US012338295B2

(12) United States Patent
Hou et al.

(10) Patent No.: US 12,338,295 B2
(45) Date of Patent: Jun. 24, 2025

(54) BINDING AGENTS TARGETING TROP2-EXPRESSING TUMOR CELLS

(71) Applicant: KisoJi Biotechnology Inc., Montréal (CA)

(72) Inventors: Wenyang Hou, Montréal (CA); Shugang Yao, Montréal (CA); Luis Da Cruz, Montréal (CA); David S. Young, Montréal (CA)

(73) Assignee: KisoJi Biotechnology Inc., Montreal (CA)

( * ) Notice: Subject to any disclaimer, the term of this patent is extended or adjusted under 35 U.S.C. 154(b) by 0 days.

(21) Appl. No.: 18/664,070

(22) Filed: May 14, 2024

(65) Prior Publication Data

US 2024/0317886 A1 Sep. 26, 2024

Related U.S. Application Data

(63) Continuation of application No. 18/620,397, filed on Mar. 28, 2024, which is a continuation of application No. PCT/CA2022/051437, filed on Sep. 28, 2022.

(60) Provisional application No. 63/249,728, filed on Sep. 29, 2021, provisional application No. 63/326,572, filed on Apr. 1, 2022.

(51) Int. Cl.
*C07K 16/30* (2006.01)
*A61K 39/00* (2006.01)
*A61P 35/00* (2006.01)

(52) U.S. Cl.
CPC .............. *C07K 16/30* (2013.01); *A61P 35/00* (2018.01); *A61K 2039/505* (2013.01); *C07K 2317/524* (2013.01); *C07K 2317/526* (2013.01); *C07K 2317/53* (2013.01); *C07K 2317/565* (2013.01); *C07K 2317/567* (2013.01); *C07K 2317/569* (2013.01); *C07K 2317/732* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 2012/0237518 A1 | 9/2012 | Yamaguchi et al. |
| 2018/0112007 A1 | 4/2018 | Bamdad et al. |

FOREIGN PATENT DOCUMENTS

| CA | 3154454 A1 | 4/2021 |
| CA | 3231574 A1 | 4/2023 |
| CN | 111518212 A | 4/2020 |
| EP | 2573120 A1 | 3/2013 |
| EP | 2799452 A1 | 11/2014 |
| WO | 20180183041 A1 | 10/2018 |
| WO | 202011868 A1 | 1/2020 |
| WO | 2021119832 A1 | 6/2021 |
| WO | 2022095851 A1 | 5/2022 |
| WO | 2022143670 A2 | 7/2022 |
| WO | 2023049999 A1 | 4/2023 |

OTHER PUBLICATIONS

Conrath, et al., "Camel Single-domain Antibodies as Modular Building Units in Bispecific and Bivalent Antibody Constructs", The Journal of Biological Chemistry, vol. 276, No. 10, 2001 (pp. 7346-7350).
Coppieters, et al., "Formatted Anti-Tumor Necrosis Factor a VHH Proteins Derived from Camelids Show Superior Potency and Targeting to Inflamed Joints in a Murine Model of Collagen-Induced Arthritis", Arthritis & Rheumatism, vol. 54, DOI 10.1002/art. 21827, No. 6 Jun. 2006 (pp. 1856-1866).
De Vlieger, et al., "Single-Domain Antibodies and Their Formatting to Combat Viral Infections", Antibodies, vol. 8, No. 1, 2019, DOI: 10.3390/antib8010001, (22 pages).
Fridy, et al., "A Robust Pipeline for Rapid Production of Versatile Nanobody Repertoires", Nature Methods, vol. 11, No. 12, Dec. 2014, DOI: 10.1038/nmeth.3170, Author Manuscript (pp. 1253-1260).
Hamers-Casterman, et al., "Naturally occurring antibodies devoid of light chains", Nature, vol. 363, Jun. 3, 1993, DOI: 10.1038/363446a0 (pp. 446-448).
Hmila, et al., "VHH, Bivalent Domains and Chimeric Heavy Chain-only Antibodies with High Neutralizing Efficacy for Scorpion Toxin Aahi", Molecular Immunology, vol. 45, No. 14, 2008, DOI: 10.1016/j.molimm.2008.04.011, (pp. 3847-3856).
Hultberg, et al., "Llama-Derived Single Domain Antibodies to Build Multivalent, Superpotent and Broadened Neutralizing Anti-Viral Molecules", PLoS One, vol. 6, No. 4, Apr. 2011, e17665, DOI: 10.1371/journal.pone.0017665 (12 pages).
Jähnichen, et al., "CXCR4 nanobodies (VHH-based single variable domains) potently inhibit chemotaxis and HIV-1 replication and mobilize stem cells", Proceedings of the National Academy of Science, vol. 107, No. 47, Nov. 23, 2010 (pp. 20565-20570).
Muyldermans, et al., "Distinct antibody species: structural differences creating therapeutic opportunities", Current Opinion in Immunology, vol. 40, Jun. 2016, DOI: 10.1016/j.coi.2016.02.003, (pp. 7-13).
Muyldermans, et al., "Sequence and structure of VH domain from naturally occurring camel heavy chain immunoglobulins lacking light chains", Protein Engineering, Design & Selection, vol. 7, No. 9, Sep. 1994, pp. 1129-1135, DOI: 10.1093/protein/7.9.1129, (7 pages).
Simmons, et al., "Dimerisation strategies for shark IgNAR single domain antibody fragments", Journal of Immunological Methods, vol. 315, No. 1-2, 2006, pp. 171-184, DOI: 10.1016/j.jim.2006.07. 019, (14 pages).

(Continued)

*Primary Examiner* — Nora M Rooney
(74) *Attorney, Agent, or Firm* — Proskauer Rose LLP

(57) ABSTRACT

The present disclosure generally relates to binding agents, such as antibodies and antigen binding fragments thereof, that are capable of binding to trophoblast cell surface antigen-2 (TROP2). Also disclosed herein are binding agents that are capable of targeting TROP2-expressing tumor cells and their use for the treatment of cancer. Single domain antibodies that specifically binds to amino acid residues of the extracellular domain of TROP2 are provided.

28 Claims, 55 Drawing Sheets

Specification includes a Sequence Listing.

(56) References Cited

OTHER PUBLICATIONS

Stepan, et al., "Expression of Trop2 Cell Surface Glycoprotein in Normal amd Tumor Tissues: Potential Implications as a Cancer Therapeutic Target", Journal of Histochemistry and Cytochemistry, 2011, 59, http://www.sagepub.com/journalsPermissions.nav DOI: 10.1369/0022155411410430 (pp. 701-710).

Vu, et al., "Comparison of Llama Vh Sequences from Conventional and Heavy Chain Antibodies", Molecular Immunology, vol. 34, No. 16-17, Dec. 4, 1997 (pp. 1121-1131).

"International Search Report" for International Application No. PCT/CA22/51437, dated Feb. 9, 2023 (7 pages).

Goldenberg, et al., "The Emergence of Trophoblast Cell-Surface Antigen 2 (TROP-2) as a Novel Cancer Target", Oncotarget, www.oncotarget.com vol. 9, No. 48, dated Jun. 22, 2018, (pp. 28989-29006).

Hu, et al., "Identification and Characterization of Specific Nanobodies against Trop-2 for Tumor Targeting", International Journal of Molecular Sciences (IJMS) Supporting Information, 2022, 23, 7942, dated Jul. 19, 2022, https://doi.org/10.3390/ijms23147942 (17 pages).

Hu, et al., "Identification and Characterization of Specific Nanobodies against Trop-2 for Tumor Targeting", International Journal of Molecular Sciences (IJMS), 2022, 23, 7942, dated Jul. 19, 2022, https://doi.org/10.3390/ijms23147942 (17 pages).

Ikeda, et al., "Cell Surface Antibody Retention Influences In Vivo Antitumor Activity Mediated by Antibody-dependent Cellular Cytotoxicity", Anticancer Research, vol. 36, No. 11, dated Nov. 2016, DOI: 10.21873/anticanres.11181 (pp. 5937-5944).

Ikeda, et al., "PrIEJ 1, a Novel Anti-Trop-2 Antibody Isolated by Adenovirus-based Antibody Screening, Recognizes a Unique Epitope", Biochemical and Biophysical Research Communications, Epub, dated Feb. 19, 2015, vol. 458, No. 4, DOI: 10.1016/j.bbrc.2015.02.051 (pp. 877-882).

Jin, et al., "Emerging New Therapeutic Antibody Derivatives for Cancer Treatment", Signal Transduction and Targeted Therapy (2022 7:39), https://doi.org/10.1038/s41392-021-00868-x, dated Feb. 7, 2022 (28 pages).

Lin, et al., "A Novel Human Fab Antibody for Trop2 Inhibits Breast Cancer Growth in Vitro and in Vivo", International Journal of Cancer, Epub vol. 134, No. 1, 19 dated Sep. 2013, DOI: 10.1002/ijc.28451 (pp. 1239-1249).

Tanaka, et al., "An Anti-TROP2 Monoclonal Antibody TrMab-6 Exerts Antitumor Activity in Breast Cancer Mouse Xenograft Models", Oncology Reports, Epub, vol. 46, No. 1, dated May 20, 2021, DOI: 10.3892/or.2021.8083 (p. 132).

De Greve, Henri et al., "Simplified monomeric VHH-Fc antibodies provide new opportunities for passive immunization," Current Opinion in Biotechnology, 61:96-101, https://doi.org/10.1016/j.copbio 2019.11.006 (Year 2020) (6 pages).

Cardillo, Thomas M., et al., "Humanized Anti-Trop-2 IgG-SN-38 Conjugate for Effective Treatment of Diverse Epithelial Cancers: Preclinical Studies in Human Cancer Xenograft Models and Monkeys", Clin Cancer Res 17(10) May 15, 2011, pp. 3157-3169 (13 pages).

Guerra, Emanuela, et al., "The anti-Trop-2 antibody-drug conjugate Sacituzumab Govitecan-effectiveness, pitfalls and promises", Ann Transl Med 2022; 10(9):501, https://dx.doi.org/10.21037/atm-22-621 (5 pages).

Liu Xinlin, et al., "Trop2-targeted therapies in solid tumors: advances and future directions", Theranostics, vol. 14, Issue 9 (2024) pp. 3674-3692 (19 pages).

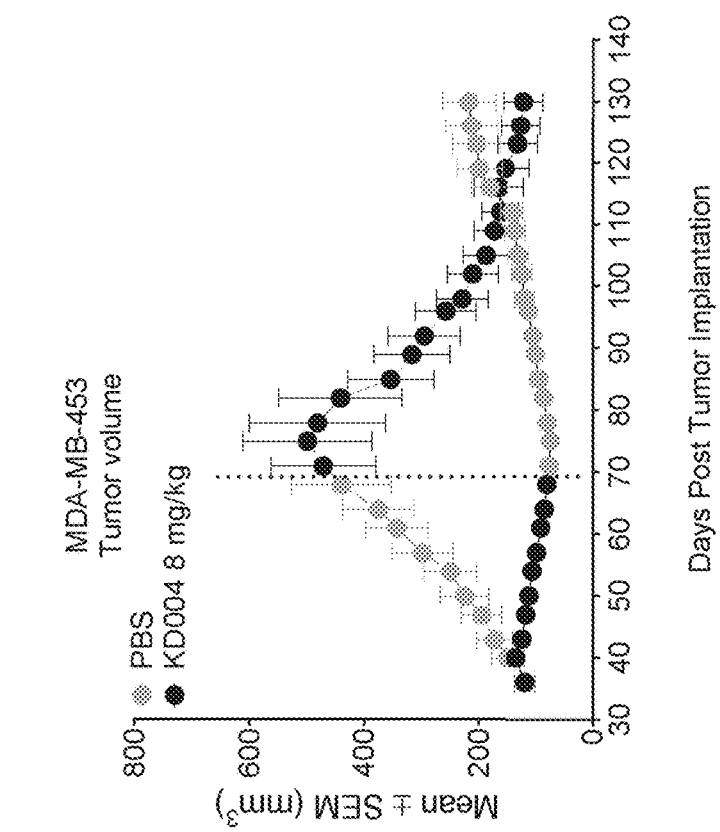
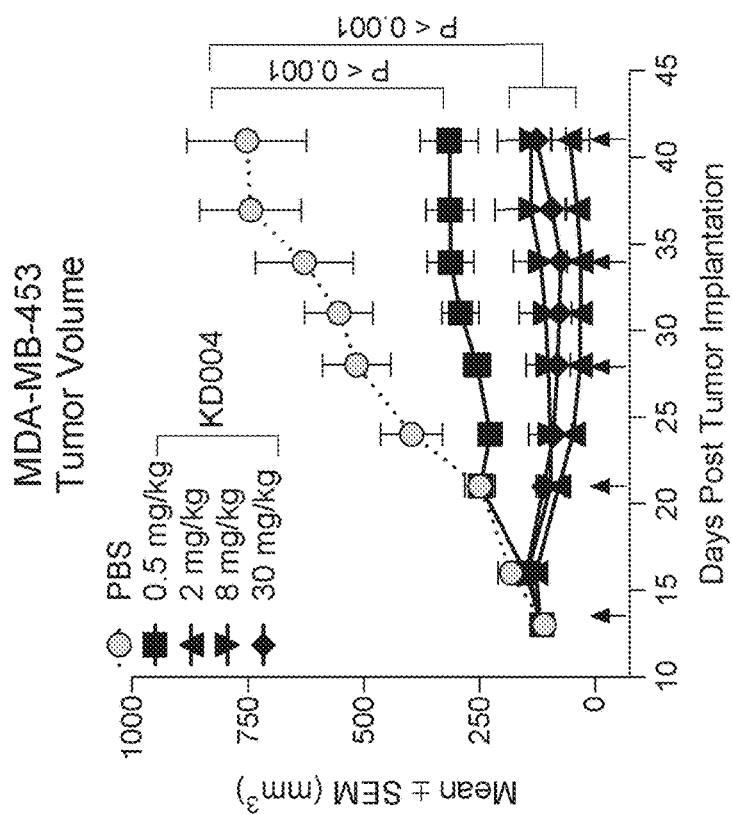
FIG. 2A
FIG. 2B

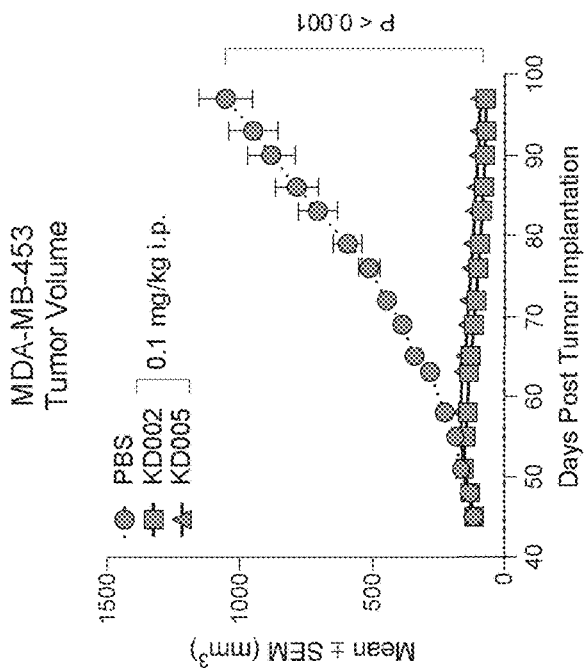
FIG. 2C
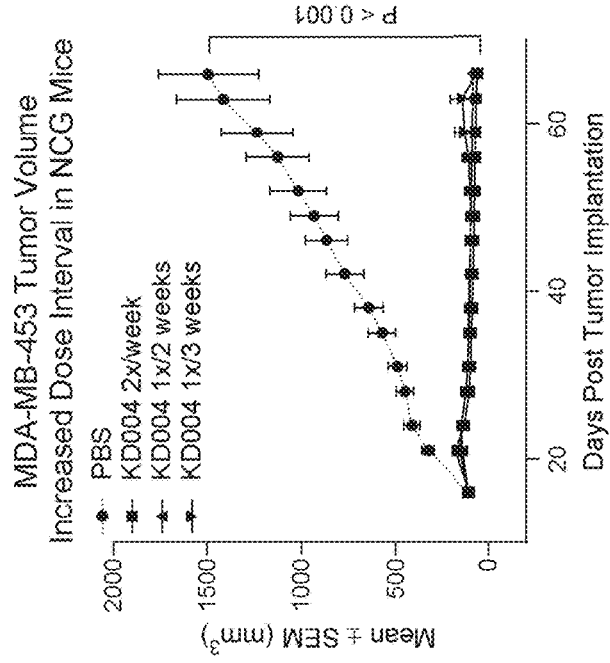
FIG. 2D
| Mouse model | Dosage (mg/kg) | Route | Cmax (ug/ml) | tmax (hours) | AUC (ug/ml*hr) | $t_{1/2}$ (hours) |
|---|---|---|---|---|---|---|
| NCG | 30 | I.V | 1096.583 | 0.08 | 13108 | 61.2 |
| | 8 | I.V | 320.221 | 0.08 | 5174.79 | 62.1 |
| | 2 | I.V | 64.89 | 0.08 | 581.58 | 22.9 |
FIG. 2E

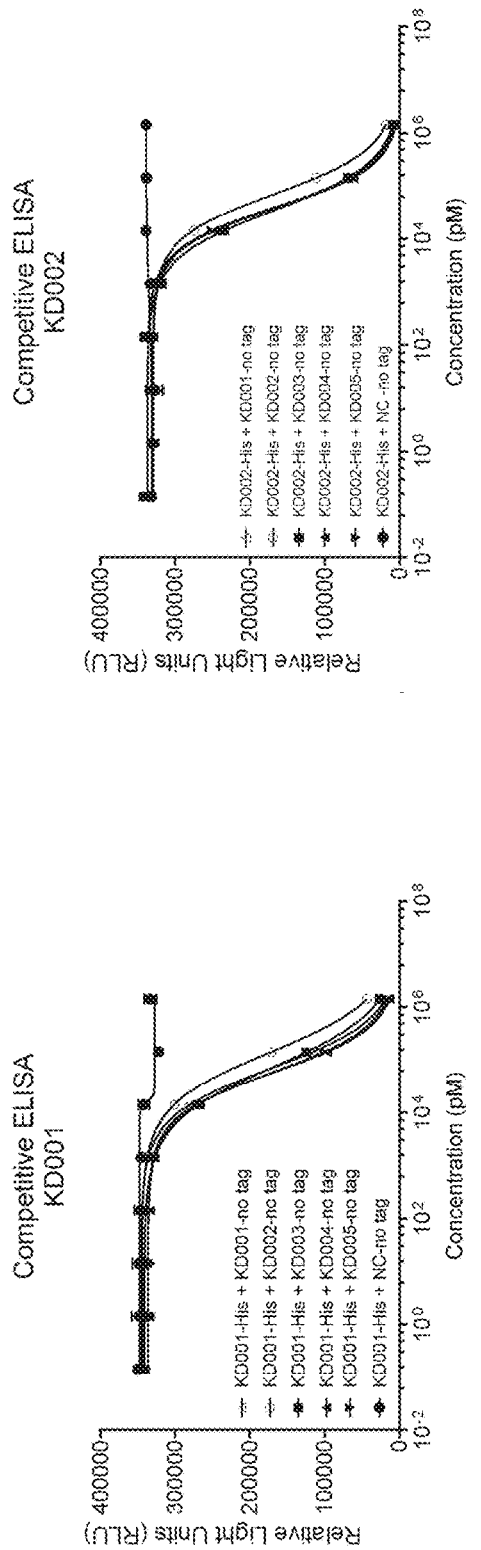
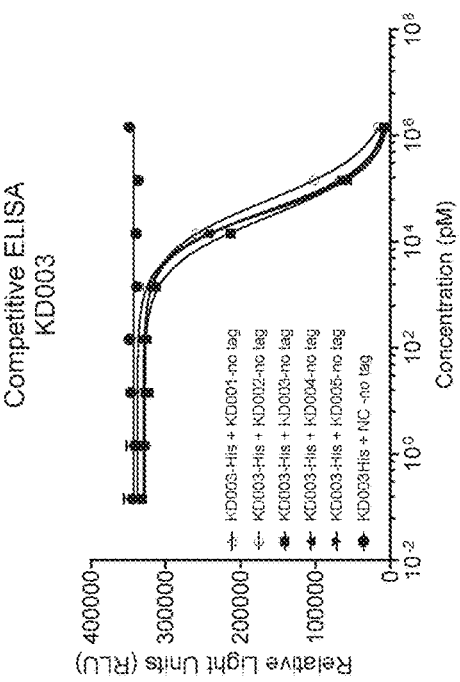
FIG. 8A
FIG. 8B
FIG. 8C

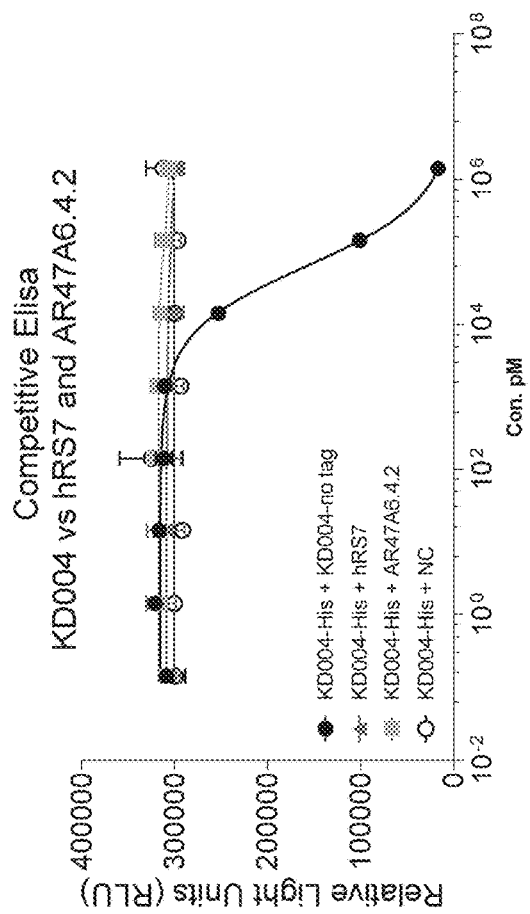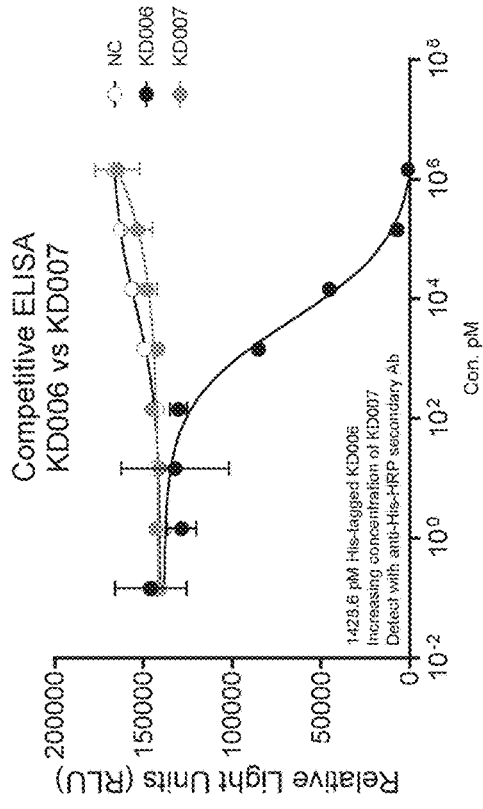

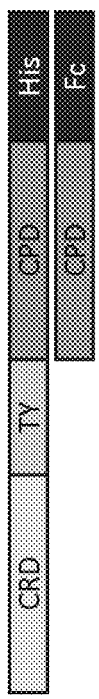
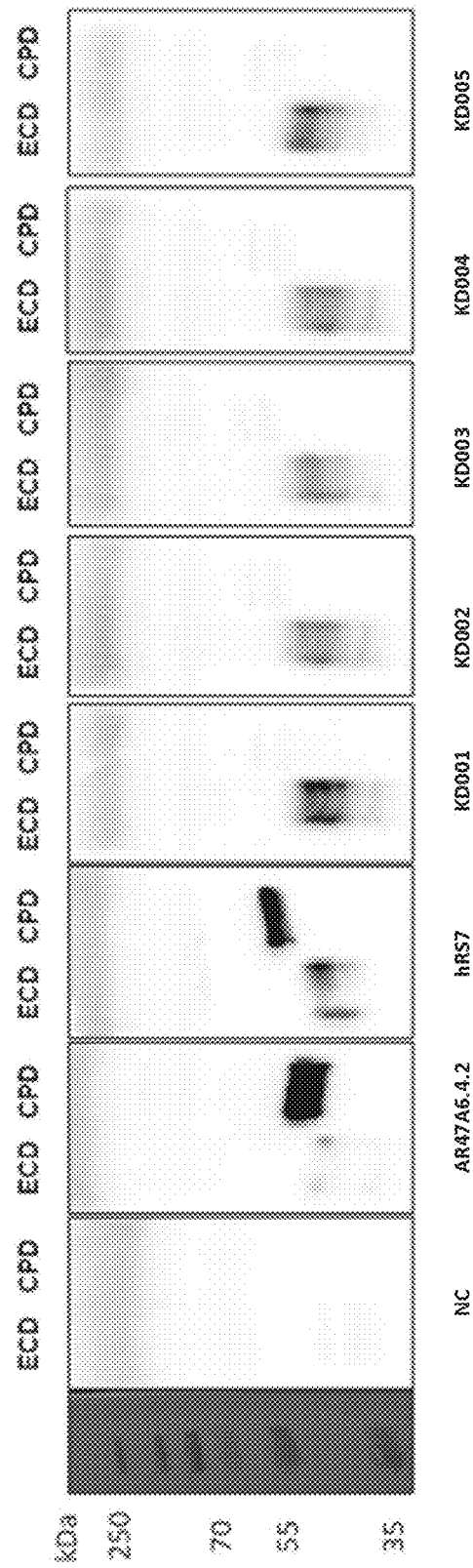
FIG. 10A
FIG. 10B

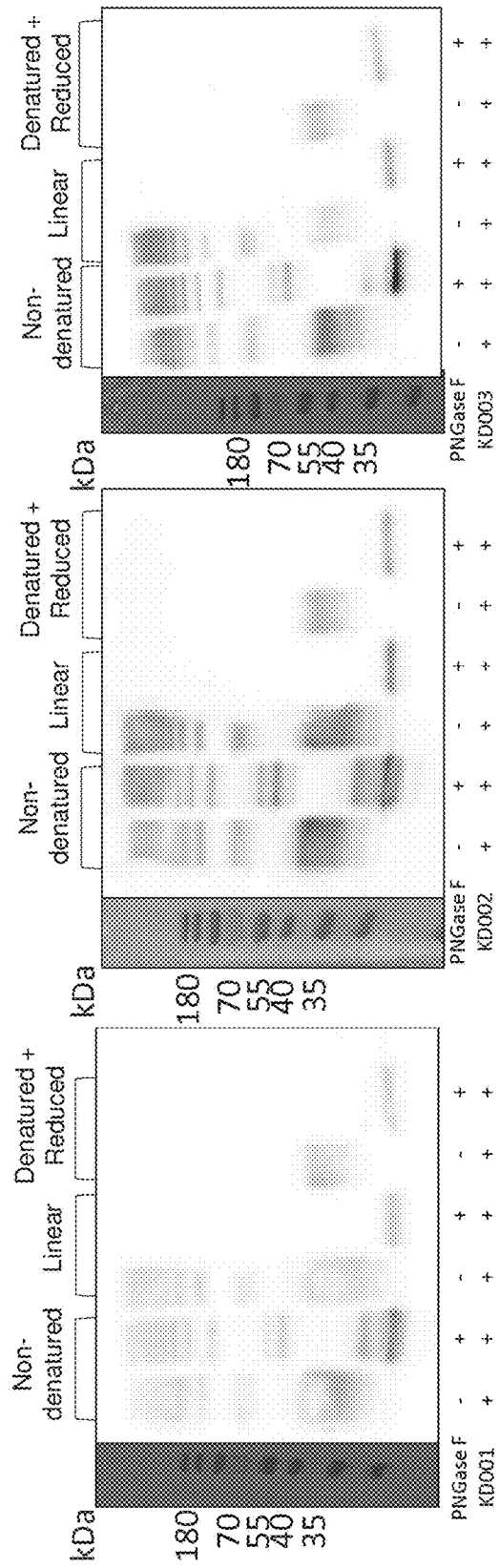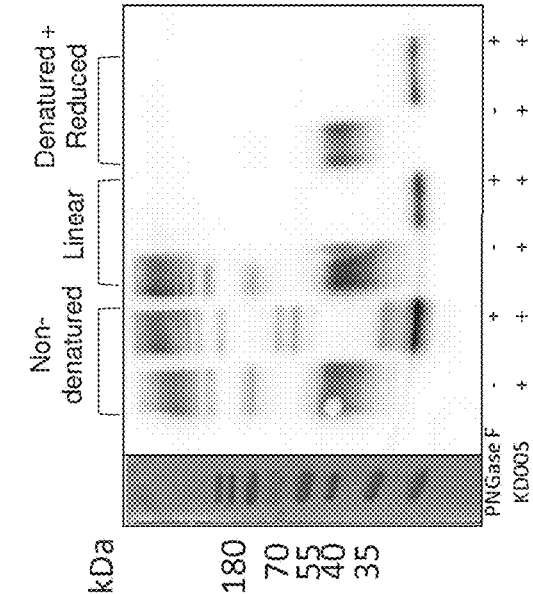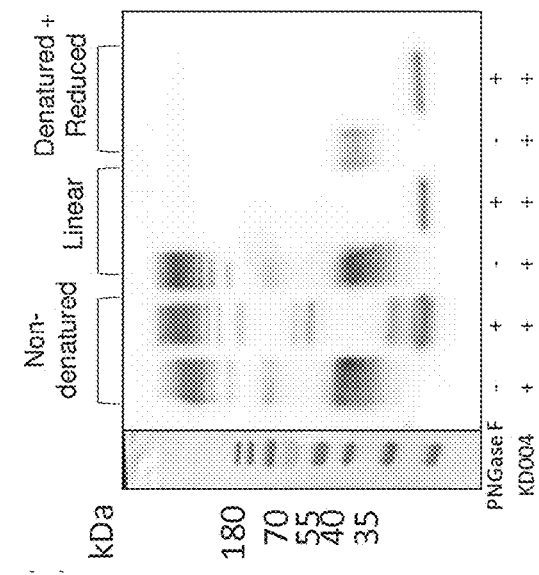

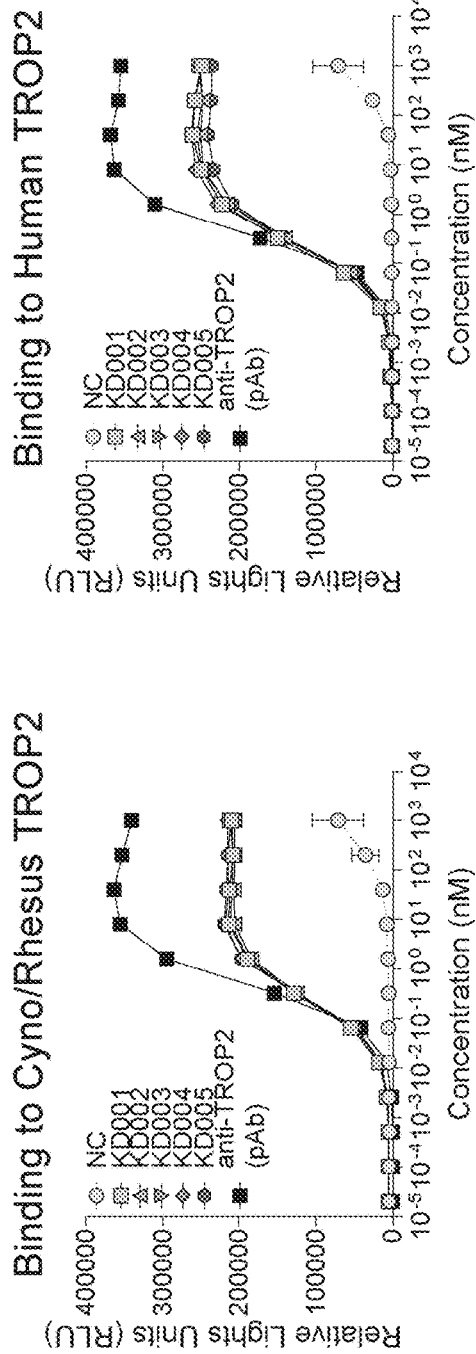
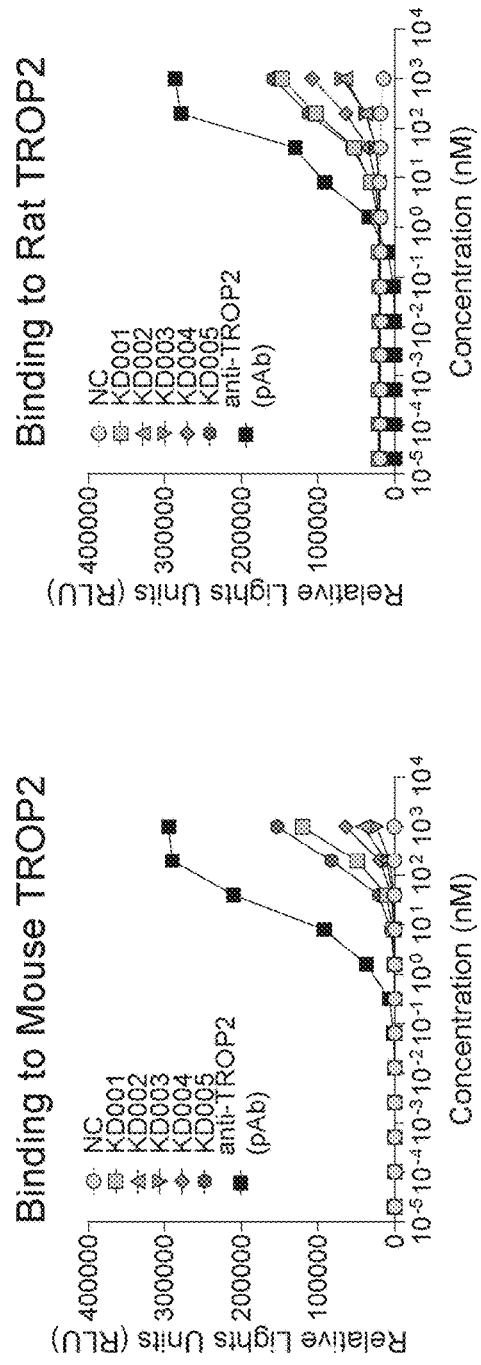
FIG. 12A
FIG. 12B
FIG. 12C
FIG. 12D

| Antibodies | Human TROP2 KD (M) | Cynomolgus TROP2 KD (M) |
|---|---|---|
| KD001 | 8.26E-11 | 2.57E-11 |
| KD002 | 4.32E-11 | 8.11E-11 |
| KD003 | 8.93E-11 | 1.69E-10 |
| KD004 | 2.94E-11 | 3.58E-11 |
| KD005 | 2.68E-11 | 5.97E-11 |

FIG. 12E

| Antibody | ka (1/Ms) | kd (1/s) | KD (M) |
|---|---|---|---|
| KD001 | 9.13E+05 | 7.54E-05 | 8.26E-11 |
| KD002 | 1.32E+06 | 5.69E-05 | 4.32E-11 |
| KD003 | 1.06E+06 | 4.88E-05 | 4.59E-11 |
| KD004 | 1.51E+06 | 4.42E-05 | 2.94E-11 |
| KD005 | 1.59E+06 | 4.27E-05 | 2.68E-11 |

FIG. 12F

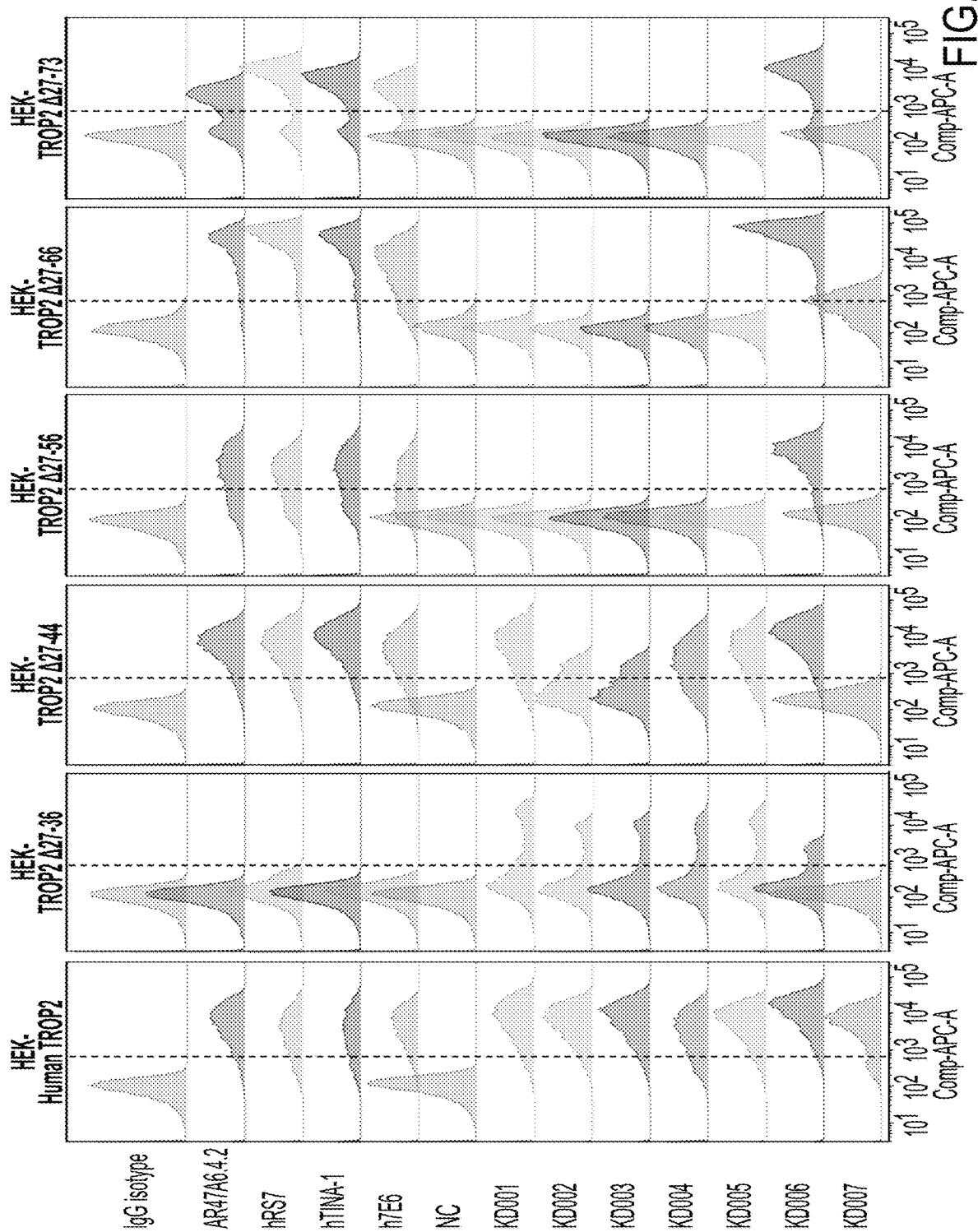

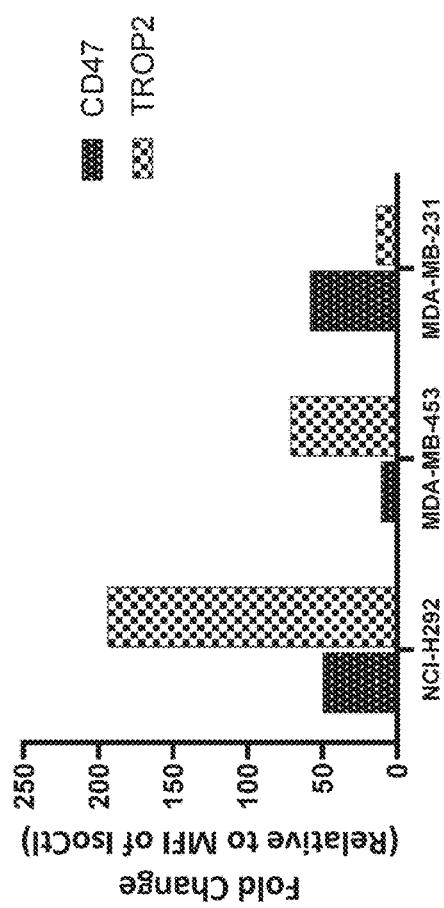
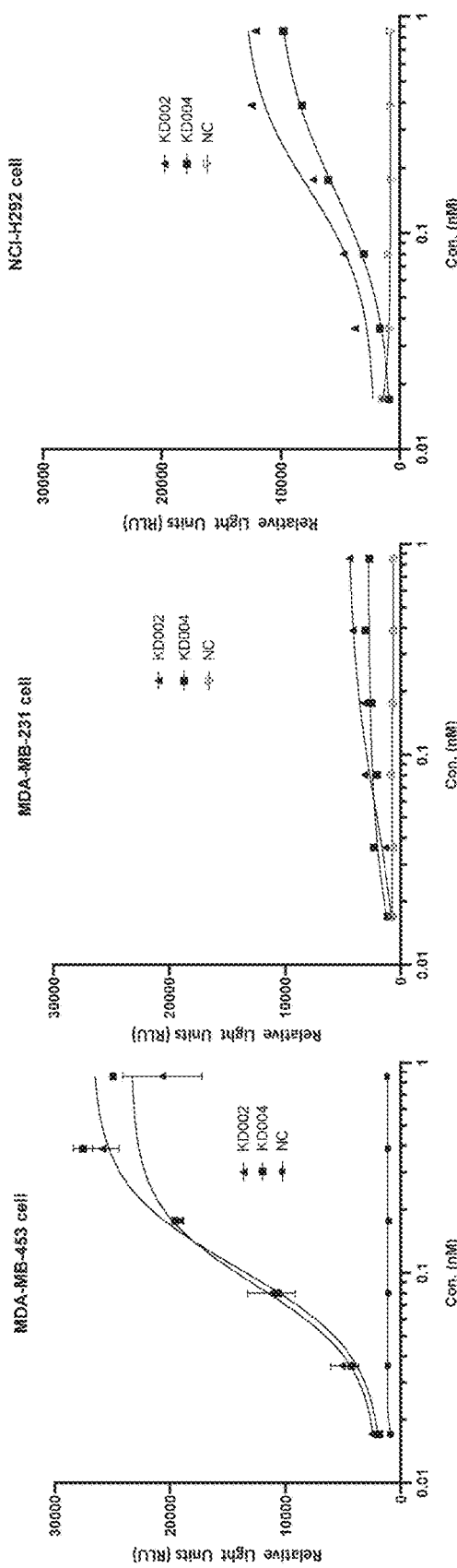
FIG. 14B
FIG. 14C
FIG. 14D
FIG. 14E

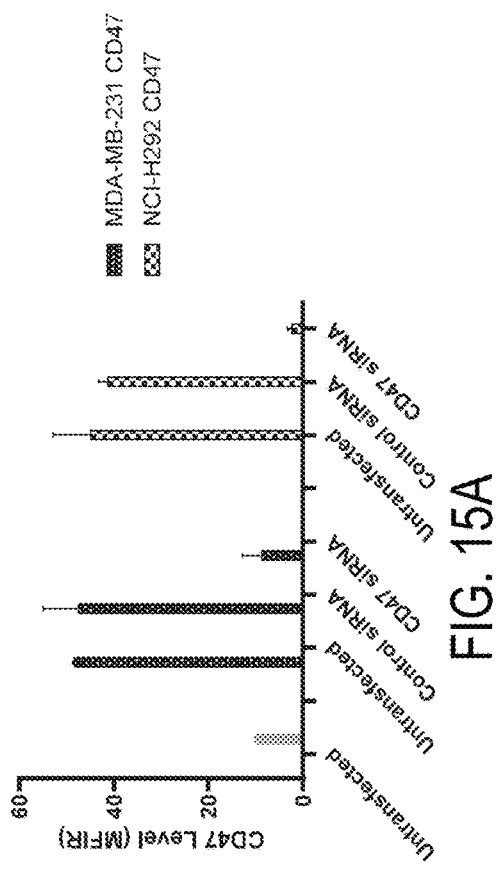
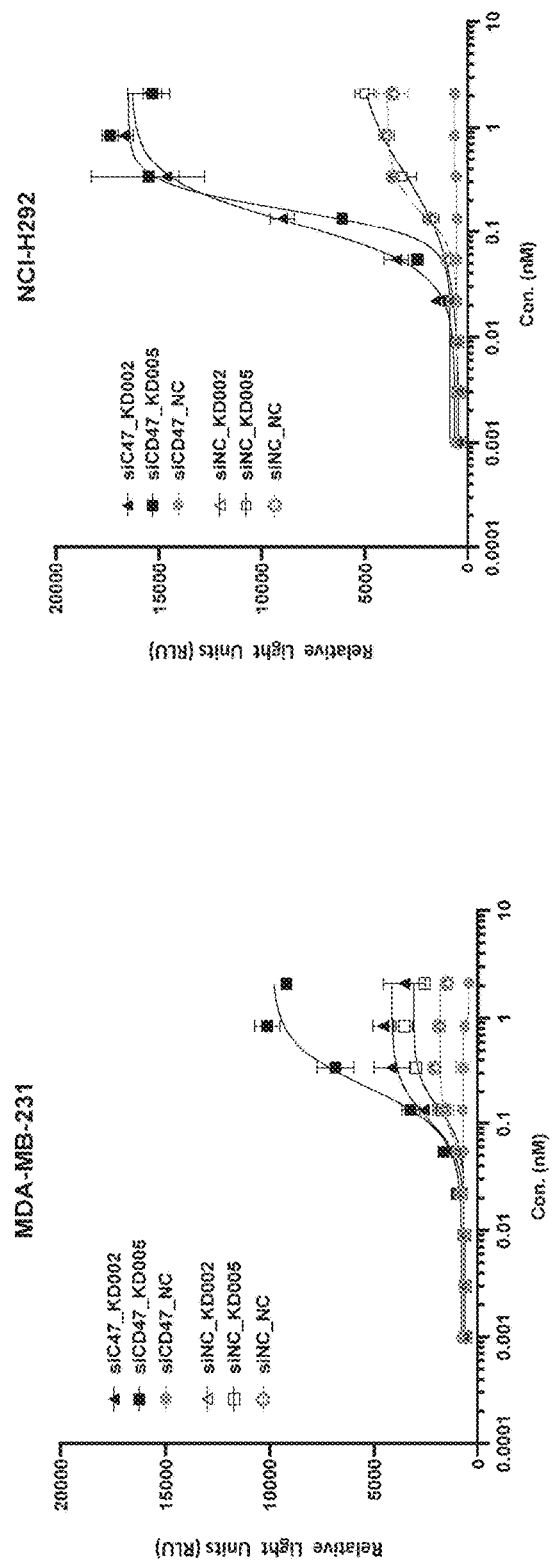

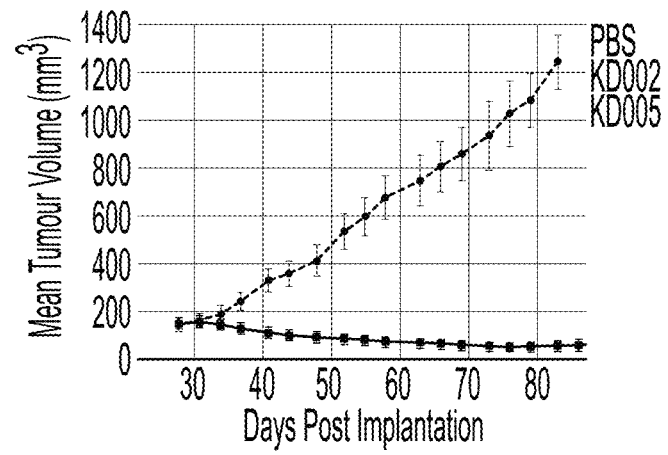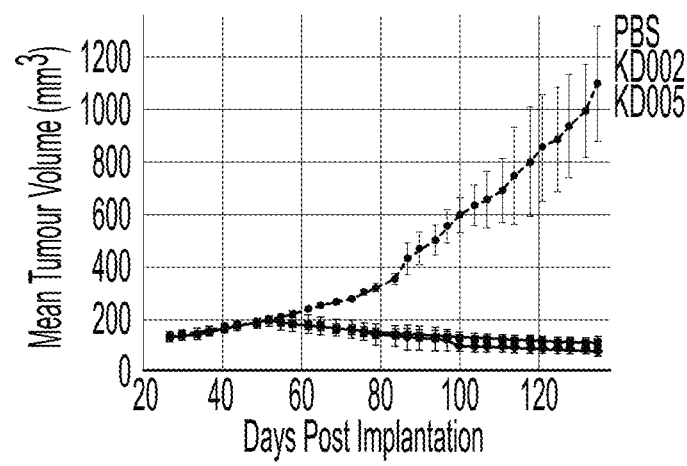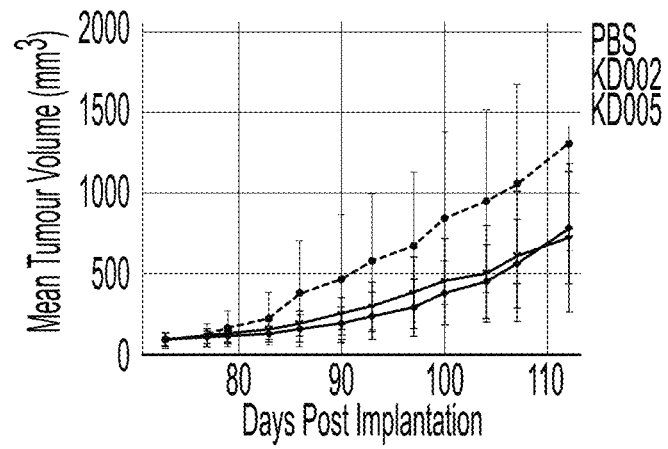
FIG. 18B

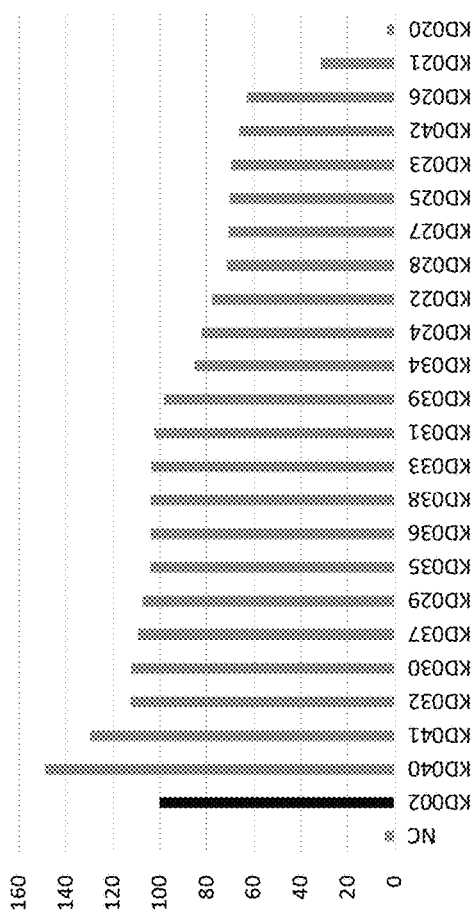
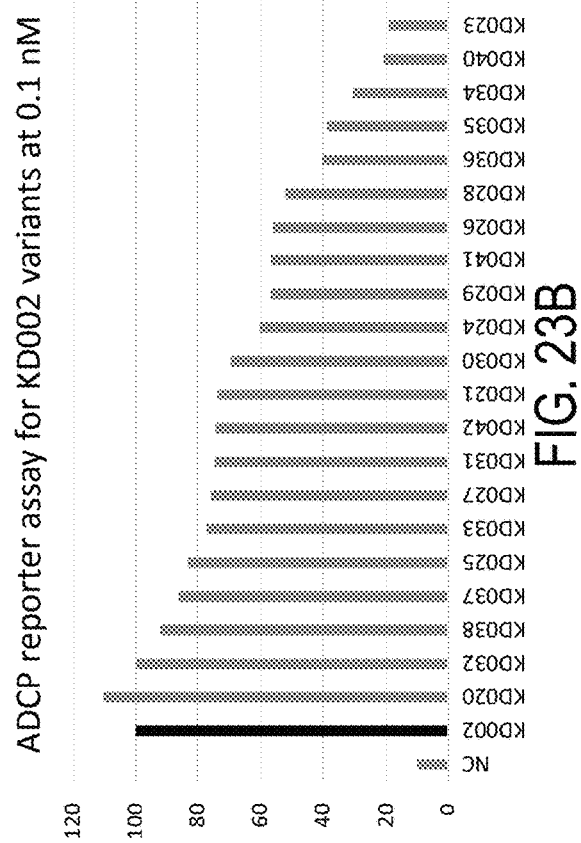
FIG. 23A
FIG. 23B

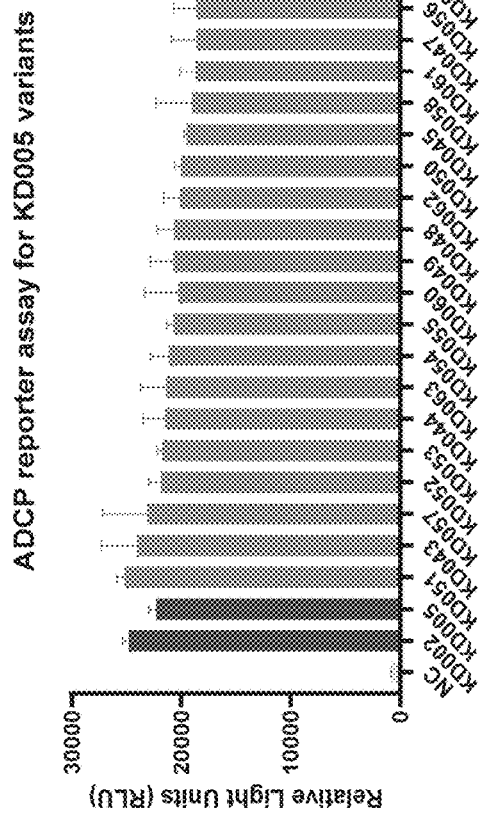
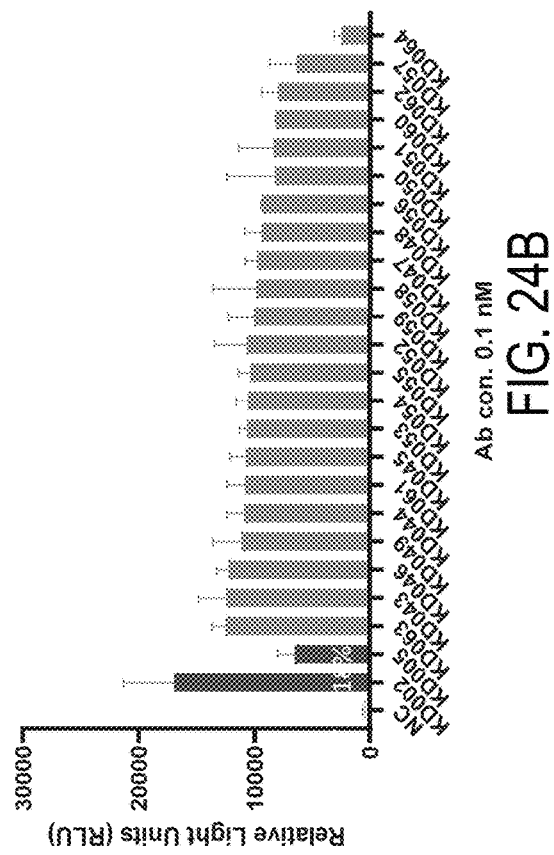

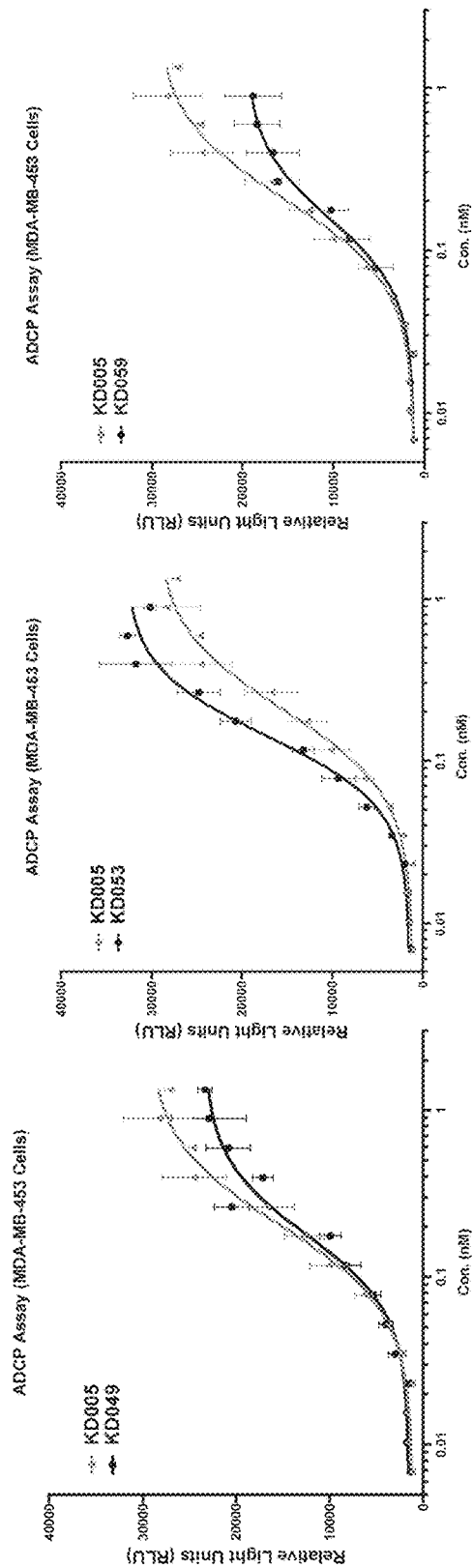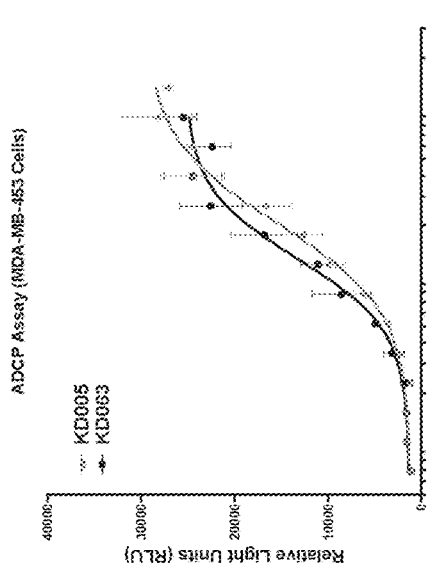

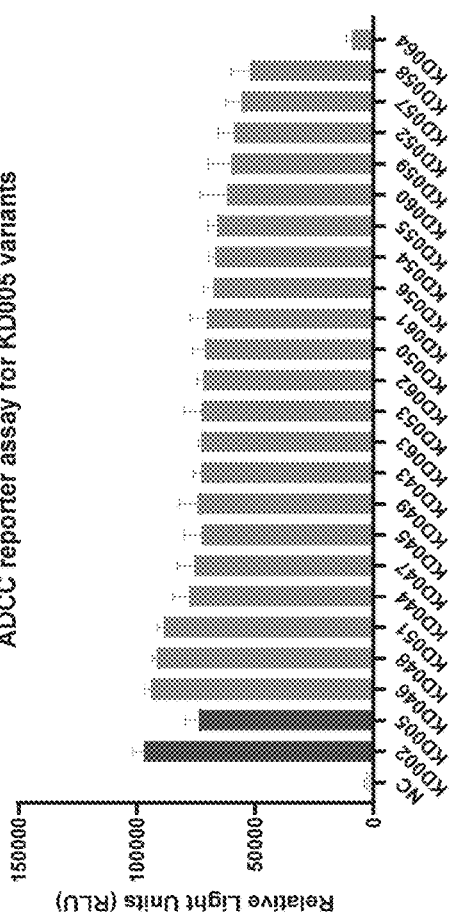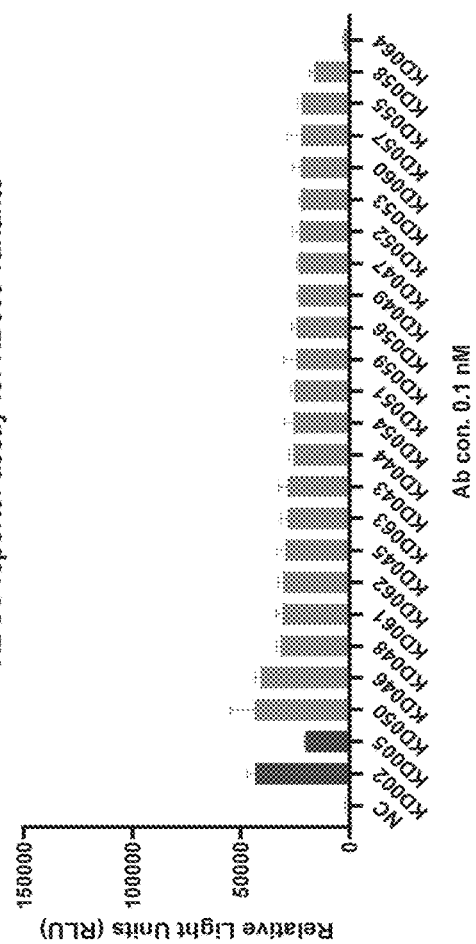

```
SEQID23  QVQLQESGGGMVQVGGSLRLSCAASGFPFSSADMSWVRQAPGKGPEWVSYINADGSKTYY  60
SEQID24  QVQLQESGGGMVQVGGSLRLSCAASGFTFSNYDMSWVRQAPGKGPEWVSYINAGGSNTDY  60
SEQID22  QVQLQESGGGMVQHPGGSLRLSCAASGFTFSGSDMSWVRQAPGKGPEWVSYITSG-GTTYY  59
SEQID26  QVQLQESGGGLVEAGGSLRLSCAASGFTFSGSDMSWVRQAPGKGPEWVSYITSG-GTTYY  59
SEQID25  QVQLQESGGGLVQPGRSLRLSCAASGFTFSGSDMSWVRQAPGKGPEWVSYITGS-GTTYY  59
         ****:****:  :.* *:**********:*:. ***************** .  .*.*

SEQID23  PDSVKGRFTISRDNAKNTLYLLLMNNLKPEDTALYRCARAKLTDTHYVEDYWGQGTQVTVS  120
SEQID24  PDSVKGRFTISRDNAKNMLYLLLMNNLKPEDTALYRCARAKLTDTHYVEDYMGQGTQVTVS  120
SEQID22  PDSVKGRFTISRDNAKNTLYLQMNSLTPDDTALYRCAKAKARLTDSHYVEDAWGQGTQVTVS  119
SEQID26  PDSVKGRFTISRDNAKNMLYLQMNSLKPDDTALYRCAKSRLTDSHYVEDAWGQGTQVTVS  119
SEQID25  PDSVKGRFTISRDNAKNMLYLQMNSLKPDDTALYRCAKARLTDSHYVEDAWGQGTQVTVS  119
         *****************:***  **.* **:*****:: .:***.*****. ********

SEQID23  S  121
SEQID24  S  121
SEQID22  S  120
SEQID26  S  120
SEQID25  S  120
```

| CODE | SEQ ID | Sequence of variable region |
|---|---|---|
| KD002 | 23 | QVQLQESGGGMVQVGGSLRLSCAASGFPFSSADMSWVRQAPGKGPEWVSYINADGSKTYYPDSVKGRFTISRDNAKNTLYLLMNNLKPEDTALYRCARAKLTDTHYVEDYWGQGTQVTVSS |
| KD022 | 73 | E\*\*\*V\*\*\*\*L\*\*P\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*A\*T\*\*\*\*\*\*\*\*\*\*\*\*\*\*\*\*\*\*\*\*\*\*\*\*Q\*\*S\*RA\*\*\*\*V\*\*\*Y\*\*\*\*\*\*\*\*\*\*\*\*\*\*\*\*\*\*\*\*\*\*\*\*\*\*\* |
| KD024 | 75 | \*\*\*\*V\*\*\*\*L\*\*P\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*Q\*\*S\*RA\*\*\*\*V\*\*\*\*\*\*\*\*\*\*\*\*\*\*\*\*\*\*\*\*\*\*\*\*\*\*\*\*\* |
| KD025 | 76 | \*\*\*\*\*V\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*T\*\*\*\*\*\*\*\*\*\*\*\*\*\*\*\*\*\*\*\*\*\*\*\*Q\*\*S\*\*\*\*\*\*V\*\*\*Y\*\*\*\*\*\*\*\*\*\*\*\*\*\*\*\*\*\*\*\*\*\*\*\*\*\*\*\*\* |
| KD026 | 77 | \*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*T\*\*\*\*\*\*\*\*\*\*\*\*\*\*\*\*\*\*\*\*\*\*\*\*Q\*\*S\*\*\*\*\*\*V\*\*\*\*\*\*\*\*\*\*\*\*\*\*\*\*\*\*\*\*\*\*\*\*\*\*\*\*\* |
| KD027 | 78 | \*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*L\*\*\*\*\*\*\*\*\*\*\*\*\*\*\*\*\*\*\*\*\*\*\*\*\*\*\*\*\*\*\*\*S\*\*\*\*Q\*\*S\*RA\*\*\*\*V\*\*\*\*\*\*\*\*\*\*\*\*\*\*\*\*\*\*\*\*\*\*\*\*\*\*\*\*\* |
| KD030 | 81 | \*\*\*\*\*\*\*\*\*\*\*\*L\*\*P\*\*\*\*\*\*\*\*\*\*\*\*\*\*\*\*\*\*\*\*\*\*\*\*\*\*\*\*\*\*\*\*\*\*\*L\*\*\*\*\*\*\*\*\*\*A\*T\*\*\*\*\*\*\*\*\*\*\*\*\*\*\*\*S\*\*\*\*Q\*\*S\*RA\*\*\*\*V\*\*\*\*\*\*\*\*\*\*\*\*\*\*\*M\*\*\*\*\*\*\*\*\*\*\*\*\*\*\*\* |
| KD031 | 82 | E\*\*\*\*\*\*\*\*\*L\*\*P\*\*\*\*\*\*\*\*\*\*\*\*\*\*\*\*\*\*\*\*\*\*\*\*\*\*\*\*\*\*\*\*\*\*\*\*L\*\*\*\*\*\*\*\*\*\*A\*T\*\*\*\*\*\*\*\*\*\*\*\*\*\*\*\*S\*\*\*\*Q\*\*S\*RA\*\*\*\*V\*\*\*\*\*\*\*\*\*\*\*\*\*\*\*M\*\*\*\*\*\*\*\*\*\*\*\*\*\*\*\* |
| KD032 | 83 | \*\*\*\*\*\*\*\*\*\*L\*\*P\*\*\*\*\*\*\*\*\*\*\*\*\*\*\*\*\*\*\*\*\*\*\*\*\*\*\*\*\*\*\*\*\*\*\*L\*\*\*\*\*\*\*\*\*\*A\*T\*\*\*\*\*\*\*\*\*\*\*\*\*\*\*\*S\*\*\*\*Q\*\*S\*RA\*\*\*\*V\*\*\*Y\*\*\*\*\*\*\*\*\*\*\*\*\*M\*\*\*\*\*\*\*\*\*\*\*\*\*\*\*\* |
| KD034 | 85 | \*\*\*\*\*\*\*\*\*\*L\*\*P\*\*\*\*\*\*\*\*\*\*\*\*\*\*\*\*\*\*\*\*\*\*\*\*\*\*\*\*\*\*\*\*\*\*\*L\*\*\*\*\*\*\*\*\*\*A\*T\*\*\*\*\*\*\*\*\*\*\*\*\*\*\*\*S\*\*\*\*Q\*\*S\*RA\*\*\*\*V\*\*\*\*\*\*\*\*\*\*\*\*\*\*\*M\*\*\*\*\*\*\*\*\*\*\*\*\*\*\*\* |
| KD038 | 89 | \*\*\*\*\*\*\*\*\*\*L\*\*P\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*A\*T\*\*\*\*\*\*\*\*\*\*\*\*\*\*\*\*S\*\*\*\*Q\*\*S\*RA\*\*\*\*V\*\*\*\*\*\*\*\*\*\*\*\*\*\*\*M\*\*\*\*\*\*\*\*\*\*\*\*\*\*\*\* |
| KD040 | 91 | \*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*QR\*\*\*\*\*\*\*\*\*\*\*\*\*A\*T\*\*\*\*\*\*\*\*\*\*\*\*\*\*\*\*S\*\*\*\*Q\*\*S\*RA\*\*\*\*V\*\*\*\*\*\*\*\*\*\*\*\*\*\*\*M\*\*\*\*\*\*\*\*\*\*\*\*\*\*\*\* |

FIG. 29

| CODE | SEQ ID | Sequence of variable region |
|---|---|---|
| KD005 | 26 | QVQLQESGGGLVEAGGSLRLSCAASGFTFSGSDMSWVRQAPGRGPEWVSYIHSGGTTYYPDSVKGRFTISRDNAKNTLYLQMNSLKPDDTALYRCAKSRLEDSHYYEDAWGQGTQVTVSS |
| KD043 | 94 | E*L****************************************************************L************A*T***********RAE*V************L*** |
| KD044 | 95 | E*L*********************QP*****************************************L************A*T***********RAE*V*I**********L*** |
| KD045 | 96 | E*L*********************QP*****************************************L************A*T***********S*RAE*V**********L*** |
| KD046 | 97 | **L*********************QP*****************************************L************A*T***********S*RAE*V**********L*** |
| KD047 | 98 | **L*********************QP*****************************************L************A*T***********S*RAE*V**********L*** |
| KD048 | 99 | ****************************QP*****************************************L************A*T***********S*RAE***V*I**********L*** |
| KD049 | 100 | ****************************QP*****************************************L************A*T***********S*RAE*V**********L*** |
| KD050 | 101 | ****************************QP*****************************************L**********T***********S*RAE*V**********L*** |
| KD051 | 102 | ****************************QP*****************************************L************A*T***********S*RAE***V*I**********L*** |
| KD052 | 103 | E*V*********************QP*****************************************L************A*T***********S*RAE***V*I**********L*** |
| KD053 | 104 | ****************************QP******************************************L***********A*T***********S*RA****V*I**********L*** |
| KD054 | 105 | ****************************QP*****************************************L************A*T***********S*RAE*V**********L*** |
| KD055 | 106 | E*L*********************QP*****************************************L************A*T***********S*RAE*V**********L*** |
| KD056 | 107 | ****************************QP*****************************************L************A*T***********S*RAE*V**********L*** |
| KD057 | 108 | ****************************QP*****************************************L************A*T***********S*RAE*V**********L*** |
| KD058 | 109 | ****************************QP*****************************************L************A*T***********S*RAE*V**********L*** |
| KD059 | 110 | ****************************QP*****************************************L************A*T***********S*RAE*V**********L*** |
| KD060 | 111 | ****************************QP*****************************************L************A*T***********S*RAE*V**********L*** |
| KD061 | 112 | ******************************I*P*******************************************L***********A*T***********S*RA**V**********L*** |
| KD062 | 113 | ****************************IQP*****************************************L***********A*T***********S*RAE*V**********L*** |
| KD063 | 114 | ****************************IQP*****************************************L***********A*T***********S*RAE*V**********L*** |
| | 144 | XVQLXESGGGLXXXGGSLXRLSCAASGFTFSGXDMSWVRQAPGRGXEWVSXIHSGGTTYYXDXVKGRFTISRDNXKNTLLQMNSLXXXDTAXYXCAKSRLXDSHYXEDAWGQGTXVTVSS |

FIG. 30

| CODE | SEQ ID | Sequence of variable region |
|---|---|---|
| KD005 | 26 | QVQLQESGGGLVEAGGSLRLSCAASGFTFSGSDMSWVRQAPGKGPEWVSYITSGGTTYYPDSVKGRFTISRDNAKNTLYLQMNSLKPEDTALYRCAKSELTDSHYVEDAWGQGTQVTVSS |
| KD043 | 94 | E*L********QP****************************************************L*****A*T***********S*************RAEVY*********************L**** |
| KD044 | 95 | E*L********QP****************************************************L*****A*T***********S*************RAEVY*********************L**** |
| KD045 | 96 | E*L********QP****************************************************L*****A*T***********S*************RAEVY*********************L**** |
| KD046 | 97 | **L********QP**************************************************************A*T***********S*************RAEVY*********************L**** |
| KD047 | 98 | **L********QP**************************************************************A*T***********S*************RAEVY*********************L**** |
| KD049 | 100 | ***************QP**************************************************************A*T***********S*************RAEVY*********************L**** |
| KD050 | 101 | ***************QP**************************************************************A*T***********S*************RAEVY*********************L**** |
| KD051 | 102 | ***************QP**************************************************************A*T***********S*************RAEVY*********************L**** |
| KD052 | 103 | E*V********IQP*************************************************************A*T***********S*************RAEVY*********************L**** |
| KD053 | 104 | **V********IQP*************************************************************A*T***********S*************RA*VY*********************L**** |
| KD054 | 105 | ***************IQP*************************************************************A*T***********S*************RAEVY*********************L**** |
| KD055 | 106 | E*V********IQP*************************************************************A*T***********S*************RAEVY*********************L**** |
| KD056 | 107 | **V********IQP*************************************************************A*T***********S*************RAEVY*********************L**** |
| KD057 | 108 | **V********IQP*********************************************L***********A*V***********S*************RAEVY*********************L**** |

FIG. 31

| CODE | SEQ ID | Sequence of variable region |
|---|---|---|
| KD005 | 26 | QVQLQESGGGLVQAGGSLRLSCAASGFTFSGSSDMSWVRQAPGKGPEWVSYITSGGTTYYPDSVKGRFTISRDNAKMTLYLQMNSLKPDDTALYRCAKSRLTDSHYVEDAWGQGTQVTVSS |
| KD043 | 94 | E*L**IQP************************************L*A****************A*T*********S*******RAE*VY*************L**** |
| KD044 | 95 | E*L**IQP************************************L*A****************A*T*********S*******RAE*VY*************L**** |
| KD045 | 96 | E*L**IQP**************************************************************A*T*********S*******RAE*VY*************L**** |
| KD046 | 97 | **L**IQP**************************************************************A*T*********S*******RAE*VY*************L**** |
| KD049 | 100 | *********IQP**************************************************************A*T*********S*******RAE*VY*************L**** |
| KD051 | 102 | E*V**IQP************************************************************T*********S*******RAE*VY*************L**** |
| KD052 | 103 | E*V**IQP************************************L*V*******************A*T*********S*******RAE*VY*************L**** |
| KD053 | 104 | *********IQP************************************L*A*******************A*T*********S*******RAVY***************L**** |
| KD054 | 105 | *********IQP**************************************************************A*T*********S*******RAE*VY*************L**** |
| KD055 | 106 | E*********IQP**************************************************************A*T*********S*******RAE*VY*************L**** |
| KD057 | 108 | *********IQP************************************L*V*******************A*T*********S*******RAE*VY*************L**** |
| KD061 | 112 | *********IQP************************************L*V*******************A*T*********S*******RAVY***************L**** |
| KD063 | 114 | ***********I*P**************************************L*********************A*T*********S*******RAE*VY********************* |

BINDING AGENTS TARGETING TROP2-EXPRESSING TUMOR CELLS

CROSS-REFERENCE TO RELATED APPLICATIONS

This application is a Continuation of U.S. patent application Ser. No. 18/620,397 filed on Mar. 28, 2024, which is a continuation of International Application No. PCT/CA2022/051437, filed on Sep. 28, 2022, which claims priority to U.S. Provisional Patent Application Ser. Nos. 63/249,728 filed on Sep. 29, 2021 and 63/326,572 filed on Apr. 1, 2022, the contents of each of which are incorporated by reference herein in entirety for all purposes.

INCORPORATION-BY-REFERENCE OF SEQUENCE LISTING

The instant application contains a Sequence Listing which has been submitted electronically in XML format and is hereby incorporated by reference in its entirety. Said XML copy, created on Mar. 25, 2024, is named TROP2 PCTCA2022051437.xml and is 30 kilobytes in size.

TECHNICAL FIELD

The present disclosure generally relates to binding agents, such as antibodies and antigen binding fragments thereof, that are capable of binding to trophoblast cell surface antigen-2 (TROP2). Also disclosed herein are binding agents that are capable of targeting TROP2-expressing tumor cells and their use for the treatment of cancer. Single domain antibodies that specifically binds to amino acid residues of the extracellular domain of TROP2 are provided.

BACKGROUND

Trophoblast cell surface antigen-2 (TROP2) is a membrane-bound protein expressed at low levels in normal adult tissues. TROP2 has pleiotropic functions including inducing cell signaling and formation of cell-cell junctions by mediating interactions with extracellular and intracellular proteins. TROP2 has an extracellular epidermal growth factor (EGF)-like domain, followed by a 23 amino acids transmembrane domain and the cytoplasmic tail. The EGF-like domain contains a cysteine-rich domain, a thyroglobulin type-1 domain, and a cysteine-poor domain. In situations of TROP2 deficiency, its role in normal tissues appears to be compensated by expression of EpCAM, which is highly related to TROP2. TROP2 is highly expressed in a wide range of late-stage epithelial cancers including breast cancer and pancreatic cancer (Stepan et al., J. Histochem and Cytochem, 2011, the entire content of which is incorporated herein by reference). Overexpression of TROP2 was shown to confer oncogenic behavior in several in vitro and in vivo models. TROP2 upregulation in solid cancers is associated with increased tumor aggressiveness, metastasis, and an overall decreased survival in large groups of difficult-to-treat cancers, making it an attractive target for cancer therapy.

TROP2 positive cancers have been successfully targeted clinically by antibody-drug conjugates (ADC) but not by naked functional antibodies. ADC's have associated drug toxicity in healthy tissues, off-target effects, and payload delivery issues. Given ADC dose-limiting side effects, narrow therapeutic windows, and efficacy limitations, there is a pressing need to improve anti-TROP2 therapeutics for patients who are poorly served by current therapies, if at all.

Camelids and cartilaginous fishes naturally produce antibodies composed of functional homodimeric heavy chain only antibodies (HCAbs) (Hamers-Casterman et al., 1993; Muyldermans and Smider, 2016). The heavy chains of HCAbs lack the first constant domain (CH1) and differs from classical antibodies by only a few amino acids substitutions normally involved in light chain pairing (Muyldermans et al., 1994; Vu et al., 1997). These substitutions (Val37Phe/Tyr, Gly44Glu, Leu45Arg, and Trp47Gly) are present in framework region 2 (FR2). The antigen-binding fragment of HCAbs is referred to as, VHH or nanobody®. VHHs have a molecular weight of around 15 kDa which makes them amenable to applications that require enhanced tissue penetration or rapid clearance, such as radioisotope-based imaging. However, for therapeutic applications, the VHH half-life usually needs to be increased so as to minimize renal clearance and optimize therapeutic efficacy (De Vlieger et al., Antibodies 8(1), 1-22, 2019). Although methods to increase VHH half-life such as PEGylation, N-glycosylation, HSA or other carrier protein fusions have been exploited, such constructs can introduce immunogenicity or have limited success.

VHHs have been exploited as building blocks to make bispecific and multispecific antibodies. In some studies, bivalent constructs have been shown to be have increased avidity or affinity compared to the monovalent form (Conrath et al., 2001; Coppieters et al., 2006; Hmila et al., 2008; Simmons et al., 2006 and Hultberg et al., 2011, Jähnichen et al. (2010), Fridy et al., 2014).

Novel TROP2 binding agents including antibodies and antigen binding fragments thereof such as single domain antibodies and antigen binding fragments thereof are disclosed herein.

SUMMARY

The present disclosure therefore generally relates to a binding agent that is capable, amongst other things, of binding trophoblast cell surface antigen-2 (TROP2). Binding agents of the present disclosure specifically bind to TROP2.

Although, the binding agents may have activity against tumor cells when unconjugated, the present disclosure also encompasses a conjugated form of such binding agents. Binding agents described herein may, in some instances, have no or low activity against tumor cells in a naked form and may thus benefit from being conjugated with a therapeutic moiety.

The present disclosure therefore provides in some aspects unconjugated binding agents. In other aspects, the present disclosure provides conjugated binding agents.

Antibodies or antigen binding fragments thereof such as single domain antibodies (sdAbs) or antigen binding fragments that specifically bind to at least one epitope comprising amino acid residues of the extracellular domain (ECD) of TROP2 are provided. The single domain antibodies (sdAbs) of the present disclosure have unique binding features and activity.

For example, the complementarity determining region 3 (CDR3) of the sdAbs forms a loop fitting into a groove within the cysteine rich domain (CRD) of the extracellular domain (ECD) of TROP2. Amino acid residues of the CDR3 and of the framework region 2 (FR2) interact with amino acid residues of TROP2 cysteine rich domain and together form a clip around the CRD as a bi-paratopic antibody. These unique properties confer high affinity and a slow dissociation rate to the sdAbs disclosed herein. Surprisingly, amino acid residues of the complementarity determining region 1 (CDR1) and of the complementarity determining region 2 (CDR2) do not appear to interact with amino acid residues of the CRD.

Moreover, the anti-TROP2 single domain antibodies of the present disclosure possess anti-tumor activity without drug conjugation.

For example, the anti-TROP2 single domain antibodies of the present disclosure are capable of inducing antibody-dependent cellular cytotoxicity (ADCC) and/or antibody-dependent cellular phagocytosis (ADCP). Moreover, the anti-TROP2 single domain antibodies of the present disclosure are also capable of internalization making them amenable to deliver drug payloads into the tumor microenvironment or into tumor cells.

The single domain antibodies of the present disclosure also interfere/block TROP2 function.

Exemplary embodiments of binding agents of the present disclosure therefore include single domain antibodies or antigen binding fragments thereof that specifically binds to at least one epitope comprising amino acids of the cysteine rich domain of TROP2. In some embodiment, the single domain antibody or antigen binding fragment thereof comprises FR2 amino acid residues and CDR3 amino acid residues that interact with amino acid residues of the CRD of TROP2. The single domain antibody or antigen binding fragment thereof may have an affinity of $\leq 10^{-6}$ M for human TROP2.

The single domain antibodies of the present disclosure may be used to treat disorders or diseases associated with expression or overexpression of TROP2, such as cancer.

The binding function of sdAbs is conferred by a single polypeptide chain namely, the heavy chain variable region. This unique property provides formatting flexibility. For example, multiple sdAbs or sdAb antigen binding domains may be fused into a single polypeptide chain conferring multivalence and/or multispecificity. In addition, multiple polypeptide chains may be assembled to increase the diversity (multi-paratopic binding) or avidity of interactions with TROP2. Moreover, the sdAbs antigen binding domains may be fused to any type of polypeptide chain including for example and without limitation, fusion with a heavy chain and/or light chain of a native antibody or antigen binding fragment thereof, with protein scaffold, with immune cell modulating agent and the like.

As such, the present disclosure not only relates to the single domain antibodies disclosed herein but also more generally to binding agents that comprise one or more antigen binding domains of the single domain antibodies disclosed herein. Accordingly, in an embodiment, the binding agent may comprise an antigen binding domain of a single domain antibody disclosed herein.

In addition, the present disclosure relates to binding agents that compete with the single domain antibodies of the present disclosure. For example, single domain antibodies that compete with one of more single domain antibodies disclosed herein for the binding of at least one epitope comprising amino acid residues of the extracellular domain (ECD) of TROP2 are provided.

In some embodiments, the binding agent of the present disclosure binds to human TROP2. In other embodiments, the binding agent of the present disclosure binds to cynomolgus or Rhesus TROP2. Accordingly, the binding agent of the present disclosure may be used in the treatment of human diseases or disorders. Moreover, the pre-clinical development of the binding agents of the present disclosure may be carried out in cynomolgus or Rhesus monkeys and other related non-human primates.

In accordance with the present disclosure, the binding agent disclosed herein is capable of targeting tumor cells expressing TROP2.

In accordance with the present disclosure, the binding agent disclosed herein is capable of causing regression of tumors expressing TROP2.

In accordance with the present disclosure, the binding agent disclosed herein is also capable of causing growth inhibition of tumors expressing TROP2.

In other embodiments, the binding agent is capable of causing inhibition of tumor growth via antibody-dependent cellular cytotoxicity (ADCC).

In other embodiments, the binding agent is capable of causing inhibition of tumor growth via antibody-dependent cellular phagocytosis (ADCP).

In yet other embodiments, the binding agent may be used to deliver a payload to tumor cells expressing TROP2. Accordingly, in some embodiments, the binding agent may be used as an antibody drug conjugate (ADC).

In some embodiments, the binding agent is capable of causing direct inhibition of tumor growth. For example, the activity of the binding agent may be independent of ADCC, ADCP or ADC function.

The present disclosure relates to a binding agent that comprises one or more antigen binding domains, wherein at least one of the one or more antigen binding domains comprises an antigen binding fragment thereof that is capable of binding to TROP2.

As such, in accordance with the present disclosure, the antigen binding fragment is from a single domain antibody (heavy chain only antibody) disclosed herein.

Also, in accordance with the present disclosure, the antigen binding fragment comprises a single domain antibody variable region.

Also, in accordance with the present disclosure, the antigen binding fragment comprises the CDRs of a single domain antibody.

Therefore, the present disclosure relates to a binding agent that comprises one or more antigen binding domains, wherein at least one of the one or more antigen binding domains comprises an antigen binding domain of a single domain antibody that is capable of binding to TROP2.

The present disclosure also particularly relates to a binding agent that comprises one or more antigen binding domains, wherein at least one of the one or more antigen binding domains specifically binds to human TROP2.

The binding agent of the present disclosure is essentially polypeptidic. In some embodiments, the binding agent of the present disclosure is essentially composed of one, two or more than two polypeptide chains. However, the binding agent may comprise non-polypeptidic moieties such as for example, small molecules, sugars, radioactive labels and the like. In some embodiments, the binding agent is composed of one heavy chain. In some embodiments, the binding agent is composed of two heavy chains. In other embodiments, the binding agent is composed of more than two heavy chains.

In some embodiments, the binding agent of the present disclosure may be capable of binding to the extracellular domain (ECD) of TROP2 (as represented by amino acids 27 to 274 of TROP2 (e.g., SEQ ID NO:39 or SEQ ID NO:40), see Goldenberg et al., 2018, Ikeda, M. et al., 2015, the entire contents of which are incorporated herein by reference). In some embodiments, the binding agent of the present disclosure binds to the extracellular domain of human TROP2. In some embodiments, the binding agent of the present disclosure may be capable of binding to an epitope comprising amino acids of the extracellular domain of TROP2. In some embodiments, the binding agent of the present disclosure binds to an epitope comprising amino acids of the extracellular domain of human TROP2.

In some embodiments, the binding agent of the present disclosure may be capable of binding to an epitope including amino acid residues comprised within amino acid sequence 27-274 of TROP2. In some embodiments, the binding agent of the present disclosure binds to an epitope including amino acid residues comprised within amino acid sequence 27-274 of human TROP2.

In some embodiments, the binding agent of the present disclosure may be capable of binding to the cysteine-rich domain (CRD) of TROP2 (as represented by amino acids 27 to 73 of TROP2 (e.g., SEQ ID NO:39 or SEQ ID NO:40)). In some embodiments, the binding agent of the present disclosure binds to the cysteine-rich domain of human TROP2.

In some embodiments, the binding agent of the present disclosure may be capable of binding to an epitope comprising amino acids of the cysteine-rich domain of TROP2. In some embodiments, the binding agent of the present disclosure binds to an epitope comprising amino acids of the cysteine-rich domain of human TROP2.

In some embodiments, the binding agent of the present disclosure may be capable of binding to the thyroglobulin type-1 domain of TROP2 (as represented by amino acids 74 to 146 of TROP2 (SEQ ID NO:39 or SEQ ID NO:40)).

In some embodiments, the binding agent of the present disclosure binds to the thyroglobulin type-1 domain of human TROP2.

In some embodiments, the binding agent of the present disclosure may be capable of binding to an epitope comprising amino acids of the thyroglobulin type-1 domain of TROP2. In some embodiments, the binding agent of the present disclosure binds to an epitope comprising amino acids of the thyroglobulin type-1 domain of human TROP2.

In an exemplary embodiment, the binding agent, or antigen binding domain(s) of the binding agent may be capable of binding to a polypeptide comprising a human TROP2 amino acid sequence consisting of amino acid residues 27-274 or a fragment thereof.

In another exemplary embodiment, the binding agent, or antigen binding domain(s) of the binding agent may be capable of binding to a polypeptide comprising a human TROP2 amino acid sequence consisting of amino acid residues 27-146 or a fragment thereof.

In another exemplary embodiment, the binding agent, or antigen binding domain(s) of the binding agent may be capable of binding to a polypeptide comprising a human TROP2 amino acid sequence consisting of amino acid residues 27-73 or a fragment thereof.

In accordance with the present disclosure the fragment may comprise at least 10 amino acid residues of human TROP2.

For example, the binding agent, or antigen binding domain(s) of the binding agent may bind to a fragment of at least 10 amino acid residues of a human TROP2 amino acid sequence consisting of amino acid residues 27-146.

In accordance with the present disclosure the fragment may comprise between 10 to 110 amino acid residues, including for example between 10 to 100 amino acid residues, between 10 to 90 amino acid residues, between 10 to 80 amino acid residues, between 10 to 70 amino acid residues, between 10 to 60 amino acid residues, between 10 to 50 amino acid residues, between 10 to 40 amino acid residues, between 10 to 30 amino acid residues, between 10 to 29 amino acid residues, between 10 to 28 amino acid residues, between 10 to 27 amino acid residues, between 10 to 26 amino acid residues, between 10 to 25 amino acid residues, between 10 to 24 amino acid residues, between 10 to 23 amino acid residues, between 10 to 22 amino acid residues, between 10 to 21 amino acid residues, between 10 to 20 amino acid residues, between 10 to 19 amino acid residues, between 10 to 18 amino acid residues, between 10 to 17 amino acid residues, between 10 to 16 amino acid residues, between 10 to 15 amino acid residues, between 10 to 14 amino acid residues, between 10 to 13 amino acid residues, between 10 to 12 amino acid residues between 10 to 11 amino acid residues of a human TROP2 amino acid sequence consisting of amino acid residues 27-146.

In another example, the binding agent, or antigen binding domain(s) of the binding agent may bind to a fragment of at least 10 amino acid residues of a human TROP2 amino acid sequence consisting of amino acid residues 27-73.

In accordance with the present disclosure the fragment may comprise of between 10 to 45 amino acid residues, including for example between 10 to 40 amino acid residues, between 10 to 35 amino acid residues, between 10 to 30 amino acid residues, between 10 to 29 amino acid residues, between 10 to 28 amino acid residues, between 10 to 27 amino acid residues, between 10 to 26 amino acid residues, between 10 to 25 amino acid residues, between 10 to 24 amino acid residues, between 10 to 23 amino acid residues, between 10 to 22 amino acid residues, between 10 to 21 amino acid residues, between 10 to 20 amino acid residues, between 10 to 19 amino acid residues, between 10 to 18 amino acid residues, between 10 to 17 amino acid residues, between 10 to 16 amino acid residues, between 10 to 15 amino acid residues, between 10 to 14 amino acid residues, between 10 to 13 amino acid residues, between 10 to 12 amino acid residues between 10 to 11 amino acid residues of a human TROP2 amino acid sequence consisting of amino acid residues 27-73.

In some instances, the binding agent, or antigen binding domain(s) of the binding agent may be capable of binding to a polypeptide comprising a human TROP2 amino acid sequence consisting of amino acid residues 27-56 of human TROP2 or a fragment thereof.

In other instances, the binding agent, or antigen binding domain(s) of the binding agent may be capable of binding to a polypeptide comprising a human TROP2 amino acid sequence consisting of amino acid residues 27-66 of human TROP2 or a fragment thereof.

In yet other instances, the binding agent, or antigen binding domain(s) of the binding agent may be capable of binding to a polypeptide comprising a human TROP2 amino acid sequence consisting of amino acid residues 47-56 of human TROP2 or a fragment thereof.

In other instances, the binding agent, or antigen binding domain(s) of the binding agent may be capable of binding to a polypeptide comprising a human TROP2 amino acid sequence consisting of amino acid residues 60-66 of human TROP2 or a fragment thereof.

In yet other instances, the binding agent, or antigen binding domain(s) of the binding agent may be capable of binding to a polypeptide comprising a human TROP2 amino acid sequence consisting of amino acid residues 47-66 of human TROP2 or a fragment thereof.

For example, the binding agent, or antigen binding domain(s) of the binding agent may be capable of binding to a polypeptide comprising a human TROP2 amino acid sequence consisting of amino acid residues 27-56, 27-66, 28-66, 29-66, 30-66, 31-66, 32-66, 33-66, 34-66, 35-66, 36-66, 37-66, 38-66, 39-66, 40-66, 41-66, 42-66, 43-66, 44-66, 45-66, 46-66 or 47-66.

For example, the binding agent, or antigen binding domain(s) of the binding agent may be capable of binding to an epitope consisting of amino acid residues 27-56, 27-66, 28-66, 29-66, 30-66, 31-66, 32-66, 33-66, 34-66, 35-66, 36-66, 37-66, 38-66, 39-66, 40-66, 41-66, 42-66, 43-66, 44-66, 45-66, 46-66 or 47-66 of TROP2.

In some embodiments, the binding agent of the present disclosure may not be capable of binding to the cysteine-poor domain (CPD) of TROP2 (as represented by amino acids 147 to 274 of TROP2). In some embodiments, the binding agent of the present disclosure does not bind to the cysteine-poor domain (CPD) of human TROP2. In some embodiments, the binding agent of the present disclosure may not be capable of significantly binding to the cysteine-poor domain (CPD) of TROP2. In some embodiments, the binding agent of the present disclosure does not significantly bind to the cysteine-poor domain (CPD) of human TROP2.

Accordingly, the binding agent, or antigen binding domain(s) or of the binding agent does not significantly bind to or is not capable of binding to a polypeptide that comprises a human TROP2 amino acid sequence consisting of amino acid residues 147-274 or a fragment thereof.

In an exemplary embodiment, the binding agent, or antigen binding domain(s) of the binding agent may not be capable of binding to one or more polypeptide selected from polypeptides comprising a human TROP2 amino acid sequence comprising deletion of at least 10 amino acid residues within amino acid residues 27-73.

In accordance with the present disclosure, the binding agent, or antigen binding domain(s) of the binding agent may not be capable of binding to one or more polypeptide selected from polypeptides comprising a human TROP2 amino acid sequence comprising deletion of amino acid residues 27-36, 27-44, 27-56, 27-66, 47-56, 47-66, 60-66 and/or 27-73.

Alternatively, the binding agent, or antigen binding domain(s) of the binding agent may have a reduced binding to one or more polypeptide selected from polypeptides comprising a human TROP2 amino acid sequence comprising deletion of amino acid residues 27-36, 27-44, 27-56, 27-66, 47-56, 47-66, 60-66 and/or 27-73 compared to a human TROP2 polypeptide that does not have such deletion including for example, the full human TROP2 polypeptide (SEQ ID NO:39).

For example, the binding agent, or antigen binding domain(s) of the binding agent may not be capable of binding to one or more polypeptide selected from polypeptides comprising a human TROP2 amino acid sequence comprising deletion of amino acid residues 28-66, 29-66, 30-66, 31-66, 32-66, 33-66, 34-66, 35-66, 36-66, 37-66, 38-66, 39-66, 40-66, 41-66, 42-66, 43-66, 44-66, 45-66, 46-66 or 47-66.

In yet another exemplary embodiment, the binding agent, or antigen binding domain(s) of the binding agent may not be capable of binding to a polypeptide comprising the amino acid sequence set forth in SEQ ID NO: 149 or have a reduced binding to such polypeptide compared to a human TROP2 polypeptide that does not have such deletion including for example, the full human TROP2 polypeptide (SEQ ID NO:39).

In an embodiment, the binding agent binds to human TROP2 protein (e.g., SEQ ID NO:39) or to a TROP2 homologue or TROP2 variant having a sequence at least 80% identical to the human TROP2 protein thereof or to a portion of human TROP2 protein (e.g., an extracellular domain of human TROP2: SEQ ID NO:164), of the homologue or variant thereof.

In some embodiment, the TROP2 homologue is a TROP2 sequence or portion thereof of a primate.

In some embodiment, the binding agent, or antigen binding domain(s) of the binding agent of the present disclosure binds to an epitope that is common to human TROP2 and to cynomolgus TROP2.

In some embodiment, the binding agent, or antigen binding domain(s) of the binding agent of the present disclosure binds to an epitope that is similar in human TROP2 and to cynomolgus TROP2.

In some embodiment, the binding agent, or antigen binding domain(s) of the binding agent of the present disclosure is capable of binding human TROP2 and cynomolgus TROP2.

In some embodiment, the binding agent, or antigen binding domain(s) of the binding agent of the present disclosure preferentially binds to human TROP2 over mouse TROP2 or has a better affinity for human TROP2 over mouse TROP2.

In some embodiment, the binding agent, or antigen binding domain(s) of the binding agent of the present disclosure preferentially binds to human TROP2 over rat TROP2 or has a better affinity for human TROP2 over rat TROP2.

In some embodiment, the binding agent, or antigen binding domain(s) of the binding agent of the present disclosure binds to amino acid residues that are common to the extracellular domain of human TROP2 and to the extracellular domain of cynomolgus TROP2.

In some embodiment, the binding agent, or antigen binding domain(s) of the binding agent of the present disclosure binds to amino acid residues that are not present in the extracellular domain of mouse TROP2.

In some embodiment, the binding agent, or antigen binding domain(s) of the binding agent of the present disclosure binds to amino acid residues that are not present in the extracellular domain of rat TROP2.

In some embodiment, the binding agent, or antigen binding domain(s) of the binding agent of the present binds to amino acid residues that are present in the extracellular domain of human TROP2, cynomolgus TROP2, mouse TROP2 and rat TROP2.

Accordingly, the binding agent, or antigen binding domain(s) of the binding agent may be capable of binding to human TROP2 and to cynomolgus TROP2.

In exemplary embodiments, the binding agent, or antigen binding domain(s) of the binding agent may be capable of binding to a denatured form human TROP2.

In another exemplary embodiments, the binding agent, or antigen binding domain(s) of the binding agent may be capable of binding to a reduced form of human TROP2.

In yet other exemplary embodiments, the binding agent, or antigen binding domain(s) of the binding agent may be capable of binding to a deglycosylated form of human TROP2.

In accordance with an embodiment, the formation of an antigen binding domain may involve amino acid residues of a single polypeptide chain. For example, the amino acid residues forming the paratope may be located on a single polypeptide chain that is able to adopt a proper configuration for interacting with the epitope.

However, in accordance with another embodiment, the formation of an antigen binding domain may involve amino acid residues of two polypeptide chains. In some instances, a complete antigen binding domain may require the association of two polypeptide chains. For example, the amino acid residues forming the paratope may be located on two polypeptide chains that are able to associate and adopt a proper configuration for interacting with the epitope.

In accordance with the present disclosure, the binding agent, or antigen binding domain(s) of the binding agent comprises an amino acid sequence of one or more CDRs of a single domain antibody (of a heavy chain only antibody).

In an exemplary embodiment, the binding agent, or the antigen binding domain(s) may comprise the amino acid sequence of a CDR1, CDR2, CDR3, FR2 or combination thereof of a heavy chain only antibody.

In an exemplary embodiment, the binding agent, or the antigen binding domain(s) may comprise the amino acid sequence of the CDR3 of single domain antibody (of a heavy chain only antibody).

In another exemplary embodiment, the binding agent, or the antigen binding domain(s) may comprise the amino acid sequence of FR2 and CDR3 of a heavy chain only antibody. In a further exemplary embodiment, the FR2 and CDR3 amino acid sequence may be on same polypeptide chain. Alternatively, the FR2 and CDR3 amino acid sequence may be on separate polypeptide chains.

In another exemplary embodiment, the binding agent, or the antigen binding domain(s) may comprise the amino acid sequence of FR2 and CDR3 of a heavy chain only antibody and optionally the amino acid sequence of CDR1 and/or CDR2.

In accordance with the present disclosure, the order of CDR1, CDR2, CDR3, and/or FR2 amino acid sequence of the antigen binding domain may be the same as that of a single domain antibody. As such, the antigen binding domain comprises in a N- to C-terminal fashion CDR1, FR2, CDR2 and/or CDR3 amino acid sequences. In some instances, the antigen binding domain comprises in a N- to C-terminal fashion FR2 and CDR3 amino acid sequences. In other instances, the antigen binding domain, comprises in a N- to C-terminal fashion CDR1, FR2 and CDR3 amino acid sequences. In other instances, the antigen binding domain, comprises in a N- to C-terminal fashion CDR2, FR2 and CDR3 amino acid sequences. In other instances, the antigen binding domain, comprises in a N- to C-terminal fashion CDR1, CDR2, FR2 and CDR3 amino acid sequences. In accordance with the present disclosure, the antigen binding domain(s) may comprise an amino acid sequence of the variable region of a heavy chain only antibody.

In some embodiments, the antigen binding domain(s) may comprise an amino acid sequence of a camelid VH or VHH. In other embodiments, the antigen binding domain(s) may comprise an amino acid sequence of a mouse VH. In yet other embodiments, the antigen binding domain(s) may comprise an amino acid sequence of human VH. In a further embodiment, the antigen binding domain(s) may comprise an amino acid sequence of humanized VH or VHH (e.g., a humanized camelid VH or VHH, or a humanized mouse VH).

The binding agent, or antigen binding domain(s) of the binding agent may come from various sources including from transgenic animals or non-transgenic animals, from screening of an antibody library etc. For example, antibodies may be obtained from hybridoma after immunization of rodents (mouse, rats etc.) or from larger mammals such as camelids. In some embodiments, the animal may be immunized with a TROP2 antigen.

In an embodiment, the amino acid sequence or nucleotide sequence of an antigen binding domain is obtained by immunization of a transgenic animal modified to express heavy chain only antibodies. In some instances, the sequence of the antigen binding domain is obtained from a transgenic mouse carrying modification at an IgH locus allowing expression of heavy chain only antibodies (see for example, WO2022/011457 A1, the entire content of which is incorporated herein by reference). In some embodiments, the transgenic animal may be immunized with a TROP2 antigen.

In an exemplary embodiment, the binding agent or the antigen binding domain(s) of the binding agent may comprise an amino acid sequence of a CDR1, CDR2 and/or CDR3 of a heavy chain variable region and/or an amino acid sequence of a CDR1, CDR2 and/or CDR3 of a light chain variable region.

In another exemplary embodiment, the binding agent or the antigen binding domain(s) of the binding agent may comprise an amino acid sequence of a CDR1, CDR2 and CDR3 of a heavy chain variable region and an amino acid sequence of a CDR1, CDR2 and CDR3 of a light chain variable region.

In an exemplary embodiment, the amino acid sequence of a CDR1, CDR2 and CDR3 of the heavy chain variable region and the amino acid sequence of a CDR1, CDR2 and CDR3 of the light chain variable region are on same polypeptide chain.

Alternatively, the amino acid sequence of CDR1, CDR2 and CDR3 of the heavy chain variable region and the amino acid sequence of CDR1, CDR2 and CDR3 of the light chain variable region are on separate polypeptide chains.

In accordance with the present disclosure, the binding agent or the antigen binding domain(s) of the binding agent may comprise a heavy chain variable region and a light chain variable region of an antibody. In an exemplary embodiment, the heavy chain variable region and the light chain variable region are on same polypeptide chain. In another exemplary embodiment, the heavy chain variable region and the light chain variable region are on separate polypeptide chains.

In accordance with the present disclosure, the CDRs may be identified using the Kabat numbering scheme (e.g., Kabat, J Immunol., 147:1709-19 (1991); Chothia C, Lesk A M, J Mol Biol. Aug 20;196(4):901-17 (1987)).

Alternatively, the CDRs may be identified using the IMGT numbering scheme (e.g., Lefranc, M.-P., The Immunologist, 7, 132-136 (1999)).

In some instances, the CDR1, CDR2, CDR3 and/or FR2 correspond to the Kabat CDR1, CDR2, CDR3 and/or FR2.

In other instances, the CDR1, CDR2, CDR3 and/or FR2 correspond to the IMGT CDR1, CDR2, CDR3 and/or FR2.

In some embodiments, the binding agent is expressed as a polypeptide chain that comprises in a N- to C-terminal fashion, a) an antigen binding domain that includes an antigen binding fragment of a single domain antibody, b) a linker and c) a dimerization domain.

In some embodiments, the binding agent is expressed as a polypeptide chain that comprises in a N- to C-terminal fashion, a) an antigen binding domain of a single domain antibody, b) a linker and c) a dimerization domain.

In some embodiments, the binding agent is expressed as a polypeptide chain that comprises in a N- to C-terminal fashion, a) a dimerization domain, b) a linker and c) an antigen binding domain that includes an antigen binding fragment of a single domain antibody.

In some embodiments, the binding agent is expressed as a polypeptide chain that comprises in a N- to C-terminal fashion, a) a dimerization domain, b) a linker and c) an antigen binding domain of a single domain antibody.

In other embodiments, the binding agent is expressed as a polypeptide chain that comprises in a N- to C-terminal fashion, a) an antigen binding domain of a single domain antibody, b) a linker, c) a dimerization domain, d) a linker and e) an antigen binding domain of a single domain antibody. In some embodiments, the antigen binding domain of a) and the antigen binding domain of e) are different. In some embodiments, the antigen binding domain of a) and the antigen binding domain of e) are the same. In some embodiments, the linker of b) and the linker of d) are the same. In some embodiments, the linker of b) and the linker of d) are different.

In accordance with the present disclosure, the binding agent may comprise additional amino acid sequence or moieties (small molecules, labels and the like) at an N- and/or C-terminus. For example, in accordance with the present disclosure, the binding agent may comprise additional antigen binding domain(s) of single domain antibody(ies) at an N- or C-terminus. The additional antigen binding domain(s) may be separated from the core by one or more linkers.

In some embodiments, the polypeptide chain may comprise additional sequences, including without limitations, additional antigen binding domains or additional linkers.

In some embodiments, the linker is an amino acid sequence of at least 5, 10, 15, 20, 25, 30, 35, 40, 45 or 50 amino acid residues in length.

In some embodiment, the linker is non-cleavable.

In some embodiments, the linker comprises one or more units of GGGGS.

In some embodiments, the linker may comprise the formula $(X(PAPAP))_n KA$ wherein n is an integer selected from 1 to 10, wherein X is present or absent and is A. In some embodiments, the linker may comprise the sequence set forth in SEQ ID NO:163.

In some embodiments, the linker is an antibody hinge or a portion thereof. For example, in some embodiments, the linker may comprise human IgG1 hinge sequence or a portion thereof. In some embodiments, the linker may comprise human IgG2 hinge sequence or a portion thereof. In some embodiments, the linker may comprise human IgG3 hinge sequence or a portion thereof. In yet other embodiment, the linker may comprise human IgG4 hinge sequence or a portion thereof.

The binding agent or antigen binding domain may comprise a sequence as set forth herein.

In accordance with the present disclosure, the binding agent, or antigen binding domain(s) of the binding agent may have the amino acid sequence set forth in SEQ ID NO: 143.

(KD002 consensus)

SEQ ID NO: 143

$X_{1a}$VQLX$_{1b}$ESGGGX$_{1c}$VQX$_{1d}$GGSLRLSCAASGFPFSSADMSWVRQAPGKX$_{1e}$

X$_{1f}$EWVSX$_{1g}$INAX$_{1h}$GSKTYYX$_{1i}$DX$_{1j}$VKGRFTISRDNX$_{1k}$KNTLYLX$_{1l}$MNX$_{1m}$

LX$_{1n}$X$_{1o}$EDTAX$_{1p}$YX$_{1q}$CARAKLTDTHYVEDYWGQGTX$_{1r}$VTVSS.

In an exemplary embodiment, any of $X_{1a}$ to $X_{1r}$ is each independently any (e.g., naturally occurring) amino acid residue.

In another exemplary embodiment, any of $X_{1a}$ to $X_{1r}$ is each independently an amino acid residue found at a corresponding position in any one of SEQ ID NO:23 or SEQ ID NOs:73-93, or conservative amino acid substitutions or non-conservative amino acid substitutions thereof. In yet another exemplary embodiment, any of $X_{1a}$ to $X_{1r}$ is each independently an amino acid residue found at a corresponding position in any one of SEQ ID NO:22, SEQ ID NO:23, SEQ ID NO:24, SEQ ID NO:25 or SEQ ID NO:26 or conservative amino acid substitutions or non-conservative amino acid substitutions thereof.

In a further exemplary embodiment, any $X_{1a}$ to $X_{1r}$ is each independently an amino acid residue most frequently found at a corresponding position in any one of SEQ ID NO:23 or SEQ ID Nos:73-93.

In another exemplary embodiment, any $X_{1a}$ to $X_{1r}$ is each independently an amino acid residue most frequently found at a corresponding position in any one of SEQ ID NO:22, SEQ ID NO:23, SEQ ID NO:24, SEQ ID NO:25 to SEQ ID NO:26.

In yet another exemplary embodiment, any of $X_{1a}$ to $X_{1r}$ is each independently an amino acid residue found at a corresponding position in any one of SEQ ID NOs: 73, 75, 76, 77, 78, 81, 82, 83, 85, 89 or 91, or conservative amino acid substitutions or non-conservative amino acid substitutions thereof.

In a further exemplary embodiment, any $X_{1a}$ to $X_{1r}$ is each independently an amino acid residue most frequently found at a corresponding position in any one of SEQ ID NOs: 73, 75, 76, 77, 78, 81, 82, 83, 85, 89 or 91.

In yet a further exemplary embodiment $X_{1a}$ is Q or E; $X_{1b}$ is Q, V or L; $X_{1c}$ is M or L; $X_{1d}$ is V or P; $X_{1e}$ is G or Q; $X_{1f}$ is P, L or R; $X_{1g}$ is Y or V; $X_{1h}$ is D, N, E; $X_{1i}$ is P or A; $X_{1j}$ is S or T; $X_{1k}$ is A or S; $X_{1l}$ is L or Q; $X_{1m}$ is N or S; $X_{1n}$ is K or R; $X_{1o}$ is P or A; $X_{1p}$ is L or V; $X_{1q}$ is R or Y; and/or $X_{1r}$ is Q or M.

In another exemplary embodiment $X_{1a}$ is Q or E; $X_{1b}$ is Q, V or L; $X_{1c}$ is M or L; $X_{1d}$ is V or P; $X_{1e}$ is G or Q; $X_{1f}$ is P, L or R; $X_{1g}$ is Y; $X_{1h}$ is D, $X_{1i}$ is P or A; $X_{1j}$ is S or T; $X_{1k}$ is A or S; $X_{1l}$ is L or Q; $X_{1m}$ is N or S; $X_{1n}$ is K or R; $X_{1o}$ is P or A; $X_{1p}$ is L or V; $X_{1q}$ is R or Y; and/or $X_{1r}$ is Q or M.

In accordance with the present disclosure, the binding agent, or antigen binding domain(s) of the binding agent may have the amino acid sequence set forth in SEQ ID NO:144.

(KD005 consensus)

SEQ ID NO: 144

$X_{2a}$VQLX$_{2b}$ESGGGLX$_{2c}$X$_{2d}$X$_{2e}$GGSLRLSCAASGFTFSGSDMSWVRQA

PGKGX$_{2f}$EWVSX$_{2g}$ITSGGTTYYX$_{2h}$DX$_{2i}$VKGRFTISRDNX$_{2j}$KNTLYL

QMNSLX$_{2k}$X$_{2l}$X$_{2m}$DTAX$_{2n}$YX$_{2o}$CAKSRLTDSHYVEDAWGQGTX$_{2p}$VTV

SS

In an exemplary embodiment, any of $X_{2a}$ to $X_{2p}$ is each independently any (e.g., naturally occurring) amino acid residue.

In another exemplary embodiment, any of $X_{2a}$ to $X_{2p}$ is each independently an amino acid residue found at a corresponding position in any one of SEQ ID NO:26 or SEQ ID NO:94-114 or conservative amino acid substitutions or non-conservative amino acid substitutions thereof.

In another exemplary embodiment, any of $X_{2a}$ to $X_{2p}$ is each independently an amino acid residue found at a corresponding position in any one of SEQ ID NO:22, SEQ ID NO:23, SEQ ID NO:24, SEQ ID NO:25 or SEQ ID NO:26 or conservative amino acid substitutions or non-conservative amino acid substitutions thereof.

In yet another exemplary embodiment, any $X_{2a}$ to $X_{2p}$ is each independently an amino acid residue most frequently found at a corresponding position in any one of SEQ ID NO:26 or SEQ ID NO:94-114.

In a further exemplary embodiment, any $X_{2a}$ to $X_{2p}$ is each independently an amino acid residue most frequently found at a corresponding position in any one of SEQ ID NO:22, SEQ ID NO:23, SEQ ID NO:24, SEQ ID NO:25 to SEQ ID NO:26.

In yet a further exemplary embodiment, any of $X_{2a}$ to $X_{2p}$ is each independently an amino acid residue found at a corresponding position in any one of SEQ ID NOs: 94, 95, 96, 97, 98, 100, 101, 102, 103, 104, 105, 106, 107 or 108 or conservative amino acid substitutions or non-conservative amino acid substitutions thereof.

In an additional exemplary embodiment, any $X_{2a}$ to $X_{2p}$ is each independently an amino acid residue most frequently found at a corresponding position in any one of SEQ ID NOs: 94, 95, 96, 97, 98, 100, 101, 102, 103, 104, 105, 106, 107 or 108.

In another exemplary embodiment, any of $X_{2a}$ to $X_{2p}$ is each independently an amino acid residue found at a corresponding position in any one of SEQ ID NOs: 94, 95, 96, 97, 100, 102, 103, 104, 105, 106, 108, 112 or 114 or conservative amino acid substitutions or non-conservative amino acid substitutions thereof.

In a further exemplary embodiment, any $X_{2a}$ to $X_{2p}$ is each independently an amino acid residue most frequently found at a corresponding position in any one of SEQ ID NOs: 94, 95, 96, 97, 100, 102, 103, 104, 105, 106, 108, 112 or 114.

In yet a further exemplary embodiment, any of $X_{2a}$ to $X_{2p}$ is each independently an amino acid residue found at a corresponding position in any one of SEQ ID NOs: 94, 95, 96, 97, 98, 99, 100, 101, 102, 104, 105, 112, 113 or 114 or conservative amino acid substitutions or non-conservative amino acid substitutions thereof.

In another exemplary embodiment, any $X_{2a}$ to $X_{2p}$ is each independently an amino acid residue most frequently found at a corresponding position in any one of SEQ ID NOs: 94, 95, 96, 97, 98, 99, 100, 101, 102, 104, 105, 112, 113 or 114.

In another exemplary embodiment, any of $X_{2a}$ to $X_{2p}$ is each independently an amino acid residue found at a corresponding position in any one of SEQ ID NOs: 94, 95, 96, 97, 102 or 105 or conservative amino acid substitutions or non-conservative amino acid substitutions thereof.

In an additional exemplary embodiment, any $X_{2a}$ to $X_{2p}$ is each independently an amino acid residue most frequently found at a corresponding position in any one of SEQ ID NOs: 94, 95, 96, 97, 102 or 105.

In another exemplary embodiment, $X_{2a}$ is Q or E; $X_{2b}$ is Q, L or V; $X_{2c}$ is V or I; $X_{2d}$ is E or Q; $X_{2e}$ is A or P; $X_{2f}$ is P, or L; $X_{2g}$ is Y, A or V; $X_{2h}$ is P or A; $X_{2i}$ is S or T; $X_{2j}$ is A or S; $X_{2k}$ is K or R; $X_{2l}$ is P or A; $X_{2m}$ is D or E; $X_{2n}$ is L or V; $X_{2o}$ is R or Y and/or $X_{2p}$ is Q or L.

In yet another exemplary embodiment, $X_{2a}$ is Q or E; $X_{2b}$ is Q or L; $X_{2c}$ is V or I; $X_{2d}$ is E or Q; $X_{2e}$ is A or P; $X_{2f}$ is P, or L; $X_{2g}$ is Y or A; $X_{2h}$ is P or A; $X_{2i}$ is S or T; $X_{2j}$ is A or S; $X_{2k}$ is K or R; $X_{2l}$ is P or A; $X_{2m}$ is D or E; $X_{2n}$ is L or V; $X_{2o}$ is R or Y and/or $X_{2p}$ is Q or L.

In accordance with the present disclosure, the binding agent, or antigen binding domain(s) of the binding agent may have the amino acid sequence set forth in SEQ ID NO:145.

```
(Consensus from KD001 to KD005
heavy chains)
                                         SEQ ID NO: 145
QVQLQESGGGX3aVX3bX3cGX3dSLRLSCAASGFX3eFSX3fX3gDMSW VRQAPGKGPEWVSYIX3hX3iX3jX3kX3lX3mTX3nYPDSVKGRFTX3o SRDNAKNX3pLYLX3qMNX3rLX3sPX3tDTALYRCAX3uX3vX3wLTD X3xHYVEDX3yWGQGTQVTVSS
```

In an exemplary embodiment any of $X_{3a}$ to $X_{3y}$ is each independently any (e.g., naturally occurring) amino acid residue.

In another exemplary embodiment, any of $X_{3a}$ to $X_{3y}$ is each independently an amino acid residue found at a corresponding position in any one of SEQ ID NO:22, SEQ ID NO:23, SEQ ID NO:24, SEQ ID NO:25 or SEQ ID NO:26 or conservative amino acid substitutions or non-conservative amino acid substitutions thereof.

In yet another exemplary embodiment, any of $X_{3a}$ to $X_{3y}$ is each independently an amino acid residue most frequently found in the group consisting of SEQ ID NO:22, SEQ ID NO:23, SEQ ID NO:24, SEQ ID NO:25 to SEQ ID NO:26.

In a further exemplary embodiment, $X_{3a}$ is M or L; $X_{3b}$ is Q, H or E; $X_{3c}$ is V, P or A; $X_{3d}$ is G or R; $X_{3e}$ is P or T; $X_{3f}$ is S, N or G; $X_{3g}$ is A, Y or S; $X_{3h}$ is N or T; $X_{3i}$ is A, S or G; $X_{3j}$ is D, G or S; $X_{3k}$ is G or absent; $X_{3l}$ is S or G; $X_{3m}$ is K, N or T; $X_{3n}$ is Y or D; $X_{3o}$ is I or T; $X_{3p}$ is T or M; $X_{3q}$ is L or Q; $X_{3r}$ is N or S; $X_{3s}$ is K or T; $X_{3t}$ is E or D; $X_{3u}$ is R or K; $X_{3v}$ is A or S; $X_{3w}$ is K or R; $X_{3x}$ is T or S; and/or $X_{3y}$ is Y or A.

In yet a further exemplary embodiment, $X_{3a}$ is M or L; $X_{3b}$ is Q, H or E; $X_{3c}$ is V, P or A; $X_{3d}$ is G or R; $X_{3e}$ is P or T; $X_{3f}$ is S, N or G; $X_{3g}$ is A, Y or S; $X_{3h}$ is N or T; $X_{3i}$ is A, S or G; $X_{3j}$ is D, G or S; $X_{3k}$ is G or absent; $X_{3l}$ is S or G; $X_{3m}$ is K, N or T; $X_{3n}$ is Y; $X_{3o}$ is I or T; $X_{3p}$ is T or M; $X_{3q}$ is L or Q; $X_{3r}$ is N or S; $X_{3s}$ is K or T; $X_{3t}$ is E or D; $X_{3u}$ is R or K; $X_{3v}$ is A or S; $X_{3w}$ is R; $X_{3x}$ is S; and/or $X_{3y}$ is A.

TABLE 1

Position of amino acid residues with reference to SEQ ID NO: 145.
SEQ ID NO: 145 amino acid residues numbering (IMGT CDR position bold underlined).
Exemplary interacting residues are indicated in each third row.

| 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|
| Q | V | Q | L | Q | E | S | G | G | G | $X_{3a}$ | V | $X_{3b}$ | $X_{3c}$ | G |
| Q | V | Q | L | | | | | | | | | | | |

| 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|
| $X_{3d}$ | S | L | R | L | S | C | A | A | S | G | F | $X_{3e}$ | F | S |

| 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|

TABLE 1-continued

Position of amino acid residues with reference to SEQ ID NO: 145.
SEQ ID NO: 145 amino acid residues numbering (IMGT CDR position bold underlined).
Exemplary interacting residues are indicated in each third row.

| $X_{3f}$ | $X_{3g}$ | D | M | S | W | V<br>V | R | Q<br>Q | A | P | G | K | G | P<br>P |
|---|---|---|---|---|---|---|---|---|---|---|---|---|---|---|
| 46 | 47 | 48 | 49 | 50 | 51 | 52 | 53 | 54 | 54a | 55 | 56 | 57 | 58 | 59 |
| E<br>E | W<br>W | V | S | Y<br>Y | I | $X_{3h}$ | $X_{3i}$ | $X_{3j}$ | $X_{3k}$ | $X_{3l}$ | $X_{3m}$ | T | $X_{3n}$<br>Y | Y |
| 60 | 61 | 62 | 63 | 64 | 65 | 66 | 67 | 68 | 69 | 70 | 71 | 72 | 73 | 74 |
| | P | D | S | V | K | G | R | F | T | $X_{3o}$ | S | R | D | N | A |
| 75 | 76 | 77 | 78 | 79 | 80 | 81 | 82 | 83 | 84 | 85 | 86 | 87 | 88 | 89 |
| K | N | $X_{3p}$ | L | Y | L | $X_{3q}$ | M | N | $X_{3r}$ | L | $X_{3s}$ | P | $X_{3t}$ | D |
| 90 | 91 | 92 | 93 | 94 | 95 | 96 | 97 | 98 | 99 | 100 | 101 | 102 | 103 | 104 |
| T | A | L | Y | R | C | A | $X_{3u}$ | $X_{3v}$ | $X_{3w}$<br>R | L<br>L | T<br>T | D<br>D | $X_{3x}$<br>S | H<br>H |
| 105 | 106 | 107 | 108 | 109 | 110 | 111 | 112 | 113 | 114 | 115 | 116 | 117 | 118 | 119 | 120 |
| Y<br>Y | V<br>V | E<br>E | D<br>D | $X_{3y}$<br>A | W<br>W | G<br>G | Q<br>Q | G | T | Q | V | T | V | S | S |

In accordance with the present disclosure, the binding agent, or antigen binding domain(s) of the binding agent may have the amino acid sequence set forth in SEQ ID NO: 146.

```
(Consensus for KD001-KD005 and
selected variants heavy chains)
                                          SEQ ID NO: 146
X4aVQLX4bESGGGX4cX4dX4eX4fGX4gSLRLSCAASGFX4hFSX4i X4jDMX4kWX4lRQAPGKX4mX4nX4oWVSX4pIX4qX4rX4sGX4tX4u TX4vYX4wDX4xVKGRFTX4ySRDNX4zKNX5aLYLX5bMNX5cLX5d X5eX5fDTAX5gYX5hCAX5iX5jX5kLTDX5lHYVEDX5mWGQGTX5nV

TVSS.
```

In an exemplary embodiment, any of $X_{4a}$ to $X_{5n}$ is each independently any (e.g., naturally occurring) amino acid residue.

In another exemplary embodiment, any of $X_{4a}$ to $X_{5n}$ is each independently an amino acid residue found at a corresponding position in any one of SEQ ID NOs:22-26, SEQ ID Nos:73-114 or conservative amino acid substitutions or non-conservative amino acid substitutions thereof.

In yet another exemplary embodiment, any of $X_{4a}$ to $X_{5n}$ is each independently an amino acid residue found at a corresponding position in any one of SEQ ID NO:22, SEQ ID NO:23, SEQ ID NO:24, SEQ ID NO:25 or SEQ ID NO:26 or conservative amino acid substitutions or non-conservative amino acid substitutions thereof.

In another exemplary embodiment, any of $X_{4a}$ to $X_{5n}$ is each independently an amino acid residue most frequently found at a corresponding position in any one of SEQ ID NOs:22-26, SEQ ID Nos:73-114.

In another exemplary embodiment, any of $X_{4a}$ to $X_{5n}$ is each independently an amino acid residue most frequently found at a corresponding position in any one of SEQ ID NO:22, SEQ ID NO:23, SEQ ID NO:24, SEQ ID NO:25 to SEQ ID NO:26.

In a further exemplary embodiment, $X_{4a}$ is Q or E, $X_{4b}$ is Q, L or V, $X_{4c}$ is M or L, $X_{4d}$ is V or I, $X_{4e}$ is Q, H or E, $X_{4f}$ is P, A or V, $X_{4g}$ is G or R, $X_{4h}$ is P or T, $X_{4i}$ is G, S or N, $X_{4j}$ is A or S, $X_{4k}$ is S or H, $X_{4l}$ is V or Y, $X_{4m}$ is G or Q, $X_{4n}$ is P, L or R, $X_{4o}$ is E or V, $X_{4p}$ is Y, A or R, $X_{4q}$ is T or N, $X_{4r}$ is A, S or G, $X_{4s}$ is G, S, D, N or E, $X_{4t}$ is absent or S, $X_{4u}$ is K or T, $X_{4v}$ is Y, D or S, $X_{4w}$ is P or A, $X_{4x}$ is S or T, $X_{4y}$ is I or T, $X_{4z}$ is S or A $X_{5a}$ is T or M $X_{5b}$ is Q or L, $X_{5c}$ is S or N, $X_{5d}$ is K, R or T, $X_{5e}$ is P or A, $X_{5f}$ is E or D, $X_{5g}$ is V or L, $X_{5h}$ is Y or R, $X_{5i}$ is R or K, $X_{5j}$ is A or S, $X_{5k}$ is K or R, $X_{5l}$ is S or T, $X_{5m}$ is Y or A, and/or $X_{5n}$ is Q, L or M.

In some embodiments, the amino acid substitution is a conservative amino acid substitution.

The present disclosure provides in further aspects and embodiments, a binding agent that comprises one or more antigen binding domains, wherein at least one of the one or more antigen binding domains is capable of binding to human trophoblast cell surface antigen-2 (human TROP2) and comprises an amino acid sequence at least 65% identical to the amino acid sequence set forth in any one of SEQ ID NOs:22-26, or SEQ ID NOs: 71-115.

In an exemplary embodiment, the binding agent or antigen binding domain(s) of the binding agent may comprise an amino acid sequence at least 70% identical, at least 75% identical, at least 80% identical, at least 85% identical, at least 90% identical, at least 95% identical, at least 99% identical to SEQ ID NO:22. More particularly, the binding agent or antigen binding domain(s) of the binding agent may comprise an amino acid sequence at least 95% identical, at least 99% identical or identical to SEQ ID NO:22. In an embodiment, the binding agent or antigen binding domain(s) of the binding agent may comprise an amino acid sequence identical to SEQ ID NO:22.

In an exemplary embodiment, the binding agent or antigen binding domain(s) of the binding agent may comprise an amino acid sequence at least 70% identical, at least 75% identical, at least 80% identical, at least 85% identical, at least 90% identical, at least 95% identical, at least 99% identical to SEQ ID NO:23. More particularly, the binding agent or antigen binding domain(s) of the binding agent may comprise an amino acid sequence at least 95% identical, at least 99% identical or identical to SEQ ID NO:23. In an embodiment, the binding agent or antigen binding domain(s) of the binding agent may comprise an amino acid sequence identical to SEQ ID NO:23.

In an exemplary embodiment, the binding agent or antigen binding domain(s) of the binding agent may comprise an amino acid sequence at least 70% identical, at least 75% identical, at least 80% identical, at least 85% identical, at least 90% identical, at least 95% identical, at least 99% identical to SEQ ID NO:24. More particularly, the binding agent or antigen binding domain(s) of the binding agent may comprise an amino acid sequence at least 95% identical, at least 99% identical or identical to SEQ ID NO:24. In an embodiment, the binding agent or antigen binding domain(s) of the binding agent may comprise an amino acid sequence identical to SEQ ID NO:24.

In an exemplary embodiment, the binding agent or antigen binding domain(s) of the binding agent may comprise an amino acid sequence at least 70% identical, at least 75% identical, at least 80% identical, at least 85% identical, at least 90% identical, at least 95% identical, at least 99% identical to SEQ ID NO:25. More particularly, the binding agent or antigen binding domain(s) of the binding agent may comprise an amino acid sequence at least 95% identical, at least 99% identical or identical to SEQ ID NO:25. In an embodiment, the binding agent or antigen binding domain(s) of the binding agent may comprise an amino acid sequence identical to SEQ ID NO:25.

In an exemplary embodiment, the binding agent or antigen binding domain(s) of the binding agent may comprise an amino acid sequence at least 70% identical, at least 75% identical, at least 80% identical, at least 85% identical, at least 90% identical, at least 95% identical, at least 99% identical to SEQ ID NO:26. More particularly, the binding agent or antigen binding domain(s) of the binding agent may comprise an amino acid sequence at least 95% identical, at least 99% identical or identical to SEQ ID NO:26. In an embodiment, the binding agent or antigen binding domain(s) of the binding agent may comprise an amino acid sequence identical to SEQ ID NO:26.

In an exemplary embodiment, the binding agent or antigen binding domain(s) of the binding agent may comprise an amino acid sequence at least 70% identical, at least 75% identical, at least 80% identical, at least 85% identical, at least 90% identical, at least 95% identical, at least 99% identical to SEQ ID NOs: 71-115. More particularly, the binding agent or antigen binding domain(s) of the binding agent may comprise an amino acid sequence at least 95% identical, at least 99% identical or identical to SEQ ID NOs: 71-115. In an embodiment, the binding agent or antigen binding domain(s) of the binding agent may comprise an amino acid sequence identical to any one of SEQ ID NOs:71-115.

In an exemplary embodiment, the binding agent or antigen binding domain(s) of the binding agent may comprise an amino acid sequence at least 70% identical, at least 75% identical, at least 80% identical, at least 85% identical, at least 90% identical, at least 95% identical, at least 99% identical to SEQ ID NOs: 73-114. More particularly, the binding agent or antigen binding domain(s) of the binding agent may comprise an amino acid sequence at least 95% identical, at least 99% identical or identical to SEQ ID NOs: 73-114. In an embodiment, the binding agent or antigen binding domain(s) of the binding agent may comprise an amino acid sequence identical to any one of SEQ ID NOs:73-114.

In accordance with the present disclosure, the binding agent or antigen binding domain(s) of the binding agent may have a sequence as set forth herein, wherein the amino acid residue at position 1 is Q, the amino acid residue at position 2 is V, the amino acid residue at position 3 is Q, the amino acid residue at position 4 is L, the amino acid residue at position 37 is V, the amino acid residue at position 39 is Q, the amino acid residue at position 45 is P, the amino acid residue at position 46 is E, the amino acid residue at position 47 is W, the amino acid residue at position 50 is Y, the amino acid residue at position 58 is Y, the amino acid residue at position 99 is R, the amino acid residue at position 100 is L, the amino acid residue at position 101 is T, the amino acid residue at position 102 is D, the amino acid residue at position 103 is S, the amino acid residue at position 104 is H, the amino acid residue at position 105 is Y, the amino acid residue at position 106 is V, the amino acid residue at position 107 is E, the amino acid residue at position 108 is D, the amino acid residue at position 109 is A, the amino acid residue at position 110 is W, the amino acid residue at position 111 is G, and/or the amino acid residue at position 112 is Q and the position is with reference to SEQ ID NO:145 (Table 1).

The binding agent, or antigen binding domain(s) of the binding agent may have an amino acid sequence as defined in any one of SEQ ID Nos:22-26, 73-114, or 143 to 146 and may comprise from one to five amino acid deletions or from one to five amino acid additions. In an exemplary embodiment, the deletion or additions are consecutive. In another exemplary embodiment, the deletion or additions are non-consecutives. In yet another exemplary embodiment, the deletion or additions are at the N-terminus. In a further exemplary embodiment, the deletion or additions are at the C-terminus. In yet a further exemplary embodiment, the deletion or additions are outside of an IMGT CDR3 sequence and/or IMGT FR2 sequence. In yet a further exemplary embodiment, the deletion or additions are outside of a Kabat CDR3 sequence and/or Kabat FR2 sequence.

In an exemplary embodiment, the binding agent or antigen binding domain(s) thereof may comprise the amino acid sequence of the CDR3 set forth in SEQ ID NO:126.

In an exemplary embodiment, the binding agent or antigen binding domain(s) thereof may comprise the amino acid sequence of the FR2 set forth in SEQ ID NO:121.

In another exemplary embodiment, the binding agent or antigen binding domain(s) thereof may comprise the amino acid sequence of the CDR3 set forth in SEQ ID NO:126 and the amino acid sequence of the FR2 set forth in SEQ ID NO:121.

In accordance with the present disclosure, the amino acid sequence of the CDR3 and the amino acid sequence of the FR2 are on a same polypeptide chain. Alternatively, in accordance with the present disclosure, the amino acid sequence of the CDR3 and the amino acid sequence of the FR2 are on separate polypeptide chains.

In accordance with the present disclosure the amino acid sequence of the CDR3 is as set forth in SEQ ID NO:48, SEQ ID NO:51, SEQ ID NO:54 or SEQ ID NO:61.

In accordance with the present disclosure the amino acid sequence of the FR2 is as set forth in SEQ ID NO:116, SEQ ID NO:117, SEQ ID NO:118, SEQ ID NO:119 or SEQ ID NO:120.

The binding agent or antigen binding domain may comprise the amino acid sequence of the CDR1 set forth in SEQ ID NO:122.

In accordance with the present disclosure, the amino acid sequence of the CDR1 is as set forth in SEQ ID NO:52, SEQ ID NO:55 or SEQ ID NO:56.

The binding agent or antigen binding domain may comprise the amino acid sequence of the CDR2 set forth in SEQ ID NO:125.

In accordance with the present disclosure, the amino acid sequence of the CDR2 is as set forth in SEQ ID NO:47, SEQ ID NO:50, SEQ ID NO:57, SEQ ID NO:60, SEQ ID NO:123 or SEQ ID NO:124.

Accordingly, the binding agent or antigen binding domain(s) of the binding agent may comprise the amino acid sequence of the CDR3 set forth in any one of SEQ ID NO:48, SEQ ID NO:51, SEQ ID NO:54, SEQ ID NO:58 or SEQ ID NO:61 and the amino acid sequence of the FR2 set forth in any one of SEQ ID NO:116, SEQ ID NO:117, SEQ ID NO:118, SEQ ID NO:119 or SEQ ID NO:120.

In exemplary embodiments, the binding agent or antigen binding domain(s) of the binding agent may comprise the amino acid sequence of the CDR3 set forth in any one of SEQ ID NO:48, SEQ ID NO:51, SEQ ID NO:54, SEQ ID NO:58 or SEQ ID NO:61, the amino acid sequence of the FR2 set forth in any one of SEQ ID NO:116, SEQ ID NO:117, SEQ ID NO:118, SEQ ID NO:119 or SEQ ID NO:120, the amino acid sequence of the CDR1 set forth in any one of SEQ ID NO: 52, SEQ ID NO: 55, SEQ ID NO:59, SEQ ID NO: 52 or SEQ ID NO: 62 and the amino acid sequence of the CDR2 set forth in any one of SEQ ID NO: 47, SEQ ID NO:50, SEQ ID NO:53, SEQ ID NO: 57, SEQ ID NO: 60, SEQ ID NO:123 or SEQ ID NO:124.

In an exemplary embodiment, the binding agent or antigen binding domain(s) thereof may comprise the amino acid sequence of the CDR3 set forth in SEQ ID NO:142.

In an exemplary embodiment, the binding agent or antigen binding domain(s) thereof may comprise the amino acid sequence of the FR2 set forth in SEQ ID NO:175.

In another exemplary embodiment, the binding agent or antigen binding domain(s) thereof may comprise the amino acid sequence of the CDR3 set forth in SEQ ID NO:142 and the amino acid sequence of the FR2 set forth in SEQ ID NO:175.

In accordance with the present disclosure, the amino acid sequence of the CDR3 and the amino acid sequence of the FR2 are on a same polypeptide chain. Alternatively, in accordance with the present disclosure, the amino acid sequence of the CDR3 and the amino acid sequence of the FR2 are on separate polypeptide chains.

In accordance with the present disclosure the amino acid sequence of the CDR3 is as set forth in SEQ ID NO:3, SEQ ID NO:6, SEQ ID NO:12, SEQ ID NO:15 or SEQ ID NO:141.

In accordance with the present disclosure the amino acid sequence of the FR2 is as set forth in SEQ ID NO:170, SEQ ID NO:171, SEQ ID NO:172, SEQ ID NO:173 or SEQ ID NO:174. In a specific embodiment, the amino acid sequence of the FR2 is as set forth in SEQ ID NO:170 or SEQ ID NO:171.

The binding agent or antigen binding domain may comprise the amino acid sequence of the CDR1 set forth in SEQ ID NO:128.

In accordance with the present disclosure, the amino acid sequence of the CDR1 is as set forth in SEQ ID NO:1, SEQ ID NO:4, SEQ ID NO:7 or SEQ ID NO:127.

The binding agent or antigen binding domain may comprise the amino acid sequence of the CDR2 set forth in SEQ ID NO:140.

In accordance with the present disclosure, the amino acid sequence of the CDR2 is as set forth in SEQ ID NO:2, SEQ ID NO:5, SEQ ID NO:8, SEQ ID NO:11, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138 or SEQ ID NO:139.

Accordingly, the binding agent or antigen binding domain(s) of the binding agent may comprise the amino acid sequence of the CDR3 set forth in any one of SEQ ID NO:3, SEQ ID NO:6, SEQ ID NO:12, SEQ ID NO:15 or SEQ ID NO:141 and the amino acid sequence of the FR2 set forth in any one of SEQ ID NO:170, SEQ ID NO:171, SEQ ID NO:172, SEQ ID NO:173 or SEQ ID NO:174.

In exemplary embodiments, the binding agent or antigen binding domain(s) of the binding agent may comprise the amino acid sequence of the CDR3 set forth in any one of SEQ ID NO:3, SEQ ID NO:6, SEQ ID NO:12, SEQ ID NO:15 or SEQ ID NO:141, the amino acid sequence of the FR2 set forth in any one of SEQ ID NO:170, SEQ ID NO:171, SEQ ID NO:172, SEQ ID NO:173 or SEQ ID NO:174, the amino acid sequence of the CDR1 set forth in any one of SEQ ID NO:1, SEQ ID NO:4, SEQ ID NO:7 or SEQ ID NO:127 and the amino acid sequence of the CDR2 set forth in any one of SEQ ID NO:2, SEQ ID NO:5, SEQ ID NO:8, SEQ ID NO:11, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138 or SEQ ID NO:139.

In more specific embodiments, the binding agent or antigen binding domain(s) of the binding agent may comprise the amino acid sequence of the CDR3 set forth in any one of SEQ ID NO:3, SEQ ID NO:6, SEQ ID NO:12, SEQ ID NO:15 or SEQ ID NO:141, the amino acid sequence of the FR2 set forth in any one of SEQ ID NO:170 or SEQ ID NO:171, the amino acid sequence of the CDR1 set forth in any one of SEQ ID NO:1, SEQ ID NO:4, SEQ ID NO:7 or SEQ ID NO:127 and the amino acid sequence of the CDR2 set forth in any one of SEQ ID NO:2, SEQ ID NO:5, SEQ ID NO:8, SEQ ID NO:11, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138 or SEQ ID NO:139.

In an exemplary embodiment, the binding agent or antigen binding domain(s) of the binding agent may comprise the amino acid sequence of the CDR3 set forth in SEQ ID NO:54 and the amino acid sequence of the FR2 set forth in SEQ ID NO:116 and optionally the amino acid sequence of the CDR1 set forth in SEQ ID NO:52 and/or the amino acid sequence of the CDR2 set forth in SEQ ID NO:53.

In an exemplary embodiment, the binding agent or antigen binding domain(s) of the binding agent may comprise the amino acid sequence of the CDR3 set forth in SEQ ID NO:48 and the amino acid sequence of the FR2 set forth in SEQ ID NO:116 and optionally the amino acid sequence of the CDR1 set forth in SEQ ID NO:55 and/or the amino acid sequence of the CDR2 set forth in SEQ ID NO:47.

In an exemplary embodiment, the binding agent or antigen binding domain(s) of the binding agent may comprise the amino acid sequence of the CDR3 set forth in SEQ ID NO:58 and the amino acid sequence of the FR2 set forth in SEQ ID NO:116 and optionally the amino acid sequence of the CDR1 set forth in SEQ ID NO:56 and/or the amino acid sequence of the CDR2 set forth in SEQ ID NO:57.

In an exemplary embodiment, the binding agent or antigen binding domain(s) of the binding agent may comprise the amino acid sequence of the CDR3 set forth in SEQ ID NO:61 and the amino acid sequence of the FR2 set forth in SEQ ID NO:116 and optionally the amino acid sequence of the CDR1 set forth in SEQ ID NO:59 and/or the amino acid sequence of the CDR2 set forth in SEQ ID NO:60.

In an exemplary embodiment, the binding agent or antigen binding domain(s) of the binding agent may comprise the amino acid sequence of the CDR3 set forth in SEQ ID NO:51 and the amino acid sequence of the FR2 set forth in SEQ ID NO:116 and optionally the amino acid sequence of the CDR1 set forth in SEQ ID NO:62 and/or the amino acid sequence of the CDR2 set forth in SEQ ID NO:50.

In an exemplary embodiment, the binding agent or antigen binding domain(s) of the binding agent may comprise the amino acid sequence of the CDR3 set forth in SEQ ID NO: 48 and the amino acid sequence of the FR2 set forth in SEQ ID NO:116 and optionally the amino acid sequence of the CDR1 set forth in SEQ ID NO:55 and/or the amino acid sequence of the CDR2 set forth in 47.

In an exemplary embodiment, the binding agent or antigen binding domain(s) of the binding agent may comprise the amino acid sequence of the CDR3 set forth in SEQ ID NO: 48 and the amino acid sequence of the FR2 set forth in SEQ ID NO:117 and optionally the amino acid sequence of the CDR1 set forth in SEQ ID NO:55 and/or the amino acid sequence of the CDR2 set forth in 47.

In an exemplary embodiment, the binding agent or antigen binding domain(s) of the binding agent may comprise the amino acid sequence of the CDR3 set forth in SEQ ID NO: 48 and the amino acid sequence of the FR2 set forth in SEQ ID NO:118 and optionally the amino acid sequence of the CDR1 set forth in SEQ ID NO:55 and/or the amino acid sequence of the CDR2 set forth in 47.

In an exemplary embodiment, the binding agent or antigen binding domain(s) of the binding agent may comprise the amino acid sequence of the CDR3 set forth in SEQ ID NO: 48 and the amino acid sequence of the FR2 set forth in SEQ ID NO:119 and optionally the amino acid sequence of the CDR1 set forth in SEQ ID NO:55 and/or the amino acid sequence of the CDR2 set forth in 47.

In an exemplary embodiment, the binding agent or antigen binding domain(s) of the binding agent may comprise the amino acid sequence of the CDR3 set forth in SEQ ID NO: 48 and the amino acid sequence of the FR2 set forth in SEQ ID NO:117 and optionally the amino acid sequence of the CDR1 set forth in SEQ ID NO:55 and/or the amino acid sequence of the CDR2 set forth in 124.

In an exemplary embodiment, the binding agent or antigen binding domain(s) of the binding agent may comprise the amino acid sequence of the CDR3 set forth in SEQ ID NO: 48 and the amino acid sequence of the FR2 set forth in SEQ ID NO:117 and optionally the amino acid sequence of the CDR1 set forth in SEQ ID NO:55 and/or the amino acid sequence of the CDR2 set forth in 123.

In an exemplary embodiment, the binding agent or antigen binding domain(s) of the binding agent may comprise the amino acid sequence of the CDR3 set forth in SEQ ID NO:51 and the amino acid sequence of the FR2 set forth in SEQ ID NO:116 and optionally the amino acid sequence of the CDR1 set forth in SEQ ID NO:62 and/or the amino acid sequence of the CDR2 set forth in SEQ ID NO:50.

In an exemplary embodiment, the binding agent or antigen binding domain(s) of the binding agent may comprise the amino acid sequence of the CDR3 set forth in SEQ ID NO:51 and the amino acid sequence of the FR2 set forth in SEQ ID NO:117 and optionally the amino acid sequence of the CDR1 set forth in SEQ ID NO:62 and/or the amino acid sequence of the CDR2 set forth in SEQ ID NO:50.

In an exemplary embodiment, the binding agent or antigen binding domain(s) of the binding agent may comprise the amino acid sequence of the CDR3 set forth in SEQ ID NO:51 and the amino acid sequence of the FR2 set forth in SEQ ID NO:118 and optionally the amino acid sequence of the CDR1 set forth in SEQ ID NO:62 and/or the amino acid sequence of the CDR2 set forth in SEQ ID NO:50.

In an exemplary embodiment, the binding agent or antigen binding domain(s) of the binding agent may comprise the amino acid sequence of the CDR3 set forth in SEQ ID NO:51 and the amino acid sequence of the FR2 set forth in SEQ ID NO:120 and optionally the amino acid sequence of the CDR1 set forth in SEQ ID NO:62 and/or the amino acid sequence of the CDR2 set forth in SEQ ID NO:50.

In an exemplary embodiment, the binding agent or antigen binding domain(s) of the binding agent may comprise the amino acid sequence of the CDR3 set forth in SEQ ID NO:6 and the amino acid sequence of the FR2 set forth in SEQ ID NO:170 and optionally the amino acid sequence of the CDR1 set forth in SEQ ID NO:4 and/or the amino acid sequence of the CDR2 set forth in SEQ ID NO:5.

In an exemplary embodiment, the binding agent or antigen binding domain(s) of the binding agent may comprise the amino acid sequence of the CDR3 set forth in SEQ ID NO:6 and the amino acid sequence of the FR2 set forth in SEQ ID NO:171 and optionally the amino acid sequence of the CDR1 set forth in SEQ ID NO:4 and/or the amino acid sequence of the CDR2 set forth in SEQ ID NO:130.

In an exemplary embodiment, the binding agent or antigen binding domain(s) of the binding agent may comprise the amino acid sequence of the CDR3 set forth in SEQ ID NO:6 and the amino acid sequence of the FR2 set forth in SEQ ID NO:170 and optionally the amino acid sequence of the CDR1 set forth in SEQ ID NO:4 and/or the amino acid sequence of the CDR2 set forth in SEQ ID NO:131.

In an exemplary embodiment, the binding agent or antigen binding domain(s) of the binding agent may comprise the amino acid sequence of the CDR3 set forth in SEQ ID NO:6 and the amino acid sequence of the FR2 set forth in SEQ ID NO:170 and optionally the amino acid sequence of the CDR1 set forth in SEQ ID NO:4 and/or the amino acid sequence of the CDR2 set forth in SEQ ID NO:133.

In an exemplary embodiment, the binding agent or antigen binding domain(s) of the binding agent may comprise the amino acid sequence of the CDR3 set forth in SEQ ID NO:6 and the amino acid sequence of the FR2 set forth in SEQ ID NO:171 and optionally the amino acid sequence of the CDR1 set forth in SEQ ID NO:4 and/or the amino acid sequence of the CDR2 set forth in SEQ ID NO:131.

In an exemplary embodiment, the binding agent or antigen binding domain(s) of the binding agent may comprise the amino acid sequence of the CDR3 set forth in SEQ ID NO:6 and the amino acid sequence of the FR2 set forth in SEQ ID NO:171 and optionally the amino acid sequence of the CDR1 set forth in SEQ ID NO:4 and/or the amino acid sequence of the CDR2 set forth in SEQ ID NO:132.

In an exemplary embodiment, the binding agent or antigen binding domain(s) of the binding agent may comprise the amino acid sequence of the CDR3 set forth in SEQ ID NO:6 and the amino acid sequence of the FR2 set forth in SEQ ID NO:171 and optionally the amino acid sequence of the CDR1 set forth in SEQ ID NO:4 and/or the amino acid sequence of the CDR2 set forth in SEQ ID NO:133.

In an exemplary embodiment, the binding agent or antigen binding domain(s) of the binding agent may comprise the amino acid sequence of the CDR3 set forth in SEQ ID NO:6 and the amino acid sequence of the FR2 set forth in SEQ ID NO:172 and optionally the amino acid sequence of the CDR1 set forth in SEQ ID NO:4 and/or the amino acid sequence of the CDR2 set forth in SEQ ID NO:133.

In an exemplary embodiment, the binding agent or antigen binding domain(s) of the binding agent may comprise the amino acid sequence of the CDR3 set forth in SEQ ID NO:6 and the amino acid sequence of the FR2 set forth in SEQ ID NO:171 and optionally the amino acid sequence of the CDR1 set forth in SEQ ID NO:4 and/or the amino acid sequence of the CDR2 set forth in SEQ ID NO:134.

In an exemplary embodiment, the binding agent or antigen binding domain(s) of the binding agent may comprise the amino acid sequence of the CDR3 set forth in SEQ ID NO:6 and the amino acid sequence of the FR2 set forth in SEQ ID NO:171 and optionally the amino acid sequence of the CDR1 set forth in SEQ ID NO:4 and/or the amino acid sequence of the CDR2 set forth in SEQ ID NO:135.

In an exemplary embodiment, the binding agent or antigen binding domain(s) of the binding agent may comprise the amino acid sequence of the CDR3 set forth in SEQ ID NO:6 and the amino acid sequence of the FR2 set forth in SEQ ID NO:174 and optionally the amino acid sequence of the CDR1 set forth in SEQ ID NO:127 and/or the amino acid sequence of the CDR2 set forth in SEQ ID NO:129.

In an exemplary embodiment, the binding agent or antigen binding domain(s) of the binding agent may comprise the amino acid sequence of the CDR3 set forth in SEQ ID NO:15 and the amino acid sequence of the FR2 set forth in SEQ ID NO:170 and optionally the amino acid sequence of the CDR1 set forth in SEQ ID NO:13 and/or the amino acid sequence of the CDR2 set forth in SEQ ID NO:14.

In an exemplary embodiment, the binding agent or antigen binding domain(s) of the binding agent may comprise the amino acid sequence of the CDR3 set forth in SEQ ID NO:15 and the amino acid sequence of the FR2 set forth in SEQ ID NO:170 and optionally the amino acid sequence of the CDR1 set forth in SEQ ID NO:13 and/or the amino acid sequence of the CDR2 set forth in SEQ ID NO:137.

In an exemplary embodiment, the binding agent or antigen binding domain(s) of the binding agent may comprise the amino acid sequence of the CDR3 set forth in SEQ ID NO:15 and the amino acid sequence of the FR2 set forth in SEQ ID NO:170 and optionally the amino acid sequence of the CDR1 set forth in SEQ ID NO:13 and/or the amino acid sequence of the CDR2 set forth in SEQ ID NO:138.

In an exemplary embodiment, the binding agent or antigen binding domain(s) of the binding agent may comprise the amino acid sequence of the CDR3 set forth in SEQ ID NO:15 and the amino acid sequence of the FR2 set forth in SEQ ID NO:171 and optionally the amino acid sequence of the CDR1 set forth in SEQ ID NO:13 and/or the amino acid sequence of the CDR2 set forth in SEQ ID NO:136.

In an exemplary embodiment, the binding agent or antigen binding domain(s) of the binding agent may comprise the amino acid sequence of the CDR3 set forth in SEQ ID NO:15 and the amino acid sequence of the FR2 set forth in SEQ ID NO:171 and optionally the amino acid sequence of the CDR1 set forth in SEQ ID NO:13 and/or the amino acid sequence of the CDR2 set forth in SEQ ID NO:137.

In an exemplary embodiment, the binding agent or antigen binding domain(s) of the binding agent may comprise the amino acid sequence of the CDR3 set forth in SEQ ID NO:15 and the amino acid sequence of the FR2 set forth in SEQ ID NO:171 and optionally the amino acid sequence of the CDR1 set forth in SEQ ID NO:13 and/or the amino acid sequence of the CDR2 set forth in SEQ ID NO:138.

In an exemplary embodiment, the binding agent or antigen binding domain(s) of the binding agent may comprise the amino acid sequence of the CDR3 set forth in SEQ ID NO:15 and the amino acid sequence of the FR2 set forth in SEQ ID NO:171 and optionally the amino acid sequence of the CDR1 set forth in SEQ ID NO:13 and/or the amino acid sequence of the CDR2 set forth in SEQ ID NO:139.

In an exemplary embodiment, the binding agent or antigen binding domain(s) of the binding agent may comprise the amino acid sequence of the CDR3 set forth in SEQ ID NO:15 and the amino acid sequence of the FR2 set forth in SEQ ID NO:173 and optionally the amino acid sequence of the CDR1 set forth in SEQ ID NO:13 and/or the amino acid sequence of the CDR2 set forth in SEQ ID NO:137.

In another exemplary embodiment, the binding agent or antigen binding domain(s) of the binding agent may comprise the amino acid sequence of the CDR1 set forth in SEQ ID NO:52, the amino acid sequence of the CDR2 set forth in SEQ ID NO:53, the amino acid sequence of the CDR3 set forth in SEQ ID NO:54 and the amino acid sequence of the FR2 set forth in SEQ ID NO:116.

In another exemplary embodiment, the binding agent or antigen binding domain(s) of the binding agent may comprise the amino acid sequence of the CDR1 set forth in SEQ ID NO:55, the amino acid sequence of the CDR2 set forth in SEQ ID NO:47, the amino acid sequence of the CDR3 set forth in SEQ ID NO:48 and the amino acid sequence of the FR2 set forth in SEQ ID NO:116.

In another exemplary embodiment, the binding agent or antigen binding domain(s) of the binding agent may comprise the amino acid sequence of the CDR1 set forth in SEQ ID NO:56, the amino acid sequence of the CDR2 set forth in SEQ ID NO:57, the amino acid sequence of the CDR3 set forth in SEQ ID NO:58 and the amino acid sequence of the FR2 set forth in SEQ ID NO:116.

In another exemplary embodiment, the binding agent or antigen binding domain(s) of the binding agent may comprise the amino acid sequence of the CDR1 set forth in SEQ ID NO:59, the amino acid sequence of the CDR2 set forth in SEQ ID NO:60, the amino acid sequence of the CDR3 set forth in SEQ ID NO:61 and the amino acid sequence of the FR2 set forth in SEQ ID NO:116.

In another exemplary embodiment, the binding agent or antigen binding domain(s) of the binding agent may comprise the amino acid sequence of the CDR1 set forth in SEQ ID NO:62, the amino acid sequence of the CDR2 set forth in SEQ ID NO:50, the amino acid sequence of the CDR3 set forth in SEQ ID NO:51 and the amino acid sequence of the FR2 set forth in SEQ ID NO:116.

In another exemplary embodiment, the binding agent or antigen binding domain(s) of the binding agent may comprise the amino acid sequence of the CDR1 set forth in SEQ ID NO:55, the amino acid sequence of the CDR2 set forth in SEQ ID NO:47, the amino acid sequence of the CDR3 set forth in SEQ ID NO: 48 and the amino acid sequence of the FR2 set forth in SEQ ID NO:116.

In another exemplary embodiment, the binding agent or antigen binding domain(s) of the binding agent may comprise the amino acid sequence of the CDR1 set forth in SEQ ID NO:55, the amino acid sequence of the CDR2 set forth in SEQ ID NO:47, the amino acid sequence of the CDR3 set forth in SEQ ID NO: 48 and the amino acid sequence of the FR2 set forth in SEQ ID NO:117.

In another exemplary embodiment, the binding agent or antigen binding domain(s) of the binding agent may comprise the amino acid sequence of the CDR1 set forth in SEQ ID NO:55, the amino acid sequence of the CDR2 set forth in SEQ ID NO: 47, the amino acid sequence of the CDR3 set forth in SEQ ID NO: 48 and the amino acid sequence of the FR2 set forth in SEQ ID NO:118.

In another exemplary embodiment, the binding agent or antigen binding domain(s) of the binding agent may comprise the amino acid sequence of the CDR1 set forth in SEQ ID NO:55, the amino acid sequence of the CDR2 set forth in SEQ ID NO:47, the amino acid sequence of the CDR3 set forth in SEQ ID NO: 48 and the amino acid sequence of the FR2 set forth in SEQ ID NO:119.

In another exemplary embodiment, the binding agent or antigen binding domain(s) of the binding agent may comprise the amino acid sequence of the CDR1 set forth in SEQ ID NO:55, the amino acid sequence of the CDR2 set forth in SEQ ID NO:124, the amino acid sequence of the CDR3 set forth in SEQ ID NO: 48 and the amino acid sequence of the FR2 set forth in SEQ ID NO:117.

In another exemplary embodiment, the binding agent or antigen binding domain(s) of the binding agent may comprise the amino acid sequence of the CDR1 set forth in SEQ ID NO:55, the amino acid sequence of the CDR2 set forth in SEQ ID NO:123, the amino acid sequence of the CDR3 set forth in SEQ ID NO: 48 and the amino acid sequence of the FR2 set forth in SEQ ID NO:117.

In another exemplary embodiment, the binding agent or antigen binding domain(s) of the binding agent may comprise the amino acid sequence of the CDR1 set forth in SEQ ID NO:62, the amino acid sequence of the CDR2 set forth in SEQ ID NO:50, the amino acid sequence of the CDR3 set forth in SEQ ID NO:51 and the amino acid sequence of the FR2 set forth in SEQ ID NO:116.

In another exemplary embodiment, the binding agent or antigen binding domain(s) of the binding agent may comprise the amino acid sequence of the CDR1 set forth in SEQ ID NO:62, the amino acid sequence of the CDR2 set forth in SEQ ID NO:50, the amino acid sequence of the CDR3 set forth in SEQ ID NO:51 and the amino acid sequence of the FR2 set forth in SEQ ID NO:117.

In another exemplary embodiment, the binding agent or antigen binding domain(s) of the binding agent may comprise the amino acid sequence of the CDR1 set forth in SEQ ID NO:62, the amino acid sequence of the CDR2 set forth in SEQ ID NO:50, amino acid sequence of the CDR3 set forth in SEQ ID NO:51 and the amino acid sequence of the FR2 set forth in SEQ ID NO:118.

In another exemplary embodiment, the binding agent or antigen binding domain(s) of the binding agent may comprise the amino acid sequence of the CDR1 set forth in SEQ ID NO:62, the amino acid sequence of the CDR2 set forth in SEQ ID NO:50, amino acid sequence of the CDR3 set forth in SEQ ID NO:51 and the amino acid sequence of the FR2 set forth in SEQ ID NO:120.

In an exemplary embodiment, the binding agent or antigen binding domain(s) of the binding agent may comprise the amino acid sequence of the CDR1 set forth in SEQ ID NO:4, the amino acid sequence of the CDR2 set forth in SEQ ID NO:5, the amino acid sequence of the CDR3 set forth in SEQ ID NO:6 and the amino acid sequence of the FR2 set forth in SEQ ID NO:170.

In an exemplary embodiment, the binding agent or antigen binding domain(s) of the binding agent may comprise the amino acid sequence of the CDR1 set forth in SEQ ID NO:4, the amino acid sequence of the CDR2 set forth in SEQ ID NO:130, the amino acid sequence of the CDR3 set forth in SEQ ID NO:6 and the amino acid sequence of the FR2 set forth in SEQ ID NO:171.

In an exemplary embodiment, the binding agent or antigen binding domain(s) of the binding agent may comprise the amino acid sequence of the CDR1 set forth in SEQ ID NO:4, the amino acid sequence of the CDR2 set forth in SEQ ID NO:131, the amino acid sequence of the CDR3 set forth in SEQ ID NO:6 and the amino acid sequence of the FR2 set forth in SEQ ID NO:170.

In an exemplary embodiment, the binding agent or antigen binding domain(s) of the binding agent may comprise the amino acid sequence of the CDR1 set forth in SEQ ID NO:4, the amino acid sequence of the CDR2 set forth in SEQ ID NO:133, the amino acid sequence of the CDR3 set forth in SEQ ID NO:6 and the amino acid sequence of the FR2 set forth in SEQ ID NO:170.

In an exemplary embodiment, the binding agent or antigen binding domain(s) of the binding agent may comprise the amino acid sequence of the CDR1 set forth in SEQ ID NO:4, the amino acid sequence of the CDR2 set forth in SEQ ID NO:131, the amino acid sequence of the CDR3 set forth in SEQ ID NO:6 and the amino acid sequence of the FR2 set forth in SEQ ID NO:171.

In an exemplary embodiment, the binding agent or antigen binding domain(s) of the binding agent may comprise the amino acid sequence of the CDR1 set forth in SEQ ID NO:4, the amino acid sequence of the CDR2 set forth in SEQ ID NO:132, the amino acid sequence of the CDR3 set forth in SEQ ID NO:6 and the amino acid sequence of the FR2 set forth in SEQ ID NO:171.

In an exemplary embodiment, the binding agent or antigen binding domain(s) of the binding agent may comprise the amino acid sequence of the CDR1 set forth in SEQ ID NO:4, the amino acid sequence of the CDR2 set forth in SEQ ID NO:133, the amino acid sequence of the CDR3 set forth in SEQ ID NO:6 and the amino acid sequence of the FR2 set forth in SEQ ID NO:171.

In an exemplary embodiment, the binding agent or antigen binding domain(s) of the binding agent may comprise the amino acid sequence of the CDR1 set forth in SEQ ID NO:4, the amino acid sequence of the CDR2 set forth in SEQ ID NO:133, the amino acid sequence of the CDR3 set forth in SEQ ID NO:6 and the amino acid sequence of the FR2 set forth in SEQ ID NO:172.

In an exemplary embodiment, the binding agent or antigen binding domain(s) of the binding agent may comprise the amino acid sequence of the CDR1 set forth in SEQ ID NO:4, the amino acid sequence of the CDR2 set forth in SEQ ID NO:134, the amino acid sequence of the CDR3 set forth in SEQ ID NO:6 and the amino acid sequence of the FR2 set forth in SEQ ID NO:171.

In an exemplary embodiment, the binding agent or antigen binding domain(s) of the binding agent may comprise the amino acid sequence of the CDR1 set forth in SEQ ID NO:4, the amino acid sequence of the CDR2 set forth in SEQ ID NO:135, the amino acid sequence of the CDR3 set forth in SEQ ID NO:6 and the amino acid sequence of the FR2 set forth in SEQ ID NO:171.

In an exemplary embodiment, the binding agent or antigen binding domain(s) of the binding agent may comprise the amino acid sequence of the CDR1 set forth in SEQ ID NO:127, the amino acid sequence of the CDR2 set forth in SEQ ID NO:129, the amino acid sequence of the CDR3 set forth in SEQ ID NO:6 and the amino acid sequence of the FR2 set forth in SEQ ID NO:174.

In an exemplary embodiment, the binding agent or antigen binding domain(s) of the binding agent may comprise the amino acid sequence of the CDR1 set forth in SEQ ID NO:13, the amino acid sequence of the CDR2 set forth in SEQ ID NO:14, the amino acid sequence of the CDR3 set forth in SEQ ID NO:15 and the amino acid sequence of the FR2 set forth in SEQ ID NO:170.

In an exemplary embodiment, the binding agent or antigen binding domain(s) of the binding agent may comprise the amino acid sequence of the CDR1 set forth in SEQ ID NO:13, the amino acid sequence of the CDR2 set forth in SEQ ID NO:137, the amino acid sequence of the CDR3 set forth in SEQ ID NO:15 and the amino acid sequence of the FR2 set forth in SEQ ID NO:170.

In an exemplary embodiment, the binding agent or antigen binding domain(s) of the binding agent may comprise the amino acid sequence of the CDR1 set forth in SEQ ID NO:13, the amino acid sequence of the CDR2 set forth in SEQ ID NO:138, the amino acid sequence of the CDR3 set forth in SEQ ID NO:15 and the amino acid sequence of the FR2 set forth in SEQ ID NO:170.

In an exemplary embodiment, the binding agent or antigen binding domain(s) of the binding agent may comprise the amino acid sequence of the CDR1 set forth in SEQ ID NO:13, the amino acid sequence of the CDR2 set forth in SEQ ID NO:136, the amino acid sequence of the CDR3 set forth in SEQ ID NO:15 and the amino acid sequence of the FR2 set forth in SEQ ID NO:171.

In an exemplary embodiment, the binding agent or antigen binding domain(s) of the binding agent may comprise the amino acid sequence of the CDR1 set forth in SEQ ID NO:13, the amino acid sequence of the CDR2 set forth in SEQ ID NO:137, the amino acid sequence of the CDR3 set forth in SEQ ID NO:15 and the amino acid sequence of the FR2 set forth in SEQ ID NO:171.

In an exemplary embodiment, the binding agent or antigen binding domain(s) of the binding agent may comprise the amino acid sequence of the CDR1 set forth in SEQ ID NO:13, the amino acid sequence of the CDR2 set forth in SEQ ID NO:138, the amino acid sequence of the CDR3 set forth in SEQ ID NO:15 and the amino acid sequence of the FR2 set forth in SEQ ID NO:171.

In an exemplary embodiment, the binding agent or antigen binding domain(s) of the binding agent may comprise the amino acid sequence of the CDR1 set forth in SEQ ID NO:13, the amino acid sequence of the CDR2 set forth in SEQ ID NO:139, the amino acid sequence of the CDR3 set forth in SEQ ID NO:15 and the amino acid sequence of the FR2 set forth in SEQ ID NO:171.

In an exemplary embodiment, the binding agent or antigen binding domain(s) of the binding agent may comprise the amino acid sequence of the CDR1 set forth in SEQ ID NO:13, the amino acid sequence of the CDR2 set forth in SEQ ID NO:137, the amino acid sequence of the CDR3 set forth in SEQ ID NO:15 and the amino acid sequence of the FR2 set forth in SEQ ID NO:173.

In an exemplary embodiment, the amino acid sequence of the CDR1, CDR2, CDR3 and/or FR2 are on a single polypeptide chain.

In another exemplary embodiment, the amino acid sequence of the CDR3 and the amino acid sequence of the FR2 are on a same polypeptide chain.

In yet another exemplary embodiment, the amino acid sequence of the CDR1, CDR2, CDR3 and FR2 are on a same polypeptide chain.

In yet another exemplary embodiment, the amino acid sequence of the CDR3 and the amino acid sequence of the FR2 are on two polypeptide chains.

The present disclosure also relates to binding agent that is capable of binding to TROP2 comprising one or more antigen binding domains or at least one antigen binding fragment of a single domain antibody, wherein at least one of the one or more antigen binding domains or at least one antigen binding fragment comprises:

a. a heavy chain complementarity determining region 1 (CDRH1) having the amino acid sequence set forth in SEQ ID NO:1, a heavy chain complementarity determining region 2 (CDRH2) having the amino acid sequence set forth in SEQ ID NO:2 and a heavy chain complementarity determining region 3 (CDRH3) having the amino acid sequence set forth in SEQ ID NO:3;

b. a CDRH1 having the amino acid sequence set forth in SEQ ID NO:4, a CDRH2 having the amino acid sequence set forth in SEQ ID NO:5 and a CDRH3 having the amino acid sequence set forth in SEQ ID NO:6;

c. a CDRH1 having the amino acid sequence set forth in SEQ ID NO:7, a CDRH2 having the amino acid sequence set forth in SEQ ID NO:8 and a CDRH3 having the amino acid sequence set forth in SEQ ID NO:9;

d. a CDRH1 having the amino acid sequence set forth in SEQ ID NO:10, a CDRH2 having the amino acid sequence set forth in SEQ ID NO:11 and a CDRH3 having the amino acid sequence set forth in SEQ ID NO:12;

e. a CDRH1 having the amino acid sequence set forth in SEQ ID NO:13, a CDRH2 having the amino acid sequence set forth in SEQ ID NO:14 and a CDRH3 having the amino acid sequence set forth in SEQ ID NO:15;

f. a CDRH1 having the amino acid sequence set forth in SEQ ID NO:16, a CDRH2 having the amino acid sequence set forth in SEQ ID NO:17 and a CDRH3 having the amino acid sequence set forth in SEQ ID NO:18;

g. a CDRH1 having the amino acid sequence set forth in SEQ ID NO:19, a CDRH2 having the amino acid sequence set forth in SEQ ID NO:20 and a CDRH3 having the amino acid sequence set forth in SEQ ID NO:21;

h. a CDRH1 having the amino acid sequence set forth in SEQ ID NO:46 or in SEQ ID NO:55, a CDRH2 having the amino acid sequence set forth in SEQ ID NO:47 and a CDRH3 having the amino acid sequence set forth in SEQ ID NO:48;

i. a CDRH1 having the amino acid sequence set forth in SEQ ID NO:49 or in SEQ ID NO: 62, a CDRH2 having the amino acid sequence set forth in SEQ ID NO:50 and a CDRH3 having the amino acid sequence set forth in SEQ ID NO:51;

j. a CDRH1 having the amino acid sequence set forth in SEQ ID NO:52, a CDRH2 having the amino acid sequence set forth in SEQ ID NO:53 and a CDRH3 having the amino acid sequence set forth in SEQ ID NO:54;

k. a CDRH1 having the amino acid sequence set forth in SEQ ID NO:56, a CDRH2 having the amino acid sequence set forth in SEQ ID NO:57 and a CDRH3 having the amino acid sequence set forth in SEQ ID NO:58;

l. a CDRH1 having the amino acid sequence set forth in SEQ ID NO:59, a CDRH2 having the amino acid sequence set forth in SEQ ID NO:60 and a CDRH3 having the amino acid sequence set forth in SEQ ID NO:61;
m. a CDRH1 having the amino acid sequence set forth in SEQ ID NO:63, a CDRH2 having the amino acid sequence set forth in SEQ ID NO:64 and a CDRH3 having the amino acid sequence set forth in SEQ ID NO:65;
n. a CDRH1 having the amino acid sequence set forth in SEQ ID NO:66, a CDRH2 having the amino acid sequence set forth in SEQ ID NO:67 and a CDRH3 having the amino acid sequence set forth in SEQ ID NO:68;
o. a CDRH1 having the amino acid sequence set forth in SEQ ID NO:127, a CDRH2 having the amino acid sequence set forth in SEQ ID NO:129 and a CDRH3 having the amino acid sequence set forth in SEQ ID NO:6;
p. a CDRH1 having the amino acid sequence set forth in SEQ ID NO:4, a CDRH2 having the amino acid sequence set forth in SEQ ID NO:130 and a CDRH3 having the amino acid sequence set forth in SEQ ID NO:6;
q. a CDRH1 having the amino acid sequence set forth in SEQ ID NO:4, a CDRH2 having the amino acid sequence set forth in SEQ ID NO:131 and a CDRH3 having the amino acid sequence set forth in SEQ ID NO:6;
r. a CDRH1 having the amino acid sequence set forth in SEQ ID NO:4, a CDRH2 having the amino acid sequence set forth in SEQ ID NO:132 and a CDRH3 having the amino acid sequence set forth in SEQ ID NO:6;
s. a CDRH1 having the amino acid sequence set forth in SEQ ID NO:4, a CDRH2 having the amino acid sequence set forth in SEQ ID NO:133 and a CDRH3 having the amino acid sequence set forth in SEQ ID NO:6;
t. a CDRH1 having the amino acid sequence set forth in SEQ ID NO:4, a CDRH2 having the amino acid sequence set forth in SEQ ID NO:134 and a CDRH3 having the amino acid sequence set forth in SEQ ID NO:6;
u. a CDRH1 having the amino acid sequence set forth in SEQ ID NO:4, a CDRH2 having the amino acid sequence set forth in SEQ ID NO:135 and a CDRH3 having the amino acid sequence set forth in SEQ ID NO:6;
v. a CDRH1 having the amino acid sequence set forth in SEQ ID NO:13, a CDRH2 having the amino acid sequence set forth in SEQ ID NO:136 and a CDRH3 having the amino acid sequence set forth in SEQ ID NO:15;
w. a CDRH1 having the amino acid sequence set forth in SEQ ID NO:13, a CDRH2 having the amino acid sequence set forth in SEQ ID NO:137 and a CDRH3 having the amino acid sequence set forth in SEQ ID NO:15;
x. a CDRH1 having the amino acid sequence set forth in SEQ ID NO:13, a CDRH2 having the amino acid sequence set forth in SEQ ID NO:138 and a CDRH3 having the amino acid sequence set forth in SEQ ID NO:15;
y. a CDRH1 having the amino acid sequence set forth in SEQ ID NO:13, a CDRH2 having the amino acid sequence set forth in SEQ ID NO:139 and a CDRH3 having the amino acid sequence set forth in SEQ ID NO:15;
z. a variable region having an amino acid sequence at least 75%, 80% 85%, 90%, 95% identical to the amino acid sequence set forth in SEQ ID NO:22;
aa. a variable region having an amino acid sequence at least 75%, 80% 85%, 90%, 95% identical to the amino acid sequence set forth in SEQ ID NO:23;
bb. a variable region having an amino acid sequence at least 75%, 80% 85%, 90%, 95% identical to the amino acid sequence set forth in SEQ ID NO:24;
cc. a variable region having an amino acid sequence at least 75%, 80% 85%, 90%, 95% identical to the amino acid sequence set forth in SEQ ID NO:25;
dd. a variable region having an amino acid sequence at least 75%, 80% 85%, 90%, 95% identical to the amino acid sequence set forth in SEQ ID NO:26;
ee. a variable region having an amino acid sequence at least 75%, 80% 85%, 90%, 95% identical to the amino acid sequence set forth in SEQ ID NO:27;
ff. a variable region having an amino acid sequence at least 75%, 80% 85%, 90%, 95% identical to the amino acid sequence set forth in SEQ ID NO:28;
gg. a variable region having an amino acid sequence at least 75%, 80% 85%, 90%, 95% identical to the amino acid sequence set forth in any one of SEQ ID NOs:73 to 114.

In yet other aspects and embodiments, the present disclosure relates to a binding agent that is capable of binding to trophoblast cell surface antigen-2 (TROP2) and that comprises at least one antigen binding fragment of a single domain antibody.

In other exemplary embodiments, the binding agent, or antigen binding domain(s) of the binding agent comprises:
a. a variable region having an amino acid sequence as set forth in SEQ ID NO:22;
b. a variable region having an amino acid sequence as set forth in SEQ ID NO:23;
c. a variable region having an amino acid sequence as set forth in SEQ ID NO:24;
d. a variable region having an amino acid sequence as set forth in SEQ ID NO:25;
e. a variable region having an amino acid sequence as set forth in SEQ ID NO:26;
f. a variable region having an amino acid sequence as set forth in SEQ ID NO:27
g. a variable region having an amino acid sequence as set forth in SEQ ID NO:28 or;
h. a variable region having an amino acid sequence as set forth in any one of SEQ ID Nos:73-114.

In other exemplary embodiments, the binding agent comprises:
a. an amino acid sequence at least 75%, 80% 85%, 90%, 95% identical to the amino acid sequence set forth in SEQ ID NO:29;
b. an amino acid sequence at least 75%, 80% 85%, 90%, 95% identical to the amino acid sequence set forth in SEQ ID NO:30;
c. an amino acid sequence at least 75%, 80% 85%, 90%, 95% identical to the amino acid sequence set forth in SEQ ID NO:31;
d. an amino acid sequence at least 75%, 80% 85%, 90%, 95% identical to the amino acid sequence set forth in SEQ ID NO:32;

e. an amino acid sequence at least 75%, 80% 85%, 90%, 95% identical to the amino acid sequence set forth in SEQ ID NO:33;
f. an amino acid sequence at least 75%, 80% 85%, 90%, 95% identical to the amino acid sequence set forth in SEQ ID NO:34;
g. an amino acid sequence at least 75%, 80% 85%, 90%, 95% identical to the amino acid sequence set forth in SEQ ID NO:35;
h. an amino acid sequence at least 75%, 80% 85%, 90%, 95% identical to the amino acid sequence set forth in SEQ ID NO:44 or,
i. an amino acid sequence at least 75%, 80% 85%, 90%, 95% identical to the amino acid sequence set forth in SEQ ID NO:45.

In further exemplary embodiments, the binding agent comprises:
a. an amino acid sequence as set forth in SEQ ID NO:29;
b. an amino acid sequence as set forth in SEQ ID NO:30;
c. an amino acid sequence as set forth in SEQ ID NO:31;
d. an amino acid sequence as set forth in SEQ ID NO:32;
e. an amino acid sequence as set forth in SEQ ID NO:33;
f. an amino acid sequence as set forth in SEQ ID NO:34;
g. an amino acid sequence as set forth in SEQ ID NO: 35;
h. an amino acid sequence as set forth in SEQ ID NO:44 or,
i. an amino acid sequence as set forth in SEQ ID NO:45.

In some embodiments, the antigen binding domain is a heavy chain variable region.

In some embodiments, the heavy chain variable region is a camelid VH or VHH.

In some embodiments, the heavy chain variable region is a human VH.

In some embodiments, the heavy chain variable region is a mouse VH.

In some embodiments, the heavy chain variable region is a rat VH.

In some embodiments, the heavy chain variable region is a humanized VH or VHH. For example, the heavy chain variable region may be a humanized camelid VH or VHH. In other example, the heavy chain variable region may be a humanized mouse VH. In other example, the heavy chain variable region may be a humanized rat VH.

In other embodiments, the antigen binding domain is a heavy chain.

In accordance with the present disclosure, the binding agent may comprise two heavy chain variable regions. Each heavy chain variable regions may be on separate heavy chains. Accordingly, the binding agent may comprise two heavy chains.

The binding agent of the present disclosure may be, for example, a single domain antibody (heavy chain only antibody).

In some exemplary embodiments, the binding agent is a heavy chain only antibody that comprises a heavy chain complementarity determining region 1 (CDRH1) having the amino acid sequence set forth in SEQ ID NO: 1, a heavy chain complementarity determining region 2 (CDRH2) having the amino acid sequence set forth in SEQ ID NO:2 and a heavy chain complementarity determining region 3 (CDRH3) having the amino acid sequence set forth in SEQ ID NO:3.

In other exemplary embodiments, the binding agent is a heavy chain only antibody that comprises a CDRH1 having the amino acid sequence set forth in SEQ ID NO:4, a CDRH2 having the amino acid sequence set forth in SEQ ID NO:5 and a CDRH3 having the amino acid sequence set forth in SEQ ID NO:6.

In yet other exemplary embodiments, the binding agent is a heavy chain only antibody that comprises a CDRH1 having the amino acid sequence set forth in SEQ ID NO:7, a CDRH2 having the amino acid sequence set forth in SEQ ID NO:8 and a CDRH3 having the amino acid sequence set forth in SEQ ID NO:9.

In further exemplary embodiments, the binding agent is a heavy chain only antibody that comprises a CDRH1 having the amino acid sequence set forth in SEQ ID NO:10, a CDRH2 having the amino acid sequence set forth in SEQ ID NO:11 and a CDRH3 having the amino acid sequence set forth in SEQ ID NO:12.

In some exemplary embodiments, the binding agent is a heavy chain only antibody that comprises a CDRH1 having the amino acid sequence set forth in SEQ ID NO:13, a CDRH2 having the amino acid sequence set forth in SEQ ID NO:14 and a CDRH3 having the amino acid sequence set forth in SEQ ID NO:15.

In additional exemplary embodiments, the binding agent is a heavy chain only antibody that comprises a CDRH1 having the amino acid sequence set forth in SEQ ID NO:16, a CDRH2 having the amino acid sequence set forth in SEQ ID NO:17 and a CDRH3 having the amino acid sequence set forth in SEQ ID NO:18.

In other exemplary embodiments, the binding agent is a heavy chain only antibody that comprises a CDRH1 having the amino acid sequence set forth in SEQ ID NO:19, a CDRH2 having the amino acid sequence set forth in SEQ ID NO:20 and a CDRH3 having the amino acid sequence set forth in SEQ ID NO:21.

In yet other exemplary embodiments, the binding agent is a heavy chain only antibody that comprises a CDRH1 having the amino acid sequence set forth in SEQ ID NO:46, a CDRH2 having the amino acid sequence set forth in SEQ ID NO:47 and a CDRH3 having the amino acid sequence set forth in SEQ ID NO:48.

In yet other exemplary embodiments, the binding agent is a heavy chain only antibody that comprises a CDRH1 having the amino acid sequence set forth in SEQ ID NO:55, a CDRH2 having the amino acid sequence set forth in SEQ ID NO:47 and a CDRH3 having the amino acid sequence set forth in SEQ ID NO:48.

In other exemplary embodiments, the binding agent is a heavy chain only antibody that comprises a CDRH1 having the amino acid sequence set forth in SEQ ID NO:49, a CDRH2 having the amino acid sequence set forth in SEQ ID NO:50 and a CDRH3 having the amino acid sequence set forth in SEQ ID NO:51.

In other exemplary embodiments, the binding agent is a heavy chain only antibody that comprises a CDRH1 having the amino acid sequence set forth in SEQ ID NO:62, a CDRH2 having the amino acid sequence set forth in SEQ ID NO:50 and a CDRH3 having the amino acid sequence set forth in SEQ ID NO:51.

In other exemplary embodiments, the binding agent is a heavy chain only antibody that comprises a CDRH1 having the amino acid sequence set forth in SEQ ID NO:52, a CDRH2 having the amino acid sequence set forth in SEQ ID NO:53 and a CDRH3 having the amino acid sequence set forth in SEQ ID NO:54.

In other exemplary embodiments, the binding agent is a heavy chain only antibody that comprises a CDRH1 having the amino acid sequence set forth in SEQ ID NO:56, a CDRH2 having the amino acid sequence set forth in SEQ ID NO:57 and a CDRH3 having the amino acid sequence set forth in SEQ ID NO:58.

In other exemplary embodiments, the binding agent is a heavy chain only antibody that comprises a CDRH1 having the amino acid sequence set forth in SEQ ID NO:59, a CDRH2 having the amino acid sequence set forth in SEQ ID NO:60 and a CDRH3 having the amino acid sequence set forth in SEQ ID NO:61.

In other exemplary embodiments, the binding agent is a heavy chain only antibody that comprises a CDRH1 having the amino acid sequence set forth in SEQ ID NO:63, a CDRH2 having the amino acid sequence set forth in SEQ ID NO:64 and a CDRH3 having the amino acid sequence set forth in SEQ ID NO:65.

In other exemplary embodiments, the binding agent is a heavy chain only antibody that comprises a CDRH1 having the amino acid sequence set forth in SEQ ID NO:66, a CDRH2 having the amino acid sequence set forth in SEQ ID NO:67 and a CDRH3 having the amino acid sequence set forth in SEQ ID NO:68.

In other exemplary embodiments, the binding agent is a heavy chain only antibody that comprises the CDRH1, CDRH2 and CDRH3 of SEQ ID NO:152.

In other exemplary embodiments, the binding agent is a heavy chain only antibody that comprises the CDRH1, CDRH2 and CDRH3 of SEQ ID NO:153.

In other exemplary embodiments, the binding agent is a heavy chain only antibody that comprises the CDRH1, CDRH2 and CDRH3 of SEQ ID NO:154.

In other exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:22.

In some exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:23.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:24.

In further exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:25.

In yet further exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:26.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:27.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:28.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:71.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:72.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:73.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:74.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:75.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:76.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NOs77.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:78.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:79.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:80.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:81.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:82.

In additional exemplary embodiments, the binding agent is a heavy chain only antibody that comprises a variable region having an amino acid sequence at least 75%, 80% 85%, 90%, 95% identical to the amino acid sequence set forth in SEQ ID NO:83.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:84.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:85.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:86.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:87.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:88.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:89.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:90.

In additional exemplary embodiments, the binding agent is a heavy chain only antibody that comprises a variable region having an amino acid sequence at least 75%, 80% 85%, 90%, 95% identical to the amino acid sequence set forth in SEQ ID NO:91.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:92.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:93.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:94.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:95.

In additional exemplary embodiments, the binding agent is a heavy chain only antibody that comprises a variable region having an amino acid sequence at least 75%, 80% 85%, 90%, v identical to the amino acid sequence set forth in SEQ ID NO:96.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:97.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:98.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:99.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:100.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:101.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:102.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:103.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:104.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:105.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:106.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:107.

In additional exemplary embodiments, the binding agent is a heavy chain only antibody that comprises a variable region having an amino acid sequence at least 75%, 80% 85%, 90%, 95% identical to the amino acid sequence set forth in SEQ ID NO:108.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:109.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:110.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:111.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:112.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:113.

In additional exemplary embodiments, the binding agent is a heavy chain only antibody that comprises a variable region having an amino acid sequence at least 75%, 80% 85%, 90%, 95%, 99% identical to the amino acid sequence set forth in SEQ ID NO:114.

In additional exemplary embodiments, the binding agent is a heavy chain only antibody that comprises a variable region having an amino acid sequence at least 75%, 80% 85%, 90%, 95%, 99% identical to the variable region of SEQ ID NO: 152.

In additional exemplary embodiments, the binding agent is a heavy chain only antibody that comprises a variable region having an amino acid sequence at least 75%, 80% 85%, 90%, 95%, 99% identical to the variable region of SEQ ID NO: 153.

In additional exemplary embodiments, the binding agent is a heavy chain only antibody that comprises a variable region having an amino acid sequence at least 75%, 80% 85%, 90%, 95%, 99% identical to the variable region of SEQ ID NO: 154.

In further exemplary embodiments, the binding agent is a heavy chain only antibody that comprises an amino acid sequence at least 75%, 80% 85%, 90%, 95%, 99% identical to the amino acid sequence set forth in SEQ ID NO:29.

In other exemplary embodiments, the binding agent is a heavy chain only antibody that comprises an amino acid sequence at least 75%, 80% 85%, 90%, 95%, 99% identical to the amino acid sequence set forth in SEQ ID NO:30.

In some exemplary embodiments, the binding agent is a heavy chain only antibody that comprises an amino acid sequence at least 75%, 80% 85%, 90%, 95%, 99% identical to the amino acid sequence set forth in SEQ ID NO:31.

In further exemplary embodiments, the binding agent is a heavy chain only antibody that comprises an amino acid sequence at least 75%, 80% 85%, 90%, 95%, 99% identical to the amino acid sequence set forth in SEQ ID NO:32.

In other exemplary embodiments, the binding agent is a heavy chain only antibody that comprises an amino acid sequence at least 75%, 80% 85%, 90%, 95%, 99% identical to the amino acid sequence set forth in SEQ ID NO:33.

In other exemplary embodiments, the binding agent is a heavy chain only antibody that comprises an amino acid sequence at least 75%, 80% 85%, 90%, 95%, 99% identical to the amino acid sequence set forth in SEQ ID NO:34.

In other exemplary embodiments, the binding agent is a heavy chain only antibody that comprises an amino acid sequence at least 75%, 80% 85%, 90%, 95%, 99% identical to the amino acid sequence set forth in SEQ ID NO:35.

In other exemplary embodiments, the binding agent is a heavy chain only antibody that comprises an amino acid sequence at least 75%, 80% 85%, 90%, 95%, 99% identical to the amino acid sequence set forth in SEQ ID NO:44.

In other exemplary embodiments, the binding agent is a heavy chain only antibody that comprises an amino acid sequence at least 75%, 80% 85%, 90%, 95% identical to the amino acid sequence set forth in SEQ ID NO:45.

In other exemplary embodiments, the binding agent is a heavy chain only antibody that comprises an amino acid sequence at least 75%, 80% 85%, 90%, 95%, 99% identical to the amino acid sequence set forth in SEQ ID NO:152.

In other exemplary embodiments, the binding agent is a heavy chain only antibody that comprises an amino acid sequence at least 75%, 80% 85%, 90%, 95%, 99% identical to the amino acid sequence set forth in SEQ ID NO:153.

In other exemplary embodiments, the binding agent is a heavy chain only antibody that comprises an amino acid sequence at least 75%, 80% 85%, 90%, 95%, 99% identical to the amino acid sequence set forth in SEQ ID NO:154.

In further exemplary embodiments, the binding agent is a heavy chain only antibody that comprises a variable region having an amino acid sequence as set forth in SEQ ID NO:22.

In other exemplary embodiments, the binding agent is a heavy chain only antibody that comprises a variable region having an amino acid sequence as set forth in SEQ ID NO:23.

In further exemplary embodiments, the binding agent is a heavy chain only antibody that comprises a variable region having an amino acid sequence as set forth in SEQ ID NO:24.

In additional exemplary embodiments, the binding agent is a heavy chain only antibody that comprises a variable region having an amino acid sequence as set forth in SEQ ID NO:25.

In other exemplary embodiments, the binding agent is a heavy chain only antibody that comprises a variable region having an amino acid sequence as set forth in SEQ ID NO:26.

In further exemplary embodiments, the binding agent is a heavy chain only antibody that comprises a variable region having an amino acid sequence as set forth in SEQ ID NO:27.

In yet further exemplary embodiments, the binding agent is a heavy chain only antibody that comprises a variable region having an amino acid sequence as set forth in SEQ ID NO:28.

In additional exemplary embodiments, the binding agent is a heavy chain only antibody that comprises an amino acid sequence as set forth in SEQ ID NO:29.

In another exemplary embodiments, the binding agent is a heavy chain only antibody that comprises an amino acid sequence as set forth in SEQ ID NO:73.

In another exemplary embodiments, the binding agent is a heavy chain only antibody that comprises an amino acid sequence as set forth in SEQ ID NO:74.

In another exemplary embodiments, the binding agent is a heavy chain only antibody that comprises an amino acid sequence as set forth in SEQ ID NO:75.

In another exemplary embodiments, the binding agent is a heavy chain only antibody that comprises an amino acid sequence as set forth in SEQ ID NO:76.

In another exemplary embodiments, the binding agent is a heavy chain only antibody that comprises an amino acid sequence as set forth in SEQ ID NO:77.

In another exemplary embodiments, the binding agent is a heavy chain only antibody that comprises an amino acid sequence as set forth in SEQ ID NO:78.

In another exemplary embodiments, the binding agent is a heavy chain only antibody that comprises an amino acid sequence as set forth in SEQ ID NO:79.

In another exemplary embodiments, the binding agent is a heavy chain only antibody that comprises an amino acid sequence as set forth in SEQ ID NO:80.

In another exemplary embodiments, the binding agent is a heavy chain only antibody that comprises an amino acid sequence as set forth in SEQ ID NO:81.

In another exemplary embodiments, the binding agent is a heavy chain only antibody that comprises an amino acid sequence as set forth in SEQ ID NO:82.

In another exemplary embodiments, the binding agent is a heavy chain only antibody that comprises an amino acid sequence as set forth in SEQ ID NO:83.

In another exemplary embodiments, the binding agent is a heavy chain only antibody that comprises an amino acid sequence as set forth in SEQ ID NO:84.

In another exemplary embodiments, the binding agent is a heavy chain only antibody that comprises an amino acid sequence as set forth in SEQ ID NO:85.

In another exemplary embodiments, the binding agent is a heavy chain only antibody that comprises an amino acid sequence as set forth in SEQ ID NO:86.

In another exemplary embodiments, the binding agent is a heavy chain only antibody that comprises an amino acid sequence as set forth in SEQ ID NO:87.

In another exemplary embodiments, the binding agent is a heavy chain only antibody that comprises an amino acid sequence as set forth in SEQ ID NO:88.

In another exemplary embodiments, the binding agent is a heavy chain only antibody that comprises an amino acid sequence as set forth in SEQ ID NO:89.

In another exemplary embodiments, the binding agent is a heavy chain only antibody that comprises an amino acid sequence as set forth in SEQ ID NO:90.

In another exemplary embodiments, the binding agent is a heavy chain only antibody that comprises an amino acid sequence as set forth in SEQ ID NO:91.

In another exemplary embodiments, the binding agent is a heavy chain only antibody that comprises an amino acid sequence as set forth in SEQ ID NO:92.

In another exemplary embodiments, the binding agent is a heavy chain only antibody that comprises an amino acid sequence as set forth in SEQ ID NO:93.

In another exemplary embodiments, the binding agent is a heavy chain only antibody that comprises an amino acid sequence as set forth in SEQ ID NO:94.

In another exemplary embodiments, the binding agent is a heavy chain only antibody that comprises an amino acid sequence as set forth in SEQ ID NO:95.

In another exemplary embodiments, the binding agent is a heavy chain only antibody that comprises an amino acid sequence as set forth in SEQ ID NO:96.

In another exemplary embodiments, the binding agent is a heavy chain only antibody that comprises an amino acid sequence as set forth in SEQ ID NO:97.

In another exemplary embodiments, the binding agent is a heavy chain only antibody that comprises an amino acid sequence as set forth in SEQ ID NO:98.

In another exemplary embodiments, the binding agent is a heavy chain only antibody that comprises an amino acid sequence as set forth in SEQ ID NO:99.

In another exemplary embodiments, the binding agent is a heavy chain only antibody that comprises an amino acid sequence as set forth in SEQ ID NO:100.

In another exemplary embodiments, the binding agent is a heavy chain only antibody that comprises an amino acid sequence as set forth in SEQ ID NO:101.

In another exemplary embodiments, the binding agent is a heavy chain only antibody that comprises an amino acid sequence as set forth in SEQ ID NO:102.

In another exemplary embodiments, the binding agent is a heavy chain only antibody that comprises an amino acid sequence as set forth in SEQ ID NO:103.

In another exemplary embodiments, the binding agent is a heavy chain only antibody that comprises an amino acid sequence as set forth in SEQ ID NO:104.

In another exemplary embodiments, the binding agent is a heavy chain only antibody that comprises an amino acid sequence as set forth in SEQ ID NO:105.

In another exemplary embodiments, the binding agent is a heavy chain only antibody that comprises an amino acid sequence as set forth in SEQ ID NO:106.

In another exemplary embodiments, the binding agent is a heavy chain only antibody that comprises an amino acid sequence as set forth in SEQ ID NO:107.

In another exemplary embodiments, the binding agent is a heavy chain only antibody that comprises an amino acid sequence as set forth in SEQ ID NO:108.

In another exemplary embodiments, the binding agent is a heavy chain only antibody that comprises an amino acid sequence as set forth in SEQ ID NO:109.

In another exemplary embodiments, the binding agent is a heavy chain only antibody that comprises an amino acid sequence as set forth in SEQ ID NO:110.

In another exemplary embodiments, the binding agent is a heavy chain only antibody that comprises an amino acid sequence as set forth in SEQ ID NO:111.

In another exemplary embodiments, the binding agent is a heavy chain only antibody that comprises an amino acid sequence as set forth in SEQ ID NO: 112.

In another exemplary embodiments, the binding agent is a heavy chain only antibody that comprises an amino acid sequence as set forth in SEQ ID NO: 113.

In additional exemplary embodiments, the binding agent is a heavy chain only antibody that comprises an amino acid sequence as set forth in SEQ ID NO: 114.

In other exemplary embodiments, the binding agent is a heavy chain only antibody that comprises an amino acid sequence as set forth in SEQ ID NO:30.

In yet other exemplary embodiments, the binding agent is a heavy chain only antibody that comprises an amino acid sequence as set forth in SEQ ID NO:31.

In further exemplary embodiments, the binding agent is a heavy chain only antibody that comprises an amino acid sequence as set forth in SEQ ID NO:32.

In yet further exemplary embodiments, the binding agent is a heavy chain only antibody that comprises an amino acid sequence as set forth in SEQ ID NO:33.

In other exemplary embodiments, the binding agent is a heavy chain only antibody that comprises an amino acid sequence as set forth in SEQ ID NO:34.

In other exemplary embodiments, the binding agent is a heavy chain only antibody that comprises an amino acid sequence as set forth in SEQ ID NO:35.

In other exemplary embodiments, the binding agent is a heavy chain only antibody that comprises an amino acid sequence as set forth in SEQ ID NO:44.

In other exemplary embodiments, the binding agent is a heavy chain only antibody that comprises an amino acid sequence as set forth in SEQ ID NO:45.

In some exemplary embodiments, the heavy chain only antibody comprises a dimerization domain as described herein. For example, the heavy chain only antibody may comprise a constant region of a human IgG or a portion thereof. The heavy chain only antibody may thus be engineered.

Accordingly, the heavy chain only antibody may be non-naturally occurring.

In some exemplary embodiments, the constant region or portion thereof is from an IgG1, an IgG2, an IgG3 or an IgG4. For example, the constant region or portion thereof is from a IgG1, an IgG2, an IgG3 or an IgG4 heavy chain.

In some embodiments, the constant region or portion thereof is from a human IgG1. For example, the constant region or portion thereof is from a IgG1 heavy chain.

In some embodiment, the constant region or portion thereof comprises a hinge.

In some embodiment, the constant region or portion thereof comprises a peptidic linker.

In some embodiments, the heavy chain only antibody comprises two heavy chains. The two chains of the heavy chain only antibody may be for example, identical.

In some embodiments, the binding agent or at least one of the one or more antigen binding domains may have an affinity of $\leq 10^{-6}$ M for human TROP2.

In some embodiments, the binding agent or at least one of the one or more antigen binding domains may have an affinity of $\leq 10^{-7}$ M for human TROP2.

In some embodiments, the binding agent or at least one of the one or more antigen binding domains may have an affinity of $10^{-8}$ M for human TROP2.

In some embodiments, the binding agent or at least one of the one or more antigen binding domains may have an affinity of $10^{-9}$ M for human TROP2.

In some embodiments, the binding agent or at least one of the one or more antigen binding domains may have an affinity of $\leq 10^{-10}$ M for human TROP2.

In some embodiments, the binding agent or at least one of the one or more antigen binding domains may have an affinity of $\leq 10^{-11}$ M for human TROP2.

In some embodiments, the binding agent or at least one of the one or more antigen binding domains may have an affinity of $\leq 10^{-12}$ M for human TROP2.

In some aspects and embodiments, the heavy chain only antibody has an affinity for human TROP2 in the picomolar range.

In some aspects and embodiments, the KD value of the heavy chain only antibody is lower than 10E-11 for human TROP2.

In an exemplary embodiment, the binding agent or at least one of the one or more antigen binding domains may have an affinity of $1\times10^{-10}$ M or lower for human TROP2.

In another exemplary embodiment, the binding agent or at least one of the one or more antigen binding domains may have an affinity of at between $1\times10^{-10}$ M and $1\times10^{-12}$ for human TROP2.

In another exemplary embodiment, the binding agent or at least one of the one or more antigen binding domains may have an affinity of at between $1\times10^{-10}$ M and $1\times10^{-11}$ for human TROP2.

In an exemplary embodiment, the binding agent or at least one of the one or more antigen binding domains may have a dissociation rate of between $1\times10^{-6}$ to $1\times10^{-4}$ for human TROP2.

In an exemplary embodiment, the binding agent or at least one of the one or more antigen binding domains may have a dissociation rate of between $1\times10^{-5}$ to $1\times10^{-4}$ for human TROP2.

In an exemplary embodiment, the binding agent or antigen binding domain(s) of the present disclosure may have ADCP activity towards cells expressing human TROP2.

In an exemplary embodiment, the binding agent or antigen binding domain(s) of the present disclosure may have ADCP activity towards cells expressing human TROP2 and Cluster of Differentiation 47 (CD47) (Uniprot Accession No. Q08722-1). An exemplary and non-limiting embodiment of a CD47 antigen is provided in SEQ ID NO:176.

In an exemplary embodiment, the binding agent or antigen binding domain(s) of the present disclosure may have ADCC activity towards cells expressing human TROP2.

In an exemplary embodiment, the binding agent or antigen binding domain(s) of the present disclosure may be internalized in cells expressing human TROP2.

In an exemplary embodiment, the binding agent or antigen binding domain(s) of the present disclosure may be capable of inhibiting the growth of tumor cells expressing human TROP2.

In an exemplary embodiment, the binding agent or antigen binding domain(s) of the present disclosure may be capable of inhibiting the growth of tumor cells expressing human TROP2 and CD47.

Accordingly, the binding agent may comprise one or more antigen binding domains that is capable of binding to CD47.

In an exemplary embodiment, the antigen binding domain that is capable of binding to CD47 may comprise:
  a. a CDRH1 having the amino acid sequence set forth in SEQ ID NO156, a CDRH2 having the amino acid sequence set forth in SEQ ID NO:157 and/or a CDRH3 having the amino acid sequence set forth in SEQ ID NO:158, or
  b. a CDRH1 having the amino acid sequence set forth in SEQ ID NO159, a CDRH2 having the amino acid sequence set forth in SEQ ID NO:160 and/or a CDRH3 having the amino acid sequence set forth in SEQ ID NO:161.

In an exemplary embodiment, the antigen binding domains that is capable of binding to CD47 may comprise an amino acid sequence at least 80% identical to the amino acid sequence set forth in SEQ ID NO:155.

In another exemplary embodiment, the antigen binding domains that is capable of binding to CD47 may comprise an amino acid sequence at least 80% identical to the amino acid sequence set forth in SEQ ID NO:150 or 151.

The present disclosure also relates to a binding agent that is capable of competing with one or more binding agents disclosed herein.

In some embodiments, the binding agent comprises at least one antigen binding domain that is capable of competing with one or more binding agent disclosed herein.

In some embodiments, the binding agent comprises at least one antigen binding fragment of a single domain antibody that is capable of competing with one or more binding agent disclosed herein.

More particularly, the binding agent is capable of competing or comprises one or more antigen binding domains that is capable of competing with a binding agent comprising:
  a. a heavy chain complementarity determining region 1 (CDRH1) having the amino acid sequence set forth in SEQ ID NO:1, a heavy chain complementarity determining region 2 (CDRH2) having the amino acid sequence set forth in SEQ ID NO:2 and a heavy chain complementarity determining region 3 (CDRH3) having the amino acid sequence set forth in SEQ ID NO:3;

b. a CDRH1 having the amino acid sequence set forth in SEQ ID NO:4, a CDRH2 having the amino acid sequence set forth in SEQ ID NO:5 and a CDRH3 having the amino acid sequence set forth in SEQ ID NO:6;

c. a CDRH1 having the amino acid sequence set forth in SEQ ID NO:7, a CDRH2 having the amino acid sequence set forth in SEQ ID NO:8 and a CDRH3 having the amino acid sequence set forth in SEQ ID NO:9;

d. a CDRH1 having the amino acid sequence set forth in SEQ ID NO:10, a CDRH2 having the amino acid sequence set forth in SEQ ID NO:11 and a CDRH3 having the amino acid sequence set forth in SEQ ID NO:12;

e. a CDRH1 having the amino acid sequence set forth in SEQ ID NO:13, a CDRH2 having the amino acid sequence set forth in SEQ ID NO:14 and a CDRH3 having the amino acid sequence set forth in SEQ ID NO:15;

f. a CDRH1 having the amino acid sequence set forth in SEQ ID NO:16, a CDRH2 having the amino acid sequence set forth in SEQ ID NO:17 and a CDRH3 having the amino acid sequence set forth in SEQ ID NO:18;

g. a CDRH1 having the amino acid sequence set forth in SEQ ID NO:19, a CDRH2 having the amino acid sequence set forth in SEQ ID NO:20 and a CDRH3 having the amino acid sequence set forth in SEQ ID NO:21;

h. a CDRH1 having the amino acid sequence set forth in SEQ ID NO:46 or SEQ ID NO:55, a CDRH2 having the amino acid sequence set forth in SEQ ID NO:47 and a CDRH3 having the amino acid sequence set forth in SEQ ID NO:48;

i. a CDRH1 having the amino acid sequence set forth in SEQ ID NO:49 or SEQ ID NO:62, a CDRH2 having the amino acid sequence set forth in SEQ ID NO:50 and a CDRH3 having the amino acid sequence set forth in SEQ ID NO:51;

j. a CDRH1 having the amino acid sequence set forth in SEQ ID NO:52, a CDRH2 having the amino acid sequence set forth in SEQ ID NO:53 and a CDRH3 having the amino acid sequence set forth in SEQ ID NO:54;

k. a CDRH1 having the amino acid sequence set forth in SEQ ID NO:56, a CDRH2 having the amino acid sequence set forth in SEQ ID NO:57 and a CDRH3 having the amino acid sequence set forth in SEQ ID NO:58;

l. a CDRH1 having the amino acid sequence set forth in SEQ ID NO:59, a CDRH2 having the amino acid sequence set forth in SEQ ID NO:60 and a CDRH3 having the amino acid sequence set forth in SEQ ID NO:61;

m. a CDRH1 having the amino acid sequence set forth in SEQ ID NO:63, a CDRH2 having the amino acid sequence set forth in SEQ ID NO:64 and a CDRH3 having the amino acid sequence set forth in SEQ ID NO:65;

n. a CDRH1 having the amino acid sequence set forth in SEQ ID NO:66, a CDRH2 having the amino acid sequence set forth in SEQ ID NO:67 and a CDRH3 having the amino acid sequence set forth in SEQ ID NO:68;

o. a CDRH1 having the amino acid sequence set forth in SEQ ID NO:127, a CDRH2 having the amino acid sequence set forth in SEQ ID NO:129 and a CDRH3 having the amino acid sequence set forth in SEQ ID NO:6;

p. a CDRH1 having the amino acid sequence set forth in SEQ ID NO:4, a CDRH2 having the amino acid sequence set forth in SEQ ID NO:130 and a CDRH3 having the amino acid sequence set forth in SEQ ID NO:6;

q. a CDRH1 having the amino acid sequence set forth in SEQ ID NO:4, a CDRH2 having the amino acid sequence set forth in SEQ ID NO:131 and a CDRH3 having the amino acid sequence set forth in SEQ ID NO:6;

r. a CDRH1 having the amino acid sequence set forth in SEQ ID NO:4, a CDRH2 having the amino acid sequence set forth in SEQ ID NO:132 and a CDRH3 having the amino acid sequence set forth in SEQ ID NO:6;

s. a CDRH1 having the amino acid sequence set forth in SEQ ID NO:4, a CDRH2 having the amino acid sequence set forth in SEQ ID NO:133 and a CDRH3 having the amino acid sequence set forth in SEQ ID NO:6;

t. a CDRH1 having the amino acid sequence set forth in SEQ ID NO:4, a CDRH2 having the amino acid sequence set forth in SEQ ID NO:134 and a CDRH3 having the amino acid sequence set forth in SEQ ID NO:6;

u. a CDRH1 having the amino acid sequence set forth in SEQ ID NO:4, a CDRH2 having the amino acid sequence set forth in SEQ ID NO:135 and a CDRH3 having the amino acid sequence set forth in SEQ ID NO:6;

v. a CDRH1 having the amino acid sequence set forth in SEQ ID NO:13, a CDRH2 having the amino acid sequence set forth in SEQ ID NO:136 and a CDRH3 having the amino acid sequence set forth in SEQ ID NO:15;

w. a CDRH1 having the amino acid sequence set forth in SEQ ID NO:13, a CDRH2 having the amino acid sequence set forth in SEQ ID NO:137 and a CDRH3 having the amino acid sequence set forth in SEQ ID NO:15;

x. a CDRH1 having the amino acid sequence set forth in SEQ ID NO:13, a CDRH2 having the amino acid sequence set forth in SEQ ID NO:138 and a CDRH3 having the amino acid sequence set forth in SEQ ID NO:15;

y. a CDRH1 having the amino acid sequence set forth in SEQ ID NO:13, a CDRH2 having the amino acid sequence set forth in SEQ ID NO:139 and a CDRH3 having the amino acid sequence set forth in SEQ ID NO:15;

z. a variable region having an amino acid sequence at least 75%, 80% 85%, 90%, 95% identical to the amino acid sequence set forth in SEQ ID NO:22;

aa. a variable region having an amino acid sequence at least 75%, 80% 85%, 90%, 95% identical to the amino acid sequence set forth in SEQ ID NO:23;

bb. a variable region having an amino acid sequence at least 75%, 80% 85%, 90%, 95% identical to the amino acid sequence set forth in SEQ ID NO:24;

cc. a variable region having an amino acid sequence at least 75%, 80% 85%, 90%, 95% identical to the amino acid sequence set forth in SEQ ID NO:25;
dd. a variable region having an amino acid sequence at least 75%, 80% 85%, 90%, 95% identical to the amino acid sequence set forth in SEQ ID NO:26;
ee. a variable region having an amino acid sequence at least 75%, 80% 85%, 90%, 95% identical to the amino acid sequence set forth in SEQ ID NO:27;
ff. a variable region having an amino acid sequence at least 75%, 80% 85%, 90%, 95% identical to the amino acid sequence set forth in SEQ ID NO:28 and/or;
gg. a variable region having an amino acid sequence at least 75%, 80% 85%, 90%, 95% identical to the amino acid sequence set forth in any one of SEQ ID NOs:73 to 114.

In accordance with the present disclosure, the binding agent comprises two antigen binding fragments.

In accordance with the present disclosure, the binding agent comprises two identical antigen binding fragments.

In accordance with the present disclosure, the binding agent comprises two antigen binding domains.

In accordance with the present disclosure, the binding agent comprises two identical antigen binding domains.

In accordance with the present disclosure, the binding agent comprises more than two antigen binding fragments.

In accordance with the present disclosure, the binding agent comprises more than two antigen binding domains.

In accordance with the present disclosure, the binding agent comprises antigen binding fragments of at least two different single domain antibodies.

In some embodiments, the at least two different single domain antibodies have the same specificity.

In other embodiments the at least two different single domain antibodies have different specificities.

In accordance with the present disclosure, the binding agent comprises two antigen binding fragments of same or different single domain antibodies.

In accordance with the present disclosure, the binding agent comprises more than two antigen binding fragments of same and/or different single domain antibodies.

In an exemplary embodiment, the binding agent may comprise a Fc or a portion thereof that is capable of binding to an Fc receptor of monocytes and/or macrophages.

In another exemplary embodiment, the binding agent may comprise a Fc or a portion thereof that is capable of binding to an Fc receptor on CD68+ macrophages.

In accordance with the present disclosure, the binding agent comprises a dimerization domain.

In some embodiments, the dimerization domain allows the formation of homodimers.

In some embodiments, the dimerization domain allows the formation of heterodimers.

In some embodiments, the dimerization domain comprises an amino acid sequence that is contiguous to the amino acid sequence of the antigen binding domain.

In some embodiments, the dimerization domain comprises an immunoglobulin dimerization domain. Other dimerization domains known to a person skilled in the art are contemplated herein including leucine zippers, etc.

In some embodiments, the dimerization domain comprises an IgG, IgM, IgA, IgD or IgE dimerization domain (from human or animal IgGss, IgM, IgAs, IgDs or IgEs).

In some embodiments, the dimerization domain comprises a constant region of an antibody or a portion thereof.

In some embodiments, the constant region or portion thereof is from an IgG1, an IgG2, an IgG3 or an IgG4 heavy chain or combination thereof. For example, the constant region or portion thereof comprises amino acid sequence of an IgG1, an IgG2, an IgG3 or an IgG4 heavy chain or combination thereof.

In some embodiments, the constant region or portion thereof is from a human IgG1 heavy chain.

In some embodiments, the constant region or portion thereof is from a human IgG2 heavy chain.

In some embodiments, the constant region or portion thereof is from a human IgG3 heavy chain.

In some embodiments, the constant region or portion thereof is from a human IgG4 heavy chain.

In some embodiments, the dimerization domain comprises a Fc region of an antibody or a portion thereof.

In some embodiments, the dimerization domain comprises a Fc region or a portion thereof that comprises Fc modification(s) or not.

In other embodiments, the dimerization domain comprises an altered or mutated Fc region or portion thereof. For example, the Fc region or portion thereof may be altered or mutated so as to modify one or more characteristics of the binding agent. In exemplary embodiments, the Fc region or portion thereof is unglycosylated. In other exemplary embodiments, the Fc region or portion thereof comprises one or more of the Fc modification(s) of Table A.

In other exemplary embodiments, the Fc region or portion thereof is altered or mutated so as to increase ADCC activity. For example, afucosylation (e.g., N297 in accordance with the EU numbering system) may result in an increased FcRgII binding on NK cells and may potently increase ADCC. Accordingly, in some embodiments, the Fc region or portion thereof may have a reduced number of fucose residues. In other embodiments, the binding agent comprises an afucosylated Fc region or portion thereof. In yet other embodiments, the Fc region or portion thereof of the binding agent lacks fucose residues. In additional embodiments, the Fc region or portion thereof of the binding agent lacks core fucose residues. In further embodiments, the Fc region or portion thereof of the binding agent fully lacks core fucose residues.

In some embodiments, the dimerization domain comprises a CH3 domain.

In some embodiments, the CH3 domain is a natural CH3 domain or a mutated CH3 domain.

In some embodiments, the dimerization domain also comprises a CH2 domain.

In some embodiments, the dimerization domain comprises a CH3 domain of an antibody. The dimerization domain may also comprise a CH2 domain of an antibody.

In some embodiments, the CH2 domain is a natural CH2 domain or a mutated CH2 domain.

In some embodiments, the dimerization domain comprises a natural CH2 domain and a natural CH3 domain.

In some embodiments, the dimerization domain comprises a natural CH2 domain and a mutated CH3 domain. Exemplary embodiments of mutated CH3 domain are provided in PCT/CA2020/051753 filed on Dec. 18, 2020, and published on Jun. 24, 2021, under No. WO2021/119832A1, the entire content of which is incorporated herein by reference.

In some embodiments, the dimerization domain comprises a mutated CH2 domain and a natural CH3 domain.

In some embodiments, the dimerization domain comprises a mutated CH2 domain and a mutated CH3 domain.

In some embodiments, the binding agent is an antibody or an antigen binding fragment thereof or a variant thereof.

In some embodiments, the antibody or an antigen binding fragment thereof is a single domain antibody or an antigen binding fragment thereof or a variant thereof.

In some embodiments, the binding agent is a competing binding agent.

In some embodiments, the binding agent is a competing antibody or antigen binding fragment thereof.

In some embodiments, the binding agent is a competing single domain antibody or antigen binding fragment thereof.

In some embodiments, the binding agent is an antibody-like molecule.

In some embodiments, the binding agent comprises a protein scaffold.

In some embodiments, the binding agent comprises an immune cell modulating agent.

In some embodiments, the antigen binding fragments of single domain antibodies are in tandem.

In some embodiments, the binding agent is naked.

In some embodiments, the binding agent is conjugated to a therapeutic moiety.

In some embodiments, the binding agent is conjugated to a detectable moiety.

In some embodiments, the binding agent is conjugated to a protein allowing an extended half-life.

In some embodiments, the binding agent is attached to a nanoparticle.

In yet other aspects, the binding agent of the present disclosure possesses anti-tumor activity. In some embodiments, the binding agent of the present disclosure may be functional when naked (unconjugated). In other embodiments, the binding agent of the present disclosure possesses antibody-dependent cellular cytotoxicity (ADCC) activity. In other embodiments, the binding agent of the present disclosure possesses antibody-dependent cellular phagocytosis activity. In yet other embodiments, the binding agent of the present disclosure possess activity as an antibody drug conjugate.

In some embodiments, the anti-TROP2 sdAbs of the present disclosure may have naked anti-tumor activity to a variety of solid tumors.

In some embodiments, the anti-TROP2 sdAbs of the present disclosure may cause tumor regression in in vivo xenograft models of multiple tumor types.

In some embodiments, the anti-TROP2 sdAbs of the present disclosure may cause tumor growth inhibition in in vivo xenograft models of multiple tumor types.

In some embodiments, the anti-TROP2 sdAbs of the present disclosure may cause in vivo tumor regression of late-stage tumors (large tumors).

In some embodiments, the anti-TROP2 sdAbs of the present disclosure may cause in vivo tumor regression of tumors.

In some embodiments, the anti-TROP2 sdAbs of the present disclosure may cause tumor regression at very low dose levels.

In some embodiments, the binding agent may have anti-tumor effect at a dose of approximately between 0.01 to 150 mg/kg, 0.01 to 100 mg/kg, 0.01 to 50 mg/kg, 0.05 to 150 mg/kg 0.05 to 100 mg/kg, 0.05 to 50 mg/kg, 0.05 to 30 mg/kg, 0.05 to 10 mg/kg, 0.1 to 50 mg/kg, 0.1 to 30 mg/kg, 0.1 to 10 m/kg, or 1.0 to 10 mg/kg.

In some embodiments, the anti-TROP2 sdAbs of the present disclosure may cause tumor regression at a dose of 0.1 mg/kg once per week.

In some embodiments, the anti-TROP2 sdAbs of the present disclosure may cause tumor regression with low frequency dosing.

In some embodiments, the anti-TROP2 sdAbs of the present disclosure may cause tumor regression with dosing once every three weeks.

In some embodiments, the anti-TROP2 sdAbs of the present disclosure may directly impact viability of tumor cells in vitro.

In some embodiments, the anti-TROP2 sdAbs of the present disclosure may elicit effector function in vitro.

In some embodiments, the anti-TROP2 sdAbs of the present disclosure may mediate their in vivo anti-tumor efficacy by an effector function-driven mechanism of action.

In some embodiments, the anti-TROP2 sdAbs of the present disclosure may mediate their in vivo anti-tumor efficacy by direct anti-tumor activity.

In some embodiments, the antigen binding fragment is partially or fully humanized.

In some embodiments, the antigen binding fragment comprises one or more human frameworks.

In some embodiments, the antigen binding domain is partially or fully humanized.

In some embodiments, the antigen binding domain comprises one or more human frameworks.

In other embodiments, the antigen binding domain comprises one or more humanized frameworks. In further embodiments, the antigen binding domain comprises one or more partially humanized frameworks.

In some embodiments, the level of humanization of a single domain antibody may be calculated based on the sequence identity to the closest human VH germline gene. Accordingly, the percentage of humanization score is based on framework regions 1-3 (FR1, FR2, FR3) and CDR1 and CDR2. In accordance with an embodiment, the sequence of CDR3 and FR4 are not accounted for assessing the level of humanization of a single domain disclosed herein.

In exemplary embodiments, the level of humanization of the antigen binding domain is at least 80%.

In other exemplary embodiments, the level of humanization of the variable region of the single domain antibody of the present disclosure is at least 80%.

Other aspects and embodiments of the present disclosure relate to a composition comprising the binding agent disclosed herein. In some embodiments, the composition of the present disclosure is composed of binding agent that have the same sequence.

Other aspects and embodiments of the present disclosure relate to a pharmaceutical composition comprising the binding agent disclosed herein and a pharmaceutically acceptable carrier. In some embodiments, the pharmaceutical composition of the present disclosure is composed of binding agent that have the same sequence.

Yet other aspects and embodiments of the present disclosure relate to a pharmaceutical composition comprising a conjugated binding agent as disclosed herein and a pharmaceutically acceptable carrier.

Yet other aspects and embodiments of the present disclosure relate to a nucleic acid or set of nucleic acids encoding the binding agent disclosed herein.

Additional aspects and embodiments of the present disclosure relate to a vector comprising a nucleic disclosed herein or a set of vectors each comprising a nucleic acid disclosed herein Further aspects and embodiments of the present disclosure relate to a cell expressing the binding agent disclosed herein.

In some embodiments, the cells are engineered to express a binding agent such as for example, an antibody or an antigen binding fragment thereof or an antibody-like molecule. Accordingly, the present disclosure encompasses isolated cells that express an antibody or an antigen binding fragment thereof or an antibody-like molecule.

In other embodiments, the cells are engineered to express a binding agent such as for example, a chimeric antigen receptor (CAR) construct. Accordingly, the present disclosure encompasses T-cells or NK cells that express a chimeric antigen receptor (CAR) construct.

Additional aspects and embodiments of the present disclosure relate to a cell comprising the nucleic acid or the vector disclosed herein.

Further aspects and embodiments of the present disclosure relate to a kit comprising the binding agent disclosed herein.

In some embodiments, the kit may comprise a binding agent that binds to TROP2 and a binding agent that binds to a macrophage marker. For example, the kit may comprise an antibody or an antigen binding fragment thereof that specifically binds to TROP2. In some instances, the kit may comprise a binding agent as described herein. The kit may also comprise an antibody that binds to a macrophage marker, such as for example and without limitations an antibody or antigen binding fragment thereof that binds to CD68 (human CD68).

Yet further aspects and embodiments of the present disclosure relate to a kit comprising the nucleic acid disclosed herein.

Yet further aspects and embodiments of the present disclosure relate to a kit comprising the vector disclosed herein.

Yet further aspects and embodiments of the present disclosure relate to a kit comprising the cells disclosed herein.

In an additional aspect and embodiments, the present disclosure relates to a method of treating a disorder or disease comprising administering the binding agent disclosed herein.

In further aspects and embodiments, the present disclosure relates to a method of treating a disorder or disease comprising administering the composition disclosed herein.

In further aspects and embodiments, the present disclosure relates to a method of treating a disorder or disease comprising administering the pharmaceutical composition disclosed herein.

In some embodiments, the TROP2 binding agent, composition or pharmaceutical composition disclosed herein is administered to a subject having cancer selected from epithetial cancer, lung cancer (such as small cell lung cancer, non small cell lung cancer), myeloma, prostate cancer, breast cancer (such as triple negative breast cancer), rectal cancer, pancreatic cancer, glioblastoma, cervical cancer, colorectal cancer, gastric cancer, ovarian cancer, thyroid cancer, stomach cancer, cancer of the urinary bladder, cancer of the uterus, esophageal cancer, head and neck cancer, blood cancer.

In other embodiments, the TROP2 binding agent, composition or pharmaceutical compositions disclosed herein is administered to a subject having a metastatic cancer.

In accordance with the present disclosure, the binding agent, composition or pharmaceutical composition may be administered to a subject having a tumor expressing TROP2.

Other aspects of the disclosure relate to a method of treating cancer, which comprises administering a drug that targets human TROP2 to a subject having a tumor expressing TROP2 and expressing one or more macrophage markers.

In some instances, the drug may be a binding agent as described herein. In other instances, the binding agent may be Sacituzumab Govitecan, hTINA-1, h7E6, and AR47A6.4.2. In other aspects, the binding agent may be a small molecule.

In some embodiments, the macrophage marker is a pan macrophage marker such as, for example and without limitations, CD68.

Therefore, in accordance with the present disclosure, the binding agent, composition or pharmaceutical composition may be administered to a subject having a tumor expressing TROP2 and a macrophage marker such as CD68.

In some instances, the eligibility of a subject to a treatment targeting TROP2 may be determined. For example, the tumor of the subject may be tested for expression of TROP2 and/or for expression of a macrophage marker prior to the administration of the binding agent, composition or pharmaceutical composition described herein.

In other instances, the efficacy of the treatment may be assessed. For example, the tumor of the subject may be tested for expression of TROP2 and for expression of a macrophage marker during and/or after treatment with the binding agent, composition or pharmaceutical composition described herein.

In other aspects and embodiments, the present disclosure relates to a method of making the binding agent disclosed herein by transforming cells with one or more vectors comprising the nucleic acid disclosed herein.

In some embodiments, the method may further comprise isolating and/or purifying the binding agent from impurities.

In some embodiments, the method further comprises conjugating the binding agent with a therapeutic moiety, detectable moiety, or a protein allowing an extended half-life or to nanoparticles.

The present disclosure also relates to the use of the binding agent disclosed herein for detecting TROP2 in tumor cells or tumor tissue.

In exemplary embodiments, the binding agent may have the CDR amino acid sequence of SEQ ID NO:152.

In another exemplary embodiments, the binding agent may have the CDR amino acid sequence of SEQ ID NO:153.

In another exemplary embodiments, the binding agent may have the CDR amino acid sequence of SEQ ID NO: 154.

In exemplary embodiments, the binding agent may have an amino acid sequence having at least 80% sequence identity with the variable region of any one of SEQ ID NO:152, SEQ ID NO:153 or SEQ ID NO:154.

In exemplary embodiments, the binding agent may have one or more CDRs of any one of SEQ ID NO:152, SEQ ID NO:153 or SEQ ID NO:154.

In exemplary embodiments, the binding agent may have the CDR1, CDR2 and CDR3 amino acid sequence of any one of SEQ ID NO:152, SEQ ID NO:153 or SEQ ID NO:154.

In exemplary embodiments, the binding agent may have an amino acid sequence identical to the variable region of any one of SEQ ID NO:152, SEQ ID NO: 153 or SEQ ID NO:154.

In yet other exemplary embodiments, the binding agent may have an amino acid sequence identical to any one of SEQ ID NO:152, SEQ ID NO:153 or SEQ ID NO:154.

The present disclosure also relates to method for identifying a binding agent capable of binding to human TROP2 and having anti-tumor activity as described herein.

Further scope, applicability and advantages of the present disclosure will become apparent from the non-restrictive detailed description given hereinafter. It should be understood, however, that this detailed description, while indicating exemplary embodiments of the disclosure, is given by way of example only, with reference to the accompanying drawings.

BRIEF DESCRIPTION OF THE DRAWINGS

FIG. 2A: graph of in vivo dose/response study of weekly treatment of KD001, KD002, KD003, KD004 or KD005 anti-TROP2 sdAbs at doses of 0.5 mg/kg, 2 mg/kg, 8 mg/kg and 30 mg/kg i.p. in MDA-MB-453 implanted NCG mice tumor model. Negative control is PBS.

FIG. 2B: graph of in vivo weekly treatment of large tumor with KD004 at 8 mg/kg, once weekly (QW) i.p. in MDA-MB-453 implanted NCG mice tumor model. Negative control is PBS. Treatment was discontinued at around day 70, and replaced with PBS, and the negative control treated mice were treated with KD004 at 8 mg/kg QW.

FIG. 2C: graph showing the anti-tumor effect of various treatment regimen with KD004 at a dose of 8 mg/kg with the indicated frequencies i.p. in MDA-MB-453 implanted NCG mice tumor model. Negative control is PBS.

FIG. 2D: graph showing the anti-tumor effect of various treatment regimen with KD002 or KD005 at a dose of 0.1 mg/kg i.p. in MDA-MB-453 implanted NCG mice tumor model. Negative control is PBS.

FIG. 2E: Anti-TROP2 in vivo pharmacokinetic parameters.

FIG. 8A-FIG. 8E: graph illustrating competition assays performed with either His tag conjugated KD001 FIG. 8A), KD002 (FIG. 8B), KD003 (FIG. 8C), KD004 (FIG. 8D) or KD005 (FIG. 8E) and each of KD001, KD002, KD003, KD004 or KD005 anti-TROP2 sdAbs for binding to human recombinant TROP2.

FIG. 9A: graph illustrating competition assays between His tag conjugated KD004 and hRS7 or AR47A6.4.2 antibodies for the binding of human recombinant TROP2.

FIG. 9B: graph illustrating competition assays between His tagged KD006 and KD007 anti-TROP2 sdAbs for the binding of human recombinant TROP2.

FIG. 10A: schematic showing the various constructs used to map the binding domain of KD001, KD002, KD003, KD004 or KD005 anti-TROP2 sdAbs.

FIG. 10B: picture of immunoblots performed with KD001, KD002, KD003, KD004 or KD005 anti-TROP2 sdAbs or with AR47A6.4.2 and hRS7 on human TROP2 extracellular domain (ECD) and human TROP2 cysteine poor domain (CPD). Negative control includes sdAb that binds HEWL (NC).

FIG. 11A-E: pictures of immunoblots performed with KD001, KD002, KD003, KD004 or KD005 anti-TROP2 sdAbs on different forms of recombinant human TROP2 (non-denaturated, linear, reduced, deglycosylated using PNGase F).

FIG. 12A-12D: graph showing binding of KD001, KD002, KD003, KD004 or KD005 anti-TROP2 sdAbs on recombinant cynomolgus/Rhesus TROP2 protein (FIG. 12A), on recombinant human TROP2 protein (FIG. 12B), on mouse TROP2 protein (FIG. 12C) or on rat TROP2 protein (FIG. 12D). Negative control includes sdAb that binds HEWL. Positive control includes anti-TROP2 polyclonal antibody.

FIG. 12E: table illustrating affinity of KD001, KD002, KD003, KD004 or KD005 anti-TROP2 sdAbs to human TROP2 and to cynomolgus TROP2 by SPR.

FIG. 12F: table illustrating affinity of KD001, KD002, KD003, KD004 or KD005 anti-TROP2 sdAbs to human TROP2 with ka, kd and KD indicated.

FIG. 13A-13B: histogram showing the binding of the indicated TROP2 antibodies at 100 nM to HEK cells transfected with TROP2 constructs with various cysteine-rich domain truncations as indicated.

FIG. 14B: graph showing CD47 and TROP2 expression level on MDA-MB-453, MDA-MB-231, and NCI-H292 cells measured by staining with anti-CD47 (Biolegend, cat #323124) and anti-TROP2 (Biolegend, cat #363804) antibodies at 1/100 dilutions. Data are shown as fold change of CD47 and TROP2 level relative to the isotype control staining.

FIG. 14C-E: graphs showing the dose-response ADCP activity of KD002 and KD004 TROP2 antibodies against the MDA-MB-453 (FIG. 14C), MDA-MB-231 (FIG. 14D), and NCI-H292 (FIG. 14E) cells. The ADCP assays were performed with the Promega ADCP assay kits (Promega, cat #CS314906). Testing antibodies were serial diluted from 1.88 nM with 1/2.2 dilution. TROP2 antibodies KD002 and KD004 showed a high level of ADCP activity against MDA-MB-453 cells, whereas relatively low ADCP activity on MDA-MB-231 and NCI-H292 cells.

FIG. 15A: graph illustrating the CD47 expression level on MDA-MB-231 and NCI-H292 cells after CD47 knockdown with siRNA. The CD47 siRNA and control siRNA were used in the knockdown assay (Thermofisher CD47 silencer select pre-designed siRNA (Cat #4392421) and silencer negative control siRNA (Cat #AM4635).

FIG. 15B-C: graphs showing the dose-response ADCP activity of KD002 and KD005 TROP2 antibodies against the MDA-MB-231 (FIG. 15B), and NCI-H292 cells (FIG. 15C) upon CD47 knockdown. Testing antibodies were serial diluted from 2.1 nM with 1/2.5 dilution.

FIG. 18B: graph showing the anti-tumor effect of KD002 and KD005 in the MDA-MB-453 (upper panel), MDA-MB-468 (middle panel), and T.T.n (lower panel) xenograft tumor models. Testing antibodies were administered with 8 mg/kg i.p., once per week.

CDRs and framework 2 are indicated with arrows.

Figures 20A, 20B:
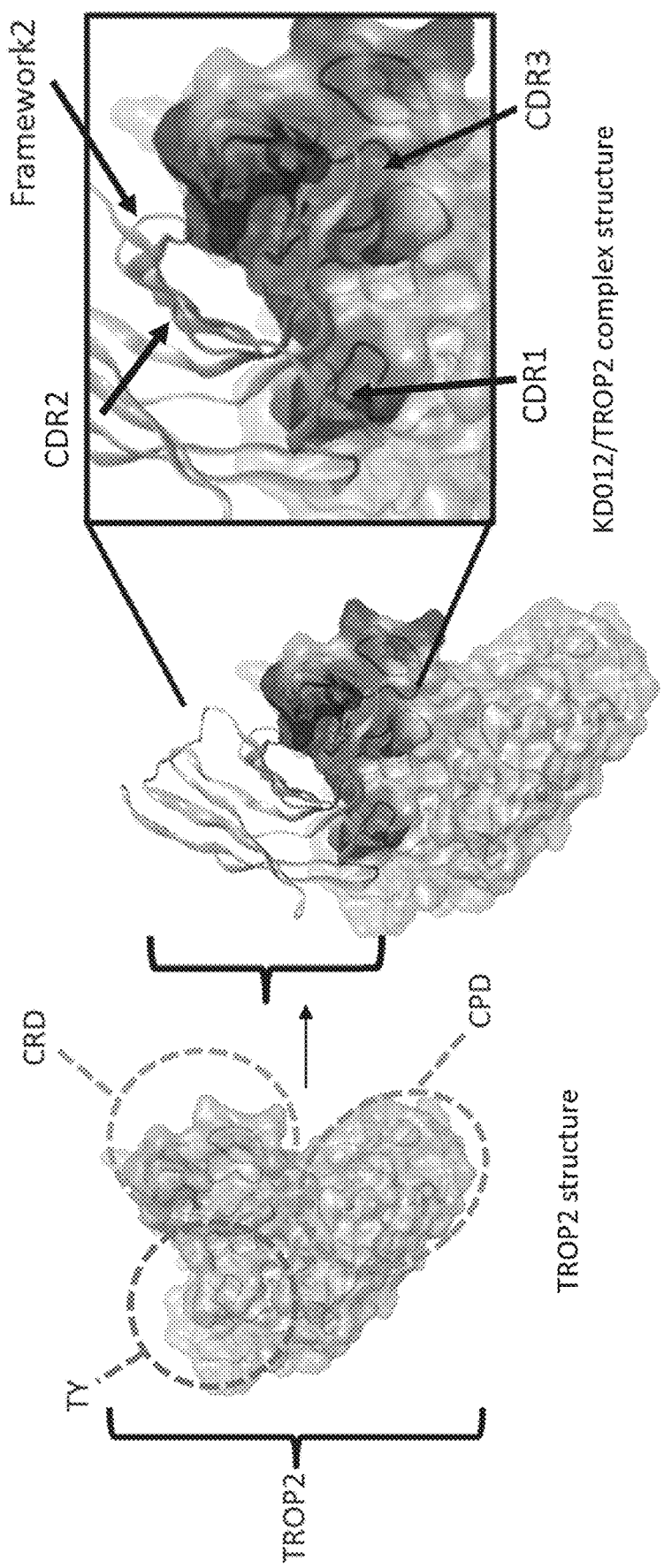
FIG. 20A: X-ray crystal structure of the extracellular domain of TROP2 protein with translucent surface rendering. The relative position of the Cystein-Rich Domain (CRD), Thyroglobulin Domain (TY-1), and Cystein-Poor Domain (CPD) are indicated.
FIG. 20B: X-ray cocrystal of KD012 with human TROP2 (surface rendering shown). The contact region on TROP2 is shown on the surface of TROP2 in dark grey. The contacts between KD012 and TROP2 occur mainly in the CRD of TROP2 and CDR3 and framework 2 of KD012.
Figure 20C:
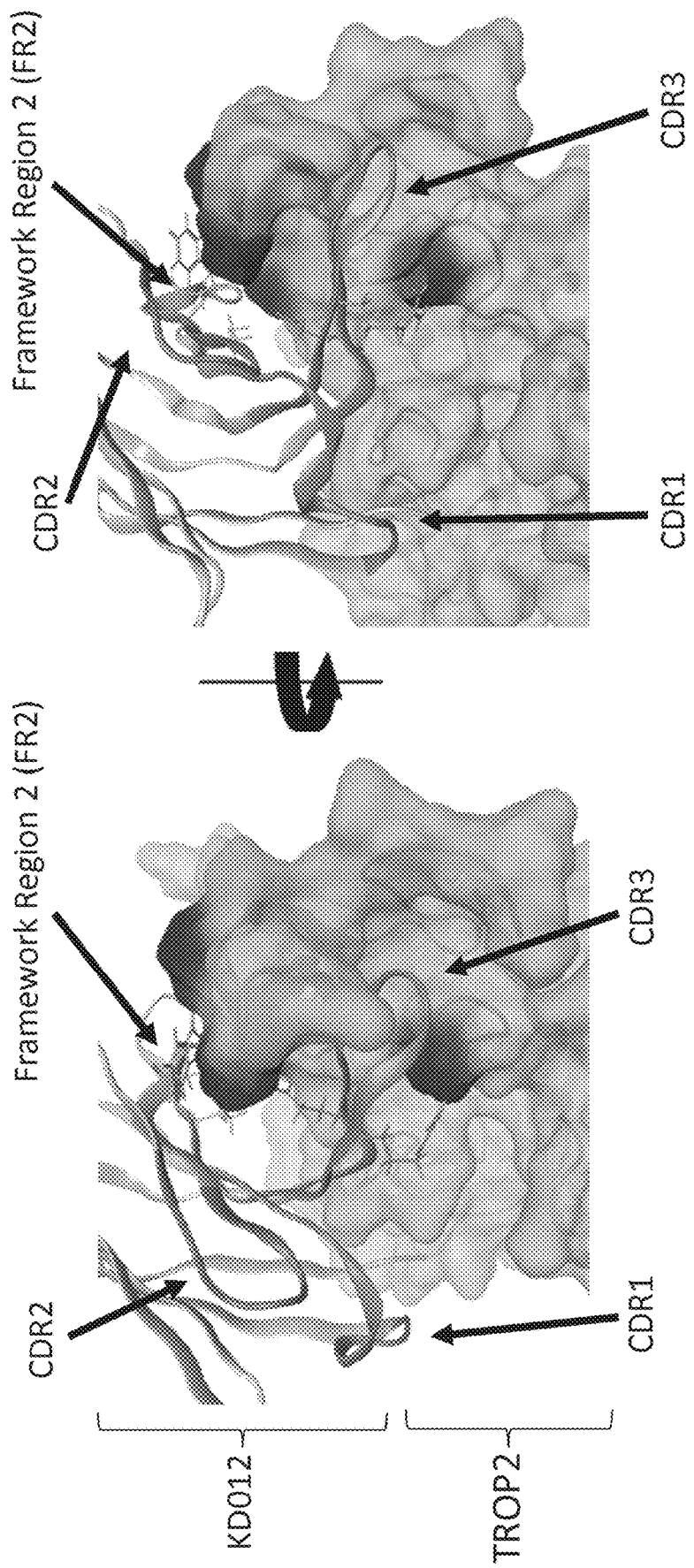

FIG. 20C: X-ray cocrystal structure of KD012 with human TROP2. KD102 is depicted as a ribbon diagram. Selected residues on KD012 are shown, with the interacting residues on TROP2 shown in dark grey.

Figure 20D:
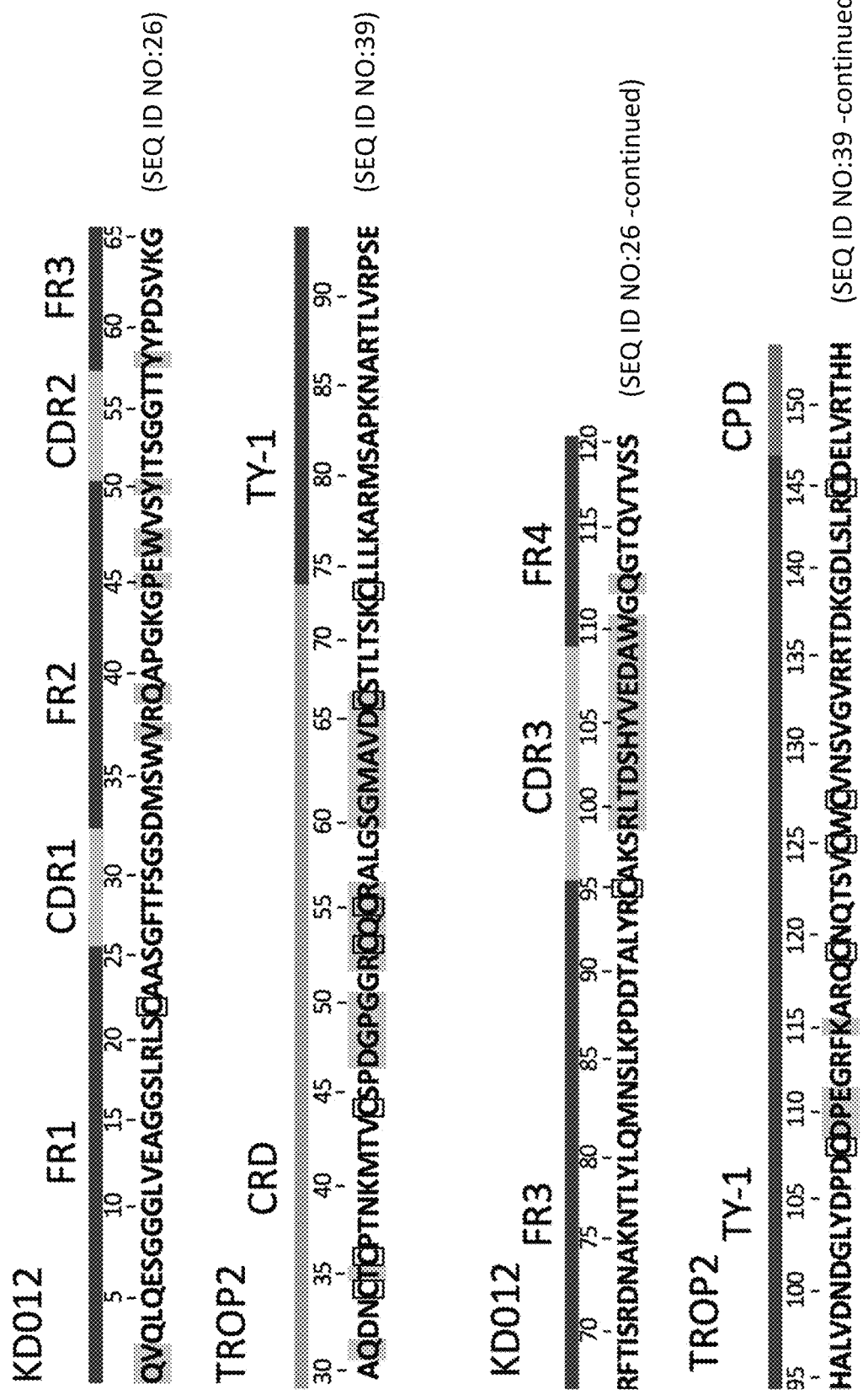

FIG. 20D: shows amino acid residues involved in the interaction between KD012 (SEQ ID NO:26) and human TROP2 (SEQ ID NO:39) (within 4.5 Å; CDRs annotated in accordance with IMGT numbering); the sequence of amino acid residues 1-29 and 154-323 of human TROP2 is not shown.

Figures 21A, 21B:
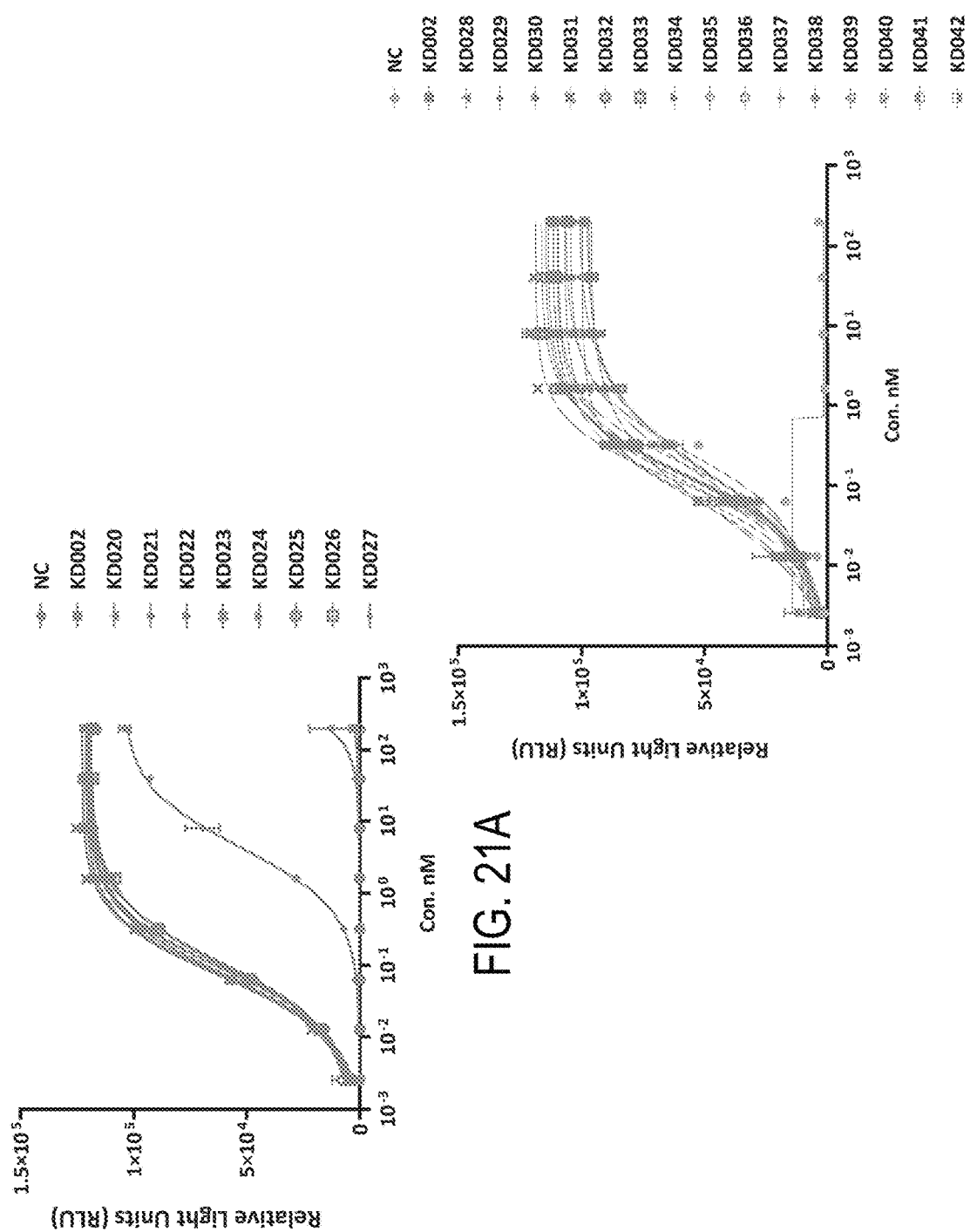

FIG. 21A-21B: represents dose-response ELISA binding of KD002 and humanized variants on human TROP2 recombinant protein. TROP2 antibodies were serially diluted from 200 nM to 0.00256 nM with ⅕ dilutions.

Figure 22A:
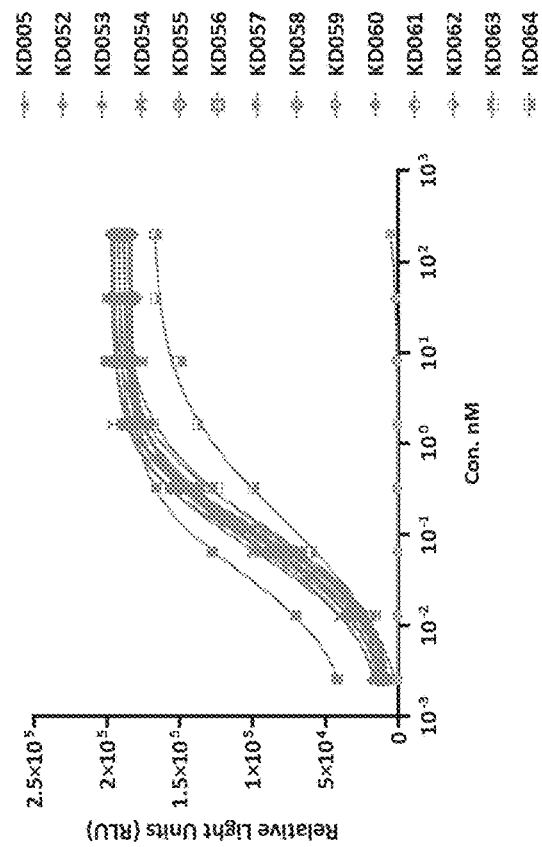
Figure 22B:
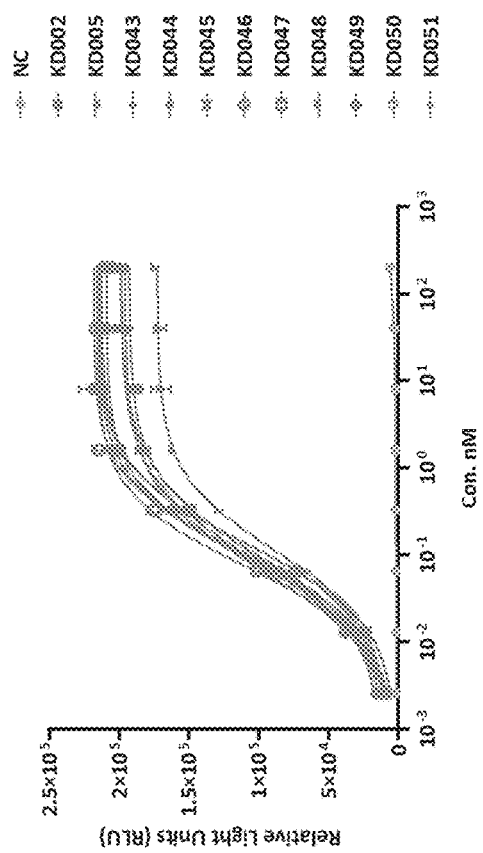

FIG. 22A-22B: represents dose-response ELISA binding of KD005 and humanized variants on human TROP2 recombinant protein. TROP2 antibodies were serially diluted from 200 nM to 0.00256 nM with ⅕ dilutions.

FIG. 23A-23B: bar graphs illustrating the relative light units of KD002 humanized variants compared to KD002 at 0.5 nM (FIG. 23A) or 0.1 nM (FIG. 23B) as measured with the Promega ADCP reporter assays.

Figures 24C, 24D, 24E:
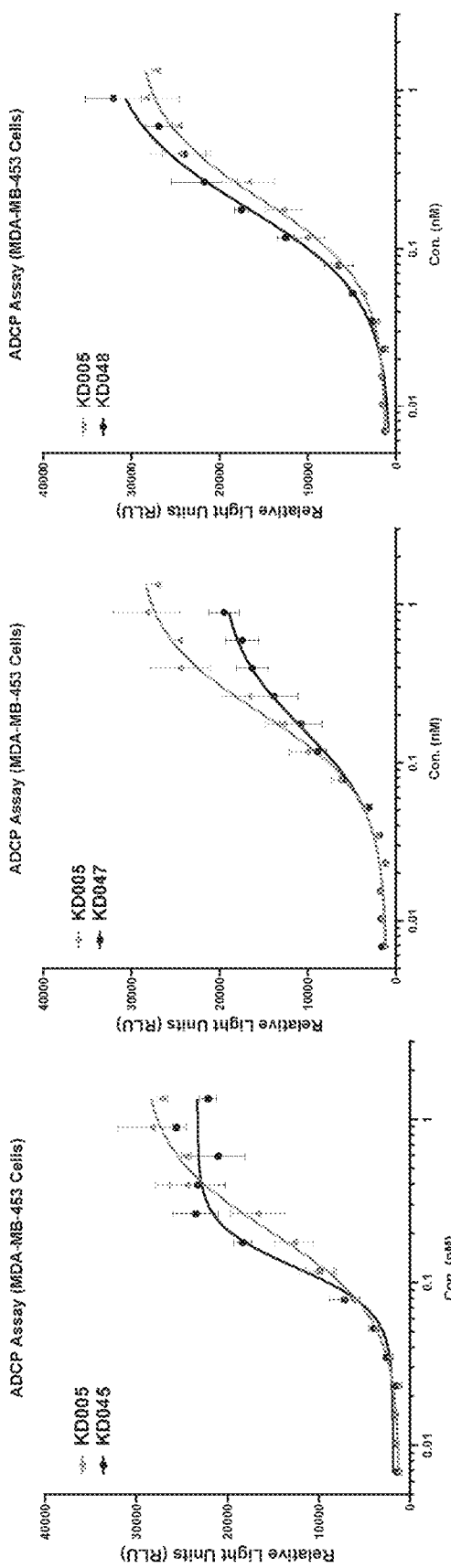

FIG. 24A-24B: bar graphs showing the relative light units of KD005 and KD005 humanized variants at 0.5 nM (24A) and 0.1 nM (FIG. 24B) as measured with the Promega ADCP reporter assays.

FIG. 24C-24I: dose-response ADCP assays carried out in MDA-MB-453 cells with KD045 (FIG. 24C), KD047 (FIG. 24D), KD048 (FIG. 24E), KD049 (24F), KD053 (24G), KD059 (24H) and KD063 (24I).

Figure 25A:
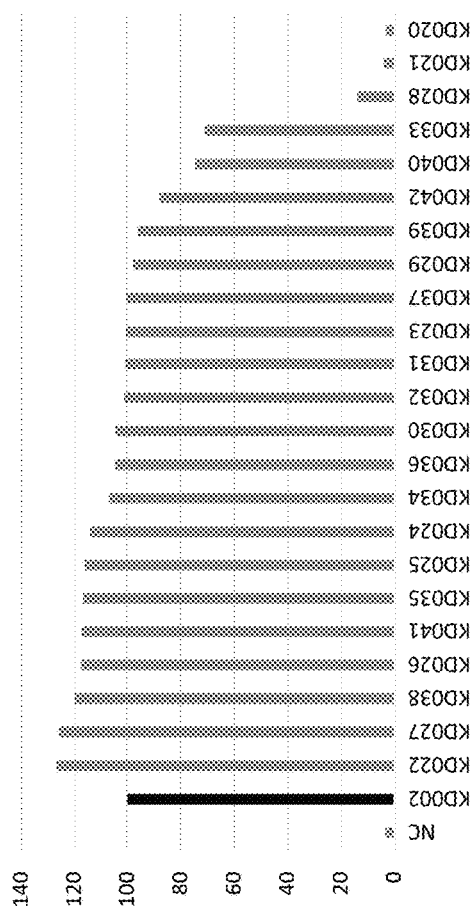
Figure 25B:
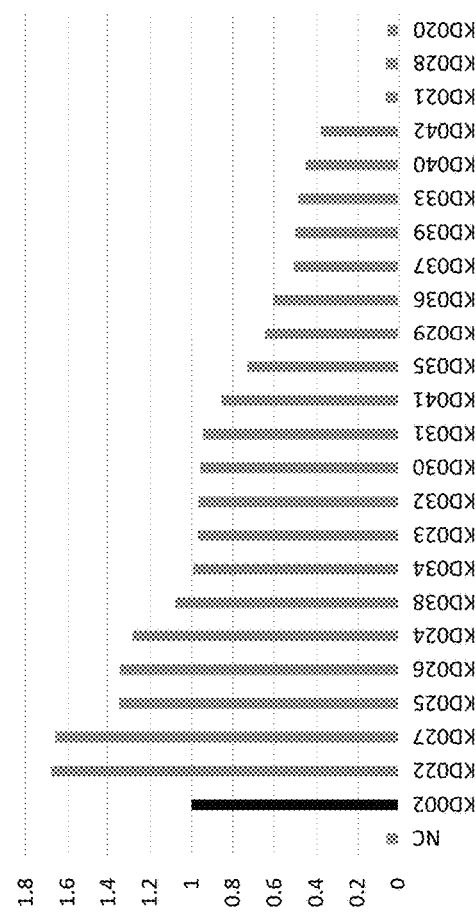

FIG. 25-25B: bar graphs showing the relative light units of KD002 humanized variants compared to KD002 at 0.5 nM (FIG. 25A) or 0.1 nM (FIG. 25B) as measured with the Promega ADCC reporter assays.

FIG. 26A-26B: bar graphs showing the relative light units of KD005 and KD005 humanized variants at 0.5 nM (FIG. 26A) and 0.1 nM (FIG. 26B) as measured with the Promega ADCC reporter assays.

FIG. 27: Alignment between KD001, KD002, KD003, KD004 and KD005 variable regions.

Figure 28:
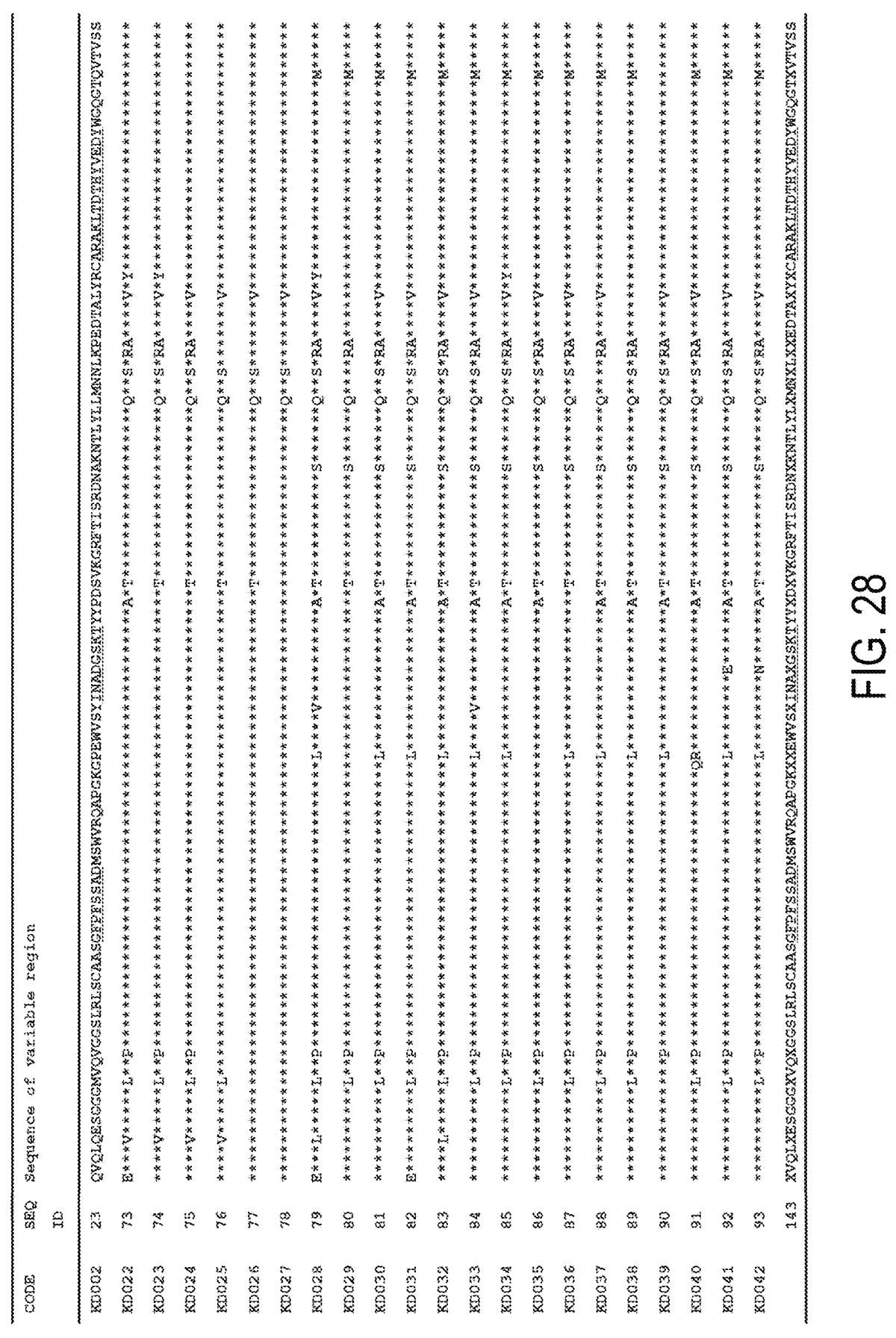

FIG. 28: Alignment and consensus sequences of KD002 variants.

FIG. 29: Alignment of KD002 variants selected for their ADCC and ADCP activity.

FIG. 30: Alignment and consensus sequences of KD005 variants.

FIG. 31: Alignment of KD005 variants selected for their binding activity.

FIG. 32: Alignment of KD005 variants selected for their ADCP activity.

Figures 33, 34:
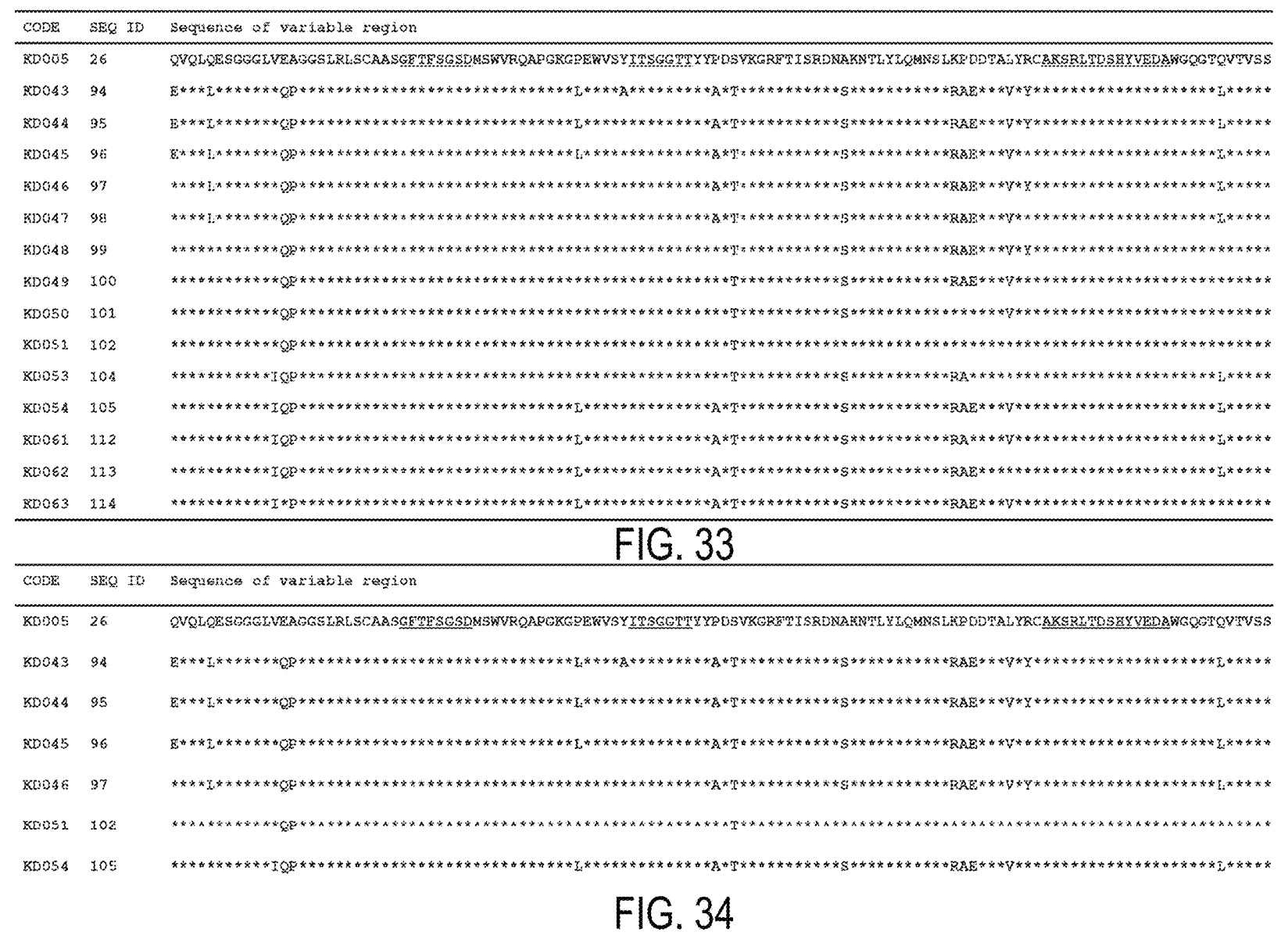

FIG. 33: Alignment of KD005 variants selected for their ADCC activity.

FIG. 34: Alignment of KD005 variants selected based on all characteristics.

DETAILED DESCRIPTION

Definitions

The use of the terms "a" and "an" and "the" and similar referents in the context of describing embodiments (especially in the context of the claims) are to be construed to cover both the singular and the plural, unless otherwise indicated herein or clearly contradicted by context.

Unless specifically stated or obvious from context, as used herein the term "or" is understood to be inclusive and covers both "or" and "and".

The term "and/or" where used herein is to be taken as specific disclosure of each of the specified features or components with or without the other.

The terms "comprising", "having", "including", and "containing" are to be construed as open-ended terms (i.e., meaning "including, but not limited to") unless otherwise noted. The term "consisting of" is to be construed as close-ended.

As used herein the term "TROP2" refers to a TROP2 protein or to a polypeptide comprising the TROP2 amino acid sequence. The term "TROP2" encompasses the human TROP2 protein and any protein having at least 80% identity with the human TROP2 protein.

The term "anti-TROP2 antibody" refers to an antibody of any format that binds to the TROP2 protein such as a TROP2 antigen or to a portion thereof and includes without limitations "anti-TROP2 single domain antibody".

The term "binding agent" refers to a molecule that comprises a polypeptidic portion (such as polypeptide chain(s)) and that is capable of specifically binding an antigen or that comprises a domain such as an antigen binding domain that is capable of specifically binding an antigen.

The term "antibody" is used in the broadest sense and encompasses various antibody formats and structures, including any immunoglobulin, monoclonal antibody, polyclonal antibody, bivalent antibody, monovalent antibody, bispecific antibody, multiple specific (multi-specific) antibody, conventional antibody, single domain antibody, single chain antibody, heavy chain only antibody, nanobody, full-length antibody, humanized antibody, chimeric antibody that binds to a specific antigen, and any antigen binding fragment that exhibits the desired antigen binding activity. An antibody can be naturally occurring (native) or the results or recombination technologies.

As used herein the expressions "single domain antibody" and "heavy chain only antibody" are used interchangeably. The term "single domain antibody" includes naturally occurring single domain antibody or heavy chain only antibody as well as single domain antibody in which the naturally occurring constant region is replaced by another dimerization domain such as for example a constant region of a human immunoglobulin (e.g., IgG) as well as variants such as humanized or chimeric single domain antibodies.

A "naturally occurring single domain antibody" includes antibodies produced by camelids (camelid antibodies) or by shark. "Naturally occurring single domain antibody(ies)" also encompass antibody(ies) that are produced by transgenic animals modified to express heavy chain only antibodies. Exemplary embodiments of transgenic animals are provided in international application No. PCT/CA2021/050951 filed on Jul. 21, 2021, and published on Jan. 20, 2022, under No. WO2022/011457, the entire content of which is incorporated herein by reference.

It is to be understood herein that any of the terms "KD001", "KD002", "KD003", "KD004", "KD005", "KD006", KD007", "KD008", "KD009", "KD010", "KD011", "KD012", "KD013", "KD014", "KD015", "KD016", "KD017", "KD018", "KD019", "KD020", "KD021", "KD022", "KD023", "KD024", "KD025", "KD026", "KD027", "KD028", "KD029", "KD030", "KD031", "KD032", "KD033", "KD034", "KD035", "KD036", "KD037", "KD038", "KD039", "KD040", "KD041", "KD042", "KD043", "KD044", "KD045", "KD046", "KD047", "KD048", "KD049", "KD050", "KD051", "KD052", "KD053", "KD054", "KD055", "KD056", "KD057", "KD058", "KD059", "KD060", "KD061", "KD062", "KD063", "KD064", "KD067", "KD068" or "KD069" refer to a single domain antibody that comprises two heavy chains, each having the corresponding heavy chain amino acid sequence set forth in Table 15, 16, 18 or 19 or, each having the corresponding variable region amino acid sequence set forth in Table 15, 16, 18 or 19.

As such, in some embodiments any one of KD001, KD002, KD003, KD004, KD005, KD006, KD007, KD008, KD009, KD010, KD011, KD012, KD013, KD014, KD015, KD016, KD017, KD018, KD019, KD020, KD021, KD022, KD023, KD024, KD025, KD026, KD027, KD028, KD029, KD030, KD031, KD032, KD033, KD034, KD035, KD036, KD037, KD038, KD039, KD040, KD041, KD042, KD043, KD044, KD045, KD046, KD047, KD048, KD049, KD050, KD051, KD052, KD053, KD054, KD055, KD056, KD057, KD058, KD059, KD060, KD061, KD062, KD063, KD064, KD067, KD068 or KD069 may have the corresponding variable region amino acid sequence set forth in Table 15, 16, 18 or 19 and a constant region that differs from that of the heavy chain amino acid sequence set forth in Table 15, 16, 18 or 19.

In other embodiments, any one of KD001, KD002, KD003, KD004, KD005, KD006, KD007, KD008, KD009, KD010, KD011, KD012, KD013, KD014, KD015, KD016, KD017, KD018, KD019, KD020, KD021, KD022, KD023, KD024, KD025, KD026, KD027, KD028, KD029, KD030, KD031, KD032, KD033, KD034, KD035, KD036, KD037, KD038, KD039, KD040, KD041, KD042, KD043, KD044, KD045, KD046, KD047, KD048, KD049, KD050, KD051, KD052, KD053, KD054, KD055, KD056, KD057, KD058, KD059, KD060, KD061, KD062, KD063, KD064, KD067, KD068 or KD069 may have the corresponding variable region amino acid sequence set forth in Table 15, 16, 18 or 19 and a constant region allowing formation of homodimers as described herein.

In yet other embodiments, any one of KD001, KD002, KD003, KD004, KD005, KD006, KD007, KD008, KD009, KD010, KD011, KD012, KD013, KD014, KD015, KD016, KD017, KD018, KD019, KD020, KD021, KD022, KD023, KD024, KD025, KD026, KD027, KD028, KD029, KD030, KD031, KD032, KD033, KD034, KD035, KD036, KD037, KD038, KD039, KD040, KD041, KD042, KD043, KD044, KD045, KD046, KD047, KD048, KD049, KD050, KD051, KD052, KD053, KD054, KD055, KD056, KD057, KD058, KD059, KD060, KD061, KD062, KD063, KD064, KD067, KD068 or KD069 may have the corresponding variable region amino acid sequence set forth in Table 15, 16, 18 or 19 and a constant region that binds to a macrophage Fc receptor.

The terms "KD065" or "KD066" refer to a binding agent that comprises two chains, each having the corresponding amino acid sequence of the polypeptide chain set forth SEQ ID NO:150 or SEQ ID NO:151 respectively or each having the corresponding variable region amino acid sequence of the polypeptide chain.

In some embodiments, any one of KD065 or KD066 may have the corresponding variable region amino acid sequence of KD065 or KD66 and a different hinge and/or dimerization domain (e.g., CH2 and/or CH3) than KD065 or KD66.

The term "subject in need" as used herein refer to a subject having, suspected of having a disorder or disease associated with TROP2, TROP2 expression (e.g., expression in tissue, cells or serum) or TROP2 overexpression. The term "subject in need" also refers to a subject having, suspected of having a disorder or disease that may benefit from treatment with a binding agent targeting TROP2. A "subject in need" include a subject having cancer or suspected of having cancer.

The term "treatment" for purposes of this disclosure refers to both therapeutic treatment and prophylactic or tumor prevention measures. Subject in need of treatment include those already with the disorder as well as those prone to have the disorder or those in whom the disorder is to be prevented. Subject in need of treatment thus include subjects that already have cancer as well as those prone to have cancer or those in whom cancer is to be managed.

The term "natural" as used in the context of a sequence refers to a sequence that occurs in nature.

The term "about" or "approximately" with respect to a given value means that variation in the value is contemplated. In some embodiments, the term "about" or "approximately" shall generally mean a range within +/−10 percent, within +/−5 percent, within +/−4 percent, within +/−3 percent, within +/−2 percent or within +/−1 percent of a given value or range.

It is to be understood herein, that expressions referring to ranges of values in the format such as "from A to B", include each individual value and any sub-range comprised and including such ranges. For example, the expression "from 1 to 10" includes sub-ranges such as and without limitations, "from 2 to 10", "from 2 to 9", "from 3 to 6", "from 5 to 7" and any individual values comprised between and including 1 and 10, i.e., 1, 2, 3, 4, 5, 6, 7, 8, 9 or 10.

It is to be understood herein that the term "at least" with respect to a given value intends to include the value and superior values. For example, the term "at least 80%" includes "at least 80%", "at least 81%", "at least 82%", "at least 83%", "at least 84%", "at least 85%", "at least 86%", "at least 87%", "at least 88%", "at least 89%", "at least 90%", "at least 91%", "at least 92%", "at least 93%", "at least 94%", "at least 95%", "at least 96%", "at least 97%", "at least 98%", "at least 99%", "at least 99.1%", "at least 99.2%", at least 99.3%" at least 99.4%" at least 99.5%", at least 99.6%", at least 99.7%" at least 99.8%", at least 99.9%" and 100%.

As used herein, the term "humanized" means that the binding agent such as an antibody or antigen binding fragment comprises CDRs or CDR amino acid residues derived from non-human animal antibodies, FR regions derived from human antibodies, and when applicable, the constant regions derived from human antibodies.

As used herein the expression "fully humanized framework region" means that the amino acid sequence of all framework regions of a given binding agent such as an antibody or antigen binding fragment is identical to that of a human antibody variable region e.g., a human germline antibody variable region sequence).

As used herein the expression "partially humanized" means that the amino acid sequence of one or more or all framework regions of the binding agent such as an antibody or antigen binding fragment is not totally identical to that of a human antibody variable region such as a germline human antibody variable region (e.g., a human germline antibody variable region sequence).

In some instances, a humanized, fully humanized or partially humanized binding agent such as an antibody or antigen binding fragment may comprises CDRs or CDR amino acid residues of a human antibody variable region (e.g., a human germline antibody variable region sequence).

A "partially humanized framework region" thus encompasses, for example and without limitations, a human framework region that contains back-mutations reintroducing an original amino acid at its original location. A "partially humanized framework region" also encompasses, for example and without limitations, a human framework region in which one or more amino acid residue has been replaced, added or deleted.

As used herein, the term "affinity" refers to the strength of non-covalent interaction between a binding agent or antigen binding domain(s) thereof and an antigen. "Affinity" is represented, for example, by KD value, i.e., the ratio of dissociation rate to association rate ($k_{off}/k_{on}$) when the binding between the antigen and the binding agent (e.g., antibody such as single domain antibody) reaches equilibrium. The affinity may be determined by using any conventional method known in the art, including but are not limited to, surface plasmon resonance method, microscale thermophoresis method, HPLC-MS method and flow cytometry (such as FACS) method. An antibody generally has a KD value of $\leq 10^{-6}$ M (e.g., $\leq 5\times 10^{-7}$ M, $\leq 2\times 10^{-7}$ M, $\leq 10^{-7}$M, $\leq 5\times 10^{-8}$M, $\leq 2\times 10^{-8}$M, $\leq 10^{-8}$M, $\leq 5\times 10^{-9}$M, $\leq 4\times 10^{-9}$M, $\leq 3\times 10^{-9}$M, $\leq 2\times 10^{-9}$ M, or $\leq 10^{-9}$ M and any value $\leq 10^{-6}$). Preferablly, an antibody has a KD value in the nanomolar range or lower (e.g., $\leq 9\times 10^{-9}$ M, $\leq 8\times 10^{-9}$ M, $\leq 7\times 10^{-9}$ M, $\leq 6\times 10^{-9}$ M, $\leq 5\times 10^{-9}$ M, $\leq 4\times 10^{-9}$ M, $\leq 3\times 10^{-9}$ M, $\leq 2\times 10^{-9}$ M, $\leq 1\times 10^{-9}$ M or lower e.g., $\leq 1\times 10^{-0}$ M, $\leq 1\times 10^{-11}$ M, $1\times 10^{-12}$ M). Even more preferablly, an antibody has a $K_D$ value in the picomolar range or lower (e.g., $\leq 9\times 10^{-12}$M, $\leq 8\times 10^{-12}$M, $\leq 7\times 10^{-12}$M, $\leq 6\times 10^{-12}$M, $\leq 5\times 10^{-12}$M, $\leq 4\times 10^{-12}$M, $\leq 3\times 10^{-12}$M, $\leq 2\times 10^{-12}$ M, $\leq 1\times 10^{-12}$ M or lower).

The term "specific binding" or "specifically binds" as used herein refers to a non-random binding reaction between two molecules, such as for example between an antibody and an antigen. Specific binding can be characterized in binding affinity, A $K_D$ value of $\leq 10^{-6}$ M (e.g., $\leq 5\times 10^{-7}$M, $\leq 2\times 10^{-7}$M, $\leq 10^{-7}$M, $\leq 5\times 10^{-8}$M, $\leq 2\times 10^{-8}$M, $\leq 10^{-8}$M, $\leq 5\times 10^{-9}$M, $\leq 4\times 10^{-9}$M, $\leq 3\times 10^{-9}$M, $\leq 2\times 10^{-9}$ M, or $\leq 10^{-9}$ M and any value $\leq 10^{-6}$) can indicate specific binding between a binding agent (e.g., antibody such as single domain antibody) and TROP2 (e.g., human TROP2).

As used herein, the term "competing for binding", "compete for binding", "compete(s) with" or "competing with" refers to the ability of a first antibody or antigen-binding fragment thereof (e.g., single domain antibody or antigen binding fragment thereof) to inhibit the binding interaction between TROP2 and a second anti-TROP2 antibody (e.g., a single domain antibody or antigen binding fragment thereof) to any detectable degree.

As used herein the term "epitope" as used herein refers to the specific group of atoms or amino acid residues on an antigen to which an antibody (e.g., single domain antibody) binds. Two antibodies may bind the same or a closely related epitope within an antigen if they exhibit competitive binding for the antigen. An epitope can be linear or conformational (i.e., including amino acid residues spaced apart). For example, if an antibody or antigen binding fragment blocks binding of a reference antibody (e.g., single domain antibody) to the antigen by at least 85%, or at least 90%, or at least 95%, then the antibody or antigen-binding fragment may be considered to bind the same/closely related epitope as the reference antibody. For example, a monoclonal, chimeric, human or humanized antibody or an antigen binding fragment thereof may compete with a single domain antibody of the present disclosure for binding to human TROP2.

As used herein, the term "sequence identity" of the present invention indicates the degree of identity between two nucleic acid or two amino acid sequences when best compared and compared when a mutation such as substitution, insertion or deletion is appropriate. The sequence identity can be at least 85%, 90% or 95%, preferably at least 95%. Non-limiting examples include 85%, 86%, 87%, 88%, 89%, 90%, 91%, $^{92}$%, 93%, 94%, 95%, 95%, 96%, 97%, 98%, 99%, and 100%.

The term "antigen binding fragment(s)" as used in the expression "antibody or antigen binding fragment thereof" or "single domain antibody or antigen binding fragment thereof" refers to a fragment of the antibody or single antibody that encompasses the antigen binding domain and that may incorporate or not, other portion(s) of the antibody or single domain antibody such as for example amino acid residues of the hinge region, amino acid residues of a constant region, portion of a Fc region. Regardless of structure, an antigen binding fragment binds to the same antigen that is recognized by the complete antibody (e.g., single domain antibody).

An antigen binding fragment of a single domain antibody includes for example the CDRs and sequences that encompass the CDRs such as the entire variable region or portion thereof or the entire heavy chain or portion thereof and may include or not, other portion(s) of the antibody.

The term "antigen binding domain" relates to the portion of an antibody that is involved in antigen binding and comprises for example, one or more CDRs, one or more framework regions (FR) or the entire variable region. The term "antigen binding domain" in the context of a single domain antibody thereof relates to the portion of single domain antibody that is involved in antigen binding and comprises for example, one or more of CDR1 (CDRH1), CDR2 (CDRH2) or CDR3 (CDRH3), one or more framework regions FR1, FR2, FR3, FR4 or the entire variable region (VH or VHH). The term "antigen binding domain"" in the context of a native antibody thereof relates to the portion of a native antibody that is involved in antigen binding and comprises for example, one or more of CDRH1, CDRH2, CDRH3, CDRL1, CDRL2 or CDRL3, one or more light chain or heavy chain framework regions FR1, FR2, FR3, FR4 or one or both entire variable regions (heavy chain variable region (VH) and/or light chain variable region (VL)).

TROP2 Antigens

Antibodies or antigen binding fragments of the present disclosure may be obtained, for example, by immunizing an animal with a TROP2 antigen.

Alternatively, the antibodies or antigen binding fragments of the present disclosure may be obtained from a library of antibodies.

Binding agents that bind to TROP2 may be identified by in silico, in vitro and/or in vivo methods. Several in vitro methods rely on the binding of candidate antibodies or antigen binding fragments thereof to an antigen. As such anti-TROP2 antibodies or antigen binding fragments thereof may be identified by methods involving binding to the TROP2 antigen disclosed herein and/or using assays disclosed herein.

In an embodiment, the TROP2 antigen is a human TROP2, a TROP2 homologue, a TROP2 variant having a sequence at least 80% identical to human TROP2 thereof or a fragment thereof.

In an exemplary embodiment, the TROP2 homologue is cynomolgus TROP2.

In another exemplary embodiment, the TROP2 homologue is Rhesus TROP2.

In some embodiments, the TROP2 antigen comprises the extracellular domain of TROP2 (e.g., of human TROP2, TROP2 homologue or variant thereof).

In some embodiments, the TROP2 antigen comprises amino acid residues 27-274 of human TROP2, or of a TROP2 homologue or a fragment thereof. Accordingly, the TROP2 antigen may comprise a polypeptide comprising a human TROP2 amino acid sequence consisting of amino acid residues 27-274 or a fragment thereof.

In other embodiments, the TROP2 antigen comprises amino acid residues 27-146 of human TROP2, or of a TROP2 homologue or a fragment thereof. Accordingly, the TROP2 antigen may comprise a polypeptide comprising a human TROP2 amino acid sequence consisting of amino acid residues 27-146 or a fragment thereof.

In yet other embodiments, the TROP2 antigen comprises amino acid residues 27-73 of human TROP2, or of a TROP2 homologue or a fragment thereof. Accordingly, the TROP2 antigen may comprise a polypeptide comprising a human TROP2 amino acid sequence consisting of amino acid residues 27-73 or a fragment thereof.

In accordance with the present disclosure, the TROP2 antigen may comprise at least 10 amino acid residues of human TROP2.

More particularly, the TROP2 antigen is a fragment of at least 10 amino acid residues of a human TROP2 amino acid sequence consisting of amino acid residues 27-146.

In accordance with the present disclosure the TROP2 antigen comprises between 10 to 110 amino acid residues, including for example between 10 to 100 amino acid residues, between 10 to 90 amino acid residues, between 10 to 80 amino acid residues, between 10 to 70 amino acid residues, between 10 to 60 amino acid residues, between 10 to 50 amino acid residues, between 10 to 40 amino acid residues, between 10 to 30 amino acid residues, 10 to 29 amino acid residues, between 10 to 28 amino acid residues, between 10 to 27 amino acid residues, between 10 to 26 amino acid residues, between 10 to 25 amino acid residues, between 10 to 24 amino acid residues, between 10 to 23 amino acid residues, between 10 to 22 amino acid residues, between 10 to 21 amino acid residues, between 10 to 20 amino acid residues, between 10 to 19 amino acid residues, between 10 to 18 amino acid residues, between 10 to 17 amino acid residues, between 10 to 16 amino acid residues, between 10 to 15 amino acid residues, between 10 to 14 amino acid residues, between 10 to 13 amino acid residues, between 10 to 12 amino acid residues between 10 to 11 amino acid residues of a human TROP2 amino acid sequence consisting of amino acid residues 27-146.

For instances, the TROP2 antigen comprises at least 10 amino acid residues of a human TROP2 amino acid sequence consisting of amino acid residues 27-73.

In accordance with the present disclosure the TROP2 antigen comprises between 10 to 45 amino acid residues, including for example between 10 to 40 amino acid residues, between 10 to 35 amino acid residues, between 10 to 30 amino acid residues, 10 to 29 amino acid residues, between 10 to 28 amino acid residues, between 10 to 27 amino acid residues, between 10 to 26 amino acid residues, between 10 to 25 amino acid residues, between 10 to 24 amino acid residues, between 10 to 23 amino acid residues, between 10 to 22 amino acid residues, between 10 to 21 amino acid residues, between 10 to 20 amino acid residues, between 10 to 19 amino acid residues, between 10 to 18 amino acid residues, between 10 to 17 amino acid residues, between 10 to 16 amino acid residues, between 10 to 15 amino acid residues, between 10 to 14 amino acid residues, between 10 to 13 amino acid residues, between 10 to 12 amino acid residues between 10 to 11 amino acid residues of a human TROP2 amino acid sequence consisting of amino acid residues 27-73.

In some instances, the TROP2 antigen comprises a human TROP2 amino acid sequence consisting of amino acid residues 27-56 of human TROP2 or a fragment thereof.

In other instances, the TROP2 antigen comprises a human TROP2 amino acid sequence consisting of amino acid residues 27-66 of human TROP2 or a fragment thereof.

In yet other instances, the TROP2 antigen comprises a human TROP2 amino acid sequence consisting of amino acid residues 47-56 of human TROP2 or a fragment thereof.

In other instances, the TROP2 antigen comprises a human TROP2 amino acid sequence consisting of amino acid residues 60-66 of human TROP2 or a fragment thereof.

In yet other instances, the TROP2 antigen comprises a human TROP2 amino acid sequence consisting of amino acid residues 47-66 of human TROP2 or a fragment thereof.

For example, the TROP2 antigen comprises a human TROP2 amino acid sequence consisting of amino acid residues 27-56, 27-66, 28-66, 29-66, 30-66, 31-66, 32-66, 33-66, 34-66, 35-66, 36-66, 37-66, 38-66, 39-66, 40-66, 41-66, 42-66, 43-66, 44-66, 45-66, 46-66 or 47-66.

In some instances, the TROP2 antigen may exclude the cysteine poor (CPD) domain of TROP2.

An exemplary and non-limiting embodiment of a TROP2 antigen is provided in SEQ ID NO:164.

Binding Agents

Exemplary embodiments of binding agents of the present disclosure includes a polypeptide chain disclosed herein.

Exemplary embodiments of binding agents of the present disclosure includes antibodies or antigen binding fragments thereof.

Exemplary embodiments of binding agents therefore include without limitations, native antibodies or antigen binding fragments thereof or single domain antibodies or antigen binding fragments thereof or variants thereof such as for example, humanized, chimeric or human antibodies or antigen binding fragments thereof or humanized or chimeric single domain antibodies or antigen binding fragments thereof.

Single domain antibodies or antigen binding fragments thereof disclosed herein are particularly contemplated as well as binding agents that comprise one or more antigen binding domain(s) of one or more single domain antibodies disclosed herein.

Single domain antibodies that compete with one or more single domain antibodies (having an amino acid sequence as disclosed herein) for the binding of a TROP2 antigen are also encompassed by the present disclosure.

Other exemplary embodiments of binding agents of the present disclosure include binding agents comprising antigen binding domain(s) such as antibody-like molecules (including single chain antibody), protein scaffold molecules and immune cell modulating agents.

Accordingly, exemplary embodiments of binding agents of the present disclosure include antibody-like molecules that comprise one or more antigen binding domain(s) of one or more single antibodies disclosed herein.

Additional exemplary embodiments of binding agents of the present disclosure include protein scaffold molecules that comprise one or more antigen binding domain(s) of one or more single antibodies disclosed herein.

Yet additional exemplary embodiments of binding agents of the present disclosure comprises immune cell modulating agents that comprise one or more antigen binding domain(s) of one or more single antibodies disclosed herein.

Binding agents including for example and without limitations, antibodies or antigen binding fragments thereof as well as single domain antibodies or antigen binding fragments thereof that competes with of a single domain antibody having an amino acid sequence disclosed herein are also encompassed by the present disclosure.

The present disclosure thus relates to a binding agent comprising one or more antigen binding domains, wherein at least one of the one or more antigen binding domains comprises an antigen binding fragment thereof that is capable of binding to trophoblast cell surface antigen-2 (TROP2).

In some embodiments, the binding agent of the present disclosure is capable of binding to the extracellular domain (ECD) of TROP2.

In some embodiments, the binding agent of the present disclosure is capable of binding to the cysteine-rich domain and/or to the thyroglobulin type-1 domain of TROP2.

In some embodiments, the binding agent of the present disclosure is capable of binding to an epitope comprising amino acids of the extracellular domain of TROP2.

In some embodiments, the binding agent of the present disclosure is capable of binding to an epitope comprising amino acids of the cysteine-rich domain and/or of the thyroglobulin type-1 domain of TROP2.

In some embodiments, the binding agent of the present disclosure is capable of binding to an epitope including amino acid residues comprised within amino acid sequence 27-274 of TROP2 or a fragment thereof.

In some embodiments, the binding agent of the present disclosure is not capable of binding to the cysteine-poor domain (CPD) of TROP2.

In some embodiments, the binding agent of the present disclosure is not capable of binding to the amino acid 146 to 274 of TROP2.

Antibodies and Antigen Binding Fragments

In some embodiments, the binding agent is an anti-TROP2 antibody or an antigen binding fragment thereof. It is to be understood herein that the following represent exemplary and non-limiting embodiments of antibodies or antigen binding fragments thereof.

Antibodies or antigen binding fragments thereof (or their sequence) may be obtained from immunization of an animal (including a transgenic animal) with a TROP2 antigen as disclosed herein. For example, single domain antibodies or antigen binding fragments thereof (or their sequence) may be obtained by immunizing an animal such as a dromedary, a camel, a llama, an alpaca, a rabbit with a TROP2 antigen (e.g., ECD or fragments thereof). Alternatively, the sequence of a single domain antibody or antigen binding domain thereof may be obtained by immunizing a transgenic animal that is able to express single domain antibodies (see international application No. PCT/CA2021/050951 filed on Jul. 12, 2021, and published on Jan. 20, 2022, under No. WO2022/011457 A1 the entire content of which is incorporated herein by reference).

In some instances, an antibody or antigen binding fragment thereof (or its sequence) is obtained from serum or tissue of immunized animals such as bone marrow, spleen and/or lymph nodes.

An hybridoma that results from fusion of cells of an immunized animal with a malignant and immortal plasma cell such as myeloma cells lacking hypoxanthine-guanine-phosphoribosyltransferase (HGPRT) an enzyme allowing cells to grow in HAT medium (hypoxanthine-aminopterin-thymidine) may be generated. Spleen cells are particularly useful to generate hybridomas. The antibody or antigen binding fragment thereof may be isolated from an hybridoma.

The nucleic acid sequence of an antibody or antigen binding fragment thereof may be obtained by PCR amplification and sequencing from cells or tissue able to express the antibody or antigen binding fragment thereof. The amino acid sequence information is obtained from the nucleic acid sequence. Due to inherent degeneracy of the genetic code, a nucleic acid molecule encoding the same amino acid sequence but having a different nucleic acid sequence compared to the original nucleic acid sequence may be generated.

Once a nucleic acid sequence encoding the amino acid sequence of an antibody is obtained, recombinant expression of an antibody is rendered possible by transfection of one or more expression vector(s) into immortalized mammalian cell lines.

Alternatively, the sequence of an antibody of antigen binding fragment thereof may also be obtained by screening an established antibody library for sequences that have desired features such as for example, homology or identity with a reference antibody.

Antibodies of the present disclosure includes native or intact antibodies that specifically bind to TROP2. A native or intact antibody includes an antibody that is recombinantly expressed, isolated from immunized animals or from an hybridoma.

Exemplary embodiments of binding agents of the present disclosure include antibodies or antigen binding fragments thereof that specifically bind to at least one epitope comprising amino acids of the extracellular domain (ECD) of TROP2. Other exemplary embodiments of binding agents of the present disclosure include antibodies or antigen binding fragments thereof that specifically bind to at least one epitope comprising amino acids of the cysteine rich domain of TROP2. In some embodiments, the antibodies or antigen binding fragments thereof bind to a TROP2 antigen disclosed herein.

In an embodiment, the antibodies of the present disclosure specifically bind to human TROP2. In another embodiment, the antibodies of the present disclosure specifically bind to cynomolgus TROP2. In another embodiment, the antibodies of the present disclosure specifically bind to Rhesus TROP2.

More particularly, the antibodies of the present disclosure specifically bind to the ECD or the CRD of human TROP2.

A native or intact antibody comprises two heavy (H) chains and two light (L) chains. Mammalian heavy chains are classified as alpha, delta, epsilon, gamma, and mu, each heavy chain consists of a variable region (VH) and a first, second, third, and optionally fourth constant region (CH1, CH2, CH3, CH4 respectively); mammalian light chains are classified as λ or κ, while each light chain consists of a variable region (VL) and a constant region. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light chain CDRs including CDRL1, CDRL2, and CDRL3, heavy chain CDRs including CDRH1, CDRH2, CDRH3). CDR boundaries for the antibodies and antigen-binding fragments disclosed herein may be defined or identified by the conventions of Kabat, IMGT, Chothia, or Al-Lazikani. The three CDRs are interposed between flanking stretches known as framework regions (FRs) (light chain FRs including LFR1, LFR2, LFR3, and LFR4, heavy chain FRs including HFR1, HFR2, HFR3, and HFR4), which are more highly conserved than the CDRs and form a scaffold to support the highly variable loops. The constant regions of the heavy and light chains are not involved in antigen-binding, but exhibit various effector functions. Antibodies are assigned to classes based on the amino acid sequences of the constant regions of their heavy chains. The five major classes or isotypes of antibodies are IgA, IgD, IgE, IgG, and IgM, which are characterized by the presence of alpha, delta, epsilon, gamma, and mu heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgA1 (alpha1 heavy chain), or IgA2 (alpha2 heavy chain).

Antibodies of the present disclosure includes chimeric antibodies that specifically bind to TROP2. A chimeric antibody is a recombinant protein that contains the variable region(s) including the complementarity determining regions (CDRs) of an antibody derived from one or more species, such as a rodent antibody, while the constant domains of the antibody molecule are derived from those of another species, such as a human antibody.

Antibodies of the present disclosure includes humanized antibodies that specifically bind to TROP2. A humanized antibody is a recombinant protein in which the CDRs or CDR residues from an antibody from one species; e.g., a rodent antibody, are transferred from the heavy and light variable chains of the rodent antibody into human heavy and light variable regions (e.g., framework region sequences). The constant domains of the antibody molecule are derived from those of a human antibody. In certain embodiments, a limited number of framework region amino acid residues from the parent (rodent) antibody may be substituted into the human antibody framework region sequences. In other examples, as simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an antibody that possesses good binding affinity to its epitope. In some embodiment the humanized antibody is a humanized single domain antibody. In some embodiments, a humanized antibody that competes with a single domain antibody disclosed herein is encompassed by the present disclosure.

Antibodies of the present disclosure includes human antibodies that specifically binds to TROP2. A fully human antibody can be obtained from a transgenic non-human animal. Methods for producing fully human antibodies using either combinatorial approaches or transgenic animals transformed with human immunoglobulin loci are known in the art. In one alternative, the phage display technique may be used to generate human antibodies. The fully human antibodies are expected to exhibit even fewer side effects than chimeric or humanized antibodies and to function in vivo as essentially endogenous human antibodies. In some embodiments, a human antibody that competes with a single domain antibody disclosed herein is encompassed by the present disclosure.

Antibodies of the present disclosure includes single domain antibodies (sdAbs) that specifically binds to TROP2. As used herein the expressions "single domain antibody" and "heavy chain only antibody" are used interchangeably. The term "single domain antibody" is used in its broad sense and includes naturally occurring single domain antibodies or variants thereof such as humanized single domain antibodies or chimeric single domain antibodies. A single domain antibody is said to be chimeric when it possesses a constant region of another species. In an embodiment, the single domain antibody is a chimeric single domain antibody. In some embodiments, the chimeric single domain antibody comprises a humanized variable region and a human constant region. In another embodiment, the chimeric single domain antibody comprises the variable region of a native single domain antibody.

A single domain antibody (sdAb) is usually composed of two heavy chains. A single domain antibody is about 12-15 kDa in size (about 110 amino acids in length). A sdAb can selectively bind to target antigens, like full-size antibodies, and have similar affinities for antigens. However, because of their much smaller size, they may be capable of better penetration into solid tumors. The smaller size also contributes to the stability of the sdAb, which is more resistant to pH and temperature extremes than full size antibodies (Van Der Linden et al., 1999, Biochim Biophys Act 1431:37-46). Single-domain antibodies were originally developed following the discovery that camelids (camels, alpacas, llamas) possess fully functional antibodies without light chains (e.g., Hamsen et al., 2007, Appl Microbiol Biotechnol 77:13-22). Naturally occurring single domain antibodies consist of a single variable region (VH or VHH) and two constant domains (CH2 and CH3). The variable region of naturally occurring single domain antibodies may be cloned and fused to a constant region of a naturally occurring antibody heavy chain. In some embodiments, the variable region of a naturally occurring single domain antibody is replaced with that of a human IgG heavy chain constant region which comprise CH1, CH2 and CH3 domains and optionally CH4 domain and may optionally comprise a hinge.

The antigen binding property of a single domain antibody is conferred by the heavy chain variable region. As such, a single heavy chain or even a single heavy variable region (VH or VHH) may be sufficient for specific binding to an antigen. However, a single domain antibody is usually composed of two heavy chains. The two heavy chains may be assembled via a dimerization domain such as for example a constant region of a class G human immunoglobulin. The two heavy chains may also be expressed as a single polypeptide chain.

Accordingly, in some embodiments, binding agents include antibodies and antigen-binding fragments thereof such as, for example and without limitations, single domain antibodies from camelids or sharks, human antibodies including IgGs (including human IgG1, human IgG2, human IgG3, human IgG4), human IgMs, human IgAs (including human IgA1 and human IgA2), human IgEs, human IgDs, animal antibodies including for example, IgGs (IgG1, IgG2a, IgG2b, IgG2c, IgG3, IgG4), IgMs, IgAs, IgEs and IgDs and variants (e.g., chimeric, humanized or human) having a similar format.

In other embodiments, binding agents of the present disclosure encompass antigen-binding fragments such as, for example and without limitations, Fab, Fab', F(ab')$_2$, complementarity determining regions, variable regions including VHs, VHHs, VLs, and the like.

An antigen binding fragment can be prepared by known techniques such as by proteolytic hydrolysis of a full-length antibody or by expression in *E. coli* or another host of the DNA coding for the fragment. An antigen binding fragment can be obtained by pepsin or papain digestion of full-length antibodies by conventional methods. For example, antigen binding fragment can be produced by enzymatic cleavage of antibodies with pepsin to provide an approximate 100 kD fragment denoted F(ab')$_2$. A F(ab')$_2$ fragment can be further cleaved using a thiol reducing agent, and optionally a blocking group for the sulfhydryl groups resulting from cleavage of disulfide linkages, to produce an approximate 50 Kd Fab' monovalent fragment. Alternatively, an enzymatic cleavage using papain produces two monovalent Fab fragments and an Fc fragment directly.

In some embodiments, antibodies that binds to TROP2 can be bispecific or multispecific. A "multispecific antibody" is an antibody that can bind simultaneously to at least two targets that are of different structure, e.g., two or more different antigens, two or more different epitopes on the same antigen, or a hapten and/or an antigen or epitope. A "multivalent antibody" is an antibody that can bind simultaneously to at least two targets that are of the same or different structure. Valency indicates how many antigen binding domains the antibody has; i.e., monovalent, bivalent, trivalent or multivalent. Multivalency provides an antibody with an advantage of multiple interactions in binding to an antigen, thus increasing the avidity of binding to the antigen. Specificity indicates how many antigens or epitopes an antibody is able to bind; i.e., monospecific, bispecific, trispecific, multispecific. Using these definitions, a native antibody (e.g., an IgG) is bivalent because it has two antigen binding domains (each binding domain being composed of amino acid residues from the light chain and heavy chain variable regions) but is monospecific because each antigen binding domain binds to the same epitope. Multispecific, multivalent antibodies include antibodies that have more than one antigen binding domain of different specificity. A "bispecific antibody" is an antibody that can bind simultaneously to two targets which are of different structure. Bispecific antibodies (bsAb) and bispecific antibody fragments (bsFab) may have at least antigen binding domain that specifically binds to TROP2.

In addition to recombinant technologies, numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site. Another method for producing bispecific antibodies uses heterobifunctional cross-linkers to chemically tether two different monoclonal antibodies.

Single Domain Antibodies

An exemplary embodiment of binding agent of the present disclosure is a single domain antibody. It is to be understood herein that the following represent exemplary and non-limiting embodiments of single domain antibodies or antigen binding fragments thereof.

The single domain antibody possesses unique binding features. For example, the complementarity determining region 3 (CDR3) of the sdAb disclosed herein forms a loop fitting into a groove within the cysteine rich domain (CRD) of the extracellular domain (ECD) of TROP2. Amino acid residues of the CDR3 and of the framework region 2 (FR2) interact with amino acid residues of TROP2 cysteine rich domain and together form a clip around the CRD. These unique properties provide a high affinity of sdAbs for TROP2 and a slow dissociation rate. Surprisingly, amino acid residues of the complementarity determining region 1 (CDR1) and of the complementarity determining region 2 (CDR2) do not appear to interact with amino acid residues of the CRD.

The single domain antibodies of the present disclosure also possess anti-cancer activity such as antibody-dependent cellular cytotoxicity (ADCC) and/or antibody-dependent cellular phagocytosis (ADCP) activity. The single domain antibodies of the present disclosure may also be conjugated for therapeutic, or detection uses.

Exemplary embodiments of binding agents of the present disclosure include single domain antibodies or antigen binding fragments thereof that specifically bind to at least one epitope comprising amino acids of the extracellular domain (ECD) of TROP2. Other exemplary embodiments of binding agents of the present disclosure include single domain antibodies or antigen binding fragments thereof that specifically bind to at least one epitope comprising amino acids of the cysteine rich domain of TROP2. In some embodiments, the single domain antibodies or antigen binding fragments thereof bind to a TROP2 antigen disclosed herein.

In an embodiment, the single domain antibodies of the present disclosure specifically bind to human TROP2. In another embodiment, the single domain antibodies of the present disclosure specifically bind to cynomolgus TROP2. In another embodiment, the single domain antibodies of the present disclosure specifically bind to Rhesus TROP2.

More particularly, the single domain antibodies of the present disclosure specifically bind to the ECD or the CRD of human TROP2.

In an exemplary embodiment, the single domain antibody or antigen binding fragment thereof comprises the amino acid sequence of the CDR3 set forth in SEQ ID NO:54 and the amino acid sequence of the FR2 set forth in SEQ ID NO:116 and optionally the amino acid sequence of the CDR1 set forth in SEQ ID NO:52 and/or the amino acid sequence of the CDR2 set forth in SEQ ID NO:53.

In an exemplary embodiment, the single domain antibody or antigen binding fragment thereof comprises the amino acid sequence of the CDR3 set forth in SEQ ID NO:48 and the amino acid sequence of the FR2 set forth in SEQ ID NO:116 and optionally the amino acid sequence of the CDR1 set forth in SEQ ID NO:55 and/or the amino acid sequence of the CDR2 set forth in SEQ ID NO:47.

In an exemplary embodiment, the single domain antibody or antigen binding fragment thereof comprises the amino acid sequence of the CDR3 set forth in SEQ ID NO:58 and the amino acid sequence of the FR2 set forth in SEQ ID NO:116 and optionally the amino acid sequence of the CDR1 set forth in SEQ ID NO:56 and/or the amino acid sequence of the CDR2 set forth in SEQ ID NO:57.

In an exemplary embodiment, the single domain antibody or antigen binding fragment thereof comprises the amino acid sequence of the CDR3 set forth in SEQ ID NO:61 and the amino acid sequence of the FR2 set forth in SEQ ID NO:116 and optionally the amino acid sequence of the CDR1 set forth in SEQ ID NO:59 and/or the amino acid sequence of the CDR2 set forth in SEQ ID NO:60.

In an exemplary embodiment, the single domain antibody or antigen binding fragment thereof comprises the amino acid sequence of the CDR3 set forth in SEQ ID NO:51 and the amino acid sequence of the FR2 set forth in SEQ ID NO:116 and optionally the amino acid sequence of the CDR1 set forth in SEQ ID NO:62 and/or the amino acid sequence of the CDR2 set forth in SEQ ID NO:50.

In an exemplary embodiment, the single domain antibody or antigen binding fragment thereof comprises the amino acid sequence of the CDR3 set forth in SEQ ID NO: 48 and the amino acid sequence of the FR2 set forth in SEQ ID NO:116 and optionally the amino acid sequence of the CDR1 set forth in SEQ ID NO:55 and/or the amino acid sequence of the CDR2 set forth in 47.

In an exemplary embodiment, the single domain antibody or antigen binding fragment thereof comprises the amino acid sequence of the CDR3 set forth in SEQ ID NO: 48 and the amino acid sequence of the FR2 set forth in SEQ ID NO:117 and optionally the amino acid sequence of the CDR1 set forth in SEQ ID NO:55 and/or the amino acid sequence of the CDR2 set forth in 47.

In an exemplary embodiment, the single domain antibody or antigen binding fragment thereof comprises the amino acid sequence of the CDR3 set forth in SEQ ID NO: 48 and the amino acid sequence of the FR2 set forth in SEQ ID NO:118 and optionally the amino acid sequence of the CDR1 set forth in SEQ ID NO:55 and/or the amino acid sequence of the CDR2 set forth in 47.

In an exemplary embodiment, the single domain antibody or antigen binding fragment thereof comprises the amino acid sequence of the CDR3 set forth in SEQ ID NO: 48 and the amino acid sequence of the FR2 set forth in SEQ ID NO:119 and optionally the amino acid sequence of the CDR1 set forth in SEQ ID NO:55 and/or the amino acid sequence of the CDR2 set forth in 47.

In an exemplary embodiment, the single domain antibody or antigen binding fragment thereof comprises the amino acid sequence of the CDR3 set forth in SEQ ID NO: 48 and the amino acid sequence of the FR2 set forth in SEQ ID NO:117 and optionally the amino acid sequence of the CDR1 set forth in SEQ ID NO:55 and/or the amino acid sequence of the CDR2 set forth in 124.

In an exemplary embodiment, the single domain antibody or antigen binding fragment thereof comprises the amino acid sequence of the CDR3 set forth in SEQ ID NO: 48 and the amino acid sequence of the FR2 set forth in SEQ ID NO:117 and optionally the amino acid sequence of the CDR1 set forth in SEQ ID NO:55 and/or the amino acid sequence of the CDR2 set forth in 123.

In an exemplary embodiment, the single domain antibody or antigen binding fragment thereof comprises the amino acid sequence of the CDR3 set forth in SEQ ID NO:51 and the amino acid sequence of the FR2 set forth in SEQ ID NO:116 and optionally the amino acid sequence of the CDR1 set forth in SEQ ID NO:62 and/or the amino acid sequence of the CDR2 set forth in SEQ ID NO:50.

In an exemplary embodiment, the single domain antibody or antigen binding fragment thereof comprises the amino acid sequence of the CDR3 set forth in SEQ ID NO:51 and the amino acid sequence of the FR2 set forth in SEQ ID NO:117 and optionally the amino acid sequence of the CDR1 set forth in SEQ ID NO:62 and/or the amino acid sequence of the CDR2 set forth in SEQ ID NO:50.

In an exemplary embodiment, the single domain antibody or antigen binding fragment thereof comprises the amino acid sequence of the CDR3 set forth in SEQ ID NO:51 and the amino acid sequence of the FR2 set forth in SEQ ID NO:118 and optionally the amino acid sequence of the CDR1 set forth in SEQ ID NO:62 and/or the amino acid sequence of the CDR2 set forth in SEQ ID NO:50.

In an exemplary embodiment, the single domain antibody or antigen binding fragment thereof comprises the amino acid sequence of the CDR3 set forth in SEQ ID NO:51 and the amino acid sequence of the FR2 set forth in SEQ ID NO:120 and optionally the amino acid sequence of the CDR1 set forth in SEQ ID NO:62 and/or the amino acid sequence of the CDR2 set forth in SEQ ID NO:50.

In an exemplary embodiment, the single domain antibody or antigen binding fragment thereof comprises the amino acid sequence of the CDR3 set forth in SEQ ID NO:6 and the amino acid sequence of the FR2 set forth in SEQ ID NO:170 and optionally the amino acid sequence of the CDR1 set forth in SEQ ID NO:4 and/or the amino acid sequence of the CDR2 set forth in SEQ ID NO:5.

In an exemplary embodiment, the single domain antibody or antigen binding fragment thereof comprises the amino acid sequence of the CDR3 set forth in SEQ ID NO:6 and the amino acid sequence of the FR2 set forth in SEQ ID NO:171 and optionally the amino acid sequence of the CDR1 set forth in SEQ ID NO:4 and/or the amino acid sequence of the CDR2 set forth in SEQ ID NO:130.

In an exemplary embodiment, the single domain antibody or antigen binding fragment thereof comprises the amino acid sequence of the CDR3 set forth in SEQ ID NO:6 and the amino acid sequence of the FR2 set forth in SEQ ID NO:170 and optionally the amino acid sequence of the CDR1 set forth in SEQ ID NO:4 and/or the amino acid sequence of the CDR2 set forth in SEQ ID NO:131.

In an exemplary embodiment, the single domain antibody or antigen binding fragment thereof comprises the amino acid sequence of the CDR3 set forth in SEQ ID NO:6 and the amino acid sequence of the FR2 set forth in SEQ ID NO:170 and optionally the amino acid sequence of the CDR1 set forth in SEQ ID NO:4 and/or the amino acid sequence of the CDR2 set forth in SEQ ID NO:133.

In an exemplary embodiment, the single domain antibody or antigen binding fragment thereof comprises the amino acid sequence of the CDR3 set forth in SEQ ID NO:6 and the amino acid sequence of the FR2 set forth in SEQ ID NO:171 and optionally the amino acid sequence of the CDR1 set forth in SEQ ID NO:4 and/or the amino acid sequence of the CDR2 set forth in SEQ ID NO:131.

In an exemplary embodiment, the single domain antibody or antigen binding fragment thereof comprises the amino acid sequence of the CDR3 set forth in SEQ ID NO:6 and the amino acid sequence of the FR2 set forth in SEQ ID NO:171 and optionally the amino acid sequence of the CDR1 set forth in SEQ ID NO:4 and/or the amino acid sequence of the CDR2 set forth in SEQ ID NO:132.

In an exemplary embodiment, the single domain antibody or antigen binding fragment thereof comprises the amino acid sequence of the CDR3 set forth in SEQ ID NO:6 and the amino acid sequence of the FR2 set forth in SEQ ID NO:171 and optionally the amino acid sequence of the CDR1 set forth in SEQ ID NO:4 and/or the amino acid sequence of the CDR2 set forth in SEQ ID NO:133.

In an exemplary embodiment, the single domain antibody or antigen binding fragment thereof comprises the amino acid sequence of the CDR3 set forth in SEQ ID NO:6 and the amino acid sequence of the FR2 set forth in SEQ ID NO:172 and optionally the amino acid sequence of the CDR1 set forth in SEQ ID NO:4 and/or the amino acid sequence of the CDR2 set forth in SEQ ID NO:133.

In an exemplary embodiment, the single domain antibody or antigen binding fragment thereof comprises the amino acid sequence of the CDR3 set forth in SEQ ID NO:6 and the amino acid sequence of the FR2 set forth in SEQ ID NO:171 and optionally the amino acid sequence of the CDR1 set forth in SEQ ID NO:4 and/or the amino acid sequence of the CDR2 set forth in SEQ ID NO:134.

In an exemplary embodiment, the single domain antibody or antigen binding fragment thereof comprises the amino acid sequence of the CDR3 set forth in SEQ ID NO:6 and the amino acid sequence of the FR2 set forth in SEQ ID NO:171 and optionally the amino acid sequence of the CDR1 set forth in SEQ ID NO:4 and/or the amino acid sequence of the CDR2 set forth in SEQ ID NO:135.

In an exemplary embodiment, the single domain antibody or antigen binding fragment thereof comprises the amino acid sequence of the CDR3 set forth in SEQ ID NO:6 and the amino acid sequence of the FR2 set forth in SEQ ID NO:174 and optionally the amino acid sequence of the CDR1 set forth in SEQ ID NO:127 and/or the amino acid sequence of the CDR2 set forth in SEQ ID NO:129.

In an exemplary embodiment, the single domain antibody or antigen binding fragment thereof comprises the amino acid sequence of the CDR3 set forth in SEQ ID NO:15 and the amino acid sequence of the FR2 set forth in SEQ ID NO:170 and optionally the amino acid sequence of the CDR1 set forth in SEQ ID NO:13 and/or the amino acid sequence of the CDR2 set forth in SEQ ID NO:14.

In an exemplary embodiment, the single domain antibody or antigen binding fragment thereof comprises the amino acid sequence of the CDR3 set forth in SEQ ID NO:15 and the amino acid sequence of the FR2 set forth in SEQ ID NO:170 and optionally the amino acid sequence of the CDR1 set forth in SEQ ID NO:13 and/or the amino acid sequence of the CDR2 set forth in SEQ ID NO:137.

In an exemplary embodiment, the single domain antibody or antigen binding fragment thereof comprises the amino acid sequence of the CDR3 set forth in SEQ ID NO:15 and the amino acid sequence of the FR2 set forth in SEQ ID NO:170 and optionally the amino acid sequence of the CDR1 set forth in SEQ ID NO:13 and/or the amino acid sequence of the CDR2 set forth in SEQ ID NO:138.

In an exemplary embodiment, the single domain antibody or antigen binding fragment thereof comprises the amino acid sequence of the CDR3 set forth in SEQ ID NO:15 and the amino acid sequence of the FR2 set forth in SEQ ID NO:171 and optionally the amino acid sequence of the CDR1 set forth in SEQ ID NO:13 and/or the amino acid sequence of the CDR2 set forth in SEQ ID NO:136.

In an exemplary embodiment, the single domain antibody or antigen binding fragment thereof comprises the amino acid sequence of the CDR3 set forth in SEQ ID NO:15 and the amino acid sequence of the FR2 set forth in SEQ ID NO:171 and optionally the amino acid sequence of the CDR1 set forth in SEQ ID NO:13 and/or the amino acid sequence of the CDR2 set forth in SEQ ID NO:137.

In an exemplary embodiment, the single domain antibody or antigen binding fragment thereof comprises the amino acid sequence of the CDR3 set forth in SEQ ID NO:15 and the amino acid sequence of the FR2 set forth in SEQ ID NO:171 and optionally the amino acid sequence of the CDR1 set forth in SEQ ID NO:13 and/or the amino acid sequence of the CDR2 set forth in SEQ ID NO:138.

In an exemplary embodiment, the single domain antibody or antigen binding fragment thereof comprises the amino acid sequence of the CDR3 set forth in SEQ ID NO:15 and the amino acid sequence of the FR2 set forth in SEQ ID NO:171 and optionally the amino acid sequence of the CDR1 set forth in SEQ ID NO:13 and/or the amino acid sequence of the CDR2 set forth in SEQ ID NO:139.

In an exemplary embodiment, the single domain antibody or antigen binding fragment thereof comprises the amino acid sequence of the CDR3 set forth in SEQ ID NO:15 and the amino acid sequence of the FR2 set forth in SEQ ID NO:173 and optionally the amino acid sequence of the CDR1 set forth in SEQ ID NO:13 and/or the amino acid sequence of the CDR2 set forth in SEQ ID NO:137.

In some embodiments single domain antibody or antigen binding fragment thereof of the present disclosure comprises the three CDRs of the single domain antibody disclosed herein.

In an exemplary embodiment, the single domain antibody or antigen binding fragment thereof comprises a CDR1 having the amino acid sequence set forth in SEQ ID NO:1, a heavy chain complementarity determining region 2 (CDRH2) having the amino acid sequence set forth in SEQ ID NO:2 and a heavy chain complementarity determining region 3 (CDRH3) having the amino acid sequence set forth in SEQ ID NO:3.

In an exemplary embodiment, the single domain antibody or antigen binding fragment thereof comprises a CDRH1 having the amino acid sequence set forth in SEQ ID NO:4, a CDRH2 having the amino acid sequence set forth in SEQ ID NO:5 and a CDRH3 having the amino acid sequence set forth in SEQ ID NO:6.

In another exemplary embodiment, the single domain antibody or antigen binding fragment thereof comprises a CDRH1 having the amino acid sequence set forth in SEQ ID NO:7, a CDRH2 having the amino acid sequence set forth in SEQ ID NO:8 and a CDRH3 having the amino acid sequence set forth in SEQ ID NO:9.

In another exemplary embodiment, the single domain antibody or antigen binding fragment thereof comprises a CDRH1 having the amino acid sequence set forth in SEQ ID NO:10, a CDRH2 having the amino acid sequence set forth in SEQ ID NO:11 and a CDRH3 having the amino acid sequence set forth in SEQ ID NO:12.

In another exemplary embodiment, the single domain antibody or antigen binding fragment thereof comprises a CDRH1 having the amino acid sequence set forth in SEQ ID NO:13, a CDRH2 having the amino acid sequence set forth in SEQ ID NO:14 and a CDRH3 having the amino acid sequence set forth in SEQ ID NO:15.

In another exemplary embodiment, the single domain antibody or antigen binding fragment thereof comprises a CDRH1 having the amino acid sequence set forth in SEQ ID NO:16, a CDRH2 having the amino acid sequence set forth in SEQ ID NO:17 and a CDRH3 having the amino acid sequence set forth in SEQ ID NO:18.

In another exemplary embodiment, the single domain antibody or antigen binding fragment thereof comprises a CDRH1 having the amino acid sequence set forth in SEQ ID NO:19, a CDRH2 having the amino acid sequence set forth in SEQ ID NO:20 and a CDRH3 having the amino acid sequence set forth in SEQ ID NO:21.

In other exemplary embodiments, the single domain antibody comprises a CDRH1 having the amino acid sequence set forth in SEQ ID NO:46, a CDRH2 having the amino acid sequence set forth in SEQ ID NO:47 and a CDRH3 having the amino acid sequence set forth in SEQ ID NO:48.

In other exemplary embodiments, the single domain antibody comprises a CDRH1 having the amino acid sequence set forth in SEQ ID NO:55, a CDRH2 having the amino acid sequence set forth in SEQ ID NO:47 and a CDRH3 having the amino acid sequence set forth in SEQ ID NO:48.

In other exemplary embodiments, the single domain antibody comprises a CDRH1 having the amino acid sequence set forth in SEQ ID NO:49, a CDRH2 having the amino acid sequence set forth in SEQ ID NO:50 and a CDRH3 having the amino acid sequence set forth in SEQ ID NO:51.

In other exemplary embodiments, the single domain antibody comprises a CDRH1 having the amino acid sequence set forth in SEQ ID NO:62, a CDRH2 having the amino acid sequence set forth in SEQ ID NO:50 and a CDRH3 having the amino acid sequence set forth in SEQ ID NO:51.

In other exemplary embodiments, the single domain antibody comprises a CDRH1 having the amino acid sequence set forth in SEQ ID NO:52, a CDRH2 having the amino acid sequence set forth in SEQ ID NO:53 and a CDRH3 having the amino acid sequence set forth in SEQ ID NO:54.

In other exemplary embodiments, the single domain antibody comprises a CDRH1 having the amino acid sequence set forth in SEQ ID NO:56, a CDRH2 having the amino acid sequence set forth in SEQ ID NO:57 and a CDRH3 having the amino acid sequence set forth in SEQ ID NO:58.

In other exemplary embodiments, the single domain antibody comprises a CDRH1 having the amino acid sequence set forth in SEQ ID NO:59, a CDRH2 having the amino acid sequence set forth in SEQ ID NO:60 and a CDRH3 having the amino acid sequence set forth in SEQ ID NO:61.

In other exemplary embodiments, the single domain antibody comprises a CDRH1 having the amino acid sequence set forth in SEQ ID NO:63, a CDRH2 having the amino acid sequence set forth in SEQ ID NO:64 and a CDRH3 having the amino acid sequence set forth in SEQ ID NO:65.

In other exemplary embodiments, the single domain antibody comprises a CDRH1 having the amino acid sequence set forth in SEQ ID NO:66, a CDRH2 having the amino acid sequence set forth in SEQ ID NO:67 and a CDRH3 having the amino acid sequence set forth in SEQ ID NO:68.

In another exemplary embodiment, the single domain antibody or antigen binding fragment thereof comprises the amino acid sequence of the CDR1 set forth in SEQ ID NO:55, the amino acid sequence of the CDR2 set forth in SEQ ID NO:123 and the amino acid sequence of the CDR3 set forth in SEQ ID NO: 48.

In another exemplary embodiment, the single domain antibody or antigen binding fragment thereof comprises the amino acid sequence of the CDR1 set forth in SEQ ID NO:55, the amino acid sequence of the CDR2 set forth in SEQ ID NO:124 and the amino acid sequence of the CDR3 set forth in SEQ ID NO: 48.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO: 130 and the amino acid sequence of the CDR3 set forth in SEQ ID NO:6.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO: 131 and the amino acid sequence of the CDR3 set forth in SEQ ID NO:6.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO: 132 and the amino acid sequence of the CDR3 set forth in SEQ ID NO:6.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO: 133 and the amino acid sequence of the CDR3 set forth in SEQ ID NO:6.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO: 134 and the amino acid sequence of the CDR3 set forth in SEQ ID NO:6.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO: 135 and the amino acid sequence of the CDR3 set forth in SEQ ID NO:6.

In an exemplary embodiment, the single domain antibody or antigen binding fragment thereof comprises the amino acid sequence of the CDR1 set forth in SEQ ID NO:127, the amino acid sequence of the CDR2 set forth in SEQ ID NO:129 and the amino acid sequence of the CDR3 set forth in SEQ ID NO:6.

In an exemplary embodiment, the single domain antibody or antigen binding fragment thereof comprises the amino acid sequence of the CDR1 set forth in SEQ ID NO:13, the amino acid sequence of the CDR2 set forth in SEQ ID NO:14 and the amino acid sequence of the CDR3 set forth in SEQ ID NO:15.

In an exemplary embodiment, the single domain antibody or antigen binding fragment thereof comprises the amino acid sequence of the CDR1 set forth in SEQ ID NO:13, the amino acid sequence of the CDR2 set forth in SEQ ID NO:136 and the amino acid sequence of the CDR3 set forth in SEQ ID NO:15.

In an exemplary embodiment, the single domain antibody or antigen binding fragment thereof comprises the amino acid sequence of the CDR1 set forth in SEQ ID NO:13, the amino acid sequence of the CDR2 set forth in SEQ ID NO:137 and the amino acid sequence of the CDR3 set forth in SEQ ID NO:15.

In an exemplary embodiment, the single domain antibody or antigen binding fragment thereof comprises the amino acid sequence of the CDR1 set forth in SEQ ID NO:13, the amino acid sequence of the CDR2 set forth in SEQ ID NO:138 and the amino acid sequence of the CDR3 set forth in SEQ ID NO:15.

In an exemplary embodiment, the single domain antibody or antigen binding fragment thereof comprises the amino acid sequence of the CDR1 set forth in SEQ ID NO:13, the amino acid sequence of the CDR2 set forth in SEQ ID NO:139 and the amino acid sequence of the CDR3 set forth in SEQ ID NO:15.

In some embodiments single domain antibody or antigen binding fragment thereof of the present disclosure comprises the CDR1, CDR2, CDR3 and the FR2 amino acid sequence of the single domain antibody disclosed herein.

In another exemplary embodiment, the single domain antibody or antigen binding fragment thereof comprises the amino acid sequence of the CDR1 set forth in SEQ ID NO:52, the amino acid sequence of the CDR2 set forth in SEQ ID NO:53, the amino acid sequence of the CDR3 set forth in SEQ ID NO:54 and the amino acid sequence of the FR2 set forth in SEQ ID NO:116.

In another exemplary embodiment, the single domain antibody or antigen binding fragment thereof comprises the amino acid sequence of the CDR1 set forth in SEQ ID NO:55, the amino acid sequence of the CDR2 set forth in SEQ ID NO:47, the amino acid sequence of the CDR3 set forth in SEQ ID NO:48 and the amino acid sequence of the FR2 set forth in SEQ ID NO:116.

In another exemplary embodiment, the single domain antibody or antigen binding fragment thereof comprises the amino acid sequence of the CDR1 set forth in SEQ ID NO:56, the amino acid sequence of the CDR2 set forth in SEQ ID NO:57, the amino acid sequence of the CDR3 set forth in SEQ ID NO:58 and the amino acid sequence of the FR2 set forth in SEQ ID NO:116.

In another exemplary embodiment, the single domain antibody or antigen binding fragment thereof comprises the amino acid sequence of the CDR1 set forth in SEQ ID NO:59, the amino acid sequence of the CDR2 set forth in SEQ ID NO:60, the amino acid sequence of the CDR3 set forth in SEQ ID NO:61 and the amino acid sequence of the FR2 set forth in SEQ ID NO:116.

In another exemplary embodiment, the single domain antibody or antigen binding fragment thereof comprises the amino acid sequence of the CDR1 set forth in SEQ ID NO:62, the amino acid sequence of the CDR2 set forth in SEQ ID NO:50, the amino acid sequence of the CDR3 set forth in SEQ ID NO:51 and the amino acid sequence of the FR2 set forth in SEQ ID NO:116.

In another exemplary embodiment, the single domain antibody or antigen binding fragment thereof comprises the amino acid sequence of the CDR1 set forth in SEQ ID NO:55, the amino acid sequence of the CDR2 set forth in SEQ ID NO:47, the amino acid sequence of the CDR3 set forth in SEQ ID NO: 48 and the amino acid sequence of the FR2 set forth in SEQ ID NO:116.

In another exemplary embodiment, the single domain antibody or antigen binding fragment thereof comprises the amino acid sequence of the CDR1 set forth in SEQ ID NO:55, the amino acid sequence of the CDR2 set forth in SEQ ID NO:47, the amino acid sequence of the CDR3 set forth in SEQ ID NO: 48 and the amino acid sequence of the FR2 set forth in SEQ ID NO:117.

In another exemplary embodiment, the single domain antibody or antigen binding fragment thereof comprises the amino acid sequence of the CDR1 set forth in SEQ ID NO:55, the amino acid sequence of the CDR2 set forth in SEQ ID NO: 47, the amino acid sequence of the CDR3 set forth in SEQ ID NO: 48 and the amino acid sequence of the FR2 set forth in SEQ ID NO:118.

In another exemplary embodiment, the single domain antibody or antigen binding fragment thereof comprises the amino acid sequence of the CDR1 set forth in SEQ ID NO:55, the amino acid sequence of the CDR2 set forth in SEQ ID NO:47, the amino acid sequence of the CDR3 set forth in SEQ ID NO: 48 and the amino acid sequence of the FR2 set forth in SEQ ID NO:119.

In another exemplary embodiment, the single domain antibody or antigen binding fragment thereof comprises the amino acid sequence of the CDR1 set forth in SEQ ID NO:55, the amino acid sequence of the CDR2 set forth in SEQ ID NO:124, the amino acid sequence of the CDR3 set forth in SEQ ID NO: 48 and the amino acid sequence of the FR2 set forth in SEQ ID NO:117.

In another exemplary embodiment, the single domain antibody or antigen binding fragment thereof comprises the amino acid sequence of the CDR1 set forth in SEQ ID NO:55, the amino acid sequence of the CDR2 set forth in SEQ ID NO:123, the amino acid sequence of the CDR3 set forth in SEQ ID NO: 48 and the amino acid sequence of the FR2 set forth in SEQ ID NO:117.

In another exemplary embodiment, the single domain antibody or antigen binding fragment thereof comprises the amino acid sequence of the CDR1 set forth in SEQ ID NO:62, the amino acid sequence of the CDR2 set forth in SEQ ID NO:50, the amino acid sequence of the CDR3 set forth in SEQ ID NO:51 and the amino acid sequence of the FR2 set forth in SEQ ID NO:116.

In another exemplary embodiment, the single domain antibody or antigen binding fragment thereof comprises the amino acid sequence of the CDR1 set forth in SEQ ID NO:62, the amino acid sequence of the CDR2 set forth in SEQ ID NO:50, the amino acid sequence of the CDR3 set forth in SEQ ID NO:51 and the amino acid sequence of the FR2 set forth in SEQ ID NO:117.

In another exemplary embodiment, the single domain antibody or antigen binding fragment thereof comprises the amino acid sequence of the CDR1 set forth in SEQ ID NO:62, the amino acid sequence of the CDR2 set forth in SEQ ID NO:50, amino acid sequence of the CDR3 set forth in SEQ ID NO:51 and the amino acid sequence of the FR2 set forth in SEQ ID NO:118.

In another exemplary embodiment, the single domain antibody or antigen binding fragment thereof comprises the amino acid sequence of the CDR1 set forth in SEQ ID NO:62, the amino acid sequence of the CDR2 set forth in SEQ ID NO:50, amino acid sequence of the CDR3 set forth in SEQ ID NO:51 and the amino acid sequence of the FR2 set forth in SEQ ID NO:120.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO:5, the amino acid sequence of the CDR3 set forth in SEQ ID NO:6 and the amino acid sequence of the FR2 set forth in SEQ ID NO:170.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO:130, the amino acid sequence of the CDR3 set forth in SEQ ID NO:6 and the amino acid sequence of the FR2 set forth in SEQ ID NO:171.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO:131, the amino acid sequence of the CDR3 set forth in SEQ ID NO:6 and the amino acid sequence of the FR2 set forth in SEQ ID NO:170.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO:133, the amino acid sequence of the CDR3 set forth in SEQ ID NO:6 and the amino acid sequence of the FR2 set forth in SEQ ID NO:170.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO:131, the amino acid sequence of the CDR3 set forth in SEQ ID NO:6 and the amino acid sequence of the FR2 set forth in SEQ ID NO:171.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO:132, the amino acid sequence of the CDR3 set forth in SEQ ID NO:6 and the amino acid sequence of the FR2 set forth in SEQ ID NO:171.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO:133, the amino acid sequence of the CDR3 set forth in SEQ ID NO:6 and the amino acid sequence of the FR2 set forth in SEQ ID NO:171.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO:133, the amino acid sequence of the CDR3 set forth in SEQ ID NO:6 and the amino acid sequence of the FR2 set forth in SEQ ID NO:172.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO:134, the amino acid sequence of the CDR3 set forth in SEQ ID NO:6 and the amino acid sequence of the FR2 set forth in SEQ ID NO:171.

In an exemplary embodiment, the single domain antibody or antigen binding fragment thereof comprises the amino acid sequence of the CDR1 set forth in SEQ ID NO:4, the amino acid sequence of the CDR2 set forth in SEQ ID NO:135, the amino acid sequence of the CDR3 set forth in SEQ ID NO:6 and the amino acid sequence of the FR2 set forth in SEQ ID NO:171.

In an exemplary embodiment, the single domain antibody or antigen binding fragment thereof comprises the amino acid sequence of the CDR1 set forth in SEQ ID NO:127, the amino acid sequence of the CDR2 set forth in SEQ ID NO:129, the amino acid sequence of the CDR3 set forth in SEQ ID NO:6 and the amino acid sequence of the FR2 set forth in SEQ ID NO:174.

In an exemplary embodiment, the single domain antibody or antigen binding fragment thereof comprises the amino acid sequence of the CDR1 set forth in SEQ ID NO:13, the amino acid sequence of the CDR2 set forth in SEQ ID NO:14, the amino acid sequence of the CDR3 set forth in SEQ ID NO:15 and the amino acid sequence of the FR2 set forth in SEQ ID NO:170.

In an exemplary embodiment, the single domain antibody or antigen binding fragment thereof comprises the amino acid sequence of the CDR1 set forth in SEQ ID NO:13, the amino acid sequence of the CDR2 set forth in SEQ ID NO:137, the amino acid sequence of the CDR3 set forth in SEQ ID NO:15 and the amino acid sequence of the FR2 set forth in SEQ ID NO:170.

In an exemplary embodiment, the single domain antibody or antigen binding fragment thereof comprises the amino acid sequence of the CDR1 set forth in SEQ ID NO:13, the amino acid sequence of the CDR2 set forth in SEQ ID NO:138, the amino acid sequence of the CDR3 set forth in SEQ ID NO:15 and the amino acid sequence of the FR2 set forth in SEQ ID NO:170.

In an exemplary embodiment, the single domain antibody or antigen binding fragment thereof comprises the amino acid sequence of the CDR1 set forth in SEQ ID NO:13, the amino acid sequence of the CDR2 set forth in SEQ ID NO:136, the amino acid sequence of the CDR3 set forth in SEQ ID NO:15 and the amino acid sequence of the FR2 set forth in SEQ ID NO:171.

In an exemplary embodiment, the single domain antibody or antigen binding fragment thereof comprises the amino acid sequence of the CDR1 set forth in SEQ ID NO:13 and/or the amino acid sequence of the CDR2 set forth in SEQ ID NO:137, the amino acid sequence of the CDR3 set forth in SEQ ID NO:15 and the amino acid sequence of the FR2 set forth in SEQ ID NO:171.

In an exemplary embodiment, the single domain antibody or antigen binding fragment thereof comprises the amino acid sequence of the CDR1 set forth in SEQ ID NO:13, the amino acid sequence of the CDR2 set forth in SEQ ID NO:138, the amino acid sequence of the CDR3 set forth in SEQ ID NO:15 and the amino acid sequence of the FR2 set forth in SEQ ID NO:171.

In an exemplary embodiment, the single domain antibody or antigen binding fragment thereof comprises the amino acid sequence of the CDR1 set forth in SEQ ID NO:13, the amino acid sequence of the CDR2 set forth in SEQ ID NO:139, the amino acid sequence of the CDR3 set forth in SEQ ID NO:15 and the amino acid sequence of the FR2 set forth in SEQ ID NO:171.

In an exemplary embodiment, the single domain antibody or antigen binding fragment thereof comprises the amino acid sequence of the CDR1 set forth in SEQ ID NO:13, the amino acid sequence of the CDR2 set forth in SEQ ID NO:137, the amino acid sequence of the CDR3 set forth in SEQ ID NO:15 and the amino acid sequence of the FR2 set forth in SEQ ID NO:173.

In another exemplary embodiment, the single domain antibody or antigen binding fragment thereof comprises the variable region of the single domain antibody disclosed herein.

In further exemplary embodiments, the single domain antibody comprises a variable region having an amino acid sequence as set forth in SEQ ID NO:22.

In other exemplary embodiments, the single domain antibody comprises a variable region having an amino acid sequence as set forth in SEQ ID NO:23.

In further exemplary embodiments, the single domain antibody comprises a variable region having an amino acid sequence as set forth in SEQ ID NO:24.

In additional exemplary embodiments, the single domain antibody comprises a variable region having an amino acid sequence as set forth in SEQ ID NO:25.

In other exemplary embodiments, the single domain antibody comprises a variable region having an amino acid sequence as set forth in SEQ ID NO:26.

In further exemplary embodiments, the single domain antibody comprises a variable region having an amino acid sequence as set forth in SEQ ID NO:27.

In yet further exemplary embodiments, the single domain antibody comprises a variable region having an amino acid sequence as set forth in SEQ ID NO:28.

In additional exemplary embodiments, the single domain antibody comprises an amino acid sequence as set forth in SEQ ID NO:29.

In additional exemplary embodiments, the single domain antibody comprises an amino acid sequence as set forth in SEQ ID NO:71.

In additional exemplary embodiments, the single domain antibody comprises an amino acid sequence as set forth in SEQ ID NO:72.

In additional exemplary embodiments, the single domain antibody comprises an amino acid sequence as set forth in SEQ ID NO:73.

In additional exemplary embodiments, the single domain antibody comprises an amino acid sequence as set forth in SEQ ID NO:74.

In additional exemplary embodiments, the single domain antibody comprises an amino acid sequence as set forth in SEQ ID NO:75.

In additional exemplary embodiments, the single domain antibody comprises an amino acid sequence as set forth in SEQ ID NO:76.

In additional exemplary embodiments, the single domain antibody comprises an amino acid sequence as set forth in SEQ ID NO:77.

In additional exemplary embodiments, the single domain antibody comprises an amino acid sequence as set forth in SEQ ID NO:78.

In additional exemplary embodiments, the single domain antibody comprises an amino acid sequence as set forth in SEQ ID NO:79.

In additional exemplary embodiments, the single domain antibody comprises an amino acid sequence as set forth in SEQ ID NO:80.

In additional exemplary embodiments, the single domain antibody comprises an amino acid sequence as set forth in SEQ ID NO:81.

In additional exemplary embodiments, the single domain antibody comprises an amino acid sequence as set forth in SEQ ID NO:82.

In additional exemplary embodiments, the single domain antibody comprises an amino acid sequence as set forth in SEQ ID NO:83.

In additional exemplary embodiments, the single domain antibody comprises an amino acid sequence as set forth in SEQ ID NO:84.

In additional exemplary embodiments, the single domain antibody comprises an amino acid sequence as set forth in SEQ ID NO:85.

In additional exemplary embodiments, the single domain antibody comprises an amino acid sequence as set forth in SEQ ID NO:86.

In additional exemplary embodiments, the single domain antibody comprises an amino acid sequence as set forth in SEQ ID NO:87.

In additional exemplary embodiments, the single domain antibody comprises an amino acid sequence as set forth in SEQ ID NO:88.

In additional exemplary embodiments, the single domain antibody comprises an amino acid sequence as set forth in SEQ ID NO:89.

In additional exemplary embodiments, the single domain antibody comprises an amino acid sequence as set forth in SEQ ID NO:90.

In additional exemplary embodiments, the single domain antibody comprises an amino acid sequence as set forth in SEQ ID NO:91.

In additional exemplary embodiments, the single domain antibody comprises an amino acid sequence as set forth in SEQ ID NO:92.

In additional exemplary embodiments, the single domain antibody comprises an amino acid sequence as set forth in SEQ ID NO:93.

In additional exemplary embodiments, the single domain antibody comprises an amino acid sequence as set forth in SEQ ID NO:94.

In additional exemplary embodiments, the single domain antibody comprises an amino acid sequence as set forth in SEQ ID NO:95.

In additional exemplary embodiments, the single domain antibody comprises an amino acid sequence as set forth in SEQ ID NO:96.

In additional exemplary embodiments, the single domain antibody comprises an amino acid sequence as set forth in SEQ ID NO:97.

In additional exemplary embodiments, the single domain antibody comprises an amino acid sequence as set forth in SEQ ID NO:98.

In additional exemplary embodiments, the single domain antibody comprises an amino acid sequence as set forth in SEQ ID NO:99.

In additional exemplary embodiments, the single domain antibody comprises an amino acid sequence as set forth in SEQ ID NO:100.

In additional exemplary embodiments, the single domain antibody comprises an amino acid sequence as set forth in SEQ ID NO:101.

In additional exemplary embodiments, the single domain antibody comprises an amino acid sequence as set forth in SEQ ID NO:012.

In additional exemplary embodiments, the single domain antibody comprises an amino acid sequence as set forth in SEQ ID NO:103.

In additional exemplary embodiments, the single domain antibody comprises an amino acid sequence as set forth in SEQ ID NO:104.

In additional exemplary embodiments, the single domain antibody comprises an amino acid sequence as set forth in SEQ ID NO:105.

In additional exemplary embodiments, the single domain antibody comprises an amino acid sequence as set forth in SEQ ID NO:106.

In additional exemplary embodiments, the single domain antibody comprises an amino acid sequence as set forth in SEQ ID NO:107.

In additional exemplary embodiments, the single domain antibody comprises an amino acid sequence as set forth in SEQ ID NO:108.

In additional exemplary embodiments, the single domain antibody comprises an amino acid sequence as set forth in SEQ ID NO:109.

In additional exemplary embodiments, the single domain antibody comprises an amino acid sequence as set forth in SEQ ID NO:110.

In additional exemplary embodiments, the single domain antibody comprises an amino acid sequence as set forth in SEQ ID NO:111.

In additional exemplary embodiments, the single domain antibody comprises an amino acid sequence as set forth in SEQ ID NO:112.

In additional exemplary embodiments, the single domain antibody comprises an amino acid sequence as set forth in SEQ ID NO:113.

In additional exemplary embodiments, the single domain antibody comprises an amino acid sequence as set forth in SEQ ID NO:114.

In additional exemplary embodiments, the single domain antibody comprises an amino acid sequence as set forth in SEQ ID NO: 115.

In another exemplary embodiment, the single domain antibody or antigen binding fragment thereof comprises the heavy chain of the single domain antibody disclosed herein.

In exemplary embodiments, the single domain antibody comprises an amino acid sequence as set forth in SEQ ID NO:30.

In yet other exemplary embodiments, the single domain antibody comprises an amino acid sequence as set forth in SEQ ID NO:31.

In further exemplary embodiments, the single domain antibody comprises an amino acid sequence as set forth in SEQ ID NO:32.

In yet further exemplary embodiments, the single domain antibody comprises an amino acid sequence as set forth in SEQ ID NO:33.

In other exemplary embodiments, the single domain antibody that an amino acid sequence as set forth in SEQ ID NO:34.

In other exemplary embodiments, the single domain antibody comprises an amino acid sequence as set forth in SEQ ID NO:35.

In other exemplary embodiments, the single domain antibody comprises an amino acid sequence as set forth in SEQ ID NO:44. In other exemplary embodiments, the single domain antibody comprises an amino acid sequence as set forth in SEQ ID NO:45.

Binding Agents Comprising Antigen Binding Domain(s) of sdAbs

Binding agents of the present disclosure comprise one or more antigen binding domain(s) of an antibody or antigen binding fragment thereof that binds to TROP2. For example, the binding agents of the present disclosure comprise one or more antigen binding domain(s) of a single domain antibody disclosed herein. It is to be understood herein that the following represent exemplary and non-limiting embodiments of binding agents comprising antigen binding domain(s) of single domain antibodies.

In some embodiments, the binding agent of the present disclosure, comprises one or more antigen binding domains that specifically bind to trophoblast cell surface antigen-2 (TROP2). In some embodiments, the binding agent of the present disclosure, comprises one or more antigen binding domains that binds to a different target than TROP2.

Exemplary embodiments of binding agents of the present disclosure include those that comprise one or more antigen binding domains that specifically bind to at least one epitope comprising amino acids of the extracellular domain (ECD) of TROP2. Other exemplary embodiments of binding agents of the present disclosure include those that comprise one or more antigen binding domains that specifically bind to at least one epitope comprising amino acids of the cysteine rich domain of TROP2. In some embodiments, the binding agent comprise one or more antigen binding domains that specifically bind to a TROP2 antigen disclosed herein.

In an embodiment, the binding agent of the present disclosure comprises one or more antigen binding domains that specifically bind to human TROP2. In another embodiment, the binding agent of the present disclosure comprises one or more antigen binding domains that specifically bind to cynomolgus TROP2. In another embodiment, the binding agent of the present disclosure comprises one or more antigen binding domains that specifically bind to Rhesus TROP2.

More particularly, the binding agent of the present disclosure comprises one or more antigen binding domains that specifically bind to the ECD or the CRD of human TROP2.

In other embodiments, the binding agents of the present disclosure comprise one or more antigen binding domain(s) of a native antibody (CDRs, and/or VL and VH) that binds to TROP2.

The CDRs or variable regions (VL and VH) of antibodies and antigen binding fragments thereof may be expressed as a single polypeptide chain to generate single chain Fv (scFV) molecules and variants. Numerous formats are contemplated as indicated below.

As well, the CDRs or variable region of multiple single domain antibodies may be expressed as a single polypeptide chain thereby providing multivalence and/or multispecificity to the binding agent. Moreover, multiple polypeptide chains may be assembled to increase the diversity or avidity of interactions with TROP2. Numerous formats are contemplated as indicated below.

Accordingly, antigen binding fragments or antigen binding domain(s) of the single domain antibodies disclosed herein may be used to generate binding agents that are monospecific, multispecific, monovalent or multivalent.

For example, the variable region or CDRs of a single domain antibody can be fused with a Fc, CH3 or CH2-CH3 domain of an antibody to allow homodimerization thereby generating a multivalent binding agent.

Alternatively, multiple copies of the variable region or CDRs of a single domain antibody can be fused in tandem with required spacers or linkers to generate a multivalent and monospecific binding agent.

For example, the variable regions or CDRs of two single domain antibodies can be fused with a Fc, CH3 or CH2-CH3 domain to allow heterodimerization thereby generating a multivalent and multispecific binding agent.

Alternatively, the variable regions or CDRs of two or more single domain antibodies may be fused in tandem with required spacers or linkers to generate a multivalent and multispecific binding agent.

Binding agents of the present disclosure may have a format of an antibody or antigen binding fragment thereof, an antibody-like molecule (native antibody fused with a single domain antibody or with an antigen binding domain of a sdAb, Fc-, CH3- fusions and the like), a fusion with protein scaffolds, immune cell modulating agents and the like.

Binding agents also include immune cell modulating agents such as for example, dual-affinity retargeting molecules (DARTs), chimeric antigen receptors (CAR) constructs, bispecific T cell engagers construct (BiTEs), bispecific killer cell engagers (BiKEs), trispecific killer cell engagers (TriKEs) containing scFvs or VHHs.

Binding agents also encompass fusion with protein scaffolds, including ankyrin repeat proteins, Z-domain of *Staphylococcus* protein-A, Type-III fibronetin, knottin and the like. Exemplary embodiments of binding agents include monospecific-, bispecifics (symmetric or asymmetric) trispecific-, or multispecific antibodies as well as monovalent, bivalent, trivalent or multivalent antibodies, single chain FVs (scFVs) and derivatives such diabody, triabody, tetrabody, tandem di-scFvs, tandem tri-scFvs, scFV-Fc, minibody (scFV-CH3), tandem diabody, di-diabody, bibody and the like, VH or VHHs and derivatives such as, tandem bispecific or multispecific VHH, bivalent VHH-Fc fusions, VHH-hinge-CH2-CH3 fusions, bivalent CH3 fusions, VHH pentabody, decabody and the like.

A single chain Fv molecule (scFv) comprises a VL domain and a VH domain. The VL and VH domains associate to form a target binding site. These two domains are further covalently linked by a peptide linker (L). A scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. Nos. 4,704,692, 4,946,778, R. Raag and M. Whitlow, "Single Chain Fvs." FASEB Vol 9:73-80 (1995) and R. E. Bird and B. W. Walker, Single Chain Antibody Variable Regions, TIBTECH, Vol 9: 132-137 (1991).

In some embodiments, the binding agents of the present disclosure may have a format as disclosed in PCT/CA2020/051753 filed on Dec. 18, 2020 and published on Jun. 24, 2021 under No. WO2021/119832A1, the entire content of which is incorporated herein by reference) such as for example, as formula Ia, formula Ib, formula Ic, formula II, formula III, formula IV, formula V, formula VI, formula VII or formula VIII and the like or formula I, formula II, formula III, formula IIIa and formula IIIb, formula IV, formula V, formula VI, formula VII or formula VIII disclosed herein.

The binding agents of the present disclosure may be formed by the assembly of two polypeptide chains having the same configuration (with same or different amino acid sequence) or having different configurations where the same or different configurations include the configuration set forth in formula I, formula II, formula III, formula IIIa and formula IIIb, formula IV, formula V, formula VI, formula VII or formula VIII disclosed herein.

In some embodiments, the binding agents of the present disclosure is monospecific. In some embodiments, the binding agents of the present disclosure is multispecific.

The binding agents of the present disclosure (including antibodies or antigen binding fragments thereof) may be monospecific, multispecific, monovalent or multivalent.

A binding agent that comprises two or more antigen binding domains of a single domain antibody is considered multivalent. A multivalent single domain antibody can be monospecific (if all antigen binding domains bind to exactly the same epitope) or multispecific (if the antigen binding domains bind to different epitopes on same target or to different epitopes or targets). A binding agent that comprises only one antigen binding domain is considered monovalent.

Production of binding agents such as antibodies or antigen binding fragments, may involve cloning procedures and recombinant expression. The antigen binding domain sequence (e.g., sequence of the variable light chain and variable heavy chain of an intact antibody or the sequence of the variable heavy chain of a single domain antibody) may be obtained by a variety of molecular cloning procedures, such as RT-PCR, 5'-RACE, and cDNA library screening. The sequence of interest may be cloned into an expression vector(s), the expression vector(s) transfected into cells and the binding agent isolated and/or purified. In the case of an intact antibody, the light chain and the heavy chain can be cloned into a single expression vector or into two separate expression vectors. Co-transfection of the separate expression vectors is necessary for the intact antibody to assemble properly. In the case of a single domain antibody, a single expression vector (expressing the heavy chain) is sufficient.

Monospecific binding agents encompass binding agents that are specific for a single epitope of a given antigen.

An exemplary embodiment of a monospecific binding agent includes a binding agent that comprise one antigen binding fragment of a single domain antibody. Another exemplary embodiment of a monospecific binding agent includes a binding agent that comprise more than one antigen binding fragments of a single domain antibody, but the antigen binding fragments have identical CDRs and framework regions. Yet another exemplary embodiment of a binding agent includes a binding agent that comprise more than one antigen binding fragments of single domain antibodies, but the variable regions have identical CDRs and different framework regions. A further exemplary embodiment of a monospecific binding agent includes a binding agent that comprise antigen binding fragments of single domain antibodies that differ in the amino acid sequence of one or more of their CDRs (e.g., conservative substitution in one or more CDRs) without affecting their ability to bind to the same antigen or epitope.

Multispecific binding agents encompass binding agents that are specific for more than one epitope (of the same antigen or different antigens) or to more than one antigen. For example, a multispecific polypeptide chain or binding agent may thus have more than one variable region of a single domain antibody, at least two of which bind to different antigens or epitopes.

The binding agents of the present disclosure may thus be bispecific, trispecific, tetraspecific, pentaspecific, hexaspecific etc. In some embodiments, each variable region may be specific for a given antigen. In some embodiments, two or more antigen binding fragments of a given binding agent may be specific for the same or different antigens. In some embodiments, three or more antigen binding fragments of a given binding agent may be specific for the same or different antigens. In some embodiments, four or more antigen binding fragments of a given binding agent may be specific for the same or different antigens. In some embodiments, five or more antigen binding fragments of a given binding agent may be specific for the same or different antigens. In some embodiments, six or more antigen binding fragments of a given binding agent may be specific for the same or different antigens. The specificity may depend on the number of antigen binding fragments present in a given binding agent.

Other exemplary non-limiting embodiments of multispecific binding agents include those having two antigen binding fragments of different specificities. Yet other exemplary non-limiting embodiments of multispecific binding agents include those having more than two antigen binding fragments that bind to two different antigens, proteins or to two different epitopes on the same antigens or proteins.

In some embodiments, the binding agent of the present disclosure is monovalent.

In some embodiments, the binding agent of the present disclosure is multivalent.

Exemplary non-limiting embodiments of multivalent binding agents include binding agents composed of multivalent polypeptide chains. Other non-limiting exemplary embodiments of multivalent binding agents include binding agents composed of more than one monovalent polypeptide chain.

In accordance with the present disclosure, a bispecific binding agent may be bivalent or multivalent depending on the number of variable regions that it contains. Exemplary non-limiting embodiments of bispecific binding agents include those comprising two identical bispecific polypeptide chains that form a dimer.

Exemplary and non-limiting embodiments of bispecific binding agents are provided herein.

In some embodiments, the bispecific binding agent comprises an antigen binding domain that binds to TROP2 and comprises formula II (see PCT/CA2020/051753 filed on Dec. 18, 2020, and published on Jun. 24, 2021, under No. WO2021/119832A1 the entire content of which is herein incorporated by reference).

In other embodiments, the binding agent comprises a polypeptide chain that comprises in a N- to C-terminal fashion, a) an antigen binding domain of a single domain antibody, b) a linker, c) a dimerization domain, d) a linker and e) an antigen binding domain of a single domain antibody, at least one of the antigen binding domain of a) or e) is an antigen binding domain that binds to TROP2.

In some embodiments, the antigen binding domain of a) and the antigen binding domain of e) are different.

In some embodiments, the antigen binding domain of a) and the antigen binding domain of e) are the same.

In some embodiments, the linker of b) and the linker of d) are the same.

In some embodiments, the linker of b) and the linker of d) are different.

In an exemplary embodiment, the antigen binding domain of a) comprises an antigen binding domain of a single domain antibody that specifically binds to human TROP2.

In another exemplary embodiment, the antigen binding domain of a) comprises an antigen binding domain of a single domain antibody that specifically binds to CD47 such as for example human CD47.

In an exemplary embodiment, the antigen binding domain of e) comprises an antigen binding domain of a single domain antibody that specifically binds to human TROP2.

In an exemplary embodiment, the antigen binding domain of e) comprises an antigen binding domain of a single domain antibody that specifically binds to CD47, such as for example human CD47.

In some embodiments, the bispecific binding agent comprises two polypeptide chains. The two polypeptide chains are non-covalently assembled by amino acid residues of the CH2 and/or CH3 domain contained therein so as to obtain a bispecific and tetravalent binding agent.

In an exemplary embodiment, the binding agent or antigen binding domain(s) of the present disclosure may be capable of inhibiting the growth of tumor cells expressing human TROP2 and CD47.

In exemplary embodiments, the binding agent comprises one or more antigen binding domains that is capable of binding to CD47.

In another exemplary embodiments, the binding agent comprises one or more antigen binding domains that is capable of binding to TROP2 and one or more antigen binding domains that is capable of binding to CD47.

In an exemplary embodiment, the antigen binding domain that is capable of binding to CD47 comprises:
a. a CDRH1 having the amino acid sequence set forth in SEQ ID NO156, a CDRH2 having the amino acid sequence set forth in SEQ ID NO:157 and a CDRH3 having the amino acid sequence set forth in SEQ ID NO:158, or
b. a CDRH1 having the amino acid sequence set forth in SEQ ID NO159, a CDRH2 having the amino acid sequence set forth in SEQ ID NO:160 and a CDRH3 having the amino acid sequence set forth in SEQ ID NO:161.

In an exemplary embodiment, the antigen binding domain that is capable of binding to CD47 comprises an amino acid sequence as set forth in SEQ ID NO:155.

In an exemplary embodiment, the binding agent is capable of binding to CD47 and TROP2 and comprises an amino acid sequence as set forth in SEQ ID NO:155 and the amino acid sequence of at least one antigen binding domain of at least one single domain antibody disclosed herein.

In other exemplary embodiments, the binding agent is capable of binding to CD47 and TROP2 and comprises an amino acid sequence as set forth in SEQ ID NO:155 and the amino acid sequence of an antigen binding domain of at least one single domain antibody set forth in any one of SEQ ID NOs:22-26 or SEQ ID Nos:73-114.

In another exemplary embodiment, the binding agent is capable of binding to CD47 and TROP2 and comprises an amino acid sequence as set forth in SEQ ID NO:150 or in SEQ ID NO:151.

Variants

Variants of the sequences disclosed herein are also encompassed by the present disclosure.

Binding agent of the present disclosure therefore encompass antibody variants (e.g., single domain antibody variants), variants of antibody-like molecule, variants of protein scaffold, variants of immune cell modulating agent. In addition, binding agents of the present disclosure may comprise an antigen binding fragment or an antigen binding domain of an antibody variant such as an antigen binding fragment or an antigen binding domain of a single domain antibody variant.

The present disclosure more particularly encompasses variants of the single domain antibody disclosed herein as well as binding agents that comprise one or more antigen binding domain of a single domain antibody variant. Variants of the binding agents disclosed herein may have the same format as the binding agent disclosed herein. As such, variants of the binding agents encompassed by the present disclosure may be multispecific and/or multivalent.

Variants encompassed by the present disclosure include those which may comprise an insertion of one or more amino acid residues at one or more position, a deletion of one or more amino acid residues at one or more position or a substitution of one or more amino acid residues at one or more position (conservative or non-conservative substitutions).

For example, naturally occurring residues are divided into groups based on common side chain properties. Conservative substitutions may be made by exchanging an amino acid from one of the groups listed below (group 1 to 6) for another amino acid of the same group. Non-conservative substitutions will entail exchanging a member of one of these groups for another.
(group 1) hydrophobic: norleucine, methionine (Met), Alanine (Ala), Valine (Val), Leucine (Leu), Isoleucine (Ile)
(group 2) neutral hydrophilic: Cysteine (Cys), Serine (Ser), Threonine (Thr), Asparagine (Asn), Glutamine (Gln),
(group 3) acidic: Aspartic acid (Asp), Glutamic acid (Glu)
(group 4) basic: Histidine (His), Lysine (Lys), Arginine (Arg)
(group 5) residues that influence chain orientation: Glycine (Gly), Proline (Pro); and
(group 6) aromatic: Tryptophan (Trp), Tyrosine (Tyr), Phenylalanine (Phe)

Other exemplary embodiments of conservative substitutions are shown in Table 2 under the heading of "preferred substitutions". If such substitutions result in an undesired property, then more substantial changes, denominated "exemplary substitutions" in Table 2, or as further described below in reference to amino acid classes, may be introduced and the products screened.

One of skill in the art will recognize that certain amino acids are less positively charged, are neutral, are negatively charged or have a reduced charge in comparison to other amino acids. Amino acids can be categorized based on net charge as indicated by an amino acid's isoelectric point. The isoelectric point is the pH at which the average net charge of the amino acid molecule is zero. When pH>pI, an amino acid has a net negative charge, and when the pH<pI, an amino acid has a net positive charge. In some embodiments, the measured pI value for an antibody is between about 3 and 9 (e.g. 3.0, 3.5, 4.0, 4.5, 5.0, 5.5, 6.0, 6.5, 7.0, 7.5, 8.0, 8.1, 8.2, 8.3, 8.4, 8.5, and 9) and any values in between. In some embodiments, the measured pI value for an antibody is between about 4 and 7 (e.g. 4.0, 4.5, 5.0, 5.5, 6.0, 6.5, 7.0), and any values in between. Exemplary isoelectric points of amino acids are shown in Table 2 below. Generally amino acids with positive electrically charged side chains include, for example, Arginine (R), Histidine (H), and Lysine (K). Amino acids with negative electrically charged side chains include, for example, Aspartic Acid (D) and Glutamic Acid (E). Amino acids with polar properties include, for example, Serine (S), Threonine (T), Asparagine (N), Glutamine (Q), and Cysteine (C), Tyrosine (Y) and Tryptophan (W). Non-polar amino acids include, for example, Alanine (A), Valine (V), Isoleucine (I), Leucine (L), Methionine (M), Phenylalanine (F), Glycine (G) and Proline (P).

In some embodiments, the isoelectric point of an antibody is modified via amino acid substitution. See, e.g. US20110076275. In some embodiments, modifying the isoelectric point of a polypeptide comprising an antibody results in a change in the antibody's half-life.

TABLE 2

Exemplary amino acid substitutions

| Original residue | Exemplary substitution | Conservative substitution | pI (isoelectric point) |
|---|---|---|---|
| Ala (A) | Val, Leu, Ile | Val | 6.0 |
| Arg (R) | Lys, Gln, Asn | Lys | 10.76 |
| Asn (N) | Gln, His, Lys, Arg, Asp | Gln | 5.41 |
| Asp (D) | Glu, Asn | Glu | 2.77 |
| Cys (C) | Ser, Ala | Ser | 5.07 |
| Gln (Q) | Asn; Glu | Asn | 5.65 |
| Glu (E) | Asp, Gln | Asp | 3.22 |
| Gly (G) | Ala | Ala | 5.97 |
| His (H) | Asn, Gln, Lys, Arg, | Arg | 7.59 |
| Ile (I) | Leu, Val, Met, Ala, Phe, norleucine | Leu | 6.02 |
| Leu (L) | Norleucine, Ile, Val, Met, Ala, Phe | Ile | 5.98 |
| Lys (K) | Arg, Gln, Asn | Arg | 9.74 |
| Met (M) | Leu, Phe, Ile | Leu | 5.74 |
| Phe (F) | Leu, Val, Ile, Ala, Tyr | Tyr | 5.48 |
| Pro (P) | Ala | Ala | 6.30 |
| Ser (S) | Thr | Thr | 5.58 |
| Thr (T) | Ser | Ser | 5.60 |
| Trp (W) | Tyr, Phe | Tyr | 5.89 |
| Tyr (Y) | Trp, Phe, Thr, Ser | Phe | 5.66 |
| Val (V) | Ile, Leu, Met, Phe, Ala, norleucine | Leu | 5.96 |

Generally, the degree of similarity and identity between variable chains is determined herein using the Blast2 sequence program (Tatiana A. Tatusova, Thomas L. Madden (1999), "Blast 2 sequences—a new tool for comparing protein and nucleotide sequences", FEMS Microbiol Lett. 174:247-250) using default settings, i.e., blastp program, BLOSUM62 matrix (open gap 11 and extension gap penalty 1; gapx dropoff 50, expect 10.0, word size 3) and activated filters.

Percent identity will therefore be indicative of amino acids which are identical in comparison with the original peptide and which may occupy the same or similar position.

Percent similarity will be indicative of amino acids which are identical and those which are replaced with conservative amino acid substitution in comparison with the original peptide at the same or similar position.

Variants of the present disclosure may therefore comprise a sequence that is at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% identical with that of an original or reference sequence or a portion of an original sequence.

In an exemplary embodiment, mutations in one or more CDRs, variable region or constant region may be performed by amino acid substitution. Exemplary embodiments of substitutions include conservative amino acid substitutions or non-conservative amino acid substitutions. Exemplary substitutions are provided in Table 2. Other exemplary substitutions are provided in Table 13. Yet other exemplary substitutions are provided in Table 14.

In some embodiments, polypeptide chains having an amino acid sequence which is at least 75%, 80% 85%, 90%, 95%, 99% identical or less than 100% identical to a given amino acid sequence, may have amino acid substitutions, additions or deletions that are generally located outside of the complementarity determining regions.

In some embodiments, a variant may have at least 80% sequence identity with a sequence disclosed herein. In other embodiments, a variant may have at least 85% sequence identity with a sequence disclosed herein. In yet embodiments, a variant may have at least 90% sequence identity with a sequence disclosed herein. In further embodiments, a variant may have at least 95% sequence identity with a sequence disclosed herein. In other embodiments, a variant may have at least 99% sequence identity with a sequence disclosed herein.

In some embodiments, variation may occur in one or more CDR. The mutations may occur for example, in CDR amino acid residues that are not involved in the interaction with TROP2. In an exemplary embodiment, amino acid residues of CDR1 and/or CDR2 may be mutated. In other exemplary embodiments, amino acid residues of CDR3 may be mutated. CDR mutations that improve affinity with TROP2 are particularly contemplated.

In other embodiments, variation may occur in the framework regions. The mutations may occur for example, in the framework amino acid residues that are not involved in the interaction with TROP2. In an exemplary embodiment, amino acid residues of FR1 and FR3 and/or FR4 may be mutated. In other exemplary embodiments, amino acid residues of FR2 may be mutated. FR2 mutations that improve affinity with TROP2 are particularly contemplated.

In other embodiments, the variations may occur in the constant region. In an exemplary embodiment, the constant region may be mutated so as to modulate ADCC activity. In another exemplary embodiment, the constant region may be mutated so as to modulate ADCP activity. In another exemplary embodiment, the constant region may be mutated so as to improve ADCP activity. In yet other exemplary embodiments, the constant region may be mutated so as to improve internalization. In yet other exemplary embodiment, the constant region may be mutated so as to improve stability.

Exemplary and non-limiting embodiments of mutations in the constant region (e.g., Fc region) that improves one or more effector function are encompassed by the present disclosure, exemplary embodiments of which, are provided in the Table A (List of Mutations Antibodies (Basel). 2020 Nov. 17; 9(4):64, the entire content of which is incorporated herein by reference).

TABLE A

| Fc Modification(s) | | Effector Function vs. WT | | |
|---|---|---|---|---|
| | ID | ADCC | ADCP | Reference |
| S298A/E333A/K334A | AAA | + | n.d. | R. J. Biol. Chem. 2001, 276, 6591-6604. |
| S239D/I332E | DE | ++ | + | Proc. Natl. Acad. Sci. USA 2006, 103, 4005-401 |
| S239D/A330L/I332E | DLE | +++ | + | Proc. Natl. Acad. Sci. USA 2006, 103, 4005-401 |
| G236A | G236A | − | + | Mol. Cancer Ther. 2008, 7, 2517-2527. |
| G236A/S239D/I332E | ADE | + | + | Mol. Cancer Ther. 2008, 7, 2517-2527. |
| F243L/R292P/Y300L/V305I/P396L | LPLIL | ++ | n.d. | Cancer Res. 2007, 67, 8882-8890. |
| L235V/F243L/R292P/Y300L/P396L | VLPLL | + | n.d. | Breast Cancer Res. 2011, 13, R123. |
| P247I/A339Q | | ++ | | Immunol. Cell Biol. 2020, 98, 287-304. |
| Afucosylation (Potelligent)* | Potelligent | ++ | n.d. | Biotechnol. Bioeng. 2004, 87, 614-622. |

*POTELLIGENT Technology involves the reduction of the amount of fucose in the carbohydrate structure of an antibody using a proprietary fucosyl transferase-knockout CHO cell line.
−: no change;
+: 2 fold increase;
++: 2-9.99 fold increase;
+++: 10-99.99;
nd: no data.

Exemplary and non-limiting embodiments of single domain antibody variants are provided herein. Binding agents comprising one or more antigen binding domain(s) of one or more single domain antibody variants are also encompassed by the present disclosure.

In an aspect of the present disclosure, single domain antibody variants include those having the amino acid sequence set forth in SEQ ID NO: 143-146.

In accordance with the present disclosure, the single domain antibody or antigen binding fragment thereof comprises the amino acid sequence set forth in SEQ ID NO: 143.

(KD002 consensus)

SEQ ID NO: 143

$X_{1a}$VQLX$_{1b}$ESGGGX$_{1c}$VQX$_{1d}$GGSLRLSCAASGFPFSSADMSWVRQAPG

KX$_{1e}$X$_{1f}$EWVSX$_{1g}$INAX$_{1h}$GSKTYYX$_{1i}$DX$_{1j}$VKGRFTISRDNX$_{1k}$KNT

LYLX$_{1l}$MNX$_{1m}$LX$_{1n}$X$_{1o}$EDTAX$_{1p}$YX$_{1q}$CARAKLTDTHYVEDYWGQGT

X$_{1r}$VTVSS.

In an exemplary embodiment, any of $X_{1a}$ to $X_{1r}$ is each independently any (e.g., naturally occurring) amino acid residue.

In another exemplary embodiment, any of $X_{1a}$ to $X_{1r}$ is each independently an amino acid residue found at a corresponding position in any one of SEQ ID NO:23 or SEQ ID NOs:73-93, or conservative amino acid substitutions or non-conservative amino acid substitutions thereof.

In yet in another exemplary embodiment, any of $X_{1a}$ to $X_{1r}$ is each independently an amino acid residue found at a corresponding position in any one of SEQ ID NO:22, SEQ ID NO:23, SEQ ID NO:24, SEQ ID NO:25 or SEQ ID NO:26 or conservative amino acid substitutions or non-conservative amino acid substitutions thereof.

In a further exemplary embodiment, any $X_{1a}$ to $X_{1r}$ is each independently an amino acid residue most frequently found at a corresponding position in any one of SEQ ID NO:23 or SEQ ID Nos:73-93.

In another exemplary embodiment, any $X_{1a}$ to $X_{1r}$ is each independently an amino acid residue most frequently found at a corresponding position in any one of SEQ ID NO:22, SEQ ID NO:23, SEQ ID NO:24, SEQ ID NO:25 to SEQ ID NO:26.

In yet another exemplary embodiment, any of $X_{1a}$ to $X_{1r}$ is each independently an amino acid residue found at a corresponding position in any one of SEQ ID NOs: 73, 75, 76, 77, 78, 81, 82, 83, 85, 89 or 91, or conservative amino acid substitutions or non-conservative amino acid substitutions thereof.

In a further exemplary embodiment, any $X_{1a}$ to $X_{1r}$ is each independently an amino acid residue most frequently found at a corresponding position in any one of SEQ ID NOs: 73, 75, 76, 77, 78, 81, 82, 83, 85, 89 or 91.

In yet a further exemplary embodiment $X_{1a}$ is Q or E; $X_{1b}$ is Q, V or L; $X_{1c}$ is M or L; $X_{1d}$ is V or P; $X_{1e}$ is G or Q; $X_{1f}$ is P, L or R; $X_{1g}$ is Y or V; $X_{1h}$ is D, N, E; $X_{1i}$ is P or A; $X_{1j}$ is S or T; $X_{1k}$ is A or S; $X_{1l}$ is L or Q; $X_{1m}$ is N or S; $X_{1n}$ is K or R; $X_{1o}$ is P or A; $X_{1p}$ is L or V; $X_{1q}$ is R or Y; and/or $X_{1r}$ is Q or M.

In another exemplary embodiment $X_{1a}$ is Q or E; $X_{1b}$ is Q, V or L; $X_{1c}$ is M or L; $X_{1d}$ is V or P; $X_{1e}$ is G or Q; $X_{1f}$ is P, L or R; $X_{1g}$ is Y; $X_{1h}$ is D, $X_{1i}$ is P or A; $X_{1j}$ is S or T; $X_{1k}$ is A or S; $X_{1l}$ is L or Q; $X_{1m}$ is N or S; $X_{1n}$ is K or R; $X_{1o}$ is P or A; $X_{1p}$ is L or V; $X_{1q}$ is R or Y; and/or $X_{1r}$ is Q or M.

In accordance with the present disclosure, the single domain antibody or antigen binding fragment thereof comprises the amino acid sequence set forth in SEQ ID NO:144.

(KD005 consensus)

SEQ ID NO: 144

$X_{2a}$VQLX$_{2b}$ESGGGLX$_{2c}$X$_{2d}$X$_{2e}$GGSLRLSCAASGFTFSGSDMSWVRQA

PGKGX$_{2f}$EWVSX$_{2g}$ITSGGTTYYX$_{2h}$DX$_{2i}$VKGRFTISRDNX$_{2j}$KNTLYL

QMNSLX$_{2k}$X$_{2l}$X$_{2m}$DTAX$_{2n}$YX$_{2o}$CAKSRLTDSHYVEDAWGQGTX$_{2p}$VTV

SS

In an exemplary embodiment, any of $X_{2a}$ to $X_{2p}$ is each independently any (e.g., naturally occurring) amino acid residue.

In another exemplary embodiment, any of $X_{2a}$ to $X_{2p}$ is each independently an amino acid residue found at a corresponding position in any one of SEQ ID NO:26 or SEQ ID NO:94-114 or conservative amino acid substitutions or non-conservative amino acid substitutions thereof.

In another exemplary embodiment, any of $X_{2a}$ to $X_{2p}$ is each independently an amino acid residue found at a corresponding position in any one of SEQ ID NO:22, SEQ ID NO:23, SEQ ID NO:24, SEQ ID NO:25 or SEQ ID NO:26 or conservative amino acid substitutions or non-conservative amino acid substitutions thereof.

In yet another exemplary embodiment, any $X_{2a}$ to $X_{2p}$ is each independently an amino acid residue most frequently found at a corresponding position in any one of SEQ ID NO:26 or SEQ ID NO:94-114.

In a further exemplary embodiment, any $X_{2a}$ to $X_{2p}$ is each independently an amino acid residue most frequently found at a corresponding position in any one of SEQ ID NO:22, SEQ ID NO:23, SEQ ID NO:24, SEQ ID NO:25 to SEQ ID NO:26.

In yet a further exemplary embodiment, any of $X_{2a}$ to $X_{2p}$ is each independently an amino acid residue found at a corresponding position in any one of SEQ ID NOs: 94, 95, 96, 97, 98, 100, 101, 102, 103, 104, 105, 106, 107 or 108 or conservative amino acid substitutions or non-conservative amino acid substitutions thereof.

In an additional exemplary embodiment, any $X_{2a}$ to $X_{2p}$ is each independently an amino acid residue most frequently found at a corresponding position in any one of SEQ ID NOs: 94, 95, 96, 97, 98, 100, 101, 102, 103, 104, 105, 106, 107 or 108.

In another exemplary embodiment, any of $X_{2a}$ to $X_{2p}$ is each independently an amino acid residue found at a corresponding position in any one of SEQ ID NOs: 94, 95, 96, 97, 100, 102, 103, 104, 105, 106, 108, 112 or 114 or conservative amino acid substitutions or non-conservative amino acid substitutions thereof.

In a further exemplary embodiment, any $X_{2a}$ to $X_{2p}$ is each independently an amino acid residue most frequently found at a corresponding position in any one of SEQ ID NOs: 94, 95, 96, 97, 100, 102, 103, 104, 105, 106, 108, 112 or 114.

In yet a further exemplary embodiment, any of $X_{2a}$ to $X_{2p}$ is each independently an amino acid residue found at a corresponding position in any one of SEQ ID NOs: 94, 95, 96, 97, 98, 99, 100, 101, 102, 104, 105, 112, 113 or 114 or conservative amino acid substitutions or non-conservative amino acid substitutions thereof.

In another exemplary embodiment, any $X_{2a}$ to $X_{2p}$ is each independently an amino acid residue most frequently found at a corresponding position in any one of SEQ ID NOs: 94, 95, 96, 97, 98, 99, 100, 101, 102, 104, 105, 112, 113 or 114.

In another exemplary embodiment, any of $X_{2a}$ to $X_{2p}$ is each independently an amino acid residue found at a corresponding position in any one of SEQ ID NOs: 94, 95, 96, 97, 102 or 105 or conservative amino acid substitutions or non-conservative amino acid substitutions thereof. In an additional exemplary embodiment, any $X_{2a}$ to $X_{2p}$ is each independently an amino acid residue most frequently found at a corresponding position in any one of SEQ ID NOs: 94, 95, 96, 97, 102 or 105.

In another exemplary embodiment, $X_{2a}$ is Q or E; $X_{2b}$ is Q, L or V; $X_{2c}$ is V or I; $X_{2d}$ is E or Q; $X_{2e}$ is A or P; $X_{2f}$ is P, or L; $X_{2g}$ is Y, A or V; $X_{2h}$ is P or A; $X_{2i}$ is S or T; $X_{2j}$ is A or S; $X_{2k}$ is K or R; $X_{2l}$ is P or A; $X_{2m}$ is D or E; $X_{2n}$ is L or V; $X_{2o}$ is R or Y and/or $X_{2p}$ is Q or L.

In yet another exemplary embodiment, $X_{2a}$ is Q or E; $X_{2b}$ is Q or L; $X_{2c}$ is V or I; $X_{2d}$ is E or Q; $X_{2e}$ is A or P; $X_{2f}$ is P, or L; $X_{2g}$ is Y or A; $X_{2h}$ is P or A; $X_{2i}$ is S or T; $X_{2j}$ is A or S; $X_{2k}$ is K or R; $X_{2l}$ is P or A; $X_{2m}$ is D or E; $X_{2n}$ is L or V; $X_{2o}$ is R or Y and/or $X_{2p}$ is Q or L.

In accordance with the present disclosure, the single domain antibody or antigen binding fragment thereof comprises the amino acid sequence set forth in SEQ ID NO:145.

```
(Consensus from KD001 to KD005
heavy chain)
                                         SEQ ID NO: 145
QVQLQESGGGX₃ₐVX₃bX₃cGX₃dSLRLSCAASGFX₃eFSX₃fX₃gDMSW

VRQAPGKGPEWVSYIX₃ₕX₃ᵢX₃ⱼX₃ₖX₃ₗX₃ₘTX₃ₙYPDSVKGRFTX₃ₒ

SRDNAKNX₃ₚLYLX₃qMNX₃ᵣLX₃ₛPX₃ₜDTALYRCAX₃ᵤX₃ᵥX₃wLTD

X₃ₓHYVEDX₃ᵧWGQGTQVTVSS
```

In an exemplary embodiment any of $X_{3a}$ to $X_{3y}$ is each independently any (e.g., naturally occurring) amino acid residue.

In another exemplary embodiment, any of $X_{3a}$ to $X_{3y}$ is each independently an amino acid residue found at a corresponding position in any one of SEQ ID NO:22, SEQ ID NO:23, SEQ ID NO:24, SEQ ID NO:25 or SEQ ID NO:26 or conservative amino acid substitutions or non-conservative amino acid substitutions thereof.

In yet another exemplary embodiment, any of $X_{3a}$ to $X_{3y}$ is each independently an amino acid residue most frequently found in the group consisting of SEQ ID NO:22, SEQ ID NO:23, SEQ ID NO:24, SEQ ID NO:25 to SEQ ID NO:26.

In a further exemplary embodiment, $X_{3a}$ is M or L; $X_{3b}$ is Q, H or E; $X_{3c}$ is V, P or A; $X_{3d}$ is G or R; $X_{3e}$ is P or T; $X_{3f}$ is S, N or G; $X_{3g}$ is A, Y or S; $X_{3h}$ is N or T; $X_{3i}$ is A, S or G; $X_{3j}$ is D, G or S; $X_{3k}$ is G or absent; $X_{3l}$ is S or G; $X_{3m}$ is K, N or T; $X_{3n}$ is Y or D; $X_{3o}$ is I or T; $X_{3p}$ is T or M; $X_{3q}$ is L or Q; $X_{3r}$ is N or S; $X_{3s}$ is K or T; $X_{3t}$ is E or D; $X_{3u}$ is R or K; $X_{3v}$ is A or S; $X_{3w}$ is K or R; $X_{3x}$ is T or S; and/or $X_{3y}$ is Y or A.

In yet a further exemplary embodiment, $X_{3a}$ is M or L; $X_{3b}$ is Q, H or E; $X_{3c}$ is V, P or A; $X_{3d}$ is G or R; $X_{3e}$ is P or T; $X_{3f}$ is S, N or G; $X_{3g}$ is A, Y or S; $X_{3h}$ is N or T; $X_{3i}$ is A, S or G; $X_{3j}$ is D, G or S; $X_{3k}$ is G or absent; $X_{3l}$ is S or G; $X_{3m}$ is K, N or T; $X_{3n}$ is Y; $X_{3o}$ is I or T; $X_{3p}$ is T or M; $X_{3q}$ is L or Q; $X_{3r}$ is N or S; $X_{3s}$ is K or T; $X_{31}$ is E or D; $X_{3u}$ is R or K; $X_{3v}$ is A or S; $X_{3w}$ is R; $X_{3x}$ is S; and/or $X_{3y}$ is A.

In accordance with the present disclosure, the single domain antibody or antigen binding fragment thereof comprises the amino acid sequence set forth in SEQ ID NO:146.

```
(Consensus for KD001-KD005 and selected
variants heavy chains)
                                         SEQ ID NO: 146
X₄ₐVQLX₄bESGGGX₄cX₄dX₄eX₄fGX₄gSLRLSCAASGFX₄ₕFSX₄ᵢ

X₄ⱼDMX₄ₖWX₄ₗRQAPGKX₄ₘX₄ₙX₄ₒWVSX₄ₚIX₄qX₄ᵣX₄ₛGX₄ₜX₄ᵤ

TX₄ᵥYX₄wDX₄ₓVKGRFTX₄ᵧSRDNX₄zKNX₅ₐLYLX₅bMNX₅cLX₅d

X₅ₑX₅fDTAX₅gYX₅ₕCAX₅ᵢX₅ⱼX₅ₖLTDX₅ₗHYVEDX₅ₘWGQGTX₅ₙV

TVSS.
```

In an exemplary embodiment, any of $X_{4a}$ to $X_{5n}$ is each independently any (e.g., naturally occurring) amino acid residue.

In another exemplary embodiment, any of $X_{4a}$ to $X_{5n}$ is each independently an amino acid residue found at a corresponding position in any one of SEQ ID NOs:22-26, SEQ ID Nos:73-114 or conservative amino acid substitutions or non-conservative amino acid substitutions thereof.

In yet another exemplary embodiment, any of $X_{4a}$ to $X_{5n}$ is each independently an amino acid residue found at a corresponding position in any one of SEQ ID NO:22, SEQ ID NO:23, SEQ ID NO:24, SEQ ID NO:25 or SEQ ID NO:26 or conservative amino acid substitutions or non-conservative amino acid substitutions thereof.

In another exemplary embodiment, any of $X_{4a}$ to $X_{5n}$ is each independently an amino acid residue most frequently found at a corresponding position in any one of SEQ ID NOs:22-26, SEQ ID Nos:73-114.

In another exemplary embodiment, any of $X_{4a}$ to $X_{5n}$ is each independently an amino acid residue most frequently found at a corresponding position in any one of SEQ ID NO:22, SEQ ID NO:23, SEQ ID NO:24, SEQ ID NO:25 to SEQ ID NO:26.

In a further exemplary embodiment, $X_{4a}$ is Q or E, $X_{4b}$ is Q, L or V, $X_{4c}$ is M or L, $X_{4d}$ is V or I, $X_{4e}$ is Q, H or E, $X_{4f}$ is P, A or V, $X_{4g}$ is G or R, $X_{4h}$ is P or T, $X_{4i}$ is G, S or N, $X_{4j}$ is A or S, $X_{4k}$ is S or H, $X_{4l}$ is V or Y, $X_{4m}$ is G or Q, $X_{4n}$ is P, L or R, $X_{4o}$ is E or V, $X_{4p}$ is Y, A or R, $X_{4q}$ is T or N, $X_{4r}$ is A, S or G, $X_{4s}$ is G, S, D, N or E, $X_{4t}$ is absent or S, $X_{4u}$ is K or T, $X_{4v}$ is Y, D or S, $X_{4w}$ is P or A, $X_{4x}$ is S or T, $X_{4y}$ is I or T, $X_{4z}$ is S or A $X_{5a}$ is T or M $X_{5b}$ is Q or L, $X_{5c}$ is S or N, $X_{5d}$ is K, R or T, $X_{5e}$ is P or A, $X_{5f}$ is E or D, $X_{5g}$ is V or L, $X_{5h}$ is Y or R, $X_{5i}$ is R or K, $X_{5j}$ is A or S, $X_{5k}$ is K or R, $X_{5l}$ is S or T, $X_{5m}$ is Y or A, and/or $X_{5n}$ is Q, L or M.

In an exemplary embodiment, the single domain antibody or antigen binding fragment thereof may have the amino acid sequence as defined in any one of SEQ ID NOs: 143 to 146, wherein the amino acid sequence of the CDR3 is as set forth in SEQ ID NO: 126.

In an exemplary embodiment, the single domain antibody or antigen binding fragment thereof may have the amino acid sequence as defined in any one of SEQ ID NOs: 143 to 146, wherein the amino acid sequence of the CDR3 is as set forth in SEQ ID NO:126 and the amino acid sequence of the FR2 is as set forth in SEQ ID NO:121. In accordance with the present disclosure, the amino acid sequence of the CDR3 and the amino acid sequence of the FR2 are on a same polypeptide chain. Alternatively, in accordance with the present disclosure, the amino acid sequence of the CDR3 and the amino acid sequence of the FR2 are on separate polypeptide chains.

In an exemplary embodiment, the single domain antibody or antigen binding fragment thereof may have the amino acid sequence as defined in any one of SEQ ID NOs: 143 to 146, wherein the CDR3 amino acid sequence is as set forth in SEQ ID NO:48, SEQ ID NO:51, SEQ ID NO:54 or SEQ ID NO:61.

In an exemplary embodiment, the single domain antibody or antigen binding fragment thereof may have the amino acid sequence as defined in any one of SEQ ID NOs: 143 to 146, wherein the FR2 amino acid sequence is as set forth in SEQ ID NO:116, SEQ ID NO:117, SEQ ID NO:118, SEQ ID NO:119 or SEQ ID NO:120.

In an exemplary embodiment, the single domain antibody or antigen binding fragment thereof may have the amino acid sequence as defined in any one of SEQ ID NOs: 143 to 146, wherein the amino acid sequence of the CDR1 is as set forth in SEQ ID NO: 122.

In an exemplary embodiment, the single domain antibody or antigen binding fragment thereof may have the amino acid sequence as defined in any one of SEQ ID NOs: 143 to 146, wherein the CDR1 amino acid sequence is as set forth in SEQ ID NO:52, SEQ ID NO:55 or SEQ ID NO:56.

In an exemplary embodiment, the single domain antibody or antigen binding fragment thereof may have the amino acid sequence as defined in any one of SEQ ID NOs: 143 to 146, wherein the amino acid sequence of the CDR2 is as set forth in SEQ ID NO:125.

In an exemplary embodiment, the single domain antibody or antigen binding fragment thereof may have the amino acid sequence as defined in any one of SEQ ID NOs: 143 to 146, wherein the CDR2 amino acid sequence is as set forth in SEQ ID NO:47, SEQ ID NO:50, SEQ ID NO:57, SEQ ID NO:60, SEQ ID NO:123 or SEQ ID NO:124.

In an exemplary embodiment, the single domain antibody or antigen binding fragment thereof may have the amino acid sequence as defined in any one of SEQ ID NOs: 143 to 146, wherein the amino acid sequence of the CDR3 is as set forth in any one of SEQ ID NO:48, SEQ ID NO:51, SEQ ID NO:54, SEQ ID NO:58 or SEQ ID NO:61 and the amino acid sequence of the FR2 is as set forth in any one of SEQ ID NO:116, SEQ ID NO:117, SEQ ID NO:118, SEQ ID NO:119 or SEQ ID NO:120.

In an exemplary embodiment, the single domain antibody or antigen binding fragment thereof may have the amino acid sequence as defined in any one of SEQ ID NOs: 143 to 146, wherein the amino acid sequence of the CDR3 is as set forth in any one of SEQ ID NO:48, SEQ ID NO:51, SEQ ID NO:54, SEQ ID NO:58 or SEQ ID NO:61, the amino acid sequence of the FR2 is as set forth in any one of SEQ ID NO:116, SEQ ID NO:117, SEQ ID NO:118, SEQ ID NO:119 or SEQ ID NO:120, the amino acid sequence of the CDR1 is as set forth in any one of SEQ ID NO: 52, SEQ ID NO: 55, SEQ ID NO:59, SEQ ID NO: 52 or SEQ ID NO: 62 and the amino acid sequence of the CDR2 is as set forth in any one of SEQ ID NO: 47, SEQ ID NO:50, SEQ ID NO:53, SEQ ID NO: 57, SEQ ID NO: 60, SEQ ID NO:123 or SEQ ID NO: 124.

In an exemplary embodiment, the single domain antibody or antigen binding fragment thereof may have the amino acid sequence as defined in any one of SEQ ID NOs: 143 to 146, wherein the amino acid sequence of the CDR3 is as set forth in SEQ ID NO: 142.

In an exemplary embodiment, the single domain antibody or antigen binding fragment thereof may have the amino acid sequence as defined in any one of SEQ ID NOs: 143 to 146, wherein the amino acid sequence of the FR2 is as set forth in SEQ ID NO:175.

In an exemplary embodiment, the single domain antibody or antigen binding fragment thereof may have the amino acid sequence as defined in any one of SEQ ID NOs: 143 to 146, wherein the amino acid sequence of the CDR3 is as set forth in SEQ ID NO:142 and the amino acid sequence of the FR2 is as set forth in SEQ ID NO:175.

In an exemplary embodiment, the single domain antibody or antigen binding fragment thereof may have the amino acid sequence as defined in any one of SEQ ID NOs: 143 to 146, wherein the CDR3 amino acid sequence is as set forth in SEQ ID NO:3, SEQ ID NO:6, SEQ ID NO:12, SEQ ID NO:15 or SEQ ID NO:141.

In an exemplary embodiment, the single domain antibody or antigen binding fragment thereof may have the amino acid sequence as defined in any one of SEQ ID NOs: 143 to 146, wherein the FR2 amino acid sequence is as set forth SEQ ID NO:170, SEQ ID NO:171, SEQ ID NO:172, SEQ ID NO:173 or SEQ ID NO:174. In a specific embodiment, the amino acid sequence of the FR2 is as set forth in SEQ ID NO:170 or SEQ ID NO:171.

In an exemplary embodiment, the single domain antibody or antigen binding fragment thereof may have the amino acid sequence as defined in any one of SEQ ID NOs: 143 to 146, wherein the amino acid sequence of the CDR1 is as set forth in SEQ ID NO:128.

In an exemplary embodiment, the single domain antibody or antigen binding fragment thereof may have the amino acid sequence as defined in any one of SEQ ID NOs: 143 to 146, wherein the CDR1 amino acid sequence is as set forth in SEQ ID NO:1, SEQ ID NO:4, SEQ ID NO:7 or SEQ ID NO:127.

In an exemplary embodiment, the single domain antibody or antigen binding fragment thereof may have the amino acid sequence as defined in any one of SEQ ID NOs: 143 to 146, wherein the amino acid sequence of the CDR2 is as set forth in SEQ ID NO: 140.

In an exemplary embodiment, the single domain antibody or antigen binding fragment thereof may have the amino acid sequence as defined in any one of SEQ ID NOs: 143 to 146, wherein the CDR2 amino acid sequence is as set forth in SEQ ID NO:2, SEQ ID NO:5, SEQ ID NO:8, SEQ ID NO:11, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138 or SEQ ID NO:139.

In an exemplary embodiment, the single domain antibody or antigen binding fragment thereof may have the amino acid sequence as defined in any one of SEQ ID NOs: 143 to 146, wherein the amino acid sequence of the CDR3 is as set forth in any one of SEQ ID NO:3, SEQ ID NO:6, SEQ ID NO:12, SEQ ID NO:15 or SEQ ID NO:141 and the amino acid sequence of the FR2 is as set forth in any one of SEQ ID NO:170, SEQ ID NO:171, SEQ ID NO:172, SEQ ID NO:173 or SEQ ID NO:174.

In an exemplary embodiment, the single domain antibody or antigen binding fragment thereof may have the amino acid sequence as defined in any one of SEQ ID NOs: 143 to 146, wherein the amino acid sequence of the CDR3 is as set forth in any one of SEQ ID NO:3, SEQ ID NO:6, SEQ ID NO:12, SEQ ID NO:15 or SEQ ID NO:141, the amino acid sequence of the FR2 is as set forth in any one of SEQ ID NO:170, SEQ ID NO:171, SEQ ID NO:172, SEQ ID NO:173 or SEQ ID NO:174, the amino acid sequence of the CDR1 is as set forth in any one of SEQ ID NO:1, SEQ ID NO:4, SEQ ID NO:7 or SEQ ID NO:127 and the amino acid sequence of the CDR2 is as set forth in any one of SEQ ID NO:2, SEQ ID NO:5, SEQ ID NO:8, SEQ ID NO:11, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138 or SEQ ID NO:139.

In an exemplary embodiment, the single domain antibody or antigen binding fragment thereof may have the amino acid sequence as defined in any one of SEQ ID NOs: 143 to 146, wherein the amino acid sequence of the CDR3 is as set forth in any one SEQ ID NO:3, SEQ ID NO:6, SEQ ID NO:12, SEQ ID NO:15 or SEQ ID NO:141, the amino acid sequence of the FR2 is as set forth in any one of SEQ ID NO:170 or SEQ ID NO:171, the amino acid sequence of the CDR1 is as set forth in any one of SEQ ID NO:1, SEQ ID NO:4, SEQ ID NO:7 or SEQ ID NO:127 and the amino acid sequence of the CDR2 is as set forth in any one of SEQ ID NO:2, SEQ ID NO:5, SEQ ID NO:8, SEQ ID NO:11, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138 or SEQ ID NO:139.

In an aspect of the present disclosure, single domain antibody variants include those comprising an amino acid sequence at least 65%, 70%, 75%, 80% 85%, 90%, 95%, 99% identical to the amino acid sequence of the antigen binding domains, variable region or single domain antibodies exemplified herein.

In some embodiments, single domain antibody variants include variants of KD001 (having a variable region as set forth in SEQ ID NO:22). In exemplary embodiments, the single domain antibody comprises a variable region having an amino acid sequence at least 75%, 80% 85%, 90%, 95% identical to the amino acid sequence set forth in SEQ ID NO:22.

Other exemplary embodiments of single domain antibody variants include variants of KD002 (having a variable region as set forth in SEQ ID NO:23). In some exemplary embodiments, the single domain antibody comprises a variable region having an amino acid sequence at least 75%, 80% 85%, 90%, 95% identical to the amino acid sequence set forth in SEQ ID NO:23. In other exemplary embodiments, the single domain antibody comprises a variable region having an amino acid sequence as set forth in any one of SEQ ID NO:71-93.

In some embodiments, single domain antibody variants include variants of KD003 (having a variable region as set forth in SEQ ID NO:24). In additional exemplary embodiments, the single domain antibody comprises a variable region having an amino acid sequence at least 75%, 80% 85%, 90%, 95% identical to the amino acid sequence set forth in SEQ ID NO:24.

In some embodiments, single domain antibody variants include variants of KD004 (having a variable region as set forth in SEQ ID NO:25). In further exemplary embodiments, the single domain antibody comprises a variable region having an amino acid sequence at least 75%, 80% 85%, 90%, 95% identical to the amino acid sequence set forth in SEQ ID NO:25.

Other exemplary embodiments of single domain antibody variants include variants of KD005 (having a variable region as set forth in SEQ ID NO:26). In some exemplary embodiments, the single domain antibody comprises a variable region having an amino acid sequence at least 75%, 80% 85%, 90%, 95% identical to the amino acid sequence set forth in SEQ ID NO:26.

In some exemplary embodiments, the single domain antibody comprises a variable region having an amino acid sequence as set forth in any one of SEQ ID NO:73-93.

In other exemplary embodiments, the single domain antibody comprises a variable region having an amino acid sequence as set forth in any one of SEQ ID NO:94-114.

Other exemplary embodiments of single domain antibody variants include those comprising an amino acid sequence at least 65% identical to the amino acid sequence set forth in any one of SEQ ID NOs:22-26, or SEQ ID NOs: 73-114.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:22. More particularly, the single domain antibody or antigen binding fragment thereof comprises an amino acid sequence at least 95% identical, at least 99% identical or identical to SEQ ID NO:22.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:23. More particularly, the single domain antibody or antigen binding fragment thereof comprises an amino acid sequence at least 95% identical, at least 99% identical or identical to SEQ ID NO:23.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:24. More particularly, the single domain antibody or antigen binding fragment thereof comprises an amino acid sequence at least 95% identical, at least 99% identical or identical to SEQ ID NO:24.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:25. More particularly, the single domain antibody or antigen binding fragment thereof comprises an amino acid sequence at least 95% identical, at least 99% identical or identical to SEQ ID NO:25.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:26. More particularly, the single domain antibody or antigen binding fragment thereof comprises an amino acid sequence at least 95% identical, at least 99% identical or identical to SEQ ID NO:26.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:71. More particularly, the single domain antibody or antigen binding fragment thereof comprises an amino acid sequence at least 95% identical, at least 99% identical or identical to SEQ ID NO:71.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:72. More particularly, the single domain antibody or antigen binding fragment thereof comprises an amino acid sequence at least 95% identical, at least 99% identical or identical to SEQ ID NO:72.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:73. More particularly, the single domain antibody or antigen binding fragment thereof comprises an amino acid sequence at least 95% identical, at least 99% identical or identical to SEQ ID NO:73.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:74. More particularly, the single domain antibody or antigen binding fragment thereof comprises an amino acid sequence at least 95% identical, at least 99% identical or identical to SEQ ID NO:74.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:75. More particularly, the single domain antibody or antigen binding fragment thereof comprises an amino acid sequence at least 95% identical, at least 99% identical or identical to SEQ ID NO:75.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:76. More particularly, the single domain antibody or antigen binding fragment thereof comprises an amino acid sequence at least 95% identical, at least 99% identical or identical to SEQ ID NO:76.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:77. More particularly, the single domain antibody or antigen binding fragment thereof comprises an amino acid sequence at least 95% identical, at least 99% identical or identical to SEQ ID NO:77.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:78. More particularly, the single domain antibody or antigen binding fragment thereof comprises an amino acid sequence at least 95% identical, at least 99% identical or identical to SEQ ID NO:78.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:79. More particularly, the single domain antibody or antigen binding fragment thereof comprises an amino acid sequence at least 95% identical, at least 99% identical or identical to SEQ ID NO:79.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:80. More particularly, the single domain antibody or antigen binding fragment thereof comprises an amino acid sequence at least 95% identical, at least 99% identical or identical to SEQ ID NO:80.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:81. More particularly, the single domain antibody or antigen binding fragment thereof comprises an amino acid sequence at least 95% identical, at least 99% identical or identical to SEQ ID NO:81.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:82. More particularly, the single domain antibody or antigen binding fragment thereof comprises an amino acid sequence at least 95% identical, at least 99% identical or identical to SEQ ID NO:82.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:83. More particularly, the single domain antibody or antigen binding fragment thereof comprises an amino acid sequence at least 95% identical, at least 99% identical or identical to SEQ ID NO:83.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:84. More particularly, the single domain antibody or antigen binding fragment thereof comprises an amino acid sequence at least 95% identical, at least 99% identical or identical to SEQ ID NO:84.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:85. More particularly, the single domain antibody or antigen binding fragment thereof comprises an amino acid sequence at least 95% identical, at least 99% identical or identical to SEQ ID NO:85.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:86. More particularly, the single domain antibody or antigen binding fragment thereof comprises may comprise an amino acid sequence at least 95% identical, at least 99% identical or identical to SEQ ID NO:86.

In an exemplary embodiment, the single domain antibody or antigen binding fragment thereof comprises may comprise an amino acid sequence at least 70% identical, at least 75% identical, at least 80% identical, at least 85% identical, at least 90% identical, at least 95% identical, at least 99% identical to SEQ ID NO:87. More particularly, the single domain antibody or antigen binding fragment thereof comprises an amino acid sequence at least 95% identical, at least 99% identical or identical to SEQ ID NO:87.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:88. More particularly, the single domain antibody or antigen binding fragment thereof comprises an amino acid sequence at least 95% identical, at least 99% identical or identical to SEQ ID NO:88.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:89. More particularly, the single domain antibody or antigen binding fragment thereof comprises an amino acid sequence at least 95% identical, at least 99% identical or identical to SEQ ID NO:89.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:90. More particularly, the single domain antibody or antigen binding fragment thereof comprises an amino acid sequence at least 95% identical, at least 99% identical or identical to SEQ ID NO:90.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:91. More particularly, the single domain antibody or antigen binding fragment thereof comprises an amino acid sequence at least 95% identical, at least 99% identical or identical to SEQ ID NO:91.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:92. More particularly, the single domain antibody or antigen binding fragment thereof comprises an amino acid sequence at least 95% identical, at least 99% identical or identical to SEQ ID NO:92.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:93. More particularly, the single domain antibody or antigen binding fragment thereof comprises an amino acid sequence at least 95% identical, at least 99% identical or identical to SEQ ID NO:93.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:94. More particularly, the single domain antibody or antigen binding fragment thereof comprises an amino acid sequence at least 95% identical, at least 99% identical or identical to SEQ ID NO:94.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:95. More particularly, the single domain antibody or antigen binding fragment thereof comprises an amino acid sequence at least 95% identical, at least 99% identical or identical to SEQ ID NO:95.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:96. More particularly, the single domain antibody or antigen binding fragment thereof comprises an amino acid sequence at least 95% identical, at least 99% identical or identical to SEQ ID NO:96.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:97. More particularly, the single domain antibody or antigen binding fragment thereof comprises an amino acid sequence at least 95% identical, at least 99% identical or identical to SEQ ID NO:97.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:98. More particularly, the single domain antibody or antigen binding fragment thereof comprises an amino acid sequence at least 95% identical, at least 99% identical or identical to SEQ ID NO:98.

In an exemplary embodiment the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:99. More particularly, the single domain antibody or antigen binding fragment thereof comprises an amino acid sequence at least 95% identical, at least 99% identical or identical to SEQ ID NO:99.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:100. More particularly, the single domain antibody or antigen binding fragment thereof comprises an amino acid sequence at least 95% identical, at least 99% identical or identical to SEQ ID NO:100.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:101. More particularly, the single domain antibody or antigen binding fragment thereof comprises an amino acid sequence at least 95% identical, at least 99% identical or identical to SEQ ID NO:101.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:102. More particularly, the single domain antibody or antigen binding fragment thereof comprises an amino acid sequence at least 95% identical, at least 99% identical or identical to SEQ ID NO:102.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:103. More particularly, the single domain antibody or antigen binding fragment thereof comprises an amino acid sequence at least 95% identical, at least 99% identical or identical to SEQ ID NO:103.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:104. More particularly, the single domain antibody or antigen binding fragment thereof comprises an amino acid sequence at least 95% identical, at least 99% identical or identical to SEQ ID NO:104.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:105. More particularly, the single domain antibody or antigen binding fragment thereof comprises an amino acid sequence at least 95% identical, at least 99% identical or identical to SEQ ID NO:105.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:106. More particularly, the single domain antibody or antigen binding fragment thereof comprises an amino acid sequence at least 95% identical, at least 99% identical or identical to SEQ ID NO:106.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:107. More particularly, the single domain antibody or antigen binding fragment thereof comprises an amino acid sequence at least 95% identical, at least 99% identical or identical to SEQ ID NO:107.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:108. More particularly, the single domain antibody or antigen binding fragment thereof comprises an amino acid sequence at least 95% identical, at least 99% identical or identical to SEQ ID NO:108.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:109. More particularly, the single domain antibody or antigen binding fragment thereof comprises an amino acid sequence at least 95% identical, at least 99% identical or identical to SEQ ID NO:109.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:110. More particularly, the single domain antibody or antigen binding fragment thereof comprises an amino acid sequence at least 95% identical, at least 99% identical or identical to SEQ ID NO:110.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:111. More particularly, the single domain antibody or antigen binding fragment thereof comprises an amino acid sequence at least 95% identical, at least 99% identical or identical to SEQ ID NO:111.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:112. More particularly, the single domain antibody or antigen binding fragment thereof comprises an amino acid sequence at least 95% identical, at least 99% identical or identical to SEQ ID NO:112.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:113. More particularly, the single domain antibody or antigen binding fragment thereof comprises an amino acid sequence at least 95% identical, at least 99% identical or identical to SEQ ID NO:113.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:114. More particularly, the single domain antibody or antigen binding fragment thereof comprises an amino acid sequence at least 95% identical, at least 99% identical or identical to SEQ ID NO:114.

In an exemplary embodiment, the single domain antibody or antigen binding fragment thereof comprises an amino acid sequence at least 70% identical, at least 75% identical, at least 80% identical, at least 85% identical, at least 90% identical, at least 95% identical, at least 99% identical to SEQ ID NO:115. More particularly, the single domain antibody or antigen binding fragment thereof comprises an amino acid sequence at least 95% identical, at least 99% identical or identical to SEQ ID NO:115.

In an exemplary embodiment, the single domain antibody or antigen binding fragment thereof comprises an amino acid sequence at least 75%, 80% 85%, 90%, 95% identical to the amino acid sequence set forth in SEQ ID NO:29.

In an exemplary embodiment, the single domain antibody or antigen binding fragment thereof comprises an amino acid sequence at least 75%, 80% 85%, 90%, 95% identical to the amino acid sequence set forth in SEQ ID NO:30.

In an exemplary embodiment, the single domain antibody or antigen binding fragment thereof comprises an amino acid sequence at least 75%, 80% 85%, 90%, 95% identical to the amino acid sequence set forth in SEQ ID NO:31.

In an exemplary embodiment, the single domain antibody or antigen binding fragment thereof comprises an amino acid sequence at least 75%, 80% 85%, 90%, 95% identical to the amino acid sequence set forth in SEQ ID NO:32.

In an exemplary embodiment, the single domain antibody or antigen binding fragment thereof comprises an amino acid sequence at least 75%, 80% 85%, 90%, 95% identical to the amino acid sequence set forth in SEQ ID NO:33.

In an exemplary embodiment, the single domain antibody or antigen binding fragment thereof comprises an amino acid sequence at least 75%, 80% 85%, 90%, 95% identical to the amino acid sequence set forth in SEQ ID NO:34.

In an exemplary embodiment, the single domain antibody or antigen binding fragment thereof comprises an amino acid sequence at least 75%, 80% 85%, 90%, 95% identical to the amino acid sequence set forth in SEQ ID NO:35.

In an exemplary embodiment, the single domain antibody or antigen binding fragment thereof comprises an amino acid sequence at least 75%, 80% 85%, 90%, 95% identical to the amino acid sequence set forth in SEQ ID NO:44.

In an exemplary embodiment, the single domain antibody or antigen binding fragment thereof comprises an amino acid sequence at least 75%, 80% 85%, 90%, 95% identical to the amino acid sequence set forth in SEQ ID NO:45.

In accordance with the present disclosure, the single domain antibody or antigen binding fragment thereof comprises a sequence as set forth herein, wherein the amino acid residue at position 37 is V, the amino acid residue at position 39 is Q, the amino acid residue at position 45 is P, the amino acid residue at position 47 is W, the amino acid residue at position 50 is Y, the amino acid residue at position 58 is Y, the amino acid residue at position 99 is R, the amino acid residue at position 100 is L, the amino acid residue at position 101 is T, the amino acid residue at position 102 is D, the amino acid residue at position 103 is S, the amino acid residue at position 104 is H, the amino acid residue at position 105 is Y, the amino acid residue at position 106 is V, the amino acid residue at position 107 is E, the amino acid residue at position 108 is D, the amino acid residue at position 109 and/or the position is with reference to SEQ ID NO:145 (Table 1).

In accordance with the present disclosure, the single domain antibody or antigen binding fragment thereof comprises a sequence as set forth herein, wherein the amino acid residue at position 1 is Q, the amino acid residue at position 2 is V, the amino acid residue at position 37 is V, the amino acid residue at position 39 is Q, the amino acid residue at position 45 is P, the amino acid residue at position 47 is W, the amino acid residue at position 50 is Y, the amino acid residue at position 58 is Y, the amino acid residue at position 99 is R, the amino acid residue at position 100 is L, the amino acid residue at position 101 is T, the amino acid residue at position 102 is D, the amino acid residue at position 103 is S, the amino acid residue at position 104 is H, the amino acid residue at position 105 is Y, the amino acid residue at position 106 is V, the amino acid residue at position 107 is E, the amino acid residue at position 108 is D, the amino acid residue at position 109 is A, the amino acid residue at position 110 is W and/or the amino acid residue at position 112 is Q and the position is with reference to SEQ ID NO:145 (Table 1).

In accordance with the present disclosure, the single domain antibody or antigen binding fragment thereof comprises a sequence as set forth herein, wherein the amino acid residue at position 1 is Q, the amino acid residue at position 2 is V, the amino acid residue at position 3 is Q, the amino acid residue at position 4 is L, the amino acid residue at position 37 is V, the amino acid residue at position 39 is Q, the amino acid residue at position 45 is P, the amino acid residue at position 46 is E, the amino acid residue at position 47 is W, the amino acid residue at position 50 is Y, the amino acid residue at position 58 is Y, the amino acid residue at position 99 is R, the amino acid residue at position 100 is L, the amino acid residue at position 101 is T, the amino acid residue at position 102 is D, the amino acid residue at position 103 is S, the amino acid residue at position 104 is H, the amino acid residue at position 105 is Y, the amino acid residue at position 106 is V, the amino acid residue at position 107 is E, the amino acid residue at position 108 is D, the amino acid residue at position 109 is A, the amino acid residue at position 110 is W, the amino acid residue at position 111 is G, and/or the amino acid residue at position 112 is Q and the position is with reference to SEQ ID NO:145 (Table 1).

Yet other exemplary embodiments of single domain antibody variants include single domain antibody or antigen binding fragment thereof having an amino acid sequence as defined in any one of SEQ ID Nos:22-26, 73-114, or 143 to 146 and may comprise from one to five amino acid deletions or from one to five amino acid additions. In an exemplary embodiment, the deletion or additions are consecutive. In another exemplary embodiment, the deletion or additions are non-consecutives. In yet another exemplary embodiment, the deletion or additions are at the N-terminus. In a further exemplary embodiment, the deletion or additions are at the C-terminus. In yet a further exemplary embodiment, the deletion or additions are outside of an IMGT CDR3 sequence and/or IMGT FR2 sequence. In yet a further exemplary embodiment, the deletion or additions are outside of a Kabat CDR3 sequence and/or Kabat FR2 sequence.

Exemplary embodiments of binding agent include for example and without limitation binding agent variants such as bispecific binding agent variants.

For example, a bispecific binding agent variant may comprise one or more antigen binding domains of one or more single domain antibody variants.

In an exemplary embodiment, the binding agent is a bispecific binding agent variant that comprises an antigen binding domain that specifically binds to CD47 and that comprises an amino acid sequence at least 80% identical, at least 85% identical, at least 90% identical, at least 95% identical, at least 99% identical to the amino acid sequence set forth in SEQ ID NO:155.

In an exemplary embodiment, the bispecific binding agent variant is capable of binding to CD47 and TROP2 and comprises an amino acid sequence at least 80% identical, at least 85% identical, at least 90% identical, at least 95% identical, at least 99% to the amino acid sequence set forth in SEQ ID NO:155 and the amino acid sequence of an antigen binding domain of a single domain antibody or of a single domain antibody variant as disclosed herein.

In other exemplary embodiments, the bispecific binding agent variant is capable of binding to CD47 and TROP2 and comprises an amino acid sequence at least 80% identical, at least 85% identical, at least 90% identical, at least 95% identical, at least 99% to the amino acid sequence set forth in SEQ ID NO:155 and the amino acid sequence of an antigen binding domain of a single domain antibody disclosed as set forth in any one of SEQ ID NOs:22-26 or SEQ ID Nos:73-114.

In another exemplary embodiment, the bispecific binding agent variant is capable of binding to CD47 and TROP2 and comprises an amino acid sequence at least 80% identical, at least 85% identical, at least 90% identical, at least 95% identical, at least 99% to the amino acid sequence set forth in SEQ ID NO:150 or in SEQ ID NO:151.

The bispecific binding agent variant may comprise:
a CDRH1 having the amino acid sequence set forth in SEQ ID NO156, a CDRH2 having the amino acid sequence set forth in SEQ ID NO:157 and a CDRH3 having the amino acid sequence set forth in SEQ ID NO:158, or
b. a CDRH1 having the amino acid sequence set forth in SEQ ID NO159, a CDRH2 having the amino acid sequence set forth in SEQ ID NO:160 and a CDRH3 having the amino acid sequence set forth in SEQ ID NO:161.

Competing Binding Agents

Binding agents of the present disclosure also encompass those that compete with a binding agent, or a single domain antibody disclosed herewith. Single domain antibodies that compete with one or more single domain antibody or antigen binding fragment thereof having an amino acid sequence as disclosed herein are provided.

In an exemplary embodiment the competing binding agent is capable of competing with a binding agent as disclosed herein.

In an exemplary embodiment the competing binding agent comprises one or more antigen binding domains that are capable of competing with the binding agent disclosed herein.

In an exemplary embodiment, a competing binding agent or competing single domain antibody may be selected based on any type of binding assays (FACS, ELISA, SPR etc.) using a TROP2 antigen as described herein.

In another exemplary embodiment, a competing binding agent or competing single domain antibody may be selected based on screening assays described herein.

In some exemplary embodiments, the competing binding agent or competing single domain antibody comprises an amino acid sequence at least 65% identical, at least 70% identical, at least 75% identical, at least 80% identical, at least 85% identical, at least 90% identical, at least 95% identical, at least 99% identical to the amino acid sequence set forth in any one of SEQ ID NOs:22-26, or SEQ ID NOs: 73-114.

In other exemplary embodiments, the competing binding agent or competing single domain antibody comprises the amino acid sequence of the CDR3 set forth in SEQ ID NO:126, the amino acid sequence of the FR2 set forth in SEQ ID NO:121.

In yet other exemplary embodiments, the competing binding agent or competing single domain antibody comprises:
a. the amino acid sequence of the CDR3 set forth in SEQ ID NO:54 and the amino acid sequence of the FR2 set forth in SEQ ID NO:116 and optionally the amino acid sequence of the CDR1 set forth in SEQ ID NO:52 and/or the amino acid sequence of the CDR2 set forth in SEQ ID NO:53;
b. the amino acid sequence of the CDR3 set forth in SEQ ID NO:48 and the amino acid sequence of the FR2 set forth in SEQ ID NO:116 and optionally the amino acid sequence of the CDR1 set forth in SEQ ID NO:55 and/or the amino acid sequence of the CDR2 set forth in SEQ ID NO:47;
c. the amino acid sequence of the CDR3 set forth in SEQ ID NO:58 and the amino acid sequence of the FR2 set forth in SEQ ID NO:116 and optionally the amino acid sequence of the CDR1 set forth in SEQ ID NO:56 and/or the amino acid sequence of the CDR2 set forth in SEQ ID NO:57;
d. the amino acid sequence of the CDR3 set forth in SEQ ID NO:61 and the amino acid sequence of the FR2 set forth in SEQ ID NO:116 and optionally the amino acid sequence of the CDR1 set forth in SEQ ID NO:59 and/or the amino acid sequence of the CDR2 set forth in SEQ ID NO:60;
e. the amino acid sequence of the CDR3 set forth in SEQ ID NO:51 and the amino acid sequence of the FR2 set forth in SEQ ID NO:116 and optionally the amino acid sequence of the CDR1 set forth in SEQ ID NO:62 and/or the amino acid sequence of the CDR2 set forth in SEQ ID NO:50,
f. the amino acid sequence of the CDR3 set forth in SEQ ID NO: 48 and the amino acid sequence of the FR2 set forth in SEQ ID NO:116 and optionally the amino acid sequence of the CDR1 set forth in SEQ ID NO:55 and/or the amino acid sequence of the CDR2 set forth in 47;
g. the amino acid sequence of the CDR3 set forth in SEQ ID NO: 48 and the amino acid sequence of the FR2 set forth in SEQ ID NO:117 and optionally the amino acid sequence of the CDR1 set forth in SEQ ID NO:55 and/or the amino acid sequence of the CDR2 set forth in 47;
h. the amino acid sequence of the CDR3 set forth in SEQ ID NO: 48 and the amino acid sequence of the FR2 set forth in SEQ ID NO:118 and optionally the amino acid sequence of the CDR1 set forth in SEQ ID NO:55 and/or the amino acid sequence of the CDR2 set forth in 47;
i. the amino acid sequence of the CDR3 set forth in SEQ ID NO: 48 and the amino acid sequence of the FR2 set forth in SEQ ID NO:119 and optionally the amino acid sequence of the CDR1 set forth in SEQ ID NO:55 and/or the amino acid sequence of the CDR2 set forth in 47;
j. the amino acid sequence of the CDR3 set forth in SEQ ID NO: 48 and the amino acid sequence of the FR2 set forth in SEQ ID NO:117 and optionally the amino acid sequence of the CDR1 set forth in SEQ ID NO:55 and/or the amino acid sequence of the CDR2 set forth in 124;
k. the amino acid sequence of the CDR3 set forth in SEQ ID NO: 48 and the amino acid sequence of the FR2 set forth in SEQ ID NO:117 and optionally the amino acid sequence of the CDR1 set forth in SEQ ID NO:55 and/or the amino acid sequence of the CDR2 set forth in 123;
l. the amino acid sequence of the CDR3 set forth in SEQ ID NO:51 and the amino acid sequence of the FR2 set forth in SEQ ID NO:116 and optionally the amino acid sequence of the CDR1 set forth in SEQ ID NO:62 and/or the amino acid sequence of the CDR2 set forth in SEQ ID NO:50;
m. the amino acid sequence of the CDR3 set forth in SEQ ID NO:51 and the amino acid sequence of the FR2 set forth in SEQ ID NO:117 and optionally the amino acid sequence of the CDR1 set forth in SEQ ID NO:62 and/or the amino acid sequence of the CDR2 set forth in SEQ ID NO:50;
n. amino acid sequence of the CDR3 set forth in SEQ ID NO:51 and the amino acid sequence of the FR2 set forth in SEQ ID NO:118 and optionally the amino acid sequence of the CDR1 set forth in SEQ ID NO:62 and/or the amino acid sequence of the CDR2 set forth in SEQ ID NO:50;

o. amino acid sequence of the CDR3 set forth in SEQ ID NO:51 and the amino acid sequence of the FR2 set forth in SEQ ID NO:120 and optionally the amino acid sequence of the CDR1 set forth in SEQ ID NO:62 and/or the amino acid sequence of the CDR2 set forth in SEQ ID NO:50;

p. a CDRH1 having the amino acid sequence set forth in SEQ ID NO:127, a CDRH2 having the amino acid sequence set forth in SEQ ID NO:129 and a CDRH3 having the amino acid sequence set forth in SEQ ID NO:6;

q. a CDRH1 having the amino acid sequence set forth in SEQ ID NO:4, a CDRH2 having the amino acid sequence set forth in SEQ ID NO:130 and a CDRH3 having the amino acid sequence set forth in SEQ ID NO:6;

r. a CDRH1 having the amino acid sequence set forth in SEQ ID NO:4, a CDRH2 having the amino acid sequence set forth in SEQ ID NO:131 and a CDRH3 having the amino acid sequence set forth in SEQ ID NO:6;

s. a CDRH1 having the amino acid sequence set forth in SEQ ID NO:4, a CDRH2 having the amino acid sequence set forth in SEQ ID NO:132 and a CDRH3 having the amino acid sequence set forth in SEQ ID NO:6;

t. a CDRH1 having the amino acid sequence set forth in SEQ ID NO:4, a CDRH2 having the amino acid sequence set forth in SEQ ID NO:133 and a CDRH3 having the amino acid sequence set forth in SEQ ID NO:6;

u. a CDRH1 having the amino acid sequence set forth in SEQ ID NO:4, a CDRH2 having the amino acid sequence set forth in SEQ ID NO:134 and a CDRH3 having the amino acid sequence set forth in SEQ ID NO:6;

v. a CDRH1 having the amino acid sequence set forth in SEQ ID NO:4, a CDRH2 having the amino acid sequence set forth in SEQ ID NO:135 and a CDRH3 having the amino acid sequence set forth in SEQ ID NO:6;

w. a CDRH1 having the amino acid sequence set forth in SEQ ID NO:13, a CDRH2 having the amino acid sequence set forth in SEQ ID NO:136 and a CDRH3 having the amino acid sequence set forth in SEQ ID NO:15;

x. a CDRH1 having the amino acid sequence set forth in SEQ ID NO:13, a CDRH2 having the amino acid sequence set forth in SEQ ID NO:137 and a CDRH3 having the amino acid sequence set forth in SEQ ID NO:15;

y. a CDRH1 having the amino acid sequence set forth in SEQ ID NO:13, a CDRH2 having the amino acid sequence set forth in SEQ ID NO:138 and a CDRH3 having the amino acid sequence set forth in SEQ ID NO:15 or, z. a CDRH1 having the amino acid sequence set forth in SEQ ID NO:13, a CDRH2 having the amino acid sequence set forth in SEQ ID NO:139 and a CDRH3 having the amino acid sequence set forth in SEQ ID NO:15.

In other exemplary embodiments, the competing binding agent or competing single domain antibody comprises:

a. the amino acid sequence of the CDR1 set forth in SEQ ID NO:52, the amino acid sequence of the CDR2 set forth in SEQ ID NO:53, the amino acid sequence of the CDR3 set forth in SEQ ID NO:54 and the amino acid sequence of the FR2 set forth in SEQ ID NO:116;

b. the amino acid sequence of the CDR1 set forth in SEQ ID NO:55, the amino acid sequence of the CDR2 set forth in SEQ ID NO:47, the amino acid sequence of the CDR3 set forth in SEQ ID NO:48 and the amino acid sequence of the FR2 set forth in SEQ ID NO:116;

c. the amino acid sequence of the CDR1 set forth in SEQ ID NO:56, the amino acid sequence of the CDR2 set forth in SEQ ID NO:57, the amino acid sequence of the CDR3 set forth in SEQ ID NO:58 and the amino acid sequence of the FR2 set forth in SEQ ID NO:116;

d. the amino acid sequence of the CDR1 set forth in SEQ ID NO:59, the amino acid sequence of the CDR2 set forth in SEQ ID NO:60, the amino acid sequence of the CDR3 set forth in SEQ ID NO:61 and the amino acid sequence of the FR2 set forth in SEQ ID NO:116;

e. the amino acid sequence of the CDR1 set forth in SEQ ID NO:62, the amino acid sequence of the CDR2 set forth in SEQ ID NO:50, the amino acid sequence of the CDR3 set forth in SEQ ID NO:51 and the amino acid sequence of the FR2 set forth in SEQ ID NO:116;

f. the amino acid sequence of the CDR1 set forth in SEQ ID NO:55, the amino acid sequence of the CDR2 set forth in 47, the amino acid sequence of the CDR3 set forth in SEQ ID NO: 48 and the amino acid sequence of the FR2 set forth in SEQ ID NO:116;

g. the amino acid sequence of the CDR1 set forth in SEQ ID NO:55, the amino acid sequence of the CDR2 set forth in 47, the amino acid sequence of the CDR3 set forth in SEQ ID NO: 48 and the amino acid sequence of the FR2 set forth in SEQ ID NO:117;

h. the amino acid sequence of the CDR1 set forth in SEQ ID NO:55, the amino acid sequence of the CDR2 set forth in 47, the amino acid sequence of the CDR3 set forth in SEQ ID NO: 48 and the amino acid sequence of the FR2 set forth in SEQ ID NO:118;

i. the amino acid sequence of the CDR1 set forth in SEQ ID NO:55, the amino acid sequence of the CDR2 set forth in 47, the amino acid sequence of the CDR3 set forth in SEQ ID NO: 48 and the amino acid sequence of the FR2 set forth in SEQ ID NO:119;

j. the amino acid sequence of the CDR1 set forth in SEQ ID NO:55, the amino acid sequence of the CDR2 set forth in 124, the amino acid sequence of the CDR3 set forth in SEQ ID NO: 48 and the amino acid sequence of the FR2 set forth in SEQ ID NO:117;

k. the amino acid sequence of the CDR1 set forth in SEQ ID NO:55, the amino acid sequence of the CDR2 set forth in 123, the amino acid sequence of the CDR3 set forth in SEQ ID NO: 48 and the amino acid sequence of the FR2 set forth in SEQ ID NO:117;

l. the amino acid sequence of the CDR1 set forth in SEQ ID NO:62, the amino acid sequence of the CDR2 set forth in SEQ ID NO:50, the amino acid sequence of the CDR3 set forth in SEQ ID NO:51 and the amino acid sequence of the FR2 set forth in SEQ ID NO:116;

m. the amino acid sequence of the CDR1 set forth in SEQ ID NO:62, the amino acid sequence of the CDR2 set forth in SEQ ID NO:50, the amino acid sequence of the CDR3 set forth in SEQ ID NO:51 and the amino acid sequence of the FR2 set forth in SEQ ID NO:117;

n. the amino acid sequence of the CDR1 set forth in SEQ ID NO:62, the amino acid sequence of the CDR2 set forth in SEQ ID NO:50, amino acid sequence of the CDR3 set forth in SEQ ID NO:51 and the amino acid sequence of the FR2 set forth in SEQ ID NO:118 or, o. the amino acid sequence of the CDR1 set forth in SEQ ID NO:62, the amino acid sequence of the CDR2 set forth in SEQ ID NO:50, amino acid sequence of the CDR3 set forth in SEQ ID NO:51 and the amino acid sequence of the FR2 set forth in SEQ ID NO:120.

In yet other exemplary embodiments, the competing binding agent or competing single domain antibody comprises the amino acid sequence as defined in any one of SEQ ID NO:143-146 and the amino acid residue at position 1 is Q, the amino acid residue at position 2 is V, the amino acid residue at position 3 is Q, the amino acid residue at position 4 is L, the amino acid residue at position 37 is V, the amino acid residue at position 39 is Q, the amino acid residue at position 45 is P, the amino acid residue at position 46 is E, the amino acid residue at position 47 is W, the amino acid residue at position 50 is Y, the amino acid residue at position 58 is Y, the amino acid residue at position 99 is R, the amino acid residue at position 100 is L, the amino acid residue at position 101 is T, the amino acid residue at position 102 is D, the amino acid residue at position 103 is S, the amino acid residue at position 104 is H, the amino acid residue at position 105 is Y, the amino acid residue at position 106 is V, the amino acid residue at position 107 is E, the amino acid residue at position 108 is D, the amino acid residue at position 109 is A, the amino acid residue at position 110 is W, the amino acid residue at position 111 is G, and/or the amino acid residue at position 112 is Q and the position is with reference to SEQ ID NO:145 (Table 1).

In yet other exemplary embodiments, the competing binding agent or competing single domain antibody has an affinity of ≤$10^{-6}$ M for human TROP2.

In other exemplary embodiments, the competing binding agent or competing single domain antibody has anti-tumor activity.

In other exemplary embodiments, the competing binding agent or competing single domain antibody competes with a single domain antibody comprising a heavy chain variable region having the amino acid sequence set forth in SEQ ID NO:26.

In other exemplary embodiments, the competing binding agent or competing single domain antibody competes with a single domain antibody comprising a heavy chain variable region having the amino acid sequence set forth in SEQ ID NO:33.

In other exemplary embodiments, the present disclosure provides an antibody or an antigen binding fragment thereof that specifically binds to an epitope comprising amino acid residues of amino acids 27-146 of TROP2; and competes for binding to TROP2 with a single domain antibody that specifically binds to an epitope formed by amino acid residues of amino acids 27-146 of TROP2.

Nucleic Acids, Vectors, Kits, Cells and Method of Making Binding Agents

The present disclosure also relates to a nucleic acid molecule or vector encoding a binding agent or a binding agent variant as disclosed herein.

In some embodiments, the nucleic acid molecule or vector encodes an antibody or an antigen binding fragment thereof or a variant thereof.

In some embodiments, the nucleic acid molecule or vector encodes a single domain antibody or an antigen binding fragment thereof or a variant thereof.

In some embodiments, the nucleic acid molecule or vector encodes a competing binding agent.

In some embodiments, the nucleic acid molecule or vector encodes a competing antibody or antigen binding fragment thereof.

In some embodiments, the nucleic acid molecule or vector encodes a competing single domain antibody or antigen binding fragment thereof.

In some embodiments, the nucleic acid molecule or vector encodes an antibody-like molecule.

In some embodiments, the nucleic acid molecule or vector encodes a protein scaffold.

In some embodiments, the nucleic acid molecule or vector encodes an immune cell modulating agent.

Nucleic acid molecules of the present disclosure may be single-stranded or double-stranded. The nucleic acid molecules disclosed herein may comprises deoxyribonucleotides, ribonucleotides, modified deoxyribonucleotides or modified ribonucleotides. The nucleic acid molecules of the present disclosure may comprise for example DNA.

In some embodiments, the nucleic acid sequence is as set forth in Table 22.

Due to the inherent degeneracy of the genetic code, DNA sequences that encode the same, substantially the same or a functionally equivalent amino acid sequence may be produced and used. As such, in some embodiments, the nucleic acid sequence may be a variant of the nucleic acid sequence set forth in Table 22. In some embodiments, the nucleic acid variant may be at least 80%, at least 85%, at least 905, at least 95%, at least 99% identical to the nucleic acid sequence set forth in Table 22 and encodes an amino acid sequence of a binding agent, antigen binding domain or a portion disclosed herein.

The nucleotide sequences of the present disclosure may be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth. Codon-optimized nucleic acids encoding the polypeptide chains described herein are encompassed by the present disclosure.

The polypeptide chains and binding agents disclosed herein may be made by a variety of methods familiar to those skilled in the art, including by recombinant DNA methods or by in vitro transcription/translation.

Generally, the polypeptide chains described herein are expressed from nucleic acid sequences inserted into an expression vector, i.e., a vector that contains the elements for transcriptional and translational control of the inserted coding sequence in a particular host. These elements may include regulatory sequences, such as enhancers, constitutive and inducible promoters, and 5' and 3' un-translated regions.

A variety of expression vector/host cell systems known to those of skill in the art may be used to express the polypeptide chains or binding agent described herein. In the event, that the binding agent is composed of distinct polypeptide chains, each of such polypeptide chain may be provided by separate expression vectors or by a unique expression vector. In accordance with the present disclosure, the two chains of a binding agent may be encoded by a single vector or by separate vectors (vector set).

Polypeptides are often expressed in mammalian cells. For long-term production of recombinant proteins, a stable expression system may be used in which the DNA segment is incorporated into the host cell genome or maintained in an episomal form by the use of selectable markers. A host cell type may be chosen for its ability to modulate expression of the inserted sequences or to process the expressed polypeptide in the desired fashion. Different host cells that have specific cellular machinery and characteristic mechanisms for post-translational activities (e.g., CHO, HeLa, MDCK, HEK293, and W138) are available commercially and from the American Type Culture Collection (ATCC) and may be chosen to ensure the correct modification and processing of the expressed polypeptide.

Other types of expression system can be used. These include, for example, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems.

The present disclosure therefore relates to isolated cells transformed or transfected with a vector, nucleic acid, sets of vectors or sets of nucleic acids encoding the binding agents (antibodies or antigen binding fragments thereof such as single domain antibodies) described herein. The present disclosure therefore also relates to isolated cells capable or expressing the binding agents (antibodies or antigen binding fragments such as single domain antibodies) thereof disclosed herein.

The present disclosure also relates to a method of making binding agents (e.g., antibodies or antigen binding fragments thereof such as single domain antibodies). The method may comprise providing a cell (e.g., a mammalian cell) with a vector or sets of vectors encoding the binding agent (e.g., antibodies or antigen binding fragments thereof such as single domain antibodies) disclosed herein and allowing expression.

The method may also comprises purifying the binding agents (e.g., antibodies or antigen binding fragments such as single domain antibodies) thereof from cells or cell debris.

In some embodiments, the method of manufacture allows to reach a purity level of at least 80%, of at least 85%, at least 90%, at least 99% (of dimers).

In some embodiments, the purity level is between 80.0% to 99.9%.

In some embodiments, the purity level is between 95.0% to 99.9%.

In some embodiments, the purity level is at least 90.0+/−5.0%.

In some embodiments, the purity level is at least 95.0+/−5.0%.

In some embodiments, the purity level is 99.0+/−1.0%.

In some embodiments, the titer of the antibodies or antigen binding fragments thereof (e.g., single domain antibody) produced by cells may be 0.1 g/L or more. In some instances, the titer of the antibodies or antigen binding fragments thereof produced by cells may be 0.5 g/L or more. In some instances, the titer of the antibodies or antigen binding fragments thereof produced by cells may be 1 g/L or more. In some instances, the titer of the antibodies or antigen binding fragments thereof produced by cells may be 2 g/L or more. In some instances, the titer of the antibodies or antigen binding fragments thereof produced by cells may be 3 g/L or more. In some instances, the titer of the antibodies or antigen binding fragments thereof produced by cells may be 4 g/L or more.

The method may also comprise a step of isolating and/or purifying the antibodies or antigen binding fragments thereof from impurities.

Conjugates

In some embodiments, the binding agent of the present disclosure may be conjugated with a therapeutic moiety or with a detectable moiety.

Although, the binding agents of the present disclosure may have activity against tumor cells when unconjugated, the present disclosure also encompasses a conjugated form of such binding agents.

Binding agents described herein may, in some instances, have no or low activity against tumor cells when unconjugated. Binding agents may thus be conjugated with a therapeutic moiety so as to deliver the therapeutic moiety to TROP2-expressing cells.

The antibodies or antigen binding fragments thereof of the present disclosure (e.g., single domain antibodies or antigen binding fragments thereof) may be conjugated, for example, with a therapeutic moiety (for therapeutic purposes) or with a detectable moiety (i.e., for detection or diagnostic purposes) or to a protein allowing an extended half-life or is attached to nanoparticle. In some instances, therapeutic or detectable moieties may be linked to at least one amino acid residues of the antibodies or antigen binding fragments thereof.

In an exemplary embodiment, the antibodies or antigen binding fragments thereof of the present disclosure is conjugated with a therapeutic moiety such as for example and without limitation, a chemotherapeutic, a cytokine, a cytotoxic agent, an anti-cancer drug (e.g., small molecule), and the like.

Therapeutic moiety may include, for example and without limitation, Yttrium-90, Scandium-47, Rhenium-186, Iodine-131, Iodine-125, and many others recognized by those skilled in the art (e.g., lutetium (e.g., $Lu^{177}$), bismuth (e.g., $Bi^{213}$), copper (e.g., $Cu^{67}$)), 5-fluorouracil, adriamycin, irinotecan, taxanes, *pseudomonas* endotoxin, ricin, auristatins (e.g., monomethyl auristatin E, monomethyl auristatin F), maytansinoids (e.g., mertansine, batansine), tubulysin B analogues (e.g., Tubl96), camptothecin, exatecan derivatives (e.g., Dxd), belotecanderivatives, irinotecan or irinotecan metabolites (e.g., SN-38) and other toxins.

In another exemplary embodiment, the antibodies or antigen binding fragments thereof of the present disclosure is conjugated with a detectable moiety including for example and without limitation, a moiety detectable by spectroscopic, photochemical, biochemical, immunochemical, chemical and/or other physical means. A detectable moiety may be coupled either directly and/or indirectly (for example via a linkage, such as, without limitation, a DOTA or NHS linkage) to the polypeptide chain or binding agent using methods well known in the art. A wide variety of detectable moieties may be used, with the choice depending on the sensitivity required, ease of conjugation, stability requirements and available instrumentation. A suitable detectable moiety includes, but is not limited to, a fluorescent label, a radioactive label (for example, without limitation, $^{125}I$, $In^{111}$, $Tc^{99}$, $I^{131}$ and including positron emitting isotopes for PET scanner etc), a nuclear magnetic resonance active label, a luminescent label, a chemiluminescent label, a chromophore label, an enzyme label (for example and without limitation horseradish peroxidase, alkaline phosphatase, etc.), quantum dots and/or a nanoparticle. Detectable moiety may cause and/or produce a detectable signal thereby allowing for a signal from the detectable moiety to be detected.

Pharmaceutical Compositions

Pharmaceutical compositions comprising binding agents of the present disclosure are also encompassed by the present disclosure.

In some embodiments, the pharmaceutical composition comprises a binding agent variant.

In some embodiments, the pharmaceutical composition comprises an antibody or an antigen binding fragment thereof or a variant thereof.

In some embodiments, the pharmaceutical composition comprises a single domain antibody or an antigen binding fragment thereof or a variant thereof.

In some embodiments, the pharmaceutical composition comprises a competing binding agent.

In some embodiments, the pharmaceutical composition comprises a competing antibody or antigen binding fragment thereof.

In some embodiments, the pharmaceutical composition comprises a competing single domain antibody or antigen binding fragment thereof.

In some embodiments, the pharmaceutical composition comprises an antibody-like molecule.

In some embodiments, the pharmaceutical composition comprises a protein scaffold.

In some embodiments, the pharmaceutical composition comprises an immune cell modulating agent or cells expressing the immune cell modulating agent.

Pharmaceutical compositions may therefore comprise the antibodies or antigen binding fragments thereof of the present disclosure (e.g., single domain antibodies or antigen. Binding fragments thereof).

The pharmaceutical composition of the present disclosure may also comprise a pharmaceutically acceptable carrier.

In some embodiments, the pharmaceutical composition comprises conjugated binding agents.

In some embodiments, the pharmaceutical composition comprises conjugated antibodies or antigen binding fragments thereof as disclosed herein (e.g., single domain antibodies or antigen binding fragment thereof). In some embodiments, the pharmaceutical composition comprises antibodies or antigen binding fragments thereof (e.g., single domain antibodies or antigen binding fragment thereof) conjugated with a therapeutic moiety. In some embodiments, the pharmaceutical composition comprises antibodies or antigen binding fragments thereof (e.g., single domain antibodies or antigen binding fragment thereof) conjugated with a detectable label.

In addition to the active ingredients, a pharmaceutical composition may contain pharmaceutically acceptable carriers comprising water, PBS, salt solutions, gelatins, oils, alcohols, and other excipients and auxiliaries that facilitate processing of the active compounds into preparations that may be used pharmaceutically. In other instances, such preparations may be sterilized.

As used herein, "pharmaceutical composition" means therapeutically effective amounts of the agent together with pharmaceutically acceptable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween™ 20, Tween™ 80, Pluronic F68, bile acid salts). Solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also encompassed by the disclosure are particulate compositions coated with polymers (e.g., poloxamers or poloxamines). Other embodiments of the compositions of the disclosure incorporate particulate forms protective coatings, protease inhibitors or permeation enhancers for various routes of administration, including parenteral, pulmonary, nasal, oral, vaginal, rectal routes. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carrier" or "pharmaceutical carrier" are known in the art and include, but are not limited to, 0.01-0.1 M or 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's orfixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

For any compound, the therapeutically effective dose may be estimated initially either in cell culture assays or in animal models such as mice, rats, rabbits, dogs, or pigs. An animal model may also be used to determine the concentration range and route of administration. Such information may then be used to determine useful doses and routes for administration in humans. These techniques are well known to one skilled in the art and a therapeutically effective dose refers to that amount of active ingredient that ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the pharmaceutical compositions described above may be applied to any subject in need of therapy, including, but not limited to, mammals such as dogs, cats, cows, horses, rabbits, monkeys, and especially humans.

The pharmaceutical compositions described herein may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In an exemplary embodiment, the pharmaceutical composition comprises a single domain antibody or an antigen binding fragment thereof selected from KD001, KD002, KD003, KD004, KD005, KD006, KD007, KD008, KD009, KD010, KD011, KD012, KD013, KD014, KD015, KD016, KD017, KD018, KD019, KD020, KD021, KD022, KD023, KD024, KD025, KD026, KD027, KD028, KD029, KD030, KD031, KD032, KD033, KD034, KD035, KD036, KD037, KD038, KD039, KD040, KD041, KD042, KD043, KD044, KD045, KD046, KD047, KD048, KD049, KD050, KD051, KD052, KD053, KD054, KD055, KD056, KD057, KD058, KD059, KD060, KD061, KD062, KD063 or KD064.

In some embodiment, the pharmaceutical composition comprises a single domain antibody or antigen binding fragment thereof selected from the group of FIG. 27.

In some embodiment, the pharmaceutical composition comprises a single domain antibody or antigen binding fragment thereof selected from the group of FIG. 28.

In some embodiment, the pharmaceutical composition comprises a single domain antibody or antigen binding fragment thereof selected from the group of FIG. 29.

In some embodiment, the pharmaceutical composition comprises a single domain antibody or antigen binding fragment thereof selected from the group of FIG. 30.

In some embodiment, the pharmaceutical composition comprises a single domain antibody or antigen binding fragment thereof selected from the group of FIG. 31.

In some embodiment, the pharmaceutical composition comprises a single domain antibody or antigen binding fragment thereof selected from the group of FIG. 32.

In some embodiment, the pharmaceutical composition comprises a single domain antibody or antigen binding fragment thereof selected from the group of FIG. 33.

In some embodiment, the pharmaceutical composition comprises a single domain antibody or antigen binding fragment thereof selected from the group of FIG. 34.

In an exemplary embodiment, the pharmaceutical composition comprises KD065 or an antigen binding fragment thereof.

In an exemplary embodiment, the pharmaceutical composition comprises KD066 or an antigen binding fragment thereof.

In another exemplary embodiment, the pharmaceutical composition comprises a single domain antibody or an antigen binding fragment thereof selected from KD067, KD068 or KD069 or an antigen binding fragment thereof.

In some embodiment, the pharmaceutical composition comprises KD001 or a binding agent that comprises the antigen binding domain of KD001. In other embodiment, the pharmaceutical composition comprises a variant of KD001 or a binding agent that comprises the antigen binding domain of a KD001 variant. In some embodiment, the pharmaceutical composition comprises a humanized version of KD001 or a binding agent that comprises the antigen binding domain of humanized version of KD001. In some embodiment, the pharmaceutical composition comprises a single domain antibody capable of competing with KD001 or a binding agent that comprises the antigen binding domain of a single domain antibody capable of competing with KD001.

In some embodiment, the pharmaceutical composition comprises KD002 or a binding agent that comprises the antigen binding domain of KD002. In other embodiment, the pharmaceutical composition comprises a variant of KD002 or a binding agent that comprises the antigen binding domain of a KD002 variant. In some embodiment, the pharmaceutical composition comprises a humanized version of KD002 or a binding agent that comprises the antigen binding domain of humanized version of KD002. In some embodiment, the pharmaceutical composition comprises a single domain antibody capable of competing with KD002 or a binding agent that comprises the antigen binding domain of a single domain antibody capable of competing with KD002.

In some embodiment, the pharmaceutical composition comprises KD003 or a binding agent that comprises the antigen binding domain of KD003. In other embodiment, the pharmaceutical composition comprises a variant of KD003 or a binding agent that comprises the antigen binding domain of a KD003 variant. In some embodiment, the pharmaceutical composition comprises a humanized version of KD003 or a binding agent that comprises the antigen binding domain of humanized version of KD003. In some embodiment, the pharmaceutical composition comprises a single domain antibody capable of competing with KD003 or a binding agent that comprises the antigen binding domain of a single domain antibody capable of competing with KD003.

In some embodiment, the pharmaceutical composition comprises KD004 or a binding agent that comprises the antigen binding domain of KD004. In other embodiment, the pharmaceutical composition comprises a variant of KD004 or a binding agent that comprises the antigen binding domain of a KD004 variant. In some embodiment, the pharmaceutical composition comprises a humanized version of KD004 or a binding agent that comprises the antigen binding domain of humanized version of KD004. In some embodiment, the pharmaceutical composition comprises a single domain antibody capable of competing with KD004 or a binding agent that comprises the antigen binding domain of a single domain antibody capable of competing with KD004.

In some embodiment, the pharmaceutical composition comprises KD005 or a binding agent that comprises the antigen binding domain of KD005. In other embodiment, the pharmaceutical composition comprises a variant of KD005 or a binding agent that comprises the antigen binding domain of a KD005 variant. In some embodiment, the pharmaceutical composition comprises a humanized version of KD005 or a binding agent that comprises the antigen binding domain of humanized version of KD005. In some embodiment, the pharmaceutical composition comprises a single domain antibody capable of competing with KD005 or a binding agent that comprises the antigen binding domain of a single domain antibody capable of competing with KD005.

In some embodiment, the pharmaceutical composition comprises KD006 or a binding agent that comprises the antigen binding domain of KD006. In other embodiment, the pharmaceutical composition comprises a variant of KD006 or a binding agent that comprises the antigen binding domain of a KD006 variant. In some embodiment, the pharmaceutical composition comprises a humanized version of KD006 or a binding agent that comprises the antigen binding domain of humanized version of KD006. In some embodiment, the pharmaceutical composition comprises a single domain antibody capable of competing with KD006 or a binding agent that comprises the antigen binding domain of a single domain antibody capable of competing with KD006.

In some embodiment, the pharmaceutical composition comprises KD007 or a binding agent that comprises the antigen binding domain of KD007. In other embodiment, the pharmaceutical composition comprises a variant of KD007 or a binding agent that comprises the antigen binding domain of a KD007 variant. In some embodiment, the pharmaceutical composition comprises a humanized version of KD007 or a binding agent that comprises the antigen binding domain of humanized version of KD007. In some embodiment, the pharmaceutical composition comprises a single domain antibody capable of competing with KD007 or a binding agent that comprises the antigen binding domain of a single domain antibody capable of competing with KD007.

In some embodiment, the pharmaceutical composition comprises KD048 or a binding agent that comprises the antigen binding domain of KD048. In other embodiment, the pharmaceutical composition comprises a variant of KD048 or a binding agent that comprises the antigen binding domain of a KD048 variant. In some embodiment, the pharmaceutical composition comprises a humanized version of KD048 or a binding agent that comprises the antigen binding domain of humanized version of KD048. In some embodiment, the pharmaceutical composition comprises a single domain antibody capable of competing with KD048 or a binding agent that comprises the antigen binding domain of a single domain antibody capable of competing with KD048.

In some embodiment, the pharmaceutical composition comprises KD053 or a binding agent that comprises the antigen binding domain of KD053. In other embodiment, the pharmaceutical composition comprises a variant of KD053 or a binding agent that comprises the antigen binding domain of a KD053 variant. In some embodiment, the pharmaceutical composition comprises a humanized version of KD053 or a binding agent that comprises the antigen binding domain of humanized version of KD053. In some embodiment, the pharmaceutical composition comprises a single domain antibody capable of competing with KD053 or a binding agent that comprises the antigen binding domain of a single domain antibody capable of competing with KD053.

Any one of KD001-KD007, including variants (e.g., including humanized version), competing single domain antibodies thereof or binding agent comprising same may comprise a single polypeptide chain, two polypeptide chains or more than two polypeptide chains.

In some instances, the pharmaceutical composition may comprise a conjugated form of a single domain antibody or an antigen binding fragment thereof selected from KD001, KD002, KD003, KD004, KD005, KD006, KD007, KD008, KD009, KD010, KD011, KD012, KD013, KD014, KD015, KD016, KD017, KD018, KD019, KD020, KD021, KD022, KD023, KD024, KD025, KD026, KD027, KD028, KD029, KD030, KD031, KD032, KD033, KD034, KD035, KD036, KD037, KD038, KD039, KD040, KD041, KD042, KD043, KD044, KD045, KD046, KD047, KD048, KD049, KD050, KD051, KD052, KD053, KD054, KD055, KD056, KD057, KD058, KD059, KD060, KD061, KD062, KD063 or KD064 or their corresponding variants, competing single domain antibodies thereof or binding agent comprising same.

Method of Use

The present disclosure also relates to the use of binding agents disclosed herein (or pharmaceutical composition comprising same) for treatment of disorders or diseases.

In some embodiments, the method comprises administering a binding agent or a variant thereof or a pharmaceutical composition comprising same to a subject in need.

In some embodiments, the binding agent is an antibody or an antigen binding fragment thereof or a variant thereof and the method comprises administering the antibody or an antigen binding fragment thereof or variant thereof or a pharmaceutical composition comprising same to a subject in need.

In some embodiments, the binding agent is a single domain antibody or an antigen binding fragment thereof or a variant thereof and the method comprises administering the single domain antibody or antigen binding fragment thereof or a variant thereof or a pharmaceutical composition comprising same to a subject in need.

In some embodiments, the binding agent is a competing binding agent and the method comprises administering the competing binding agent or a pharmaceutical composition comprising same to a subject in need.

In some embodiments, the binding agent is a competing antibody or antigen binding fragment thereof and the method comprises administering the competing antibody or antigen binding fragment thereof or a pharmaceutical composition comprising same to a subject in need.

In some embodiments, the binding agent is a competing single domain antibody or antigen binding fragment thereof and the method comprises administering the competing single domain antibody or antigen binding fragment thereof or a pharmaceutical composition comprising same to a subject in need.

In some embodiments, the binding agent is an antibody-like molecule and the method comprises administering the antibody-like molecule or a pharmaceutical composition comprising same to a subject in need.

In In some embodiments, the binding agent comprises a protein scaffold and the method comprises administering the protein scaffold or a pharmaceutical composition comprising same to a subject in need.

In some embodiments, the binding agent is an immune cell modulating agent and the method comprises administering an immune cell modulating agent or a pharmaceutical composition comprising same to a subject in need or cells modified to express the immune cell modulating agent thereof.

The binding agents of the present disclosure may be used for treatment of disorders or diseases. In some embodiments, the binding agent of the present disclosure is a single domain antibody be used for treating disorders or diseases.

In some embodiments, the binding agent may be used to target therapeutics and/or diagnostics to a target cell, circulating protein or tissue. Accordingly, in some embodiments, the binding agent of the present disclosure is a single domain antibody used to target therapeutics and/or diagnostics to a target cell, circulating protein or tissue.

In some embodiments, the binding agent may be conjugated with a therapeutic moiety and used for therapeutic methods. Accordingly, in some embodiments, the binding agent of the present disclosure is a single domain antibody used for therapeutic methods.

In some embodiments, the binding agent may be conjugated with a detectable moiety and used for detection or diagnostic methods. Accordingly, in some embodiments, the binding agent of the present disclosure is a single domain antibody used for detection or diagnostic methods.

In some embodiments, the binding agent (e.g., antibody or antigen binding fragment thereof such as, for example, single domain antibody or antigen binding fragment thereof) of the present disclosure may be used for targeting tumors in vivo.

In some embodiments, the binding agent (e.g., antibody or antigen binding fragment thereof such as, for example, single domain antibody or antigen binding fragment thereof) may be used for promoting tumor regression and/or reducing tumor volume in vivo.

The binding agent of the present disclosure (e.g., antibody or antigen binding fragment thereof such as, for example, single domain antibody or antigen binding fragment thereof) may thus be used for cancer treatment.

The method of the present disclosure may comprise a step of administering the binding agent (e.g., antibody or antigen binding fragment thereof such as, for example, single domain antibody or antigen binding fragment thereof) or a pharmaceutical composition comprising the binding agent to an individual in need.

In some embodiments, the binding agent (e.g., antibody or antigen binding fragment thereof such as, for example, single domain antibody or antigen binding fragment thereof) is administered in combination with a chemotherapeutic.

In accordance with the present disclosure, the individual in need may be a human. Further in accordance with the present disclosure, the individual in need may be an animal.

In some embodiment, treatment of disorders or diseases that are caused or associated with expression of TROP2 are particularly contemplated. In some embodiment, treatment of disorders or diseases that are caused or associated with overexpression of TROP2 are also particularly contemplated.

In some embodiments, the disorder or disease may be cancer.

In some embodiments, the binding agent of the present disclosure (including for example and without limitations, an antibody or antigen binding fragment thereof such as, for example, a single domain antibody or antigen binding fragment thereof) is administered intravenously, intra-muscularly, or by fusion.

In some embodiment, the antibodies or antigen binding fragments thereof (e.g., single domain antibody or antigen binding fragment thereof) is administered intravenously.

In some embodiment, the antibodies or antigen binding fragments thereof (e.g., single domain antibody or antigen binding fragment thereof) is administered intra-muscularly.

In some embodiment, the antibodies or antigen binding fragments thereof (e.g., single domain antibody or antigen binding fragment thereof) is administered by infusion.

In some embodiments, the binding agent (including for example and without limitations, an antibody or antigen binding fragment thereof such as, for example, a single domain antibody or antigen binding fragment thereof) is administered at a dose of approximately between 0.01 to 150 mg/kg, 0.01 to 100 mg/kg, 0.01 to 50 mg/kg, 0.05 to 150 mg/kg, 0.05 to 100 mg/kg, 0.05 to 50 mg/kg, 0.05 to 30 mg/kg, 0.05 to 10 mg/kg, 0.1 to 50 mg/kg, 0.1 to 30 mg/kg, 0.1 to 10 m/kg, or 1.0 to 10 mg/kg.

In some embodiments, the binding agent (including for example and without limitations, an antibody or antigen binding fragment thereof such as, for example, a single domain antibody or antigen binding fragment thereof) is administered at a dose of approximately between 0.05 to 100 mg/kg.

In some embodiments, the binding agent (including for example and without limitations, an antibody or antigen binding fragment thereof such as, for example, a single domain antibody or antigen binding fragment thereof) is administered at a dose of approximately between 0.05 to 50 mg/kg.

In other embodiments, the binding agent (including for example and without limitations, an antibody or antigen binding fragment thereof such as, for example, a single domain antibody or antigen binding fragment thereof) is administered at a dose of approximately between 0.05 to 30 mg/kg.

In yet other embodiments, the binding agent (including for example and without limitations, an antibody or antigen binding fragment thereof such as, for example, a single domain antibody or antigen binding fragment thereof) is administered at a dose of approximately between 0.05 to 10 mg/kg.

In yet other embodiments, the binding agent (including for example and without limitations, an antibody or antigen binding fragment thereof such as, for example, a single domain antibody or antigen binding fragment thereof) is administered at a dose of approximately between 0.1 to 10 mg/kg.

Accordingly, in exemplary embodiments, the dose of the binding agent may be approximately 0.1 mg/kg. In other exemplary embodiments, the dose of the binding agent may be approximately 0.2 mg/kg. In yet other exemplary embodiments, the dose of the binding agent may be approximately 0.3 mg/kg. In other exemplary embodiments, the dose of the binding agent may be approximately 0.4 mg/kg. In other exemplary embodiments, the dose of the binding agent may be approximately 0.5 mg/kg. In yet other exemplary embodiments, the dose of the binding agent may be approximately 1 mg/kg. In further exemplary embodiments, the dose of the binding agent may be approximately 2 mg/kg. In yet further exemplary embodiments, the dose of the binding agent may be approximately 3 mg/kg. In additional exemplary embodiments, the dose of the binding agent may be approximately 4 mg/kg. In other exemplary embodiments, the dose of the binding agent may be approximately 5 mg/kg. In yet other exemplary embodiments, the dose of the binding agent may be approximately 6 mg/kg. In further exemplary embodiments, the dose of the binding agent may be approximately 7 mg/kg. In yet further exemplary embodiments, the dose of the binding agent may be approximately 8 mg/kg. In additional exemplary embodiments, the dose of the binding agent may be approximately 9 mg/kg. In other exemplary embodiments, the dose of the binding agent may be approximately 10 mg/kg. In yet other exemplary embodiments, the dose of the binding agent may be more than 10 mg/kg.

Accordingly, in exemplary embodiments, the dose of the single domain antibody may be approximately 0.1 mg/kg. In other exemplary embodiments, the dose of the single domain antibody may be approximately 0.2 mg/kg. In yet other exemplary embodiments, the dose of the single domain antibody may be approximately 0.3 mg/kg. In other exemplary embodiments, the dose of single domain antibody may be approximately 0.4 mg/kg. In other exemplary embodiments, the dose of the single domain antibody may be approximately 0.5 mg/kg. In yet other exemplary embodiments, the dose of the single domain antibody may be approximately 1 mg/kg. In further exemplary embodiments, the dose of the single domain antibody may be approximately 2 mg/kg. In yet further exemplary embodiments, the dose of the single domain antibody may be approximately 3 mg/kg. In additional exemplary embodiments, the dose of the single domain antibody may be approximately 4 mg/kg. In other exemplary embodiments, the dose of single domain antibody may be approximately 5 mg/kg. In yet other exemplary embodiments, the dose of the single domain antibody may be approximately 6 mg/kg. In further exemplary embodiments, the dose of the single domain antibody may be approximately 7 mg/kg. In yet further exemplary embodiments, the dose of the single domain antibody may be approximately 8 mg/kg. In additional exemplary embodiments, the dose of the single domain antibody may be approximately 9 mg/kg. In other exemplary embodiments, the dose of the single domain antibody may be approximately 10 mg/kg. In yet other exemplary embodiments, the dose of the single domain antibody may be more than 10 mg/kg.

In accordance with the present disclosure, the binding agent (including for example and without limitations, an antibody or antigen binding fragment thereof such as, for example, a single domain antibody or antigen binding fragment thereof) may be administered once weekly, more often than once a week (e.g., twice a week), once every two weeks, once every three weeks, once every month, or once every two months.

In accordance with the present disclosure, the binding agent (including for example and without limitations, an antibody or antigen binding fragment thereof such as, for example, a single domain antibody or antigen binding fragment thereof) may be administered once weekly.

In accordance with the present disclosure, the binding agent (including for example and without limitations, an antibody or antigen binding fragment thereof such as, for example, a single domain antibody or antigen binding fragment thereof) may be administered more often than once a week (e.g., twice a week).

Also in accordance with the present disclosure, the binding agent (including for example and without limitations, an antibody or antigen binding fragment thereof such as, for example, a single domain antibody or antigen binding fragment thereof) may be administered once every two weeks.

In accordance with the present disclosure, the binding agent (including for example and without limitations, an antibody or antigen binding fragment thereof such as, for example, a single domain antibody or antigen binding fragment thereof) may be administered once every three weeks.

In accordance with the present disclosure, the binding agent (including for example and without limitations, an antibody or antigen binding fragment thereof such as, for example, a single domain antibody or antigen binding fragment thereof) may be administered once every month.

The binding agent of the present disclosure particularly encompasses single domain antibodies which are administered to a subject having a disorder or disease associated with TROP2 expression or with TROP2 overexpression.

In some embodiments, the anti-TROP2 single domain antibodies disclosed herein is administered to a subject having cancer selected from epithetial cancer, lung cancer (such as small cell lung cancer, non small cell lung cancer), myeloma, prostate cancer, breast cancer (such as triple negative breast cancer), rectal cancer, pancreatic cancer, glioblastoma, cervical cancer, colorectal cancer, gastric cancer, ovarian cancer, thyroid cancer, stomach cancer, cancer of the urinary bladder, cancer of the uterus, esophageal cancer, head and neck cancer, blood cancer.

In other embodiments, the anti-TROP2 single domain antibodies disclosed herein is administered to a subject having a metastatic cancer.

In an exemplary embodiment, the method comprises administering a single domain antibody or an antigen binding fragment thereof or a pharmaceutical composition comprising the single domain antibody or an antigen binding fragment thereof selected from KD001, KD002, KD003, KD004, KD005, KD006, KD007, KD008, KD009, KD010, KD011, KD012, KD013, KD014, KD015, KD016, KD017, KD018, KD019, KD020, KD021, KD022, KD023, KD024, KD025, KD026, KD027, KD028, KD029, KD030, KD031, KD032, KD033, KD034, KD035, KD036, KD037, KD038, KD039, KD040, KD041, KD042, KD043, KD044, KD045, KD046, KD047, KD048, KD049, KD050, KD051, KD052, KD053, KD054, KD055, KD056, KD057, KD058, KD059, KD060, KD061, KD062, KD063 or KD064 or an antigen binding fragment thereof.

In some embodiment, the method comprises administering a single domain antibody or an antigen binding fragment thereof or a pharmaceutical composition comprising the single domain antibody or an antigen binding fragment thereof selected from the group of FIG. 27.

In some embodiment, the method comprises administering a single domain antibody or an antigen binding fragment thereof or a pharmaceutical composition comprising the single domain antibody or an antigen binding fragment thereof selected from the group of FIG. 28.

In some embodiment, the method comprises administering a single domain antibody or an antigen binding fragment thereof or a pharmaceutical composition comprising the single domain antibody or an antigen binding fragment thereof selected from the group of FIG. 29.

In some embodiment, the method comprises administering a single domain antibody or an antigen binding fragment thereof or a pharmaceutical composition comprising the single domain antibody or an antigen binding fragment thereof selected from the group of FIG. 30.

In some embodiment, the method comprises administering a single domain antibody or an antigen binding fragment thereof or a pharmaceutical composition comprising the single domain antibody or an antigen binding fragment thereof selected from the group of FIG. 31.

In some embodiment, the method comprises administering a single domain antibody or an antigen binding fragment thereof or a pharmaceutical composition comprising the single domain antibody or an antigen binding fragment thereof selected from the group of FIG. 32.

In some embodiment, the method comprises administering a single domain antibody or an antigen binding fragment thereof or a pharmaceutical composition comprising the single domain antibody or an antigen binding fragment thereof selected from the group of FIG. 33.

In some embodiment, the method comprises administering a single domain antibody or an antigen binding fragment thereof or a pharmaceutical composition comprising the single domain antibody or an antigen binding fragment thereof selected from the group of FIG. 34.

In an exemplary embodiment, the method comprises administering KD065 or an antigen binding fragment thereof or a pharmaceutical composition comprising KD065 or an antigen binding fragment thereof.

In an exemplary embodiment, the method comprises administering KD066 or an antigen binding fragment thereof or a pharmaceutical composition comprising KD066 or an antigen binding fragment thereof.

In another exemplary embodiment, the pharmaceutical composition comprises a single domain antibody or an antigen binding fragment thereof selected from KD067, KD068 or KD069 or an antigen binding fragment thereof.

In an exemplary embodiment, the method comprises administering a single domain antibody or an antigen binding fragment thereof or a pharmaceutical composition comprising the single domain antibody or an antigen binding fragment thereof selected from KD067, KD068 or KD069 or an antigen binding fragment thereof.

In some embodiment, the binding agent (including for example and without limitations, an antibody or antigen binding fragment thereof such as, for example, a single domain antibody or antigen binding fragment thereof) used in the method of treatment is KD001, comprises KD001 or comprises the antigen binding domain of KD001. In some embodiment, the binding agent used in the method of treatment is a KD001 variant, comprises a KD001 variant or comprises the antigen binding domain of a KD001 variant. In some embodiment, the binding agent used in the method of treatment is a humanized version of KD001, comprises a humanized version of KD001 or comprises the antigen binding domain of a humanized version of KD001. In some embodiment, the binding agent used in the method of treatment is single domain antibody capable of competing with KD001, comprises a single domain antibody capable of competing with KD001 or comprises the antigen binding domain of a single domain antibody capable of competing with KD001.

In some embodiment, the binding agent (including for example and without limitations, an antibody or antigen binding fragment thereof such as, for example, a single domain antibody or antigen binding fragment thereof) used in the method of treatment is KD002, comprises KD002 or comprises the antigen binding domain of KD002. In other embodiment, the binding agent used in the method of treatment is a variant of KD002, comprise a variant of KD002 or comprises the antigen binding domain of a KD002 variant. In some embodiment, the binding agent used in the method of treatment is a humanized version of KD002, comprises a humanized version of KD002 or comprises the antigen binding domain of humanized version of KD002. In some embodiment, the binding agent used in the method of treatment is a single domain antibody capable of competing with KD002, comprises a single domain antibody capable of competing with KD002 or comprises the antigen binding domain of a single domain antibody capable of competing with KD002.

In some embodiment, the binding agent (including for example and without limitations, an antibody or antigen binding fragment thereof such as, for example, a single domain antibody or antigen binding fragment thereof) used in the method of treatment is KD003, comprises KD003 or comprises the antigen binding domain of KD003. In other embodiment, the binding agent used in the method of treatment is a variant of KD003, comprise a variant of KD003 or comprises the antigen binding domain of a KD003 variant. In some embodiment, the binding agent used in the method of treatment is a humanized version of KD003, comprises a humanized version of KD003 or comprises the antigen binding domain of humanized version of KD003. In some embodiment, the binding agent used in the method of treatment is a single domain antibody capable of competing with KD003, comprises a single domain antibody capable of competing with KD003 or comprises the antigen binding domain of a single domain antibody capable of competing with KD003.

In some embodiment, the binding agent (including for example and without limitations, an antibody or antigen binding fragment thereof such as, for example, a single domain antibody or antigen binding fragment thereof) used in the method of treatment is KD004, comprises KD004 or comprises the antigen binding domain of KD004. In other embodiment, the binding agent used in the method of treatment is a variant of KD004, comprise a variant of KD004 or comprises the antigen binding domain of a KD004 variant. In some embodiment, the binding agent used in the method of treatment is a humanized version of KD004, comprises a humanized version of KD004 or comprises the antigen binding domain of humanized version of KD004. In some embodiment, the binding agent used in the method of treatment is a single domain antibody capable of competing with KD004, comprises a single domain antibody capable of competing with KD004 or comprises the antigen binding domain of a single domain antibody capable of competing with KD004.

In some embodiment, the binding agent (including for example and without limitations, an antibody or antigen binding fragment thereof such as, for example, a single domain antibody or antigen binding fragment thereof) used in the method of treatment is KD005, comprises KD005 or comprises the antigen binding domain of KD005. In other embodiment, the binding agent used in the method of treatment is a variant of KD005, comprise a variant of KD005 or comprises the antigen binding domain of a KD005 variant. In some embodiment, the binding agent used in the method of treatment is a humanized version of KD005, comprises a humanized version of KD005 or comprises the antigen binding domain of humanized version of KD005. In some embodiment, the binding agent used in the method of treatment is a single domain antibody capable of competing with KD005, comprises a single domain antibody capable of competing with KD005 or comprises the antigen binding domain of a single domain antibody capable of competing with KD005.

In some embodiment, the binding agent (including for example and without limitations, an antibody or antigen binding fragment thereof such as, for example, a single domain antibody or antigen binding fragment thereof) used in the method of treatment is KD006, comprises KD006 or comprises the antigen binding domain of KD006. In other embodiment, the binding agent used in the method of treatment is a variant of KD006, comprise a variant of KD006 or comprises the antigen binding domain of a KD006 variant. In some embodiment, the binding agent used in the method of treatment is a humanized version of KD006, comprises a humanized version of KD006 or comprises the antigen binding domain of humanized version of KD006. In some embodiment, the binding agent used in the method of treatment is a single domain antibody capable of competing with KD006, comprises a single domain antibody capable of competing with KD006 or comprises the antigen binding domain of a single domain antibody capable of competing with KD006.

In some embodiment, the binding agent (including for example and without limitations, an antibody or antigen binding fragment thereof such as, for example, a single domain antibody or antigen binding fragment thereof) used in the method of treatment is KD007, comprises KD007 or comprises the antigen binding domain of KD007. In other embodiment, the binding agent used in the method of treatment is a variant of KD007, comprise a variant of KD007 or comprises the antigen binding domain of a KD007 variant. In some embodiment, the binding agent used in the method of treatment is a humanized version of KD007, comprises a humanized version of KD007 or comprises the antigen binding domain of humanized version of KD007. In some embodiment, the binding agent used in the method of treatment is a single domain antibody capable of competing with KD007, comprises a single domain antibody capable of competing with KD007 or comprises the antigen binding domain of a single domain antibody capable of competing with KD007.

In some embodiment, the binding agent (including for example and without limitations, an antibody or antigen binding fragment thereof such as, for example, a single domain antibody or antigen binding fragment thereof) used in the method of treatment is KD048, comprises KD048 or comprises the antigen binding domain of KD048. In other embodiment, the binding agent used in the method of treatment is a variant of KD048, comprise a variant of KD048 or comprises the antigen binding domain of a KD048 variant. In some embodiment, the binding agent used in the method of treatment is a humanized version of KD048, comprises a humanized version of KD048 or comprises the antigen binding domain of humanized version of KD048. In some embodiment, the binding agent used in the method of treatment is a single domain antibody capable of competing with KD007, comprises a single domain antibody capable of competing with KD048 or comprises the antigen binding domain of a single domain antibody capable of competing with KD048.

In some embodiment, the binding agent (including for example and without limitations, an antibody or antigen binding fragment thereof such as, for example, a single domain antibody or antigen binding fragment thereof) used in the method of treatment is KD053, comprises KD053 or comprises the antigen binding domain of KD053. In other embodiment, the binding agent used in the method of treatment is a variant of KD053, comprise a variant of KD053 or comprises the antigen binding domain of a KD053 variant. In some embodiment, the binding agent used in the method of treatment is a humanized version of KD053, comprises a humanized version of KD053 or comprises the antigen binding domain of humanized version of KD053. In some embodiment, the binding agent used in the method of treatment is a single domain antibody capable of competing with KD007, comprises a single domain antibody capable of competing with KD053 or comprises the antigen binding domain of a single domain antibody capable of competing with KD053.

In some embodiments, the binding agent is a single domain antibody and is used at a dose of approximately between 0.1 to 10 mg/kg once a week.

In some embodiments, KD001 or KD001 variant (such as humanized KD001 variant) is used at a dose of approximately between 0.1 to 10 mg/kg once a week.

In some embodiments, KD001 or KD001 variant (such as humanized KD001 variant) is used at a dose of approximately between 0.1 to 10 mg/kg once every two weeks.

In some embodiments, KD001 or KD001 variant (such as humanized KD001 variant) is used at a dose of approximately between 0.1 to 10 mg/kg once every three weeks.

In some embodiments, KD002 or KD002 variant (such as humanized KD002 variant) is used at a dose of approximately between 0.1 to 10 mg/kg once a week.

In some embodiments, KD002 or KD002 variant (such as humanized KD002 variant) is used at a dose of approximately between 0.1 to 10 mg/kg once every two weeks.

In some embodiments, KD002 or KD002 variant (such as humanized KD002 variant) is used at a dose of approximately between 0.1 to 10 mg/kg once every three weeks.

In some embodiments, KD003 or KD003 variant (such as humanized KD003 variant) is used at a dose of approximately between 0.1 to 10 mg/kg once a week.

In some embodiments, KD003 or KD003 variant (such as humanized KD003 variant) is used at a dose of approximately between 0.1 to 10 mg/kg once every two weeks.

In some embodiments, KD003 or KD003 variant (such as humanized KD003 variant) is used at a dose of approximately between 0.1 to 10 mg/kg once every three weeks.

In some embodiments, KD004 or KD004 variant (such as humanized KD004 variant) is used at a dose of approximately between 0.1 to 10 mg/kg once a week.

In some embodiments, KD004 or KD004 variant (such as humanized KD004 variant) is used at a dose of approximately between 0.1 to 10 mg/kg once every two weeks.

In some embodiments, KD004 or KD004 variant (such as humanized KD004 variant) is used at a dose of approximately between 0.1 to 10 mg/kg once every three weeks.

In some embodiments, KD005 or KD005 variant (such as humanized KD005 variant) is used at a dose of approximately between 0.1 to 10 mg/kg once a week.

In some embodiments, KD005 or KD005 variant (such as humanized KD005 variant) is used at a dose of approximately between 0.1 to 10 mg/kg once every two weeks.

In some embodiments, KD005 or KD005 variant (such as humanized KD005 variant) is used at a dose of approximately between 0.1 to 10 mg/kg once every three weeks.

In some embodiments, KD006 or KD006 variant (such as humanized KD006 variant) is used at a dose of approximately between 0.1 to 10 mg/kg once a week.

In some embodiments, KD006 or KD006 variant (such as humanized KD006 variant) is used at a dose of approximately between 0.1 to 10 mg/kg once every two weeks.

In some embodiments, KD006 or KD006 variant (such as humanized KD006 variant) is used at a dose of approximately between 0.1 to 10 mg/kg once every three weeks.

In some embodiments, KD007 or KD007 variant (such as humanized KD007 variant) is used at a dose of approximately between 0.1 to 10 mg/kg once a week.

In some embodiments, KD007 or KD007 variant (such as humanized KD007 variant) is used at a dose of approximately between 0.1 to 10 mg/kg once every two weeks.

In some embodiments, KD007 or KD007 variant (such as humanized KD007 variant) is used at a dose of approximately between 0.1 to 10 mg/kg once every three weeks.

In some instances, the method of the present disclosure comprises administering a pharmaceutical composition comprising a conjugated form of a single domain antibody or an antigen binding fragment thereof selected from KD001, KD002, KD003, KD004, KD005, KD006, KD007, KD008, KD009, KD010, KD011, KD012, KD013, KD014, KD015, KD016, KD017, KD018, KD019, KD020, KD021, KD022, KD023, KD024, KD025, KD026, KD027, KD028, KD029, KD030, KD031, KD032, KD033, KD034, KD035, KD036, KD037, KD038, KD039, KD040, KD041, KD042, KD043, KD044, KD045, KD046, KD047, KD048, KD049, KD050, KD051, KD052, KD053, KD054, KD055, KD056, KD057, KD058, KD059, KD060, KD061, KD062, KD063 or KD064 or their corresponding variants, competing single domain antibodies thereof or binding agent comprising same.

The binding agent (e.g., antibodies or antigen binding fragments thereof) of the present disclosure may be used for detection purposes.

Detection of a particular target may be performed in vitro by contacting a sample, containing or suspected of containing the target with the binding agent (e.g., antibodies or antigen binding fragments thereof) described herein and quantifying a signal associated with positive or negative binding using a detection apparatus.

The sample may originate from a mammal (e.g., a human). The sample may be a tissue sample obtained from the mammal or a cell culture supernatant.

In some embodiments, the sample may be a serum sample, a plasma sample, a blood sample, semen or ascitic fluid obtained from the mammal.

Detection of a particular target may be performed in vivo by administering the antibodies or antigen binding fragments thereof to an individual and quantifying a signal associated with positive or negative binding using a detection apparatus.

Upon detecting the presence of the target in the sample or in the individual, a drug (e.g., antibody, small molecule, antibodies or antigen binding fragments thereof disclosed herein) may be administered to the individual.

Companion Diagnostic

The present application also provides a test and medical device that may be used as a companion diagnostic.

The test may be used to evaluate the expression of TROP2 in tumor or tumor cells and/or the presence of macrophages in a tumor.

In some embodiments, the test may be carried out prior to treating a subject with a drug targeting TROP2. Accordingly, the test may be carried out to determine whether a subject would be eligible for treatment with the drug.

In other embodiments, the test may be carried out during or subsequent to treatment with a drug targeting TROP2. Accordingly, the test may be carried out to determine whether the subject respond to treatment or not and/or to monitor ongoing treatment.

In some embodiments, the test may be used as a companion diagnostic to treatment with any type of drug targeting TROP2 such as for example and without limitation, small molecules and biologics including the binding agents disclosed herein or any therapeutic antibodies against TROP2.

The test may be particularly used as a companion diagnostic to treatment with a binding agent described herein.

The test may help identify subjects who are most likely to benefit from treatment with the binding agent disclosed herewith.

In some embodiments, the test may be used to determine the level of TROP2 expressing cells in a tumor. In other embodiments, the test may be used to determine the level of TROP2 expression in tumor cells. In another embodiment, the test may be used to determine the presence of macrophages in a tumor.

In some embodiments, the test is based on immunodetection of markers. Accordingly, the test uses a binding agent targeting TROP2 and optionally a binding agent targeting one or more macrophage markers.

In an exemplary embodiment, the test is an immunohistochemical assay. In another exemplary embodiment, the test is an immunocytochemical assay. In yet other embodiments, the test is a flow cytometry assay. In yet other embodiments, the test is a Western blot. In yet other embodiments, the assay is an ELISA.

In other embodiments, the test is based on detection of nucleic acids. Accordingly, the test may comprise nucleic acid molecules that are capable of specific hybridization with nucleic acids encoding TROP2 or their complement thereof and optionally nucleic acid molecules that are capable of binding to one or more macrophages markers.

In some embodiments, the test is based on in situ hybridization.

In another embodiment, the test is based on polymerase chain reaction.

The test may be carried out, for example, on a tumor biopsy obtained from a patient and the level of selected biomarker expression may assessed. In an embodiment, expression of TROP2 is determined and may be scored as low, moderate or high by IHC staining with the TROP2 binding agent. In another embodiment, the human macrophage infiltration, is determined and may be scored as low, moderate or high by IHC staining. The characterization of TROP2 expression as low, moderate and high may be determined, for example, by a trained pathologist.

Figure 16A:
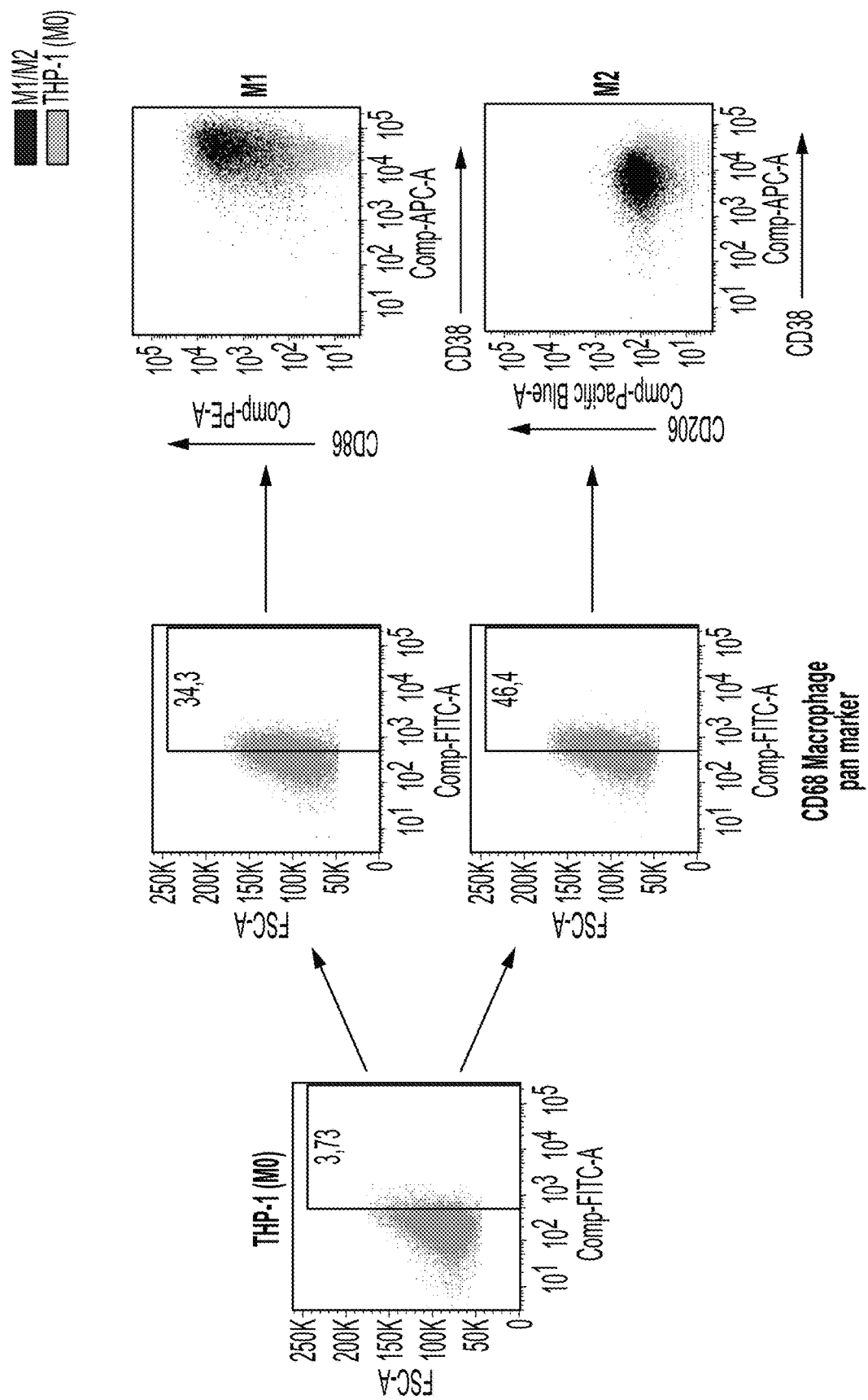
FIG. 16A: plots showing the THP-1 differentiated M1 and M2 macrophages upon treatment with PMA and cytokines. THP-1 cells showed upregulation of CD68 after PMA treatment. The M1 cells showed upregulation of CD38 and CD86 after treatment with IFN-7 and LPS. M2 macrophages showed upregulation of CD206 and downregulation of CD38 after treatment with IL-4 and IL-13.
Figure 16B:
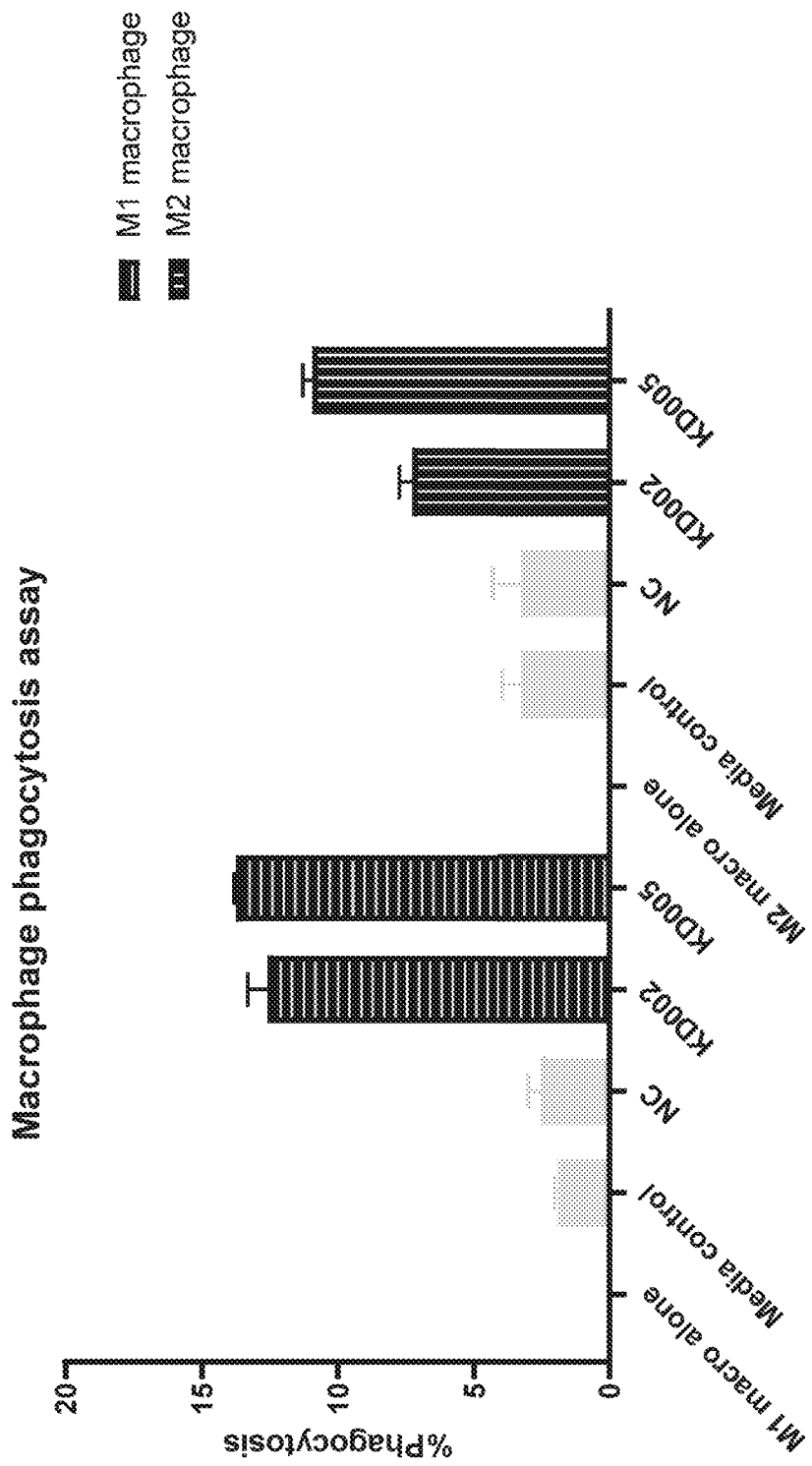
FIG. 16B: bar graph showing the percentage of phagocytosed M1 or M2 macrophages upon treatment with KD002, KD004 or KD005 at 10 nM as illustrated by gating on the pHrodo positive and Celltrace Violet positive cells.

Based on the FIG. 16B indicating that both M1 and M2 macrophages lead to phagocytosis, a pan macrophage marker may be used to evaluate the macrophage infiltration level and the potential efficacy prediction. In an exemplary embodiment, the presence of macrophages in tumors may be assessed with the pan marker CD68.

The binding agent or pharmaceutical composition of the present disclosure may be administered to patients carrying tumors with high TROP2/high CD68 expression, low CD68/high TROP2 expression, low CD68/low TROP2 expression.

The present disclosure therefore relates to a kit that comprise a binding agent that specifically binds to TROP2 and a binding agent that binds to a macrophage marker.

The kit may more particularly comprise a binding agent that specifically binds to TROP2 and a binding agent that binds to a pan macrophage marker. Exemplary embodiments of pan macrophages markers include for example and without limitations, CD68, CD80, and CD11c.

Screening Assay

Binding agents having same or similar property(ies) as any one of KD001-KD005 and/or KD001-KD005 such as KD002 variants or KD005 variants can be identify by performing one or more of the assays described herein.

For example, candidate binding agents may be submitted to binding assays (e.g., ELISA, FACS etc.) for identifying those that bind to the same or overlapping region of TROP2 as any one of KD001, KD002, KD003, KD004, KD005, KD002 variants or KD005 variants.

The binding assay may measure positive binding to a specific region of TROP2 or to specific amino acid residues of TROP2 or loss of binding when a specific region of TROP2 is deleted or when specific amino acid residues of TROP2 are mutated or deleted.

The binding assays may be carried out on recombinant polypeptides or on cells expressing the polypeptides.

In some embodiments, a binding agent may be identified by contacting a candidate binding agent with a polypeptide comprising a sequence at least 80% identical, at least 85% identical, at least 90% identical, at least 95% identical, at least 99% identical or identical to the human TROP2 amino acid sequence, or a fragment thereof or with a cell expressing such polypeptide or fragment thereof.

Due to their high level of identity, a binding agent that binds to human TROP2 may be identified by contacting a candidate binding agent with a polypeptide comprising a cynomolgus TROP2 amino acid sequence or a fragment thereof or with a cell expressing such polypeptide or fragment thereof.

In an exemplary embodiment, the candidate binding agent is contacted with a polypeptide comprising a sequence consisting of amino acid residues 27-73 of human TROP2 or of cynomolgus TROP2 or a fragment thereof or with a cell expressing such polypeptide or fragment thereof.

In an exemplary embodiment, the candidate binding agent is contacted with a polypeptide comprising a sequence consisting of amino acid residues 27-56 of human TROP2 or of cynomolgus TROP2 or a fragment thereof or with a cell expressing such polypeptide or fragment thereof.

In an exemplary embodiment, the candidate binding agent is contacted with a polypeptide comprising a sequence consisting of amino acid residues 27-66 of human TROP2 or of cynomolgus TROP2 or a fragment thereof or with a cell expressing such polypeptide or fragment thereof.

The present disclosure therefore relates to a method of identifying a binding agent that comprises a) contacting a candidate binding agent with a polypeptide comprising i) a TROP2 amino acid sequence consisting of amino acid residues 27-146 of human TROP2 or of cynomolgus TROP2, ii) a polypeptide comprising a sequence at least 80% identical to the TROP2 amino acid sequence of i) or iii) a fragment of i) or ii) thereof and b) selecting a binding agent that binds to the polypeptide. The method of the present disclosure may also be carried out by contacting a candidate binding agent with cell expressing such polypeptide or fragment thereof.

The binding agent may also be selected for not being capable of binding to a polypeptide that comprises a human TROP2 amino acid sequence consisting of amino acid residues 147-274 or a fragment thereof or for having a reduced binding to said polypeptide compared to the full human TROP2 polypeptide.

For example, the binding agent may be selected for not being capable of binding to one or more polypeptide comprising a human TROP2 amino acid sequence carrying from 5 to 70 amino acid deletions in the amino acid sequence defined by residues 1-73 of human TROP2 or for having a reduced binding to said polypeptide compared to a human TROP2 polypeptide having no such deletion.

For example, the binding agent may be selected for not being capable of binding to one or more polypeptide selected from polypeptides comprising a human TROP2 amino acid sequence carrying deletion of amino acid residues 27-36, 27-44, 27-56, 27-66 or 27-73 or for having a reduced binding to said polypeptide compared to a human TROP2 polypeptide having no such deletion.

More particularly, the binding agent may be selected for not being capable of binding to a polypeptide comprising the amino acid sequence set forth in SEQ ID NO: 149.

Binding agents may also be selected based on their ability to compete with one or more of binding agents or antigen binding domains disclosed herein. More particularly, binding agents may also be identified based on their ability to compete with any one of KD001, KD002, KD003, KD004, KD005, KD002 variants or KD005 variants.

In some embodiments, the binding agent or antigen binding domain does not compete with Sacituzumab, hTINA-1, h7E6, and/or AR47A6.4.2.

For example, the method of the present disclosure may comprise a) performing a competition assay between a candidate binding agent and the binding agent of any one of SEQ ID NO:22-26 or SEQ ID NO:94-114 for binding to i) human TROP2, ii) cynomolgus TROP2, iii) a polypeptide comprising a sequence at least 80% identical to human TROP2, iv) a polypeptide comprising a sequence at least 80% identical to cynomolgus TROP2 or v) a fragment of any one of i) to iv) thereof and b) selecting a competing binding agent.

In an exemplary embodiment, the competition assay is performed with a polypeptide comprising a sequence consisting of amino acid residues 27-146 of human TROP2 or of cynomolgus TROP2 or a fragment thereof.

In an exemplary embodiment, the competition assay is performed with a polypeptide comprising a sequence consisting of amino acid residues 27-73 of human TROP2 or of cynomolgus TROP2 or a fragment thereof.

In an exemplary embodiment, the competition assay is performed with a polypeptide comprising a sequence consisting of amino acid residues 27-56 of human TROP2 or of cynomolgus TROP2 or a fragment thereof.

In an exemplary embodiment, the competition assay is performed with a polypeptide comprising a sequence consisting of amino acid residues 27-66 of human TROP2 or of cynomolgus TROP2 or a fragment thereof.

In a particular embodiment, binding agents that compete with any one of KD001, KD002, KD003, KD004, KD005, KD002 variants or KD005 variants are selected. In other particular embodiments, binding agents that compete with KD002 and/or KD005 are particularly selected.

In an exemplary embodiment, the TROP2 amino acid sequence used in the binding experiments and/or in the competition assay is a human TROP2 amino acid sequence.

In an exemplary embodiment, the TROP2 amino acid sequence used in the binding experiments and/or in the competition assay is a cynomolgus TROP2 amino acid sequence.

In an exemplary embodiment, the TROP2 fragment used in the binding experiments and/or in the competition assay is a fragment of at least 10 amino acid residues.

In an exemplary embodiment, the TROP2 fragment used in the binding experiments and/or in the competition assay is a fragment of between 10 to 30 amino acid residues, including for example a fragment of between 10 to 25 amino acid residues, a fragment of between 10 to 20 amino acid residues, a fragment of between 10 to 15 amino acid residues etc.

In an embodiment, the human TROP2 amino acid sequence used in the binding experiments and/or in the competition assay may include for example, amino acid residues 47-56 of human TROP2.

In another embodiment, the human TROP2 amino acid sequence used in the binding experiments and/or in the competition assay may include for example, amino acid residues 60-66 of human TROP2.

In yet another embodiment, the human TROP2 amino acid sequence used in the binding experiments and/or in the competition assay may include for example, amino acid residues 47-66 of human TROP2.

The candidate binding agent may comprise the antigen binding domain of an antibody or antigen binding fragment thereof, of an antibody-like molecule, of a fusion with protein scaffolds or of an immune cell modulating agent or the like.

Alternatively, the candidate binding agent may be selected from an antibody or antigen binding fragment thereof, an antibody-like molecule, a fusion with protein scaffolds or an immune cell modulating agent.

In an exemplary embodiment, the candidate binding agent may comprise an antibody having a light chain variable region and a heavy chain variable region or an antigen binding domain of said antibody.

In another exemplary embodiment, the candidate binding agent may comprise a heavy chain only antibody or an antigen binding domain of said heavy chain only antibody.

In some embodiments, the binding agent is selected for its affinity for human TROP2.

In some embodiments, the binding agent is selected for its affinity for cynomolgus TROP2.

In some embodiments, the binding agent is selected for having an affinity for human TROP2 that is similar (with+/−

25% variation) to that of KD001, KD002, KD003, KD004, KD005 or to a variable region thereof.

In other embodiments, the binding agent is selected for having an affinity for human TROP2 that is identical or superior to that of KD001, KD002, KD003, KD004, KD005 or to a variable region thereof.

In some embodiments, the binding agent is selected for having a dissociation rate that is similar (with+/−25% variation) to that of KD001, KD002, KD003, KD004, KD005 or to a variable region thereof for human TROP2.

In some embodiments, the binding agent is selected for having a dissociation rate that is identical or lower to that of KD001, KD002, KD003, KD004, KD005 or to a variable region thereof for human TROP2.

In some embodiments, the candidate binding agent or at least one of the one or more antigen binding domains of the candidate binding agent has an affinity of $\leq 10^{-6}$ M.

In some embodiments, the candidate binding agent or at least one of the one or more antigen binding domains of the candidate binding agent has an affinity of $\leq 10^{-7}$ M.

In some embodiments, the candidate binding agent or at least one of the one or more antigen binding domains of the candidate binding agent has an affinity of $\leq 10^{-8}$ M.

In some embodiments, the candidate binding agent or at least one of the one or more antigen binding domains of the candidate binding agent has an affinity of $\leq 10^{-9}$ M.

In some embodiments, the candidate binding agent or at least one of the one or more antigen binding domains of the candidate binding agent has an affinity of $\leq 10^{-10}$ M.

In some embodiments, the candidate binding agent or at least one of the one or more antigen binding domains of the candidate binding agent has an affinity of $\leq 10^{-11}$ M.

In some embodiments, the candidate binding agent or at least one of the one or more antigen binding domains of the candidate binding agent has an affinity of at least $1 \times 10^{-10}$ M for human TROP2.

In some embodiments, the candidate binding agent or at least one of the one or more antigen binding domains of the candidate binding agent has an affinity of between $1 \times 10^{-10}$ M and $1 \times 10^{-12}$ for human TROP2.

In some embodiments, the candidate binding agent or at least one of the one or more antigen binding domains of the candidate binding agent has an affinity of between $1 \times 10^{-10}$ M and $1 \times 10^{-11}$ for human TROP2.

In some embodiments, the candidate binding agent or at least one of the one or more antigen binding domains of the candidate binding agent has a dissociation rate of between $1 \times 10^{-6}$ to $1 \times 10^{-4}$.

In some embodiments, the candidate binding agent or at least one of the one or more antigen binding domains of the candidate binding agent has a dissociation rate of between $1 \times 10^{-5}$ to $1 \times 10^{-4}$.

In accordance with the present disclosure, the affinity may be measured on recombinant human TROP2 protein or on cells expressing human TROP2 protein. The affinity may be measured on full length human TROP2 protein.

The binding agents can also be submitted to in vitro or in vivo assays to assess function. Exemplary assays include internalization, ADCC, ADCP, cell viability, in vitro tumor growth inhibition experiments and/or in vivo tumor growth inhibition experiments as described herein.

In some embodiments, the binding agent is selected for in vitro potency against tumor cells.

In some embodiments, the binding agent is selected for in vivo potency against tumor cells.

Binding agents having similar (+/−25%) or better activity as any one of KD001, KD002, KD003, KD004, KD005, KD002 variants or KD005 variants are particularly selected. However, Binding agents having reduced activity compared with any one of KD001, KD002, KD003, KD004, KD005, KD002 variants or KD005 variants (e.g., 10% activity, 20% activity, 30% activity, 40% activity, 50% activity, between 50% and 75% activity, between 50% and 85% activity, between 50% and 95% activity of a reference antibody) may still be functional and may be selected.

In some embodiments, the binding agent may be selected for having at least one pharmacokinetic parameter similar to that of any one of KD001, KD002, KD003, KD004 or KD005.

In some embodiments, the binding agent may be selected for having at least one pharmacokinetic parameter equivalent to that of any one of as any one of KD001, KD002, KD003, KD004, KD005, KD002 variants or KD005 variants.

In some embodiments, the binding agent may be selected for having a sequence as set forth in any one of SEQ ID NOs:143-147.

Examples

Example 1—Animal Immunization and Immune Library Construction

Single domain antibodies were generated by immunizing transgenic mouse carrying CH1 deletions at an immunoglobulin heavy chain (IgH) locus (see international application No. PCT/CA2021/050951 filed on Jul. 12, 2021, and published on Jan. 20, 2022, under No. WO2022/011457 A1 the entire content of which is incorporated herein by reference) with the extracellular domain of human TROP2 protein (aa 1-274) comprising His tag (e.g., SEQ ID NO:164) (Sino Biological, Cat. No. 10428-H08H: GenBank Acc. No. NP_002344.2)).

Sequences of single-domain antibodies were uncovered from clone picking after phage display panning of reconstituted immune libraries against the antigens.

DNA fragments encoding VHHs or VHs were generally subcloned into constructs comprising a constant region of a human antibody (e.g., human IgG1 Fc) for expression and in vitro and in vivo testing.

Example 2—Production and Purification of sdAbs sdAbs were expressed in cells and isolated as protein dimers. The sdAbs identified in the experimental section and/or Figures as KD001 to KD068 are composed of two heavy chains. Unless, specifically mentioned otherwise each of KD001 to KD068 have the corresponding heavy chain amino acid sequence set forth in in Table 15, 16, 18 or 19.

Protein dimers (e.g., homodimers) were expressed in 2.5 mL or 400 mL culture volume from the DNA construct using the ExpiCHO™ Expression System (Thermo Fisher, Cat. no. A29133) or the Expi293™ Expression System (Thermo Fisher, Cat. no. A14635).

Freshly thawed ExpiCHO-s cells were allowed to recover in culture for two or more passages before transfection. Cells were then passaged every 3-4 days until they reach $4 \times 10^6$-$6 \times 10^6$ cells/mL at which time they were diluted to $2 \times 10^5$-$3 \times 10^5$ cells/mL in ExpiCHO™ Expression Medium pre-warmed to 37° C. The day prior to transfection, cells were diluted to $3 \times 10^6$-$4 \times 10^6$ cells/mL and on the day of transfection, cells were further diluted to $6. \times 10^6$ cells/mL. 1 µg of DNA/mL of culture volume was diluted with cold OptiPRO™ medium (100 µL for 2.5 mL of culture volume;

16 mL for 400 mL of culture volume). ExpiFectamine™ CHO Reagent (8 µL for 2.5 mL of culture volume; 1280 µL for 400 mL of culture volume) was added to medium containing DNA and incubated with ExpiFectamine™/DNA complexes at room temperature for 1-5 min. Then the DNA complex was transferred to culture (at $6\times10^6$ cells/mL) while swirling. The cells were incubated at 37° C. under 8% $CO_2$ and 80% humidity with shaking (INFORS HT shaker, 125 rpm). 18-22 h after onset of transfection, ExpiCHO™ feed (0.6 mL for 2.5 mL of culture volume; 96 mL for 400 mL of culture volume) and ExpiCHO™ enhancer (15 µL for 2.5 mL of culture volume; 2.4 mL for 400 mL of culture volume) were added to the cells. The cells were returned to INFORS HT incubator set at 37° C. under 8% $CO_2$ and 80% humidity with shaking at 125 rpm (25 mm orbit). 8 days post-transfection, supernatants were clarified by centrifugation at 4000×g for 30 min. Supernatants were filter-sterilized using a Nalgene™ Rapid-Flow™ Sterile Disposable Filter Units 1000 mL filter unit (Thermo Scientific, Cat. no. 567-0020) and were stored at 4° C. or frozen for later analysis.

Freshly thawed Expi293F cells were allowed to recover in culture for two or more passages before transfection. Cells were then passaged every 3-4 days until they reach $3\times10^6$-$5\times10^6$ cells/mL at which time they were diluted to $3\times10^5$-$5\times10^5$ cells/mL in Expi293™ Expression Medium pre-warmed to 37° C. The day prior to transfection, cells were diluted to $2.5\times10^6$-$3\times10^6$ and on the day of transfection, cells were further diluted to $3\times10^6$ viable cells/mL. 1 µg of DNA/mL of culture volume was diluted with Opti-MEM™ I Reduced Serum medium to get a final volume of 150 µL for 2.5 mL of culture volume and 24 mL for 400 mL of culture volume. ExpiFectamine™ 293 Reagent (8 µL for 2.5 mL of culture volume; 1.3 mL for 400 mL of culture volume) was added to medium Opti-MEM™ I Reduced Serum medium (140 µL for 2.5 mL of culture volume; 22.5 mL for 400 mL of culture volume) to incubate at room temperature for 5 minutes. Diluted ExpiFectamine™ was added to diluted DNA and incubate for 15 minutes at room temperature. ExpiFectamine™/DNA solution was transferred to culture drop by drop (at $3\times10^6$ cells/mL) while swirling. The cells were incubated at 37° C. under 8% $CO_2$ and 80% humidity with overnight shaking (INFORS HT shaker, 125 rpm). 18-22 h after onset of transfection, ExpiFectamine™ 293 Transfection Enhancer 1 (15 µL for 2.5 mL of culture volume; 2.4 mL for 400 mL of culture volume) and ExpiFectamine™ 293 Transfection Enhancer 2 (50 µL for 2.5 mL of culture volume; 24 mL for 400 mL of culture volume) were added to the cells. The cells were returned to INFORS HT incubator set at 37° C. under 8% $CO_2$ and 80% humidity with shaking at 125 rpm (25 mm orbit). 5 days post-transfection, supernatants were clarified by centrifugation at 4000×g for 30 min. Supernatants were filter-sterilized using a Nalgene™ Rapid-Flow™ Sterile Disposable Filter Units 1000 mL filter unit (Thermo Scientific, Cat. no. 567-0020) and were stored at 4° C. or frozen for later analysis.

Proteins are purified using 3-mL MabSelect SuRe resin (GE Healthcare, Cat. No. 17-5438-02) with gravity columns or 40-mL MabSelect SuRe resin with AKTA PURE (GE Healthcare, Piscataway, NJ) depending on the supernatant volume. Resin was incubated with 0.5 NaOH for one hour and equilibrated with Tris-base buffer pH 7.4 (50 mM Tris-HCl, 150 mM NaCl, pH 7.4) prior injection. Supernatant was applied on gravity columns or the at 5 mL/min on 40-mL column. Resin column was washed with 3 CV (column volume) with Tris-base buffer pH 7.4 at flow rate of 10 mL/min. Protein was eluted with 3 CV of 0.1M citrate acid pH 3 at 10 mL/min. Fractions identified with protein from the visual output of the chromatogram (absorbance at 280 nm) were pooled together. Pooled fractions were neutralized with 1 M Tris-HCl pH 9 to achieve the pH ~5-6 before transferring into PBS (Phosphate-buffered saline) pH 6 buffer prepared from PBS 10×pH 7.2 (15 mM Potassium Phosphate monobasic 1552 mM Sodium Chloride 27 mM Sodium Phosphate dibasic, ThermoFisher, Cat. no. 70013073) or 20 mM Histidine 7% Sucrose 0.02% Polysorbate80 pH 5.5.

Buffer exchange was carried out by sample concentrators for proteins purified from gravity columns or either by dialysis or by desalting column for proteins purified from AKTA PURE. Proteins purified from gravity columns were concentrated with sample concentrator VivaSpin 2, 50 kDa MWCO (GE Healthcare, Cat. no. 28932257) by centrifugation at 3,500-4,000×g at 4° C. then, diluted with PBS pH 6 to achieve 4-fold and repeated until sample reached 200-fold. Dialysis was carried out in 4 L of PBS pH 6 overnight at 4° C. using 7 kDa molecular weight cut-off dialysis tubing (ThermoFisher, Cat. no. 68799). On the other hand, desalting column was incubated with 0.5 NaOH overnight and equilibrated with PBS pH 6. Volume of 15 mL of neutralized protein sample was loaded into the HiPrep 26/10 desalting column (GE Healthcare, Cat. no. 17-5087-02) at 0.5 mL/min then, protein was eluted with 2 CV of PBS pH 6. Loading and elution steps were repeated until no neutralized protein sample from elution of affinity column remained. Fractions identified with protein from the visual output of the chromatogram (absorbance at 280 nm) were pooled together.

Sample was filter-sterilized using a Nalgene™ Rapid-Flow™ Sterile Disposable Filter Units 150 mL filter unit (Thermo Scientific, Cat. no. 565-0010). Final protein sample was quantified by optical density at 280 nanometer and tested for endotoxin level with Endosafe® LAL Reagent cartridges (Charles River Cat. no. PTS2005). Final protein sample was analyzed on SDS-PAGE gels under reducing or non-reducing conditions (see section SDS PAGE and Western Blotting).

Example 3—In Vivo Anti-Tumor Effect

The anti-tumor effect of the sdAbs of the present disclosure was tested in established tumor models in mice.

NCG mice (5-6 weeks old, female) were purchased from Charles River Laboratories (St. Constant, QC). CB-17 Fox Chase SCID mice (6-8 weeks old, female) were purchased either from Charles River Laboratories (St. Constant, QC) or from UHN (Toronto, ON). Mice were housed in a pathogen-free environment at the animal facility in UHN. The animal work was conducted according to the guidelines of the Canadian Council on Animal Care (CCAC) and the Animal Use Protocol approved by the Animal Care Committee at UHN.

Briefly, SCID mice or NCG mice were implanted subcutaneously with 5 or 10 million tumor cells. Animals were randomized into experimental groups when tumor volumes reached 100 mm³ and were then treated (arrows) with the human IgG1 fusion construct of the KD001-KD005 or with PBS (negative control). Tumor volume was measured twice per week.

Figure 1A:
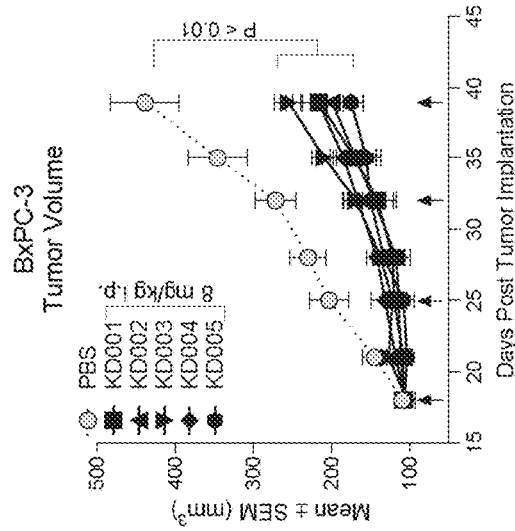
FIG. 1A-D: graphs illustrating the tumor volume over time of SCID mice bearing MDA-MB-453 (FIG. 1A), MDA-MB-231 (FIG. 1B), BxPC-3 (FIG. 1C) or T.Tn (FIG. 1D) treated with the KD001, KD002, KD003, KD004 or KD005 anti-TROP2 sdAbs or with PBS.
Figure 1B:
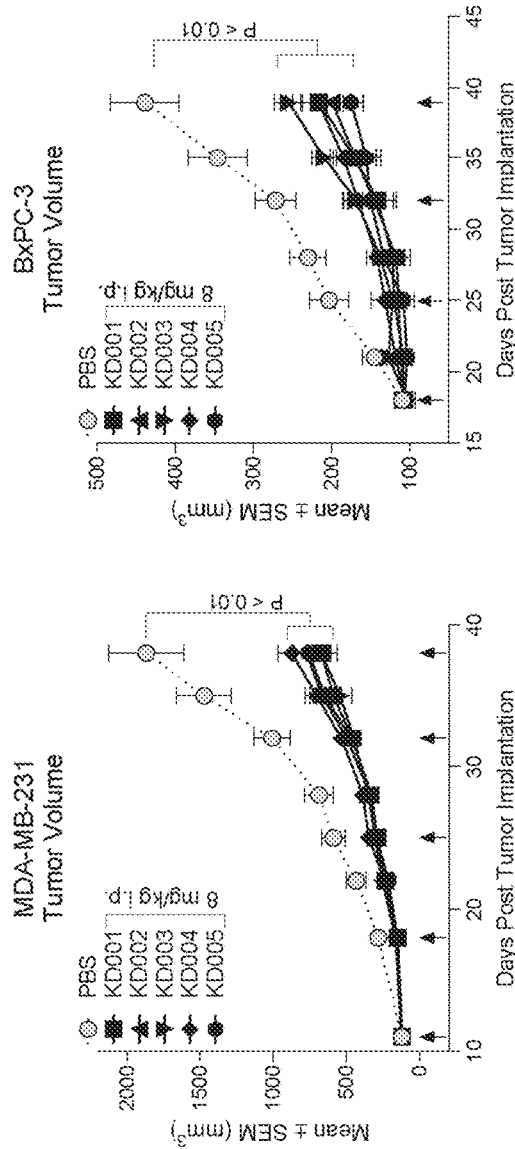
Figure 1C:
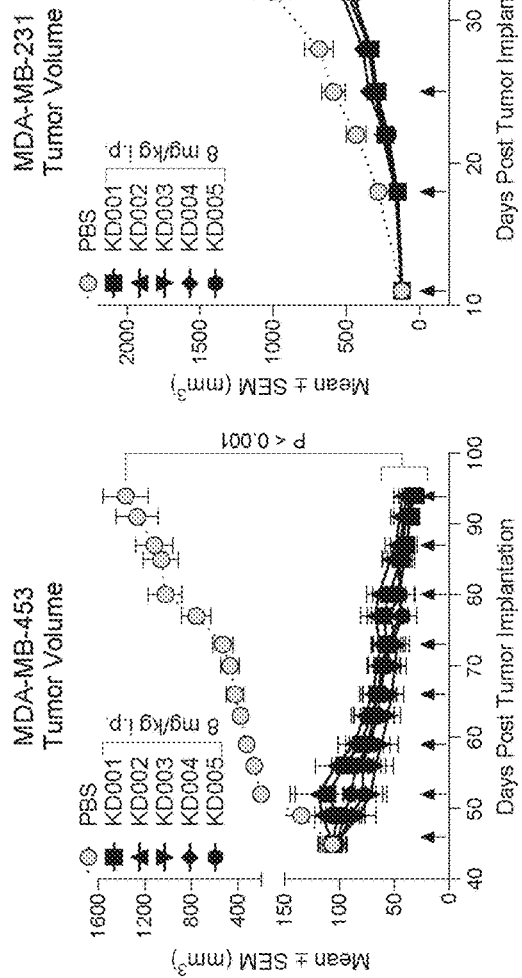
Figure 1D:
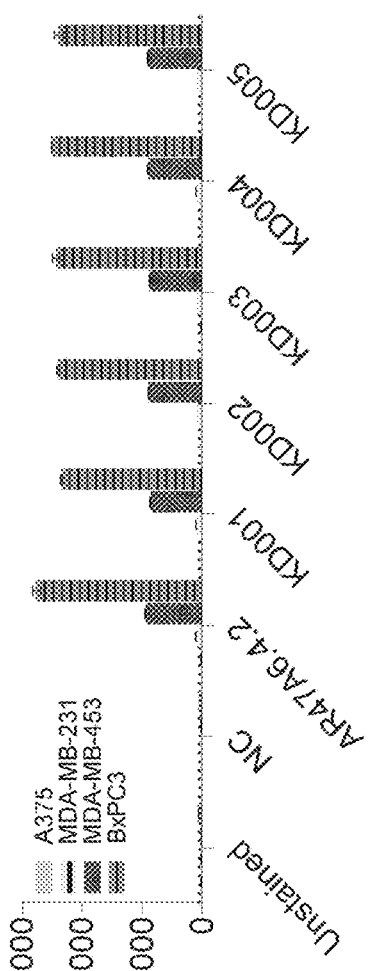
Figure 3:
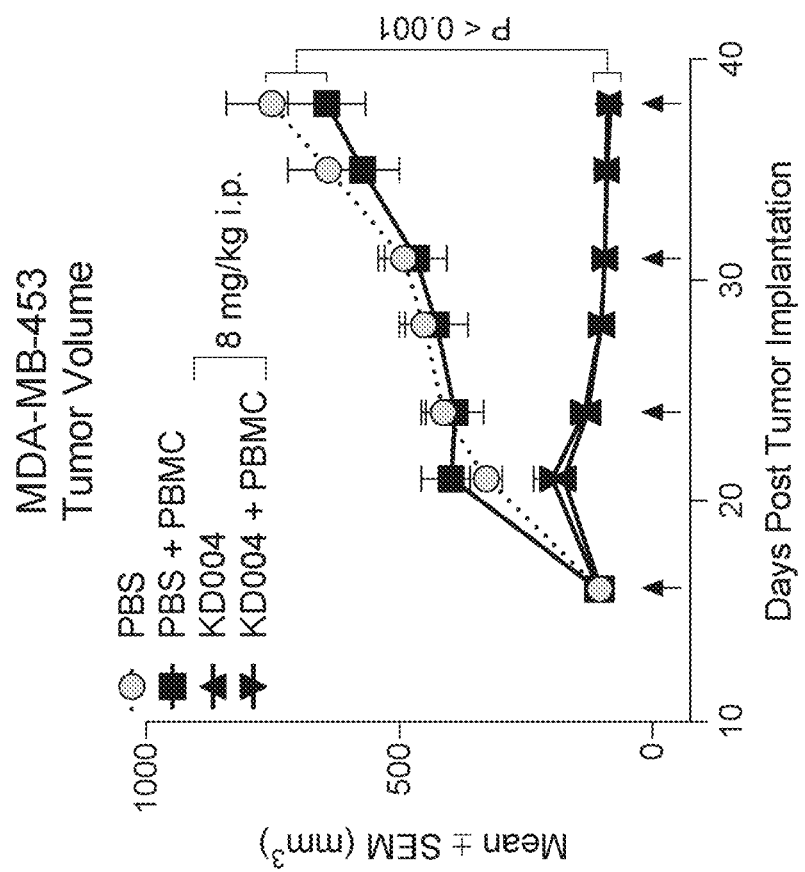
FIG. 3: graph showing tumor volume over time of MDA-MB-453 implanted NCG mice treated with KD004 at 8 mg/kg i.p. at the indicated intervals in the presence or absence of human PBMCs. Negative control is PBS.

Antibody efficacy was tested in SCID or in NCG mice bearing MDA-MB-453, MDA-MB-231, BxPC-3, T.Tn tumors or MDA-MB-468 tumors. In FIG. 1A, the NCG mice were treated with testing articles at 8 mg/kg, once per week for 8 doses. In FIG. 1B to 1D, the SCID mice were treated with testing articles at 8 mg/kg, once per week for 8 doses. In FIG. 2A, the NCG mice were treated with testing articles at 0.5, 2, 8, 30 mg/kg once per week for 8 doses. The PBS control arm were treated with testing articles at 8 mg/kg in FIG. 2B. In FIG. 2C, the NCG mice were treated with KD004 at 8 mg/kg with different dosing frequencies, including twice per week, every two weeks, and every three weeks. In FIG. 2D, the SCID mice were treated with testing articles at 0.1 mg/kg once per week for 6 doses. In FIG. 3, the NCG mice were engrafted with or without 10 million PBMC and then treated with KD004 at 8 mg/kg, twice per week for 8 doses. In FIG. 13C, SCID mice were treated with testing articles at 8 mg/kg once per week for 6 doses. In FIG. 15E, SCID mice were treated with testing articles at 8 mg/kg once per week for 6 doses.

No signs of toxicity were observed throughout the studies. All sdAb-treated mice had significantly smaller tumors compared to the PBS-treated animals (FIG. 1A-1D).

Figure 1E:
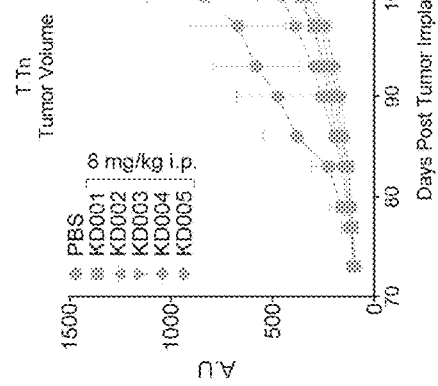
FIG. 1E: histogram showing binding of KD001, KD002, KD003, KD004 or KD005 anti-TROP2 sdAbs to MDA-MB-453, MDA-MB-231, BxPC3, and A375 cells compared with AR47A6.4.2 anti-TROP2 monoclonal antibody as analyzed by flow cytometry. Negative control is sdAb that binds HEWL (NC).

The binding of anti-TROP2 sdAbs to several cancer cell lines including MDA-MB-453, MDA-MB-231, BxPC3, and A375 cells were analyzed by flow cytometry (FIG. 1E). $1 \times 10^5$ cells were incubated with an Fc receptor blocking antibody (1/100 dilution) for 10 minutes at room temperature. Anti-TROP2 antibodies were diluted in FACS staining buffer to 10 nM and added and incubated with cells for 30 minutes on ice. After washing three times with FACS staining buffer, FITC-conjugated secondary antibodies recognizing the human Fc region (Biolegend) were mixed with cells. After staining for 30 minutes, cells were washed three times, followed by resuspension into 100 μL of 7-Amino-Actinomycin D (7-AAD) solution (1/100 dilution). Cells were analyzed by BD FACSCanto™ II Flow cytometer (BD Bioscience). Data were analyzed with FlowJo via gating on single cells and live cells.

As illustrated in FIG. 1E, all the tested anti-TROP2 antibodies exhibited similar binding to tested cancer cell lines. All the tested anti-TROP2 antibodies showed the highest binding to BxPC3 cells, intermediate binding to MDA-MB-453 cells, and weak binding to MDA-MB-231 cells. None of the TROP2 antibodies bound to low TROP2 expression cell lines A375, illustrating the binding specificity of tested antibodies to TROP2. The binding of TROP2 sdAbs showed comparable binding to MDA-MB-231, MDA-MB453, and BxPC3 as AR47A6.4.2 TROP2 antibody (see Truong et al., 2008).

Example 4—Dose-Response, Schedule, Regimen and Pharmacokinetics

In FIGS. 2A and 2B, all the NCG mice were humanized with human PBMCs (10 million cells, i.v.) the day before treatment initiated, represented by the first time point in the graphs. In FIGS. 2C and 2D, the NCG mice were not humanized with human PBMCs. Human PBMC cells (10 million cells/mouse were injected i.v.) were received from HemaCare Corporation (Northridge, CA). Tumor cells were implanted in NCG mice in a similar fashion to SCID mice. In all models, tumor volumes were measured using vernier calipers and the mice were weighed one or two times weekly. Tumor volume was calculated using the formula: $\frac{1}{2}(Length \times Width^2)$.

As illustrated in FIG. 2A, the in vivo dose/response study indicates that weekly treatment of sdAbs KD004 (0.5 mg/kg, 2 mg/kg, 8 mg/kg and 30 mg/kg) prevents the growth of MDA-MB-453 implanted in NCG mice (5 million cells s.c.). No signs of toxicity were observed when animals were treated with higher doses.

Late intervention with anti-TROP2 therapy caused tumor regression in tumors of very large size (average 500 mm³) when dosed with KD004 at 8 mg/kg, once weekly (QW) in the MDA-MB-453 tumor model in NCG mice. (FIG. 2B).

Potent tumor regression was also achieved even when anti-TROP2 sdAb KD004 was administered once every three weeks in the MDA-MB-453 tumor model, in NCG mice, at a dose of 8 mg/kg (FIG. 2C).

Treatment with KD002 or KD005 at a dose of 0.1 mg/kg (i.p.) in MDA-MB-453 implanted NCG mice tumor model also led to tumor regression (FIG. 2D). The data indicated a strong anti-tumor activity of KD002 and KD005 in the pre-clinical MDA-MB-453 model. Such a strong activity may be explained by the higher binding affinity and potent ADCP activity mediated by macrophages.

Different groups of NCG mice were administered a single dose of KD004 at 2, 8 or 30 mg/kg dose level. Blood samples were collected at different time points and serum was prepared. Level of KD004 in serum was measured by ELISA and the pharmacokinetic parameters were calculated using the WinNonLin software. The anti-TROP2 in vivo pharmacokinetic parameters show that the half-life of KD004 is approximately 60 hours when administered at a dose of 8-30 mg/kg i.v. in NCG mice (FIG. 2E).

As illustrated in FIG. 3, the sdAb of the present disclosure possess anti-tumor activity as a naked antibody but may also induce ADCC.

The mechanism of action of the sdAbs of the present disclosure was further investigated.

Example 5—Cell Viability

Figure 4B:
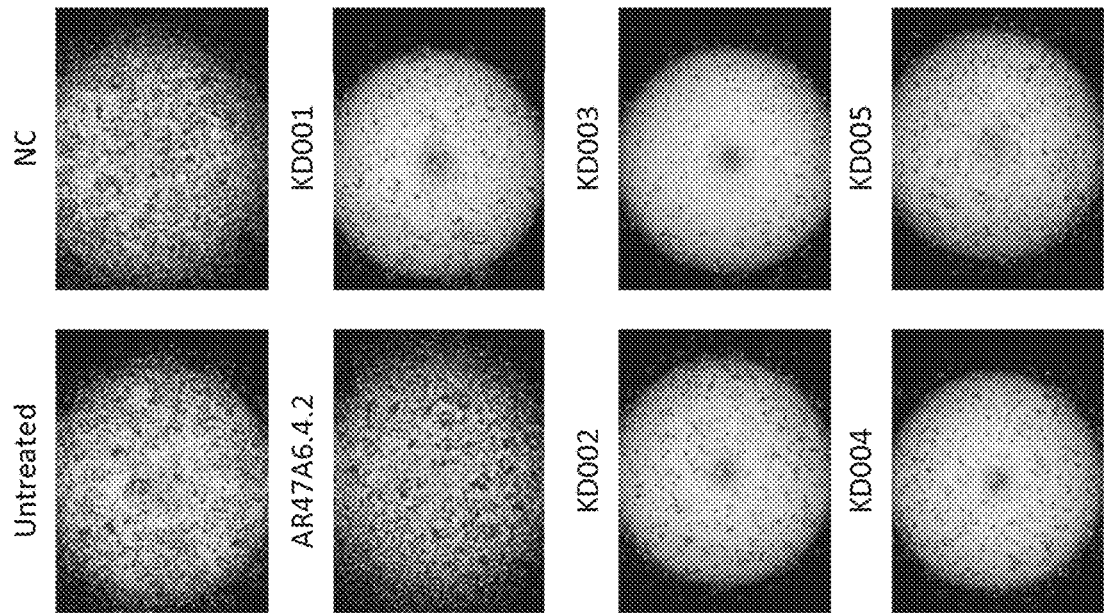
FIG. 4B image of MDA-MB-453 cells at 4×resolution after 12 days of treatment with KD001, KD002, KD003, KD004 or KD005 anti-TROP2 sdAb. Negative controls include sdAb that binds HEWL (NC) or untreated cells.
Figure 4A:
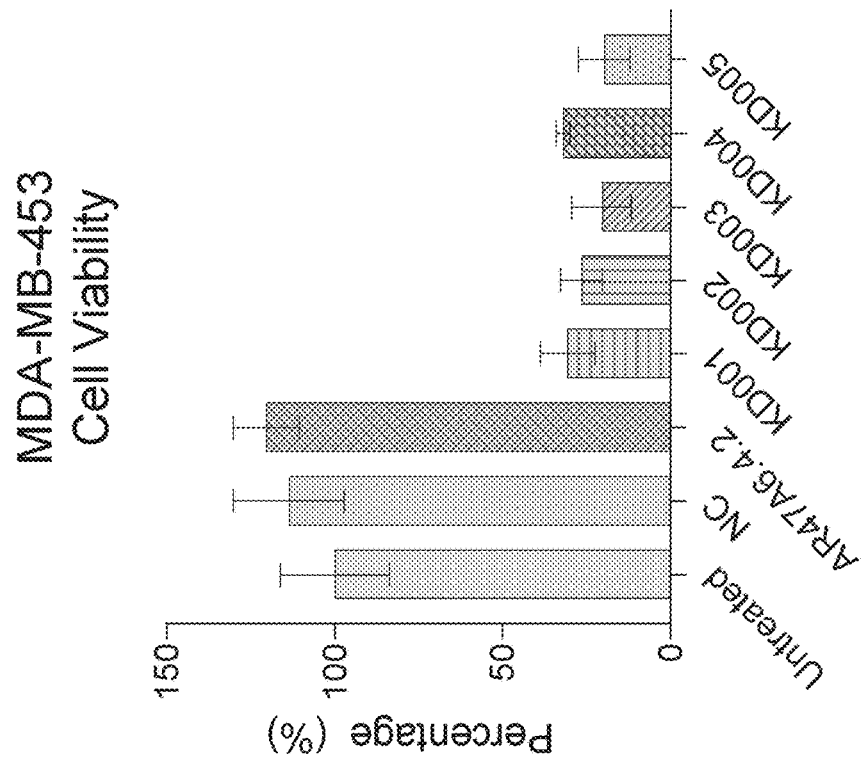
FIG. 4A: histogram showing cell viability of MDA-MB-453 cells following 12 days treatment with 1 µM KD001, KD002, KD003, KD004 or KD005 anti-TROP2 sdAbs in comparison with AR47A6.4.2 anti-TROP2 monoclonal antibody. Negative controls include sdAb that binds HEWL (NC) or untreated cells.

Cell viability of MDA-MB-453 cells following 12 days treatment with 1 μM TROP2 sdAbs was analyzed using the Promega CellTitre-Glo luminescent assay (FIG. 4A-FIG. 4B). FIG. 4A. MDA-MB-453 cells were seeded in 96-well plates at $5 \times 10^3$ cells per well and incubated overnight at 37° C., 5% $CO_2$. Cells were treated with 1 μM TROP2 sdAbs for 12 days. Following treatment cell viability was assessed using CellTitre-Glo luminescent assay (Promega) according to manufacturer's instructions. Negative control wells were treated with isotype control sdAb (sdAb with VHH specific for HEWL). AR47A6.4.2 TROP2 antibody was used for comparison purposes. Control wells containing cells which did not receive any treatment were used for signal normalization and calculation of percentage cell viability following treatment. Background luminescence was determined using wells containing medium without cells. Values represent the mean±S.D. of three replicates for each treatment. FIG. 4B shows cells imaged at 4× resolution after 12 days of treatment with TROP2 sdAb. Images were captured using EVOS XL Core Imaging System.

As shown in FIG. 4A-4B, the TROP2 sdAbs of the present disclosure (KD001, KD002, KD003, KD004 and KD005) directly inhibited MDA-MB-453 cell viability more than 50% compared to AR47A6.4.2 TROP2 antibody (which in turn did not directly affect cell viability) and the negative control (sdAb with VHH specific for HEWL).

Example 6—ADCC Activity

The ADCC activity of sdAbs was further characterized using the Promega ADCC reporter assay kit (Promega, G7015). In brief, the target cells MDA-MB-453 cells were collected and using TrypLE and resuspended at the concentration of 3 million/mL. 12,500 cells were seeded into each well and incubated overnight. The next day, testing antibodies were diluted into the assay medium, with a final testing concentration of 1 μg/mL. The ADCC effector cells were thawed gently in a 37° C. water bath and resuspended into the assay medium. The ratio between effector cells and target cells used was 1:10. Thus 1,250 effector cells were transferred to each well. Plates were incubated at 37° C. incubator for 24 hours. 24 hours later, plates were equilibrated to room temperature. The Bio-Glo luciferase assay substrate was added to each well. Incubate the plate at room temperature for 5-30 minutes. Luminescence signal was measured by SpectraMax i3x plate reader. Data were analyzed by signal fold change upon untreated control wells.

Figures 5A, 5B:
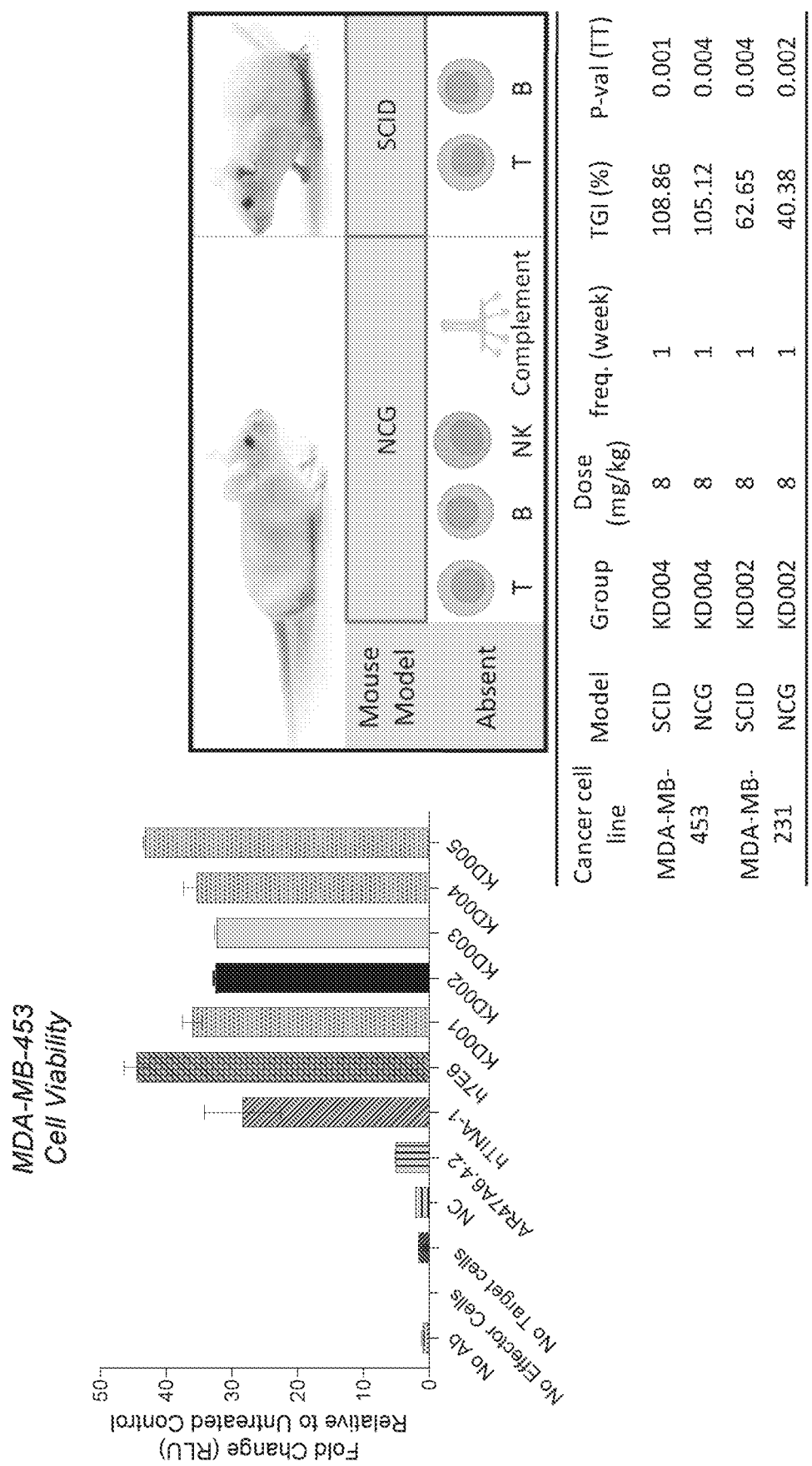
FIG. 5A: histogram showing cell viability of MDA-MB-453 cells reflecting the ADCC activity of KD001, KD002, KD003, KD004 or KD005 anti-TROP2 sdAbs. Negative controls include untreated cells (No Ab), no effector cells, no target cells or sdAb that binds HEWL (NC). Comparisons includes cells treated with human IgG1 anti-TROP2 antibodies generated with the sequences from clones hTINA-1 and h7E6.
FIG. 5B: sdAbs tumor growth inhibition (TGI) was tested in vivo in NCG and SCID mice having different effector function background and implanted with either MDA-MB-231 or MDA-MB-453 cells s.c. Administration of KD002 or KD004 was initiated when average tumor volume reached 100 mm³.

As shown in FIG. 5A, the tested anti-TROP2 sdAbs showed high ADCC capability against MDA-MB-453 cells. This ADCC reporter assay also indicates that KD001, KD002, KD003, KD004 or KD005 anti-TROP2 sdAbs are capable of inducing ADCC comparable to the human IgG1 anti-TROP2 antibodies generated with the sequences from clones hTINA-1 and h7E6.

NCG and SCID mice were implanted with either MDA-MB-231 or MDA-MB-453 cells s.c.. Anti-TROP2 sdAb (KD002 or KD004) administration was initiated when the average tumor volume reached 100 mm$^3$. As illustrated in FIG. 5B, sdAbs in vivo activity is similar in mouse strains with different effector function components.

Example 7—Internalization

The internalization assay was divided into two steps. First, the anti-TROP2 sdAbs were conjugated with Promega pHAb Amine reactive dye (Promega, G9841) using on-bead antibody conjugation. Second, the internalization assay was carried out and analyzed by flow cytometry.

For pHAb amine-reactive dye labeling, anti-TROP2 sdAbs were conjugated to the protein A beads. anti-TROP2 sdAbs were mixed with protein A beads and incubated for 60 minutes at room temperature. The antibody/bead mix was then washed with the washing buffer and resuspended in the amine/thiol conjugation buffer. The pHAb amine-reactive dye was added into the tubes containing antibody/bead mix with a 20 molar excess of dye and incubated at room temperature for 60 minutes. Tubes were placed in the magnetic stand and supernatant was discarded. Beads were washed another two times with washing buffer before elution into the elution buffer. Eluted antibody was resuspended into the neutralization buffer from the kit.

The internalization assay was performed with MDA-MB-453 cells in a flow-based format. The MDA-MB-453 cells were collected and diluted to 300,000 cells/mL. 100 μL of cell solution (30,000) was transferred to the 96-well plates. Cells were incubated in the incubator overnight. The next day, pH conjugated antibodies were diluted to 10 μg/mL concentration. 50 μL of the pH conjugated antibodies were distributed into the corresponding wells and incubated to the indicated timepoints (4 hours and 24 hours). Plates were washed 1× with flow buffer (DPBS containing 2% serum) and cells were resuspended in 100 μL of flow buffer containing 7-AAD at 1:100 dilution. Plates were analyzed by BD FACSCanto II. Antibody internalized cells were gated based on 7-AAD negative and PE positive cells.

Figures 6A, 6B:
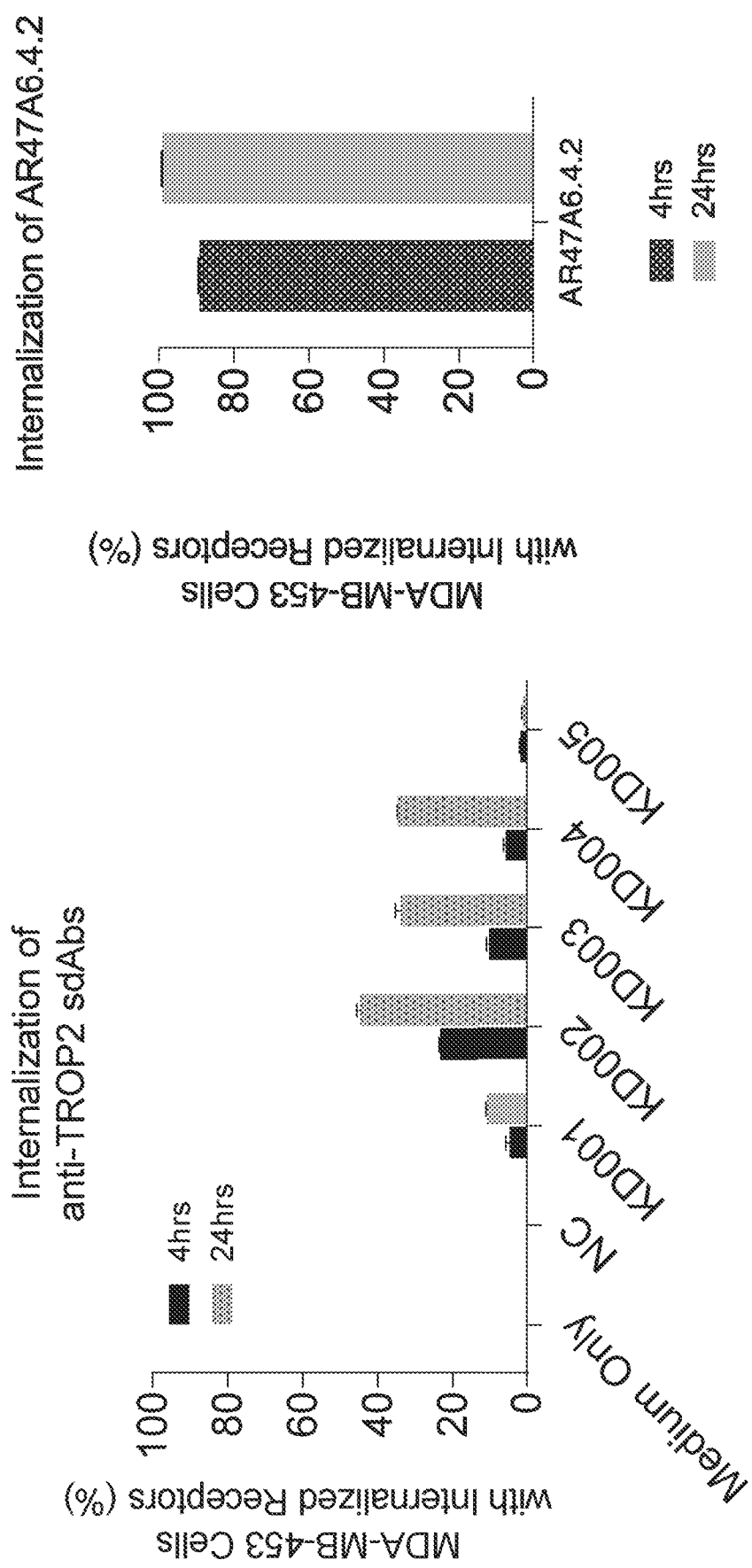
FIG. 6A-B: histograms illustrating internalization of KD001, KD002, KD003, KD004 or KD005 anti-TROP2 sdAbs (FIG. 6A) or AR47A6.4.2 (FIG. 6B) in MDA-MB-453 cells after 4 or 24 hours. Negative controls include sdAb that binds HEWL (NC) or medium only.

As illustrated in FIG. 6A and FIG. 6B, the positive control anti-TROP2 antibody AR47A6.4.2 showed internalization at 4 hours after incubation. The internalization of anti-TROP2 sdAbs was detected at 4 hours for KD002, KD003, and KD004. Increased internalization was observed at 24 hours for KD002, KD003, and KD004. KD002 showed the highest internalization among the anti-TROP2 sdAbs. Interestingly, KD005 was not internalized although it bound a similar epitope to the other anti-TROP2 sdAbs.

Figure 6C:
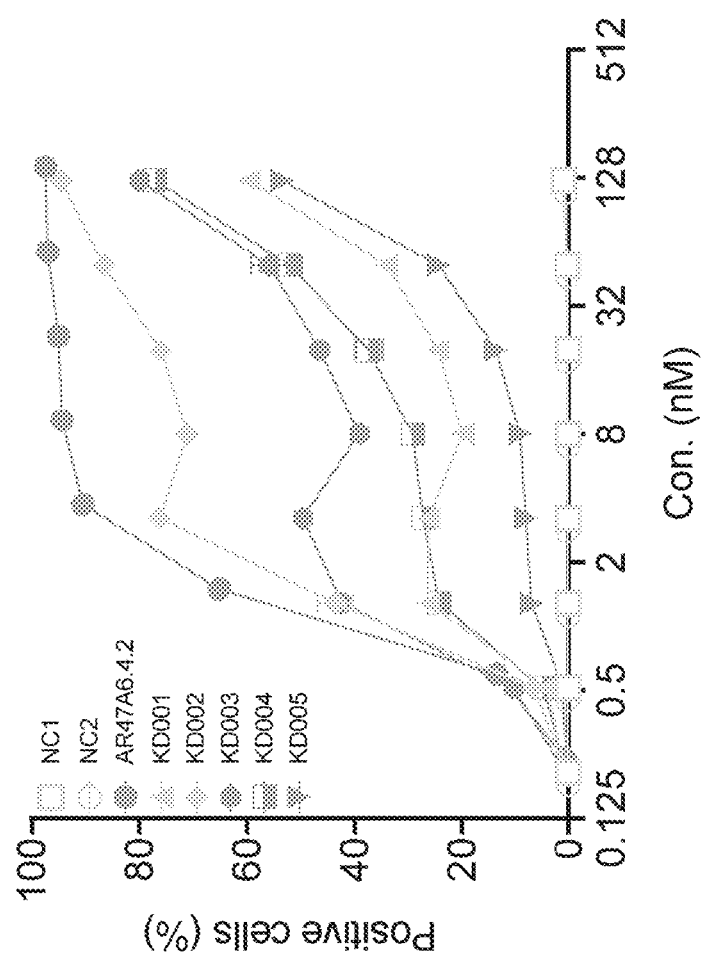
FIG. 6C: graph illustrating internalization of KD001, KD002, KD003, KD004 or KD005 anti-TROP2 sdAbs in MDA-MB-453. Internalization was assessed by conjugation of HCAbs with a pH-sensitive probe and monitored by flow cytometry (Em. 560 nm).
Figure 6D:
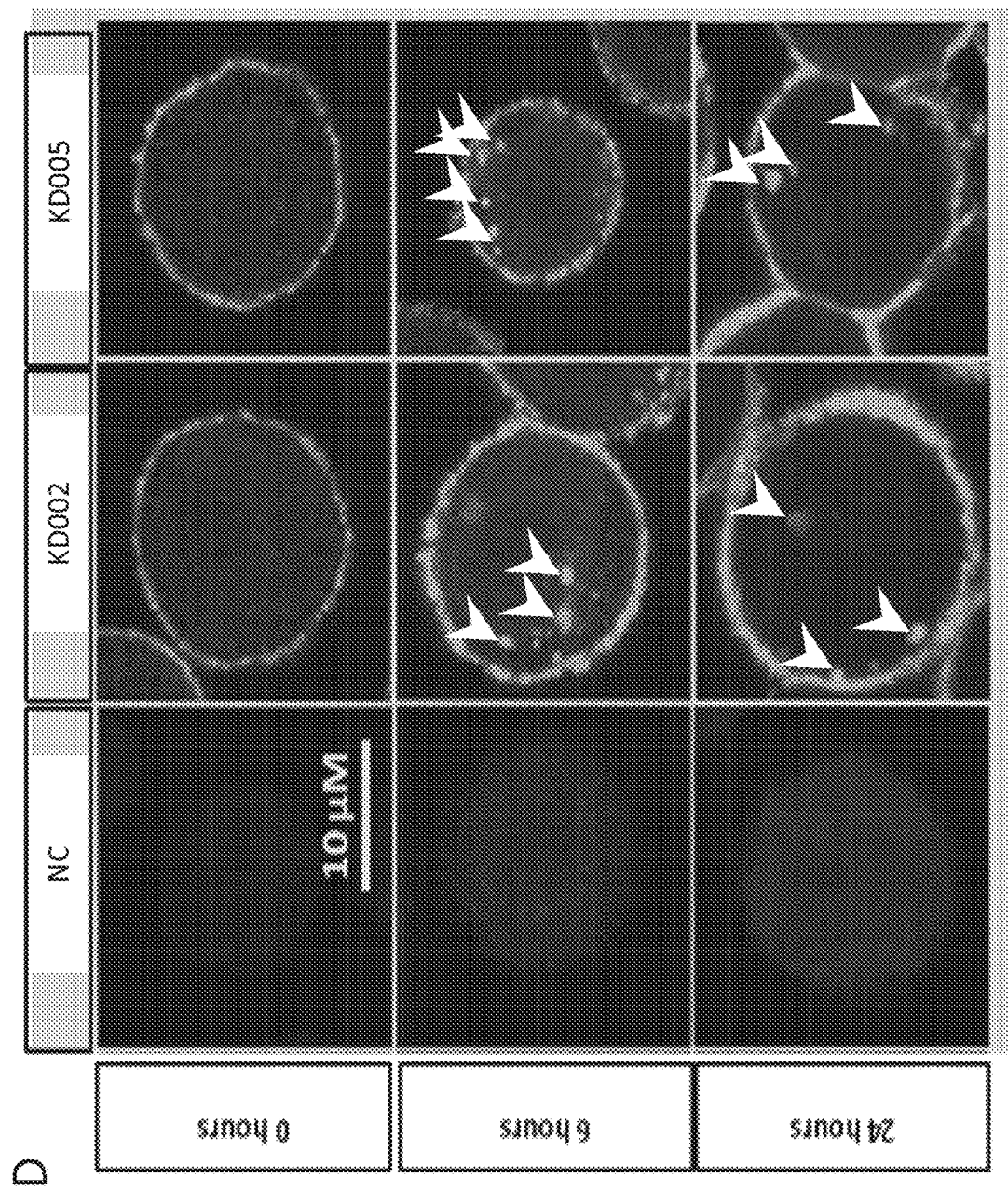
FIG. 6D: Confocal microscopy images of MDA-MB-453 cells showing KD002 and KD005 antibody binding and internalization were taken at 0, 6 and 24 hours. For each time point, one representative cell is shown. The cells were stained with anti-human IgG Fc-FITC and the nuclei were counterstained with DAPI. Images were obtained using confocal fluorescence microscopy. Scale bar, 10 µM.

As illustrated in FIG. 6C, which represents the results from a dose-response internalization experiment in MDA-MB-231 cells, it was observed that each of the anti-TROP2 sdAbs KD001-KD005 (0.125 nM-128 nM range) display a unique dose-response internalization profile. Some sdAbs internalized only to a very small extent (e.g., KD005), whereas others showed internalization levels comparable to that of monoclonal antibodies known to internalize efficiently (e.g., KD002). Internalization was assessed by conjugation of sdAbs with a pH-sensitive probe and monitored by flow cytometry (Em. 560 nm) after 24 hours. This internalization process was also visualized by microscopy as illustrated by FIG. 6D. MDA-MB-453 cells were treated with αTROP2 sdAbs and internalization was monitored at 0 hours (after 15 minutes at 4° C.), 6 hours or 24 hours by confocal microscopy. Cells were stained with anti-human IgG Fc antibody and counterstained for nuclei (DAPI). Isotype negative control HCAb (NC) showed no binding to cells. Whereas anti-TROP2 sdAb staining is restricted to membrane at 0 h, and at 6 and 24 hours punctate green staining is observed (arrowheads) revealing antibody internalization.

These results indicate that the sdAbs of the present disclosure may be used as a naked antibody or as an antibody drug conjugate.

Example 8—Specificity, Epitope Characterization and Domain Binding

The binding of anti-TROP2 sdAbs to cells was assessed by flow cytometry. To determine the binding specificity of anti-TROP2 sdAbs, the CHO and HEK parental cells were transiently transfected with human TROP2 by lipofectamine. 24 hours after transfection, cells were collected and stained with anti-TROP2 antibodies. In brief, 1×10$^5$ cells were incubated with an Fc receptor blocking antibody (1/100 dilution) for 10 minutes at room temperature. Anti-TROP2 antibodies were diluted in FACS staining buffer to 100 nM and added and incubated with cells for 30 minutes on ice. After washing three times with FACS staining buffer, APC-conjugated secondary antibodies recognizing the human Fc region (Biolegend) were mixed with cells. After staining for 30 minutes, cells were washed three times, followed by resuspension into 100 μL of 7-Amino-Actinomycin D (7-AAD) solution (1/100 dilution). Cells were analyzed by BD FACSCanto™ II Flow cytometer (BD Bioscience). Data were analyzed with FlowJo via gating on single cells and live cells.

As illustrated in FIG. 7A-FIG. 7D, all anti-TROP2 antibodies did not bind to the HEK and CHO parental cells, which is similar to the negative control. After TROP2 transient transfection, all anti-TROP2 sdAbs showed specific binding to the HEK-TROP2 and CHO-TROP2 cells as also observed for comparator antibodies, AR47A6.4.2, hTINA-1, h7E6, hRS7 (see Cardillo et al. 2011).

Figure 7D:
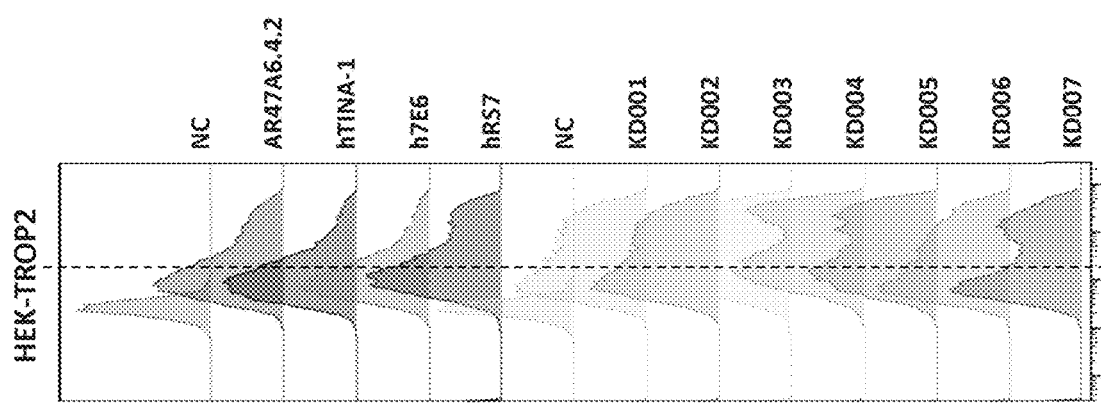
FIG. 7A-D: binding of KD001, KD002, KD003, KD004, KD005, KD006 or KD007 anti-TROP2 sdAbs to CHO (FIG. 7A) or HEK parental cells (FIG. 7C) or CHO (FIG. 7B) or HEK cells expressing human TROP2 (FIG. 7D) compared with negative control (sdAb that binds HEWL (NC)) or comparator monoclonal antibodies AR47A6.4.2, hTINA-1, h7E6 and hRS7 as assessed by flow cytometry.
Figure 7C:
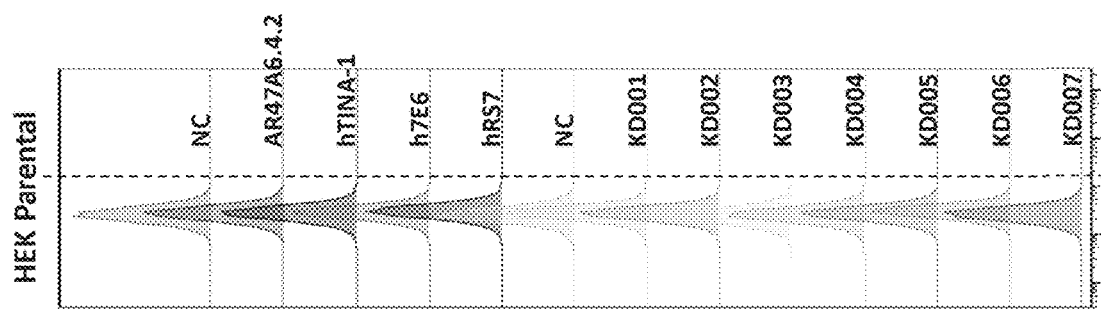
Figure 7B:
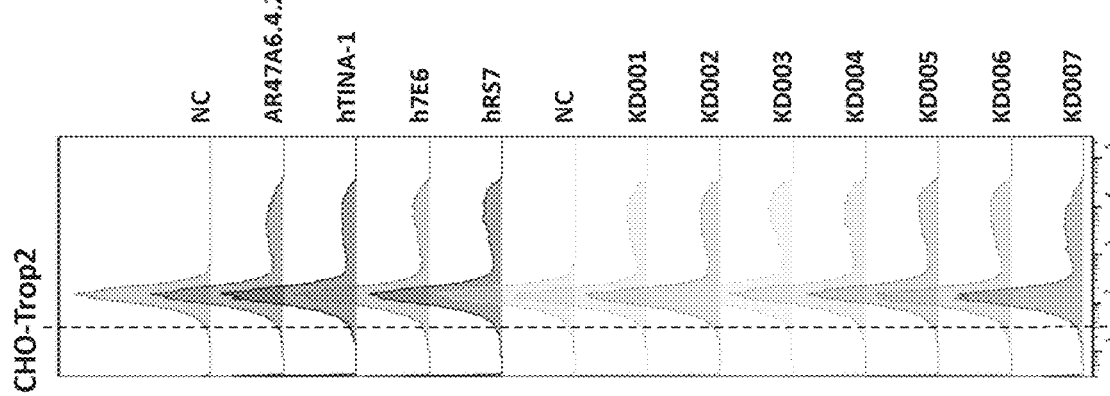
Figure 7A:
Figure 7E:
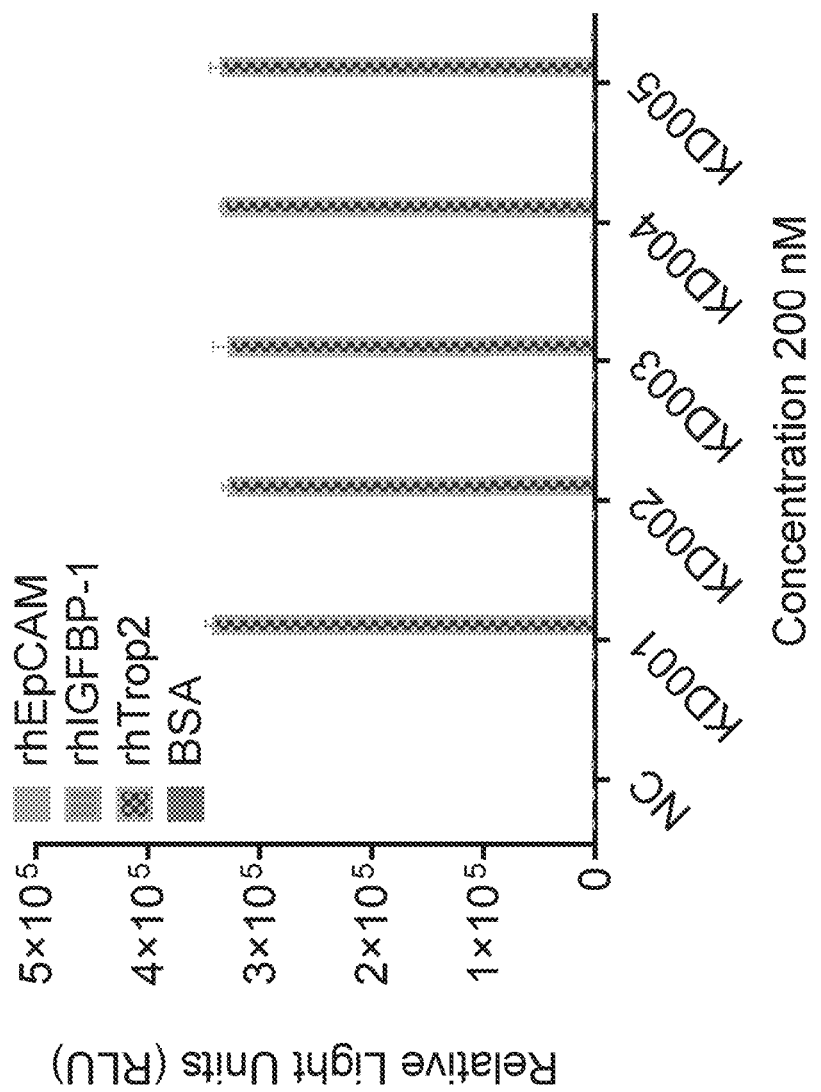
FIG. 7E: Bar graph illustrating binding of KD001, KD002, KD003, KD004, KD005, KD006 or KD007 anti-TROP2 sdAbs to recombinant human EpCAM (rhEpCAM) and to recombinant human IGFBP-1 (rhIGFB-1) proteins.

Also as illustrated in FIG. 7E, binding of anti-TROP2 sdAbs is highly specific, as they did not bind to the highly related EpCAM and IGFBP-1 proteins, by ELISA.

Figures 8D, 8E:
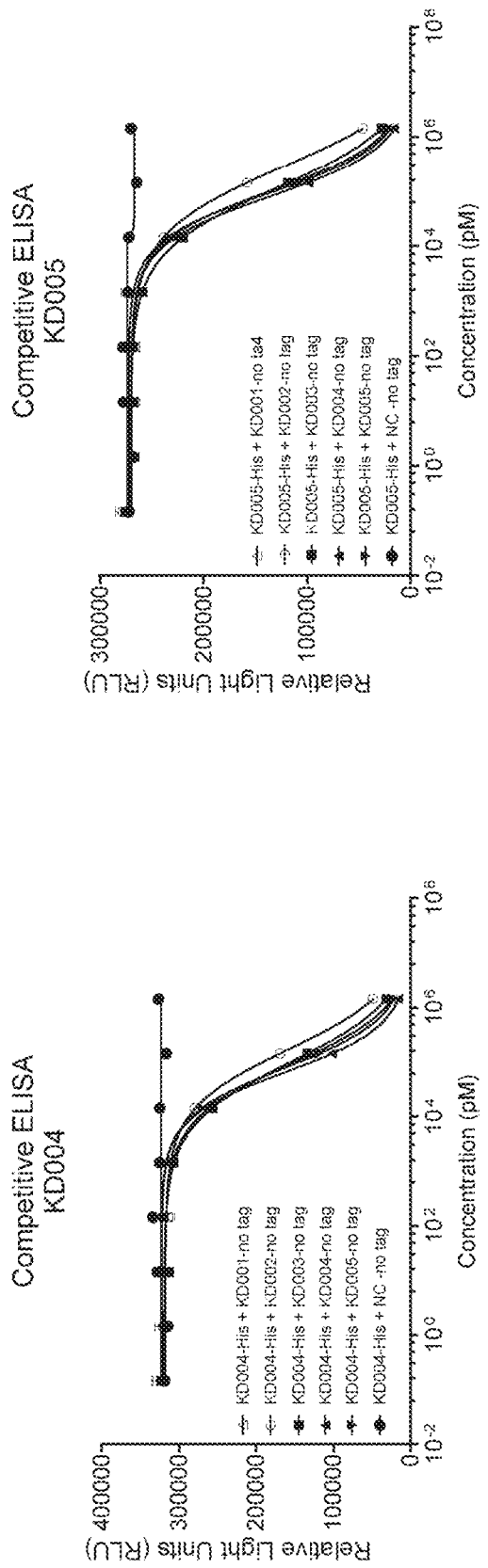

The epitope characterization was assessed by competitive ELISA (FIG. 8 and FIG. 9). Microplates were coated with human recombinant TROP2 at 4° C. overnight. After washing, plates were blocked with blocking buffer (PBS+2% BSA), for 1 hour at room temperature. Meanwhile, the dilution for anti-TROP2 VHH sdAbs was prepared with blocking buffer making two different dilutions depending on the tag. For sdAbs with His tag, the antibody was diluted to 28571.4 μM. For sdAbs without tag, antibodies were serially diluted from 2857142.9 µM to 0.29 µM (8 dilutions, 10×). After that, equal volume of the his-tagged sdAbs and serial diluted non-tagged sdAbs were mixed, to make the final concentration of his-tagged sdAbs 14285.7 µM and non-tagged sdAbs from 1428571.4 µM to 0.14 µM. After washing two times, the mixed antibody contents were added into the wells and the plates were incubated for 2 hours at room temperature. The HRP-conjugated anti-6× His was diluted to 1:5000 and added to the wells after washing three times. Any unbound conjugate was removed by washing after 1 hour incubation at room temperature, and the colorimetric reaction was performed by adding the same volume of Supersignal ELISA Pico Luminol/Enhancer and SuperSignal ELISA Pico Stable Peroxide Solution and detected on SpectraMax i3x Microplate Reader. Positive and negative controls were included in each plate.

As illustrated in FIG. 8A-FIG. 8E, anti-TROP2 sdAbs KD001, KD002, KD003, KD004, and KD005 compete with each other for binding to human TROP2 recombinant protein, suggesting they bind to very similar epitopes binding of TROP2 or bind to overlapping epitopes.

Anti-TROP2 sdAb KD004 did not compete with hRS7 and AR47A6.4.2 for binding to human TROP2 recombinant protein, as illustrated in FIG. 9A, implying that KD004 binds different epitopes from hRS7 and AR47A6.4.2.

Anti-TROP2 sdAbs KD006 and KD007 did not compete for binding to human TROP2 recombinant protein (FIG. 9B), implying that KD006 binds a different epitope from KD007.

KD006 and KD007 do not compete with KD001-KD005 in these experiments (data not shown).

In order to decipher the domain specificity of TROP2 sdAbs, immunoblots were performed with various TROP2 constructs including the extracellular domain of TROP2 and the cysteine poor domain of TROP2 (FIG. 10A).

Recombinant protein of human TROP2 extracellular domain (ECD) (Sino Biological, Cat. No. 10428-H08H) was incubated with PNGase F enzyme (NEB, Cat. No. P0704) for the deglycosylation reaction under both denatured and non-denatured conditions as per the manufacturer's protocol. Samples were prepared for SDS-PAGE analysis under reduced conditions premixed with NuPAGE™ sample reducing agent (ThermoFisher Cat. No. NP0004) or non-reducing conditions without reducing agent.

Samples of recombinant proteins of human TROP2 extracellular domain (ECD) (Sino Biological, Cat. no. 10428-H08H) and human TROP2 cysteine poor domain (CPD) were prepared for SDS-PAGE analysis under reducing or non-reducing conditions with NuPAGE™ LDS Sample Buffer (ThermoFisher Cat. no NP0007) with NuPAGE™ Sample Reducing Agent (ThermoFisher Cat. no. NP0004) or without reducing agent. Samples under reducing condition were denatured by heating at 70° C. for 10 minutes. Samples (16 µL) were loaded onto 4-12% Bis-Tris mini-gels (1.5 mm, 15 wells) or 250 ng of samples were loaded onto 14% Tris-glycine mini-gels alongside a BSA standard. Electrophoresis was conducted using a X-Cell SureLock™ mini-gel device at 125 volts for approximately 1 hour. Gels were stained using GelCode™ staining reagent (Thermo Fisher, Cat. no. 24594).

Electrophoresis was conducted using a X-Cell SureLock™ mini-gel device at 125 volts for 1 hour. Proteins were transferred to nitrocellulose membranes using the iBlot™ system (Thermo Fisher, Cat. no. IB301031) according to the manufacturer's instructions. Membranes were blocked by incubation in PBS/0.1% Tween™ 20/5% Milk for 1 hour at room temperature with shaking, followed by incubation with 1 µg/mL of Anti-TROP2 antibodies or the isotype control (IgG1 isotype) in 20 mL of PBS/0.1% Tween™ 20/5% milk. Membranes were washed three times for 10 minutes with PBS/0.1% Tween™ 20. Membranes were incubated with HRP-conjugated goat anti-human IgG antibody (Sigma-Aldrich, AP113P) diluted at 1:10000 in blocking buffer for 1 hour at room temperature with shaking. Membranes were washed three times for 10 minutes with PBS/0.1% Tween™ 20. The signal was visualized using Super Signal™ West Pico PLUS (Thermo Fisher, Cat. no. 34080) according to the manufacturer's instructions. Images were captured using the Azure Biosystem imaging system.

As illustrated in FIG. 10B, all sdAbs tested bound to the extracellular domain of human TROP2 but did not bind to the cysteine poor domain of human TROP2 contrary to other MAbs such as AR47A6.4.2 or hRS7.

The epitope recognized by the sdAbs of the present disclosure involves the CRD/TY-1 region of TROP2.

Western blots using recombinant human TROP2 in different forms (non-denatured, linear, reduced, deglycosylated using PNGase F) confirm that the sdAbs of the present disclosure effectively bind to TROP2 (FIG. 11A-FIG. 11E).

The specificity of sdAb for different TROP2 species was also investigated.

TROP2 full-length extracellular domain recombinant proteins including cynomolgus/Rhesus (FIG. 12A), human (FIG. 12B), mouse (FIG. 12C), and rat (FIG. 12D) were coated on 96-well ELISA plates at the concentration of 1 µg/mL. Plates were covered with adhesive plate cover and stored at 4° C. overnight. The next day, plates were washed 3× with washing buffer (PBS with 0.1% Tween™ 20). Plates were blocked with 2% fat-free BSA in washing buffer for 1 hour at 37° C. During the incubation time, the anti-TROP2 sdAbs were diluted in the blocking buffer to the indicated concentrations. In brief, the anti-TROP2 sdAbs starting concentration was 1000 nM and serial diluted 1 in 5 to 0.02048 µM. After blocking, the blocking buffer was removed from the wells and 100 µL of anti-TROP2 sdAbs dilutions were transferred to the corresponding wells. Plates were covered with adhesive plates cover and incubated at 37° C. for 1 hour. During the primary antibody incubation, the secondary antibody (goat anti-human IgG, HRP conjugated) was diluted 1 in 5000 with the blocking buffer. Plates were washed 3× with blocking buffer, followed by secondary antibody incubation for another 1 hour at 37° C. After the secondary antibody incubation, plates were washed 3× with washing buffer and added with 100 µL of ELISA chemiluminescent substrate (Thermofisher). The luminescence signal was detected by SpectraMax i3x at 425 nM.

As shown in FIG. 12A-FIG. 12D, the human anti-TROP2 sdAbs showed cross-reactivity to the cynomolgus/Rhesus TROP2, and a lower binding activity to mouse and rat TROP2 by ELISA.

All anti-TROP2 sdAbs have very high affinity, as shown by surface plasmon resonance (SPR) assay, both for human and cynomolgus TROP2 (low pM) (FIG. 12E). All anti-TROP2 sdAbs showed a very slow dissociation rate as indicated by the kd rate (FIG. 12F).

In order to determine the region of TROP2 targeted by the anti-TROP2 antibodies, the binding of anti-TROP2 antibodies to cells expressing TROP2 truncation was assessed by flow cytometry.

Figure 13B:
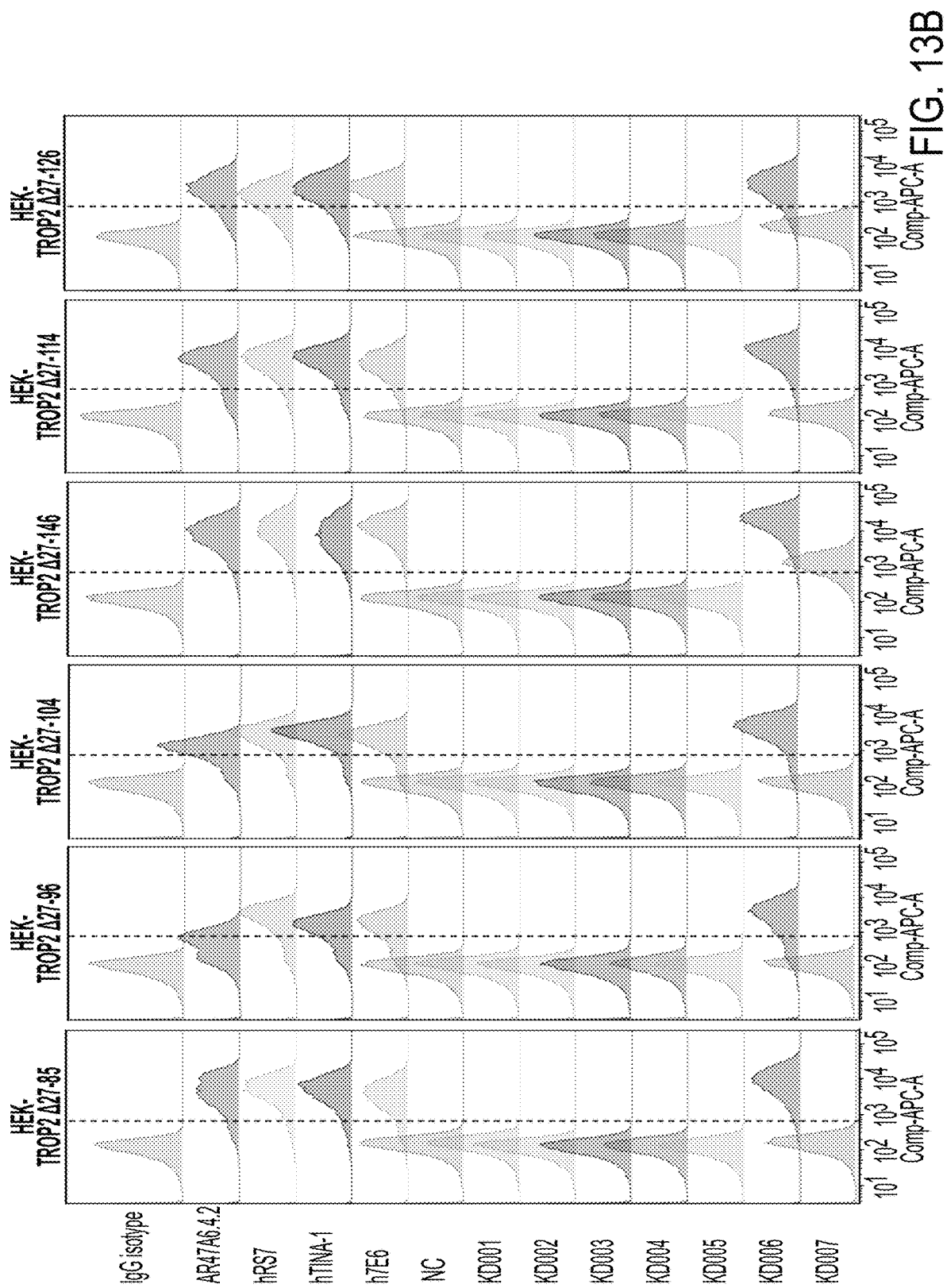
Figure 13C:
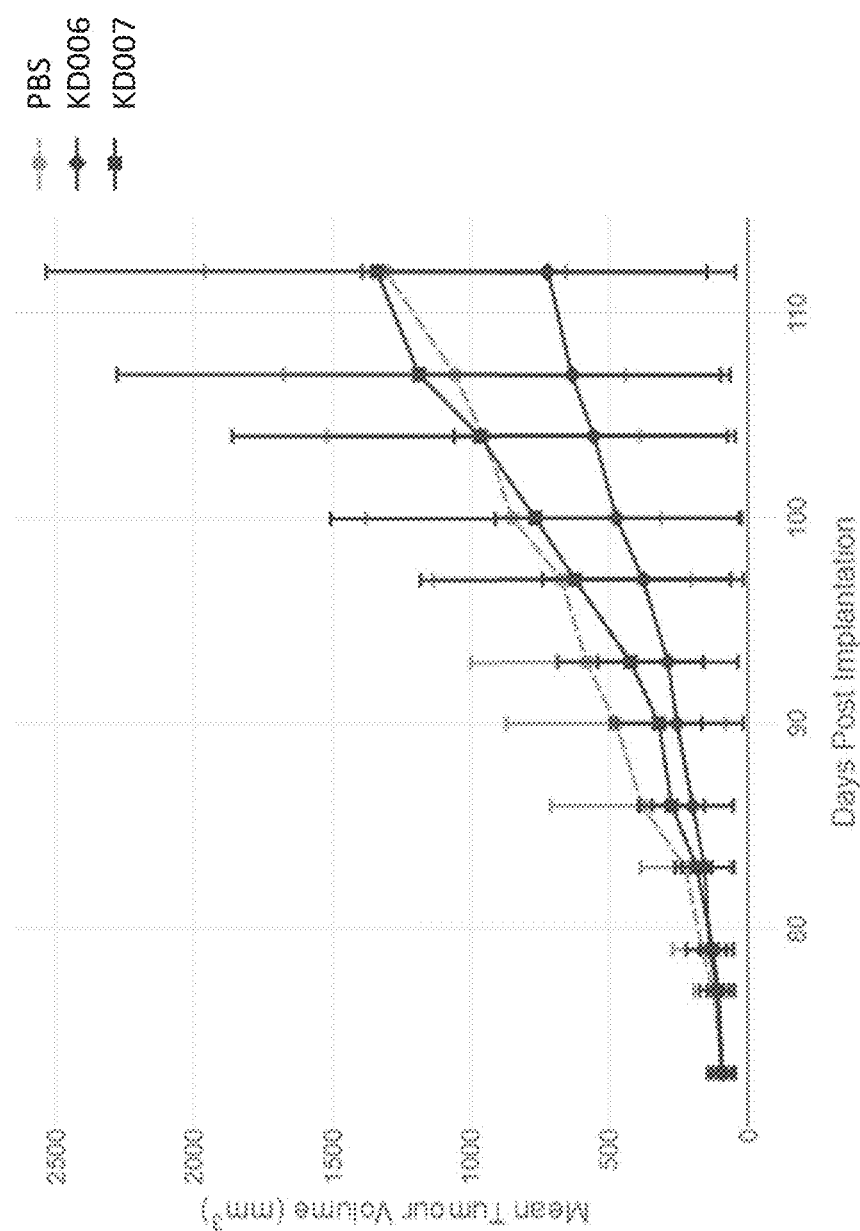
FIG. 13C: graph showing the tumor growth of in the xenograft model of T.Tn in the SCID mice upon treatment with anti-TROP2 antibodies at 8 mg/kg i.p., once per week. Treatment with KD006 led to a tumor growth inhibition of 48.6% in the xenograft model of T.Tn.

To determine the effect of TROP2 truncations on the binding ability of anti-TROP2 sdAbs, the HEK parental cells were transiently transfected with human TROP2 mutants by lipofectamine. 24 hours after transfection, cells were collected and stained with anti-TROP2 antibodies (FIG. 13A and FIG. 13B). In brief, 1×10⁵ cells were incubated with an Fc receptor blocking antibody (1/100 dilution) for 10 minutes at room temperature. Anti-TROP2 antibodies were diluted in FACS staining buffer to 100 nM and added and incubated with cells for 30 minutes on ice. After washing three times with FACS staining buffer, APC-conjugated secondary antibodies recognizing the human Fc region (Biolegend, Cat #410712) were mixed with cells. After staining for 30 minutes, cells were washed three times, followed by resuspension into 100 µL of 7-Amino-Actinomycin D (7-AAD) solution (BD Biosciences, Cat #559925).

As illustrated in FIG. 13A and FIG. 13B, clone AR47A6.4.2, hRS7, hTINA-1, h7E6 and KD006 binding to TROP2 was not affected by TROP2 truncation in the cysteine-rich domain. KD001, KD002, KD003, KD004, and KD005 lost their binding to TROP2 on HEK cells when TROP2 27-56 regions were truncated, implying that KD001-KD005 binding to TROP2 involves the TROP2 27-56 region.

Different from KD001 to KD005, KD006 and KD007 bound to another region to TROP2 proteins. Similar to other benchmark TROP2 antibodies, KD006 was able to bind to all TROP2 CRD truncations, implying that binding of these antibodies to TROP2 involves the TY-1 and/or CPD region. KD007 did not bind to any of the TROP2 CRD truncations, indicating that KD007 binding to TROP2 may involve TROP2 N-terminal 1-27 amino acids.

Treatment with KD006 led to a tumor growth inhibition of 48.6% in the xenograft model of T.Tn whereas KD007 did not show efficacy in this model (FIG. 13C).

Example 9—ADCP

The ADCP assays were performed with the Promega ADCP kits (cat #CS314906). In brief, 200,000 target cells, including MDA-MB-453, MDA-MB-231 (, NCI-H292, MDA-MB-468, T.Tn tumor cells were seeded into the 96-well plates overnight. The next day, testing antibodies were serial diluted (1 in 2 dilutions starting from 2 nM) into the RPMI 1640 culture medium. 25 µL of the serial diluted testing antibody was added to the wells containing appropriate adherent target cells.

THP-1 cells (ADCP Reporter Bioassay Effector Cells) were taken from −140° C. storage and transferred to the bench on dry ice. The effector cells were thawed in a 37° C. water bath until cells are just thawed (about 2-3 minutes). While thawing, the vial was gently agitated and visually inspected. The cell suspension was mixed in the vial by pipetting up and down and 0.5 ml cells was transferred to the tube containing 4.5 ml assay buffer. The tube was mixed by gently inverting.

The ADCP Reporter Bioassay Effector Cells (THP-1) suspension were transferred to a sterile reagent reservoir and 25 µl of the cell suspension was dispensed to all the wells containing target cells and antibodies. The lid was placed on the plates and the plate was incubated for 4 hours at 37° C. in a CO₂ incubator. 4 hours later, the Bio-Glo-NL™ Luciferase assay reagent was freshly prepared and reconstituted and equilibrated at room temperature. Using a manual multichannel pipette, 75 µl of io-Glo-NL™ Luciferase assay reagent was added to the assay plates while avoiding creating any bubbles. The plate was incubated at ambient temperature for 5-30 minutes and then luminescence was measured using a plate reader with glow-type luminescence read capabilities.

Figure 14A:
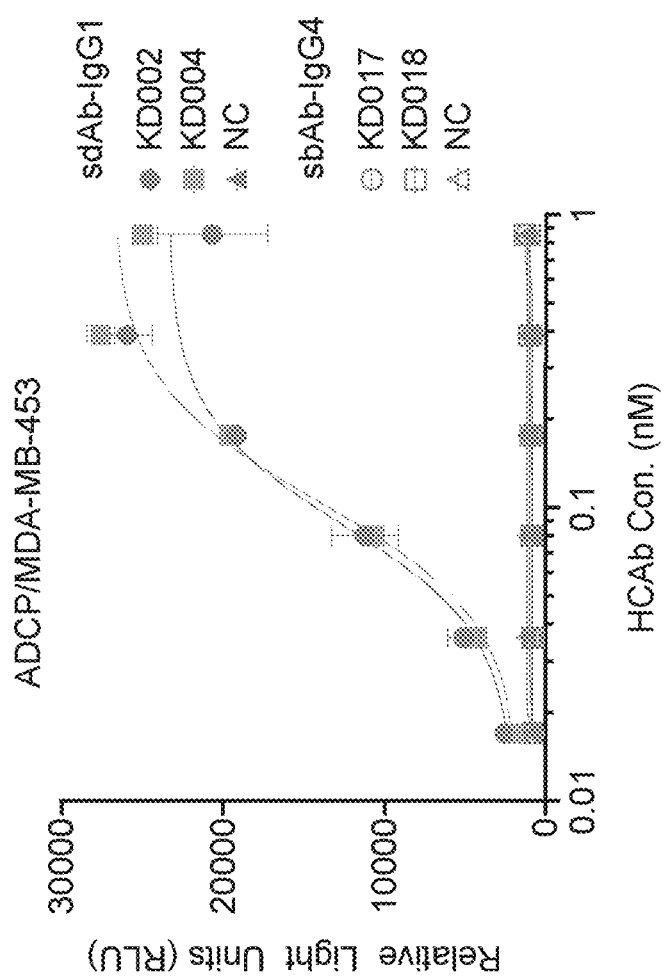
FIG. 14A: graph of the antibody-mediated cellular phagocytosis activity of IgG1- or IgG4 versions of KD002 and KD004 against MDA-MB-453 tumors.

Experiments with KD002 and KD004 as well as corresponding versions in which the IgG1 Fc portion of KD002 and KD004 (KD017 and KD018) was replaced for an IgG4 Fc, were tested for antibody-dependent cellular phagocytosis (ADCP). As illustrated in FIG. 14A, the anti-TROP2 sdAbs IgG1 but not the IgG4 version elicited ADCP in vitro in a dose-response test (0.01 nM to 1 nM range). Antibodies' stock (20 nM) was serially diluted and added to the wells containing target and effector reporter THP-1 cells. MDA-MB-453 cells (target) were seeded at 20,000 cell/well overnight. The ADCP effector cells (THP-1 cells) were dispensed at an E:T ratio of 3:2.

Since CD47 is a checkpoint for macrophage ADCP activity, we assessed the level of CD47 expression in various cancer cells lines expressing TROP2 to evaluate the impact on the efficacy of anti-TROP2 sdAbs.

As illustrated in FIG. 14B, MDA-MB-453 cells showed the lowest CD47 expression, whereas the level of cell surface CD47 expression in NCI-H292 and MDA-MB-231 is similar. The level of TROP2 expression is higher in NCI-H292, followed by MDA-MB-453 and MDA-MB-231.

The ADCP assays were performed with the Promega ADCP kits (cat #CS314906). 200,000 target cells, including MDA-MB-453 (FIG. 14C and FIG. 18A-upper panel), MDA-MB-231 (FIG. 14D), NCI-H292 (FIG. 14E), MDA-MB-468 (FIG. 18A-middle panel) or T.Tn tumor cells (FIG. 18A-lower panel) were seeded into the 96-well plates overnight. The next day, testing antibodies (KD002 or KD004) were serial diluted (1 in 2.2 dilutions starting from 2 nM) into RPMI 1640 culture medium. 25 µL of the serial diluted testing antibody was added to the wells containing appropriate adherent target cells.

As illustrated in FIG. 14C-FIG. 14E, TROP2 antibodies KD002 and KD004 showed a high level of ADCP activity against MDA-MB-453 cells and lower ADCP activity on MDA-MB-231 and NCI-H292 cells.

As shown in the FIG. 14C, the EC50 of the two antibodies KD002 and KD004 are close to each other at around 0.1 nM, but MDA-MB-453 there was a higher RLUmax than the MDA-MB-231 and NCI-H292 cells, which may be explained by the lower expression of CD47 on MDA-MB-453 cells.

Figure 14F:
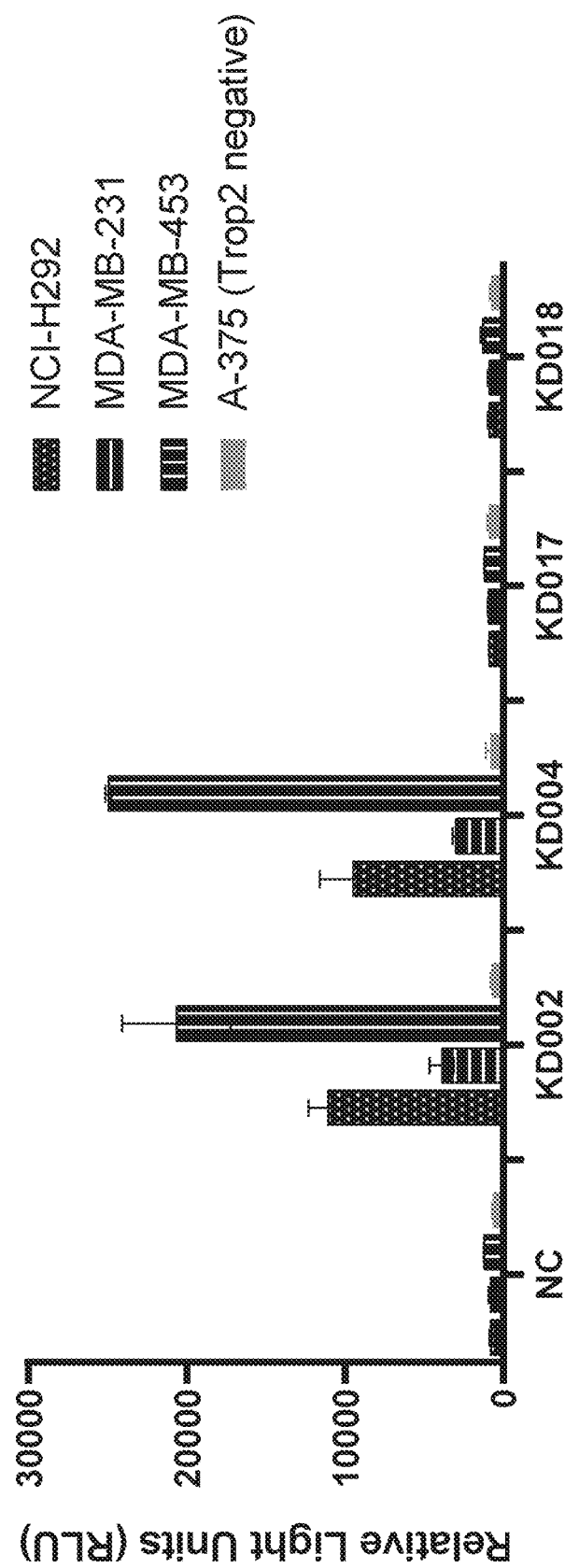
FIG. 14F: graph illustrating the ADCP activity of KD002 and KD004 and the corresponding IgG4 version; KD017 and KD018 against MDA-MB-453, MDA-MB-231, and NCI-H292 cells. Assay was performed at the antibody concentration of 1 nM.

As shown in FIG. 14F, IgG4 versions of the KD002 and KD004 antibodies (KD017 and KD018) have lost ADCP activity against MDA-MB-453, MDA-MB-231 and NCI-H292 cells in a similar experiment. These in vitro data suggest the ADCP mechanism of the TROP2 antibodies may be dependent on the Fc receptor.

Expression of CD47 was knocked down using small interfering RNA (siRNA) and similar ADCP assay were performed. MDA-MB-231 cells and NIC-H292 cells were transfected with CD47 siRNA (Thermofisher, Cat #4392421) or control siRNA (Thermofisher, Cat #AM4635) by the lipofectamine transfection kits. 48 hours after transfection, cells were collected and CD47 expression level was determined by flow cytometry. Once CD47 knockdown was confirmed, cells were used as the target cells in ADCP assays.

Expression level of CD47 and TROP2 on NCI-H292, MDA-MB-453 and MDA-MB-231 cells after CD47 knockdown was determined (FIG. 15A). 1×10⁵ cells were incubated with an Fc receptor blocking antibody (1/100 dilution) for 10 minutes at room temperature. Diluted APC-conjugated anti-CD47, PE-conjugated anti-TROP2 antibodies (Biolegend) (1/100 dilution) were mixed with cells. After staining for 30 minutes, cells were washed three times, followed by resuspension into 100 µL of 7-Amino-Actinomycin D (7-AAD) solution (1/100 dilution).

Cells were analyzed by BD FACSCanto™ II Flow cytometer (BD Bioscience). Data were analyzed with FlowJo via gating on single cells and live cells.

As illustrated in FIG. 15A, transfection with CD47 siRNA led to a significant reduction of CD47 expression in MDA-MB-231 and NCI-H292 cells.

Figure 15D:
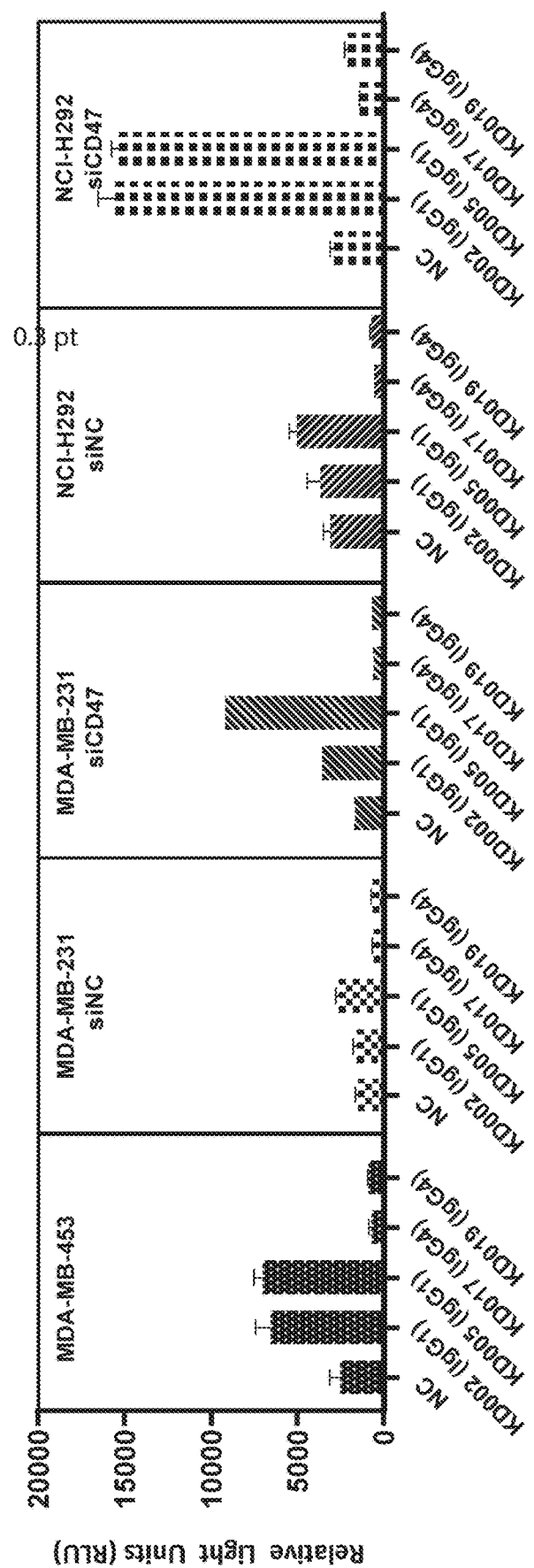
FIG. 15D: graphs illustrating the ADCP activity of KD002 and KD005 and the corresponding IgG4 version, KD017 and KD019 against the MDA-MB-453, MDA-MB-231, and NCI-H292 cells upon inhibition of CD47 expression with siRNA (siCD47) or not (siNC). Assay was performed at the antibody concentration of 1 nM.
Figure 15E:
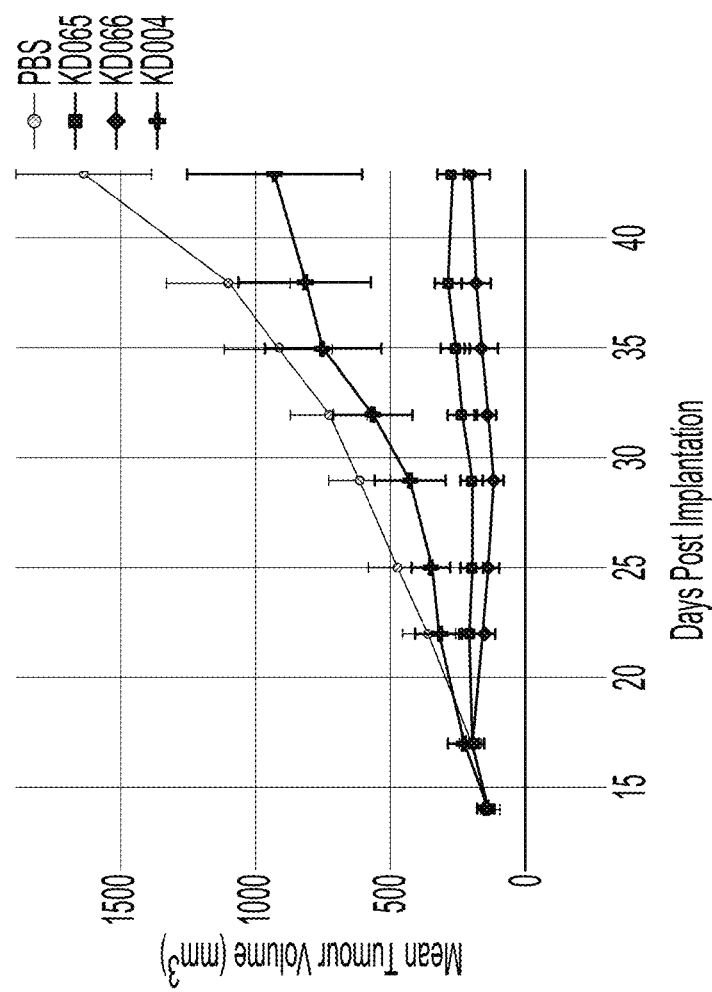
FIG. 15E: graphs showing in vivo efficacy of TROP2-CD47 bispecific antibodies in the xenograft model of MDA-MB-231 in SCID mice. Mice were treated with KD004 at 8 mg/kg, once per week and KD065 and KD066 were administered at the same molarity (11 mg/kg) i.p.

As illustrated in FIG. 15B-FIG. 15D, CD47 knockdown by siRNA increased ADCP activity (phagocytosis) of KD002 and KD005 in both MDA-MB-231 and NCI-H292 cells. In MDA-MB-231 KD005 appears to have higher ADCP activity than KD002 and also show ADCP activity even without inhibition of CD47.

Moreover, as illustrated in FIG. 15D, in comparison to KD002 and KD005, the IgG4 versions of KD002 and KD005 antibodies (KD017 and KD019) have lost ADCP activity against MDA-MB-231 and NCI-H292 tumor cells even when CD47 expression is inhibited.

These results indicated that knockdown of CD47 significantly enhanced the maximal signal of the ADCP assay. Since CD47 is a checkpoint for macrophage ADCP activity, the higher expression of CD47 on MDA-MB-231 and NCI-H292 may explain the relatively low ADCP activity. This is consistent with data showing that higher CD47 expression led to the lower ADCP activity.

The in vivo ADCP mechanism and the potential enhancing ADCP activity was also verified with an anti-CD47 antibody. Briefly two bispecific antibodies comprising either KD011 at the N-terminus and KD070 at the C-terminus of Fc or KD011 at the C-terminus and KD070 at the N-terminus of Fc were generated. Both KD065 and KD066 showed increased anti-tumor activity compared to KD004 that does not include the anti-CD47 module (FIG. 15E).

These data suggest that potency of anti-TROP2 antibodies may be increased by inhibiting CD47. Bispecific or multi-specific antibodies comprising an anti-TROP2 antigen binding domain and a CD47 antigen binding domain may therefore be used for treating cancer associated with TROP2 expression.

THP-1 Differentiation

THP-1 cells were differentiated into macrophages in the six-well plates. Two million cells were plated in the six-well plates and stimulated with PMA (Sigma, P8139-1MG) at the concentration of 150 nM for 24 hours. Cells were washed with PBS and treated with cytokines for 72 hours in the cell culture medium. For M1 cell differentiation, cells were treated with 20 ng/ml IFN-gamma (Cedarlane, 285-IF-100) and 10 μg/ml LPS (Cedarlane, 437628-1MG). For M2 cell differentiation, cells were treated with 20 ng/ml IL-4 (Cedarlane, 204-IL-010) and 20 ng/ml IL-13 (Cedarlane, 213-ILB-010).

Before running macrophage phagocytosis assay, cells were collected with TrypLE and washed twice with PBS. The target cells MDA-MB-453 were stained with pHrodo SE (Invitrogen, P36600) at 120 ng/ml for 30 minutes at room temperature. The M1 or M2 macrophages were stained with Celltrace Violet (Invitrogen, C34557 A) at 5 μM for 30 minutes at room temperature. Cells. Cells were washed with PBS and resuspended in the RPMI complete medium. M1 or M2 macrophages were mixed with MDA-MB-453 cells at the E:T ratio of 2:1 and treated with the indicated antibodies for 4 hours. After the incubation, cells were washed with PBS and resuspended in the FACS buffer with 1/100 dilution of 7-AAD. Cells were analyzed by the FACS CantoII cytometer and double positive cells were gated as the phagocytosed macrophages.

FIG. 16A shows that THP-1 cells differentiate into M1 and M2 macrophages upon treatment with PMA and cytokines. THP-1 cells showed upregulation of CD68 after PMA treatment. The M1 cells showed upregulation of CD38 and CD86 after treatment with IFN-7 and LPS. M2 macrophages showed upregulation of CD206 and downregulation of CD38 after treatment with IL-3 and IL-13.

As illustrated in FIG. 16B, both M1 and M2 macrophages lead to phagocytosis of target cells MDA-MB-453 by KD002 and KD005.

Example 10—In Vivo Mechanism of Action

The mechanism of action was further investigated in vivo.

Figure 17B:
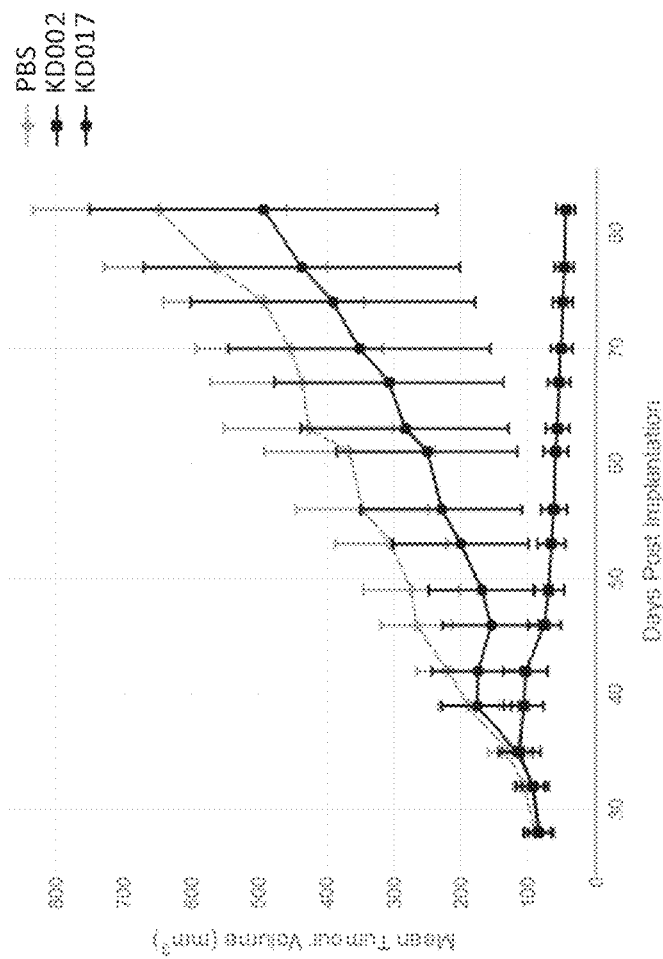
FIG. 17B: graph showing the anti-tumor effect of KD002 and KD017 at a dose of 8 mg/kg i.v. in MDA-MB-453 implanted NCG mice tumor model. Negative control is PBS.
Figure 17A:
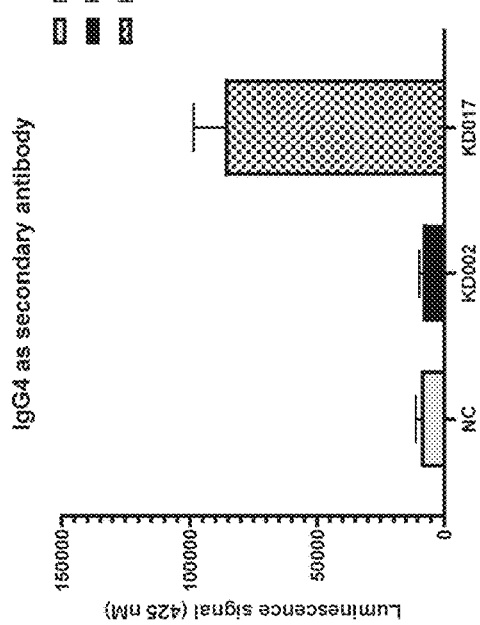
FIG. 17A: bar graph illustrating the binding of TROP2 antibodies at 25 nM to TROP2 recombinant proteins by ELISA using an anti-IgG4 Fc secondary antibody.

As illustrated in FIG. 17A KD017 which is the IgG4 version of KD002 was detected by the secondary antibody while as expected, the IgG1 version KD002 was not. KD017 is thus able to bind to recombinant human TROP2. However, as illustrated in FIG. 17B, KD017 has lost the anti-tumor effect in the MDA-MB-453 xenograft tumor model. These data suggest that KD002 anti-tumor function is a Fc receptor-dependent activity. Since the NCG mice only has myeloid cells but lack all B cell, T cell and NK cells, this Fc-dependent cellular activity is likely mediated by macrophage ADCP.

Figure 18A:
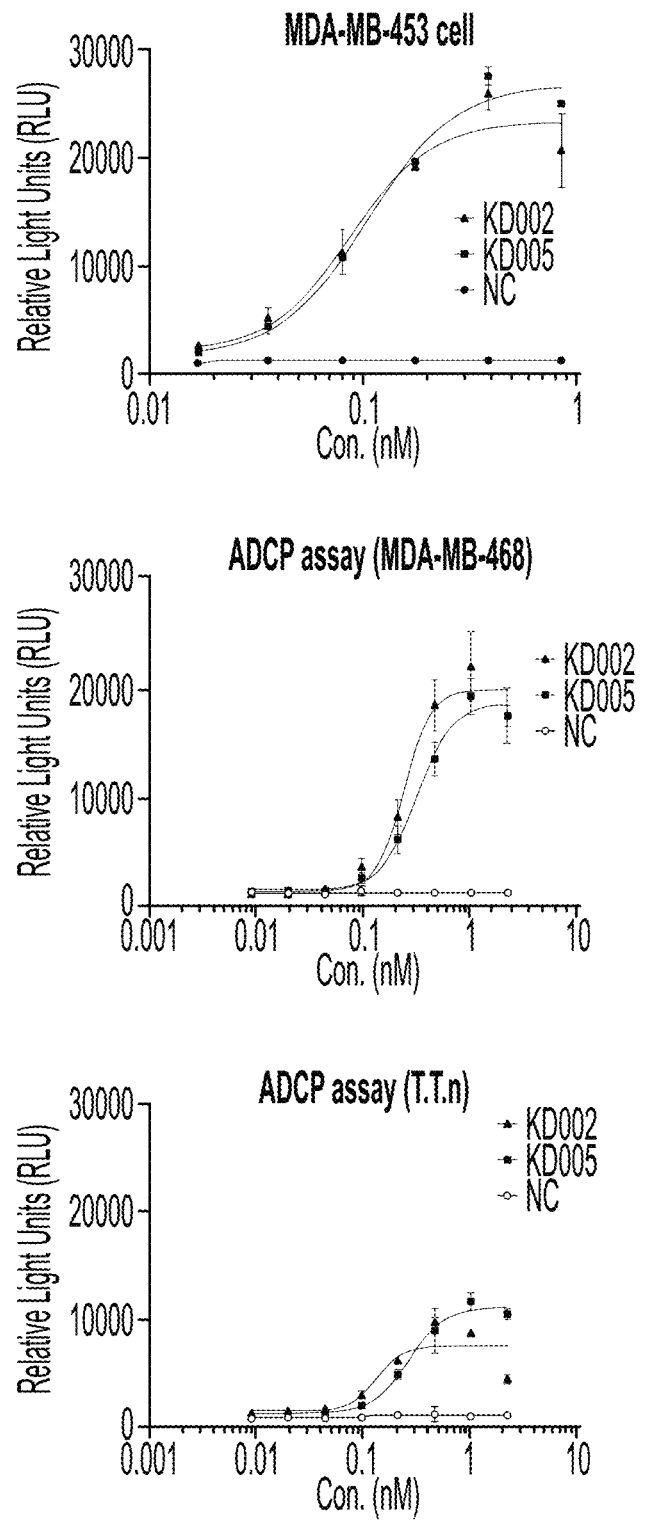
FIG. 18A: graph showing the dose-response ADCP activity of KD002 and KD005 TROP2 antibodies against the MDA-MB-453 (upper panel), MDA-MB-468 (middle panel), and T.Tn cells (lower panel). The ADCP assays were performed using the Promega ADCP assay kits (Promega, cat #CS314906).

As illustrated in FIG. 18A, TROP2 antibodies KD002 and KD005 showed a high level of ADCP activity against MDA-MB-453 cells (upper panel) and MDA-MB-468 cells (middle panel) and a medium level of ADCP activity against T.T.n cells (lower panel). Corresponding to the higher in vitro ADCP activity, KD002 and KD005 treatment led to complete tumor regression in the MDA-MB-453 (upper panel), and MDA-MB-468 (middle panel) xenograft model (FIG. 18B). KD002 and KD005 led to a partial response in T.Tn xenograft tumor model with a tumor growth inhibition of 60% (FIG. 18B-lower panel).

Figure 19A:
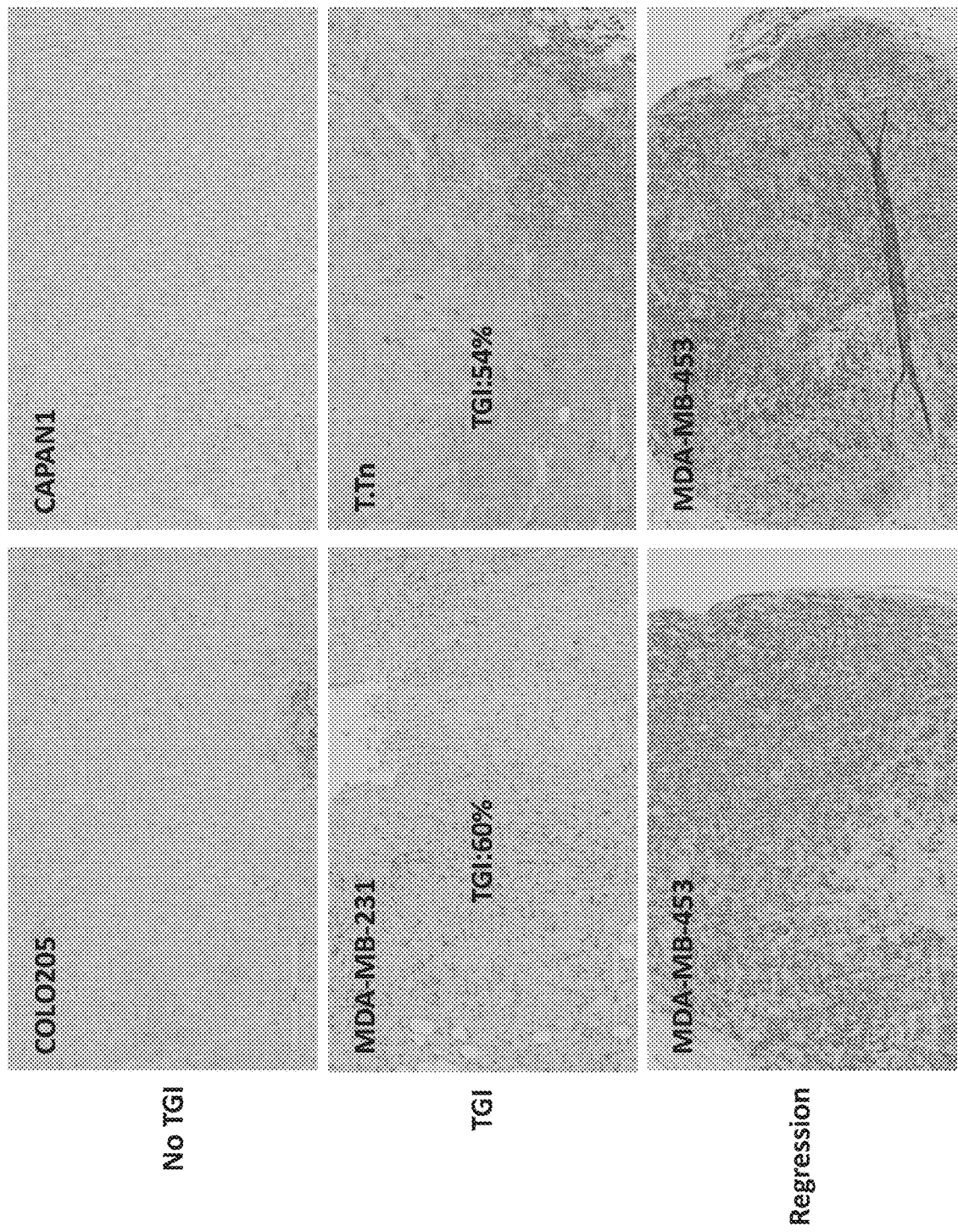
FIG. 19A: Photomicrographs of IHC staining of mouse macrophages with F4/80 antibody on the xenograft tumors collected from COLO205, CAPAN1, MDA-MB-231, T.T.n and MDA-MB-453 xenograft models treated with the TROP2 antibodies KD002 and KD005 at the dose level of 8 mg/kg. Tumors were collected at the end of the study.
Figure 19B:
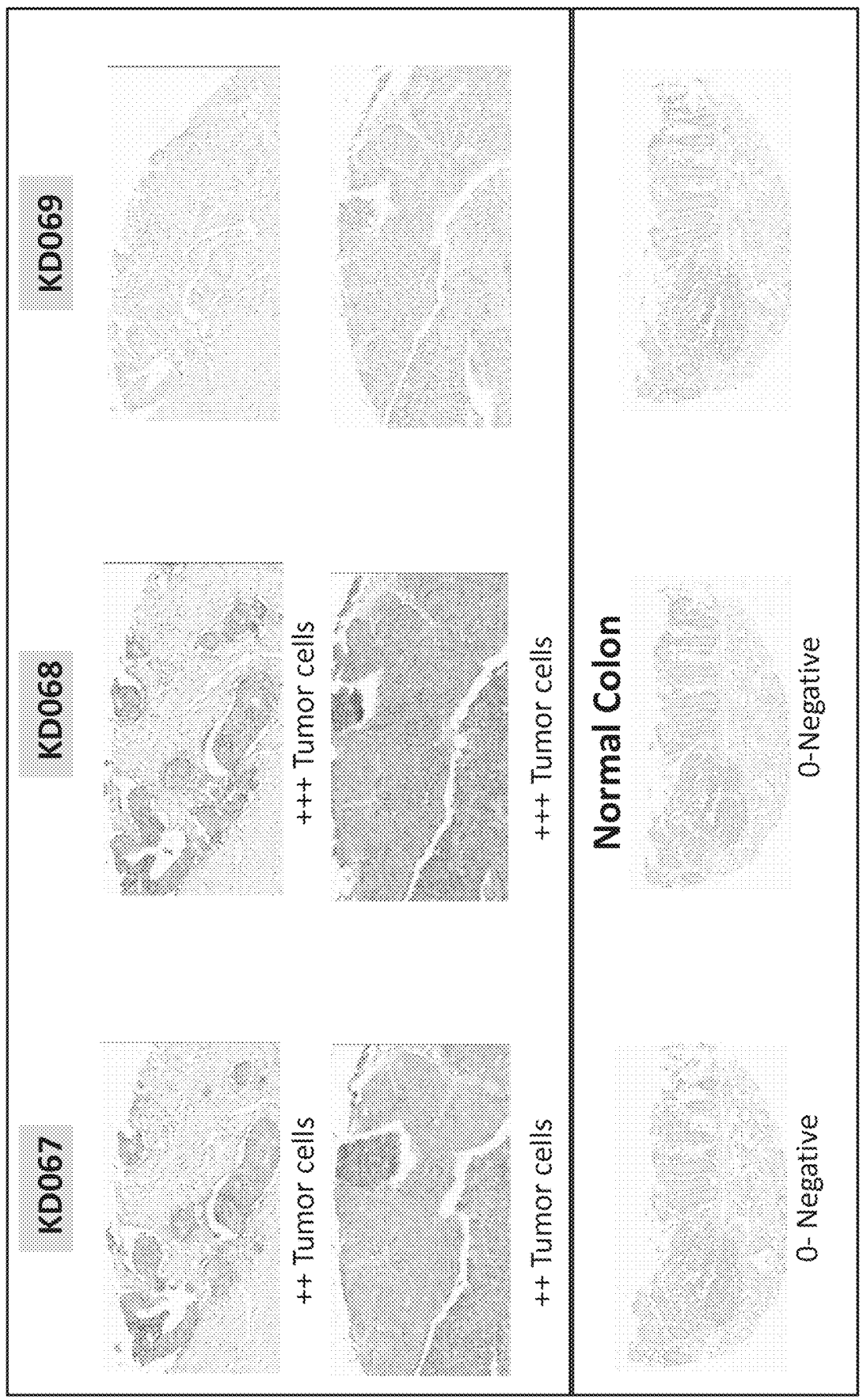
FIG. 19B: Human colon adenocarcinoma tumor tissue microarray with KD067, KD068 or isotype control KD069 antibody. The human multiple tumor tissue microarray was purchased from Novus Biologics (cat #NBP2-42056) and stained with the antibodies at 2 µg/ml.
Figure 19C:
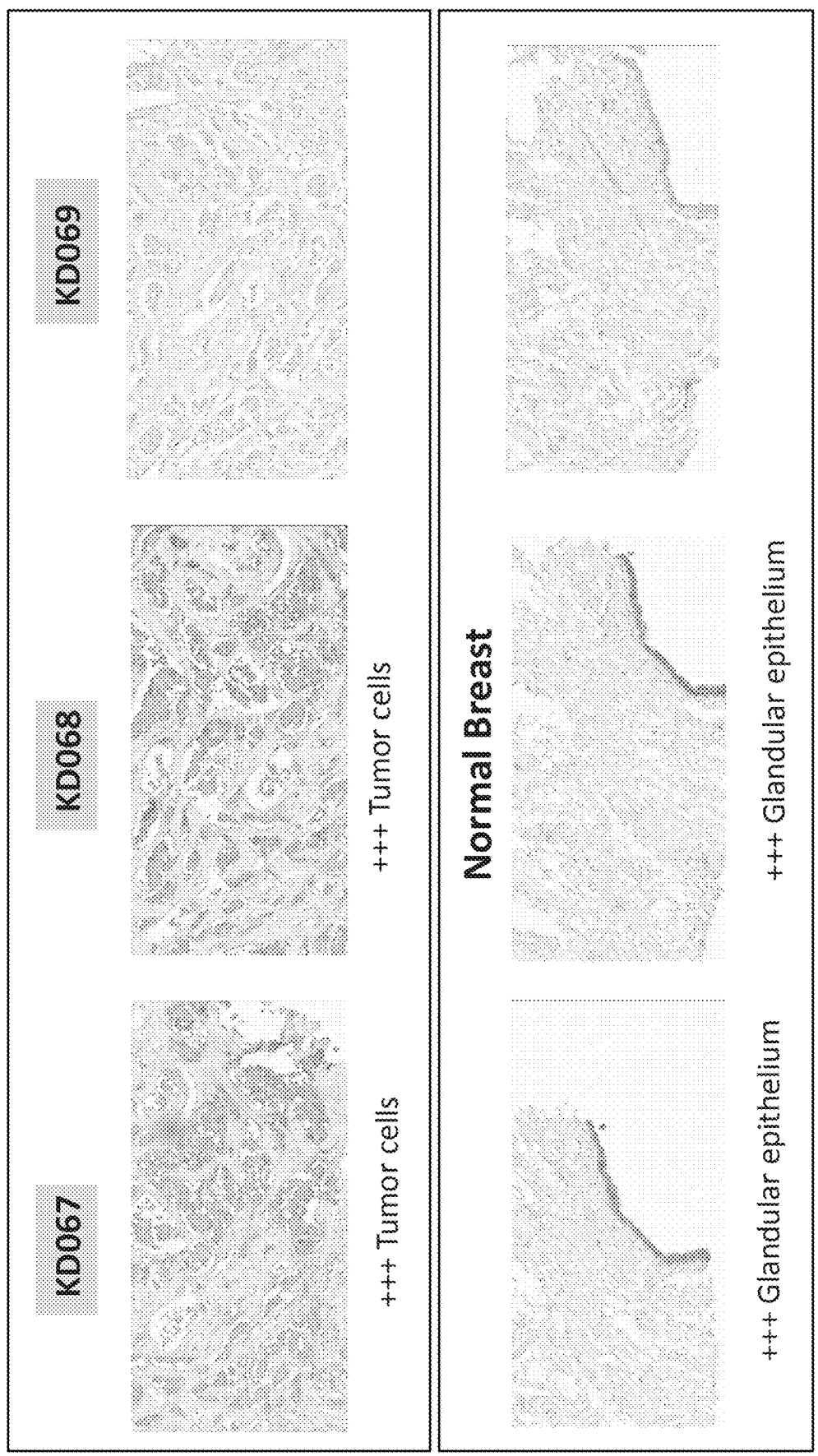
FIG. 19C: Human breast invasive ductal carcinoma tumor tissue microarray with KD067, KD068 or isotype control KD069 antibody. The human multiple tumor tissue microarray was purchased from Novus Biologics (cat #NBP2-42052) and stained with the antibodies at 2 µg/ml.
Figure 19D:
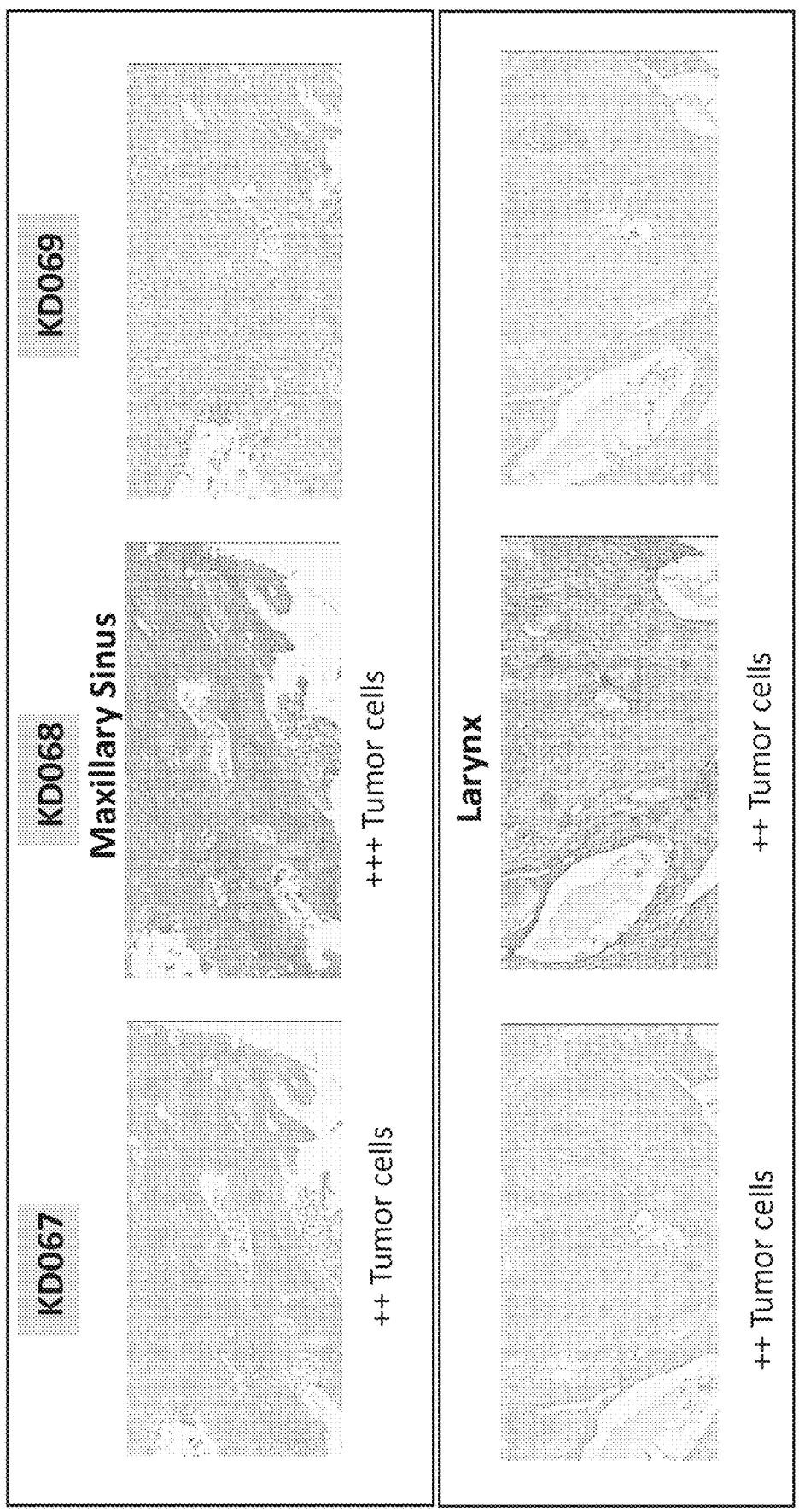
FIG. 19D: Human head and neck tumor tissue microarray with KD067, KD068 or isotype control KD069 antibody (H&N squamous cell carcinoma). The human multiple tumor tissue microarray was purchased from Novus Biologics (cat #NBP2-42056) and stained with the antibodies at 2 µg/ml.
Figure 19E:
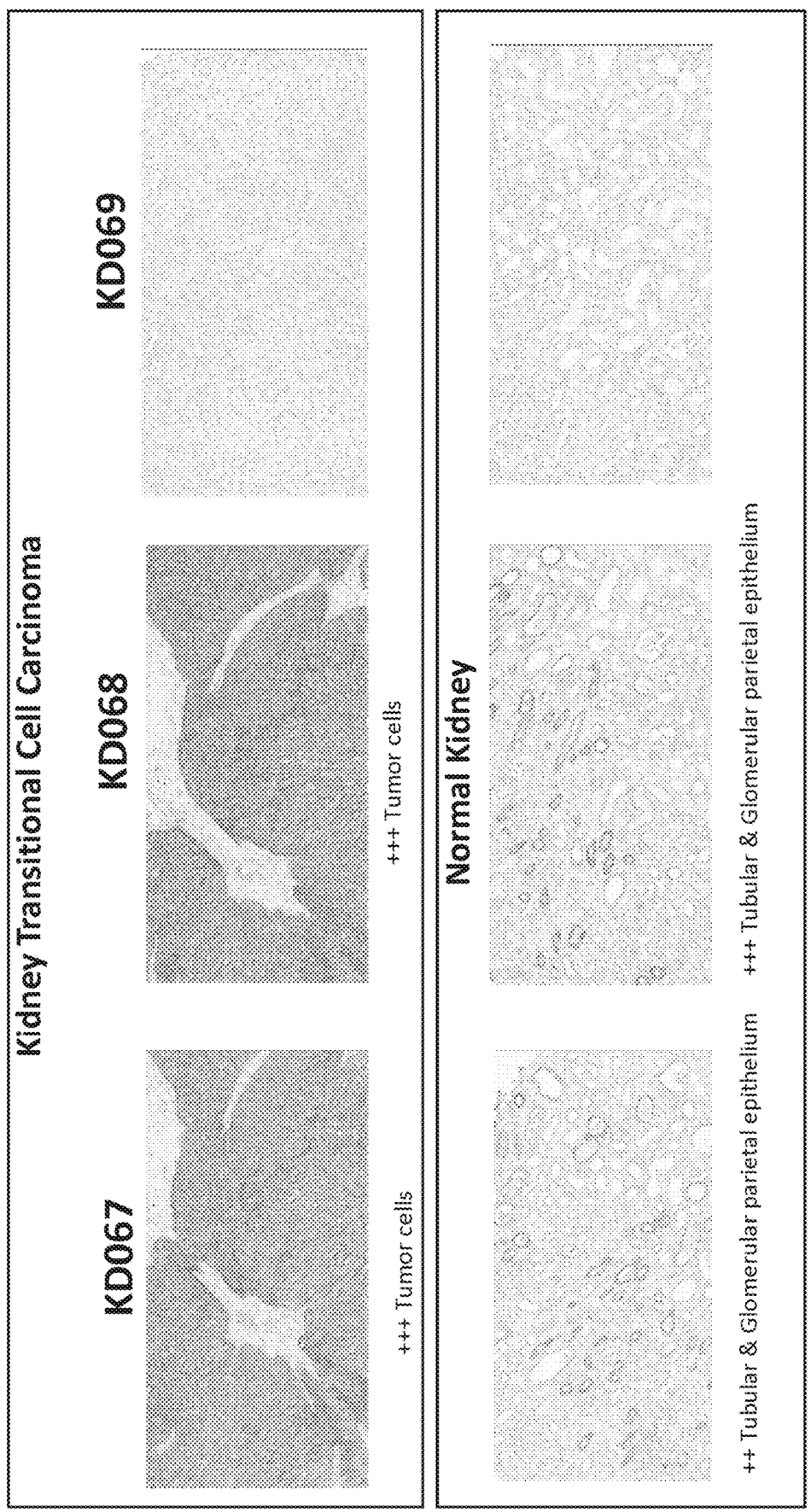
FIG. 19E: Human kidney transitional cell carcinoma microarray with KD067, KD068 or isotype control KD069 antibody. The human multiple tumor tissue microarray was purchased from Novus Biologics (cat #NBP2-42052) and stained with the antibodies at 2 µg/ml.

For mouse macrophage IHC staining, tumor samples including COLO205, CAPAN1, MDA-MB-231, T.Tn and MDA-MB-453 were collected from the xenograft models and formalin-fixed paraffin-embedded. Samples were stained with the mouse macrophage marker F4/80 followed by the secondary antibody-HRP (FIG. 19A). There was a correlation between the degree of macrophage infiltration and the potency of TROP2 antibodies. In the MDA-MB-453 xenograft model in which TROP2 antibodies treatment led to a complete regression, macrophage showed massive infiltration into the tumors confirmed by IHC. In the MDA-MB-231 and T.Tn xenograft model in which TROP2 antibodies showed a 50%-60% tumor growth inhibition, macrophage exhibited a medium level of macrophage infiltration. COLO205 and CAPAN1 xenograft model showed little macrophage infiltration and no tumor growth inhibition (TGI).

CD47 showed a higher expression in most of the tumors confirmed by IHC. However, overall, we observed a correlation between TROP2 antibodies efficacy and macrophage infiltration (FIG. 19A).

These data indicate that the TROP2 antibody potency involves macrophage infiltration into the tumors. TROP2 expression and macrophage infiltration could represent clinical biomarkers to achieve optimal treatment result.

Example 11—TROP2 Expression in Selected Tumors

TROP2 IHC Staining

To understand the TROP2 expression prevalence across different cancer types, we stained TROP2 expression with TROP2 antibodies at 2 mg/ml on the FFPE cancer tissue microarrays (Novus Biologics, cat #NBP2-42052 & NBP2-42056) and frozen colon cancer microarray (Biochain, T6235090) (FIG. 19B-FIG. 19E). In the Novus Biologics FFPE cancer tissue microarrays, TROP2 antibody showed high positive staining on ovary cancer (71%), bladder cancer (100%), breast cancer (100%), uterus cancer (83.3%), head and neck cancer (78%), and stomach cancer (77.8%) (Table 3). We confirmed the head and neck cancer by staining with Biomax head and neck cancer microarrays containing over 150 patient samples (85% positive). The trop2 staining on FFPE colon cancer microarray was low, which might be due to the antigen retrieval method. To verify the colon cancer prevalence, we stained with frozen colon cancer arrays and showed 94% positive by TROP2 antibody staining. These data suggested the positive TROP2 epitope, a potential TROP2 biomarker by IHC staining and clinical indication of cancer types for the clinical trials and treatment.

TABLE 3

IHC Summary of KD005/All Tumors TMAs

| Arrays | Organ | No. of positive Tumors/Total (%) | + | ++ | +++ |
|---|---|---|---|---|---|
| TMA #1* | Ovary | 5/7 (71.4) | 2 | 1 | 2 |
| NBPS-45052 & | Bladder | 8/8 (100) | 0 | 3 | 5 |
| 45056 | Breast | 8/8 (100) | 4 | 0 | 4 |
|  | Kidney | 1/13 (7.7) | 0 | 0 | 1 |
|  | Uterus | 5/6 (83.3) | 1 | 3 | 1 |
|  | Lung | 7/9 (100) | 2 | 3 | 4 |
|  | Colon** | 3/8 (37.5) | 1 | 0 | 2 |
|  | Esophagus | 7/9 (77.8) | 0 | 1 | 6 |
|  | Liver | 2/9 (22.2) | 1 | 0 | 1 |
|  | Rectum | 2/9 (22.2) | 1 | 1 | 0 |
|  | Stomach | 7/9 (77.8) | 2 | 4 | 1 |
|  | Total Positive | 57/89 (64) | 14 | 16 | 27 |
| TMA #2* (H&N) Biomax HN602 & HN601d | Head and Neck | 101/119 (85) | 40 | 53 | 8 |
| TMA Frozen Array Biochain T6235090 | Colon Cancer | 33/35 (94) | 7 | 15 | 11 |

Example 12—Crystallization and Structure Determination

Crystallization

Crystals were obtained by the vapor diffusion method at 18° C., by mixing equal volumes of protein plus well solution.

The TROP2 ECD:VHH 3572 crystals grew in 55.5 mM MES, 45.5 mM Imidazole, 10 mM D-Galactose, 10 mM D-Glucose, 10 mM D-Mannose, 10 mM D-Xylose, 10 mM L-Fucose, 10 mM N-acetyl-D-glucosamine, 7% (w/v) PEG 20,000 and 14% (w/v) PEG 500 MME. For cryoprotection, crystals were generally transferred to a solution of mother liquor with the precipitant increased to 10% (w/v) PEG 20,000 and 20% (w/v) PEG 500 MME.

Data sets were collected at the European Synchrotron Radiation Facility (beamline MASSIF-1). Data was processed using XDS (Kabsch, W. (2010a/b) Acta Cryst D66, 125-132) and AIMLESS (Evans, P. R. and Murshudov, G. N. (2013) Acta Cryst D69, 1204-1214) from the CCP4 Suite (Winn, M., et al. (2011) Acta Cryst D67, 235-242).

The crystal structure was solved by molecular replacement using Phaser (McCoy et al., (2005) Acta Cryst D 61, 458-64), using atomic models generated using Alphafold2-multimer (Evans et al., (2022) bioRxiv doi:10.1101/2021.10.04.463034). Atomic models were built using Coot (Emsley, P. & Cowtan, K. Coot, (2004) Acta Cryst D60, 2126-32) and refined with Refmac (Murshudov, et al., (1997) Acta Cryst D53, 240-255) Co-crystals of TROP2 ECD and VHH M100Y were refined to 1.75 Å resolution after merging three datasets (Table 4).

TABLE 4

|  | TROP2 + 3572 |
|---|---|
| Data Collection |  |
| Beamline | ESRF MASSIF-1 |
| Wavelength | 0.965459 |
| Space Group | P $3_2$21 |
| Cell Dimensions |  |
| a, b, c (Å), α, β, γ (o) | 81.5, 81.5, 113.6, 90, 90, 120 |
| Resolution Å | 70.56-1.75 |
| Rmerge | 0.150 (3.923) |
| CC ½ | 0.994 (0.293) |
| I/σI | 7.2 (0.8) |
| Completeness (%) | 100.0 (99.9) |
| Redundancy | 9.4 (6.6) |
| Refinement |  |
| No. of Reflections | 412573 |
| No. of Unique | 43744 |
| Rfactor/Rfree (%) | 19.9 (25.8) |
| Wilson B-factors (Å) | 39.11 |
| B-factors (Å) |  |
| Protein | 52.23 |
| R.M.S. Deviations |  |
| Bond lengths (Å) | 0.0079 |
| Bond angles (°) | 1.458 |

As can be seen from FIG. 20A-FIG. 20C, the CDR3 and FR2 region of the variable region of KD005 (i.e., KD012) appears to surround a knob formed by the cysteine-rich domain of TROP2. The CDR3 of KD012 forms a clip fitting into a groove within the CRD of the TROP2 protein which may explain the high-affinity binding and slow dissociation rate. Furthermore, the framework region 2 of the KD012 sdAb also contributes to the binding to TROP2 which appears to be an unusual feature.

Since KD001, KD002, KD003, KD004 and KD005 compete with each other, it is expected that they all form a similar structure and have similar binding affinity. It is also unique that the framework 2 of KD012 contribute to the binding to TROP2 protein.

These structural data supported the high affinity of these anti-TROP2 sdAbs and potent in vivo efficacy.

The co-crystal structured revealed amino acid residues of KD012 and TROP2 that are involved in this interaction (FIG. 20D).

Table 5A shows the amino acid residues of the variable region of KD005 (i.e., corresponding to KD012: SEQ ID NO:26) that interact with human TROP2.

TABLE 5A

| Type | Position KD012 | Location KD012 | Residues KD012 | Position TROP2 | Location TROP2 | Residues TROP2 | Energy | Distance |
|---|---|---|---|---|---|---|---|---|
| D | 1 | FR1 | Gln1 | 80 | TY-1 | Asp109 | −0.22 | 3.81 |
| D | 1 | FR1 | Gln1 | 81 | TY-1 | Pro110 | −0.1 | 3.9 |
| D | 1 | FR1 | Gln1 | 82 | TY-1 | Glu111 | −0.27 | 3.86 |
| D | 2 | FR1 | Val2 | 81 | TY-1 | Pro110 | −0.31 | 4.01 |
| DH | 2 | FR1 | Val2 | 82 | TY-1 | Glu111 | −6.95 | 3.82 |
| D | 37 | FR2 | Val37 | 27 | CRD | Arg56 | −0.98 | 4.13 |
| D | 39 | FR2 | Gln39 | 31 | CRD | Ser60 | 0.01 | 4.26 |
| D | 45 | FR2 | Pro45 | 27 | CRD | Arg56 | 1.14 | 4.09 |
| D | 45 | FR2 | Pro45 | 31 | CRD | Ser60 | −0.01 | 4.2 |
| D | 45 | FR2 | Pro45 | 32 | CRD | Gly61 | 0.94 | 3.95 |
| DH | 47 | FR2 | Trp47 | 18 | CRD | Asp47 | −5.09 | 3.68 |
| D | 47 | FR2 | Trp47 | 19 | CRD | Gly48 | 0.66 | 3.92 |
| DA | 47 | FR2 | Trp47 | 20 | CRD | Pro49 | −4.89 | 3.97 |
| D | 47 | FR2 | Trp47 | 25 | CRD | Gln54 | 1.92 | 3.87 |
| D | 47 | FR2 | Trp47 | 27 | CRD | Arg56 | 0.7 | 4.09 |
| D | 50 | FR2 | Tyr50 | 20 | CRD | Pro49 | 2.66 | 3.93 |
| D | 58 | FR3 | Tyr58 | 20 | CRD | Pro49 | 0.71 | 4.23 |
| D | 58 | FR3 | Tyr58 | 21 | CRD | Gly50 | 1.96 | 3.91 |
| DIH | 99 | CDR3 | Arg99 | 36 | CRD | Asp65 | −19.2 | 3.47 |
| D | 100 | CDR3 | Leu100 | 20 | CRD | Pro49 | −0.54 | 4.35 |
| D | 100 | CDR3 | Leu100 | 23 | CRD | Arg52 | −1.27 | 4.03 |
| DH | 101 | CDR3 | Thr101 | 23 | CRD | Arg52 | −9.92 | 3.69 |
| D | 101 | CDR3 | Thr101 | 36 | CRD | Asp65 | −0.68 | 4.06 |
| D | 102 | CDR3 | Asp102 | 23 | CRD | Arg52 | −0.04 | 3.92 |
| D | 103 | CDR3 | Ser103 | 2 | CRD | Gln31 | −0.02 | 4.13 |
| D | 103 | CDR3 | Ser103 | 23 | CRD | Arg52 | −0.43 | 4.03 |
| D | 103 | CDR3 | Ser103 | 24 | CRD | Cys53 | −0.12 | 3.85 |
| DH | 104 | CDR3 | His104 | 6 | CRD | Thr35 | −4.23 | 3.51 |
| D | 104 | CDR3 | His104 | 23 | CRD | Arg52 | 0.28 | 4.02 |
| DH | 104 | CDR3 | His104 | 24 | CRD | Cys53 | −1.17 | 3.91 |
| DH | 104 | CDR3 | His104 | 26 | CRD | Cys55 | −0.97 | 3.93 |
| DA | 104 | CDR3 | His104 | 37 | CRD | Cys66 | 0.07 | 3.88 |
| D | 105 | CDR3 | Tyr105 | 19 | CRD | Gly48 | 0.32 | 4.49 |
| D | 105 | CDR3 | Tyr105 | 20 | CRD | Pro49 | 2.68 | 4.06 |
| D | 105 | CDR3 | Tyr105 | 23 | CRD | Arg52 | 1.8 | 4.11 |
| DH | 105 | CDR3 | Tyr105 | 24 | CRD | Cys53 | −5.53 | 3.87 |
| D | 105 | CDR3 | Tyr105 | 25 | CRD | Gln54 | 0.77 | 4.13 |
| D | 105 | CDR3 | Tyr105 | 27 | CRD | Arg56 | 1.5 | 3.69 |
| D | 105 | CDR3 | Tyr105 | 34 | CRD | Ala63 | 0.75 | 4.1 |
| D | 105 | CDR3 | Tyr105 | 35 | CRD | Val64 | 0.03 | 4.13 |
| D | 106 | CDR3 | Val106 | 34 | CRD | Ala63 | −0.3 | 3.97 |
| D | 106 | CDR3 | Val106 | 35 | CRD | Val64 | −0.27 | 4.09 |
| D | 106 | CDR3 | Val106 | 36 | CRD | Asp65 | −0.64 | 4.16 |
| DIH | 107 | CDR3 | Glu107 | 27 | CRD | Arg56 | −37.12 | 3.27 |
| D | 107 | CDR3 | Glu107 | 32 | CRD | Gly61 | 0.02 | 4.16 |
| D | 107 | CDR3 | Glu107 | 33 | CRD | Met62 | −1.04 | 3.89 |
| DH | 107 | CDR3 | Glu107 | 34 | CRD | Ala63 | −9.04 | 3.9 |
| D | 108 | CDR3 | Asp108 | 33 | CRD | Met62 | −0.27 | 4.43 |
| D | 108 | CDR3 | Asp108 | 81 | TY-1 | Pro110 | 0.01 | 4.29 |
| D | 108 | CDR3 | Asp108 | 82 | TY-1 | Glu111 | −0.47 | 3.81 |
| D | 109 | CDR3 | Ala109 | 33 | CRD | Met62 | −0.79 | 4.25 |
| D | 109 | CDR3 | Ala109 | 81 | TY-1 | Pro110 | −0.68 | 3.78 |
| D | 109 | CDR3 | Ala109 | 82 | TY-1 | Glu111 | 0.01 | 4.2 |
| D | 110 | FR4 | Trp110 | 27 | CRD | Arg56 | −0.26 | 4.37 |
| D | 110 | FR4 | Trp110 | 31 | CRD | Ser60 | −0.65 | 3.79 |
| D | 110 | FR4 | Trp110 | 32 | CRD | Gly61 | −0.48 | 4.11 |
| D | 110 | FR4 | Trp110 | 33 | CRD | Met62 | −5.73 | 4.1 |
| DH | 110 | FR4 | Trp110 | 81 | TY-1 | Pro110 | −3.73 | 3.94 |
| D | 112 | FR4 | Gln112 | 86 | TY-1 | Lys115 | −0.09 | 4.22 |

TABLE 5B

| | | |
|---|---|---|
| D | distance | VdW distance interaction energies. |
| A | arene | Arene interactions in the list, these include π:π, π-H, and π:cation contacts |
| I | ionic | Ionic bond contacts in the list |
| H | hbond | Hydrogen bond contacts |

KD102 Annotated According to IMGT Numbering

This data is one representative example of protein-protein interactions determined from the co-crystal structure done in triplicate. Slight variation in the distance and energy values are likely due to the energy minimization step performed in QuickPrep in MOE.

Example 13—Antibody Humanization and Characterization

ELISA Binding Assay

Human TROP2 recombinant proteins were coated on 96-well ELISA plates at the concentration of 1 μg/mL. Plates were covered with adhesive plate cover and stored at 4° C. overnight. The next day, plates were washed 3× with washing buffer (PBS with 0.1% Tween™ 20). Plates were blocked with 2% fat-free BSA in washing buffer for 1 hour at 37° C. During the incubation time, the TROP2 reference antibodies, as well as the humanized variants, were diluted in the blocking buffer to the indicated concentrations. In brief, the anti-TROP2 sdAbs starting concentration was 200 nM and serial diluted 1 in 5 to 0.00256 nM. After blocking, the blocking buffer was removed from the wells and 100 µL of anti-TROP2 sdAbs dilutions were transferred to the corresponding wells. Plates were covered with adhesive plates cover and incubated at 37° C. for 1 hour. During the primary antibody incubation, the secondary antibody (goat anti-human IgG, HRP conjugated) was diluted 1 in 5000 with the blocking buffer. Plates were washed 3× with blocking buffer, followed by secondary antibody incubation for another 1 hour at 37° C. After the secondary antibody incubation, plates were washed 3× with washing buffer and added with 100 µL of ELISA chemiluminescent substrate (Thermofisher). The luminescence signal was detected by SpectraMax i3x at 425 nM.

As illustrated in FIG. 21, all humanized variants of KD002 showed similar binding to KD002 except for KD021 and KD020, which showed reduced binding to recombinant human TROP2 protein in this assay. EC50 values are provided in Table 6.

TABLE 6

| KD002 variants | EC50 (nM) |
|---|---|
| KD002 | 0.07 |
| KD020 | N/A |
| KD021 | 4.30 |
| KD022 | 0.07 |
| KD023 | 0.08 |
| KD024 | 0.09 |
| KD025 | 0.11 |
| KD026 | 0.10 |
| KD027 | 0.09 |
| KD028 | 0.14 |
| KD029 | 0.16 |
| KD030 | 0.12 |
| KD031 | 0.11 |
| KD032 | 0.15 |
| KD033 | 0.13 |
| KD034 | 0.13 |
| KD035 | 0.12 |
| KD036 | 0.13 |
| KD037 | 0.18 |
| KD038 | 0.26 |
| KD039 | 0.15 |
| KD040 | 0.05 |
| KD041 | 0.15 |
| KD042 | 0.07 |

As illustrated in FIGS. 22A and 22B, all humanized variants showed similar binding to KD005 except for KD064, which showed reduced binding EC50 and maximum binding signal in this assay. Since the amino acid changes in KD064 are at the framework 2, this implies the importance of framework binding to TROP2 in addition to the CDR3. EC50 values and 00 EC50 value compared to KD005 are presented in Table 7.

TABLE 7

| Code name | EC50 (nM) | EC50% to KD005 | RMax |
|---|---|---|---|
| KD002 | 0.055 | 0.6875 | 199906.5 |
| KD005 | 0.08 | 1 | 202140.5 |
| KD043 | 0.09 | 1.125 | 195093 |
| KD044 | 0.08 | 1 | 200020 |
| KD045 | 0.09 | 1.125 | 206168.5 |

TABLE 7-continued

| Code name | EC50 (nM) | EC50% to KD005 | RMax |
|---|---|---|---|
| KD046 | 0.08 | 1 | 206369.5 |
| KD047 | 0.14 | 1.75 | 207446.5 |
| KD048 | 0.11 | 1.375 | 173921.5 |
| KD049 | 0.14 | 1.75 | 212138 |
| KD050 | 0.1 | 1.25 | 211592 |
| KD051 | 0.12 | 1.5 | 211126 |
| KD052 | 0.07 | 0.875 | 189730 |
| KD053 | 0.1 | 1.25 | 198757 |
| KD054 | 0.07 | 0.875 | 195032.5 |
| KD055 | 0.08 | 1 | 194513 |
| KD056 | 0.09 | 1.125 | 190663.5 |
| KD057 | 0.09 | 1.125 | 183824.5 |
| KD058 | 0.1 | 1.25 | 183885.5 |
| KD059 | 0.1 | 1.25 | 188315.5 |
| KD060 | 0.11 | 1.375 | 190929 |
| KD061 | 0.12 | 1.5 | 191304 |
| KD062 | 0.14 | 1.75 | 189381 |
| KD063 | 0.12 | 1.5 | 184553 |
| KD064 | 0.14 | 1.75 | 167056.5 |

ADCP assays were carried out as described above. Results of assays for ADCP activity for KD002 and humanized variants are presented in FIG. 23A and FIG. 23B. Antibody concentration of 0.1 nM and 0.5 nM were selected as 0.1 nM is close to the EC50 and 0.5 nM is close to the plateau observed. As illustrated in FIG. 23A and FIG. 23B, the humanized variants KD020 and KD021 had a significantly reduced ADCP activity, consistent with the binding data. Some of the amino acid substitution in KD020 are located in the framework 2 and may help explaining the decreased binding as framework 2 contributes to TROP2 binding as revealed by the structure data.

Results of assays for ADCP activity for KD005 and humanized variants are presented in FIG. 24A and FIG. 24B. The antibody concentration of 0.1 nM and 0.5 nM were selected as 0.1 nM is close to the EC50 and 0.5 nM is close to the plateau. At concentration of 0.1 nM, the majority of KD005 humanized variants exhibited better ADCP activity than the reference antibody KD005 except for the KD064. At concentration of 0.5 nM, the activity appeared essentially equivalent except for the KD064. These results are consistent with the binding data as KD064 significantly reduced the binding to TROP2 after framework2 mutation.

However, dose-response ADCP analysis FIG. 24C-FIG. 24I carried out on selected KD005 humanized variants (KD045, KD047, KD048, KD049, KD053, Kd059 and KD063) revealed that some had slightly ADCP better activity, while others had similar ADCP activity or lower ADCP activity.

The ADCC activity of the humanized variants was evaluated as described above. Results of ADCC activity for KD002 and KD002 humanized variants are presented in FIG. 25A and FIG. 25B. Antibody concentration of 0.1 nM and 0.5 nM were selected as 0.1 nM is close to the EC50 and 0.5 nM is close to the plateau. At 0.5 nM concentration, the majority of humanized variants had similar ADCC activity to KD002 except for KD020 and KD021. The explanation is that the ADCC activity showed saturation at 0.5 nM close to the plateau. ADCC activity at 0.1 nM showed greater variability than at 0.5 nM. The humanized variants KD022, KD027, KD025, KD026, and KD024 exhibited better ADCC activity than KD002. Whereas KD028, KD020 and KD021 have a significantly reduced ADCC activity, which was consistent with the binding data.

Results of ADCC activity for KD005 and KD005 humanized variants are presented in FIG. 26A and FIG. 26B.

Antibody concentration of 0.1 nM and 0.5 nM were selected as 0.1 nM is close to the EC50 and 0.5 nM is close to the plateau. At the concentration of 0.1 nM, the majority of KD005 humanized variants exhibited similar or better ADCC activity than the reference antibody KD005 except for the KD064. This is consistent with the binding data as KD064 significantly reduced the binding to TROP2 after framework2 mutation.

Based on the above results KD002 and KD005 humanized variants were ranked according to binding data, ADCP activity and/or ADCC activity.

For example, based on ELISA binding data, it appears that KD056, KD057, KD050, KD055, KD043, KD045, KD052, KD054, KD044, KD046 have a EC50 that is similar to or better than KD005, whereas KD054, KD043, KD053, KD044, KD045, KD046, KD047, KD051, KD050 and KD049 have a Rmax that is similar to or better than KD005.

Therefore, based on binding data, it appears that KD043, KD044, KD045, KD046, KD047, KD049, KD050, KD051, KD052, KD053, KD054, KD055, KD056, and KD057 represent the best binders.

The binding EC50 and the maximum binding signal (Rmax) of selected KD005 humanized variants based on the ELISA binding curve is presented in Table 8. The binding EC50 and Rmax were normalized to the reference antibody KD005.

TABLE 8

| Variant Designation | EC50 (% KD005) | Variant Designation | Rmax (% KD005) |
| --- | --- | --- | --- |
| KD056 | 1.21 | KD054 | 0.964 |
| KD057 | 1.15 | KD043 | 0.965 |
| KD050 | 1.12 | KD053 | 0.983 |
| KD055 | 1.12 | KD054 | 0.990 |
| KD043 | 1.01 | KD005 | 1 |
| KD045 | 1.01 | KD045 | 1.0199 |
| KD005 | 1 | KD046 | 1.0209 |
| KD052 | 0.93 | KD047 | 1.0262 |
| KD054 | 0.93 | KD051 | 1.0445 |
| KD044 | 0.9 | KD050 | 1.0468 |
| KD046 | 0.9 | KD049 | 1.0495 |

Based on ADCP assays performed herein, it appears that KD043, KD044, KD045, KD046, KD048, KD049, KD051, KD052, KD053, KD054, KD055, KD057, KD061, and KD063 have the best ADCP activity.

The ADCP activity of KD005 humanized variants at 0.1 nM and 0.5 nM are presented in Table 9 and Table 10. The data was normalized to the reference antibody KD005.

TABLE 9

ADCP activity measured at 0.1 nM and 0.5 nM relative to KD005 ranked based on highest value at 0.1 nM.

| | 0.5 nM (% KD005) | 0.1 nM (% KD005) |
| --- | --- | --- |
| KD063 | 96.1 | 189.9 |
| KD043 | 108.1 | 189.0 |
| KD046 | 72.1 | 186.4 |
| KD049 | 92.8 | 169.1 |
| KD044 | 96.4 | 165.0 |
| KD061 | 83.8 | 164.7 |
| KD045 | 87.3 | 163.5 |
| KD052 | 98.2 | 162.6 |
| KD053 | 97.6 | 161.7 |
| KD054 | 94.9 | 160.5 |
| KD005 | 100.0 | 100.0 |

TABLE 10

ADCP activity measured at 0.1 nM and 0.5 nM relative to KD005 ranked based on highest value at 0.5 nM.

| | 0.5 nM (% KD005) | 0.1 nM (% KD005) |
| --- | --- | --- |
| KD051 | 113.1 | 126.9 |
| KD043 | 108.1 | 189.0 |
| KD057 | 103.9 | 96.6 |
| KD005 | 100.0 | 100.0 |
| KD052 | 98.2 | 162.6 |
| KD053 | 97.6 | 161.7 |
| KD044 | 96.4 | 165.0 |
| KD063 | 96.1 | 189.9 |
| KD054 | 94.9 | 160.5 |
| KD055 | 93.0 | 157.9 |
| KD049 | 92.8 | 169.1 |

Based on ADCC assay performed at 0.1 nM and 0.5 nM (EC50 and % Emax relative to KD005), it appears that KD043, KD044, KD045, KD046, KD047, KD048, KD049, KD55), KD051, KD053, KD054, KD61, KD062, and KD063 have the best ADCC activity.

Tables 11 and Table 12 summarize the ADCC activity of KD005 humanized variants at 0.1 nM and 0.5 nM. The data was normalized to the reference antibody KD005.

TABLE 11

ADCC activity measured at 0.1 nM and 0.5 nM relative to KD005 ranked based on highest value at 0.1 nM.

| | 0.5 nM (% KD005) | 0.1 nM (% KD005) |
| --- | --- | --- |
| KD050 | 96.3 | 214.3 |
| KD046 | 127.8 | 199.9 |
| KD048 | 124.2 | 154.5 |
| KD061 | 95.5 | 151.4 |
| KD062 | 97.5 | 150.1 |
| KD045 | 98.3 | 145.7 |
| KD063 | 98.7 | 140.1 |
| KD043 | 98.8 | 139.8 |
| KD044 | 105.4 | 127.3 |
| KD054 | 90.3 | 126.8 |
| KD005 | 100.0 | 100.0 |

TABLE 12

ADCC activity measured at 0.1 nM and 0.5 nM relative to KD005 ranked based on highest value at 0.5 nM.

| | 0.5 nM (% KD005) | 0.1 nM (% KD005) |
| --- | --- | --- |
| KD046 | 127.8 | 199.9 |
| KD048 | 124.2 | 154.5 |
| KD051 | 120.0 | 124.5 |
| KD044 | 105.4 | 127.3 |
| KD047 | 102.5 | 115.5 |
| KD049 | 100.8 | 115.7 |
| KD005 | 100.0 | 100.0 |
| KD043 | 98.8 | 139.8 |
| KD063 | 98.7 | 140.1 |
| KD053 | 98.3 | 110.8 |
| KD045 | 98.3 | 145.7 |

Example 14—Sequence Analysis

Co-crystallization of the variable region of KD005 with human TROP2 reveals that amino acid residues of CDRH3 and FR2 are in close contact with the CRD region of TROP2

(see Table 5 and FIG. 20B-FIG. 20D). Amino acid residues of TY-1 (74-146) appear to be involved in the interaction but to a lesser extent, whereas it appears that there is no significant interaction with amino acid residues of the CPD (147-274).

The competition assays and FACS analysis indicate that KD001-KD005 all bind to the same or overlapping regions of TROP2. Therefore, KD001, KD002, KD003 and KD004 may likely bind some or all interacting amino acid residues of human TROP2 identified for KD005.

Since KD002 variants have similar properties as KD002, it is expected that KD002 variants also bind to the CRD region of TROP2. As well, since KD005 variants have similar properties as KD002, it is expected that KD005 variants also bind to the CRD region of TROP2.

An alignment between the variable regions of KD001-KD005 (FIG. 27: SEQ ID NO:22, SEQ ID NO:23, SEQ ID NO:24, SEQ ID NO:25 or SEQ ID NO:26) was generated. The alignment was used to generate an exemplary consensus sequence (SEQ ID NO:145) carrying 25 amino acid substitutions out of 120 or 121 positions.

KD001-KD005 are therefore approximately 80% identical to each other over the entire length of the polypeptide.

As illustrated in FIG. 27, the variable region of KD001-KD005 have at least 80% sequence identity to each other over the entire length of the polypeptide.

In the alignment of FIG. 27 as well as in other alignments presented herein a colon (:) indicates conservation between groups of strongly similar properties as below—roughly equivalent to scoring >0.5 in the Gonnet PAM 250 matrix (Table 13). A period (.) indicates conservation between groups of weakly similar properties as below—roughly equivalent to scoring=<0.5 and >0 in the Gonnet PAM 250 matrix (Table 14). For example, it may be possible to substitute an amino acid residue identified as being part of a group in Table 13 for another of the same group. Similarly, it may be possible to substitute an amino acid residue identified as being part of a group in Table 14 for another of the same group.

An empty space indicates that the amino acid may be a non-conservative amino acid substitution.

TABLE 13

| (:) |
|---|
| STA |
| NEQK |
| NHQK |
| NDEQ |
| QHRK |
| MILV |
| MILF |
| HY |
| FYW |

TABLE 14

| (.) |
|---|
| CSA |
| ATV |
| SAG |
| STNK |
| STPA |
| SGND |
| SNDEQK |
| NDEQHK |
| NEQHRK |
| FVLIM |
| HFY |

Upon analysis of the sequence, it appears that KD001-KD005 all have an identical IMGT FR2 amino acid sequence, but different IMGT CDRH1, IMGT CDRH2 and IMGT CDRH3 or different combinations of IMGT CDRH1, IMGT CDRH2 and IMGT CDRH3.

For example, KD001, KD004 and KD005 have identical IMGT CDRH1 (SEQ ID Nos: 52, 59 and 62 are identical) whereas KD002 and KD003 have unique IMGT CDRH1 sequences.

KD001 and KD005 have identical IMGT CDRH2 (SEQ ID Nos: 50 and 53 are identical) whereas KD002, KD003 and KD004 have unique IMGT CDRH2 sequences.

KD002 and KD003 have identical IMGT CDRH3 (SEQ ID NO:48 and 58 are identical) and KD001 and KD004 have identical IMGT CDRH3, whereas KD005 has a unique IMGT CDRH3.

There is a high level of variability between KD001-KD005 IMGT CDRH1 indicating that this region may not be involved in binding as also illustrated by the co-crystallization experiments.

There is also substantial variability in IMGT CDRH2 indicating that this region may not be involved in binding as also illustrated by the co-crystallization experiments.

There is, however a high level of similarity between the IMGT CDRH3 of KD001-KD005. An alignment between the different IMGT CDRH3 shows that 9/14 amino acid residues are identical and 4/14 amino acid residues are conservative amino acid substitutions. Nevertheless, these alignments show that some level of variation may be tolerated in CDRH3 as well.

The amino acid sequence of KD002 and KD005 variants was also analyzed.

The IMGT CDRH1 (SEQ ID NO:55) and IMGT CDRH3 (SEQ ID NO:48) of KD002 variants is identical to that of KD002.

The CDRH2 of most variants is identical to that of KD002 (SEQ ID NO:47) except for 2 variants having a sequence illustrated in SEQ ID:123 and SEQ ID NO:124 that each includes one amino acid substitution.

Several KD002 variants have an IMGT FR2 identical to that of KD002 (SEQ ID NO:116) while others have one or two amino acid substitutions. Variations in KD002 IMGT FR2 are illustrated in SEQ ID NO: 117, SEQ ID NO: 118 and SEQ ID NO: 119.

The IMGT CDRH1, CDRH2 and CDRH3 of KD005 variants are identical to that of KD005.

Several KD005 variants have an IMGT FR2 identical to that of KD005 while others have one or two amino acid substitutions. Variations in KD005 IMGT FR2 are illustrated in SEQ ID NO: 117, SEQ ID NO: 118 and SEQ ID NO:120.

An alignment between the IMGT FR2 sequences of all tested variants shows that 14/17 amino acid residues are identical. The binding and/or function of these variants was not affected by these substitutions suggesting that FR2 can sustain some level of variation.

However, the amino acid substitutions introduced in the IMGT FR2 of KD064 lead to a reduced binding and activity. The co-crystallization experiment confirms that amino acid residues 37, 45, 47, and 50 of IMGT FR2 are involved in binding with human TROP2. Based on the results obtained for KD064, amino acid substitution V/Y at position 37 and amino acid substitution P/R at position 45 may affect binding.

Overall, the results presented herein show that CDRH3 and FR2 are important for binding to TROP2 but that some level of variation may be tolerated and that CDRH1 and CDRH2 do not appear to be involved in binding to human TROP2.

An alignment between the entire variable region of KD002 (SEQ ID NO:23) and the entire variable region of exemplary embodiments of KD002 variants (FIG. 28) was made. The alignment was used to generate an exemplary consensus sequence (SEQ ID NO:143) carrying 18 amino acid substitutions out of the 121 positions.

KD002 and KD002 variants are therefore approximately 85% identical to each other over the entire length of the polypeptide.

KD002 variants selected for their ADCC and ADCP activity are also illustrated in FIG. 29.

An alignment between the variable region of KD005 (SEQ ID NO:26) and the variable region of exemplary embodiments of KD005 variants (FIG. 30) was also made. The alignment was used to generate an exemplary consensus sequence (SEQ ID NO:144) carrying 16 amino acid substitutions out of the 120 positions.

KD005 and KD005 variants are therefore approximately 85% identical to each other over the entire length of the polypeptide.

KD005 variants selected for their binding activity are illustrated in FIG. 31.

KD005 variants selected for their ADCP activity are illustrated in FIG. 24C-FIG. 24I and in FIG. 32.

KD005 variants selected for their ADCC activity are illustrated in FIG. 33.

KD005 variants selected for their binding activity, ADCP activity and ADCC activity are illustrated in FIG. 34.

Since they have similar activity and sequences, an alignment between the variable regions of KD001-KD005 (SEQ ID NOs:22-26 and variants (SEQ ID NOs: 94-115) was generated. The alignment was used to generate an exemplary consensus sequence (SEQ ID NO:146) carrying 40 amino acid substitutions out of 121 positions.

All variants are therefore approximately 65% identical to each other over the entire length of the polypeptide. In addition to the embodiments described and provided in this disclosure, the following non-limiting embodiments are particularly contemplated.

Example 15—Dose Range Finding Intravenous Toxicity Study in Cynomolgus Monkey The potential toxicity of the TROP2 testing articles was evaluated in the naïve cynomolgus monkeys. All procedures and protocols were carried out under the institutional guidelines of Sinclair Research Center in Missouri, USA. The design is in an accelerated, increasing dosing study. The naïve cynomolgus monkey was first administered intravenously with KD002 or KD005 at the dosing level of 25 mg/kg. If the animal tolerated the first 25 mg/kg dose well, the next dose, 100 mg/kg, was given one week later. If the animal also tolerated 100 mg/kg dose, another two repeating dose of 100 mg/kg were given to the animal once per week.

During the study, animals were examined by the veterinary staff as warranted by clinical signs or other changes. In-cage observations were performed twice daily in the AM and PM (with at least 4 hours between observations) during the in-life study period to assess general health, mortality, or moribundity. Each animal underwent a physical examination, including assessment of behavior, general body condition, condition of major body systems, and skin/coat. Detailed clinical observations were performed at least five times following each dose at 1, 2, 6, 12, and 24 hours post dose and daily on non-dosing days starting after each animal's first dosing event. Serum samples for hematology and clinical chemistry were collected at 2 and 7 days after each dose.

For both KD002 and KD005 testing articles, there were no instances of moribundity or unscheduled deaths during the study. All animals underwent a physical examination and were deemed satisfactory for study inclusion. There were no test article-related effects on body weight relative to dose group. Throughout the dosing phase, all animals had body weights remained with 10% of their weights in the acclimation phase. There were no instances of inappetence either during the study. There were no test article-related findings for any hematology parameters for both KD002 and KD005 studies. All the serum chemistry parameters were in the normal range during the dosing phase to the acclimation phase values for each animal.

Based on the above observations, 100 mg/kg of KD002 and KD005 once weekly for up to at least three doses were well tolerated in cynomolgus non-human primates.

In addition to the embodiments described and provided in this disclosure, the following non-limiting embodiments are contemplated.

1. A binding agent comprising one or more antigen binding domains, wherein at least one of the one or more antigen binding domains specifically binds to the extracellular domain (ECD) of trophoblast cell surface antigen-2 (TROP2).
2. A single domain antibody that specifically binds to at least one epitope comprising amino acid residues of the extracellular domain (ECD) of trophoblast cell surface antigen-2 (TROP2).
3. A binding agent comprising one or more antigen binding domains, wherein at least one of the one or more antigen binding domains specifically binds to the extracellular domain (ECD) of trophoblast cell surface antigen-2 (TROP2) and comprises an amino acid sequence at least 80% identical to the amino acid sequence set forth in SEQ ID NO:22.
4. A binding agent comprising one or more antigen binding domains, wherein at least one of the one or more antigen binding domains specifically binds to the extracellular domain (ECD) of trophoblast cell surface antigen-2 (TROP2) and comprises an amino acid sequence at least 80% identical to the amino acid sequence set forth in SEQ ID NO:23.
5. A binding agent comprising one or more antigen binding domains, wherein at least one of the one or more antigen binding domains specifically binds to the extracellular domain (ECD) of trophoblast cell surface antigen-2 (TROP2) and comprises an amino acid sequence at least 80% identical to the amino acid sequence set forth in SEQ ID NO:24.
6. A binding agent comprising one or more antigen binding domains, wherein at least one of the one or more antigen binding domains specifically binds to the extracellular domain (ECD) of trophoblast cell surface antigen-2 (TROP2) and comprises an amino acid sequence at least 80% identical to the amino acid sequence set forth in SEQ ID NO:25.
7. A binding agent comprising one or more antigen binding domains, wherein at least one of the one or more antigen binding domains specifically binds to the extracellular domain (ECD) of trophoblast cell surface antigen-2 (TROP2) and comprises an amino acid sequence at least 80% identical to the amino acid sequence set forth in SEQ ID NO:26.
8. A binding agent comprising one or more antigen binding domains, wherein at least one of the one or more antigen binding domains specifically binds to the extracellular domain (ECD) of trophoblast cell surface antigen-2 (TROP2) and comprises an amino acid sequence at least 80% identical to the amino acid sequence set forth in SEQ ID NO:27.
9. A binding agent comprising one or more antigen binding domains, wherein at least one of the one or more antigen binding domains specifically binds to the extracellular domain (ECD) of trophoblast cell surface antigen-2 (TROP2) and comprises an amino acid sequence at least 80% identical to the amino acid sequence set forth in SEQ ID NO:28.
10. The binding agent of any of the preceding embodiments, wherein the one or more antigen binding domains are one or more antigen binding domains of a single domain antibody.
11. The binding agent of any of the preceding embodiments, wherein the binding agent is a single domain antibody.
12. The binding agent of any of the preceding embodiments, wherein the one or more antigen binding domains comprise a CDR3 amino acid sequence as set forth in SEQ ID NO:126 or in SEQ ID NO:142.
13. The binding agent of any of the preceding embodiments, wherein the one or more antigen binding domains comprise a FR2 amino acid sequence as set forth in SEQ ID NO:121 or in SEQ ID NO: 175.
14. The binding agent of any of the preceding embodiments, wherein the binding agent or at least one of the one or more antigen binding domains comprises the amino acid sequence set forth in SEQ ID NO:145 and wherein any of $X_{3a}$ to $X_{3y}$ is each independently any amino acid residue.
15. The binding agent of any of the preceding embodiments, wherein the binding agent or at least one of the one or more antigen binding domains comprises the amino acid sequence set forth in SEQ ID NO:145 and wherein:
    a. any of $X_{3a}$ to $X_{3y}$ is each independently an amino acid residue found at a corresponding position in any one of SEQ ID NO:22, SEQ ID NO:23, SEQ ID NO:24, SEQ ID NO:25 or SEQ ID NO:26 or conservative amino acid substitutions or non-conservative amino acid substitutions thereof or;
    b. wherein any of $X_{3a}$ to $X_{3y}$ is each independently an amino acid residue most frequently found at a corresponding position in any one of SEQ ID NO:22, SEQ ID NO:23, SEQ ID NO:24, SEQ ID NO:25 to SEQ ID NO:26.
16. The binding agent of any of the preceding embodiments, wherein the binding agent or at least one of the one or more antigen binding domains comprises the amino acid sequence set forth in SEQ ID NO:145 and wherein $X_{3a}$ is M or L; $X_{3b}$ is Q, H or E; $X_{3c}$ is V, P or A; $X_{3d}$ is G or R; $X_{3e}$ is P or T; $X_{3f}$ is S, N or G; $X_{3g}$ is A, Y or S; $X_{3h}$ is N or T; $X_{3i}$ is A, S or G; $X_{3j}$ is D, G or S; $X_{3k}$ is G or absent; $X_{3l}$ is S or G; $X_{3m}$ is K, N or T; $X_{3n}$ is Y or D; $X_{3o}$ is I or T; $X_{3p}$ is T or M; $X_{3q}$ is L or Q; $X_{3r}$ is N or S; $X_{3s}$ is K or T; $X_{3t}$ is E or D; $X_{3u}$ is R or K; $X_{3v}$ is A or S; $X_{3w}$ is K or R; $X_{3x}$ is T or S; and/or $X_{3y}$ is Y or A.
17. The binding agent of any of the preceding embodiments, wherein the binding agent or at least one of the one or more antigen binding domains comprises the amino acid sequence set forth in SEQ ID NO:145 and wherein $X_{3a}$ is M or L; $X_{3b}$ is Q, H or E; $X_{3c}$ is V, P or A; $X_{3d}$ is G or R; $X_{3e}$ is P or T; $X_{3f}$ is S, N or G; $X_{3g}$ is A, Y or S; $X_{3h}$ is N or T; $X_{3i}$ is A, S or G; $X_{3j}$ is D, G or S; $X_{3k}$ is G or absent; $X_{3l}$ is S or G; $X_{3m}$ is K, N or T; $X_{3n}$ is Y; $X_{3o}$ is I or T; $X_{3p}$ is T or M; $X_{3q}$ is L or Q; $X_{3r}$ is N or S; $X_{3s}$ is K or T; $X_{3t}$ is E or D; $X_{3u}$ is R or K; $X_{3v}$ is A or S; $X_{3w}$ is R; $X_{3x}$ is S; and/or $X_{3y}$ is A.
18. The binding agent of any of the preceding embodiments, wherein at least one of the one or more antigen binding domains comprises the amino acid sequence set forth in SEQ ID NO:144 and wherein any of $X_{2a}$ to $X_{2p}$ is each independently any amino acid residue.
19. The binding agent of any of the preceding embodiments, wherein the binding agent or at least one of the one or more antigen binding domains comprises the amino acid sequence set forth in SEQ ID NO:144 and wherein,
    a. any of $X_{2a}$ to $X_{2p}$ is each independently an amino acid residue found at a corresponding position in any one of SEQ ID NO:26 or SEQ ID NO:94-114 or conservative amino acid substitutions or non-conservative amino acid substitutions thereof
    b. any of $X_{2a}$ to $X_{2p}$ is each independently an amino acid residue found at a corresponding position in any one of SEQ ID NO:22, SEQ ID NO:23, SEQ ID NO:24, SEQ ID NO:25 or SEQ ID NO:26 or conservative amino acid substitutions or non-conservative amino acid substitutions thereof;
    c. wherein any $X_{2a}$ to $X_{2p}$ is each independently an amino acid residue most frequently found at a corresponding position in any one of SEQ ID NO:26 or SEQ ID NO:94-114 or;
    d. wherein any $X_{2a}$ to $X_{2p}$ is each independently an amino acid residue most frequently found at a corresponding position in any one of SEQ ID NO:22, SEQ ID NO:23, SEQ ID NO:24, SEQ ID NO:25 to SEQ ID NO:26.
20. The binding agent of any of the preceding embodiments, wherein the binding agent or at least one of the one or more antigen binding domains comprises the amino acid sequence set forth in SEQ ID NO:144 and wherein:
    a. any of $X_{2a}$ to $X_{2p}$ is each independently an amino acid residue found at a corresponding position in any one of SEQ ID NOs: 94, 95, 96, 97, 98, 100, 101, 102, 103, 104, 105, 106, 107 or 108 or conservative amino acid substitutions or non-conservative amino acid substitutions thereof or;

b. wherein any $X_{2a}$ to $X_{2p}$ is each independently an amino acid residue most frequently found at a corresponding position in any one of SEQ ID NOs: 94, 95, 96, 97, 98, 100, 101, 102, 103, 104, 105, 106, 107 or 108.

21. The binding agent of any of the preceding embodiments, wherein the binding agent or at least one of the one or more antigen binding domains comprises the amino acid sequence set forth in SEQ ID NO:144 and wherein:
   a. any of $X_{2a}$ to $X_{2p}$ is each independently an amino acid residue found at a corresponding position in any one of SEQ ID NOs: 94, 95, 96, 97, 100, 102, 103, 104, 105, 106, 108, 112 or 114 or conservative amino acid substitutions or non-conservative amino acid substitutions thereof or;
   b. wherein any $X_{2a}$ to $X_{2p}$ is each independently an amino acid residue most frequently found at a corresponding position in any one of SEQ ID NOs: 94, 95, 96, 97, 100, 102, 103, 104, 105, 106, 108, 112 or 114.

22. The binding agent of any of the preceding embodiments, wherein the binding agent or at least one of the one or more antigen binding domains comprises the amino acid sequence set forth in SEQ ID NO:144 and wherein:
   a. any of $X_{2a}$ to $X_{2p}$ is each independently an amino acid residue found at a corresponding position in any one of SEQ ID NOs: 94, 95, 96, 97, 98, 99, 100, 101, 102, 104, 105, 112, 113 or 114 or conservative amino acid substitutions or non-conservative amino acid substitutions thereof or;
   b. wherein any $X_{2a}$ to $X_{2p}$ is each independently an amino acid residue most frequently found at a corresponding position in any one of SEQ ID NOs: 94, 95, 96, 97, 98, 99, 100, 101, 102, 104, 105, 112, 113 or 114.

23. The binding agent of any of the preceding embodiments, wherein the binding agent or at least one of the one or more antigen binding domains comprises the amino acid sequence set forth in SEQ ID NO:144 and wherein:
   a. any of $X_{2a}$ to $X_{2p}$ is each independently an amino acid residue found at a corresponding position in any one of SEQ ID NOs: 94, 95, 96, 97, 102 or 105 or conservative amino acid substitutions or non-conservative amino acid substitutions thereof or;
   b. wherein any $X_{2a}$ to $X_{2p}$ is each independently an amino acid residue most frequently found at a corresponding position in any one of SEQ ID NOs: 94, 95, 96, 97, 102 or 105.

24. The binding agent of any of the preceding embodiments, wherein the binding agent or at least one of the one or more antigen binding domains comprises the amino acid sequence set forth in SEQ ID NO:144 and wherein $X_{2a}$ is Q or E; $X_{2b}$ is Q, L or V; $X_{2c}$ is V or I; $X_{2d}$ is E or Q; $X_{2e}$ is A or P; $X_{2f}$ is P, or L; $X_{2g}$ is Y, A or V; $X_{2h}$ is P or A; $X_{2i}$ is S or T; $X_{2j}$ is A or S; $X_{2k}$ is K or R; $X_{2l}$ is P or A; $X_{2m}$ is D or E; $X_{2n}$ is L or V; $X_{2o}$ is R or Y and/or $X_{2p}$ is Q or L.

25. The binding agent of any of the preceding embodiments, wherein the binding agent or at least one of the one or more antigen binding domains comprises the amino acid sequence set forth in SEQ ID NO:144 and wherein $X_{2a}$ is Q or E; $X_{2b}$ is Q or L; $X_{2c}$ is V or I; $X_{2d}$ is E or Q; $X_{2e}$ is A or P; $X_{2f}$ is P, or L; $X_{2g}$ is Y or A; $X_{2h}$ is P or A; $X_{2i}$ is S or T; $X_{2j}$ is A or S; $X_{2k}$ is K or R; $X_{2l}$ is P or A; $X_{2m}$ is D or E; $X_{2n}$ is L or V; $X_{2o}$ is R or Y and/or $X_{2p}$ is Q or L.

26. The binding agent of any one of the preceding embodiments, wherein the amino acid residue at position 1 is Q, the amino acid residue at position 2 is V, the amino acid residue at position 3 is Q, the amino acid residue at position 4 is L, the amino acid residue at position 37 is V, the amino acid residue at position 39 is Q, the amino acid residue at position 45 is P, the amino acid residue at position 46 is E, the amino acid residue at position 47 is W, the amino acid residue at position 50 is Y, the amino acid residue at position 58 is Y, the amino acid residue at position 99 is R, the amino acid residue at position 100 is L, the amino acid residue at position 101 is T, the amino acid residue at position 102 is D, the amino acid residue at position 103 is S, the amino acid residue at position 104 is H, the amino acid residue at position 105 is Y, the amino acid residue at position 106 is V, the amino acid residue at position 107 is E, the amino acid residue at position 108 is D, the amino acid residue at position 109 is A, the amino acid residue at position 110 is W, the amino acid residue at position 111 is G, and/or the amino acid residue at position 112 is Q and the position is with reference to SEQ ID NO:145 (Table 1)

27. The binding agent of any one of the preceding embodiments, wherein the at least one of the one or more antigen binding domains comprises the amino acid sequence of the CDR3 set forth in any one of SEQ ID NO:48, SEQ ID NO:51, SEQ ID NO:54, SEQ ID NO:58 or SEQ ID NO:61, the amino acid sequence of the FR2 set forth in any one of SEQ ID NO:116, SEQ ID NO:117, SEQ ID NO:118, SEQ ID NO:119 or SEQ ID NO:120 and optionally the amino acid sequence of the CDR1 set forth in any one of SEQ ID NO: 52, SEQ ID NO: 55, SEQ ID NO:59, SEQ ID NO: 52 or SEQ ID NO: 62 and/or the amino acid sequence of the CDR2 set forth in any one of SEQ ID NO: 47, SEQ ID NO:50, SEQ ID NO:53, SEQ ID NO: 57, SEQ ID NO: 60, SEQ ID NO:123 or SEQ ID NO:124 or;

28. The binding agent of any one of the preceding embodiments, wherein the at least one of the one or more antigen binding domains comprises the amino acid sequence of the CDR3 set forth in any one of SEQ ID NO:3, SEQ ID NO:6, SEQ ID NO:12, SEQ ID NO:15 or SEQ ID NO:141, the amino acid sequence of the FR2 set forth in any one of SEQ ID NO:170, SEQ ID NO:171, SEQ ID NO:172, SEQ ID NO:173 or SEQ ID NO:174 and optionally the amino acid sequence of the CDR1 set forth in any one of SEQ ID NO:1, SEQ ID NO:4, SEQ ID NO:7 or SEQ ID NO:127 and/or the amino acid sequence of the CDR2 set forth in any one of SEQ ID NO:2, SEQ ID NO:5, SEQ ID NO:8, SEQ ID NO:11, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138 or SEQ ID NO:139.

29. The binding agent of any one of the preceding embodiments, wherein the binding agent or at least one of the one or more antigen binding domains has an affinity of $\leq 10^{-6}$ M for TROP2.

30. The binding agent of any one of the preceding embodiments, wherein the binding agent or at least one of the one or more antigen binding domains has an affinity of $\leq 10^{-10}$ M for human TROP2.

31. The binding agent of any one of the preceding embodiments, wherein the binding agent or at least one of the one or more antigen binding domains has an affinity of at between $1\times10^{-10}$ M and $1\times10^{-12}$ for human TROP2.
32. The binding agent of any one of the preceding embodiments, wherein the binding agent or at least one of the one or more antigen binding domains has a dissociation rate of between $1\times10^{-6}$ to $1\times10^{-4}$.
33. The binding agent of any of the preceding embodiments, wherein the binding agent comprises partially humanized framework regions.
34. The binding agent of any of the preceding embodiments, wherein the binding agent comprises fully humanized framework regions.
35. The binding agent of any one of the preceding embodiments, wherein the binding agent or at least one of the one or more antigen binding domains has ADCP activity towards cells expressing human TROP2.
36. The binding agent of any one of the preceding embodiments, wherein the binding agent or at least one of the one or more antigen binding domains has ADCP activity towards cells expressing human TROP2 and CD47.
37. The binding agent of any one of the preceding embodiments, wherein the binding agent or at least one of the one or more antigen binding domains has ADCC activity towards cells expressing human TROP2.
38. The binding agent of any one of the preceding embodiments, wherein the binding agent or at least one of the one or more antigen binding domains is internalized in cells expressing human TROP2.
39. The binding agent of any one of the preceding embodiments, wherein the binding agent or at least one of the one or more antigen binding domains is capable of inhibiting the growth of tumor cells expressing human TROP2.
40. The binding agent of any one of the preceding embodiments, wherein the binding agent or at least one of the one or more antigen binding domains is capable of inhibiting the growth of tumor cells expressing human TROP2 and CD47.
41. The binding agent of any one of the preceding embodiments, wherein the binding agent comprises one or more antigen binding domains that specifically binds to CD47.
42. The binding agent of any one of the preceding embodiments, wherein the binding agent comprises a Fc portion that is capable of binding to an Fc receptor of monocytes and/or macrophages.
43. The binding agent of any one of the preceding embodiments, wherein the binding agent comprises a dimerization domain.
44. The binding agent of any of the preceding embodiments, wherein the binding agent is naked.
45. The binding agent of any of the preceding embodiments, wherein the binding agent is conjugated to a therapeutic moiety.
46. The binding agent of any of the preceding embodiments, wherein the binding agent is conjugated to a detectable moiety.
47. The binding agent of any one of the preceding embodiments, wherein the binding agent or one or more of the antigen binding domains specifically binds to human TROP2.
48. The binding agent of any one of the preceding embodiments, wherein the binding agent comprises two antigen binding domains or more.
49. The binding agent of any one of the preceding embodiments, wherein the binding agent is monospecific.
50. The binding agent of any one of the preceding embodiments, wherein the binding agent is bispecific.
51. The binding agent of any one of the preceding embodiments, wherein the binding agent is multispecific.
52. The binding agent of any one of the preceding embodiments, wherein the binding agent is capable of competing with a single domain antibody comprising the amino acid sequence set forth in SEQ ID NO:26.
53. The binding agent of any one of the preceding embodiments, wherein the binding agent specifically binds to a polypeptide comprising a human TROP2 amino acid sequence consisting of amino acid residues 27-146 or a fragment thereof.
54. The binding agent of any one of the preceding embodiments, wherein the binding agent specifically binds to a polypeptide comprising a human TROP2 amino acid sequence consisting of amino acid residues 27-73 or a fragment thereof.
55. The binding agent of any one of the preceding embodiments, wherein the binding agent does not significantly bind to or is not capable of binding to a) a polypeptide that comprises a human TROP2 amino acid sequence consisting of amino acid residues 147-274 or a fragment thereof, b) a human TROP2 amino acid sequence comprising deletion of amino acid residues 27-36, 27-44, 27-56, 27-66 or 27-73 or has a reduced binding to said polypeptide compared to the full human TROP2 polypeptide and/or a polypeptide comprising the amino acid sequence set forth in SEQ ID NO: 149.
56. A single domain antibody that competes with the binding agent of any one of the preceding embodiments.
57. A composition comprising the binding agent or single domain antibody of any of the preceding embodiments.
58. A pharmaceutical composition comprising the binding agent or single domain antibody of any of the preceding embodiments and a pharmaceutically acceptable carrier.
59. A nucleic acid or vector encoding the binding agent or single domain antibody of any of the preceding embodiments.
60. A cell expressing the binding agent or single domain antibody of any of the preceding embodiments.
61. A cell comprising the nucleic acid or the vector of any of the preceding embodiments.
62. A kit comprising the binding agent or single domain antibody of any of the preceding embodiments.
63. A kit comprising the nucleic acid or the vector of any of the preceding embodiments.
64. A method of treating a disorder or disease comprising administering the binding agent or single domain antibody of any one of the preceding embodiments or a pharmaceutical composition comprising the binding agent or single domain antibody of any one of the preceding embodiments.
65. The method of the preceding embodiments, wherein the disorder or disease is cancer, solid tumor, epithetial cancer, lung cancer, metastatic lung cancer, small cell lung cancer, non-small cell lung cancer, myeloma, prostate cancer, breast cancer, triple negative breast cancer, rectal cancer, pancreatic cancer, glioblastoma, cervical cancer, colorectal cancer, gastric cancer, ovarian cancer, thyroid cancer, stomach cancer, urinary bladder cancer, cancer of the uterus, esophegeal cancer, blood cancer, or head and neck cancer.

66. The method of any of the preceding embodiments, wherein the binding agent or single domain antibody is administered at a dose of approximately between 0.05 to 150 mg/kg.
67. The method of any of the preceding embodiments, wherein the binding agent or single domain antibody is administered once weekly.
68. The method of any of the preceding embodiments, wherein the binding agent or single domain antibody is administered once every two weeks, once every three weeks, once every month or less frequently.
69. The method of any of the preceding embodiments, wherein the binding agent or single domain antibody is administered by intra-veinous injection, by intra-muscular injection or by infusion.
70. The method of any of the preceding embodiments, wherein the binding agent or single domain antibody is administered to a subject having a tumor or tumor cells expressing TROP2 and optionally expressing a macrophages marker.

The embodiments and examples described herein are illustrative and are not meant to limit the scope of the claims. Variations of the foregoing embodiments, including alternatives, modifications and equivalents, are intended by the inventors to be encompassed by the claims.

Citations listed in the present application are incorporated herein by reference.

REFERENCES

The entire content of all patents, patent applications and publications referred to throughout the application are incorporated herein by reference.

Angal, S. et al., A Single Amino Acid Substitution Abolishes the Heterogeneity of Chimeric Mouse/human IgG4 Antibody, Mol Immunol 30, 105-108, 1993

Cardillo et al., Clinical Cancer Research, Humanized Anti-Trop-2 IgG-SN-38 Conjugate for Effective Treatment of Diverse Epithelial Cancers: Preclinical Studies in Human Cancer Xenograft Models and Monkeys, May 2011 17:10

Chen X et al., Fusion Protein Linkers: Properties, Design and Functionality, Adv Drug Deliv Rev. 2013; 65(10): 1357-1369.

De Vlieger et al., Single-domain Antibodies and their Formatting to Combat Viral Infections, Antibodies 8(1), 1-22, 2019

Deyev, S et al., Multivalency: the hallmark of antibodies used for optimization of tumor targeting by design, BioEssays, 30:904-918, 2008.

Godar M et al. Therapeutic Bispecific Antibody Formats: a Patent Applications Review (1994-2017) Expert Opinion on Therapeutic patents, 2018; 28(3):251-276

Goldenberg et al., The emergence of trophoblast cell-surface antigen 2 (TROP-2) as a novel cancer target, Oncotarget, 2018; 9:28989-29006

Goldenberg et al., Trop-2 is a novel target for solid cancer therapy with Sacituzumab govitecan (IMMU-132), antibody-drug conjugate (ADC), Oncotarget, 2015, 6:22496-22512

Ha, J -H et al. Immunoglobulin Fc Heterodimer Platform Technology: From Design to Applications in Therapeutic Antibodies and Proteins, Front Immunol, 2016; 7:394.

Hamers-Casterman C, et al., Naturally-occurring Antibodies Devoid of Light-chains. Nature 1993, 363:446-448.

Ikeda, M. et al., Pr1E11, a novel anti-TROP2 antibody isolated by adenovirus-based antibody screening, recognizes a unique epitope, Biochemical and Biophysical Research Communications, 458 (2015) 877-882.

Kovalenko O V et al. Atypical Antigen Recognition Mode of a Shark Immunoglobulin New Antigen Receptor (IgNAR) Variable Domain Characterized by Humanization and Structural Analysis, J Biol Chem. 2013, 288:17408-17419

Muyldermans, S and Smider, 2016. Distinct Antibody Species: Structural Differences Creating Therapeutic Opportunities. Current Opinion in Immunology 2016, 40:7-13

Muyldermans, S et al., 1994. Sequence and Structure of VH Domain From Naturally Occurring Camel Heavy Chain Immunoglobulins Lacking Light Chains. Protein Eng. 7: 1129-1135.

Perrone et al., Frontiers in Oncology, Preclinical Activity of Sacituzumab Govitecan, an Antibody-Drug Conjugate Targeting Trophoblast Cell-Surface Antigen 2 (Trop-2) Linked to the Active Metabolite of Irinotecan (SN-38), in Ovarian Cancer, Feb. 12 2020

Saunders K. O., Conceptual Approach to Modulating Antibody Effector Functions and Circuation Half-Life, Front. Immunol. 10:1296, 2019.

Stepan L. P., et al., Expression of Trop2 cell surface glycoprotein in normal amd tumor tissues: Potential implications as a cancer therapeutic target, Journal of Histochemistry and Cytochemistry, 2011; 59:701-710

Tatusova, T. A, et al. (1999), BLAST 2 Sequences, a New Tool for Comparing Protein and Nucleotide Sequences, FEMS Microbiol Lett. 174:247-250)

Truong, A. et al., AR47A6.4.2, a naked monoclonal antibody targeting Trop-2, exhibits anti-tumor efficacy in multiple human cancer models as a monotherapeutic agent and demonstrates efficacy in combination therapy, Experimental and Molecular Therapeutics, AACR Annual Meeting, volume 68 (9), Abstract 3990, 2008.

Vincke C. et al. General Strategy to Humanize a Camelid Single-Domain Antibody and Identification of a Universal Humanized Nanobody Scaffold, J.Biol Chem. 2009, 284 (5):3273-3284

Vu, K. B., et al., 1997. Comparison of Llama VH Sequences from Conventional and Heavy Chain Antibodies. Mol. Immunol. 34: 1121-1131.

Sequence Tables

TABLE 15 anti-TROP2 sequences
(KD001-KD005 and exemplary CDR sequences are provided)

| Anti-TROP2 | CDR1 | CDR2 | CDR3 |
|---|---|---|---|
| KD008 and KD001 Kabat CDRs | GSDMS (SEQ ID NO: 1) | YITSGGTTYYPDSVKG (SEQ ID NO: 2) | ARLTDSHYVEDA (SEQ ID NO: 3) |
| KD008 and KD001 IMGT CDRs | GFTFSGSD (SEQ ID NO: 52) | ITSGGTT (SEQ ID NO: 53) | AKARLTDSHYVEDA (SEQ ID NO: 54) |

TABLE 15-continued anti-TROP2 sequences
(KD001-KD005 and exemplary CDR sequences are provided)

| Anti-TROP2 | CDR1 | CDR2 | CDR3 |
|---|---|---|---|
| KD008 (VHH) (KD001 variable region) (SEQ ID NO: 22) | QVQLQESGGGMVHPGGSLRLSCAASGFTFSGSDMSWVRQAPGKGPEWVSYITSGGTTYYPDSVKGRFTISRDNAKNTLYLQMNSLTPDDTALYRCAKARLTDSHYVEDAWGQGTQVTVSS | | |
| KD001 heavy chain (SEQ ID NO: 29) | QVQLQESGGGMVHPGGSLRLSCAASGFTFSGSDMSWVRQAPGKGPEWVSYITSGGTTYYPDSVKGRFTISRDNAKNTLYLQMNSLTPDDTALYRCAKARLTDSHYVEDAWGQGTQVTVSSEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | | |
| KD009 and KD002 Kabat CDRs | SADMS (SEQ ID NO: 4) | YINADGSKTYYPDS VKG (SEQ ID NO: 5) | AKLTDTHYVEDY (SEQ ID NO: 6) |
| KD009 and KD002 IMGT CDRs | GFPFSSADMS (SEQ ID NO: 46) or GFPFSSAD (SEQ ID NO: 55) | INADGSKT (SEQ ID NO: 47) | ARAKLTDTHYVEDY (SEQ ID NO: 48) |
| KD009 (VHH) (KD002 variable region) (SEQ ID NO: 23) | QVQLQESGGGMVQVGGSLRLSCAASGFPFSSADMSWVRQAPGKGPEWVSYINADGSKTYYPDSVKGRFTISRDNAKNTLYLLMNNLKPEDTALYRCARAKLTDTHYVEDYWGQGTQVTVSS | | |
| KD002 heavy chain (SEQ ID NO: 30) | QVQLQESGGGMVQVGGSLRLSCAASGFPFSSADMSWVRQAPGKGPEWVSYINADGSKTYYPDSVKGRFTISRDNAKNTLYLLMNNLKPEDTALYRCARAKLTDTHYVEDYWGQGTQVTVSSEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | | |
| KD010 and KD003 Kabat CDRs | NYDMS (SEQ ID NO: 7) | YINAGGSNTDYPDS AKLTDTHYVEDY VKG (SEQ ID NO: 8) | (SEQ ID NO: 9) |
| KD010 and KD003 IMGT CDRs | GFTFSNYD (SEQ ID NO: 56) | INAGGSNT (SEQ ID NO: 57) | ARAKLTDTHYVEDY (SEQ ID NO: 58) |
| KD010 (VHH) (KD003 variable region) (SEQ ID NO: 24) | QVQLQESGGGMVQPGGSLRLSCAASGFTFSNYDMSWVRQAPGKGPEWVSYINAGGSNTDYPDSVKGRFTISRDNAKNMLYLLMNNLKPEDTALYRCARAKLTDTHYVEDYWGQGTQVTVSS | | |
| KD003 heavy chain (SEQ ID NO: 31) | QVQLQESGGGMVQPGGSLRLSCAASGFTFSNYDMSWVRQAPGKGPEWVSYINAGGSNTDYPDSVKGRFTISRDNAKNMLYLLMNNLKPEDTALYRCARAKLTDTHYVEDYWGQGTQVTVSSEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | | |
| KD011 and KD004 Kabat CDRs | GSDMS (SEQ ID NO: 10) | YITGSGTTYYPDSV KG (SEQ ID NO: 11) | ARLTDSHYVEDA (SEQ ID NO: 12) |
| KD011 and KD004 IMGT CDRs | GFTFSGSD (SEQ ID NO: 59) | ITGSGTT (SEQ ID NO: 60) | AKARLTDSHYVEDA (SEQ ID NO: 61) |

TABLE 15-continued anti-TROP2 sequences
(KD001-KD005 and exemplary CDR sequences are provided)

| Anti-TROP2 | CDR1 | CDR2 | CDR3 |
|---|---|---|---|
| KD011 (VHH) (KD004 variable region) (SEQ ID NO: 25) | QVQLQESGGGLVQPGRSLRLSCAASGFTFSGSDMSWVRQAPGKG PEWVSYITGSGTTYYPDSVKGRFTTSRDNAKNMLYLQMNSLKPD DTALYRCAKARLTDSHYVEDAWGQGTQVTVSS | | |
| KD004 heavy chain (SEQ ID NO: 32) | QVQLQESGGGLVQPGRSLRLSCAASGFTFSGSDMSWVRQAPGKG PEWVSYITGSGTTYYPDSVKGRFTTSRDNAKNMLYLQMNSLKPD DTALYRCAKARLTDSHYVEDAWGQGTQVTVSSEPKSCDKTHTCP PCPAPELLGGPSVFLFPPKPKDTLMISRTPEVTCVVVDVSHEDP EVKFNWYVDGVEVHNAKTKPREEQYNSTYRVVSVLTVLHQDWLN GKEYKCKVSNKALPAPIEKTISKAKGQPREPQVYTLPPSREEMT KNQVSLTCLVKGFYPSDIAVEWESNGQPENNYKTTPPVLDSDGS FFLYSKLTVDKSRWQQGNVFSCSVMHEALHNHYTQKSLSLSPGK | | |
| KD012 and KD005 Kabat CDRs | GSDMS (SEQ ID NO: 13) | YITSGGTTYYPDSV KG (SEQ ID NO: 14) | SRLTDSHYVEDA (SEQ ID NO: 15) |
| KD012 and KD005 IMGT CDRs | GFTFSGSDMS (SEQ ID NO: 49) or GFTFSGSD (SEQ ID NO: 62) | ITSGGTT (SEQ ID NO: 50) | AKSRLTDSHYVED A (SEQ ID NO: 51) |
| KD012 (VHH) (KD005 variable region) (SEQ ID NO: 26) | QVQLQESGGGLVEAGGSLRLSCAASGFTFSGSDMSWVRQAPGKG PEWVSYITSGGTTYYPDSVKGRFTISRDNAKNTLYLQMNSLKPD DTALYRCAKSRLTDSHYVEDAWGQGTQVTVSS | | |
| KD005 heavy chain (SEQ ID NO: 33) | QVQLQESGGGLVEAGGSLRLSCAASGFTFSGSDMSWVRQAPGKG PEWVSYITSGGTTYYPDSVKGRFTISRDNAKNTLYLQMNSLKPD DTALYRCAKSRLTDSHYVEDAWGQGTQVTVSSEPKSCDKTHTCP PCPAPELLGGPSVFLFPPKPKDTLMISRTPEVTCVVVDVSHEDP EVKFNWYVDGVEVHNAKTKPREEQYNSTYRVVSVLTVLHQDWLN GKEYKCKVSNKALPAPIEKTISKAKGQPREPQVYTLPPSREEMT KNQVSLTCLVKGFYPSDIAVEWESNGQPENNYKTTPPVLDSDGS FFLYSKLTVDKSRWQQGNVFSCSVMHEALHNHYTQKSLSLSPGK | | |
| KD015 heavy chain (SEQ ID NO: 44) IgG4 version of KD002 | QVQLQESGGGMVQVGGSLRLSCAASGFPFSSADMSWVRQAPGKG PEWVSYINADGSKTYYPDSVKGRFTISRDNAKNTLYLLMNNLKP EDTALYRCARAKLTDTHYVEDYWGQGTQVTVSSESKYGPPCPPC PAPEAAGGPSVFLFPPKPKDTLMISRTPEVTCVVVDVSQEDPEV QFNWYVDGVEVHNAKTKPREEQFNSTYRVVSVLTVLHQDWLNGK EYKCKVSNKGLPSSIEKTISKAKGQPREPQVYTLPPSQEEMTKN QVSLTCLVKGFYPSDIAVEWESNGQPENNYKTTPPVLDSDGSFF LYSRLTVDKSRWQEGNVFSCSVMHEALHNHYTQKSLSLSLGK | | |
| KD016 heavy chain (SEQ ID NO: 45) IgG4 version of KD004 | QVQLQESGGGLVQPGRSLRLSCAASGFTFSGSDMSWVRQAPGKG PEWVSYITGSGTTYYPDSVKGRFTTSRDNAKNMLYLQMNSLKPD DTALYRCAKARLTDSHYVEDAWGQGTQVTVSSESKYGPPCPPCP APEAAGGPSVFLFPPKPKDTLMISRTPEVTCVVVDVSQEDPEVQ FNWYVDGVEVHNAKTKPREEQFNSTYRVVSVLTVLHQDWLNGKE YKCKVSNKGLPSSIEKTISKAKGQPREPQVYTLPPSQEEMTKNQ VSLTCLVKGFYPSDIAVEWESNGQPENNYKTTPPVLDSDGSFFL YSRLTVDKSRWQEGNVFSCSVMHEALHNHYTQKSLSLSLGK | | |
| KD017 heavy chain (SEQ ID NO: 155) | QVQLQESGGGMVQVGGSLRLSCAASGFPFSSADMSWVRQAPGKG PEWVSYINADGSKTYYPDSVKGRFTISRDNAKNTLYLLMNNLKP EDTALYRCARAKLTDTHYVEDYWGQGTQVTVSSESKYGPPCPPC PAPEAAGGPSVFLFPPKPKDTLMISRTPEVTCVVVDVSQEDPEV QFNWYVDGVEVHNAKTKPREEQFNSTYRVVSVLTVLHQDWLNGK EYKCKVSNKGLPSSIEKTISKAKGQPREPQVYTLPPSQEEMTKN QVSLTCLVKGFYPSDIAVEWESNGQPENNYKTTPPVLDSDGSFF LYSRLTVDKSRWQEGNVFSCSVMHEALHNHYTQKSLSLSLGK | | |
| KD018 heavy chain (SEQ ID NO: 156) | QVQLQESGGGLVQPGRSLRLSCAASGFTFSGSDMSWVRQAPGKG PEWVSYITGSGTTYYPDSVKGRFTTSRDNAKNMLYLQMNSLKPD DTALYRCAKARLTDSHYVEDAWGQGTQVTVSSESKYGPPCPPCP APEAAGGPSVFLFPPKPKDTLMISRTPEVTCVVVDVSQEDPEVQ FNWYVDGVEVHNAKTKPREEQFNSTYRVVSVLTVLHQDWLNGKE YKCKVSNKGLPSSIEKTISKAKGQPREPQVYTLPPSQEEMTKNQ VSLTCLVKGFYPSDIAVEWESNGQPENNYKTTPPVLDSDGSFFL YSRLTVDKSRWQEGNVFSCSVMHEALHNHYTQKSLSLSLGK | | |

TABLE 15-continued anti-TROP2 sequences
(KD001-KD005 and exemplary CDR sequences are provided)

| Anti-TROP2 | CDR1 | CDR2 | CDR3 |
|---|---|---|---|
| KD019 heavy chain (SEQ ID NO: 162) | QVQLQESGGGLVEAGGSLRLSCAASGFTFSGSDMSWVRQAPGKG PEWVSYITSGGTTYYPDSVKGRFTISRDNAKNTLYLQMNSLKPD DTALYRCAKSRLTDSHYVEDAWGQGTQVTVSSESKYGPPCPPCP APEAAGGPSVFLFPPKPKDTLMISRTPEVTCVVVDVSQEDPEVQ FNWYVDGVEVHNAKTKPREEQFNSTYRVVSVLTVLHQDWLNGKE YKCKVSNKGLPSSIEKTISKAKGQPREPQVYTLPPSQEEMTKNQ VSLTCLVKGFYPSDIAVEWESNGQPENNYKTTPPVLDSDGSFFL YSRLTVDKSRWQEGNVFSCSVMHEALHNHYTQKSLSLSLGK | | |

TABLE 16 anti-TROP2 sequences
(KD006, KD007: Exemplary CDR sequences are provided)

| | CDR1 | CDR2 | CDR3 |
|---|---|---|---|
| KD013 and KD006 Kabat CDRs | TKAMG (SEQ ID NO: 16) | AISESGSTYYADSV KD (SEQ ID NO: 17) | KWYSGSFDDTRSY DY (SEQ ID NO: 18) |
| KD013 and KD006 IMGT CDRs | VRTFSTKA (SEQ ID NO: 63) | ISESGST (SEQ ID NO: 64) | GVKWYSGSFDDTR SYDY (SEQ ID NO: 65) |
| KD013 (VHH) (KD006 variable region) (SEQ ID NO: 27) | QVQLQESGGGLVQAGNSLRLSCVASVRTFSTKAMGWFRQAPGKE REFTAAISESGSTYYADSVKDRFTISRDNVKNTVYLQMNSLKPE DTAVYYCGVKWYSGSFDDTRSYDYWGQGTQVTVSS | | |
| KD006 heavy chain (SEQ ID NO: 34) | QVQLQESGGGLVQAGNSLRLSCVASVRTFSTKAMGWFRQAPGKE REFTAAISESGSTYYADSVKDRFTISRDNVKNTVYLQMNSLKPE DTAVYYCGVKWYSGSFDDTRSYDYWGQGTQVTVSSEPKSCDKTH TCPPCPAPELLGGPSVFLFPPKPKDTLMISRTPEVTCVVVDVSH EDPEVKFNWYVDGVEVHNAKTKPREEQYNSTYRVVSVLTVLHQD WLNGKEYKCKVSNKALPAPIEKTISKAKGQPREPQVYTLPPSRE EMTKNQVSLTCLVKGFYPSDIAVEWESNGQPENNYKTTPPVLDS DGSFFLYSKLTVDKSRWQQGNVFSCSVMHEALHNHYTQKSLSLS PGK | | |
| KD014 and KD007 Kabat CDRs | FYAMA (SEQ ID NO: 19) | TITAYGNTNYADSV KG (SEQ ID NO: 20) | NLPSASHNY (SEQ ID NO: 21) |
| KD014 and KD007 IMGT CDRs | GFAFSFYA (SEQ ID NO: 66) | ITAYGNT (SEQ ID NO: 67) | NANLPSASHNY (SEQ ID NO: 68) |
| KD014 (VHH) (KD007 variable region) (SEQ ID NO: 28) | QVQLQESGGGLVQPGGSLRLSCAASGFAFSFYAMAWYRQAPGKQ RDMVATITAYGNTNYADSVKGRFTTSRDNAKNTVYLQMNSLKPE DTAVYVCNANLPSASHNYWGQGTQVTVSS | | |
| KD007 heavy chain (SEQ ID NO: 35) | QVQLQESGGGLVQPGGSLRLSCAASGFAFSFYAMAWYRQAPGKQ RDMVATITAYGNTNYADSVKGRFTTSRDNAKNTVYLQMNSLKPE DTAVYVCNANLPSASHNYWGQGTQVTVSSEPKSCDKTHTCPPCP APELLGGPSVFLFPPKPKDTLMISRTPEVTCVVVDVSHEDPEVK FNWYVDGVEVHNAKTKPREEQYNSTYRVVSVLTVLHQDWLNGKE YKCKVSNKALPAPIEKTISKAKGQPREPQVYTLPPSREEMTKNQ VSLTCLVKGFYPSDIAVEWESNGQPENNYKTTPPVLDSDGSFFL YSKLTVDKSRWQQGNVFSCSVMHEALHNHYTQKSLSLSPGK | | |

TABLE 17 anti-CD47 sequences

| | CDR1 | CDR2 | CDR3 |
|---|---|---|---|
| KD070 Kabat CDRs | VNDIR (SEQ ID NO: 156) | RITGGGRTDYADSV KG (SEQ ID NO: 157) | WGRGY (SEQ ID NO: 158) |

TABLE 17-continued anti-CD47 sequences

| | | | |
|---|---|---|---|
| KD070 IMGT CDRs | RFDFSVND (SEQ ID NO: 159) | ITGGGRT (SEQ ID NO: 160) | WGRGY (SEQ ID NO: 161) |

KD070 (VHH) Variable region (SEQ ID NO: 155)

QVQLQESGGGLVQPGGSLRLSCAASRFDFSVNDIRWYRQAPGNE
RELVARITGGGRTDYADSVKGRFTISRDNAKNTVYLQMNNLKPE
DTAVYYCWGRGYWGQGTQVTVSS

TABLE 18

KD002 and variants amino acid sequence

| Code No. | SEQUENCE<br>IMGT CDRs: bold and underlined<br>FR2: twice underlined |
|---|---|
| KD002 heavy chain (SEQ ID NO: 30) | QVQLQESGGGMVQVGGSLRLSCAASGFPFSSADMSWVRQAPGKG PEWVSYINADGSKTYYPDSVKGRFTISRDNAKNTLYLLMNNLKP EDTALYRCARAKLTDTHYVEDYWGQGTQVTVSSEPKSCDKTHTC PPCPAPELLGGPSVFLFPPKPKDTLMISRTPEVTCVVVDVSHED PEVKFNWYVDGVEVHNAKTKPREEQYNSTYRVVSVLTVLHQDWL NGKEYKCKVSNKALPAPIEKTISKAKGQPREPQVYTLPPSREEM TKNQVSLTCLVKGFYPSDIAVEWESNGQPENNYKTTPPVLDSDG SFFLYSKLTVDKSRWQQGNVFSCSVMHEALHNHYTQKSLSLSPG K |
| KD020 variable region (SEQ ID NO: 71) | EVQLVESGGGLVQPGGSLRLSCAASGFPFSSADMHWVRQAPGKG LVWVSRINADGSKTSYADTVKGRFTISRDNAKNTLYLQMNSLRA EDTAVYYCARAKLTDTHYVEDYWGQGTLVTVSS |
| KD021 variable region (SEQ ID NO: 72) | EVQLVESGGGLVQPGGSLRLSCAASGFPFSSADMSWVRQAPGKG LEWVSYINADGSKTSYADTVKGRFTISRDNAKNTLYLQMNSLRA EDTAVYYCARAKLTDTHYVEDYWGQGTLVTVSS |
| KD022 variable region (SEQ ID NO: 73) | EVQLVESGGGLVQPGGSLRLSCAASGFPFSSADMSWVRQAPGKG PEWVSYINADGSKTYYADTVKGRFTISRDNAKNTLYLQMNSLRA EDTAVYYCARAKLTDTHYVEDYWGQGTQVTVSS |
| KD023 variable region (SEQ ID NO: 74) | QVQLVESGGGLVQPGGSLRLSCAASGFPFSSADMSWVRQAPGKG PEWVSYINADGSKTYYPDTVKGRFTISRDNAKNTLYLQMNSLRA EDTAVYYCARAKLTDTHYVEDYWGQGTQVTVSS |
| KD024 variable region (SEQ ID NO: 75) | QVQLVESGGGLVQPGGSLRLSCAASGFPFSSADMSWVRQAPGKG PEWVSYINADGSKTYYPDTVKGRFTISRDNAKNTLYLQMNSLRA EDTAVYRCARAKLTDTHYVEDYWGQGTQVTVSS |
| KD025 variable region (SEQ ID NO: 76) | QVQLVESGGGLVQVGGSLRLSCAASGFPFSSADMSWVRQAPGKG PEWVSYINADGSKTYYPDTVKGRFTISRDNAKNTLYLQMNSLKP EDTAVYRCARAKLTDTHYVEDYWGQGTQVTVSS |
| KD026 variable region (SEQ ID NO: 77) | QVQLQESGGGMVQVGGSLRLSCAASGFPFSSADMSWVRQAPGKG PEWVSYINADGSKTYYPDTVKGRFTISRDNAKNTLYLQMNSLKP EDTAVYRCARAKLTDTHYVEDYWGQGTQVTVSS |
| KD027 variable region (SEQ ID NO: 78) | QVQLQESGGGMVQVGGSLRLSCAASGFPFSSADMSWVRQAPGKG PEWVSYINADGSKTYYPDSVKGRFTISRDNAKNTLYLQMNSLKP EDTAVYRCARAKLTDTHYVEDYWGQGTQVTVSS |
| KD028 variable region (SEQ ID NO: 79) | EVQLLESGGGLVQPGGSLRLSCAASGFPFSSADMSWVRQAPGKG LEWVSVINADGSKTYYADTVKGRFTISRDNSKNTLYLQMNSLRA EDTAVYYCARAKLTDTHYVEDYWGQGTMVTVSS |
| KD029 variable region (SEQ ID NO: 80) | QVQLQESGGGLVQPGGSLRLSCAASGFPFSSADMSWVRQAPGKG PEWVSYINADGSKTYYPDTVKGRFTISRDNSKNTLYLQMNNLRA EDTALYRCARAKLTDTHYVEDYWGQGTMVTVSS |
| KD030 variable region (SEQ ID NO: 81) | QVQLQESGGGLVQPGGSLRLSCAASGFPFSSADMSWVRQAPGKG LEWVSYINADGSKTYYADTVKGRFTISRDNSKNTLYLQMNSLRA EDTAVYRCARAKLTDTHYVEDYWGQGTMVTVSS |
| KD031 variable region (SEQ ID NO: 82) | EVQLQESGGGLVQPGGSLRLSCAASGFPFSSADMSWVRQAPGKG LEWVSYINADGSKTYYADTVKGRFTISRDNSKNTLYLQMNSLRA EDTAVYRCARAKLTDTHYVEDYWGQGTMVTVSS |

TABLE 18-continued

KD002 and variants amino acid sequence

| Code No. | SEQUENCE<br>IMGT CDRs: bold and underlined<br>FR2: twice underlined |
|---|---|
| KD032 variable region (SEQ ID NO: 83) | QVQLLESGGGLVQPGGSLRLSCAASGFPFSSAD<u><u>MSWVRQAPGKG LEWVSY</u></u>INADGSKTYYADTVKGRFTISRDNSKNTLYLQMNSLRA EDTAVYRCARAKLTDTHYVEDYWGQGTMVTVSS |
| KD033 variable region (SEQ ID NO: 84) | QVQLQESGGGLVQPGGSLRLSCAASGFPFSSAD<u><u>MSWVRQAPGKG LEWVSY</u></u>INADGSKTYYADTVKGRFTISRDNSKNTLYLQMNSLRA EDTAVYRCARAKLTDTHYVEDYWGQGTMVTVSS |
| KD034 variable region (SEQ ID NO: 85) | QVQLQESGGGLVQPGGSLRLSCAASGFPFSSAD<u><u>MSWVRQAPGKG LEWVSY</u></u>INADGSKTYYADTVKGRFTISRDNSKNTLYLQMNSLRA EDTAVYYCARAKLTDTHYVEDYWGQGTMVTVSS |
| KD035 variable region (SEQ ID NO: 86) | QVQLQESGGGLVQPGGSLRLSCAASGFPFSSAD<u><u>MSWVRQAPGKG PEWVSY</u></u>INADGSKTYYADTVKGRFTISRDNSKNTLYLQMNSLRA EDTAVYRCARAKLTDTHYVEDYWGQGTMVTVSS |
| KD036 variable region (SEQ ID NO: 87) | QVQLQESGGGLVQPGGSLRLSCAASGFPFSSAD<u><u>MSWVRQAPGKG LEWVSY</u></u>INADGSKTYYPDTVKGRFTISRDNSKNTLYLQMNSLRA EDTAVYRCARAKLTDTHYVEDYWGQGTMVTVSS |
| KD037 variable region (SEQ ID NO: 88) | QVQLQESGGGLVQPGGSLRLSCAASGFPFSSAD<u><u>MSWVRQAPGKG LEWVSY</u></u>INADGSKTYYADTVKGRFTISRDNSKNTLYLQMNNLRA EDTAVYRCARAKLTDTHYVEDYWGQGTMVTVSS |
| KD038 variable region (SEQ ID NO: 89) | QVQLQESGGGLVQPGGSLRLSCAASGFPFSSAD<u><u>MSWVRQAPGKG LEWVSY</u></u>INADGSKTYYADTVKGRFTISRDNSKNTLYLQMNSLRA EDTALYRCARAKLTDTHYVEDYWGQGTMVTVSS |
| KD039 variable region (SEQ ID NO: 90) | QVQLQESGGGMVQPGGSLRLSCAASGFPFSSAD<u><u>MSWVRQAPGKG LEWVSY</u></u>INADGSKTYYADTVKGRFTISRDNSKNTLYLQMNSLRA EDTAVYRCARAKLTDTHYVEDYWGQGTQVTVSS |
| KD040 variable region (SEQ ID NO: 91) | QVQLQESGGGLVQPGGSLRLSCAASGFPFSSAD<u><u>MSWVRQAPGKQ REWVSY</u></u>INADGSKTYYADTVKGRFTISRDNSKNTLYLQMNSLRA EDTAVYRCARAKLTDTHYVEDYWGQGTMVTVSS |
| KD041 variable region (SEQ ID NO: 92) | QVQLQESGGGLVQPGGSLRLSCAASGFPFSSAD<u><u>MSWVRQAPGKG LEWVSY</u></u>INAEGSKTYYADTVKGRFTISRDNSKNTLYLQMNSLRA EDTAVYRCARAKLTDTHYVEDYWGQGTMVTVSS |
| KD042 variable region (SEQ ID NO: 93) | QVQLQESGGGLVQPGGSLRLSCAASGFPFSSAD<u><u>MSWVRQAPGKG LEWVSY</u></u>INANGSKTYYADTVKGRFTISRDNSKNTLYLQMNSLRA EDTAVYRCARAKLTDTHYVEDYWGQGTMVTVSS |

TABLE 19

KD005 and variants amino acid sequence

| Code | SEQUENCE<br>IMGT CDRs: bold and underlined<br>FR2: twice underlined |
|---|---|
| KD005 heavy chain (SEQ ID NO: 33) | QVQLQESGGGLVEAGGSLRLSCAASGFTFSGSD<u><u>MSWVRQAPGKG PEWVSY</u></u>ITSGGTTYYPDSVKGRFTISRDNAKNTLYLQMNSLKPD DTALYRCAKSRLTDSHYVEDAWGQGTQVTVSSEPKSCDKTHTCP PCPAPELLGGPSVFLFPPKPKDTLMISRTPEVTCVVVDVSHEDP EVKFNWYVDGVEVHNAKTKPREEQYNSTYRVVSVLTVLHQDWLN GKEYKCKVSNKALPAPIEKTISKAKGQPREPQVYTLPPSREEMT KNQVSLTCLVKGFYPSDIAVEWESNGQPENNYKTTPPVLDSDGS FFLYSKLTVDKSRWQQGNVFSCSVMHEALHNHYTQKSLSLSPGK |
| KD043 variable region (SEQ ID NO: 94) | EVQLLESGGGLVQPGGSLRLSCAASGFTFSGSD<u><u>MSWVRQAPGKG LEWVSA</u></u>ITSGGTTYYADTVKGRFTISRDNSKNTLYLQMNSLRAE DTAVYYCAKSRLTDSHYVEDAWGQGTLVTVSS |
| KD044 variable region (SEQ ID NO: 95) | EVQLLESGGGLVQPGGSLRLSCAASGFTFSGSD<u><u>MSWVRQAPGKG LEWVSY</u></u>ITSGGTTYYADTVKGRFTISRDNSKNTLYLQMNSLRAE DTAVYYCAKSRLTDSHYVEDAWGQGTLVTVSS |

TABLE 19-continued

KD005 and variants amino acid sequence

| Code | SEQUENCE<br>IMGT CDRs: bold and underlined<br>FR2: twice underlined |
|---|---|
| KD045 variable region (SEQ ID NO: 96) | EVQLLESGGGLVQPGGSLRLSCAASGFTFSGSD<u><u>MSWVRQAPGKG LEWVSY</u></u>ITSGGTTYYADTVKGRFTISRDNSKNTLYLQMNSLRAE DTAVYRCAKSRLTDSHYVEDAWGQGTLVTVSS |
| KD046 variable region (SEQ ID NO: 97) | QVQLLESGGGLVQPGGSLRLSCAASGFTFSGSD<u><u>MSWVRQAPGKG PEWVSY</u></u>ITSGGTTYYADTVKGRFTISRDNSKNTLYLQMNSLRAE DTAVYYCAKSRLTDSHYVEDAWGQGTLVTVSS |
| KD047 variable region (SEQ ID NO: 98) | QVQLLESGGGLVQPGGSLRLSCAASGFTFSGSD<u><u>MSWVRQAPGKG PEWVSY</u></u>ITSGGTTYYADTVKGRFTISRDNSKNTLYLQMNSLRAE DTAVYRCAKSRLTDSHYVEDAWGQGTLVTVSS |
| KD048 variable region (SEQ ID NO: 99) | QVQLQESGGGLVQPGGSLRLSCAASGFTFSGSD<u><u>MSWVRQAPGKG PEWVSY</u></u>ITSGGTTYYPDTVKGRFTISRDNSKNTLYLQMNSLRAE DTAVYYCAKSRLTDSHYVEDAWGQGTQVTVSS |
| KD049 variable region (SEQ ID NO: 100) | QVQLQESGGGLVQPGGSLRLSCAASGFTFSGSD<u><u>MSWVRQAPGKG PEWVSY</u></u>ITSGGTTYYPDTVKGRFTISRDNSKNTLYLQMNSLRAE DTAVYRCAKSRLTDSHYVEDAWGQGTQVTVSS |
| KD050 variable region (SEQ ID NO: 101) | QVQLQESGGGLVQPGGSLRLSCAASGFTFSGSD<u><u>MSWVRQAPGKG PEWVSY</u></u>ITSGGTTYYPDTVKGRFTISRDNSKNTLYLQMNSLKPD DTAVYRCAKSRLTDSHYVEDAWGQGTQVTVSS |
| KD051 variable region (SEQ ID NO: 102) | QVQLQESGGGLVQPGGSLRLSCAASGFTFSGSD<u><u>MSWVRQAPGKG PEWVSY</u></u>ITSGGTTYYPDTVKGRFTISRDNAKNTLYLQMNSLKPD DTALYRCAKSRLTDSHYVEDAWGQGTQVTVSS |
| KD052 variable region (SEQ ID NO: 103) | EVQLVESGGGLIQPGGSLRLSCAASGFTFSGSD<u><u>MSWVRQAPGKG LEWVSV</u></u>ITSGGTTYYADTVKGRFTISRDNSKNTLYLQMNSLRAE DTAVYYCAKSRLTDSHYVEDAWGQGTLVTVSS |
| KD053 variable region (SEQ ID NO: 104) | QVQLQESGGGLIQPGGSLRLSCAASGFTFSGSD<u><u>MSWVRQAPGKG PEWVSY</u></u>ITSGGTTYYPDTVKGRFTISRDNSKNTLYLQMNSLRAD DTALYRCAKSRLTDSHYVEDAWGQGTLVTVSS |
| KD054 variable region (SEQ ID NO: 105) | QVQLQESGGGLIQPGGSLRLSCAASGFTFSGSD<u><u>MSWVRQAPGKG LEWVSY</u></u>ITSGGTTYYADTVKGRFTISRDNSKNTLYLQMNSLRAE DTAVYRCAKSRLTDSHYVEDAWGQGTLVTVSS |
| KD055 variable region (SEQ ID NO: 106) | EVQLQESGGGLIQPGGSLRLSCAASGFTFSGSD<u><u>MSWVRQAPGKG LEWVSY</u></u>ITSGGTTYYADTVKGRFTISRDNSKNTLYLQMNSLRAE DTAVYRCAKSRLTDSHYVEDAWGQGTLVTVSS |
| KD056 variable region (SEQ ID NO: 107) | QVQLVESGGGLIQPGGSLRLSCAASGFTFSGSD<u><u>MSWVRQAPGKG LEWVSY</u></u>ITSGGTTYYADTVKGRFTISRDNSKNTLYLQMNSLRAE DTAVYRCAKSRLTDSHYVEDAWGQGTLVTVSS |
| KD057 variable region (SEQ ID NO: 108) | QVQLQESGGGLIQPGGSLRLSCAASGFTFSGSD<u><u>MSWVRQAPGKG LEWVSV</u></u>ITSGGTTYYADTVKGRFTISRDNSKNTLYLQMNSLRAE DTAVYRCAKSRLTDSHYVEDAWGQGTLVTVSS |
| KD058 variable region (SEQ ID NO: 109) | QVQLQESGGGLIQPGGSLRLSCAASGFTFSGSD<u><u>MSWVRQAPGKG LEWVSY</u></u>ITSGGTTYYADTVKGRFTISRDNSKNTLYLQMNSLRAE DTAVYYCAKSRLTDSHYVEDAWGQGTLVTVSS |
| KD059 variable region (SEQ ID NO: 110) | QVQLQESGGGLIQPGGSLRLSCAASGFTFSGSD<u><u>MSWVRQAPGKG PEWVSY</u></u>ITSGGTTYYADTVKGRFTISRDNSKNTLYLQMNSLRAE DTAVYRCAKSRLTDSHYVEDAWGQGTLVTVSS |
| KD060 variable region (SEQ ID NO: 111) | QVQLQESGGGLIQPGGSLRLSCAASGFTFSGSD<u><u>MSWVRQAPGKG LEWVSY</u></u>ITSGGTTYYPDTVKGRFTISRDNSKNTLYLQMNSLRAE DTAVYRCAKSRLTDSHYVEDAWGQGTLVTVSS |
| KD061 variable region (SEQ ID NO: 112) | QVQLQESGGGLIQPGGSLRLSCAASGFTFSGSD<u><u>MSWVRQAPGKG LEWVSY</u></u>ITSGGTTYYADTVKGRFTISRDNSKNTLYLQMNSLRAD DTAVYRCAKSRLTDSHYVEDAWGQGTLVTVSS |
| KD062 variable region (SEQ ID NO: 113) | QVQLQESGGGLIQPGGSLRLSCAASGFTFSGSD<u><u>MSWVRQAPGKG LEWVSY</u></u>ITSGGTTYYADTVKGRFTISRDNSKNTLYLQMNSLRAE DTALYRCAKSRLTDSHYVEDAWGQGTLVTVSS |

TABLE 19-continued

KD005 and variants amino acid sequence

| Code | SEQUENCE<br>IMGT CDRs: bold and underlined<br>FR2: twice underlined |
|---|---|
| KD063 variable region (SEQ ID NO: 114) | QVQLQESGGGLIEPGGSLRLSCAASGFTFSGSDMSWVRQAPGKG<br>LEWVSYITSGGTTYYADTVKGRFTISRDNSKNTLYLQMNSLRAE<br>DTAVYRCAKSRLTDSHYVEDAWGQGTQVTVSS |
| KD064 variable region (SEQ ID NO: 115) | QVQLQESGGGLIQPGGSLRLSCAASGFTFSGSDMSWYRQAPGKG<br>REWVSYITSGGTTYYADTVKGRFTISRDNSKNTLYLQMNSLRAE<br>DTAVYRCAKSRLTDSHYVEDAWGQGTLVTVSS |

Table 20A-D: Alignment of IMGT CDRs or FR2 Sequences of KD001-KD005 and Variants

TABLE 20A

| IMGT CDRH1 | KD001-KD005 original sequences |
|---|---|
| | GFTFSGSD (SEQ ID NOs: 52, 59 and 62) |
| | GFPFSSAD (SEQ ID NO: 55) |
| | GFTFSNYD (SEQ ID NO: 56) |

| IMGT CDRH1 Alignment, Consensus, Examples | Alignment | | |
|---|---|---|---|
| | 52 | GFTFSGSD | 8 |
| | 56 | GFTFSNYD | 8 |
| | 55 | GFPFSSAD | 8 |
| | | ** **. * | |

Consensus
GFX$_{7a}$FSX$_{7b}$X$_{7c}$D (SEQ ID NO: 122)
Examples
a) Wherein any one of X$_{7a}$ to X$_{7c}$ is any amino acid.
b) Wherein X$_{7a}$ is any amino acid;
Wherein X$_{7b}$ is G, N, S or D and/or
Wherein X$_{7c}$ is any amino acid.
c) Wherein X$_{7a}$ is T or P;
Wherein X$_{7b}$ is G, N or S and/or
Wherein X$_{7c}$ is S, Y or A.

TABLE 20B

| IMGT CDRH2 | KD001-KD005 original sequences |
|---|---|
| | INADGSKT (SEQ ID NO: 47) |
| | ITSGGTT (SEQ ID NOs: 50 and 53) |
| | INAGGSNT (SEQ ID NO: 57) |
| | ITGSGTT (SEQ ID NO: 60) |
| | KD002 Variants |
| | INANGSKT (SEQ ID NO: 123) |
| | INAEGSKT (SEQ ID NO: 124) |

| IMGT CDRH2 Alignment, Consensus, Examples | Alignment | | |
|---|---|---|---|
| | 47 | INADGSKT | 8 |
| | 124 | INANGSKT | 8 |
| | 123 | INAEGSKT | 8 |
| | 57 | INAGGSNT | 8 |
| | 50 | ITSGGTT- | 7 |
| | 60 | ITGSGTT- | 7 |
| | | *.. *:. | |

Consensus
IX$_{8a}$X$_{8b}$X$_{8c}$GX$_{8d}$X$_{8e}$X$_{8f}$ (SEQ ID NO: 125)
Examples
a) Wherein any one of X$_{8a}$ to X$_{8f}$ is any amino acid.
b) Wherein X$_{8a}$ is S, T, N or K;
Wherein X$_{8b}$ is A, S or G;
Wherein X$_{8c}$ is any amino acid;
Wherein X$_{8d}$ is S, T or A;
Wherein X$_{8e}$ is S, T, N or K and/or
Wherein X$_{8f}$ is any amino acid or absent.
c) Wherein X$_{8a}$ is N or T;
Wherein X$_{8b}$ is A, S or G;
Wherein X$_{8c}$ is D, N, E, G or S;
Wherein X$_{8d}$ is S or T;
Wherein X$_{8e}$ is K, N or T and/or
Wherein X$_{8f}$ is T or absent.

TABLE 20C

| IMGT CDRH3 | KD001-KD005 original sequences |
|---|---|
| | ARAKLTDTHYVEDY (SEQ ID NOs: 48 and 58) |
| | AKSRLTDSHYVEDA (SEQ ID NO: 51) |
| | AKARLTDSHYVEDA (SEQ ID NO: 54) |
| | AKARLTDSHYVEDA (SEQ ID NO: 61) |

| IMGT CDRH3 Alignment, Consensus, Examples | Alignment | | |
|---|---|---|---|
| | 48 | ARAKLTDTHYVEDY | 14 |
| | 51 | AKSRLTDSHYVEDA | 14 |
| | 54 | AKARLTDSHYVEDA | 14 |
| | 61 | AKARLTDSHYVEDA | 14 |
| | | *::: *:*** | |

Consensus
AX$_{9a}$X$_{9b}$X$_{9c}$LTDX$_{9d}$HYVEDX$_{9e}$ (SEQ ID NO: 126)
Examples
a) Wherein any one of X$_{9a}$ to X$_{9e}$ is any amino acid.
b) Wherein X$_{9a}$ is Q, H, R or K;
Wherein X$_{9b}$ is S, T or A;
Wherein X$_{9c}$ is Q, H, R or K;
Wherein X$_{9d}$ is S, T or A and/or
Wherein X$_{9e}$ is any amino acid or absent.
c) Wherein X$_{9a}$ is R or K;
Wherein X$_{9b}$ is A or S;
Wherein X$_{9c}$ is K or R;
Wherein X$_{9d}$ is T or S and/or
Wherein X$_{9e}$ is Y, A or absent.

TABLE 20D

| IMGT FR2 | KD001-KD005 original sequences<br>(e.g., aa 34-50 of SEQ ID NO: 33) |
|---|---|
| | MSWVRQAPGKGPEWVSY (SEQ ID: 116) |
| | KD002 variants |
| | MSWVRQAPGKGLEWVSY (SEQ ID: 117) |
| | MSWVRQAPGKGLEWVSV (SEQ ID: 118) |
| | MSWVRQAPGKQREWVSY (SEQ ID: 119) |
| | KD005 variants |
| | MSWVRQAPGKGLEWVSA (SEQ ID: 120) |
| | MSWVRQAPGKGLEWVSV (SEQ ID: 118) |
| | MSWVRQAPGKGLEWVSY (SEQ ID: 117) |

| IMGT FR2 Alignment, Consensus, Examples | Alignment | | |
|---|---|---|---|
| | 119 | MSWVRQAPGKQREWVSY | 17 |
| | 120 | MSWVRQAPGKGLEWVSA | 17 |
| | 118 | MSWVRQAPGKGLEWVSV | 17 |
| | 116 | MSWVRQAPGKGPEWVSY | 17 |
| | 117 | MSWVRQAPGKGLEWVSY | 17 |
| | | ********** **** | |

TABLE 20D-continued

Consensus
MSWVRQAPGKX$_{6a}$X$_{6b}$EWVSX$_{6c}$
(consensus SEQ ID NO: 121)
Examples
a) Wherein any one of X$_{6a}$ to X$_{6c}$ is any amino acid.
b) Wherein X$_{6a}$ is Q or G;
Wherein X$_{6b}$ is R, L or P and/or
Wherein X$_{6c}$ is Y, A or V.

Table 21A-C: Alignment of Kabat CDRs or FR2 Sequences of KD001-KD005 and Variants

TABLE 21A

| Kabat CDRH1 | KD001-KD005 original sequences |
|---|---|
| | GSDMS (SEQ ID NOs: 1, 10 and 13) |
| | SADMS (SEQ ID NO: 4) |
| | NYDMS (SEQ ID NO: 7) |
| | KD002 variants |
| | SADMH (SEQ ID NO: 127) |

| Kabat CDRH1 Alignment, Consensus, Examples | Alignment | | |
|---|---|---|---|
| | 7 | NYDMS | 5 |
| | 1 | GSDMS | 5 |
| | 4 | SADMS | 5 |
| | 127 | SADMH | 5 |
| | | . ** | |

Consensus
X$_{10a}$X$_{10b}$DMX$_{10c}$ (SEQ ID NO: 128)
Examples
a) Wherein any one of X$_{10a}$ to X$_{10c}$ is any amino acid.
b) Wherein X$_{10a}$ is S, G, N or D;
Wherein X$_{10b}$ is any amino acid and/or
Wherein X$_{10c}$ is any amino acid.
c) Wherein X$_{10a}$ is N, G or S;
Wherein X$_{10b}$ is Y, S or A and/or
Wherein X$_{10c}$ is S or H.

TABLE 21B

| Kabat CDRH2 | KD001-KD005 original sequences |
|---|---|
| | YITSGGTTYYPDSVKG (SEQ ID NOs: 2 and 14) |
| | YINADGSKTYYPDSVKG (SEQ ID NO: 5) |
| | YINAGGSNTDYPDSVKG (SEQ ID NO: 8) |
| | YITGSGTTYYPDSVKG (SEQ ID NO: 11) |
| | KD002 variants |
| | RINADGSKTSYADTVKG (SEQ ID NO: 129) |
| | YINADGSKTSYADTVKG (SEQ ID NO: 130) |
| | YINADGSKTYYPDTVKG (SEQ ID NO: 131) |
| | VINADGSKTYYADTVKG (SEQ ID NO: 132) |
| | YINADGSKTYYADTVKG (SEQ ID NO: 133) |
| | YINAEGSKTYYADTVKG (SEQ ID NO: 134) |
| | YINANGSKTYYADTVKG (SEQ ID NO: 135) |
| | KD005 variants |
| | AITSGGTTYYADTVKG (SEQ ID NO: 136) |
| | YITSGGTTYYADTVKG (SEQ ID NO: 137) |
| | YITSGGTTYYPDTVKG (SEQ ID NO: 138) |
| | VITSGGTTYYADTVKG (SEQ ID NO: 139) |

| Kabat CDRH2 Alignment, Consensus, Examples | Alignment | | |
|---|---|---|---|
| | 11 | YI-TGSGTTYYPDSVKG | 16 |
| | 2 | YI-TSGGTTYYPDSVKG | 16 |
| | 138 | YI-TSGGTTYYPDTVKG | 16 |
| | 136 | AI-TSGGTTYYADTVKG | 16 |
| | 135 | YI-TSGGTTYYADTVKG | 16 |
| | 139 | VI-TSGGTTYYADTVKG | 16 |
| | 8 | YINAGGSNTDYPDSVKG | 17 |
| | 129 | RINADGSKTSYADTVKG | 17 |
| | 130 | YINADGSKTSYADTVKG | 17 |
| | 5 | YINADGSKTYYPDSVKG | 17 |
| | 131 | YINADGSKTYYPDTVKG | 17 |
| | 135 | YINANGSKTYYADTVKG | 17 |
| | 134 | YINAEGSKTYYADTVKG | 17 |
| | 132 | VINADGSKTYYADTVKG | 17 |
| | 133 | YINADGSKTYYADTVKG | 17 |
| | | * : ...* * *:*** | |

Consensus
X$_{11a}$IX$_{11b}$X$_{11c}$X$_{11d}$X$_{11e}$X$_{11f}$X$_{11g}$TX$_{11h}$YX$_{11i}$DX$_{11j}$VKG
(SEQ ID NO: 140)
Examples
a) Wherein any one of X$_{11a}$ to X$_{11j}$ is any amino acid.
b) Wherein X$_{11a}$ is any amino acid;
Wherein X$_{11b}$ is any amino acid or absent;
Wherein X$_{11c}$ is S, T or A;
Wherein X$_{11d}$ is any amino acid;
Wherein X$_{11e}$ is S, A or G;
Wherein X$_{11f}$ S, A or G;
Wherein X$_{11g}$ is S, T, N or K;
Wherein X$_{11h}$ is any amino acid;
Wherein X$_{11i}$ is any amino acid;
Wherein X$_{11j}$ is S, T, or A.
c) Wherein X$_{11a}$ is Y, A, V or R;
Wherein X$_{11b}$ is absent or N;
Wherein X$_{11c}$ is T or A;
Wherein X$_{11d}$ is G, S, D, N or E;
Wherein X$_{11e}$ is S or G;
Wherein X$_{11f}$ is G or S;
Wherein X$_{11g}$ is T, N or K;
Wherein X$_{11h}$ is Y, D or S;
Wherein X$_{11i}$ is P or A and/or
Wherein X$_{11j}$ is S or T.

TABLE 21C

| Kabat CDRH3 | KD001-KD005 original sequences |
|---|---|
| | ARLTDSHYVED (SEQ ID NO: 3) |
| | AKLTDTHYVEDY (SEQ ID NOs: 6 and 9) |
| | ARLTDSHYVEDA (SEQ ID NO: 12) |
| | SRLTDSHYVED (SEQ ID NO: 15) |
| | KD005 variants |
| | SRLTDSHYVEDA (SEQ ID NO: 141) |

| Kabat CDRH3 Alignment, Consensus, Examples | Alignment | | |
|---|---|---|---|
| | 6 | AKLTDTHYVEDY | 12 |
| | 3 | ARLTDSHYVED- | 11 |
| | 12 | ARLTDSHYVEDA | 12 |
| | 15 | SRLTDSHYVED- | 11 |
| | 140 | SRLTDSHYVEDA | 12 |
| | | :*:*** | |

Consensus
X$_{12a}$X$_{12b}$LTDX$_{12c}$HYVEDX$_{12d}$ (SEQ ID NO: 142)
Examples
a) Wherein any one of X$_{12a}$ to X$_{12d}$ is any amino acid.
b) Wherein X$_{12a}$ is S, T or A;
Wherein X$_{12b}$ is Q, H, R or K;
Wherein X$_{12c}$ is S, T or A and/or
Wherein X$_{12d}$ is any amino acid or absent.
c) Wherein X$_{12a}$ is A or S;
Wherein X$_{12b}$ is K or R;
Wherein X$_{12c}$ is T or S and/or
Wherein X$_{12d}$ is Y, A or absent.

TABLE 21D

| Kabat FR2 | WVRQAPGKGPEWVS (SEQ ID NO: 170) |
|---|---|
| | WVRQAPGKGLEWVS (SEQ ID NO: 171) |
| | WVRQAPGKQREWVS (SEQ ID NO: 172) |
| | WYRQAPGKGREWVS (SEQ ID NO: 173) |
| | WVRQAPGKGLVWVS (SEQ ID NO: 174) |

| Kabat FR2 Alignment, Consensus, Examples | Alignment | |
|---|---|---|
| | 173 | WYRQAPGKGREWVS |
| | 172 | WVRQAPGKQREWVS |
| | 174 | WVRQAPGKGLVWVS |

TABLE 21D-continued

| | |
|---|---|
| 170 | WVRQAPGKGPEWVS |
| 171 | WVRQAPGKGLEWVS |
| | * ***** *** |

Consensus
WX$_{13a}$RQAPGKX$_{13b}$X$_{13c}$X$_{13d}$WVS
(SEQ ID NO: 175)
Examples
a) Wherein any one of X$_{13a}$ to X$_{13d}$ is any amino acid.
b) Wherein X$_{13a}$ is V or Y;
  wherein X$_{13b}$ is G or Q;
  wherein X$_{13c}$ is P, L or R and;
  wherein X$_{13d}$ is E or V
c) Wherein X$_{13a}$ is V;
  wherein X$_{13b}$ is G or Q and;
  wherein X$_{13c}$ is P, L or R
  wherein X$_{13d}$ is E SEQ ID NO: 36 Human IgG1 hinge AA sequences:
EPKSCDKTHTCPPCP SEQ ID NO: 37 Human IgG1 CH2 AA sequences:
APELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNK

ALPAPIEKTISKAK

SEQ ID NO: 38 Human IgG1 CH3 AA sequences:
GQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHY

TQKSLSLSPG

SEQ ID NO: 39 human TROP2
MARGPGLAPPPLRLPLLLLVLAAVTGHTAAQDNCTCPTNKMTVCSPDG

PGGRCQCRALGSGMAVDCSTLTSKCLLLKARMSAPKNARTLVRPSEHA

LVDNDGLYDPDCDPEGRFKARQCNQTSVCWCVNSVGVRRTDKGDLSLR

CDELVRTHHILIDLRHRPTAGAFNHSDLDAELRRLFRERYRLHPKFVA

AVHYEQPTIQIELRQNTSQKAAGDVDIGDAAYYFERDIKGESLFQGRG

GLDLRVRGEPLQVERTLIYYLDEIPPKFSMKRLTAGLIAVIVVVVAL

VAGMAVLVITNRRKSGKYKKVEIKELGELRKEPSL

SEQ ID NO: 40 cynomolgus TROP2
MARGPGLAPPPLRLPLLLLLLAAVTGHTAAQDNCTCPTNKMTVCSPDG

PGGRCQCRALGSGVAVDCSTLTSKCLLLKARMSAPKNARTLVRPNEHA

LVDNDGLYDPDCDPEGRFKARQCNQTSVCWCVNSVGVRRTDKGDLSLR

CDELVRTHHILIDLRHRPTAGAFNHSDLDAELRRLFRERYRLHPKFVA

AVHYEQPTIQIELRQNTSQKAAGDVDIGDAAYYFERDVKGESLFQGRG

GLDLRVRGEPLQVERTLIYYLDEIPPKFSMKRLTAGLIAVIVVVVAL

VAGVAVLVISNRRKSGKYKKVEIKELGELRKEPSL

SEQ ID NO: 41 mouse TROP2
MARGLDLAPLLLLLLAMATRFCTAQSNCTCPTNKMTVCDTNGPGGVCQ

CRAMGSQVLVDCSTLTSKCLLLKARMSARKGSRSLVMPSEHAILDNDG

LYDPECDDKGRFKARQCNQTSVCWCVNSVGVRRTDKGDQSLRCDEVVR

THHILIELRHRPTDRAFNHSDLDSELRRLFQERYKLHPSFLSAVHYEE

PTIQIELRQNASQKGLRDVDIADAAYYFERDIKGESLFMGRRGLDVQV

RGEPLHVERTLIYYLDEKPPQFSMKRLTAGVIAVIAVVSVAVVAGVVV

LVVTKRRKSGKYKKVELKELGEMRSEPSL

SEQ ID NO: 42 Human IgG4 hinge AA sequences:
ESKYGPPCPPCP

SEQ ID NO: 34 Human IgG4 CH2 AA sequences:
APEAAGGPSVFLFPPKPKDTLMISRTPEVTCVVVDVSQEDPEVQFNWY

VDGVEVHNAKTKPREEQFNSTYRVVSVLTVLHQDWLNGKEYKCKVSNK

GLPSSIEKTISKAK

SEQ ID NO: 43 Human IgG4 CH3 AA sequences:
GQPREPQVYTLPPSQEEMTKNQVSLTCLVKGFYPSDIAVEWESNGQPE

NNYKTTPPVLDSDGSFFLYSRLTVDKSRWQEGNVFSCSVMHEALHNHY

TQKSLSLSLGK

SEQ ID NO: 143 (KD002 consensus)
X$_{1a}$VQLX$_{1b}$ESGGGX$_{1c}$VQX$_{1d}$GGSLRLSCAASGFPFSSADMSWVRQAPGK X$_{1e}$X$_{1f}$WVSX$_{1g}$INAX$_{1h}$GSKTYYX$_{1i}$DX$_{1j}$VKGRFTISRDNX$_{1k}$KNTLYLX$_{1l}$ MNX$_{1m}$LX$_{1n}$X$_{1o}$EDTAX$_{1p}$YX$_{1q}$CARAKLTDTHYVEDYWGQGTX$_{1r}$VTVSS SEQ ID NO: 144 (KD005 consensus)
X$_{2a}$VQLX$_{2b}$ESGGGLX$_{2c}$X$_{2d}$X$_{2e}$GGSLRLSCAASGFTFSGSDMSWVRQAP GKGX$_{2f}$EWVSX$_{2g}$ITSGGTTYYX$_{2h}$DX$_{2i}$VKGRFTISRDNX$_{2j}$KNTLYLQM NSLX$_{2k}$X$_{2l}$X$_{2m}$DTAX$_{2n}$YX$_{2o}$CAKSRLTDSHYVEDAWGQGTX$_{2p}$VTVSS SEQ ID NO: 145 (Consensus from KD001 to KD005)
QVQLQESGGGX$_{3a}$VX$_{3b}$X$_{3c}$GX$_{3d}$SLRLSCAASGFX$_{3e}$FSX$_{3f}$X$_{3g}$DMSWVRQ APGKGPEWVSYIX$_{3h}$X$_{3i}$X$_{3j}$X$_{3k}$X$_{3l}$X$_{3m}$TX$_{3n}$YPDSVKGRFTX$_{3o}$SRDNAK NX$_{3p}$LYLX$_{3q}$MNX$_{3r}$LX$_{3s}$PX$_{3t}$DTALYRCAX$_{3u}$X$_{3v}$X$_{3w}$LTDX$_{3x}$HYVEDX$_{3y}$W

GQGTQVTVSS

SEQ ID NO: 146 (Consensus for KD001-KD005 and selected variants)
X$_{4a}$VQLX$_{4b}$ESGGGX$_{4c}$X$_{4d}$X$_{4e}$X$_{4f}$GX$_{4g}$SLRLSCAASGFX$_{4h}$FSX$_{4i}$X$_{4j}$DM X$_{4k}$WX$_{4l}$RQAPGKX$_{4m}$X$_{4n}$X$_{4o}$WVSX$_{4p}$IX$_{4q}$X$_{4r}$X$_{4s}$GX$_{4t}$X$_{4u}$TX$_{4v}$YX$_{4w}$DX$_{4x}$V KGRFTX$_{4y}$SRDNX$_{4z}$KNX$_{5a}$LYLX$_{5b}$MNX$_{5c}$LX$_{5d}$X$_{5e}$X$_{5f}$DTAX$_{5g}$YX$_{5h}$CAX$_{5i}$ X$_{5j}$X$_{5k}$LTDX$_{5l}$HYVEDX$_{5m}$WGQGTX$_{5n}$VTVSS.

SEQ ID NO: 147 (TROP2 delta 27-36)
MARGPGLAPPPLRLPLLLLVLAAVTGPTNKMTVCSPDGPGGRCQCRAL

GSGMAVDCSTLTSKCLLLKARMSAPKNARTLVRPSEHALVDNDGLYDP

DCDPEGRFKARQCNQTSVCWCVNSVGVRRTDKGDLSLRCDDLVRTHHI

LIDLRHRPTAGAFNHSDLDAELRRLFRERYRLHPKFVAAVHYEQPTIQ

IELRQNTSQKAAGEVDIGDAAYYFERDIKGESLFQGRGGLDLRVRGEP

LQVERTLIYYLDEIPPKFSMKRLTAGLIAVIVVVVALVAGMAVLVIT

NRRKSGKYKKVEIKELGELRKE PSL

SEQ ID NO: 148 (TROP2 delta 27-44)
MARGPGLAPPPLRLPLLLLVLAAVTGSPDGPGGRCQCRALGSGMAVDC

STLTSKCLLLKARMSAPKNARTLVRPSEHALVDNDGLYDPDCDPEGRF

KARQCNQTSVCWCVNSVGVRRTDKGDLSLRCDDLVRTHHILIDLRHRP

TAGAFNHSDLDAELRRLFRERYRLHPKFVAAVHYEQPTIQIELRQNTS

QKAAGEVDIGDAAYYFERDIKGESLFQGRGGLDLRVRGEPLQVERTLI

YYLDEIPPKFSMKRLTAGLIAVIVVVVVALVAGMAVLVITNRKSGKYK

KVEIKELGELRKEPSL

SEQ ID NO: 149 (TROP2 delta 27-56)
MARGPGLAPPPLRLPLLLLVLAAVTGALGSGMAVDCSTLTSKCLLLKA

RMSAPKNARTLVRPSEHALVDNDGLYDPDCDPEGRFKARQCNQTSVCW

CVNSVGVRRTDKGDLSLRCDDLVRTHHILIDLRHRPTAGAFNHSDLDA

ELRRLFRERYRLHPKFVAAVHYEQPTIQIELRQNTSQKAAGEVDIGDA

AYYFERDIKGESLFQGRGGLDLRVRGEPLQVERTLIYYLDEIPPKFSM

KRLTAGLIAVIVVVVVALVAGMAVLVITNRRKSGKYKKVEIKELGELR

KEPSL

SEQ ID NO: 150 (KD065: TROP2-CD47 bispecific,
TROP2 VHH at the N-terminal- variable
regions underlined)
QVQLQESGGGLVQPGRSLRLSCAASGFTFSGSDMSWVRQAPGKGPEWV

SYITGSGTTYYPDSVKGRFTTSRDNAKNMLYLQMNSLKPDDTALYRCA

KARLTDSHYVEDAWGQGTQVTVSSEPKSCDKTHTCPPCPAPELLGGPS

VFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEA

LHNHYTQKSLSLSPGKAPAPAPAPAPAPAPAPAPAPKAQVQLQESGGG

LVQPGGSLRLSCAASREDESVNDIRWYRQAPGNERELVARITGGGRTD

YADSVKGRFTISRDNAKNTVYLQMNNLKPEDTAVYYCWGRGYWGQGTQ

VTVSS

SEQ ID NO: 151 (KD066: TROP2-CD47 bispecific,
TROP2 VHH at the C-terminal-- variable
regions underlined)
QVQLQESGGGLVQPGGSLRLSCAASRFDFSVNDIRWYRQAPGNERELV

ARITGGGRTDYADSVKGRFTISRDNAKNTVYLQMNNLKPEDTAVYYCW

GRGYWGQGTQVTVSSEPKSCDKTHTCPPCPAPELLGGPSVFLFPPKPK

DTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYK

TTPPVLDSDGSFFLYSKLTVDKSRWQQGNVFSCSVMHEALHNHYTQKS

LSLSPGKAPAPAPAPAPAPAPAPAPKAQVQLQESGGGLVQPGRSLR

LSCAASGFTFSGSDMSWVRQAPGKGPEWVSYITGSGTTYYPDSVKGRF

TTSRDNAKNMLYLQMNSLKPDDTALYRCAKARLTDSHYVEDAWGQGTQ

VTVSS

SEQ ID NO: 152: KD067 (variable region 1-140-
mouse hinge- mouse constant region -IMGT
CDRH1, CDRH2 and CDRH3 in bold and underlined)
QVQLQESGGGMVQGGSLRLSCAASGFPFSSADMSWVRQAPGKGPEWV

SYINADGSKTYYPDSVKGRFTISRDNAKNTYLLMNNLKPEDTALYRC

ARAKLTDTHYVEDYWGQGTQVTVSSVPRDCGCKPCICTVPEVSSVFIF

PPKPKDVLTITLTPKVTCVVVDISKDDPEVQFSWFVDDVEVHTAQTQP

REEQFNSTFRSVSELPIMHQDWLNGKEFKCRVNSAAFPAPIEKTISKT

KGRPKAPQVYTIPPPKEQMAKDKVSLTCMITDFFPEDITVEWQWNGQP

AENYKNTQPIMNTNGSYFVYSKLNVQKSNWEAGNTFTCSVLHEGLHNH

HTEKSLSHSPGK

SEQ ID NO: 153: KD068 (variable region 1-139-
mouse hinge- mouse constant region -IMGT
CDRH1, CDRH2 and CDRH3 in bold and underlined)
QVQLQESGGGLVEAGGSLRLSCAASGFTFSGSDMSWVRQAPGKGPEWV

SYITSGGTTYYPDSVKGRFTISRDNAKNTLYLQMNSLKPDDTALYRCA

KSRLTDSHYVEDAWGQGTQVTVSSVPRDCGCKPCICTVPEVSSVFIFP

PKPKDVLTITLTPKVTCVVVDISKDDPEVQFSWFVDDVEVHTAQTQPR

EEQFNSTFRSVSELPIMHQDWLNGKEFKCRVNSAAFPAPIEKTISKTK

GRPKAPQVYTIPPPKEQMAKDKVSLTCMITDFFPEDITVEWQWNGQPA

ENYKNTQPIMNTNGSYFVYSKLNVQKSNWEAGNTFTCSVLHEGLHNHH

TEKSLSHSPGK

SEQ ID NO: 154: KD069 (variable region 1-146-
mouse hinge- mouse constant region -IMGT CDRH1,
CDRH2 and CDRH3 in bold and underlined)
DVQLVESGGGSVQAGGSLRLSCAASGSTDSIEYMTWFRQAPGKAREGV

AALYTHTGNTYYTDSVKGRFTISQDKAKNMAYLRMDSVKSEDTAIYTC

GATRKYVPVRFALDQSSYDYWGQGTQVTVSSVPRDCGCKPCICTVPEV

SSVFIFPPKPKDVLTITLTPKVTCVVVDISKDDPEVQFSWFVDDVEVH

TAQTQPREEQFNSTFRSVSELPIMHQDWLNGKEFKCRVNSAAFPAPIE

KTISKTKGRPKAPQVYTIPPPKEQMAKDKVSLTCMITDFFPEDITVEW

QWNGQPAENYKNTQPIMNINGSYFVYSKLNVQKSNWEAGNTFTCSVLH

EGLHNHHTEKSLSHSPGK

SEQ ID NO: 163 (linker)
APAPAPAPAPAPAPAPAPKA

SEQ ID NO: 164 (amino acid sequence 1 to 274 of
human TROP2)
MARGPGLAPPPLRLPLLLLVLAAVTGHTAAQDNCTCPTNKMTVCSPDG

PGGRCQCRALGSGMAVDCSTLTSKCLLLKARMSAPKNARTLVRPSEHA

LVDNDGLYDPDCDPEGRFKARQCNQTSVCWCVNSVGVRRTDKGDLSLR

CDELVRTHHILIDLRHRPTAGAFNHSDLDAELRRLFRERYRLHPKFVA

AVHYEQPTIQIELRQNTSQKAAGDVDIGDAAYYFERDIKGESLFQGRG

GLDLRVRGEPLQVERTLIYYLDEIPPKFSMKRLT

TABLE 22

Exemplary nucleotide sequence
encoding the heavy chains of KD001-KD005

| Anti-TROP2 | Nucleotide Sequence |
|---|---|
| KD001<br>Heavy chain<br>SEQ ID NO: 165 | CAGGTGCAATTGCAAGAGTCTGGCGGCGGAATGGTGCACCCTG<br>GTGGATCTCTGAGACTGTCTTGTGCCGCCTCCGGCTTCACCTTC<br>TCTGGCTCTGATATGTCCTGGGTCCGACAGGCTCCTGGCAAGG<br>GACCTGAATGGGTGTCCTACATCACCTCCGGCGGCACCACCTA<br>CTATCCCGACTCTGTGAAGGGCAGATTCACCATCTCTCGGGAC<br>AACGCCAAGAACACCCTGTACCTGCAGATGAACTCTCTGACCC<br>CTGACGACACAGCCCTGTACAGATGTGCCAAGGCCAGACTGAC<br>CGACAGCCACTACGTGGAAGATGCTTGGGGCCAGGGAACACA<br>GGTCACCGTGTCTAGTGAACCCAAGTCCTGCGACAAGACCCAC<br>ACCTGTCCTCCATGTCCTGCTCCAGAACTGCTCGGCGGACCTTC<br>CGTGTTCCTGTTTCCTCCAAAGCCTAAGGACACCCTGATGATCT<br>CTCGGACCCCTGAAGTGACCTGCGTGGTGGTGGATGTGTCTCA<br>CGAGGATCCCGAAGTGAAGTTCAATTGGTACGTGGACGGCGTG<br>GAAGTGCACAACGCCAAGACCAAGCCTAGAGAGGAACAGTAC<br>AACTCCACCTACAGAGTGGTGTCCGTGCTGACCGTGCTGCACC<br>AGGATTGGCTGAACGGCAAAGAGTACAAGTGCAAGGTGTCCA<br>ACAAGGCCCTGCCTGCTCCTATCGAAAAGACCATCTCCAAGGC<br>CAAGGGCCAGCCTAGGGAACCCCAGGTTTACACCCTGCCTCCA<br>AGCCGGGAAGAGATGACCAAGAACCAGGTGTCCCTGACCTGCC<br>TGGTCAAGGGCTTCTACCCTTCCGATATCGCCGTGGAATGGGA<br>GAGCAATGGCCAGCCTGAGAACAACTACAAGACAACCCCTCCT<br>GTGCTGGACTCCGACGGCTCATTCTTCCTGTACTCCAAGCTGAC<br>AGTGGACAAGTCCAGATGGCAGCAGGGCAACGTGTTCTCCTGC<br>TCCGTGATGCACGAGGCCCTGCACAATCACTACACCCAGAAGT<br>CCCTGTCTCTGTCCCCTGGCAAA |
| KD002<br>Heavy chain<br>SEQ ID NO: 166 | CAGGTGCAATTGCAAGAGTCTGGCGGCGGAATGGTGCAAGTCG<br>GCGGATCTCTGAGACTGTCTTGTGCCGCCTCTGGCTTCCCCTTC<br>TCCTCCGCCGATATGTCCTGGGTCCGACAGGCTCCTGGAAAGG<br>GACCTGAGTGGGTGTCCTACATCAACGCCGACGGCTCCAAGAC<br>CTACTATCCCGACTCTGTGAAGGGCAGATTCACCATCTCTCGGG<br>ACAACGCCAAGAACACCCTGTACCTGCTGATGAACAACCTGAA<br>GCCTGAGGACACAGCCCTGTACAGATGCGCCAGAGCCAAGCTG<br>ACCGACACACACTACGTGGAAGATTACTGGGGCCAGGGCACAC<br>AGGTCACCGTGTCTAGTGAACCCAAGTCCTGCGACAAGACCCA<br>CACCTGTCCTCCATGTCCTGCTCCAGAACTGCTCGGCGGACCTT<br>CCGTGTTCCTGTTTCCTCCAAAGCCTAAGGACACCCTGATGATC<br>TCTCGGACCCCTGAAGTGACCTGCGTGGTGGTGGATGTGTCTC<br>ACGAGGATCCCGAAGTGAAGTTCAATTGGTACGTGGACGGCGT<br>GGAAGTGCACAACGCCAAGACCAAGCCTAGAGAGGAACAGTA<br>CAACTCCACCTACAGAGTGGTGTCCGTGCTGACCGTGCTGCAC<br>CAGGATTGGCTGAACGGCAAAGAGTACAAGTGCAAGGTGTCC<br>AACAAGGCCCTGCCTGCTCCTATCGAAAAGACCATCTCCAAGG<br>CCAAGGGCCAGCCTAGGGAACCCCAGGTTTACACCCTGCCTCC<br>AAGCCGGGAAGAGATGACCAAGAACCAGGTGTCCCTGACCTG<br>CCTGGTCAAGGGCTTCTACCCTTCCGATATCGCCGTGGAATGG<br>GAGAGCAATGGCCAGCCTGAGAACAACTACAAGACAACCCCT<br>CCTGTGCTGGACTCCGACGGCTCATTCTTCCTGTACTCCAAGCT<br>GACAGTGGACAAGTCCAGATGGCAGCAGGGCAACGTGTTCTCC<br>TGCTCCGTGATGCACGAGGCCCTGCACAATCACTACACCCAGA<br>AGTCCCTGTCTCTGTCCCCTGGCAAA |
| KD003<br>Heavy chain<br>SEQ ID NO: 167 | CAGGTGCAATTGCAAGAGTCTGGCGGCGGAATGGTGCAGCCTG<br>GTGGATCTCTGAGACTGTCTTGTGCCGCCTCCGGCTTCACCTTC<br>TCCAACTACGACATGTCCTGGGTCCGACAGGCTCCTGGAAAGG<br>GACCTGAGTGGGTGTCCTACATCAACGCTGGCGGCTCCAACAC<br>CGACTATCCCGACTCTGTGAAGGGCAGATTCACCATCTCTCGG<br>GACAACGCCAAGAACATGCTGTACCTGCTGATGAACAACCTGA<br>AGCCTGAGGACACAGCCCTGTACAGATGCGCCAGAGCCAAGCT<br>GACCGACACACACTACGTGGAAGATTACTGGGGCCAGGGCAC<br>ACAGGTCACCGTGTCTAGTGAACCCAAGTCCTGCGACAAGACC<br>CACACCTGTCCTCCATGTCCTGCTCCAGAACTGCTCGGCGGACC<br>TTCCGTGTTCCTGTTTCCTCCAAAGCCTAAGGACACCCTGATGA<br>TCTCTCGGACCCCTGAAGTGACCTGCGTGGTGGTGGATGTGTCT<br>CACGAGGATCCCGAAGTGAAGTTCAATTGGTACGTGGACGGCG<br>TGGAAGTGCACAACGCCAAGACCAAGCCTAGAGAGGAACAGT<br>ACAACTCCACCTACAGAGTGGTGTCCGTGCTGACCGTGCTGCA<br>CCAGGATTGGCTGAACGGCAAAGAGTACAAGTGCAAGGTGTCC<br>AACAAGGCCCTGCCTGCTCCTATCGAAAAGACCATCTCCAAGG<br>CCAAGGGCCAGCCTAGGGAACCCCAGGTTTACACCCTGCCTCC<br>AAGCCGGGAAGAGATGACCAAGAACCAGGTGTCCCTGACCTG<br>CCTGGTCAAGGGCTTCTACCCTTCCGATATCGCCGTGGAATGG<br>GAGAGCAATGGCCAGCCTGAGAACAACTACAAGACAACCCCT |

TABLE 22-continued

Exemplary nucleotide sequence
encoding the heavy chains of KD001-KD005

| Anti-TROP2 | Nucleotide Sequence |
|---|---|
| | CCTGTGCTGGACTCCGACGGCTCATTCTTCCTGTACTCCAAGCT
GACAGTGGACAAGTCCAGATGGCAGCAGGGCAACGTGTTCTCC
TGCTCCGTGATGCACGAGGCCCTGCACAATCACTACACCCAGA
AGTCCCTGTCTCTGTCCCCTGGCAAA |
| KD004
Heavy chain
SEQ ID NO: 168 | CAGGTGCAATTGCAAGAGTCTGGCGGCGGACTGGTGCAGCCTG
GAAGATCTCTGAGACTGTCCTTGTGCCGCCTCCGGCTTCACCTTC
TCTGGCTCTGATATGTCCTGGGTCCGACAGGCTCCTGGCAAGG
GACCTGAATGGGTGTCCTACATCACCGGCTCCGGCACCACCTA
CTATCCCGACTCTGTGAAGGGCAGATTCACCACCTCCAGAGAC
AACGCCAAGAACATGCTGTACCTGCAGATGAACTCCCTGAAGC
CTGACGACACAGCCCTGTACAGATGCGCCAAGGCCAGACTGAC
CGACAGCCACTACGTGGAAGATGCTTGGGGCCAGGGAACACA
GGTCACCGTGTCTAGTAACCCAAGTCCTGCGACAAGACCCAC
ACCTGTCCTCCATGTCCTGCTCCAGAACTGCTCGGCGGACCTTC
CGTGTTCCTGTTTCCTCCAAAGCCTAAGGACACCCTGATGATCT
CTCGGACCCCTGAAGTGACCTGCGTGGTGGTGGATGTGTCTCA
CGAGGATCCCGAAGTGAAGTTCAATTGGTACGTGGACGGCGTG
GAAGTGCACAACGCCAAGACCAAGCCTAGAGAGGAACAGTAC
AACTCCACCTACAGAGTGGTGTCCGTGCTGACCGTGCTGCACC
AGGATTGGCTGAACGGCAAAGAGTACAAGTGCAAGGTGTCCA
ACAAGGCCCTGCCTGCTCCTATCGAAAAGACCATCTCCAAGGC
CAAGGGCCAGCCTAGGGAACCCCAGGTTTACACCCTGCCTCCA
AGCCGGGAAGAGATGACCAAGAACCAGGTGTCCCTGACCTGCC
TGGTCAAGGGCTTCTACCCTTCCGATATCGCCGTGGAATGGGA
GAGCAATGGCCAGCCTGAGAACAACTACAAGACAACCCCTCCT
GTGCTGGACTCCGACGGCTCATTCTTCCTGTACTCCAAGCTGAC
AGTGGACAAGTCCAGATGGCAGCAGGGCAACGTGTTCTCCTGC
TCCGTGATGCACGAGGCCCTGCACAATCACTACACCCAGAAGT
CCCTGTCTCTGTCCCCTGGCAAA |
| KD005
Heavy chain
SEQ ID NO: 169 | CAGGTGCAATTGCAAGAGTCTGGCGGCGGACTGGTGGAAGCTG
GTGGATCTCTGAGACTGTCTTGTGCCGCCTCCGGCTTCACCTTC
TCTGGCTCTGATATGTCCTGGGTCCGACAGGCTCCTGGCAAGG
GACCTGAATGGGTGTCCTACATCACCTCCGGCGGCACCACCTA
CTATCCCGACTCTGTGAAGGGCAGATTCACCATCTCTCGGGAC
AACGCCAAGAACACCCTGTACCTGCAGATGAACTCCCTGAAGC
CTGACGACACAGCCCTGTACAGATGCGCCAAGTCTCGGCTGAC
CGACAGCCACTACGTGGAAGATGCTTGGGGCCAGGGAACACA
GGTCACCGTGTCTAGTAACCCAAGTCCTGCGACAAGACCCAC
ACCTGTCCTCCATGTCCTGCTCCAGAACTGCTCGGCGGACCTTC
CGTGTTCCTGTTTCCTCCAAAGCCTAAGGACACCCTGATGATCT
CTCGGACCCCTGAAGTGACCTGCGTGGTGGTGGATGTGTCTCA
CGAGGATCCCGAAGTGAAGTTCAATTGGTACGTGGACGGCGTG
GAAGTGCACAACGCCAAGACCAAGCCTAGAGAGGAACAGTAC
AACTCCACCTACAGAGTGGTGTCCGTGCTGACCGTGCTGCACC
AGGATTGGCTGAACGGCAAAGAGTACAAGTGCAAGGTGTCCA
ACAAGGCCCTGCCTGCTCCTATCGAAAAGACCATCTCCAAGGC
CAAGGGCCAGCCTAGGGAACCCCAGGTTTACACCCTGCCTCCA
AGCCGGGAAGAGATGACCAAGAACCAGGTGTCCCTGACCTGCC
TGGTCAAGGGCTTCTACCCTTCCGATATCGCCGTGGAATGGGA
GAGCAATGGCCAGCCTGAGAACAACTACAAGACAACCCCTCCT
GTGCTGGACTCCGACGGCTCATTCTTCCTGTACTCCAAGCTGAC
AGTGGACAAGTCCAGATGGCAGCAGGGCAACGTGTTCTCCTGC
TCCGTGATGCACGAGGCCCTGCACAATCACTACACCCAGAAGT
CCCTGTCTCTGTCCCCTGGCAAA |

(CD47 Antigen)
SEQ ID NO: 176
MWPLVAALLLGSACCGSAQLLFNKTKSVEFTFCNDTVVIPCFVTN
MEAQNTTEVYVKWKFKGRDIYTFDGALNKSTVPTDFSSAKIEVSQ -continued

LLKGDASLKMDKSDAVSHTGNYTCEVTELTREGETIIELKYRVVS
WFSP

The invention claimed is:

1. A single domain antibody (sdAb) that binds to TROP2 comprising a VHH, wherein the VHH comprises:
   a CDRH1 having the amino acid sequence set forth in SEQ ID NO:62,
   a CDRH2 having the amino acid sequence set forth in SEQ ID NO:50, and
   a CDRH3 having the amino acid sequence set forth in SEQ ID NO:51.

2. The sdAb of claim 1 further comprising a framework region comprising the sequence set forth in SEQ ID NO: 117.

3. The sdAb of claim 1, wherein the VHH comprises a sequence at least 95% identical to the sequence set forth in SEQ ID NO: 26.

4. The sdAb of claim 3, wherein the VHH comprises the sequence set forth in SEQ ID NO: 26.

5. The sdAb of claim 1, wherein the VHH comprises a sequence at least 95% identical to the sequence set forth in SEQ ID NO: 96.

6. The sdAb of claim 5, wherein the VHH comprises the sequence set forth in SEQ ID NO: 96.

7. The sdAb of claim 1, wherein the sdAb further comprises a hinge domain, a CH2 domain and a CH3 domain.

8. The sdAb of claim 7, wherein the hinge domain, CH2 domain and CH3 domain are derived from human IgG1.

9. The sdAb of claim 7, wherein the hinge domain comprises the sequence set forth in SEQ ID NO: 36.

10. The sdAb of claim 7, wherein the CH2 domain comprises the sequence set forth in SEQ ID NO: 37.

11. The sdAb of claim 7, wherein the CH3 domain comprises the sequence set forth in SEQ ID NO: 38.

12. The sdAb of claim 1, wherein the sdAb is a homodimer.

13. A single domain antibody (sdAb) that binds to TROP2 comprising two identical polypeptide chains, each comprising a VHH, a hinge domain, a CH2 domain and a CH3 domain,
wherein the VHH comprises:
   a CDRH1 having the amino acid sequence set forth in SEQ ID NO:62,
   a CDRH2 having the amino acid sequence set forth in SEQ ID NO:50, and
   a CDRH3 having the amino acid sequence set forth in SEQ ID NO:51.

14. The sdAb of claim 13, wherein the VHH comprises a sequence at least 95% identical to the sequence set forth in SEQ ID NO: 26.

15. The sdAb of claim 14, wherein the VHH comprises the sequence set forth in SEQ ID NO: 26.

16. The sdAb of claim 13, wherein the VHH comprises a sequence at least 95% identical to the sequence set forth in SEQ ID NO: 96.

17. The sdAb of claim 16, wherein the VHH comprises the sequence set forth in SEQ ID NO: 96.

18. The sdAb of claim 13, wherein the hinge domain, CH2 domain and CH3 domain are derived from human IgG1.

19. The sdAb of claim 13, wherein the hinge domain comprises the sequence set forth in SEQ ID NO: 36.

20. The sdAb of claim 13, wherein the CH2 domain comprises the sequence set forth in SEQ ID NO: 37.

21. The sdAb of claim 13, wherein the CH3 domain comprises the sequence set forth in SEQ ID NO: 38.

22. A single domain antibody (sdAb) that binds to TROP2 comprising a VHH, wherein the VHH comprises:
   a CDRH1 having the amino acid sequence set forth in SEQ ID NO:13,
   a CDRH2 having the amino acid sequence set forth in SEQ ID NO:14, and
   a CDRH3 having the amino acid sequence set forth in SEQ ID NO:15.

23. The sdAb of claim 22, wherein the sdAb further comprises a hinge domain, a CH2 domain and a CH3 domain.

24. The sdAb of claim 22, wherein the hinge domain, CH2 domain and CH3 domain are derived from human IgG1.

25. The sdAb of claim 22, wherein the hinge domain comprises the sequence set forth in SEQ ID NO: 36.

26. The sdAb of claim 21, wherein the CH2 domain comprises the sequence set forth in SEQ ID NO: 37.

27. The sdAb of claim 21, wherein the CH3 domain comprises the sequence set forth in SEQ ID NO: 38.

28. A single domain antibody (sdAb) that binds to TROP2 comprising a VHH, wherein the VHH comprises:
- a CDRH1 having the amino acid sequence set forth in SEQ ID NO:49,
- a CDRH2 having the amino acid sequence set forth in SEQ ID NO:50, and
- a CDRH3 having the amino acid sequence set forth in SEQ ID NO:51.

* * * * *

SEQUENCE LISTING

Sequence total quantity: 214
SEQ ID NO: 1         moltype = AA  length = 5
FEATURE              Location/Qualifiers

```
                    source                  1..5
                                            mol_type = protein
                                            organism = synthetic construct
                    SEQUENCE: 1
                    GSDMS                                                            5

SEQ ID NO: 2            moltype = AA  length = 16
                    FEATURE                 Location/Qualifiers
                    source                  1..16
                                            mol_type = protein
                                            organism = synthetic construct
                    SEQUENCE: 2
                    YITSGGTTYY PDSVKG                                                16

SEQ ID NO: 3            moltype = AA  length = 12
                    FEATURE                 Location/Qualifiers
                    source                  1..12
                                            mol_type = protein
                                            organism = synthetic construct
                    SEQUENCE: 3
                    ARLTDSHYVE DA                                                    12

SEQ ID NO: 4            moltype = AA  length = 5
                    FEATURE                 Location/Qualifiers
                    source                  1..5
                                            mol_type = protein
                                            organism = synthetic construct
                    SEQUENCE: 4
                    SADMS                                                            5

SEQ ID NO: 5            moltype = AA  length = 17
                    FEATURE                 Location/Qualifiers
                    source                  1..17
                                            mol_type = protein
                                            organism = synthetic construct
                    SEQUENCE: 5
                    YINADGSKTY YPDSVKG                                               17

SEQ ID NO: 6            moltype = AA  length = 12
                    FEATURE                 Location/Qualifiers
                    source                  1..12
                                            mol_type = protein
                                            organism = synthetic construct
                    SEQUENCE: 6
                    AKLTDTHYVE DY                                                    12

SEQ ID NO: 7            moltype = AA  length = 5
                    FEATURE                 Location/Qualifiers
                    source                  1..5
                                            mol_type = protein
                                            organism = synthetic construct
                    SEQUENCE: 7
                    NYDMS                                                            5

SEQ ID NO: 8            moltype = AA  length = 17
                    FEATURE                 Location/Qualifiers
                    source                  1..17
                                            mol_type = protein
                                            organism = synthetic construct
                    SEQUENCE: 8
                    YINAGGSNTD YPDSVKG                                               17

SEQ ID NO: 9            moltype = AA  length = 12
                    FEATURE                 Location/Qualifiers
                    source                  1..12
                                            mol_type = protein
                                            organism = synthetic construct
                    SEQUENCE: 9
                    AKLTDTHYVE DY                                                    12

SEQ ID NO: 10           moltype = AA  length = 5
                    FEATURE                 Location/Qualifiers
                    source                  1..5
                                            mol_type = protein
                                            organism = synthetic construct
                    SEQUENCE: 10
                    GSDMS                                                            5

SEQ ID NO: 11           moltype = AA  length = 16
```

```
FEATURE                 Location/Qualifiers
source                  1..16
                        mol_type = protein
                        organism = synthetic construct
SEQUENCE: 11
YITGSGTTYY PDSVKG                                                       16

SEQ ID NO: 12           moltype = AA  length = 12
FEATURE                 Location/Qualifiers
source                  1..12
                        mol_type = protein
                        organism = synthetic construct
SEQUENCE: 12
ARLTDSHYVE DA                                                           12

SEQ ID NO: 13           moltype = AA  length = 5
FEATURE                 Location/Qualifiers
source                  1..5
                        mol_type = protein
                        organism = synthetic construct
SEQUENCE: 13
GSDMS                                                                   5

SEQ ID NO: 14           moltype = AA  length = 16
FEATURE                 Location/Qualifiers
source                  1..16
                        mol_type = protein
                        organism = synthetic construct
SEQUENCE: 14
YITSGGTTYY PDSVKG                                                       16

SEQ ID NO: 15           moltype = AA  length = 12
FEATURE                 Location/Qualifiers
source                  1..12
                        mol_type = protein
                        organism = synthetic construct
SEQUENCE: 15
SRLTDSHYVE DA                                                           12

SEQ ID NO: 16           moltype = AA  length = 5
FEATURE                 Location/Qualifiers
source                  1..5
                        mol_type = protein
                        organism = synthetic construct
SEQUENCE: 16
TKAMG                                                                   5

SEQ ID NO: 17           moltype = AA  length = 16
FEATURE                 Location/Qualifiers
source                  1..16
                        mol_type = protein
                        organism = synthetic construct
SEQUENCE: 17
AISESGSTYY ADSVKD                                                       16

SEQ ID NO: 18           moltype = AA  length = 15
FEATURE                 Location/Qualifiers
source                  1..15
                        mol_type = protein
                        organism = synthetic construct
SEQUENCE: 18
KWYSGSFDDT RSYDY                                                        15

SEQ ID NO: 19           moltype = AA  length = 5
FEATURE                 Location/Qualifiers
source                  1..5
                        mol_type = protein
                        organism = synthetic construct
SEQUENCE: 19
FYAMA                                                                   5

SEQ ID NO: 20           moltype = AA  length = 16
FEATURE                 Location/Qualifiers
source                  1..16
                        mol_type = protein
                        organism = synthetic construct
SEQUENCE: 20
TITAYGNTNY ADSVKG                                                       16
```

| | | |
|---|---|---|
| SEQ ID NO: 21 | moltype = AA length = 9 | |
| FEATURE | Location/Qualifiers | |
| source | 1..9 | |
| | mol_type = protein | |
| | organism = synthetic construct | |
| SEQUENCE: 21 | | |
| NLPSASHNY | | 9 |
| | | |
| SEQ ID NO: 22 | moltype = AA length = 120 | |
| FEATURE | Location/Qualifiers | |
| source | 1..120 | |
| | mol_type = protein | |
| | organism = synthetic construct | |
| SEQUENCE: 22 | | |
| QVQLQESGGG MVHPGGSLRL SCAASGFTFS GSDMSWVRQA PGKGPEWVSY ITSGGTTYYP | | 60 |
| DSVKGRFTIS RDNAKNTLYL QMNSLTPDDT ALYRCAKARL TDSHYVEDAW GQGTQVTVSS | | 120 |
| | | |
| SEQ ID NO: 23 | moltype = AA length = 121 | |
| FEATURE | Location/Qualifiers | |
| source | 1..121 | |
| | mol_type = protein | |
| | organism = synthetic construct | |
| SEQUENCE: 23 | | |
| QVQLQESGGG MVQVGGSLRL SCAASGFPFS SADMSWVRQA PGKGPEWVSY INADGSKTYY | | 60 |
| PDSVKGRFTI SRDNAKNTLY LLMNNLKPED TALYRCARAK LTDTHYVEDY WGQGTQVTVS | | 120 |
| S | | 121 |
| | | |
| SEQ ID NO: 24 | moltype = AA length = 121 | |
| FEATURE | Location/Qualifiers | |
| source | 1..121 | |
| | mol_type = protein | |
| | organism = synthetic construct | |
| SEQUENCE: 24 | | |
| QVQLQESGGG MVQPGGSLRL SCAASGFTFS NYDMSWVRQA PGKGPEWVSY INAGGSNTDY | | 60 |
| PDSVKGRFTI SRDNAKNMLY LLMNNLKPED TALYRCARAK LTDTHYVEDY WGQGTQVTVS | | 120 |
| S | | 121 |
| | | |
| SEQ ID NO: 25 | moltype = AA length = 120 | |
| FEATURE | Location/Qualifiers | |
| source | 1..120 | |
| | mol_type = protein | |
| | organism = synthetic construct | |
| SEQUENCE: 25 | | |
| QVQLQESGGG LVQPGRSLRL SCAASGFTFS GSDMSWVRQA PGKGPEWVSY ITGSGTTYYP | | 60 |
| DSVKGRFTTS RDNAKNMLYL QMNSLKPDDT ALYRCAKARL TDSHYVEDAW GQGTQVTVSS | | 120 |
| | | |
| SEQ ID NO: 26 | moltype = AA length = 120 | |
| FEATURE | Location/Qualifiers | |
| source | 1..120 | |
| | mol_type = protein | |
| | organism = synthetic construct | |
| SEQUENCE: 26 | | |
| QVQLQESGGG LVEAGGSLRL SCAASGFTFS GSDMSWVRQA PGKGPEWVSY ITSGGTTYYP | | 60 |
| DSVKGRFTIS RDNAKNTLYL QMNSLKPDDT ALYRCAKSRL TDSHYVEDAW GQGTQVTVSS | | 120 |
| | | |
| SEQ ID NO: 27 | moltype = AA length = 123 | |
| FEATURE | Location/Qualifiers | |
| source | 1..123 | |
| | mol_type = protein | |
| | organism = synthetic construct | |
| SEQUENCE: 27 | | |
| QVQLQESGGG LVQAGNSLRL SCVASVRTFS TKAMGWFRQA PGKEREFTAA ISESGSTYYA | | 60 |
| DSVKDRFTIS RDNVKNTVYL QMNSLKPEDT AVYYCGVKWY SGSFDDTRSY DYWGQGTQVT | | 120 |
| VSS | | 123 |
| | | |
| SEQ ID NO: 28 | moltype = AA length = 117 | |
| FEATURE | Location/Qualifiers | |
| source | 1..117 | |
| | mol_type = protein | |
| | organism = synthetic construct | |
| SEQUENCE: 28 | | |
| QVQLQESGGG LVQPGGSLRL SCAASGFAFS FYAMAWYRQA PGKQRDMVAT ITAYGNTNYA | | 60 |
| DSVKGRFTTS RDNAKNTVYL QMNSLKPEDT AVYYCNANLP SASHNYWGQG TQVTVSS | | 117 |
| | | |
| SEQ ID NO: 29 | moltype = AA length = 352 | |
| FEATURE | Location/Qualifiers | |
| source | 1..352 | |
| | mol_type = protein | |
| | organism = synthetic construct | |

```
SEQUENCE: 29
QVQLQESGGG MVHPGGSLRL SCAASGFTFS GSDMSWVRQA PGKGPEWVSY ITSGGTTYYP   60
DSVKGRFTIS RDNAKNTLYL QMNSLTPDDT ALYRCAKARL TDSHYVEDAW GQGTQVTVSS  120
EPKSCDKTHT CPPCPAPELL GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNH YTQKSLSLSP GK          352

SEQ ID NO: 30           moltype = AA   length = 353
FEATURE                 Location/Qualifiers
source                  1..353
                        mol_type = protein
                        organism = synthetic construct
SEQUENCE: 30
QVQLQESGGG MVQVGGSLRL SCAASGFPFS SADMSWVRQA PGKGPEWVSY INADGSKTYY   60
PDSVKGRFTI SRDNAKNTLY LLMNNLKPED TALYRCARAK LTDTHYVEDY WGQGTQVTVS  120
SEPKSCDKTH TCPPCPAPEL LGGPSVFLFP PKPKDTLMIS RTPEVTCVVV DVSHEDPEVK  180
FNWYVDGVEV HNAKTKPREE QYNSTYRVVS VLTVLHQDWL NGKEYKCKVS NKALPAPIEK  240
TISKAKGQPR EPQVYTLPPS REEMTKNQVS LTCLVKGFYP SDIAVEWESN GQPENNYKTT  300
PPVLDSDGSF FLYSKLTVDK SRWQQGNVFS CSVMHEALHN HYTQKSLSLS PGK          353

SEQ ID NO: 31           moltype = AA   length = 353
FEATURE                 Location/Qualifiers
source                  1..353
                        mol_type = protein
                        organism = synthetic construct
SEQUENCE: 31
QVQLQESGGG MVQPGGSLRL SCAASGFTFS NYDMSWVRQA PGKGPEWVSY INAGGSNTDY   60
PDSVKGRFTI SRDNAKNMLY LLMNNLKPED TALYRCARAK LTDTHYVEDY WGQGTQVTVS  120
SEPKSCDKTH TCPPCPAPEL LGGPSVFLFP PKPKDTLMIS RTPEVTCVVV DVSHEDPEVK  180
FNWYVDGVEV HNAKTKPREE QYNSTYRVVS VLTVLHQDWL NGKEYKCKVS NKALPAPIEK  240
TISKAKGQPR EPQVYTLPPS REEMTKNQVS LTCLVKGFYP SDIAVEWESN GQPENNYKTT  300
PPVLDSDGSF FLYSKLTVDK SRWQQGNVFS CSVMHEALHN HYTQKSLSLS PGK          353

SEQ ID NO: 32           moltype = AA   length = 352
FEATURE                 Location/Qualifiers
source                  1..352
                        mol_type = protein
                        organism = synthetic construct
SEQUENCE: 32
QVQLQESGGG LVQPGRSLRL SCAASGFTFS GSDMSWVRQA PGKGPEWVSY ITSGTTYYP    60
DSVKGRFTTS RDNAKNMLYL QMNSLKPDDT ALYRCAKARL TDSHYVEDAW GQGTQVTVSS  120
EPKSCDKTHT CPPCPAPELL GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNH YTQKSLSLSP GK          352

SEQ ID NO: 33           moltype = AA   length = 352
FEATURE                 Location/Qualifiers
source                  1..352
                        mol_type = protein
                        organism = synthetic construct
SEQUENCE: 33
QVQLQESGGG LVEAGGSLRL SCAASGFTFS GSDMSWVRQA PGKGPEWVSY ITSGGTTYYP   60
DSVKGRFTIS RDNAKNTLYL QMNSLKPDDT ALYRCAKSRL TDSHYVEDAW GQGTQVTVSS  120
EPKSCDKTHT CPPCPAPELL GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNH YTQKSLSLSP GK          352

SEQ ID NO: 34           moltype = AA   length = 355
FEATURE                 Location/Qualifiers
source                  1..355
                        mol_type = protein
                        organism = synthetic construct
SEQUENCE: 34
QVQLQESGGG LVQAGNSLRL SCVASVRTFS TKAMGWFRQA PGKEREFTAA ISESGSTYYA   60
DSVKDRFTIS RDNVKNTVYL QMNSLKPEDT AVYYCGVKWY SGSFDDTRSY DYWGQGTQVT  120
VSSEPKSCDK THTCPPCPAP ELLGGPSVFL FPPKPKDTLM ISRTPEVTCV VVDVSHEDPE  180
VKFNWYVDGV EVHNAKTKPR EEQYNSTYRV VSVLTVLHQD WLNGKEYKCK VSNKALPAPI  240
EKTISKAKGQ PREPQVYTLP PSREEMTKNQ VSLTCLVKGF YPSDIAVEWE SNGQPENNYK  300
TTPPVLDSDG SFFLYSKLTV DKSRWQQGNV FSCSVMHEAL HNHYTQKSLS LSPGK        355

SEQ ID NO: 35           moltype = AA   length = 349
FEATURE                 Location/Qualifiers
source                  1..349
                        mol_type = protein
                        organism = synthetic construct
SEQUENCE: 35
```

-continued

```
QVQLQESGGG LVQPGGSLRL SCAASGFAFS FYAMAWYRQA PGKQRDMVAT ITAYGNTNYA    60
DSVKGRFTTS RDNAKNTVYL QMNSLKPEDT AVYVCNANLP SASHNYWGQG TQVTVSSEPK   120
SCDKTHTCPP CPAPELLGGP SVFLFPPKPK DTLMISRTPE VTCVVVDVSH EDPEVKFNWY   180
VDGVEVHNAK TKPREEQYNS TYRVVSVLTV LHQDWLNGKE YKCKVSNKAL PAPIEKTISK   240
AKGQPREPQV YTLPPSREEM TKNQVSLTCL VKGFYPSDIA VEWESNGQPE NNYKTTPPVL   300
DSDGSFFLYS KLTVDKSRWQ QGNVFSCSVM HEALHNHYTQ KSLSLSPGK              349

SEQ ID NO: 36            moltype = AA  length = 15
FEATURE                  Location/Qualifiers
source                   1..15
                         mol_type = protein
                         organism = synthetic construct
SEQUENCE: 36
EPKSCDKTHT CPPCP                                                    15

SEQ ID NO: 37            moltype = AA  length = 110
FEATURE                  Location/Qualifiers
source                   1..110
                         mol_type = protein
                         organism = synthetic construct
SEQUENCE: 37
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK             110

SEQ ID NO: 38            moltype = AA  length = 106
FEATURE                  Location/Qualifiers
source                   1..106
                         mol_type = protein
                         organism = synthetic construct
SEQUENCE: 38
GQPREPQVYT LPPSREEMTK NQVSLTCLVK GFYPSDIAVE WESNGQPENN YKTTPPVLDS    60
DGSFFLYSKL TVDKSRWQQG NVFSCSVMHE ALHNHYTQKS LSLSPG                 106

SEQ ID NO: 39            moltype = AA  length = 323
FEATURE                  Location/Qualifiers
source                   1..323
                         mol_type = protein
                         organism = synthetic construct
SEQUENCE: 39
MARGPGLAPP PLRLPLLLLV LAAVTGHTAA QDNCTCPTNK MTVCSPDGPG GRCQCRALGS    60
GMAVDCSTLT SKCLLLKARM SAPKNARTLV RPSEHALVDN DGLYDPDCDP EGRFKARQCN   120
QTSVCWCVNS VGVRRTDKGD LSLRCDELVR THHILIDLRH RPTAGAFNHS DLDAELRRLF   180
RERYRLHPKF VAAVHYEQPT IQIELRQNTS QKAAGDVDIG DAAYYFERDI KGESLFQGRG   240
GLDLRVRGEP LQVERTLIYY LDEIPPKFSM KRLTAGLIAV IVVVVVALVA GMAVLVITNR   300
RKSGKYKKVE IKELGELRKE PSL                                         323

SEQ ID NO: 40            moltype = AA  length = 323
FEATURE                  Location/Qualifiers
source                   1..323
                         mol_type = protein
                         organism = synthetic construct
SEQUENCE: 40
MARGPGLAPP PLRLPLLLLL LAAVTGHTAA QDNCTCPTNK MTVCSPDGPG GRCQCRALGS    60
GVAVDCSTLT SKCLLLKARM SAPKNARTLV RPNEHALVDN DGLYDPDCDP EGRFKARQCN   120
QTSVCWCVNS VGVRRTDKGD LSLRCDELVR THHILIDLRH RPTAGAFNHS DLDAELRRLF   180
RERYRLHPKF VAAVHYEQPT IQIELRQNTS QKAAGDVDIG DAAYYFERDV KGESLFQGRG   240
GLDLRVRGEP LQVERTLIYY LDEIPPKFSM KRLTAGLIAV IVVVVVALVA GVAVLVISNR   300
RKSGKYKKVE IKELGELRKE PSL                                         323

SEQ ID NO: 41            moltype = AA  length = 317
FEATURE                  Location/Qualifiers
source                   1..317
                         mol_type = protein
                         organism = synthetic construct
SEQUENCE: 41
MARGLDLAPL LLLLLAMATR FCTAQSNCTC PTNKMTVCDT NGPGGVCQCR AMGSQVLVDC    60
STLTSKCLLL KARMSARKSG RSLVMPSEHA ILDNDGLYDP ECDDKGRFKA RQCNQTSVCW   120
CVNSVGVRRT DKGDQSLRCD EVVRTHHILI ELRHRPTDRA FNHSDLDSEL RRLFQERYKL   180
HPSFLSAVHY EEPTIQIELR QNASQKGLRD VDIADAAYYF ERDIKGESLF MGRRGLDVQV   240
RGEPLHVERT LIYYLDEKPP QFSMKRLTAG VIAVIAVVSV AVVAGVVVLV VTKRRKSGKY   300
KKVELKELGE MRSEPSL                                                 317

SEQ ID NO: 42            moltype = AA  length = 12
FEATURE                  Location/Qualifiers
source                   1..12
                         mol_type = protein
                         organism = synthetic construct
SEQUENCE: 42
ESKYGPPCPP CP                                                       12
```

```
SEQ ID NO: 43            moltype = AA   length = 107
FEATURE                  Location/Qualifiers
source                   1..107
                         mol_type = protein
                         organism = synthetic construct
SEQUENCE: 43
GQPREPQVYT LPPSQEEMTK NQVSLTCLVK GFYPSDIAVE WESNGQPENN YKTTPPVLDS     60
DGSFFLYSRL TVDKSRWQEG NVFSCSVMHE ALHNHYTQKS LSLSLGK                  107

SEQ ID NO: 44            moltype = AA   length = 350
FEATURE                  Location/Qualifiers
source                   1..350
                         mol_type = protein
                         organism = synthetic construct
SEQUENCE: 44
QVQLQESGGG MVQVGGSLRL SCAASGFPFS SADMSWVRQA PGKGPEWVSY INADGSKTYY     60
PDSVKGRFTI SRDNAKNTLY LLMNNLKPED TALYRCARAK LTDTHYVEDY WGQGTQVTVS    120
SESKYGPPCP PCPAPEAAGG PSVFLFPPKP KDTLMISRTP EVTCVVVDVS QEDPEVQFNW    180
YVDGVEVHNA KTKPREEQFN STYRVVSVLT VLHQDWLNGK EYKCKVSNKG LPSSIEKTIS    240
KAKGQPREPQ VYTLPPSQEE MTKNQVSLTC LVKGFYPSDI AVEWESNGQP ENNYKTTPPV    300
LDSDGSFFLY SRLTVDKSRW QEGNVFSCSV MHEALHNHYT QKSLSLSLGK              350

SEQ ID NO: 45            moltype = AA   length = 349
FEATURE                  Location/Qualifiers
source                   1..349
                         mol_type = protein
                         organism = synthetic construct
SEQUENCE: 45
QVQLQESGGG LVQPGRSLRL SCAASGFTFS GSDMSWVRQA PGKGPEWVSY ITGSGTTYYP     60
DSVKGRFTTS RDNAKNMLYL QMNSLKPDDT ALYRCAKARL TDSHYVEDAW GQGTQVTVSS    120
ESKYGPPCPP CPAPEAAGGP SVFLFPPKPK DTLMISRTPE VTCVVVDVSQ EDPEVQFNWY    180
VDGVEVHNAK TKPREEQFNS TYRVVSVLTV LHQDWLNGKE YKCKVSNKGL PSSIEKTISK    240
AKGQPREPQV YTLPPSQEEM TKNQVSLTCL VKGFYPSDIA VEWESNGQPE NNYKTTPPVL    300
DSDGSFFLYS RLTVDKSRWQ EGNVFSCSVM HEALHNHYTQ KSLSLSLGK               349

SEQ ID NO: 46            moltype = AA   length = 10
FEATURE                  Location/Qualifiers
source                   1..10
                         mol_type = protein
                         organism = synthetic construct
SEQUENCE: 46
GFPFSSADMS                                                            10

SEQ ID NO: 47            moltype = AA   length = 8
FEATURE                  Location/Qualifiers
source                   1..8
                         mol_type = protein
                         organism = synthetic construct
SEQUENCE: 47
INADGSKT                                                               8

SEQ ID NO: 48            moltype = AA   length = 14
FEATURE                  Location/Qualifiers
source                   1..14
                         mol_type = protein
                         organism = synthetic construct
SEQUENCE: 48
ARAKLTDTHY VEDY                                                       14

SEQ ID NO: 49            moltype = AA   length = 10
FEATURE                  Location/Qualifiers
source                   1..10
                         mol_type = protein
                         organism = synthetic construct
SEQUENCE: 49
GFTFSGSDMS                                                            10

SEQ ID NO: 50            moltype = AA   length = 7
FEATURE                  Location/Qualifiers
source                   1..7
                         mol_type = protein
                         organism = synthetic construct
SEQUENCE: 50
ITSGGTT                                                                7

SEQ ID NO: 51            moltype = AA   length = 14
FEATURE                  Location/Qualifiers
source                   1..14
```

```
                            mol_type = protein
                            organism = synthetic construct
SEQUENCE: 51
AKSRLTDSHY VEDA                                                              14

SEQ ID NO: 52               moltype = AA   length = 8
FEATURE                     Location/Qualifiers
source                      1..8
                            mol_type = protein
                            organism = synthetic construct
SEQUENCE: 52
GFTFSGSD                                                                      8

SEQ ID NO: 53               moltype = AA   length = 7
FEATURE                     Location/Qualifiers
source                      1..7
                            mol_type = protein
                            organism = synthetic construct
SEQUENCE: 53
ITSGGTT                                                                       7

SEQ ID NO: 54               moltype = AA   length = 14
FEATURE                     Location/Qualifiers
source                      1..14
                            mol_type = protein
                            organism = synthetic construct
SEQUENCE: 54
AKARLTDSHY VEDA                                                              14

SEQ ID NO: 55               moltype = AA   length = 8
FEATURE                     Location/Qualifiers
source                      1..8
                            mol_type = protein
                            organism = synthetic construct
SEQUENCE: 55
GFPFSSAD                                                                      8

SEQ ID NO: 56               moltype = AA   length = 8
FEATURE                     Location/Qualifiers
source                      1..8
                            mol_type = protein
                            organism = synthetic construct
SEQUENCE: 56
GFTFSNYD                                                                      8

SEQ ID NO: 57               moltype = AA   length = 8
FEATURE                     Location/Qualifiers
source                      1..8
                            mol_type = protein
                            organism = synthetic construct
SEQUENCE: 57
INAGGSNT                                                                      8

SEQ ID NO: 58               moltype = AA   length = 14
FEATURE                     Location/Qualifiers
source                      1..14
                            mol_type = protein
                            organism = synthetic construct
SEQUENCE: 58
ARAKLTDTHY VEDY                                                              14

SEQ ID NO: 59               moltype = AA   length = 8
FEATURE                     Location/Qualifiers
source                      1..8
                            mol_type = protein
                            organism = synthetic construct
SEQUENCE: 59
GFTFSGSD                                                                      8

SEQ ID NO: 60               moltype = AA   length = 7
FEATURE                     Location/Qualifiers
source                      1..7
                            mol_type = protein
                            organism = synthetic construct
SEQUENCE: 60
ITGSGTT                                                                       7

SEQ ID NO: 61               moltype = AA   length = 14
FEATURE                     Location/Qualifiers
```

```
source                  1..14
                        mol_type = protein
                        organism = synthetic construct
SEQUENCE: 61
AKARLTDSHY VEDA                                                              14

SEQ ID NO: 62           moltype = AA   length = 8
FEATURE                 Location/Qualifiers
source                  1..8
                        mol_type = protein
                        organism = synthetic construct
SEQUENCE: 62
GFTFSGSD                                                                      8

SEQ ID NO: 63           moltype = AA   length = 8
FEATURE                 Location/Qualifiers
source                  1..8
                        mol_type = protein
                        organism = synthetic construct
SEQUENCE: 63
VRTFSTKA                                                                      8

SEQ ID NO: 64           moltype = AA   length = 7
FEATURE                 Location/Qualifiers
source                  1..7
                        mol_type = protein
                        organism = synthetic construct
SEQUENCE: 64
ISESGST                                                                       7

SEQ ID NO: 65           moltype = AA   length = 17
FEATURE                 Location/Qualifiers
source                  1..17
                        mol_type = protein
                        organism = synthetic construct
SEQUENCE: 65
GVKWYSGSFD DTRSYDY                                                           17

SEQ ID NO: 66           moltype = AA   length = 8
FEATURE                 Location/Qualifiers
source                  1..8
                        mol_type = protein
                        organism = synthetic construct
SEQUENCE: 66
GFAFSFYA                                                                      8

SEQ ID NO: 67           moltype = AA   length = 7
FEATURE                 Location/Qualifiers
source                  1..7
                        mol_type = protein
                        organism = synthetic construct
SEQUENCE: 67
ITAYGNT                                                                       7

SEQ ID NO: 68           moltype = AA   length = 11
FEATURE                 Location/Qualifiers
source                  1..11
                        mol_type = protein
                        organism = synthetic construct
SEQUENCE: 68
NANLPSASHN Y                                                                 11

SEQ ID NO: 69           moltype =     length =
SEQUENCE: 69
000

SEQ ID NO: 70           moltype =     length =
SEQUENCE: 70
000

SEQ ID NO: 71           moltype = AA   length = 121
FEATURE                 Location/Qualifiers
source                  1..121
                        mol_type = protein
                        organism = synthetic construct
SEQUENCE: 71
EVQLVESGGG LVQPGGSLRL SCAASGFPFS SADMHWVRQA PGKGLVWVSR INADGSKTSY            60
ADTVKGRFTI SRDNAKNTLY LQMNSLRAED TAVYYCARAK LTDTHYVEDY WGQGTLVTVS           120
S                                                                          121
```

```
SEQ ID NO: 72           moltype = AA  length = 121
FEATURE                 Location/Qualifiers
source                  1..121
                        mol_type = protein
                        organism = synthetic construct
SEQUENCE: 72
EVQLVESGGG LVQPGGSLRL SCAASGFPFS SADMSWVRQA PGKGLEWVSY INADGSKTSY    60
ADTVKGRFTI SRDNAKNTLY LQMNSLRAED TAVYYCARAK LTDTHYVEDY WGQGTLVTVS   120
S                                                                   121

SEQ ID NO: 73           moltype = AA  length = 121
FEATURE                 Location/Qualifiers
source                  1..121
                        mol_type = protein
                        organism = synthetic construct
SEQUENCE: 73
EVQLVESGGG LVQPGGSLRL SCAASGFPFS SADMSWVRQA PGKGPEWVSY INADGSKTYY    60
ADTVKGRFTI SRDNAKNTLY LQMNSLRAED TAVYYCARAK LTDTHYVEDY WGQGTQVTVS   120
S                                                                   121

SEQ ID NO: 74           moltype = AA  length = 121
FEATURE                 Location/Qualifiers
source                  1..121
                        mol_type = protein
                        organism = synthetic construct
SEQUENCE: 74
QVQLVESGGG LVQPGGSLRL SCAASGFPFS SADMSWVRQA PGKGPEWVSY INADGSKTYY    60
PDTVKGRFTI SRDNAKNTLY LQMNSLRAED TAVYYCARAK LTDTHYVEDY WGQGTQVTVS   120
S                                                                   121

SEQ ID NO: 75           moltype = AA  length = 121
FEATURE                 Location/Qualifiers
source                  1..121
                        mol_type = protein
                        organism = synthetic construct
SEQUENCE: 75
QVQLVESGGG LVQPGGSLRL SCAASGFPFS SADMSWVRQA PGKGPEWVSY INADGSKTYY    60
PDTVKGRFTI SRDNAKNTLY LQMNSLRAED TAVYRCARAK LTDTHYVEDY WGQGTQVTVS   120
S                                                                   121

SEQ ID NO: 76           moltype = AA  length = 121
FEATURE                 Location/Qualifiers
source                  1..121
                        mol_type = protein
                        organism = synthetic construct
SEQUENCE: 76
QVQLVESGGG LVQVGGSLRL SCAASGFPFS SADMSWVRQA PGKGPEWVSY INADGSKTYY    60
PDTVKGRFTI SRDNAKNTLY LQMNSLKPED TAVYRCARAK LTDTHYVEDY WGQGTQVTVS   120
S                                                                   121

SEQ ID NO: 77           moltype = AA  length = 121
FEATURE                 Location/Qualifiers
source                  1..121
                        mol_type = protein
                        organism = synthetic construct
SEQUENCE: 77
QVQLQESGGG MVQVGGSLRL SCAASGFPFS SADMSWVRQA PGKGPEWVSY INADGSKTYY    60
PDTVKGRFTI SRDNAKNTLY LQMNSLKPED TAVYRCARAK LTDTHYVEDY WGQGTQVTVS   120
S                                                                   121

SEQ ID NO: 78           moltype = AA  length = 121
FEATURE                 Location/Qualifiers
source                  1..121
                        mol_type = protein
                        organism = synthetic construct
SEQUENCE: 78
QVQLQESGGG MVQVGGSLRL SCAASGFPFS SADMSWVRQA PGKGPEWVSY INADGSKTYY    60
PDSVKGRFTI SRDNAKNTLY LQMNSLKPED TAVYRCARAK LTDTHYVEDY WGQGTQVTVS   120
S                                                                   121

SEQ ID NO: 79           moltype = AA  length = 121
FEATURE                 Location/Qualifiers
source                  1..121
                        mol_type = protein
                        organism = synthetic construct
SEQUENCE: 79
EVQLLESGGG LVQPGGSLRL SCAASGFPFS SADMSWVRQA PGKGLEWVSV INADGSKTYY    60
ADTVKGRFTI SRDNSKNTLY LQMNSLRAED TAVYYCARAK LTDTHYVEDY WGQGTMVTVS   120
```

```
SEQ ID NO: 80            moltype = AA  length = 121
FEATURE                  Location/Qualifiers
source                   1..121
                         mol_type = protein
                         organism = synthetic construct
SEQUENCE: 80
QVQLQESGGG LVQPGGSLRL SCAASGFPFS SADMSWVRQA PGKGPEWVSY INADGSKTYY   60
PDTVKGRFTI SRDNSKNTLY LQMNNLRAED TALYRCARAK LTDTHYVEDY WGQGTMVTVS  120
S                                                                 121

SEQ ID NO: 81            moltype = AA  length = 121
FEATURE                  Location/Qualifiers
source                   1..121
                         mol_type = protein
                         organism = synthetic construct
SEQUENCE: 81
QVQLQESGGG LVQPGGSLRL SCAASGFPFS SADMSWVRQA PGKGLEWVSY INADGSKTYY   60
ADTVKGRFTI SRDNSKNTLY LQMNSLRAED TAVYRCARAK LTDTHYVEDY WGQGTMVTVS  120
S                                                                 121

SEQ ID NO: 82            moltype = AA  length = 121
FEATURE                  Location/Qualifiers
source                   1..121
                         mol_type = protein
                         organism = synthetic construct
SEQUENCE: 82
EVQLQESGGG LVQPGGSLRL SCAASGFPFS SADMSWVRQA PGKGLEWVSY INADGSKTYY   60
ADTVKGRFTI SRDNSKNTLY LQMNSLRAED TAVYRCARAK LTDTHYVEDY WGQGTMVTVS  120
S                                                                 121

SEQ ID NO: 83            moltype = AA  length = 121
FEATURE                  Location/Qualifiers
source                   1..121
                         mol_type = protein
                         organism = synthetic construct
SEQUENCE: 83
QVQLLESGGG LVQPGGSLRL SCAASGFPFS SADMSWVRQA PGKGLEWVSY INADGSKTYY   60
ADTVKGRFTI SRDNSKNTLY LQMNSLRAED TAVYRCARAK LTDTHYVEDY WGQGTMVTVS  120
S                                                                 121

SEQ ID NO: 84            moltype = AA  length = 121
FEATURE                  Location/Qualifiers
source                   1..121
                         mol_type = protein
                         organism = synthetic construct
SEQUENCE: 84
QVQLQESGGG LVQPGGSLRL SCAASGFPFS SADMSWVRQA PGKGLEWVSV INADGSKTYY   60
ADTVKGRFTI SRDNSKNTLY LQMNSLRAED TAVYRCARAK LTDTHYVEDY WGQGTMVTVS  120
S                                                                 121

SEQ ID NO: 85            moltype = AA  length = 121
FEATURE                  Location/Qualifiers
source                   1..121
                         mol_type = protein
                         organism = synthetic construct
SEQUENCE: 85
QVQLQESGGG LVQPGGSLRL SCAASGFPFS SADMSWVRQA PGKGLEWVSY INADGSKTYY   60
ADTVKGRFTI SRDNSKNTLY LQMNSLRAED TAVYYCARAK LTDTHYVEDY WGQGTMVTVS  120
S                                                                 121

SEQ ID NO: 86            moltype = AA  length = 121
FEATURE                  Location/Qualifiers
source                   1..121
                         mol_type = protein
                         organism = synthetic construct
SEQUENCE: 86
QVQLQESGGG LVQPGGSLRL SCAASGFPFS SADMSWVRQA PGKGPEWVSY INADGSKTYY   60
ADTVKGRFTI SRDNSKNTLY LQMNSLRAED TAVYRCARAK LTDTHYVEDY WGQGTMVTVS  120
S                                                                 121

SEQ ID NO: 87            moltype = AA  length = 121
FEATURE                  Location/Qualifiers
source                   1..121
                         mol_type = protein
                         organism = synthetic construct
SEQUENCE: 87
QVQLQESGGG LVQPGGSLRL SCAASGFPFS SADMSWVRQA PGKGLEWVSY INADGSKTYY   60
```

```
PDTVKGRFTI SRDNSKNTLY LQMNSLRAED TAVYRCARAK LTDTHYVEDY WGQGTMVTVS    120
S                                                                   121

SEQ ID NO: 88           moltype = AA  length = 121
FEATURE                 Location/Qualifiers
source                  1..121
                        mol_type = protein
                        organism = synthetic construct
SEQUENCE: 88
QVQLQESGGG LVQPGGSLRL SCAASGFPFS SADMSWVRQA PGKGLEWVSY INADGSKTYY    60
ADTVKGRFTI SRDNSKNTLY LQMNNLRAED TAVYRCARAK LTDTHYVEDY WGQGTMVTVS    120
S                                                                   121

SEQ ID NO: 89           moltype = AA  length = 121
FEATURE                 Location/Qualifiers
source                  1..121
                        mol_type = protein
                        organism = synthetic construct
SEQUENCE: 89
QVQLQESGGG LVQPGGSLRL SCAASGFPFS SADMSWVRQA PGKGLEWVSY INADGSKTYY    60
ADTVKGRFTI SRDNSKNTLY LQMNSLRAED TALYRCARAK LTDTHYVEDY WGQGTMVTVS    120
S                                                                   121

SEQ ID NO: 90           moltype = AA  length = 121
FEATURE                 Location/Qualifiers
source                  1..121
                        mol_type = protein
                        organism = synthetic construct
SEQUENCE: 90
QVQLQESGGG MVQPGGSLRL SCAASGFPFS SADMSWVRQA PGKGLEWVSY INADGSKTYY    60
ADTVKGRFTI SRDNSKNTLY LQMNSLRAED TAVYRCARAK LTDTHYVEDY WGQGTQVTVS    120
S                                                                   121

SEQ ID NO: 91           moltype = AA  length = 121
FEATURE                 Location/Qualifiers
source                  1..121
                        mol_type = protein
                        organism = synthetic construct
SEQUENCE: 91
QVQLQESGGG LVQPGGSLRL SCAASGFPFS SADMSWVRQA PGKQREWVSY INADGSKTYY    60
ADTVKGRFTI SRDNSKNTLY LQMNSLRAED TAVYRCARAK LTDTHYVEDY WGQGTMVTVS    120
S                                                                   121

SEQ ID NO: 92           moltype = AA  length = 121
FEATURE                 Location/Qualifiers
source                  1..121
                        mol_type = protein
                        organism = synthetic construct
SEQUENCE: 92
QVQLQESGGG LVQPGGSLRL SCAASGFPFS SADMSWVRQA PGKGLEWVSY INAEGSKTYY    60
ADTVKGRFTI SRDNSKNTLY LQMNSLRAED TAVYRCARAK LTDTHYVEDY WGQGTMVTVS    120
S                                                                   121

SEQ ID NO: 93           moltype = AA  length = 121
FEATURE                 Location/Qualifiers
source                  1..121
                        mol_type = protein
                        organism = synthetic construct
SEQUENCE: 93
QVQLQESGGG LVQPGGSLRL SCAASGFPFS SADMSWVRQA PGKGLEWVSY INANGSKTYY    60
ADTVKGRFTI SRDNSKNTLY LQMNSLRAED TAVYRCARAK LTDTHYVEDY WGQGTMVTVS    120
S                                                                   121

SEQ ID NO: 94           moltype = AA  length = 120
FEATURE                 Location/Qualifiers
source                  1..120
                        mol_type = protein
                        organism = synthetic construct
SEQUENCE: 94
EVQLLESGGG LVQPGGSLRL SCAASGFTFS GSDMSWVRQA PGKGLEWVSA ITSGGTTYYA    60
DTVKGRFTIS RDNSKNTLYL QMNSLRAEDT AVYYCAKSRL TDSHYVEDAW GQGTLVTVSS   120

SEQ ID NO: 95           moltype = AA  length = 120
FEATURE                 Location/Qualifiers
source                  1..120
                        mol_type = protein
                        organism = synthetic construct
SEQUENCE: 95
EVQLLESGGG LVQPGGSLRL SCAASGFTFS GSDMSWVRQA PGKGLEWVSY ITSGGTTYYA    60
```

```
DTVKGRFTIS RDNSKNTLYL QMNSLRAEDT AVYYCAKSRL TDSHYVEDAW GQGTLVTVSS    120

SEQ ID NO: 96              moltype = AA  length = 120
FEATURE                    Location/Qualifiers
source                     1..120
                           mol_type = protein
                           organism = synthetic construct
SEQUENCE: 96
EVQLLESGGG LVQPGGSLRL SCAASGFTFS GSDMSWVRQA PGKGLEWVSY ITSGGTTYYA     60
DTVKGRFTIS RDNSKNTLYL QMNSLRAEDT AVYRCAKSRL TDSHYVEDAW GQGTLVTVSS    120

SEQ ID NO: 97              moltype = AA  length = 120
FEATURE                    Location/Qualifiers
source                     1..120
                           mol_type = protein
                           organism = synthetic construct
SEQUENCE: 97
QVQLLESGGG LVQPGGSLRL SCAASGFTFS GSDMSWVRQA PGKGPEWVSY ITSGGTTYYA     60
DTVKGRFTIS RDNSKNTLYL QMNSLRAEDT AVYYCAKSRL TDSHYVEDAW GQGTLVTVSS    120

SEQ ID NO: 98              moltype = AA  length = 120
FEATURE                    Location/Qualifiers
source                     1..120
                           mol_type = protein
                           organism = synthetic construct
SEQUENCE: 98
QVQLLESGGG LVQPGGSLRL SCAASGFTFS GSDMSWVRQA PGKGPEWVSY ITSGGTTYYA     60
DTVKGRFTIS RDNSKNTLYL QMNSLRAEDT AVYRCAKSRL TDSHYVEDAW GQGTLVTVSS    120

SEQ ID NO: 99              moltype = AA  length = 120
FEATURE                    Location/Qualifiers
source                     1..120
                           mol_type = protein
                           organism = synthetic construct
SEQUENCE: 99
QVQLQESGGG LVQPGGSLRL SCAASGFTFS GSDMSWVRQA PGKGPEWVSY ITSGGTTYYP     60
DTVKGRFTIS RDNSKNTLYL QMNSLRAEDT AVYYCAKSRL TDSHYVEDAW GQGTQVTVSS    120

SEQ ID NO: 100             moltype = AA  length = 120
FEATURE                    Location/Qualifiers
source                     1..120
                           mol_type = protein
                           organism = synthetic construct
SEQUENCE: 100
QVQLQESGGG LVQPGGSLRL SCAASGFTFS GSDMSWVRQA PGKGPEWVSY ITSGGTTYYP     60
DTVKGRFTIS RDNSKNTLYL QMNSLRAEDT AVYRCAKSRL TDSHYVEDAW GQGTQVTVSS    120

SEQ ID NO: 101             moltype = AA  length = 120
FEATURE                    Location/Qualifiers
source                     1..120
                           mol_type = protein
                           organism = synthetic construct
SEQUENCE: 101
QVQLQESGGG LVQPGGSLRL SCAASGFTFS GSDMSWVRQA PGKGPEWVSY ITSGGTTYYP     60
DTVKGRFTIS RDNSKNTLYL QMNSLKPDDT AVYRCAKSRL TDSHYVEDAW GQGTQVTVSS    120

SEQ ID NO: 102             moltype = AA  length = 120
FEATURE                    Location/Qualifiers
source                     1..120
                           mol_type = protein
                           organism = synthetic construct
SEQUENCE: 102
QVQLQESGGG LVQPGGSLRL SCAASGFTFS GSDMSWVRQA PGKGPEWVSY ITSGGTTYYP     60
DTVKGRFTIS RDNAKNTLYL QMNSLKPDDT ALYRCAKSRL TDSHYVEDAW GQGTQVTVSS    120

SEQ ID NO: 103             moltype = AA  length = 120
FEATURE                    Location/Qualifiers
source                     1..120
                           mol_type = protein
                           organism = synthetic construct
SEQUENCE: 103
EVQLVESGGG LIQPGGSLRL SCAASGFTFS GSDMSWVRQA PGKGLEWVSV ITSGGTTYYA     60
DTVKGRFTIS RDNSKNTLYL QMNSLRAEDT AVYYCAKSRL TDSHYVEDAW GQGTLVTVSS    120

SEQ ID NO: 104             moltype = AA  length = 120
FEATURE                    Location/Qualifiers
source                     1..120
                           mol_type = protein
                           organism = synthetic construct
```

```
SEQUENCE: 104
QVQLQESGGG LIQPGGSLRL SCAASGFTFS GSDMSWVRQA PGKGPEWVSY ITSGGTTYYP    60
DTVKGRFTIS RDNSKNTLYL QMNSLRADDT ALYRCAKSRL TDSHYVEDAW GQGTLVTVSS   120

SEQ ID NO: 105          moltype = AA  length = 120
FEATURE                 Location/Qualifiers
source                  1..120
                        mol_type = protein
                        organism = synthetic construct
SEQUENCE: 105
QVQLQESGGG LIQPGGSLRL SCAASGFTFS GSDMSWVRQA PGKGLEWVSY ITSGGTTYYA    60
DTVKGRFTIS RDNSKNTLYL QMNSLRAEDT AVYRCAKSRL TDSHYVEDAW GQGTLVTVSS   120

SEQ ID NO: 106          moltype = AA  length = 120
FEATURE                 Location/Qualifiers
source                  1..120
                        mol_type = protein
                        organism = synthetic construct
SEQUENCE: 106
EVQLQESGGG LIQPGGSLRL SCAASGFTFS GSDMSWVRQA PGKGLEWVSY ITSGGTTYYA    60
DTVKGRFTIS RDNSKNTLYL QMNSLRAEDT AVYRCAKSRL TDSHYVEDAW GQGTLVTVSS   120

SEQ ID NO: 107          moltype = AA  length = 120
FEATURE                 Location/Qualifiers
source                  1..120
                        mol_type = protein
                        organism = synthetic construct
SEQUENCE: 107
QVQLVESGGG LIQPGGSLRL SCAASGFTFS GSDMSWVRQA PGKGLEWVSY ITSGGTTYYA    60
DTVKGRFTIS RDNSKNTLYL QMNSLRAEDT AVYRCAKSRL TDSHYVEDAW GQGTLVTVSS   120

SEQ ID NO: 108          moltype = AA  length = 120
FEATURE                 Location/Qualifiers
source                  1..120
                        mol_type = protein
                        organism = synthetic construct
SEQUENCE: 108
QVQLQESGGG LIQPGGSLRL SCAASGFTFS GSDMSWVRQA PGKGLEWVSV ITSGGTTYYA    60
DTVKGRFTIS RDNSKNTLYL QMNSLRAEDT AVYRCAKSRL TDSHYVEDAW GQGTLVTVSS   120

SEQ ID NO: 109          moltype = AA  length = 120
FEATURE                 Location/Qualifiers
source                  1..120
                        mol_type = protein
                        organism = synthetic construct
SEQUENCE: 109
QVQLQESGGG LIQPGGSLRL SCAASGFTFS GSDMSWVRQA PGKGLEWVSY ITSGGTTYYA    60
DTVKGRFTIS RDNSKNTLYL QMNSLRAEDT AVYYCAKSRL TDSHYVEDAW GQGTLVTVSS   120

SEQ ID NO: 110          moltype = AA  length = 120
FEATURE                 Location/Qualifiers
source                  1..120
                        mol_type = protein
                        organism = synthetic construct
SEQUENCE: 110
QVQLQESGGG LIQPGGSLRL SCAASGFTFS GSDMSWVRQA PGKGPEWVSY ITSGGTTYYA    60
DTVKGRFTIS RDNSKNTLYL QMNSLRAEDT AVYRCAKSRL TDSHYVEDAW GQGTLVTVSS   120

SEQ ID NO: 111          moltype = AA  length = 120
FEATURE                 Location/Qualifiers
source                  1..120
                        mol_type = protein
                        organism = synthetic construct
SEQUENCE: 111
QVQLQESGGG LIQPGGSLRL SCAASGFTFS GSDMSWVRQA PGKGLEWVSY ITSGGTTYYP    60
DTVKGRFTIS RDNSKNTLYL QMNSLRAEDT AVYRCAKSRL TDSHYVEDAW GQGTLVTVSS   120

SEQ ID NO: 112          moltype = AA  length = 120
FEATURE                 Location/Qualifiers
source                  1..120
                        mol_type = protein
                        organism = synthetic construct
SEQUENCE: 112
QVQLQESGGG LIQPGGSLRL SCAASGFTFS GSDMSWVRQA PGKGLEWVSY ITSGGTTYYA    60
DTVKGRFTIS RDNSKNTLYL QMNSLRADDT AVYRCAKSRL TDSHYVEDAW GQGTLVTVSS   120

SEQ ID NO: 113          moltype = AA  length = 120
FEATURE                 Location/Qualifiers
source                  1..120
```

```
                                mol_type = protein
                                organism = synthetic construct
SEQUENCE: 113
QVQLQESGGG LIQPGGSLRL SCAASGFTFS GSDMSWVRQA PGKGLEWVSY ITSGGTTYYA      60
DTVKGRFTIS RDNSKNTLYL QMNSLRAEDT ALYRCAKSRL TDSHYVEDAW GQGTLVTVSS     120

SEQ ID NO: 114                  moltype = AA  length = 120
FEATURE                         Location/Qualifiers
source                          1..120
                                mol_type = protein
                                organism = synthetic construct
SEQUENCE: 114
QVQLQESGGG LIEPGGSLRL SCAASGFTFS GSDMSWVRQA PGKGLEWVSY ITSGGTTYYA      60
DTVKGRFTIS RDNSKNTLYL QMNSLRAEDT AVYRCAKSRL TDSHYVEDAW GQGTQVTVSS     120

SEQ ID NO: 115                  moltype = AA  length = 120
FEATURE                         Location/Qualifiers
source                          1..120
                                mol_type = protein
                                organism = synthetic construct
SEQUENCE: 115
QVQLQESGGG LIQPGGSLRL SCAASGFTFS GSDMSWYRQA PGKGREWVSY ITSGGTTYYA      60
DTVKGRFTIS RDNSKNTLYL QMNSLRAEDT AVYRCAKSRL TDSHYVEDAW GQGTLVTVSS     120

SEQ ID NO: 116                  moltype = AA  length = 17
FEATURE                         Location/Qualifiers
source                          1..17
                                mol_type = protein
                                organism = synthetic construct
SEQUENCE: 116
MSWVRQAPGK GPEWVSY                                                     17

SEQ ID NO: 117                  moltype = AA  length = 17
FEATURE                         Location/Qualifiers
source                          1..17
                                mol_type = protein
                                organism = synthetic construct
SEQUENCE: 117
MSWVRQAPGK GLEWVSY                                                     17

SEQ ID NO: 118                  moltype = AA  length = 17
FEATURE                         Location/Qualifiers
source                          1..17
                                mol_type = protein
                                organism = synthetic construct
SEQUENCE: 118
MSWVRQAPGK GLEWVSV                                                     17

SEQ ID NO: 119                  moltype = AA  length = 17
FEATURE                         Location/Qualifiers
source                          1..17
                                mol_type = protein
                                organism = synthetic construct
SEQUENCE: 119
MSWVRQAPGK QREWVSY                                                     17

SEQ ID NO: 120                  moltype = AA  length = 17
FEATURE                         Location/Qualifiers
source                          1..17
                                mol_type = protein
                                organism = synthetic construct
SEQUENCE: 120
MSWVRQAPGK GLEWVSA                                                     17

SEQ ID NO: 121                  moltype = AA  length = 17
FEATURE                         Location/Qualifiers
source                          1..17
                                mol_type = protein
                                organism = synthetic construct
VARIANT                         11..17
                                note = Xaa is any amino acid
SEQUENCE: 121
MSWVRQAPGK XXEWVSX                                                     17

SEQ ID NO: 122                  moltype = AA  length = 8
FEATURE                         Location/Qualifiers
source                          1..8
                                mol_type = protein
                                organism = synthetic construct
```

```
VARIANT                   3..7
                          note = Xaa is any amino acid
SEQUENCE: 122
GFXFSXXD                                                               8

SEQ ID NO: 123            moltype = AA  length = 8
FEATURE                   Location/Qualifiers
source                    1..8
                          mol_type = protein
                          organism = synthetic construct
SEQUENCE: 123
INANGSKT                                                               8

SEQ ID NO: 124            moltype = AA  length = 8
FEATURE                   Location/Qualifiers
source                    1..8
                          mol_type = protein
                          organism = synthetic construct
SEQUENCE: 124
INAEGSKT                                                               8

SEQ ID NO: 125            moltype =     length =
SEQUENCE: 125
000

SEQ ID NO: 126            moltype = AA  length = 14
FEATURE                   Location/Qualifiers
source                    1..14
                          mol_type = protein
                          organism = synthetic construct
VARIANT                   2..14
                          note = Xaa is any amino acid
SEQUENCE: 126
AXXXLTDXHY VEDX                                                       14

SEQ ID NO: 127            moltype = AA  length = 5
FEATURE                   Location/Qualifiers
source                    1..5
                          mol_type = protein
                          organism = synthetic construct
SEQUENCE: 127
SADMH                                                                  5

SEQ ID NO: 128            moltype =     length =
SEQUENCE: 128
000

SEQ ID NO: 129            moltype = AA  length = 17
FEATURE                   Location/Qualifiers
source                    1..17
                          mol_type = protein
                          organism = synthetic construct
SEQUENCE: 129
RINADGSKTS YADTVKG                                                    17

SEQ ID NO: 130            moltype = AA  length = 17
FEATURE                   Location/Qualifiers
source                    1..17
                          mol_type = protein
                          organism = synthetic construct
SEQUENCE: 130
YINADGSKTS YADTVKG                                                    17

SEQ ID NO: 131            moltype = AA  length = 17
FEATURE                   Location/Qualifiers
source                    1..17
                          mol_type = protein
                          organism = synthetic construct
SEQUENCE: 131
YINADGSKTY YPDTVKG                                                    17

SEQ ID NO: 132            moltype = AA  length = 17
FEATURE                   Location/Qualifiers
source                    1..17
                          mol_type = protein
                          organism = synthetic construct
SEQUENCE: 132
VINADGSKTY YADTVKG                                                    17
```

| | | |
|---|---|---|
| SEQ ID NO: 133<br>FEATURE<br>source | moltype = AA  length = 17<br>Location/Qualifiers<br>1..17<br>mol_type = protein<br>organism = synthetic construct | |
| SEQUENCE: 133<br>YINADGSKTY YADTVKG | | 17 |
| SEQ ID NO: 134<br>FEATURE<br>source | moltype = AA  length = 17<br>Location/Qualifiers<br>1..17<br>mol_type = protein<br>organism = synthetic construct | |
| SEQUENCE: 134<br>YINAEGSKTY YADTVKG | | 17 |
| SEQ ID NO: 135<br>FEATURE<br>source | moltype = AA  length = 17<br>Location/Qualifiers<br>1..17<br>mol_type = protein<br>organism = synthetic construct | |
| SEQUENCE: 135<br>YINANGSKTY YADTVKG | | 17 |
| SEQ ID NO: 136<br>FEATURE<br>source | moltype = AA  length = 16<br>Location/Qualifiers<br>1..16<br>mol_type = protein<br>organism = synthetic construct | |
| SEQUENCE: 136<br>AITSGGTTYY ADTVKG | | 16 |
| SEQ ID NO: 137<br>FEATURE<br>source | moltype = AA  length = 16<br>Location/Qualifiers<br>1..16<br>mol_type = protein<br>organism = synthetic construct | |
| SEQUENCE: 137<br>YITSGGTTYY ADTVKG | | 16 |
| SEQ ID NO: 138<br>FEATURE<br>source | moltype = AA  length = 16<br>Location/Qualifiers<br>1..16<br>mol_type = protein<br>organism = synthetic construct | |
| SEQUENCE: 138<br>YITSGGTTYY PDTVKG | | 16 |
| SEQ ID NO: 139<br>FEATURE<br>source | moltype = AA  length = 16<br>Location/Qualifiers<br>1..16<br>mol_type = protein<br>organism = synthetic construct | |
| SEQUENCE: 139<br>VITSGGTTYY ADTVKG | | 16 |
| SEQ ID NO: 140<br>FEATURE<br>source<br><br>VARIANT | moltype = AA  length = 17<br>Location/Qualifiers<br>1..17<br>mol_type = protein<br>organism = synthetic construct<br>1..14<br>note = Xaa is any amino acid | |
| SEQUENCE: 140<br>XIXXXXXXTX YXDXVKG | | 17 |
| SEQ ID NO: 141<br>FEATURE<br>source | moltype = AA  length = 12<br>Location/Qualifiers<br>1..12<br>mol_type = protein<br>organism = synthetic construct | |
| SEQUENCE: 141<br>SRLTDSHYVE DA | | 12 |
| SEQ ID NO: 142<br>FEATURE<br>source | moltype = AA  length = 12<br>Location/Qualifiers<br>1..12<br>mol_type = protein<br>organism = synthetic construct | |

```
VARIANT                 1..12
                        note = Xaa is any amino acid
SEQUENCE: 142
XXLTDXHYVE DX                                                            12

SEQ ID NO: 143          moltype = AA   length = 121
FEATURE                 Location/Qualifiers
source                  1..121
                        mol_type = protein
                        organism = synthetic construct
VARIANT                 1..116
                        note = Xaa is any amino acid
SEQUENCE: 143
XVQLXESGGG XVQXGGSLRL SCAASGFPFS SADMSWVRQA PGKXXEWVSX INAXGSKTYY         60
XDXVKGRFTI SRDNXKNTLY LXMNXLXXED TAXYXCARAK LTDTHYVEDY WGQGTXVTVS        120
S                                                                        121

SEQ ID NO: 144          moltype = AA   length = 120
FEATURE                 Location/Qualifiers
source                  1..120
                        mol_type = protein
                        organism = synthetic construct
VARIANT                 1..115
                        note = Xaa is any amino acid
SEQUENCE: 144
XVQLXESGGG LXXXGGSLRL SCAASGFTFS GSDMSWVRQA PGKGXEWVSX ITSGGTTYYX         60
DXVKGRFTIS RDNXKNTLYL QMNSLXXXDT AXYXCAKSRL TDSHYVEDAW GQGTXVTVSS        120

SEQ ID NO: 145          moltype = AA   length = 121
FEATURE                 Location/Qualifiers
source                  1..121
                        mol_type = protein
                        organism = synthetic construct
VARIANT                 11..110
                        note = Xaa is any amino acid
SEQUENCE: 145
QVQLQESGGG XVXXGXSLRL SCAASGFXFS XXDMSWVRQA PGKGPEWVSY IXXXXXXTXY         60
PDSVKGRFTX SRDNAKNXLY LXMNXLXPXD TALYRCAXXX LTDXHYVEDX WGQGTQVTVS        120
S                                                                        121

SEQ ID NO: 146          moltype = AA   length = 121
FEATURE                 Location/Qualifiers
source                  1..121
                        mol_type = protein
                        organism = synthetic construct
VARIANT                 1..116
                        note = Xaa is any amino acid
SEQUENCE: 146
XVQLXESGGG XXXXGXSLRL SCAASGFXFS XXDMXWXRQA PGKXXXWVSX IXXXGXXTXY         60
XDXVKGRFTX SRDNXKNXLY LXMNXLXXXD TAXYXCAXXX LTDXHYVEDX WGQGTXVTVS        120
S                                                                        121

SEQ ID NO: 147          moltype = AA   length = 313
FEATURE                 Location/Qualifiers
source                  1..313
                        mol_type = protein
                        organism = synthetic construct
SEQUENCE: 147
MARGPGLAPP PLRLPLLLLV LAAVTGPTNK MTVCSPDGPG GRCQCRALGS GMAVDCSTLT         60
SKCLLLKARM SAPKNARTLV RPSEHALVDN DGLYDPDCDP EGRFKARQCN QTSVCWCVNS        120
VGVRRTDKGD LSLRCDDLVR THHILIDLRH RPTAGAFNHS DLDAELRRLF RERYRLHPKF        180
VAAVHYEQPT IQIELRQNTS QKAAGEVDIG DAAYYFERDI KGESLFQGRG GLDLRVRGEP        240
LQVERTLIYY LDEIPPKFSM KRLTAGLIAV IVVVVALVA GMAVLITNR RKSGKYKKVE          300
IKELGELRKE PSL                                                           313

SEQ ID NO: 148          moltype = AA   length = 304
FEATURE                 Location/Qualifiers
source                  1..304
                        mol_type = protein
                        organism = synthetic construct
SEQUENCE: 148
MARGPGLAPP PLRLPLLLLV LAAVTGSPDG PGGRCQCRAL GSGMAVDCST LTSKCLLLKA         60
RMSAPKNART LVRPSEHALV DNDGLYDPDC DPEGRFKARQ CNQTSVCWCV NSVGVRRTDK        120
GDLSLRCDDL VRTHHILIDL RHRPTAGAFN HSDLDAELRR LFRERYRLHP KFVAAVHYEQ        180
PTIQIELRQN TSQKAAGEVD IGDAAYYFER DIKGESLFQG RGGLDLRVRG EPLQVERTLI        240
YYLDEIPPKF SMKRLTAGLI AVIVVVVVAL VAGMAVLVIT NRKSGKYKKV EIKELGELRK        300
EPSL                                                                     304

SEQ ID NO: 149          moltype = AA   length = 293
```

```
FEATURE                 Location/Qualifiers
source                  1..293
                        mol_type = protein
                        organism = synthetic construct
SEQUENCE: 149
MARGPGLAPP PLRLPLLLLV LAAVTGALGS GMAVDCSTLT SKCLLLKARM SAPKNARTLV     60
RPSEHALVDN DGLYDPDCDP EGRFKARQCN QTSVCWCVNS VGVRRTDKGD LSLRCDDLVR    120
THHILIDLRH RPTAGAFNHS DLDAELRRLF RERYRLHPKF VAAVHYEQPT IQIELRQNTS    180
QKAAGEVDIG DAAYYFERDI KGESLFQGRG GLDLRVRGEP LQVERTLIYY LDEIPPKFSM    240
KRLTAGLIAV IVVVVALVA GMAVLVITNR RKSGKYKKVE IKELGELRKE PSL            293

SEQ ID NO: 150          moltype = AA   length = 485
FEATURE                 Location/Qualifiers
source                  1..485
                        mol_type = protein
                        organism = synthetic construct
SEQUENCE: 150
QVQLQESGGG LVQPGRSLRL SCAASGFTFS GSDMSWVRQA PGKGPEWVSY ITGSGTTYYP     60
DSVKGRFTTS RDNAKNMLYL QMNSLKPDDT ALYRCAKARL TDSHYVEDAW GQGTQVTVSS    120
EPKSCDKTHT CPPCPAPELL GGPSVFLFPP KPKDTLMISR TPEVTCVVVD VSHEDPEVKF    180
NWYVDGVEVH NAKTKPREEQ YNSTYRVVSV LTVLHQDWLN GKEYKCKVSN KALPAPIEKT    240
ISKAKGQPRE PQVYTLPPSR EEMTKNQVSL TCLVKGFYPS DIAVEWESNG QPENNYKTTP    300
PVLDSDGSFF LYSKLTVDKS RWQQGNVFSC SVMHEALHNH YTQKSLSLSP GKAPAPAPAP    360
APAPAPAPAP APKAQVQLQE SGGGLVQPGG SLRLSCAASR FDFSVNDIRW YRQAPGNERE    420
LVARITGGGR TDYADSVKGR FTISRDNAKN TVYLQMNNLK PEDTAVYYCW GRGYWGQGTQ    480
VTVSS                                                                485

SEQ ID NO: 151          moltype = AA   length = 485
FEATURE                 Location/Qualifiers
source                  1..485
                        mol_type = protein
                        organism = synthetic construct
SEQUENCE: 151
QVQLQESGGG LVQPGGSLRL SCAASRFDFS VNDIRWYRQA PGNERELVAR ITGGGRTDYA     60
DSVKGRFTIS RDNAKNTVYL QMNNLKPEDT AVYYCWGRGY WGQGTQVTVS SEPKSCDKTH    120
TCPPCPAPEL LGGPSVFLFP PKPKDTLMIS RTPEVTCVVV DVSHEDPEVK FNWYVDGVEV    180
HNAKTKPREE QYNSTYRVVS VLTVLHQDWL NGKEYKCKVS NKALPAPIEK TISKAKGQPR    240
EPQVYTLPPS REEMTKNQVS LTCLVKGFYP SDIAVEWESN GQPENNYKTT PPVLDSDGSF    300
FLYSKLTVDK SRWQQGNVFS CSVMHEALHN HYTQKSLSLS PGKAPAPAPA PAPAPAPAPA    360
PAPKAQVQLQ ESGGGLVQPG RSLRLSCAAS GFTFSGSDMS WVRQAPGKGP EWVSYITGSG    420
TTYYPDSVKG RFTTSRDNAK NMLYLQMNSL KPDDTALYRC AKARLTDSHY VEDAWGQGTQ    480
VTVSS                                                                485

SEQ ID NO: 152          moltype = AA   length = 348
FEATURE                 Location/Qualifiers
source                  1..348
                        mol_type = protein
                        organism = synthetic construct
SEQUENCE: 152
QVQLQESGGG MVQVGGSLRL SCAASGFPFS SADMSWVRQA PGKGPEWVSY INADGSKTYY     60
PDSVKGRFTI SRDNAKNTLY LLMNNLKPED TALYRCARAK LTDTHYVEDY WGQGTQVTVS    120
SVPRDCGCKP CICTVPEVSS VFIFPPKPKD VLTITLTPKV TCVVVDISKD DPEVQFSWFV    180
DDDVEVHTAQT QPREEQFNST FRSVSELPIM HQDWLNGKEF KCRVNSAAFP APIEKTISKT    240
KGRPKAPQVY TIPPPKEQMA KDKVSLTCMI TDFFPEDITV EWQWNGQPAE NYKNTQPIMN    300
TNGSYFVYSK LNVQKSNWEA GNTFTCSVLH EGLHNHHTEK SLSHSPGK                348

SEQ ID NO: 153          moltype = AA   length = 347
FEATURE                 Location/Qualifiers
source                  1..347
                        mol_type = protein
                        organism = synthetic construct
SEQUENCE: 153
QVQLQESGGG LVEAGGSLRL SCAASGFTFS GSDMSWVRQA PGKGPEWVSY ITSGGTTYYP     60
DSVKGRFTIS RDNAKNTYL QMNSLKPDDT ALYRCAKSRL TDSHYVEDAW GQGTQVTVSS    120
VPRDCGCKPC ICTVPEVSSV FIFPPKPKDV LTITLTPKVT CVVVDISKDD PEVQFSWFVD    180
DVEVHTAQTQ PREEQFNSTF RSVSELPIMH QDWLNGKEFK CRVNSAAFPA PIEKTISKTK    240
GRPKAPQVYT IPPPKEQMAK DKVSLTCMIT DFFPEDITVE WQWNGQPAEN YKNTQPIMNT    300
NGSYFVYSKL NVQKSNWEAG NTFTCSVLHE GLHNHHTEKS LSHSPGK                 347

SEQ ID NO: 154          moltype = AA   length = 354
FEATURE                 Location/Qualifiers
source                  1..354
                        mol_type = protein
                        organism = synthetic construct
SEQUENCE: 154
DVQLVESGGG SVQAGGSLRL SCAASGSTDS IEYMTWFRQA PGKAREGVAA LYTHTGNTYY     60
TDSVKGRFTI SQDKAKNMAY LRMDSVKSED TAIYTCGATR KYVPVRFALD QSSYDYWGQG    120
TQVTVSSVPR DCGCKPCICT VPEVSSVFIF PPKPKDVLTI TLTPKVTCVV VDISKDDPEV    180
QFSWFVDDVE VHTAQTQPRE EQFNSTFRSV SELPIMHQDW LNGKEFKCRV NSAAFPAPIE    240
```

-continued

```
KTISKTKGRP KAPQVYTIPP PKEQMAKDKV SLTCMITDFF PEDITVEWQW NGQPAENYKN    300
TQPIMNTNGS YFVYSKLNVQ KSNWEAGNTF TCSVLHEGLH NHHTEKSLSH SPGK          354

SEQ ID NO: 155             moltype = AA   length = 111
FEATURE                    Location/Qualifiers
source                     1..111
                           mol_type = protein
                           organism = synthetic construct
SEQUENCE: 155
QVQLQESGGG LVQPGGSLRL SCAASRFDFS VNDIRWYRQA PGNERELVAR ITGGGRTDYA    60
DSVKGRFTIS RDNAKNTVYL QMNNLKPEDT AVYYCWGRGY WGQGTQVTVS S             111

SEQ ID NO: 156             moltype = AA   length = 5
FEATURE                    Location/Qualifiers
source                     1..5
                           mol_type = protein
                           organism = synthetic construct
SEQUENCE: 156
VNDIR                                                                5

SEQ ID NO: 157             moltype = AA   length = 16
FEATURE                    Location/Qualifiers
source                     1..16
                           mol_type = protein
                           organism = synthetic construct
SEQUENCE: 157
RITGGGRTDY ADSVKG                                                    16

SEQ ID NO: 158             moltype = AA   length = 5
FEATURE                    Location/Qualifiers
source                     1..5
                           mol_type = protein
                           organism = synthetic construct
SEQUENCE: 158
WGRGY                                                                5

SEQ ID NO: 159             moltype = AA   length = 8
FEATURE                    Location/Qualifiers
source                     1..8
                           mol_type = protein
                           organism = synthetic construct
SEQUENCE: 159
RFDFSVND                                                             8

SEQ ID NO: 160             moltype = AA   length = 7
FEATURE                    Location/Qualifiers
source                     1..7
                           mol_type = protein
                           organism = synthetic construct
SEQUENCE: 160
ITGGGRT                                                              7

SEQ ID NO: 161             moltype = AA   length = 5
FEATURE                    Location/Qualifiers
source                     1..5
                           mol_type = protein
                           organism = synthetic construct
SEQUENCE: 161
WGRGY                                                                5

SEQ ID NO: 162             moltype = AA   length = 349
FEATURE                    Location/Qualifiers
source                     1..349
                           mol_type = protein
                           organism = synthetic construct
SEQUENCE: 162
QVQLQESGGG LVEAGGSLRL SCAASGFTFS GSDMSWVRQA PGKGPEWVSY ITSGGTTYYP    60
DSVKGRFTIS RDNAKNTLYL QMNSLKPDDT ALYRCAKSRL TDSHYVEDAW GQGTQVTVSS    120
ESKYGPPCPP CPAPEAAGGP SVFLFPPKPK DTLMISRTPE VTCVVVDVSQ EDPEVQFNWY    180
VDGVEVHNAK TKPREEQFNS TYRVVSVLTV LHQDWLNGKE YKCKVSNKGL PSSIEKTISK    240
AKGQPREPQV YTLPPSQEEM TKNQVSLTCL VKGFYPSDIA VEWESNGQPE NNYKTTPPVL    300
DSDGSFFLYS RLTVDKSRWQ EGNVFSCSVM HEALHNHYTQ KSLSLSLGK                349

SEQ ID NO: 163             moltype = AA   length = 22
FEATURE                    Location/Qualifiers
source                     1..22
                           mol_type = protein
                           organism = synthetic construct
SEQUENCE: 163
```

```
APAPAPAPAP APAPAPAPAP KA                                                    22

SEQ ID NO: 164           moltype = AA  length = 274
FEATURE                  Location/Qualifiers
source                   1..274
                         mol_type = protein
                         organism = synthetic construct
SEQUENCE: 164
MARGPGLAPP PLRLPLLLLV LAAVTGHTAA QDNCTCPTNK MTVCSPDGPG GRCQCRALGS    60
GMAVDCSTLT SKCLLLKARM SAPKNARTLV RPSEHALVDN DGLYDPDCDP EGRFKARQCN   120
QTSVCWCVNS VGVRRTDKGD LSLRCDELVR THHILIDLRH RPTAGAFNHS DLDAELRRLF   180
RERYRLHPKF VAAVHYEQPT IQIELRQNTS QKAAGDVDIG DAAYYFERDI KGESLFQGRG   240
GLDLRVRGEP LQVERTLIYY LDEIPPKFSM KRLT                              274

SEQ ID NO: 165           moltype = DNA  length = 1056
FEATURE                  Location/Qualifiers
source                   1..1056
                         mol_type = other DNA
                         organism = synthetic construct
SEQUENCE: 165
caggtgcaat tgcaagagtc tggcggcgga atggtgcacc tggtggatc tctgagactg     60
tcttgtgccg cctccggctt cacctttctct ggctctgata tgtcctgggt ccgacaggct  120
cctggcaagg gacctgaatg ggtgtcctac atcacctccg gcggcaccac ctactatccc  180
gactctgtga agggcagatt caccatctct cgggacaacg ccaagaacac cctgtacctg  240
cagatgaact ctctgacccc tgacgacaca gccctgtaca gatgtgccaa ggccagactg  300
accgacagcc actacgtgga agatgcttgg ggccaggaca caggtcac cgtgtctagt    360
gaacccaagt cctgcgacaa gacccacacc tgtcctccat gtcctgctcc agaactgctc  420
ggcggacctt ccgtgttcct gtttcctcca aagcctaagg acaccctgat gatctctcgg  480
accccctgaag tgacctgcgt ggtggtggat gtgtctcacg aggatcccga agtgaagttc  540
aattggtacg tggacggcgt ggaagtgcac aacgccaagc ccaagcctag agaggaacag  600
tacaactcca cctacagagt ggtgtccgtg ctgaccgtgc tgcaccagga ttggctgaac  660
ggcaaagagt acaagtgcaa ggtgtccaac aaggccctgc ctgctcctat cgaaaagacc  720
atctccaagg ccaggggcca gcctaggaa ccccaggttt acaccctgcc tccaagccgg   780
gaagagatga ccaagaacca ggtgtccctg acctgcctgg tcaagggctt ctaccttcc   840
gatatcgccg tggaatggga gagcaatggc cagcctgaga acaactacaa gacaacccct  900
cctgtgctgg actccgacgg ctcattcttc ctgtactcca agctgacagt ggacaagtcc  960
agatggcagc agggcaacgt gttcctcctgc tccgtgatgc acgaggccct gcacaatcac 1020
tacacccaga agtccctgtc tctgtccct ggcaaa                            1056

SEQ ID NO: 166           moltype = DNA  length = 1059
FEATURE                  Location/Qualifiers
source                   1..1059
                         mol_type = other DNA
                         organism = synthetic construct
SEQUENCE: 166
caggtgcaat tgcaagagtc tggcggcgga atggtgcaag tcggcggatc tctgagactg    60
tcttgtgccg cctctggctt ccctttctcc tccgccgata tgtcctgggt ccgacaggct  120
cctggaaagg gacctgagtg ggtgtcctac atcaacgccg acggctccaa gacctactat  180
cccgactctg tgaagggcag attcaccatc tctcgggaca cgccaagaa caccctgtac  240
ctgctgatga caacctgaa gcctgaggac acagccctgt acagatgcgc cagagccaag  300
ctgaccgaca cacactacgt ggaagattac tgggggcagg gcacacaggt gaccgtgtct  360
agtgaaccca gtcctgcgca aagacccac acctgtcctc catgtcctgc tccagaactg  420
ctcggcggac cttccgtgtt cctgtttcct ccaaagccta ggacaccct gatgatctct   480
cggacccctg aagtgacctg cgtggtggtg gatgtgtctc acgaggatcc cgaagtgaag  540
ttcaattggt acgtggacgg cgtggaagtg cacaacgcca agcccaagcc tagagaggaa  600
cagtacaact ccacctacag agtggtgtcc gtgctgaccg tgctgcacca ggattggctg  660
aacggcaaag agtacaagtg caaggtgtcc aacaaggccc tgcctgctcc tatcgaaaag  720
accatctcca aggccaaggg ccagcctagg aaccccaggt ttacaccct gcctccaagc   780
cgggaagaga tgaccaagaa ccaggtgtcc tgacctgcc tggtcaaggg cttctaccct  840
tccgatatcg ccgtggaatg ggagagcaat ggccagcctg agaacaacta caagacaacc  900
cctcctgtgc tggactccga cggctcattc ttcctgtact ccaagctgac agtggacaag  960
tccagatggc agcagggcaa cgtgttcctc tgctccgtga tgcacgaggc cctgcacaat 1020
cactacaccc agaagtccct gtctctgtcc cctggcaaa                        1059

SEQ ID NO: 167           moltype = DNA  length = 1059
FEATURE                  Location/Qualifiers
source                   1..1059
                         mol_type = other DNA
                         organism = synthetic construct
SEQUENCE: 167
caggtgcaat tgcaagagtc tggcggcgga atggtgcagc tggtggatc tctgagactg    60
tcttgtgccg cctccggctt caccttctcc aactacgaca tgtcctgggt ccgacaggct  120
cctggaaagg gacctgagtg ggtgtcctac atcaacgctg cggctccaa caccgactat   180
cccgactctg tgaagggcag attcaccatc tctcgggaca cgccaagaa caccctgtac  240
ctgctgatga caacctgaa gcctgaggac acagccctgt acagatgcgc cagagccaag  300
ctgaccgaca cacactacgt ggaagattac tgggggcagg gcacacaggt caccgtgtct  360
agtgaaccca gtcctgcgca aagacccac acctgtcctc catgtcctgc tccagaactg  420
ctcggcggac cttccgtgtt cctgtttcct ccaaagccta ggacaccct gatgatctct   480
cggacccctg aagtgacctg cgtggtggtg gatgtgtctc acgaggatcc cgaagtgaag  540
```

```
ttcaattggt acgtggacgg cgtggaagtg cacaacgcca agaccaagcc tagagaggaa    600
cagtacaact ccacctacag agtggtgtcc gtgctgaccg tgctgcacca ggattggctg    660
aacggcaaag agtacaagtg caaggtgtcc aacaaggccc tgcctgctcc tatcgaaaag    720
accatctcca aggccaaggg ccagcctagg aacccccagg tttacaccct gcctccaagc    780
cgggaagaga tgaccaagaa ccaggtgtcc ctgacctgcc tggtcaaggg cttctaccct    840
tccgatatcg ccgtggaatg ggagagcaat ggccagcctg agaacaacta caagacaacc    900
cctcctgtgc tggactccga cggctcattc ttcctgtact ccaagctgac agtggacaag    960
tccagatggc agcagggcaa cgtgttctcc tgctccgtga tgcacgaggc cctgcacaat   1020
cactacaccc agaagtccct gtctctgtcc cctggcaaa                          1059

SEQ ID NO: 168           moltype = DNA   length = 1056
FEATURE                  Location/Qualifiers
source                   1..1056
                         mol_type = other DNA
                         organism = synthetic construct SEQUENCE: 168
caggtgcaat tgcaagagtc tggcggcgga ctggtgcagc ctggaagatc tctgagactg     60
tcttgtgccg cctccggctt cacctttctct ggctctgtga tgtcctgggt ccgacaggct   120
cctggcaagg gacctgaatg ggtgtcctac atcaccggct ccggcaccac ctactatccc    180
gactctgtga agggcagatt caccacctcc agagacaacg ccaagaacat gctgtacctg    240
cagatgaact ccctgaagcc tgacgacaca gccctgtaca gatgcgccaa ggccagactg    300
accgacagcc actacgtgga agatgcttgg ggccagggaa cacaggtcac cgtgtctagt    360
gaacccaagt cctgcgacaa gacccacacc tgtcctccat gtcctgctcc agaactgctc    420
ggcggacctt ccgtgttcct gtttcctcca aagcctaagg acaccctgat gatctctcgg    480
accccctgaag tgacctgcgt ggtggtggat gtgtctcacg aggatcccga agtgaagttc    540
aattggtacg tggacggcgt ggaagtgcac aacgccaaga ccaagcctag agaggaacag    600
tacaactcca cctacagagt ggtgtccgtg ctgaccgtgc tgcaccagga ttggctgaac    660
ggcaaagagt acaagtgcaa ggtgtccaac aaggccctgc ctgctcctat cgaaaagacc    720
atctccaagg ccaagggcca gcctaggaa ccccaggttt acaccctgcc tccaagccgg    780
gaagagatga ccaagaacca ggtgtcctg acctgcctgg tcaagggctt ctaccctttcc   840
gatatcgccg tggaatggga gagcaatggc cagcctgaga acaactacaa gacaacccct    900
cctgtgctgg actccgacgg ctcattcttc ctgtactcca agctgacagt ggacaagtcc    960
agatggcagc agggcaacgt gttctcctgc tccgtgatgc acgaggccct gcacaatcac   1020
tacacccaga agtccctgtc tctgtcccct ggcaaa                             1056

SEQ ID NO: 169           moltype = DNA   length = 1056
FEATURE                  Location/Qualifiers
source                   1..1056
                         mol_type = other DNA
                         organism = synthetic construct SEQUENCE: 169
caggtgcaat tgcaagagtc tggcggcgga ctggtggaag ctggtggatc tctgagactg     60
tcttgtgccg cctccggctt cacctttctct ggctctgata tgtcctgggt ccgacaggct   120
cctggcaagg gacctgaatg ggtgtcctac atcacctccg gcggcaccac ctactatccc    180
gactctgtga agggcagatt caccatctct cgggacaacg ccaagaacac cctgtacctg    240
cagatgaact ccctgaagcc tgacgacaca gccctgtaca gatgcgccaa gtctcggctg    300
accgacagcc actacgtgga agatgcttgg ggccagggaa cacaggtcac cgtgtctagt    360
gaacccaagt cctgcgacaa gacccacacc tgtcctccat gtcctgctcc agaactgctc    420
ggcggacctt ccgtgttcct gtttcctcca aagcctaagg acaccctgat gatctctcgg    480
accccctgaag tgacctgcgt ggtggtggat gtgtctcacg aggatcccga agtgaagttc    540
aattggtacg tggacggcgt ggaagtgcac aacgccaaga ccaagcctag agaggaacag    600
tacaactcca cctacagagt ggtgtccgtg ctgaccgtgc tgcaccagga ttggctgaac    660
ggcaaagagt acaagtgcaa ggtgtccaac aaggccctgc ctgctcctat cgaaaagacc    720
atctccaagg ccaagggcca gcctaggaa ccccaggttt acaccctgcc tccaagccgg    780
gaagagatga ccaagaacca ggtgtcctg acctgcctgg tcaagggctt ctaccctttcc   840
gatatcgccg tggaatggga gagcaatggc cagcctgaga acaactacaa gacaacccct    900
cctgtgctgg actccgacgg ctcattcttc ctgtactcca agctgacagt ggacaagtcc    960
agatggcagc agggcaacgt gttctcctgc tccgtgatgc acgaggccct gcacaatcac   1020
tacacccaga agtccctgtc tctgtcccct ggcaaa                             1056

SEQ ID NO: 170           moltype = AA    length = 14
FEATURE                  Location/Qualifiers
source                   1..14
                         mol_type = protein
                         organism = synthetic construct SEQUENCE: 170
WVRQAPGKGP EWVS                                                       14

SEQ ID NO: 171           moltype = AA    length = 14
FEATURE                  Location/Qualifiers
source                   1..14
                         mol_type = protein
                         organism = synthetic construct SEQUENCE: 171
WVRQAPGKGL EWVS                                                       14

SEQ ID NO: 172           moltype = AA    length = 14
FEATURE                  Location/Qualifiers
source                   1..14
```

```
                        mol_type = protein
                        organism = synthetic construct
SEQUENCE: 172
WVRQAPGKQR EWVS                                                              14

SEQ ID NO: 173          moltype = AA  length = 14
FEATURE                 Location/Qualifiers
source                  1..14
                        mol_type = protein
                        organism = synthetic construct
SEQUENCE: 173
WYRQAPGKGR EWVS                                                              14

SEQ ID NO: 174          moltype = AA  length = 14
FEATURE                 Location/Qualifiers
source                  1..14
                        mol_type = protein
                        organism = synthetic construct
SEQUENCE: 174
WVRQAPGKGL VWVS                                                              14

SEQ ID NO: 175          moltype = AA  length = 14
FEATURE                 Location/Qualifiers
source                  1..14
                        mol_type = protein
                        organism = synthetic construct
VARIANT                 2..11
                        note = Xaa is any amino acid
SEQUENCE: 175
WXRQAPGKXX XWVS                                                              14

SEQ ID NO: 176          moltype = AA  length = 139
FEATURE                 Location/Qualifiers
source                  1..139
                        mol_type = protein
                        organism = synthetic construct
SEQUENCE: 176
MWPLVAALLL GSACCGSAQL LFNKTKSVEF TFCNDTVVIP CFVTNMEAQN TTEVYVKWKF            60
KGRDIYTFDG ALNKSTVPTD FSSAKIEVSQ LLKGDASLKM DKSDAVSHTG NYTCEVTELT            120
REGETIIELK YRVVSWFSP                                                         139

SEQ ID NO: 177          moltype = AA  length = 350
FEATURE                 Location/Qualifiers
source                  1..350
                        mol_type = protein
                        organism = synthetic construct
SEQUENCE: 177
QVQLQESGGG MVQVGGSLRL SCAASGFPFS SADMSWVRQA PGKGPEWVSY INADGSKTYY            60
PDSVKGRFTI SRDNAKNTLY LLMNNLKPED TALYRCARAK LTDTHYVEDY WGQGTQVTVS            120
SESKYGPPCP PCPAPEAAGG PSVFLFPPKP KDTLMISRTP EVTCVVVDVS QEDPEVQFNW            180
YVDGVEVHNA KTKPREEQFN STYRVVSVLT VLHQDWLNGK EYKCKVSNKG LPSSIEKTIS            240
KAKGQPREPQ VYTLPPSQEE MTKNQVSLTC LVKGFYPSDI AVEWESNGQP ENNYKTTPPV            300
LDSDGSFFLY SRLTVDKSRW QEGNVFSCSV MHEALHNHYT QKSLSLSLGK                       350

SEQ ID NO: 178          moltype = AA  length = 349
FEATURE                 Location/Qualifiers
source                  1..349
                        mol_type = protein
                        organism = synthetic construct
SEQUENCE: 178
QVQLQESGGG LVQPGRSLRL SCAASGFTFS GSDMSWVRQA PGKGPEWVSY ITGSGTTYYP            60
DSVKGRFTTS RDNAKNMLYL QMNSLKPDDT ALYRCAKARL TDSHYVEDAW GQGTQVTVSS            120
ESKYGPPCPP CPAPEAAGGP SVFLFPPKPK DTLMISRTPE VTCVVVDVSQ EDPEVQFNWY            180
VDGVEVHNAK TKPREEQFNS TYRVVSVLTV LHQDWLNGKE YKCKVSNKGL PSSIEKTISK            240
AKGQPREPQV YTLPPSQEEM TKNQVSLTCL VKGFYPSDIA VEWESNGQPE NNYKTTPPVL            300
DSDGSFFLYS RLTVDKSRWQ EGNVFSCSVM HEALHNHYTQ KSLSLSLGK                        349

SEQ ID NO: 179          moltype = AA  length = 110
FEATURE                 Location/Qualifiers
source                  1..110
                        mol_type = protein
                        organism = synthetic construct
SEQUENCE: 179
APEAAGGPSV FLFPPKPKDT LMISRTPEVT CVVVDVSQED PEVQFNWYVD GVEVHNAKTK            60
PREEQFNSTY RVVSVLTVLH QDWLNGKEYK CKVSNKGLPS SIEKTISKAK                       110

SEQ ID NO: 180          moltype = AA  length = 17
FEATURE                 Location/Qualifiers
source                  1..17
```

```
                        mol_type = protein
                        organism = synthetic construct
VARIANT                 11
                        note = Q or G
VARIANT                 12
                        note = R, L or P
VARIANT                 17
                        note = Y, A or V
SEQUENCE: 180
MSWVRQAPGK XXEWVSX                                                           17

SEQ ID NO: 181          moltype = AA  length = 8
FEATURE                 Location/Qualifiers
source                  1..8
                        mol_type = protein
                        organism = synthetic construct
VARIANT                 6
                        note = G, N, S or D
VARIANT                 3
                        note = Xaa is any amino acid
VARIANT                 7
                        note = Xaa is any amino acid
SEQUENCE: 181
GFXFSXXD                                                                      8

SEQ ID NO: 182          moltype = AA  length = 8
FEATURE                 Location/Qualifiers
source                  1..8
                        mol_type = protein
                        organism = synthetic construct
VARIANT                 3
                        note = T or P
VARIANT                 6
                        note = G, N or S
VARIANT                 7
                        note = S, Y or A
SEQUENCE: 182
GFXFSXXD                                                                      8

SEQ ID NO: 183          moltype =   length =
SEQUENCE: 183
000

SEQ ID NO: 184          moltype =   length =
SEQUENCE: 184
000

SEQ ID NO: 185          moltype = AA  length = 14
FEATURE                 Location/Qualifiers
source                  1..14
                        mol_type = protein
                        organism = synthetic construct
VARIANT                 2
                        note = Q, H, R or K
VARIANT                 3
                        note = S, T or A
VARIANT                 4
                        note = Q, H, R or K
VARIANT                 8
                        note = S, T or A
VARIANT                 14
                        note = any amino acid or absent
SEQUENCE: 185
AXXXLTDXHY VEDX                                                              14

SEQ ID NO: 186          moltype = AA  length = 14
FEATURE                 Location/Qualifiers
source                  1..14
                        mol_type = protein
                        organism = synthetic construct
VARIANT                 2
                        note = R or K
VARIANT                 3
                        note = A or S
VARIANT                 4
                        note = K or R
VARIANT                 8
                        note = T or S
VARIANT                 14
```

```
                                         note = Y, A or absent
SEQUENCE: 186
AXXXLTDXHY VEDX                                                                               14

SEQ ID NO: 187           moltype =    length =
SEQUENCE: 187
000

SEQ ID NO: 188           moltype =    length =
SEQUENCE: 188
000

SEQ ID NO: 189           moltype = AA   length = 17
FEATURE                  Location/Qualifiers
source                   1..17
                         mol_type = protein
                         organism = synthetic construct
VARIANT                  3
                         note = any amino acid or absent
VARIANT                  4
                         note = S, T or A
VARIANT                  6
                         note = S, A or G
VARIANT                  7
                         note = S, A or G
VARIANT                  8
                         note = S, T, N or K
VARIANT                  14
                         note = S, T or A
VARIANT                  1
                         note = Xaa is any amino acid
VARIANT                  5
                         note = Xaa is any amino acid
VARIANT                  10
                         note = Xaa is any amino acid
VARIANT                  12
                         note = Xaa is any amino acid
SEQUENCE: 189
XIXXXXXXTX YXDXVKG                                                                            17

SEQ ID NO: 190           moltype = AA   length = 17
FEATURE                  Location/Qualifiers
source                   1..17
                         mol_type = protein
                         organism = synthetic construct
VARIANT                  1
                         note = Y, A, V or R
VARIANT                  3
                         note = absent or N
VARIANT                  4
                         note = T or A
VARIANT                  5
                         note = G, S, D, N or E
VARIANT                  6
                         note = S or G
VARIANT                  7
                         note = G or S
VARIANT                  8
                         note = T, N or K
VARIANT                  10
                         note = Y, D or S
VARIANT                  12
                         note = P or A
VARIANT                  14
                         note = S or T
SEQUENCE: 190
XIXXXXXXTX YXDXVKG                                                                            17

SEQ ID NO: 191           moltype = AA   length = 12
FEATURE                  Location/Qualifiers
source                   1..12
                         mol_type = protein
                         organism = synthetic construct
VARIANT                  1
                         note = S, T or A
VARIANT                  2
                         note = Q, H, R or K
VARIANT                  6
                         note = S, T or A
```

```
VARIANT                 12
                        note = any amino acid or absent
SEQUENCE: 191
XXLTDXHYVE DX                                                               12

SEQ ID NO: 192          moltype = AA  length = 12
FEATURE                 Location/Qualifiers
source                  1..12
                        mol_type = protein
                        organism = synthetic construct
VARIANT                 1
                        note = A or S
VARIANT                 2
                        note = K or R
VARIANT                 6
                        note = T or S
VARIANT                 12
                        note = Y, A or absent
SEQUENCE: 192
XXLTDXHYVE DX                                                               12

SEQ ID NO: 193          moltype = AA  length = 14
FEATURE                 Location/Qualifiers
source                  1..14
                        mol_type = protein
                        organism = synthetic construct
VARIANT                 2
                        note = V or Y
VARIANT                 9
                        note = G or Q
VARIANT                 10
                        note = P, L or R
VARIANT                 11
                        note = E or V
SEQUENCE: 193
WXRQAPGKXX XWVS                                                             14

SEQ ID NO: 194          moltype = AA  length = 14
FEATURE                 Location/Qualifiers
source                  1..14
                        mol_type = protein
                        organism = synthetic construct
VARIANT                 9
                        note = G or Q
VARIANT                 10
                        note = P, L or R
SEQUENCE: 194
WVRQAPGKXX EWVS                                                             14

SEQ ID NO: 195          moltype = AA  length = 121
FEATURE                 Location/Qualifiers
source                  1..121
                        mol_type = protein
                        organism = synthetic construct
VARIANT                 11
                        note = M or L
VARIANT                 14
                        note = V, P or A
VARIANT                 54
                        note = D, G or S
VARIANT                 82
                        note = L or Q
VARIANT                 85
                        note = N or S
VARIANT                 87
                        note = K or T
SEQUENCE: 195
QVQLQESGGG XVQXGGSLRL SCAASGFPFS SADMSWVRQA PGKGPEWVSY INAXGSKTYY            60
PDSVKGRFTI SRDNAKNTLY LXMNXLXPED TALYRCARAK LTDTHYVEDY WGQGTQVTVS           120
S                                                                          121

SEQ ID NO: 196          moltype = AA  length = 121
FEATURE                 Location/Qualifiers
source                  1..121
                        mol_type = protein
                        organism = synthetic construct
VARIANT                 1
                        note = Q or E
VARIANT                 5
```

```
                        note = Q, V or L
VARIANT                 11
                        note = M or L
VARIANT                 14
                        note = V or P
VARIANT                 44
                        note = G or Q
VARIANT                 45
                        note = P, L or R
VARIANT                 50
                        note = Y or V
VARIANT                 54
                        note = D, N or E
VARIANT                 61
                        note = P or A
VARIANT                 63
                        note = S or T
VARIANT                 75
                        note = A or S
VARIANT                 82
                        note = L or Q
VARIANT                 85
                        note = N or S
VARIANT                 87
                        note = K or R
VARIANT                 88
                        note = P or A
VARIANT                 93
                        note = L or V
VARIANT                 95
                        note = R or Y
VARIANT                 116
                        note = Q or M
SEQUENCE: 196
XVQLXESGGG XVQXGGSLRL SCAASGFPFS SADMSWVRQA PGKXXEWVSX INAXGSKTYY     60
XDXVKGRFTI SRDNXKNTLY LXMNXLXXED TAXYXCARAK LTDTHYVEDY WGQGTXVTVS   120
S                                                                   121

SEQ ID NO: 197          moltype = AA   length = 121
FEATURE                 Location/Qualifiers
source                  1..121
                        mol_type = protein
                        organism = synthetic construct
VARIANT                 1
                        note = Q or E
VARIANT                 5
                        note = Q, V or L
VARIANT                 11
                        note = M or L
VARIANT                 14
                        note = V or P
VARIANT                 44
                        note = G or Q
VARIANT                 45
                        note = P, L or R
VARIANT                 61
                        note = P or A
VARIANT                 63
                        note = S or T
VARIANT                 75
                        note = A or S
VARIANT                 82
                        note = L or Q
VARIANT                 85
                        note = N or S
VARIANT                 87
                        note = K or R
VARIANT                 88
                        note = P or A
VARIANT                 93
                        note = L or V
VARIANT                 95
                        note = R or Y
VARIANT                 116
                        note = Q or M
SEQUENCE: 197
XVQLXESGGG XVQXGGSLRL SCAASGFPFS SADMSWVRQA PGKXXEWVSY INADGSKTYY     60
XDXVKGRFTI SRDNXKNTLY LXMNXLXXED TAXYXCARAK LTDTHYVEDY WGQGTXVTVS   120
S                                                                   121
```

```
SEQ ID NO: 198         moltype = AA  length = 120
FEATURE                Location/Qualifiers
source                 1..120
                       mol_type = protein
                       organism = synthetic construct
VARIANT                13
                       note = Q, H or E
VARIANT                14
                       note = V, P or A
VARIANT                86
                       note = K or T
VARIANT                88
                       note = E or D
SEQUENCE: 198
QVQLQESGGG LVXXGGSLRL SCAASGFTFS GSDMSWVRQA PGKGPEWVSY ITSGGTTYYP   60
DSVKGRFTIS RDNAKNTLYL QMNSLXPXDT ALYRCAKSRL TDSHYVEDAW GQGTQVTVSS  120

SEQ ID NO: 199         moltype = AA  length = 120
FEATURE                Location/Qualifiers
source                 1..120
                       mol_type = protein
                       organism = synthetic construct
VARIANT                1
                       note = Q or E
VARIANT                5
                       note = Q, L or V
VARIANT                12
                       note = V or I
VARIANT                13
                       note = E or Q
VARIANT                14
                       note = A or P
VARIANT                45
                       note = P or L
VARIANT                50
                       note = Y, A or V
VARIANT                60
                       note = P or A
VARIANT                62
                       note = S or T
VARIANT                74
                       note = A or S
VARIANT                86
                       note = K or R
VARIANT                87
                       note = P or A
VARIANT                115
                       note = Q or L
VARIANT                92
                       note = L or V
VARIANT                94
                       note = R or Y
VARIANT                88
                       note = D or E
SEQUENCE: 199
XVQLXESGGG LXXXGGSLRL SCAASGFTFS GSDMSWVRQA PGKGXEWVSX ITSGGTTYYX   60
DXVKGRFTIS RDNXKNTLYL QMNSLXXXDT AXYXCAKSRL TDSHYVEDAW GQGTXVTVSS  120

SEQ ID NO: 200         moltype = AA  length = 120
FEATURE                Location/Qualifiers
source                 1..120
                       mol_type = protein
                       organism = synthetic construct
VARIANT                1
                       note = Q or E
VARIANT                5
                       note = Q or L
VARIANT                12
                       note = V or I
VARIANT                13
                       note = E or Q
VARIANT                14
                       note = A or P
VARIANT                45
                       note = P or L
VARIANT                50
                       note = Y or A
VARIANT                60
```

```
                        note = P or A
VARIANT                 62
                        note = S or T
VARIANT                 74
                        note = A or S
VARIANT                 86
                        note = K or R
VARIANT                 87
                        note = P or A
VARIANT                 88
                        note = D or E
VARIANT                 92
                        note = L or V
VARIANT                 94
                        note = R or Y
VARIANT                 115
                        note = Q or L
SEQUENCE: 200
XVQLXESGGG LXXXGGSLRL SCAASGFTFS GSDMSWVRQA PGKGXEWVSX ITSGGTTYYX    60
DXVKGRFTIS RDNXKNTLYL QMNSLXXXDT AXYXCAKSRL TDSHYVEDAW GQGTXVTVSS   120

SEQ ID NO: 201          moltype = AA   length = 121
FEATURE                 Location/Qualifiers
source                  1..121
                        mol_type = protein
                        organism = synthetic construct
VARIANT                 11
                        note = M or L
VARIANT                 13
                        note = Q, H or E
VARIANT                 14
                        note = V, P or A
VARIANT                 16
                        note = G or R
VARIANT                 28
                        note = P or T
VARIANT                 31
                        note = S, N or G
VARIANT                 32
                        note = A, Y or S
VARIANT                 52
                        note = N or T
VARIANT                 53
                        note = A, S or G
VARIANT                 54
                        note = D, G or S
VARIANT                 55
                        note = G or absent
VARIANT                 56
                        note = S or G
VARIANT                 57
                        note = K, N or T
VARIANT                 59
                        note = Y or D
VARIANT                 70
                        note = I or T
VARIANT                 78
                        note = T or M
VARIANT                 82
                        note = L or Q
VARIANT                 85
                        note = N or S
VARIANT                 87
                        note = K or T
VARIANT                 89
                        note = E or D
VARIANT                 98
                        note = R or K
VARIANT                 99
                        note = A or S
VARIANT                 100
                        note = K or R
VARIANT                 104
                        note = T or S
VARIANT                 110
                        note = Y or A
SEQUENCE: 201
QVQLQESGGG XVXXGXSLRL SCAASGFXFS XXDMSWVRQA PGKGPEWVSY IXXXXXXTXY    60
PDSVKGRFTX SRDNAKNXLY LXMNXLXPXD TALYRCAXXX LTDXHYVEDX WGQGTQVTVS   120
```

|   |   |   |
|---|---|---|
| S | | 121 |
| SEQ ID NO: 202 | moltype = AA length = 121 | |
| FEATURE | Location/Qualifiers | |
| source | 1..121 | |
| | mol_type = protein | |
| | organism = synthetic construct | |
| VARIANT | 11 | |
| | note = M or L | |
| VARIANT | 13 | |
| | note = Q, H or E | |
| VARIANT | 14 | |
| | note = V, P or A | |
| VARIANT | 16 | |
| | note = G or R | |
| VARIANT | 28 | |
| | note = P or T | |
| VARIANT | 31 | |
| | note = S, N or G | |
| VARIANT | 32 | |
| | note = A, Y or S | |
| VARIANT | 52 | |
| | note = N or T | |
| VARIANT | 53 | |
| | note = A, S or G | |
| VARIANT | 54 | |
| | note = D, G or S | |
| VARIANT | 55 | |
| | note = G or absent | |
| VARIANT | 56 | |
| | note = S or G | |
| VARIANT | 57 | |
| | note = K, N or T | |
| VARIANT | 59 | |
| | note = Y or D | |
| VARIANT | 70 | |
| | note = I or T | |
| VARIANT | 78 | |
| | note = T or M | |
| VARIANT | 82 | |
| | note = L or Q | |
| VARIANT | 85 | |
| | note = N or S | |
| VARIANT | 87 | |
| | note = K or T | |
| VARIANT | 89 | |
| | note = E or D | |
| VARIANT | 98 | |
| | note = R or K | |
| VARIANT | 99 | |
| | note = A or S | |
| VARIANT | 100 | |
| | note = K or R | |
| VARIANT | 104 | |
| | note = T or S | |
| VARIANT | 110 | |
| | note = Y or A | |
| SEQUENCE: 202 | | |
| QVQLQESGGG XVXXGXSLRL SCAASGFXFS XXDMSWVRQA PGKGPEWVSY IXXXXXXTXY | | 60 |
| PDSVKGRFTX SRDNAKNXLY LXMNXLXPXD TALYRCAXXX LTDXHYVEDX WGQGTQVTVS | | 120 |
| S | | 121 |
| SEQ ID NO: 203 | moltype = AA length = 121 | |
| FEATURE | Location/Qualifiers | |
| source | 1..121 | |
| | mol_type = protein | |
| | organism = synthetic construct | |
| VARIANT | 11 | |
| | note = M or L | |
| VARIANT | 13 | |
| | note = Q, H or E | |
| VARIANT | 14 | |
| | note = V, P or A | |
| VARIANT | 16 | |
| | note = G or R | |
| VARIANT | 28 | |
| | note = P or T | |
| VARIANT | 31 | |
| | note = S, N or G | |

```
VARIANT                 32
                        note = A, Y or S
VARIANT                 52
                        note = N or T
VARIANT                 53
                        note = A, S or G
VARIANT                 54
                        note = D, G or S
VARIANT                 55
                        note = G or absent
VARIANT                 56
                        note = S or G
VARIANT                 57
                        note = K, N or T
VARIANT                 70
                        note = I or T
VARIANT                 78
                        note = T or M
VARIANT                 82
                        note = L or Q
VARIANT                 85
                        note = N or S
VARIANT                 87
                        note = K or T
VARIANT                 89
                        note = E or D
VARIANT                 98
                        note = R or K
VARIANT                 99
                        note = A or S
SEQUENCE: 203
QVQLQESGGG XVXXGXSLRL SCAASGFXFS XXDMSWVRQA PGKGPEWVSY IXXXXXXTYY      60
PDSVKGRFTX SRDNAKNXLY LXMNXLXPXD TALYRCAXXR LTDSHYVEDA WGQGTQVTVS     120
S                                                                    121

SEQ ID NO: 204          moltype = AA  length = 121
FEATURE                 Location/Qualifiers
source                  1..121
                        mol_type = protein
                        organism = synthetic construct
VARIANT                 11
                        note = M or L
VARIANT                 13
                        note = Q, H or E
VARIANT                 14
                        note = V, P or A
VARIANT                 16
                        note = G or R
VARIANT                 28
                        note = P or T
VARIANT                 31
                        note = S, N or G
VARIANT                 32
                        note = A, Y or S
VARIANT                 52
                        note = N or T
VARIANT                 53
                        note = A, S or G
VARIANT                 54
                        note = D, G or S
VARIANT                 56
                        note = S or G
VARIANT                 57
                        note = K, N or T
VARIANT                 59
                        note = Y or D
VARIANT                 70
                        note = I or T
VARIANT                 78
                        note = T or M
VARIANT                 82
                        note = L or Q
VARIANT                 85
                        note = N or S
VARIANT                 87
                        note = K or T
VARIANT                 89
                        note = E or D
VARIANT                 98
```

-continued

```
VARIANT           note = R or K
                  99
                  note = A or S
VARIANT           100
                  note = K or R
VARIANT           104
                  note = T or S
VARIANT           110
                  note = Y or A
SEQUENCE: 204
QVQLQESGGG XVXXGXSLRL SCAASGFXFS XXDMSWVRQA PGKGPEWVSY IXXXGXXTXY    60
PDSVKGRFTX SRDNAKNXLY LXMNXLXPXD TALYRCAXXX LTDXHYVEDX WGQGTQVTVS   120
S                                                                  121

SEQ ID NO: 205    moltype = AA  length = 121
FEATURE           Location/Qualifiers
source            1..121
                  mol_type = protein
                  organism = synthetic construct
VARIANT           1
                  note = Q or E
VARIANT           5
                  note = Q, L or V
VARIANT           11
                  note = M or L
VARIANT           12
                  note = V or I
VARIANT           13
                  note = Q, H or E
VARIANT           14
                  note = P, A or V
VARIANT           16
                  note = G or R
VARIANT           28
                  note = P or T
VARIANT           31
                  note = G, S or N
VARIANT           32
                  note = A or S
VARIANT           35
                  note = S or H
VARIANT           37
                  note = V or Y
VARIANT           44
                  note = G or Q
VARIANT           45
                  note = P, L or R
VARIANT           46
                  note = E or V
VARIANT           50
                  note = Y, A or R
VARIANT           52
                  note = T or N
VARIANT           53
                  note = A, S or G
VARIANT           54
                  note = G, S, D, N or E
VARIANT           56
                  note = absent or S
VARIANT           57
                  note = K or T
VARIANT           59
                  note = Y, D or S
VARIANT           61
                  note = P or A
VARIANT           63
                  note = S or T
VARIANT           70
                  note = I or T
VARIANT           75
                  note = S or A
VARIANT           78
                  note = T or M
VARIANT           82
                  note = Q or L
VARIANT           85
                  note = S or N
VARIANT           87
                  note = K, R or T
```

```
VARIANT                 88
                        note = P or A
VARIANT                 89
                        note = E or D
VARIANT                 93
                        note = V or L
VARIANT                 95
                        note = Y or R
VARIANT                 99
                        note = A or S
VARIANT                 100
                        note = K or R
VARIANT                 104
                        note = S or T
VARIANT                 110
                        note = Y or A
VARIANT                 116
                        note = Q, L or M
VARIANT                 98
                        note = R or K
SEQUENCE: 205
XVQLXESGGG XXXXGXSLRL SCAASGFXFS XXDMXWXRQA PGKXXXWVSX IXXXGXXTXY       60
XDXVKGRFTX SRDNXKNXLY LXMNXLXXXD TAXYXCAXXX LTDXHYVEDX WGQGTXVTVS      120
S                                                                     121

SEQ ID NO: 206          moltype = AA   length = 5
FEATURE                 Location/Qualifiers
source                  1..5
                        mol_type = protein
                        organism = synthetic construct
SEQUENCE: 206
GGGGS                                                                   5

SEQ ID NO: 207          moltype = AA   length = 8
FEATURE                 Location/Qualifiers
source                  1..8
                        mol_type = protein
                        organism = synthetic construct
REPEAT                  2..6
                        note = amino acid residues 2-6 can be repeated from one to
                         ten times
VARIANT                 1
                        note = Xaa is absent or A
SEQUENCE: 207
XPAPAPKA                                                                8

SEQ ID NO: 208          moltype = AA   length = 121
FEATURE                 Location/Qualifiers
source                  1..121
                        mol_type = protein
                        organism = synthetic construct
VARIANT                 1
                        note = Q or E
VARIANT                 5
                        note = Q, V or L
VARIANT                 11
                        note = M or L
VARIANT                 14
                        note = V or P
VARIANT                 44
                        note = G or Q
VARIANT                 45
                        note = P, L or R
VARIANT                 61
                        note = P or A
VARIANT                 63
                        note = S or T
VARIANT                 75
                        note = A or S
VARIANT                 87
                        note = K or R
VARIANT                 88
                        note = P or A
VARIANT                 93
                        note = L or V
VARIANT                 95
                        note = R or Y
VARIANT                 116
                        note = Q or M
```

```
SEQUENCE: 208
XVQLXESGGG XVQXGGSLRL SCAASGFPFS SADMSWVRQA PGKXXEWVSY INADGSKTYY      60
XDXVKGRFTI SRDNXKNTLY LQMNSLXXED TAXYXCARAK LTDTHYVEDY WGQGTXVTVS     120
S                                                                    121

SEQ ID NO: 209          moltype = AA  length = 120
FEATURE                 Location/Qualifiers
source                  1..120
                        mol_type = protein
                        organism = synthetic construct
VARIANT                 1
                        note = Q or E
VARIANT                 5
                        note = Q, L or V
VARIANT                 12
                        note = V or I
VARIANT                 45
                        note = P or L
VARIANT                 50
                        note = Y, A or V
VARIANT                 60
                        note = P or A
VARIANT                 74
                        note = A or S
VARIANT                 86
                        note = K or R
VARIANT                 87
                        note = P or A
VARIANT                 88
                        note = D or E
VARIANT                 92
                        note = L or V
VARIANT                 94
                        note = R or Y
VARIANT                 115
                        note = Q or L
SEQUENCE: 209
XVQLXESGGG LXQPGGSLRL SCAASGFTFS GSDMSWVRQA PGKGXEWVSX ITSGGTTYYX      60
DTVKGRFTIS RDNXKNTLYL QMNSLXXXDT AXYXCAKSRL TDSHYVEDAW GQGTXVTVSS    120

SEQ ID NO: 210          moltype = AA  length = 120
FEATURE                 Location/Qualifiers
source                  1..120
                        mol_type = protein
                        organism = synthetic construct
VARIANT                 1
                        note = Q or E
VARIANT                 5
                        note = Q, L or V
VARIANT                 12
                        note = V or I
VARIANT                 13
                        note = E or Q
VARIANT                 45
                        note = P or L
VARIANT                 50
                        note = Y, A or V
VARIANT                 60
                        note = P or A
VARIANT                 74
                        note = A or S
VARIANT                 86
                        note = K or R
VARIANT                 87
                        note = P or A
VARIANT                 88
                        note = D or E
VARIANT                 92
                        note = L or V
VARIANT                 94
                        note = R or Y
VARIANT                 115
                        note = Q or L
SEQUENCE: 210
XVQLXESGGG LXXPGGSLRL SCAASGFTFS GSDMSWVRQA PGKGXEWVSX ITSGGTTYYX      60
DTVKGRFTIS RDNXKNTLYL QMNSLXXXDT AXYXCAKSRL TDSHYVEDAW GQGTXVTVSS    120

SEQ ID NO: 211          moltype = AA  length = 65
FEATURE                 Location/Qualifiers
```

```
source                  1..65
                        mol_type = protein
                        organism = synthetic construct
SEQUENCE: 211
QVQLQESGGG LVEAGGSLRL SCAASGFTFS GSDMSWVRQA PGKGPEWVSY ITSGGTTYYP    60
DSVKG                                                                65

SEQ ID NO: 212          moltype = AA  length = 65
FEATURE                 Location/Qualifiers
source                  1..65
                        mol_type = protein
                        organism = synthetic construct
SEQUENCE: 212
AQDNCTCPTN KMTVCSPDGP GGRCQCRALG SGMAVDCSTL TSKCLLLKAR MSAPKNARTL    60
VRPSE                                                                65

SEQ ID NO: 213          moltype = AA  length = 54
FEATURE                 Location/Qualifiers
source                  1..54
                        mol_type = protein
                        organism = synthetic construct
SEQUENCE: 213
RFTISRDNAK NTLYLQMNSL KPDDTALYRC AKSRLTDSHY VEDAWGQGTQ VTVS           54

SEQ ID NO: 214          moltype = AA  length = 57
FEATURE                 Location/Qualifiers
source                  1..57
                        mol_type = protein
                        organism = synthetic construct
SEQUENCE: 214
HALVDNDGLY DPDCDPEGRF KARQCQQVCW CVNSVGVRRT DKGDLSLRCD ELVRTHH       57
```